United States Patent
Bryan et al.

(10) Patent No.: US 11,034,698 B2
(45) Date of Patent: *Jun. 15, 2021

(54) PYRAZOLO[1,5A]PYRIMIDINE DERIVATIVES AS IRAK4 MODULATORS

(71) Applicant: Genentech, Inc., South San Francisco, CA (US)

(72) Inventors: Marian C. Bryan, South San Francisco, CA (US); Steven Do, South San Francisco, CA (US); Joy Drobnick, South San Francisco, CA (US); Alberto Gobbi, South San Francisco, CA (US); Tamiko Katsumoto, Millbrae, CA (US); James Richard Kiefer, Jr., South San Francisco, CA (US); Jun Liang, South San Francisco, CA (US); Naomi S. Rajapaksa, South San Francisco, CA (US); Yongsheng Chen, Shanghai (CN); Liqiang Fu, Shanghai (CN); Kwong Wah Lai, Shanghai (CN); Zhiguo Liu, Shanghai (CN); John Wai, Shanghai (CN); Fei Wang, Shanghai (CN)

(73) Assignee: Genentech, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/715,933

(22) Filed: Dec. 16, 2019

(65) Prior Publication Data

US 2020/0123166 A1    Apr. 23, 2020

Related U.S. Application Data

(63) Continuation of application No. PCT/EP2018/066320, filed on Jun. 19, 2018.

(30) Foreign Application Priority Data

Jun. 21, 2017  (WO) ............... PCT/CN2017/089358

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .......................... C07D 487/04; C07D 519/00
See application file for complete search history.

(56) References Cited

U.S. PATENT DOCUMENTS

2012/0015962 A1    1/2012   Arora et al.

FOREIGN PATENT DOCUMENTS

| WO | 2012/007375 | 1/2012 |
|----|-------------|--------|
| WO | 2015/193846 A1 | 12/2015 |
| WO | 2016/144846 A1 | 9/2016 |
| WO | 2016/144848 A1 | 9/2016 |
| WO | 2016/144849 A1 | 9/2016 |
| WO | 2017/108723 A2 | 6/2017 |

OTHER PUBLICATIONS

Chaudhary, D., et al., "Recent Advances in the Discovery of Small Molecule Inhibitors of Interlekin-1 Receptor-Associated Kinase 4 (IRAK4) as a Therapeutic Target for Inflammation and Oncology Disorders" J Med Chem 58(1):96-110 (Jan. 8, 2015).
"International Preliminary Report on Patentability—PCT/EP2018/066320":pp. 1-11 (Jan. 2, 2020).
"International Search Report—PCT/EP2018/066320":pp. 1-19 (Nov. 7, 2018).
Lim, J., et al., "Discovery of 5-Amino-N-(1H-parazol-4yl)pyrazolo(1.5-a)pyrimidine-3carboxamide Inhibitors of IRAK4" ACS Med Chem Lett 6(6):683-688 (Jun. 11, 2015).

*Primary Examiner* — Golam M Shameem

(57) ABSTRACT

Compounds of Formula I, Formula II, Formula III, Formula IV, Formula V, Formula VI, Formula VII, Formula VIII, and methods of use as Interleukin-1 Receptor Associated Kinase (IRAK4) inhibitors are described herein.

16 Claims, No Drawings

PYRAZOLO[1,5A]PYRIMIDINE DERIVATIVES AS IRAK4 MODULATORS

CROSS-REFERENCE TO RELATED APPLICATION

This application is a continuation application of PCT/EP2018/066320, filed Jun. 19, 2018 that claims the benefit of priority to International Patent Application No. PCT/CN2017/089358, filed Jun. 21, 2017, which is incorporated by reference herein in its entirety.

FIELD OF THE INVENTION

This invention pertains to compounds useful for inhibition of Interleukin-1 Receptor Associated Kinase 4 (IRAK4).

BACKGROUND OF THE INVENTION

TIR-domain (Toll-Interleukin 1 Receptor-domain) containing cell surface receptors such as the Toll-like receptors (TLR) and the IL-1 and IL-18 receptors play critical roles in innate immunity and have been implicated in the pathogenesis of autoimmunity. TLRs, for example, recognize pathogenic or endogenous ligands and provide a requisite signal for dendritic cell maturation and antigen presentation to T cell. Similarly, proteins that mediate signaling from these receptors have also been shown to play important roles in the pathogenesis of autoimmune disorders. For example mice deficient in MyD88, an adaptor protein that directly interacts with the TIR domain, are more susceptible to bacterial, fungal and parasitic infections. In addition, MyD88 deficient mice are resistant to experimental autoimmune encephalomyelitis (EAE) and streptococcal cell wall-induced arthritis.

The Interleukin-1 Receptor Associated Kinase (IRAK) family is comprised of four family members IRAK1, IRAK2, IRAK3 (also termed IRAK-M), and IRAK4. These proteins are characterized by a typical N-terminal death domain that mediates interaction with MyD88-family adaptor proteins and a centrally located kinase domain. Whereas IRAK1 and IRAK4 have kinase activity, IRAK2 and IRAK3 are catalytically inactive. Upon activation of their upstream cognate receptors, IRAK4 is thought to phosphorylate IRAK1, resulting in the activation and autophosphorylation of IRAK1 and subsequent phosphorylation of downstream substrates. The hyperphosphorylation of IRAK1 directs its dissociation from the receptor complex and its eventual ubiquitylation and proteasomal degradation. Phosphorylation of downstream substrates such as Pellino-2 ultimately leads to the activation of the MAPKs such as p38 and c-Jun N-terminal kinase (JNK) and NF-kB followed by production of pro-inflammatory cytokines, chemokines, and destructive enzyme.

The role of IRAK4 in innate immunity and in the pathogenesis of autoimmune diseases is emerging. See, e.g., Li et al., "IRAK-4: A novel member of the IRAK family with the properties of an IRAK-kinase," PNAS 2002, 99(8), 5567-5572; Flannery et al., "The interleukin-1 receptor-associated kinases: Critical regulators of innate immune signaling," Biochem Pharm 2010, 80(12), 1981-1991. Patients with destabilizing or null mutations in IRAK4 demonstrate defects in TLR signaling and the production of pro-inflammatory cytokines such as IL-1 and TNF as well as antiviral cytokines such as IFNα and IFNβ. These patients demonstrate an increased susceptibility to gram-positive bacterial infections although they are generally resistant to gram-negative bacterial, viral, and fungal infections. Similarly, IRAK4 deficient mice have defects in TLR- and IL-1-mediated cytokine production and exhibit an increased susceptibility to infection. IRAK1 deficient mice demonstrate a loss of responsiveness to lipopolysaccharides (LPS), IL-1, and IL-18 as well as impaired Th1 development. These mice were resistant to experimental autoimmune encephalomyelitis, exhibiting little or no CNS inflammation.

Accordingly, compounds that modulate the function of IRAK4 represent an attractive approach to the development of therapeutic agents for the treatment of diseases such as inflammatory, cell proliferative and immune-related conditions and diseases associated with IRAK-mediated signal transduction, such as rheumatoid arthritis, inflammatory bowel disease, multiple sclerosis, lupus, diabetes, obesity, allergic disease, psoriasis, asthma, graft rejection, cancer and sepsis.

SUMMARY OF THE INVENTION

One aspect of the invention includes a compound of Formula I:

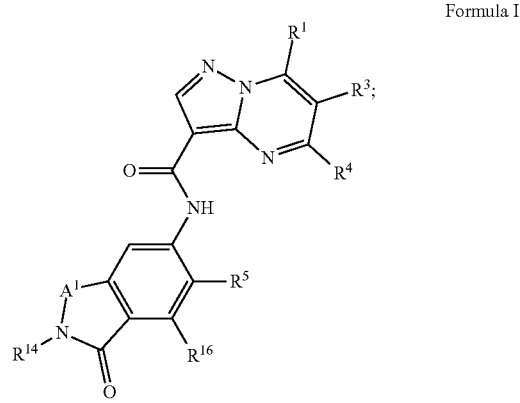

Formula I or a stereoisomer or a pharmaceutically acceptable salt thereof, wherein:

$A^1$ is $CH_2$ or NH;

$R^1$ is hydrogen;

$R^3$ is hydrogen, halogen, —OH, or $C_{1-3}$alkyl;

$R^4$ is hydrogen, halogen, —$NR^8R^9$, —$C(O)NR^8R^9$, or a 3-7 membered monocyclic saturated or partially saturated heterocyclic group optionally substituted with one or more substituents selected from oxo, —$NR^8R^9$, or $R^{13}$;

$R^5$ is selected from the group consisting of —$NHCH_3$, —$N(CH_3)_2$, —$C(CH_3)_2OH$, —$OCH_3$, —$OCH(CH_3)_2$, —$OC(CH_3)_3$, —$OCH_2CH_3$, —$OCHF_2$, —$OCH_2CF_3$, —$OCH_2CHF_2$, —$CH_2OCHF_2$, —CN,

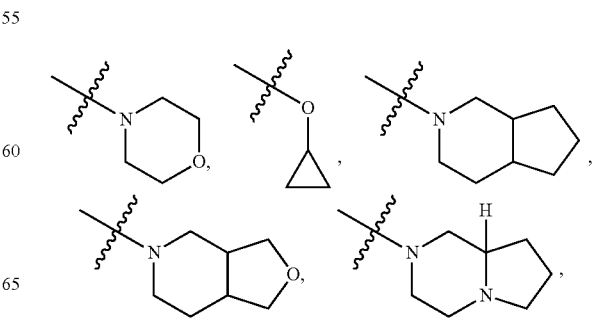

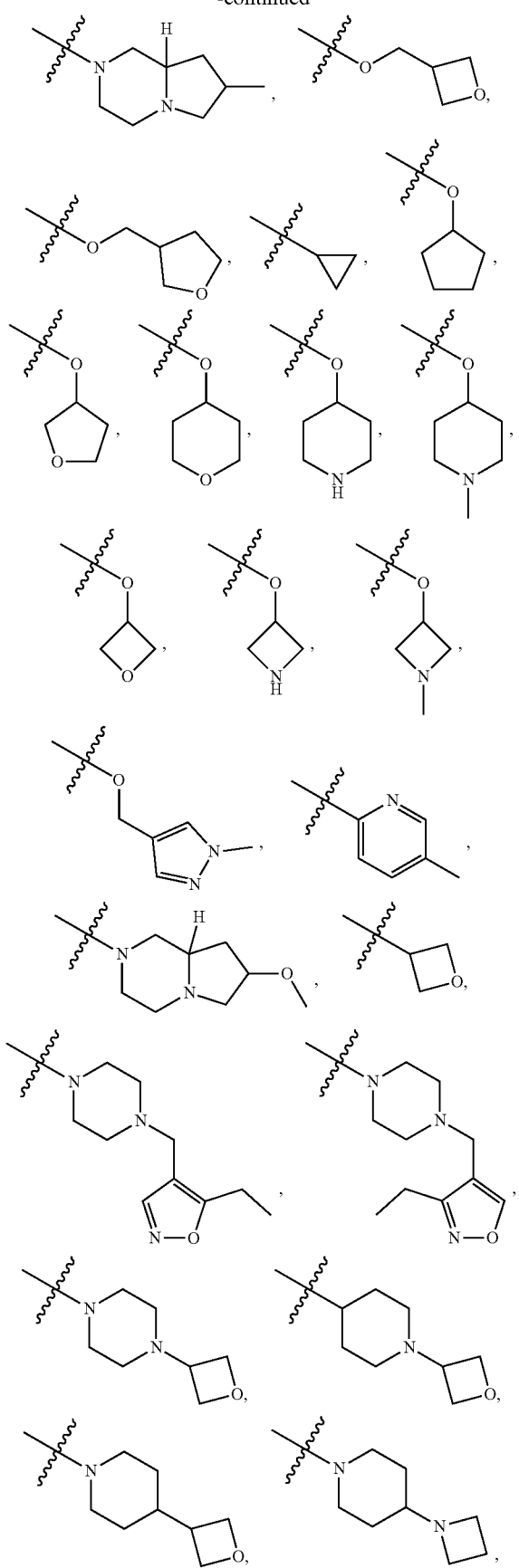
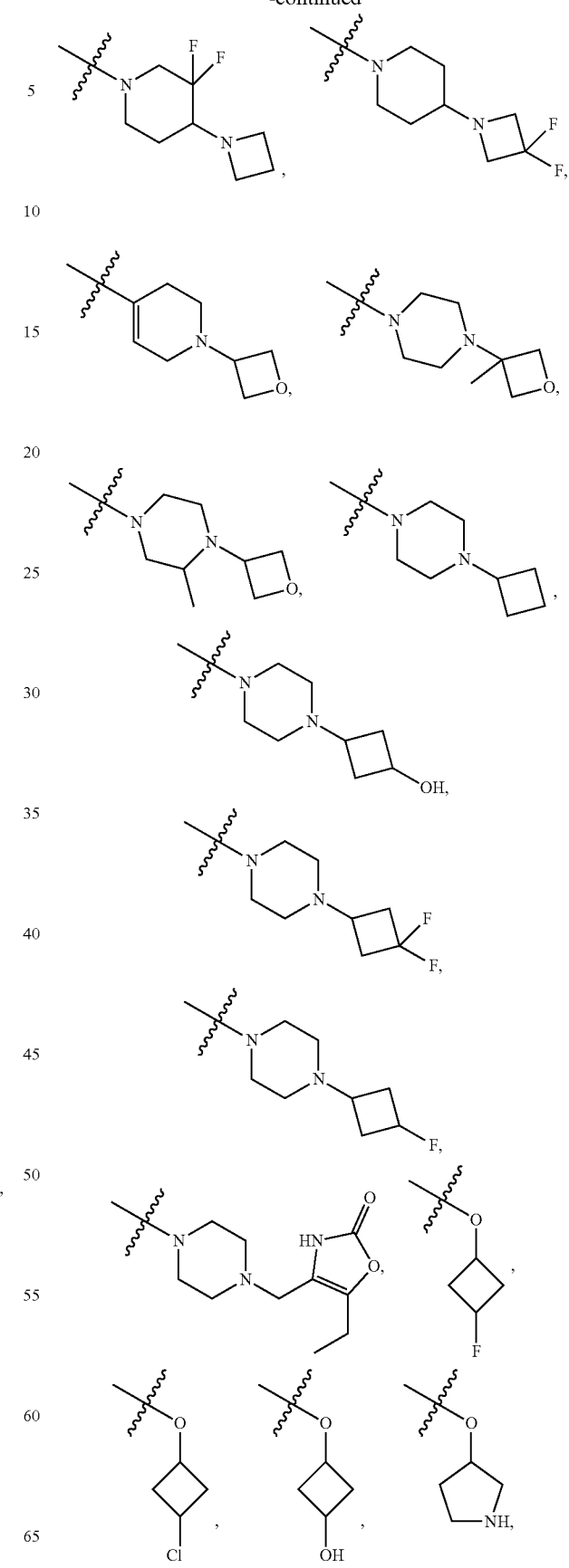

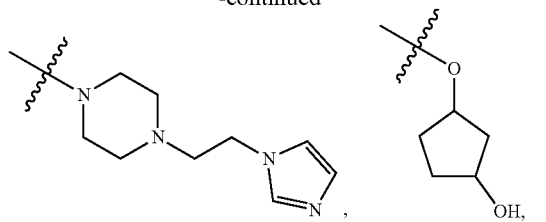
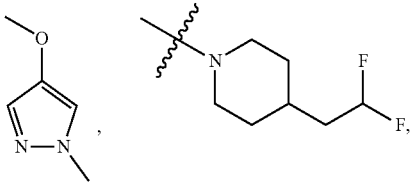
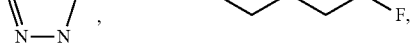
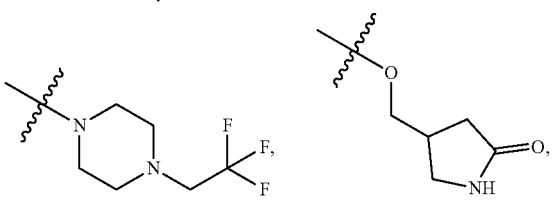
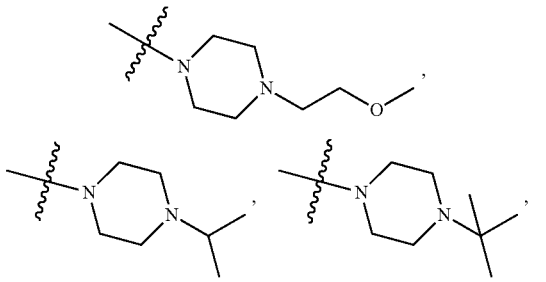
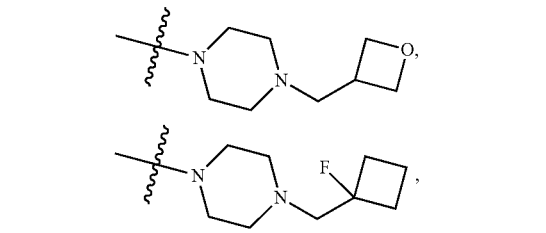
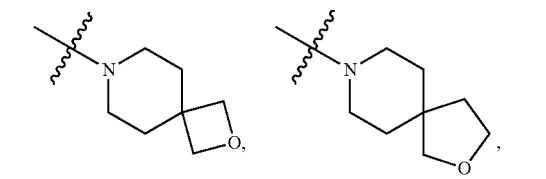
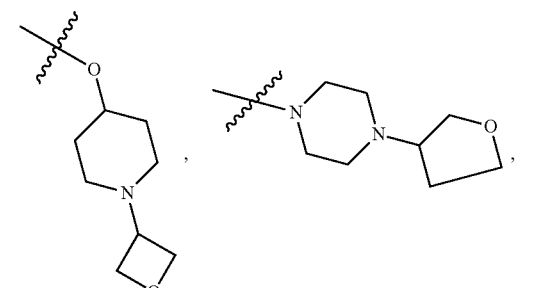
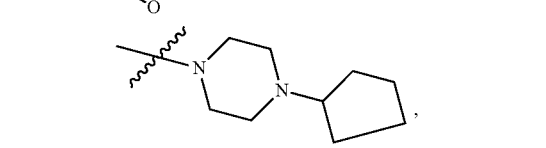

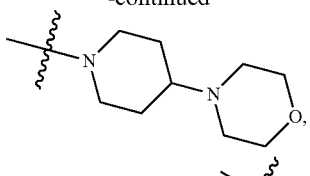
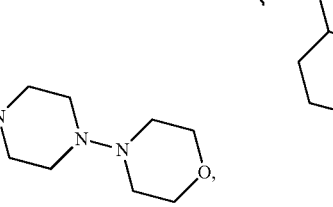
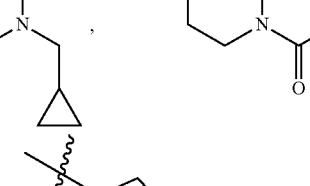

$R^8$ and $R^9$ are, independently at each occurrence, hydrogen, $C_{1-6}$alkyl optionally substituted with $R^{13}$, —C(O)$R^{13}$, $C_{3-6}$cycloalkyl group, or a 3-7 membered saturated or partially saturated heterocyclic group;

$R^{13}$ is, independently at each occurrence, $C_{1-6}$alkyl, —NH$_2$, or halogen;

$R^{14}$ is selected from the group consisting of

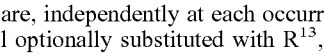
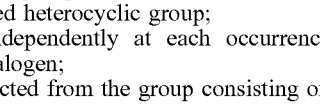
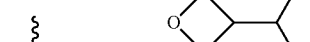

and
$R^{16}$ is hydrogen, or $C_{1-3}$alkyl optionally substituted with —NH$_2$ or —OH.

Another aspect of the invention includes a compound of Formula II:

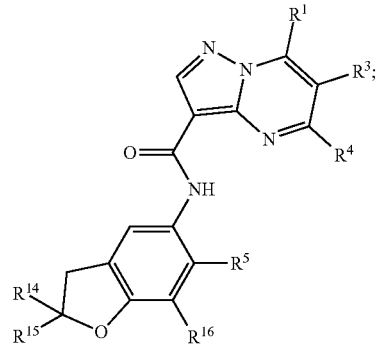

Formula II or a stereoisomer or a pharmaceutically acceptable salt thereof, wherein:
R¹ is hydrogen;
R³ is hydrogen, halogen, —OH, or $C_{1-3}$alkyl;
R⁴ is hydrogen, halogen, —NR⁸R⁹, —C(O)NR⁸R⁹, or a 3-7 membered monocyclic saturated or partially saturated heterocyclic group optionally substituted with one or more substituents selected from oxo, —NR⁸R⁹, or R¹³;
R⁵ is selected from the group consisting of hydrogen, —OCH₃, —CH₂NH₂,

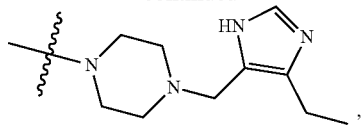

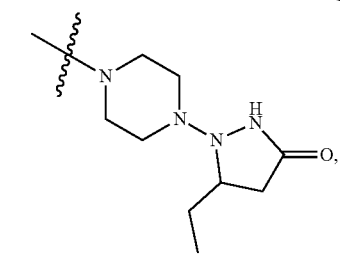

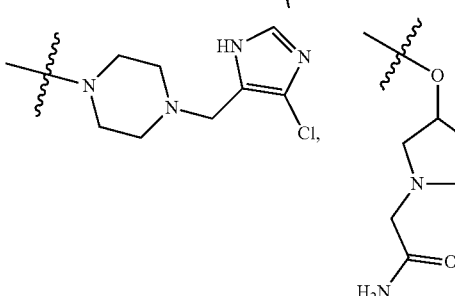
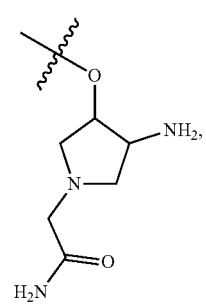

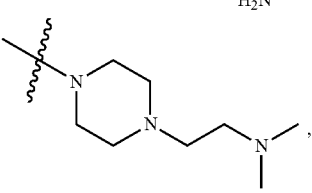

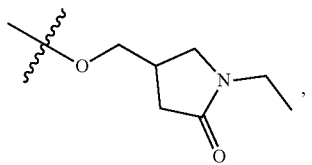

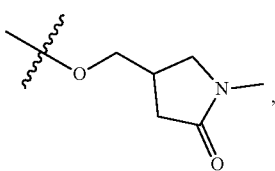

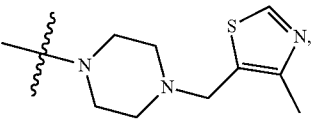

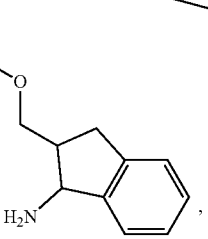
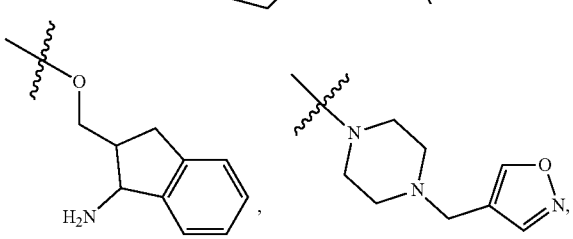

-continued

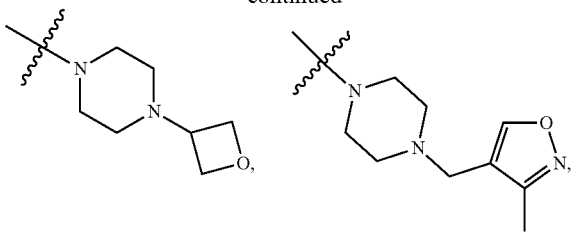

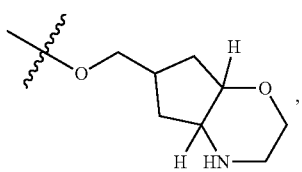

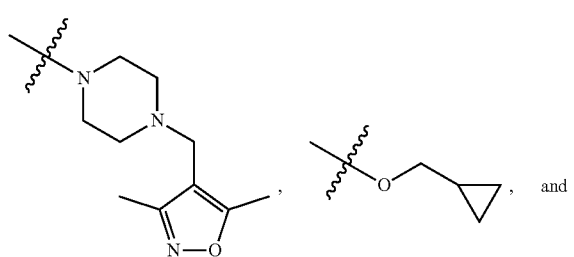

$R^8$ and $R^9$ are, independently at each occurrence, hydrogen, $C_{1-6}$alkyl optionally substituted with $R^{13}$, —C(O)$R^{13}$, $C_{3-6}$cycloalkyl group, or a 3-7 membered saturated or partially saturated heterocyclic group;

$R^{13}$ is, independently at each occurrence, $C_{1-6}$alkyl, —NH$_2$, or halogen;

$R^{14}$, $R^{15}$ are, independently at each occurrence, methyl or —CH$_2$OH, or taken together form a 6-membered, spiro bonded heterocyclic group with the carbon to which they are bonded; and $R^{16}$ is hydrogen, or $C_{1-3}$alkyl optionally substituted with —NH$_2$ or —OH, wherein no more than one of $R^5$ or $R^{16}$ can be hydrogen.

Yet another aspect of the invention includes a compound of Formula III:

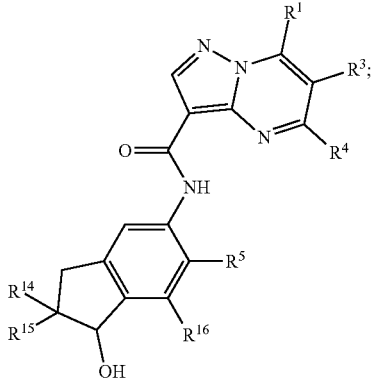

Formula III or a stereoisomer or a pharmaceutically acceptable salt thereof, wherein:

$R^1$ is hydrogen;

$R^3$ is hydrogen, halogen, —OH, or $C_{1-3}$alkyl;

$R^4$ is hydrogen, halogen, —NR$^8$R$^9$, —C(O)NR$^8$R$^9$, or a 3-7 membered monocyclic saturated or partially saturated heterocyclic group optionally substituted with one or more substituents selected from oxo, —NR$^8$R$^9$, or $R^{13}$;

$R^5$ is selected from the group consisting of hydrogen, —NHCH$_3$, —N(CH$_3$)$_2$, —C(CH$_3$)$_2$OH, —OCH$_3$, —OCH(CH$_3$)$_2$, —OC(CH$_3$)$_3$, —OCH$_2$CH$_3$, —OCHF$_2$, —OCH$_2$CF$_3$, —OCH$_2$CHF$_2$, —CH$_2$OCHF$_2$, —CN, —CH$_2$NH$_2$,

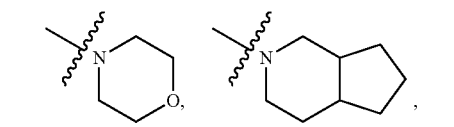


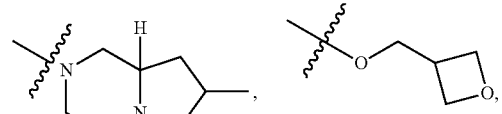

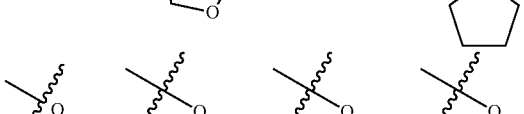

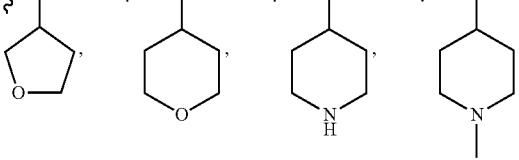

-continued
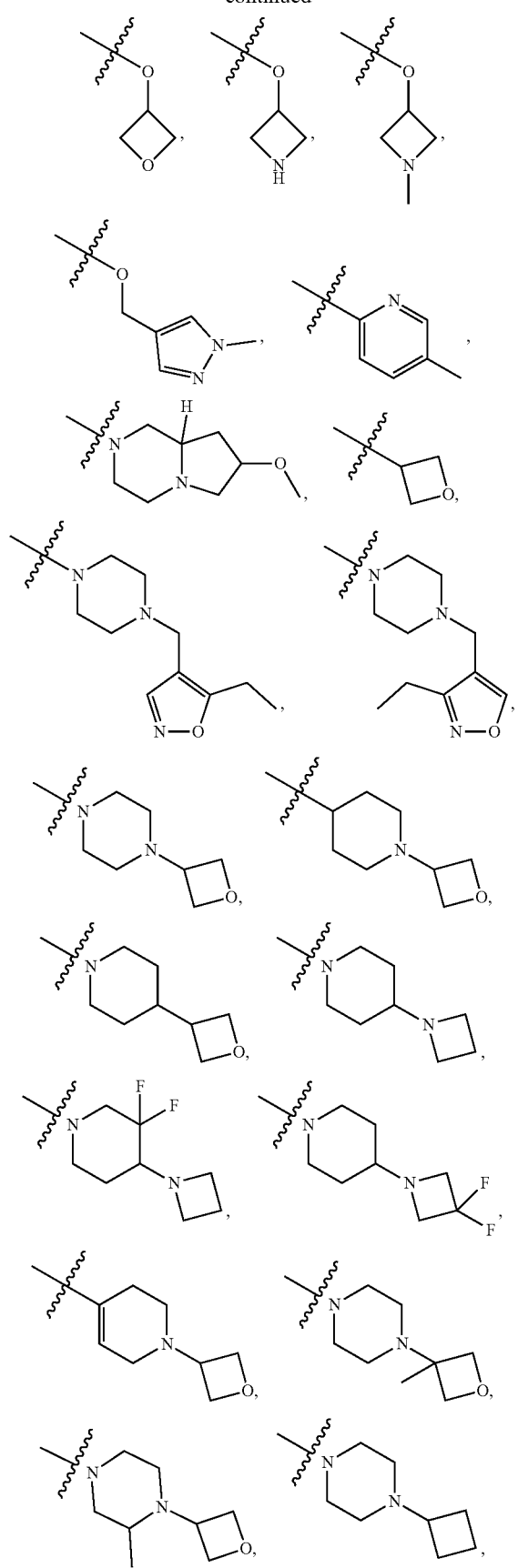
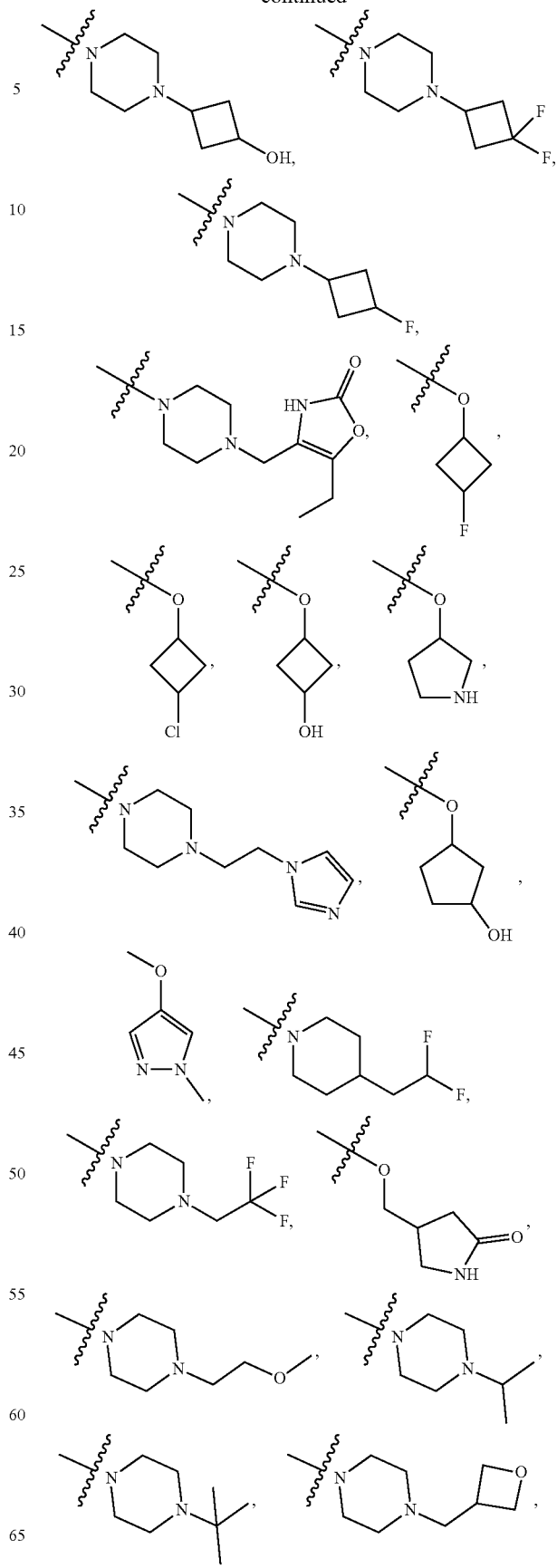

-continued
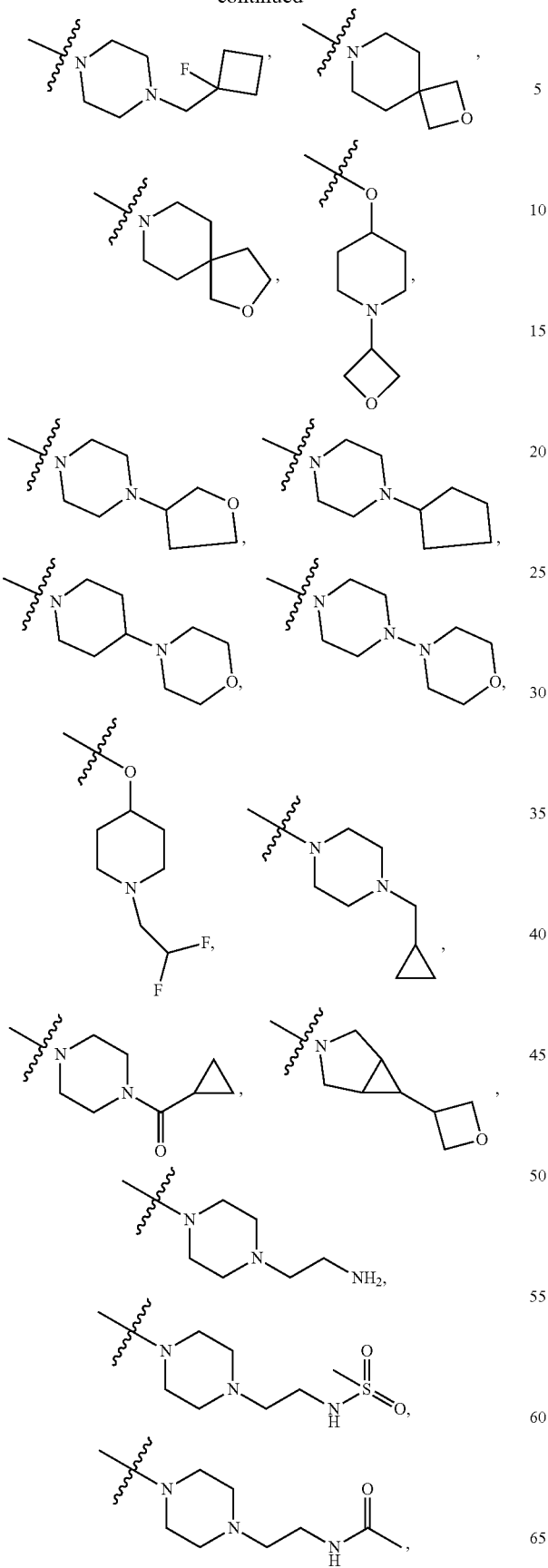
-continued
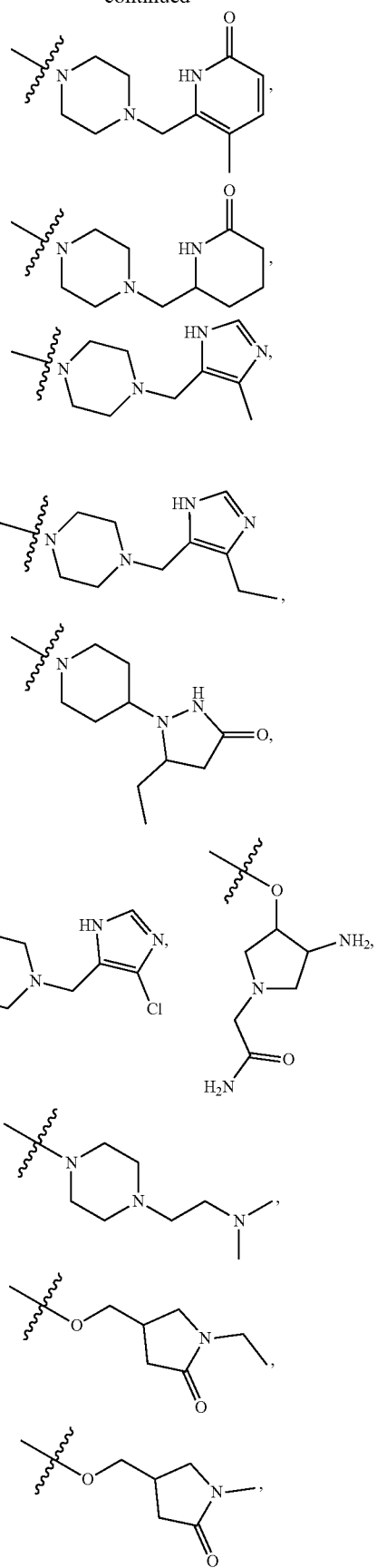

-continued

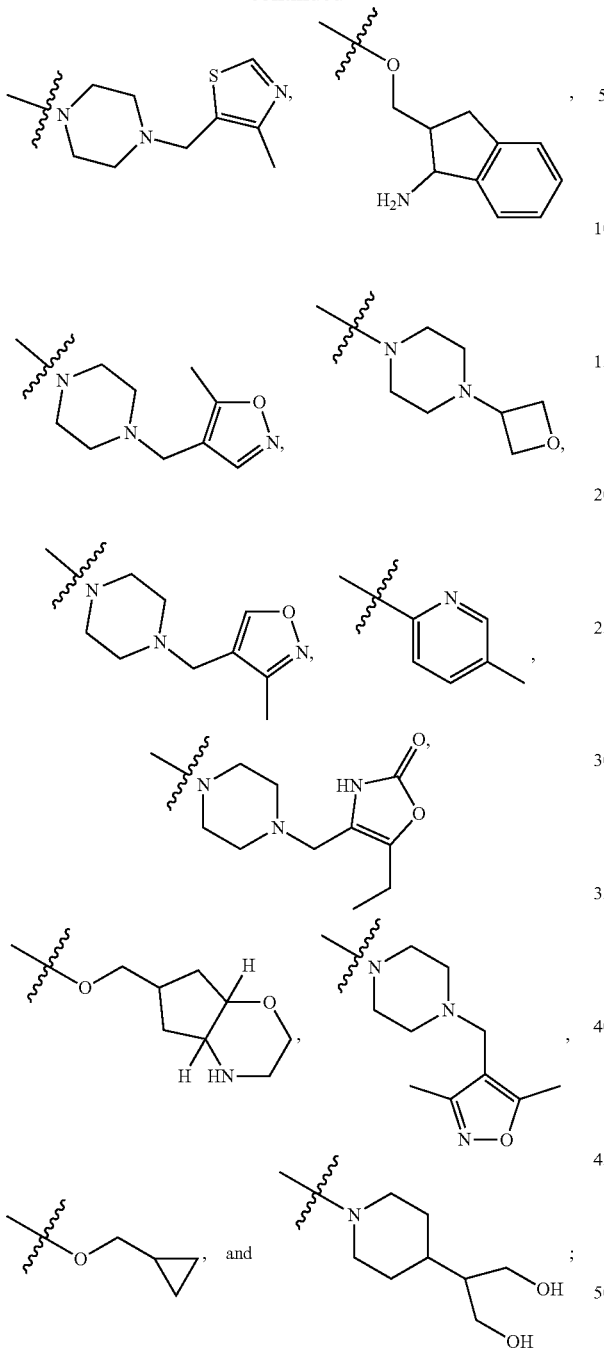

R[8] and R[9] are, independently at each occurrence, hydrogen, $C_{1-6}$alkyl optionally substituted with R[13], —C(O)R[13], $C_{3-6}$cycloalkyl group, or a 3-7 membered saturated or partially saturated heterocyclic group;

R[13] is, independently at each occurrence, $C_{1-6}$alkyl, —NH$_2$, or halogen;

R[14], R[15] are, independently at each occurrence, methyl or —CH$_2$OH, or taken together form a 6-membered, spiro bonded heterocyclic group with the carbon to which they are bonded; and R[16] is hydrogen, or $C_{1-3}$alkyl optionally substituted with —NH$_2$ or —OH.

Yet another aspect of the invention includes a compound of Formula IV:

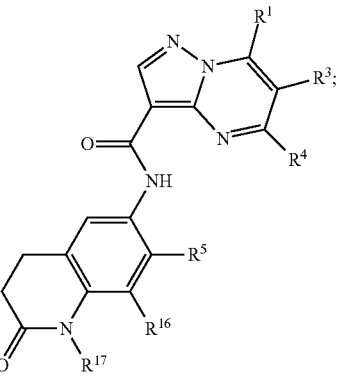

Formula IV or a stereoisomer or a pharmaceutically acceptable salt thereof, wherein:

R[1] is hydrogen;

R[3] is hydrogen, halogen, —OH, or $C_{1-3}$alkyl;

R[4] is hydrogen, halogen, —NR[8]R[9], —C(O)NR[8]R[9], or a 3-7 membered monocyclic saturated or partially saturated heterocyclic group optionally substituted with one or more substituents selected from oxo, —NR[8]R[9], or R[13];

R[5] is selected from the group consisting of hydrogen, —NHCH$_3$, —N(CH$_3$)$_2$, —C(CH$_3$)$_2$OH, —OCH$_3$, —OCH(CH$_3$)$_2$, —OC(CH$_3$)$_3$, —OCH$_2$CH$_3$, —OCHF$_2$, —OCH$_2$CF$_3$, —OCH$_2$CHF$_2$, —CH$_2$OCHF$_2$, —CN, —CH$_2$NH$_2$,

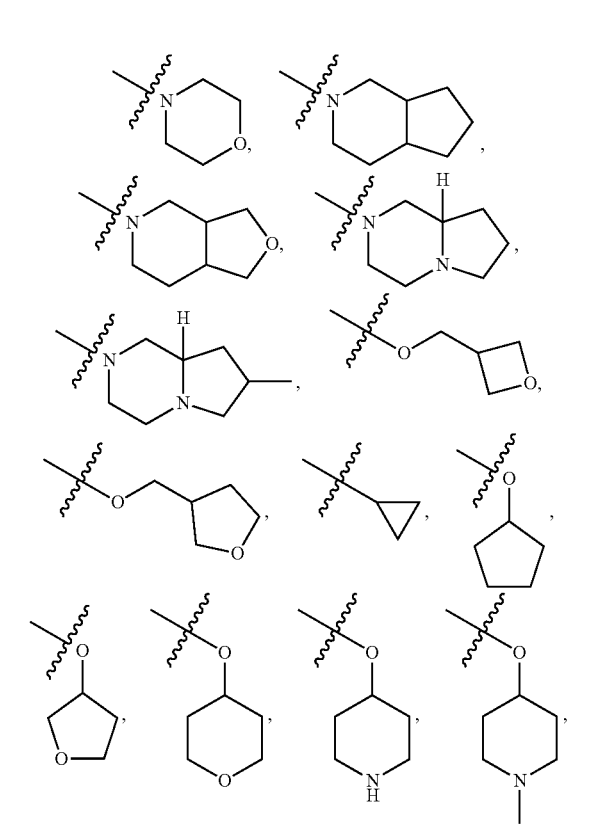

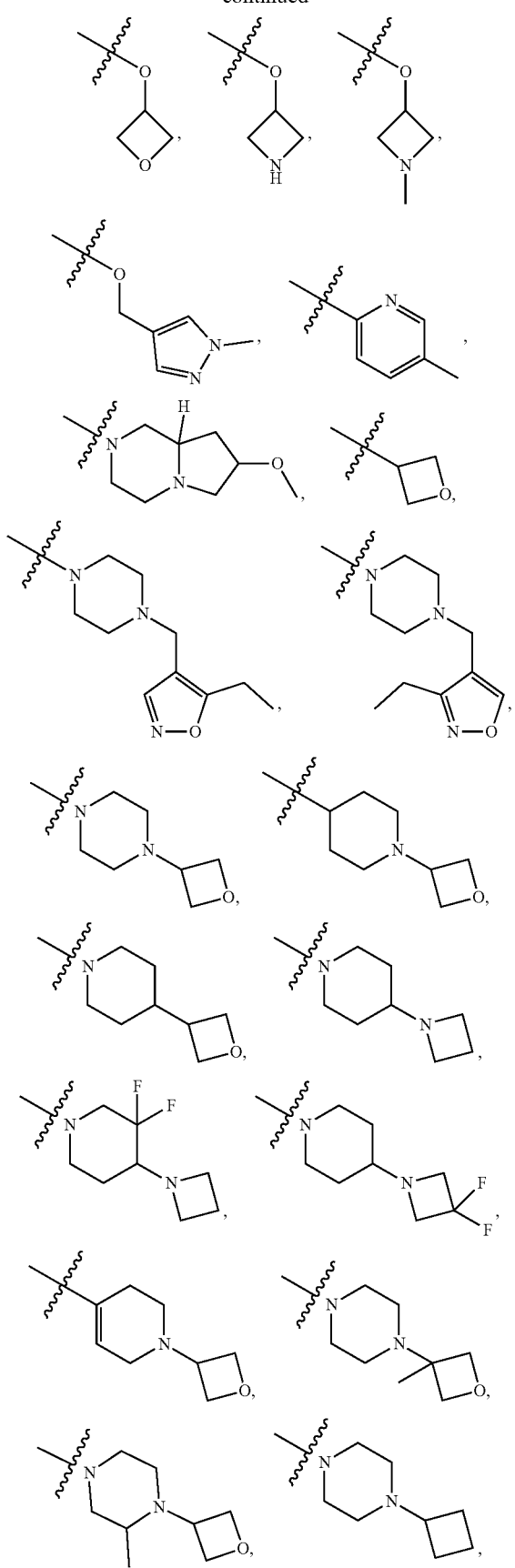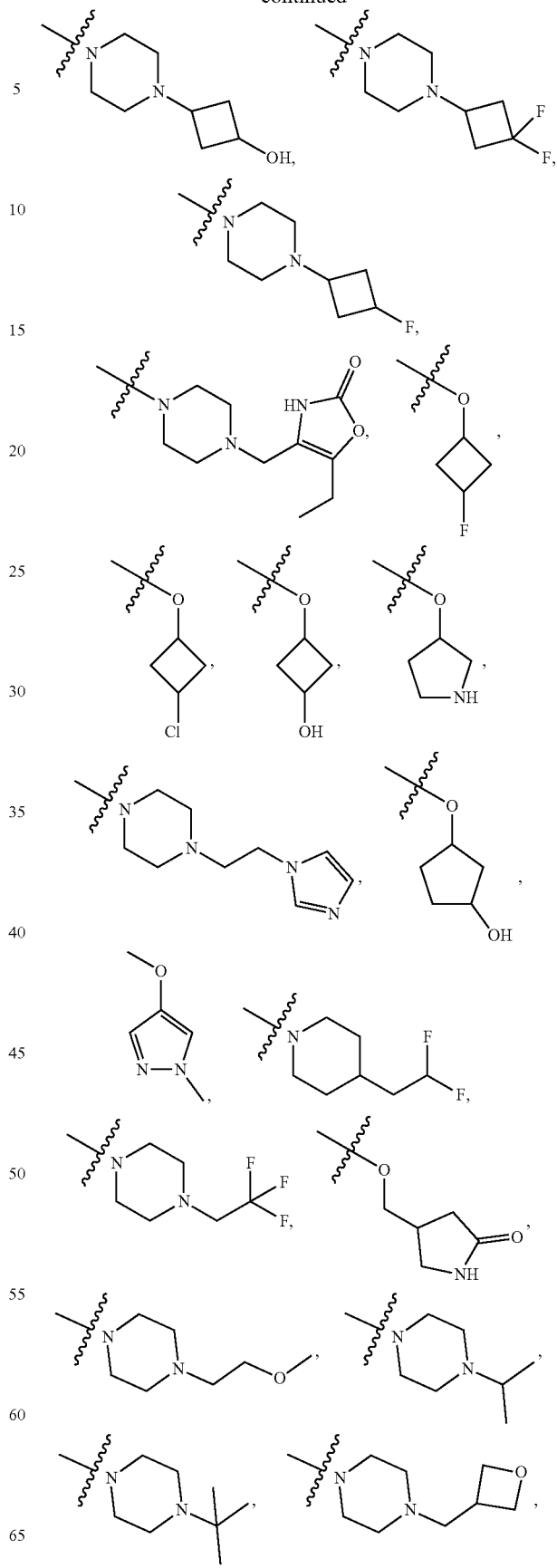

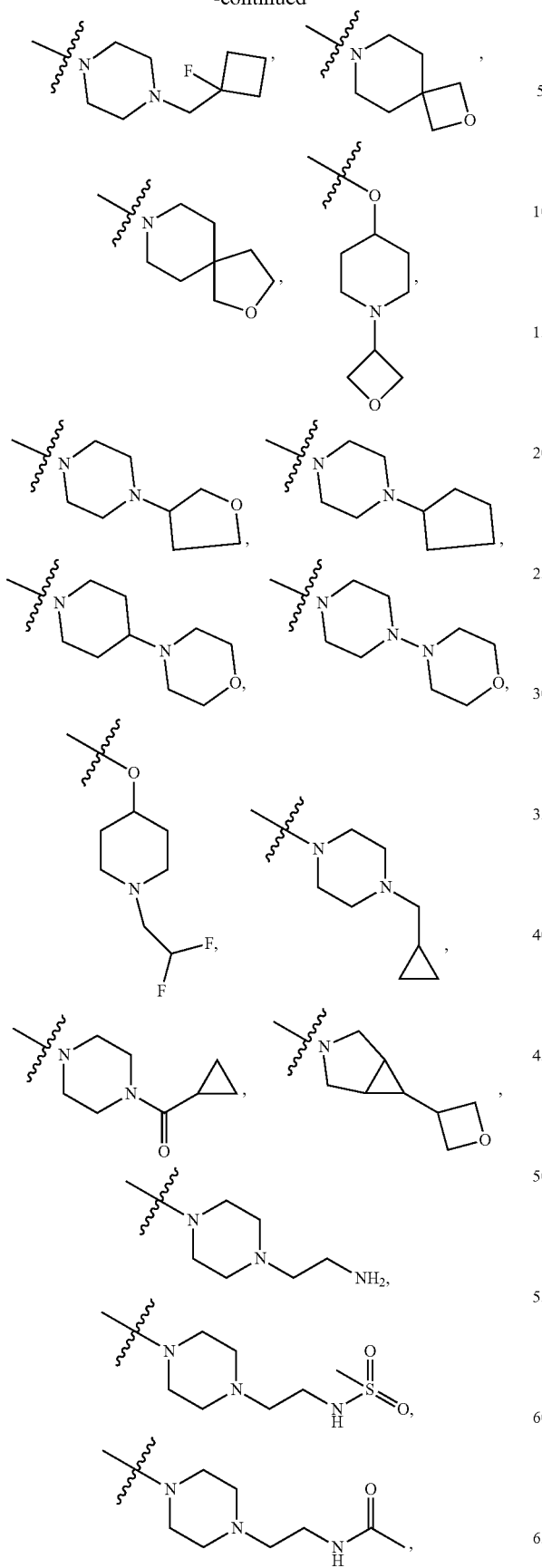
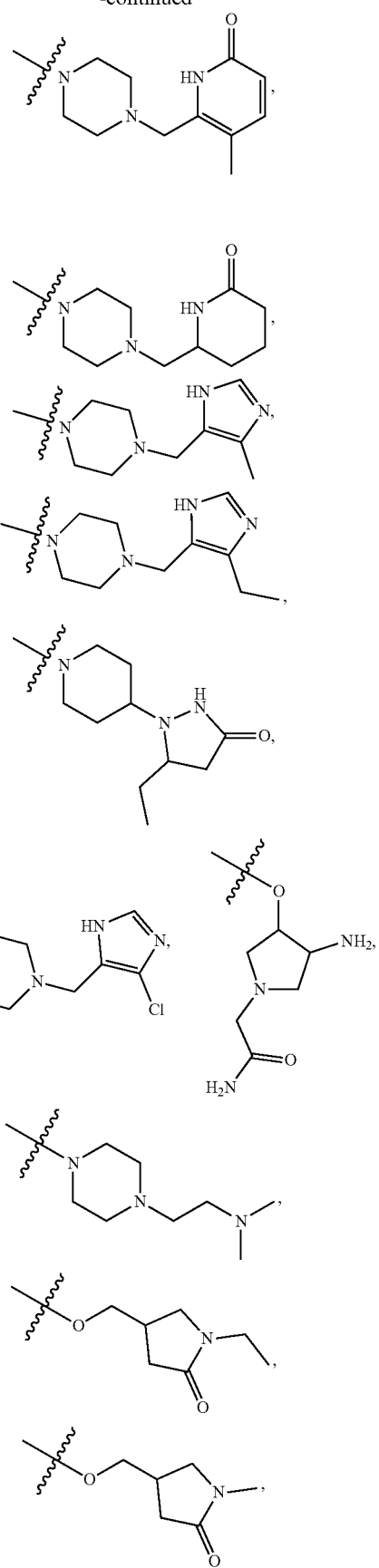

21

-continued

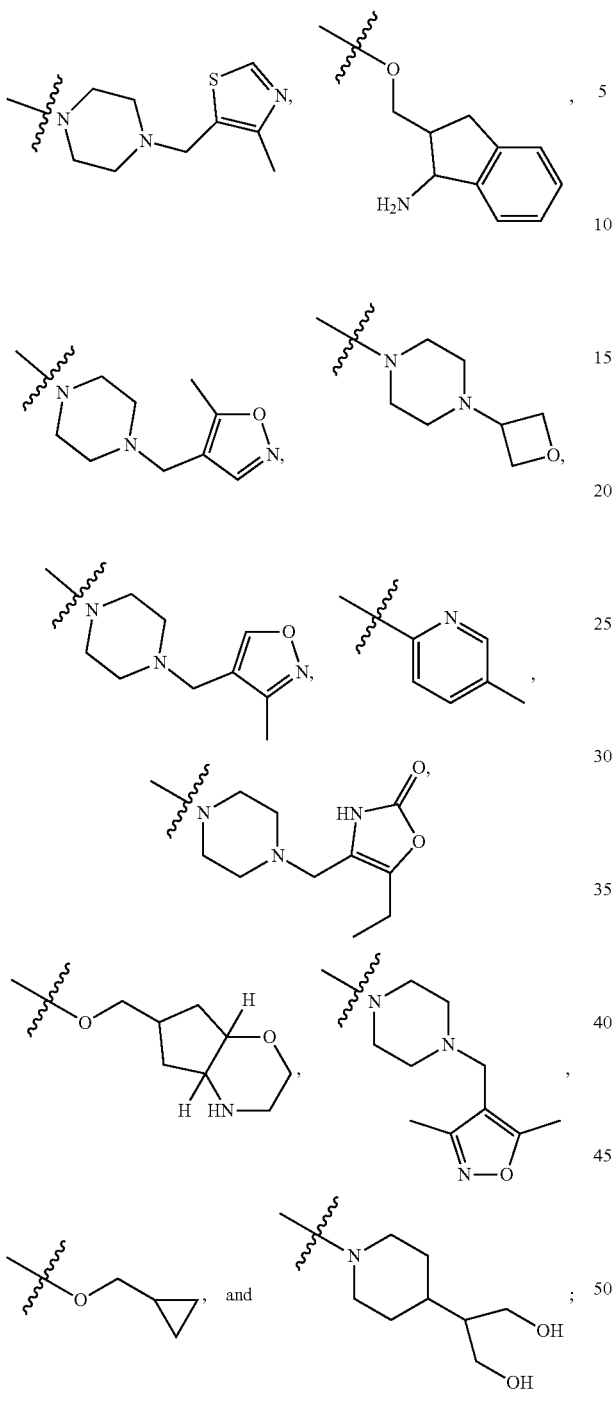

$R^8$ and $R^9$ are, independently at each occurrence, hydrogen, $C_{1-6}$alkyl optionally substituted with $R^{13}$, —C(O)$R^{13}$, $C_{3-6}$cycloalkyl group, or a 3-7 membered saturated or partially saturated heterocyclic group;

$R^{13}$ is, independently at each occurrence, $C_{1-6}$alkyl, —NH$_2$, or halogen;

$R^{16}$ is hydrogen, or $C_{1-3}$alkyl optionally substituted with —NH$_2$ or —OH; and $R^{17}$ is hydrogen or $C_{1-3}$alkyl optionally substituted with —NH$_2$ or —OH.

22

Yet another aspect of the invention includes a compound of Formula V:

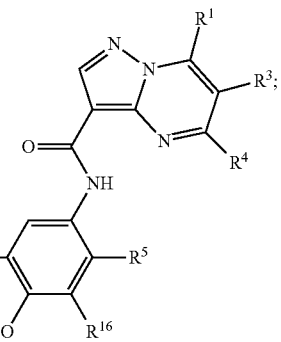

Formula V or a stereoisomer or a pharmaceutically acceptable salt thereof, wherein:

$R^1$ is hydrogen;

$R^3$ is hydrogen, halogen, —OH, or $C_{1-3}$alkyl;

$R^4$ is hydrogen, halogen, —NR$^8$R$^9$, —C(O)NR$^8$R$^9$, or a 3-7 membered monocyclic saturated or partially saturated heterocyclic group optionally substituted with one or more substituents selected from oxo, —NR$^8$R$^9$, or $R^{13}$;

$R^5$ is selected from the group consisting of hydrogen, —NHCH$_3$, —N(CH$_3$)$_2$, —C(CH$_3$)$_2$OH, —OCH$_3$, —OCH(CH$_3$)$_2$, —OC(CH$_3$)$_3$, —OCH$_2$CH$_3$, —OCHF$_2$, —OCH$_2$CF$_3$, —OCH$_2$CHF$_2$, —CH$_2$OCHF$_2$, —CN, —CH$_2$NH$_2$,

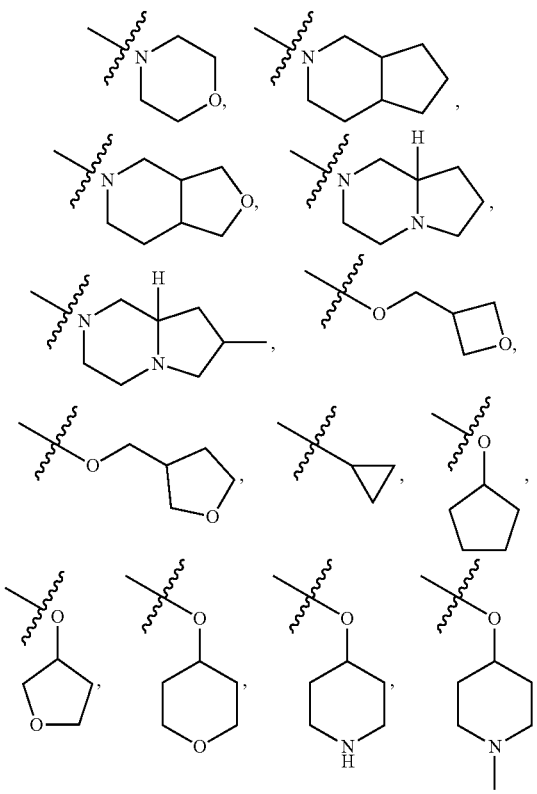

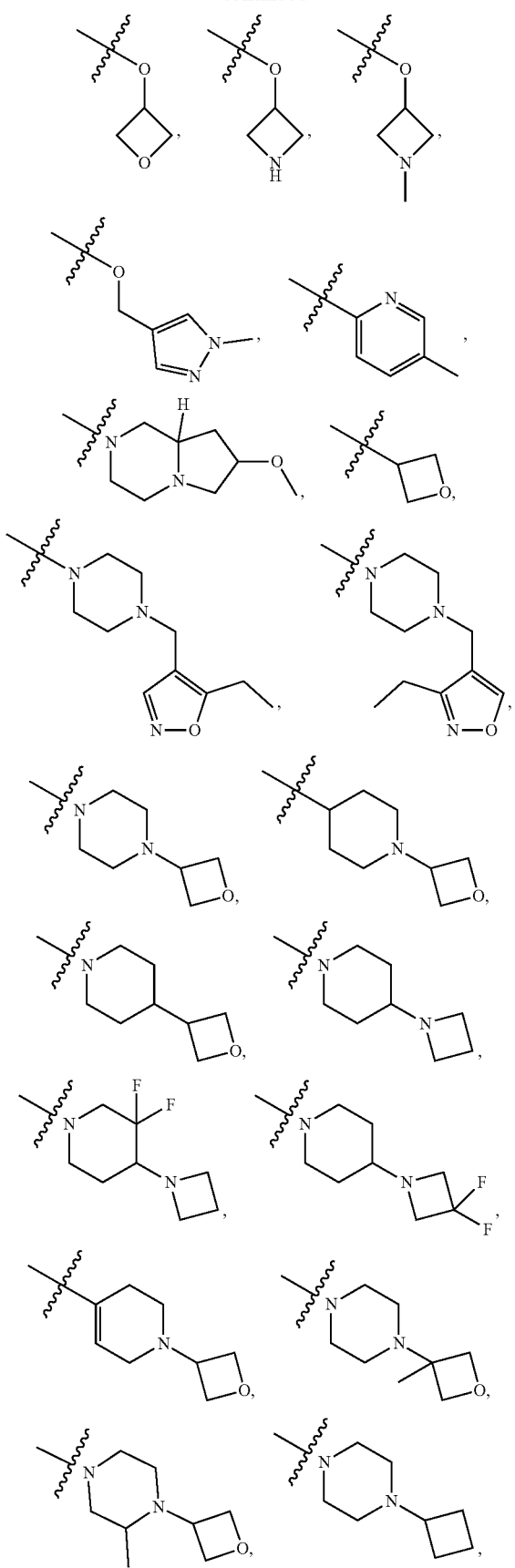
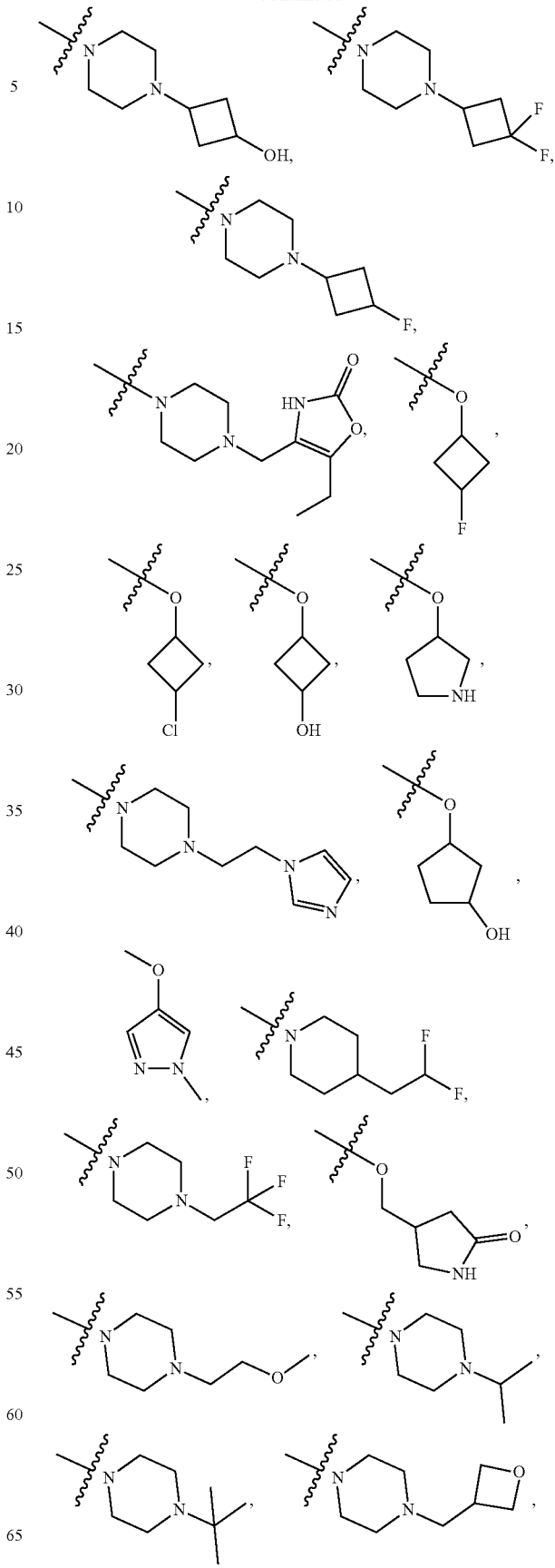

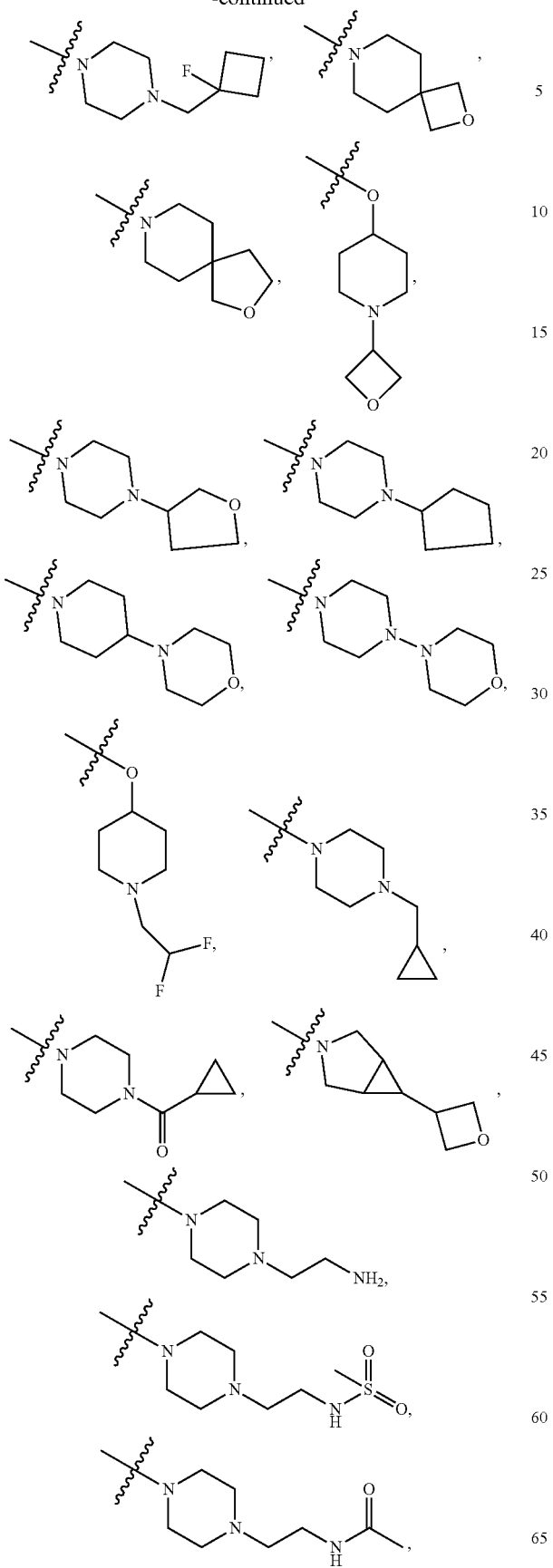
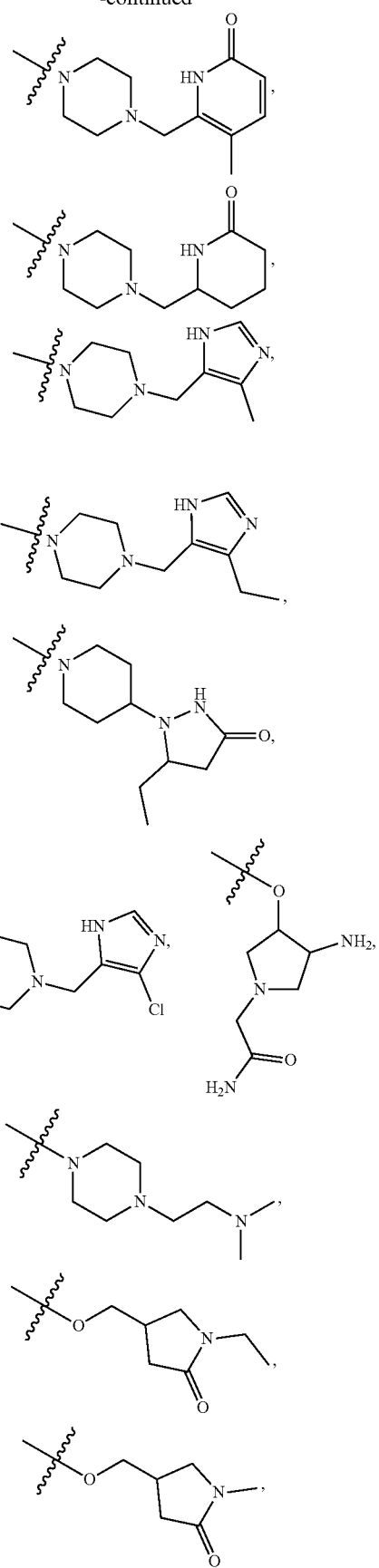

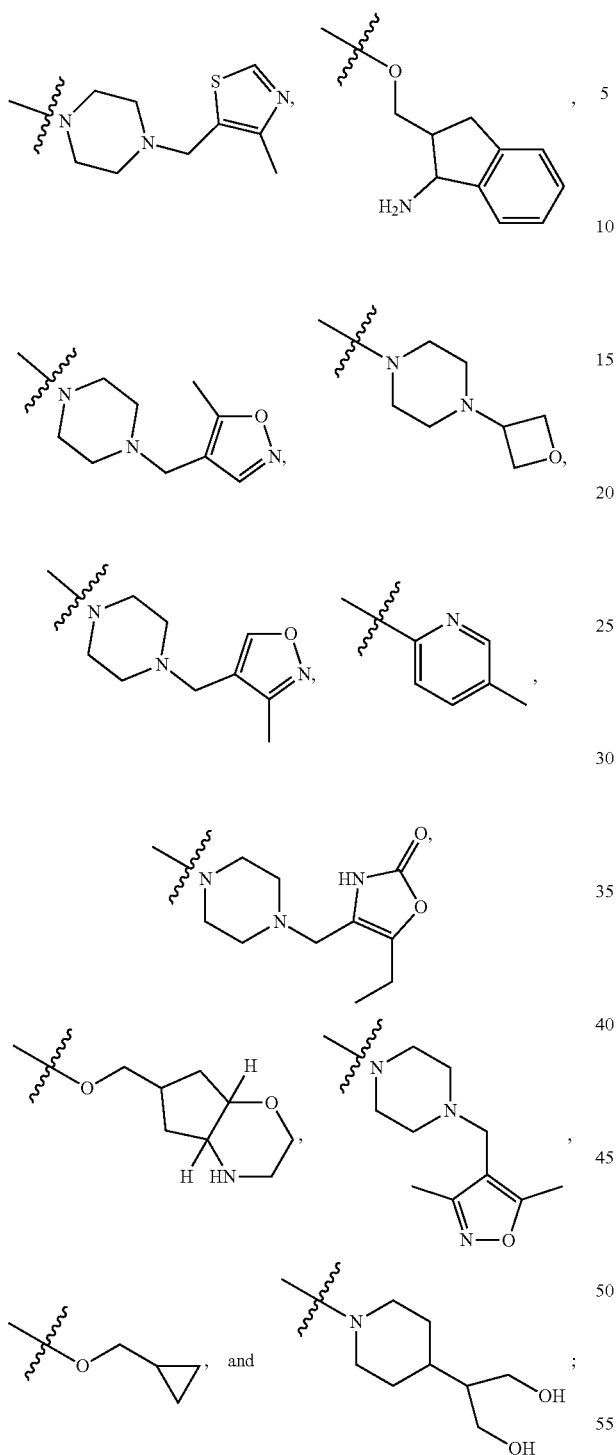

Yet another aspect of the invention includes a compound of Formula VI:

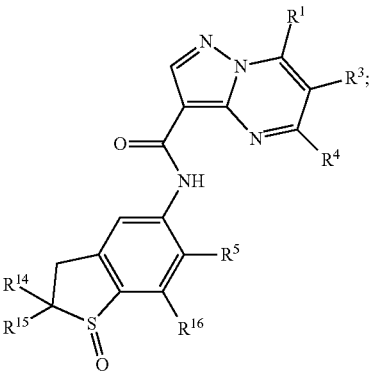

Formula VI or a stereoisomer or a pharmaceutically acceptable salt thereof, wherein:

$R^1$ is hydrogen;

$R^3$ is hydrogen, halogen, —OH, or $C_{1-3}$alkyl;

$R^4$ is hydrogen, halogen, —$NR^8R^9$, —$C(O)NR^8R^9$, or a 3-7 membered monocyclic saturated or partially saturated heterocyclic group optionally substituted with one or more substituents selected from oxo, —$NR^8R^9$, or $R^{13}$;

$R^5$ is selected from the group consisting of hydrogen, —$NHCH_3$, —$N(CH_3)_2$, —$C(CH_3)_2OH$, —$OCH_3$, —$OCH(CH_3)_2$, —$OC(CH_3)_3$, —$OCH_2CH_3$, —$OCHF_2$, —$OCH_2CF_3$, —$OCH_2CHF_2$, —$CH_2OCHF_2$, —CN, —$CH_2NH_2$,

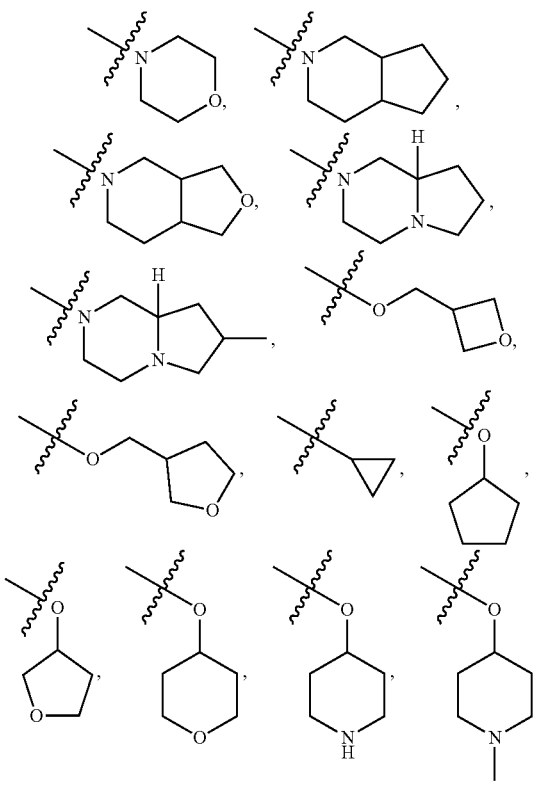

$R^8$ and $R^9$ are, independently at each occurrence, hydrogen, $C_{1-6}$alkyl optionally substituted with $R^{13}$, —$C(O)R^{13}$, $C_{3-6}$cycloalkyl group, or a 3-7 membered saturated or partially saturated heterocyclic group;

$R^{13}$ is, independently at each occurrence, $C_{1-6}$alkyl, —$NH_2$, or halogen; and $R^{16}$ is hydrogen, or $C_{1-3}$alkyl optionally substituted with —$NH_2$ or —OH.

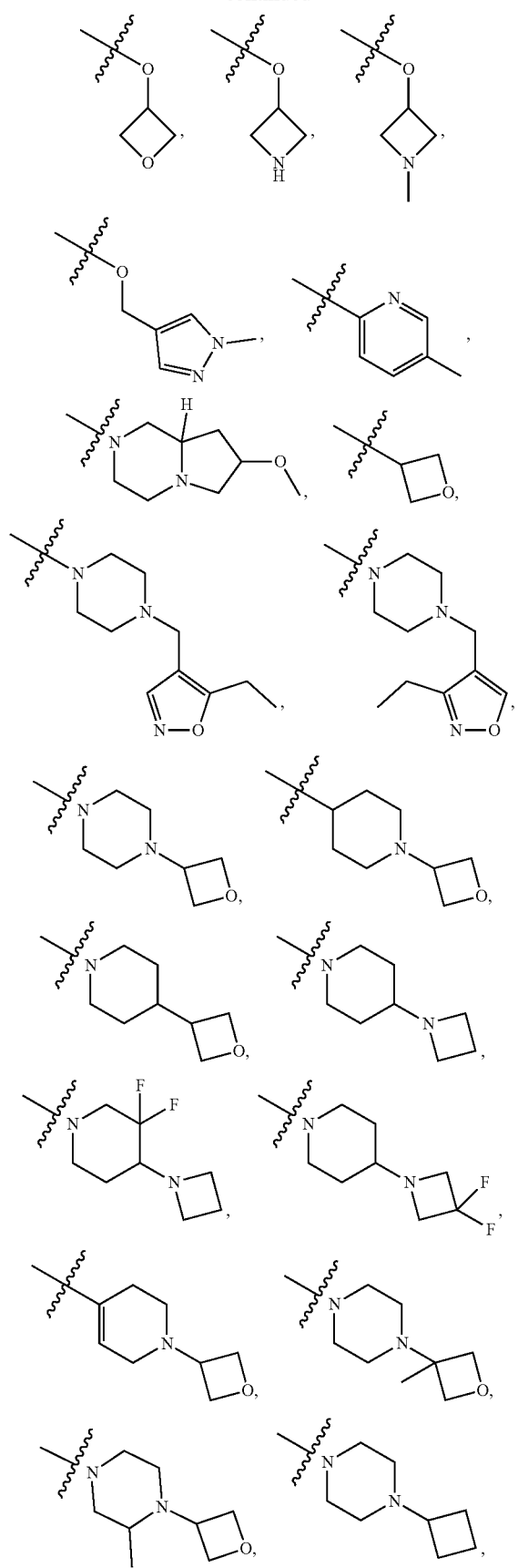
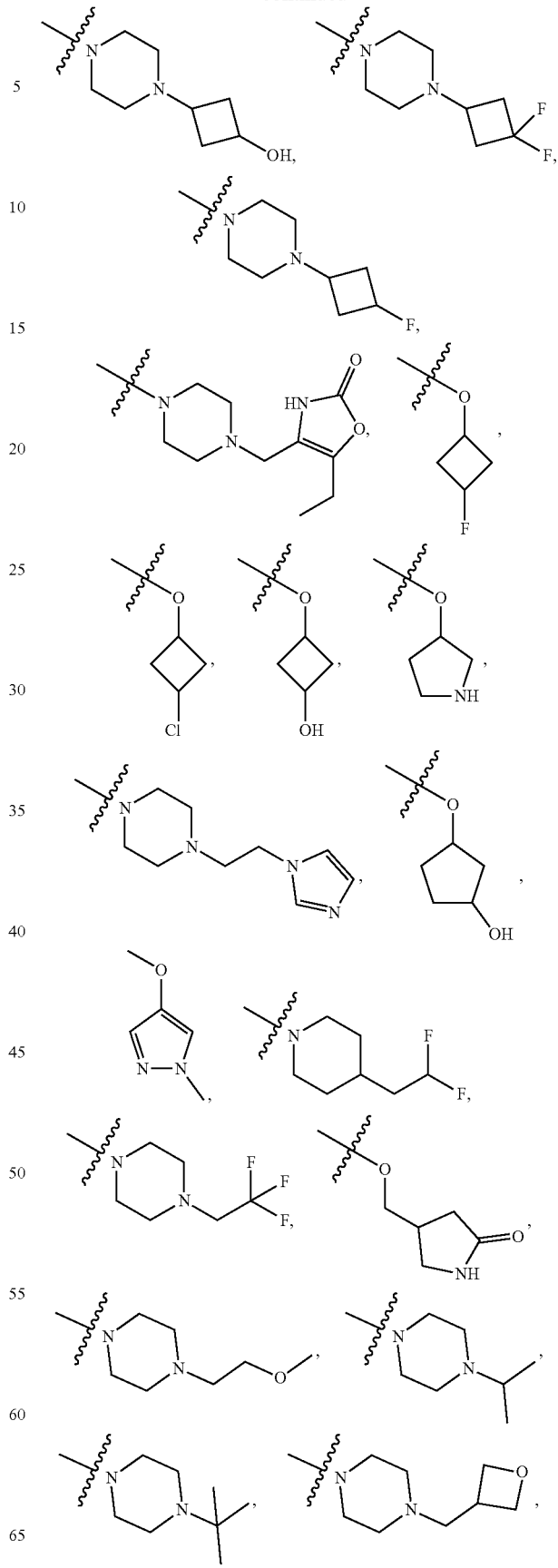

-continued
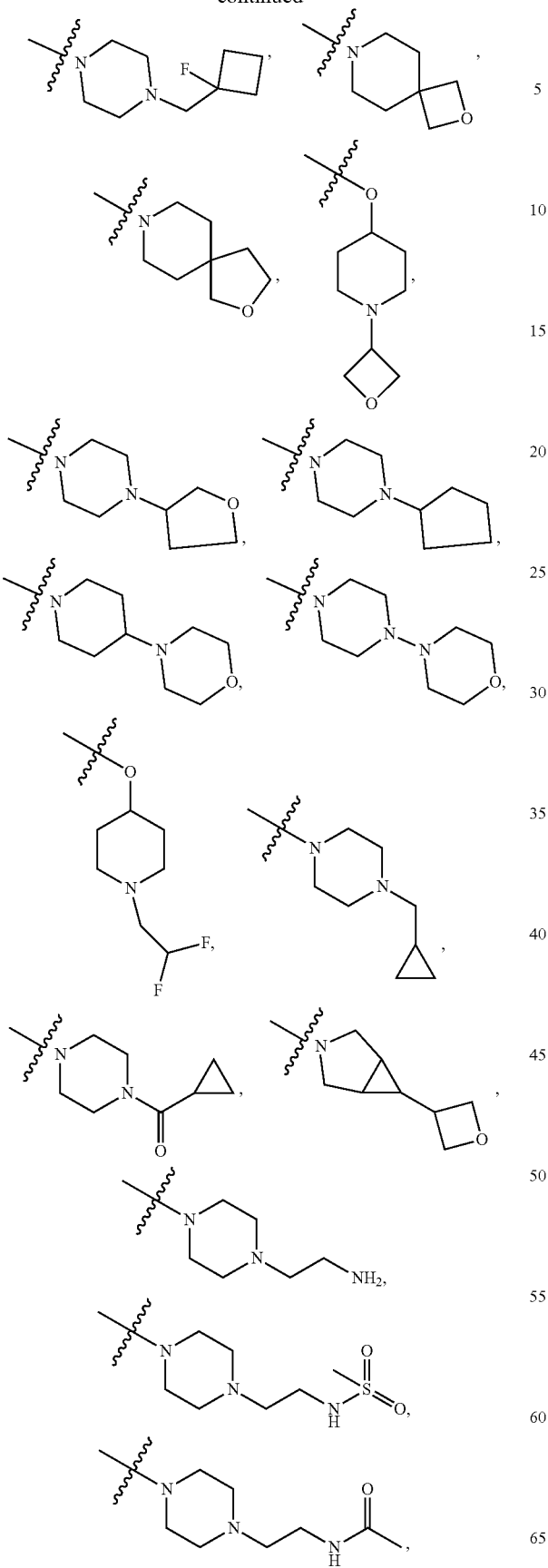
-continued
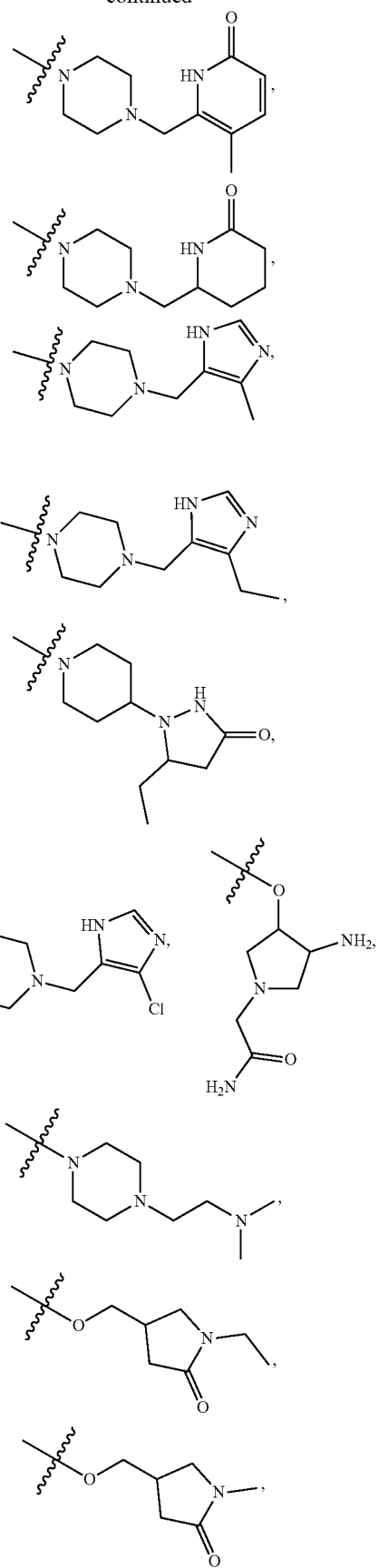

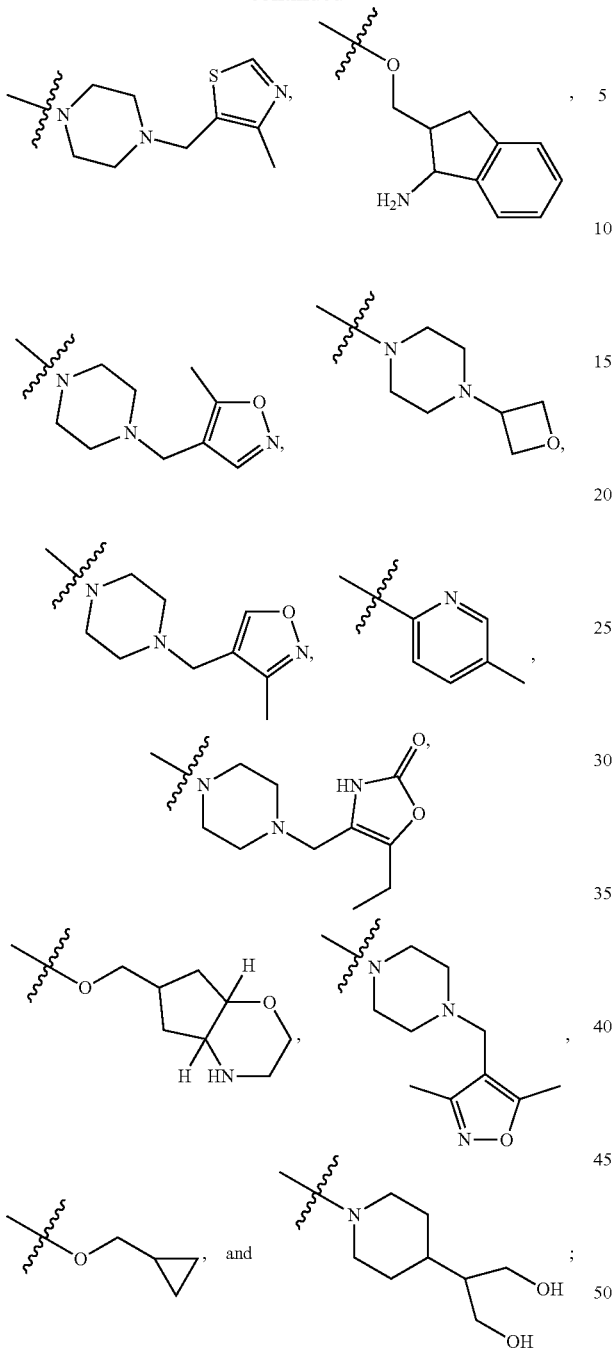

Yet another aspect of the invention includes a compound of Formula VII:

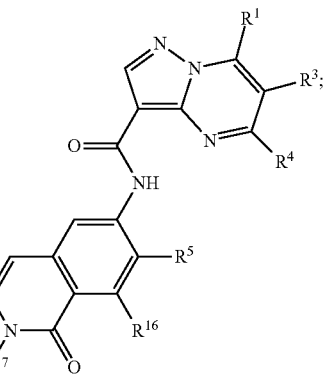

Formula VII or a stereoisomer or a pharmaceutically acceptable salt thereof, wherein:

$R^1$ is hydrogen;

$R^3$ is hydrogen, halogen, —OH, or $C_{1-3}$alkyl;

$R^4$ is hydrogen, halogen, —$NR^8R^9$, —$C(O)NR^8R^9$, or a 3-7 membered monocyclic saturated or partially saturated heterocyclic group optionally substituted with one or more substituents selected from oxo, —$NR^8R^9$, or $R^{13}$;

$R^5$ is selected from the group consisting of hydrogen, —$NHCH_3$, —$N(CH_3)_2$, —$C(CH_3)_2OH$, —$OCH_3$, —$OCH(CH_3)_2$, —$OC(CH_3)_3$, —$OCH_2CH_3$, —$OCHF_2$, —$OCH_2CF_3$, —$OCH_2CHF_2$, —$CH_2OCHF_2$, —CN, —$CH_2NH_2$,

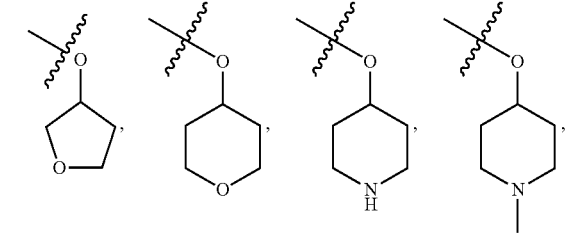

$R^8$ and $R^9$ are, independently at each occurrence, hydrogen, $C_{1-6}$alkyl optionally substituted with $R^{13}$, —$C(O)R^{13}$, $C_{3-6}$cycloalkyl group, or a 3-7 membered saturated or partially saturated heterocyclic group;

$R^{13}$ is, independently, at each occurrence, $C_{1-6}$alkyl, —$NH_2$, or halogen;

$R^{14}$, $R^{15}$ are, independently at each occurrence, methyl or —$CH_2OH$, or taken together form a 6-membered, spiro bonded heterocyclic group with the carbon to which they are bonded; and $R^{16}$ is hydrogen, or $C_{1-3}$alkyl optionally substituted with —$NH_2$ or —OH.

-continued
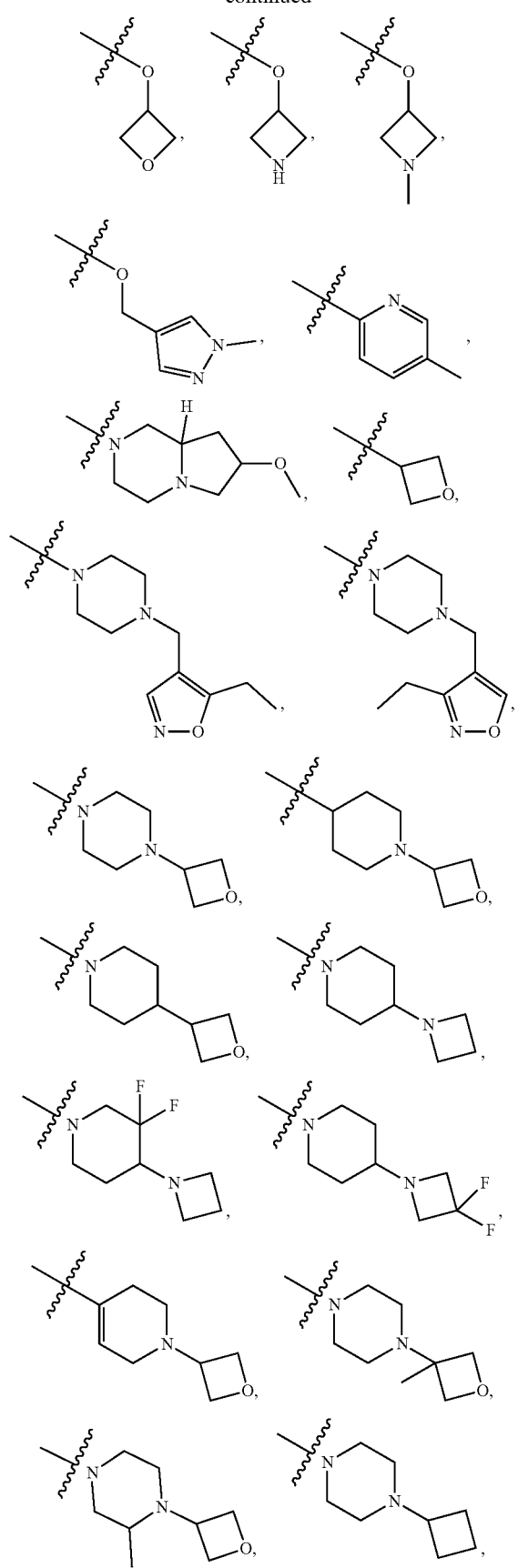
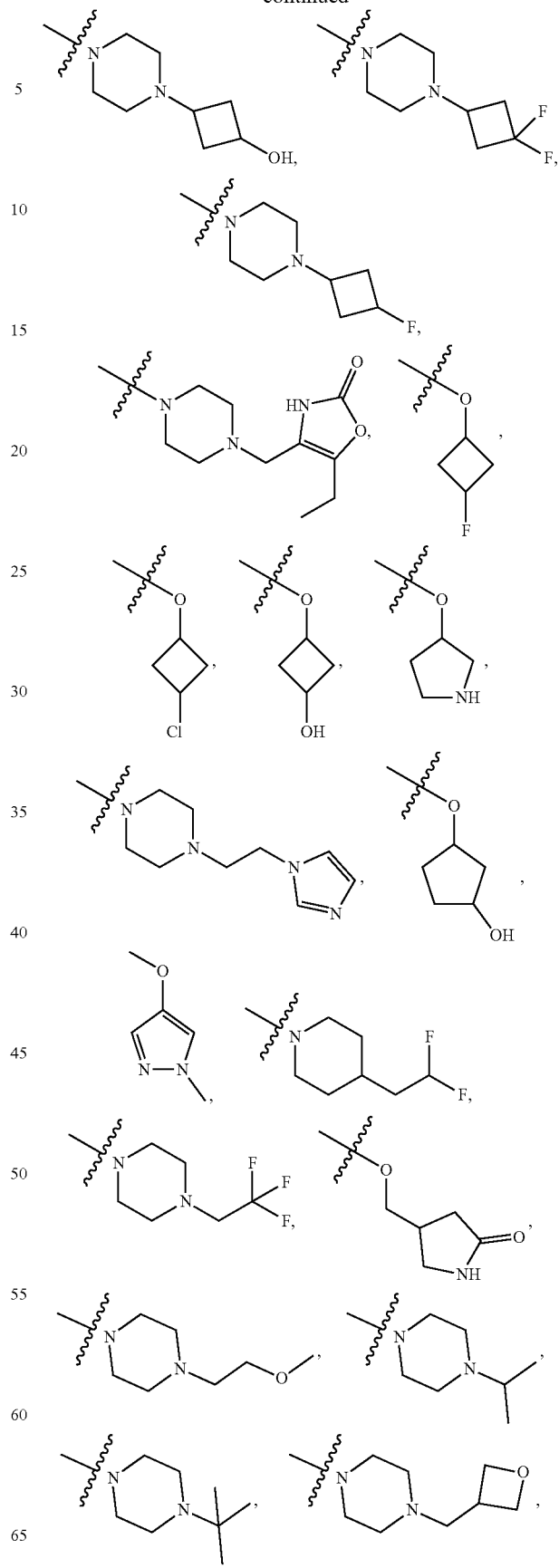

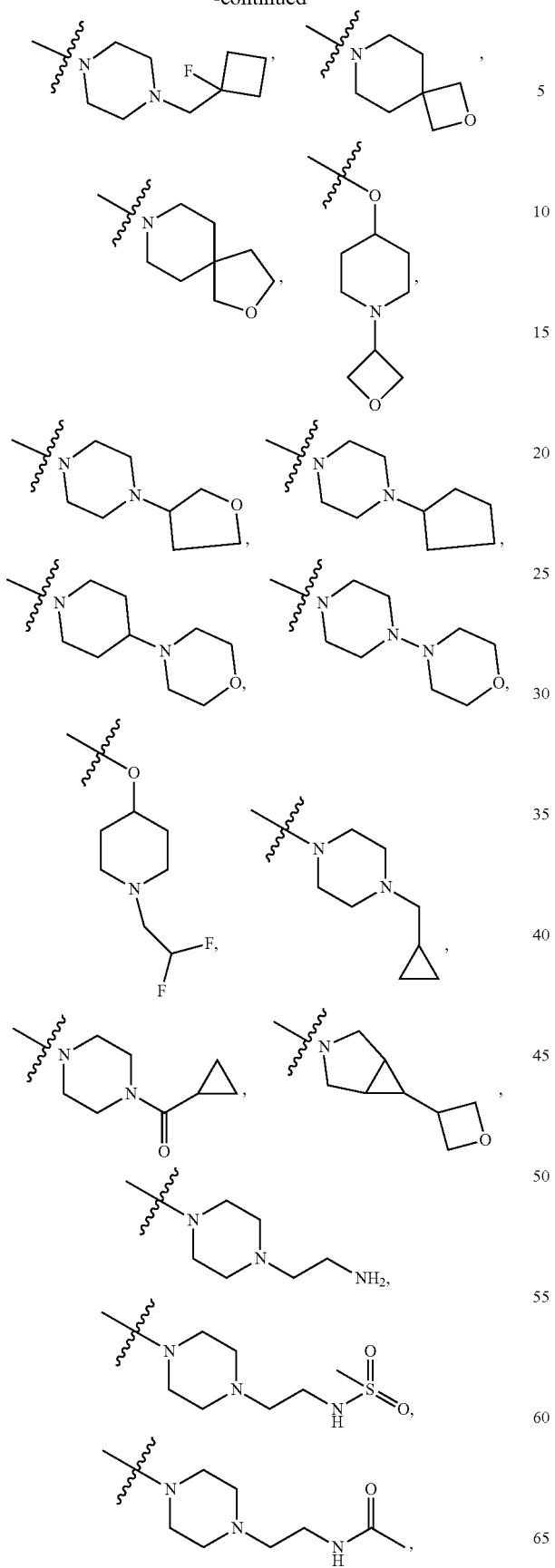
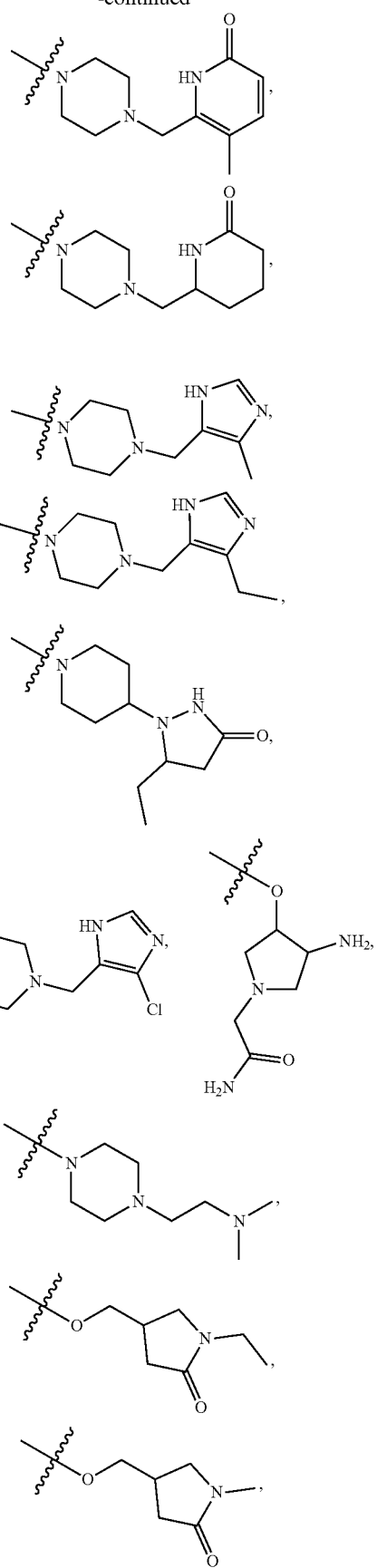

-continued

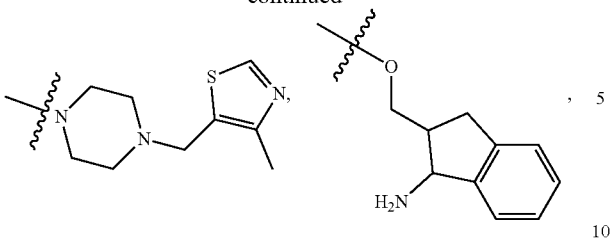

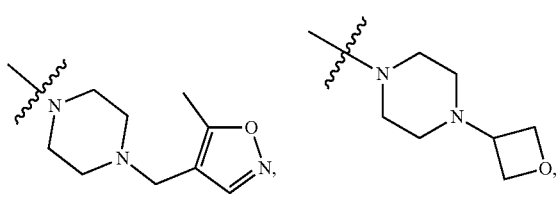

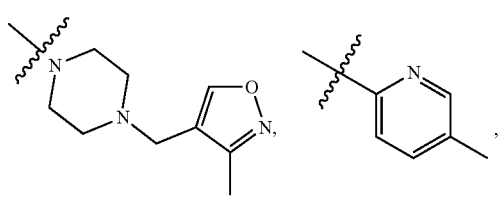

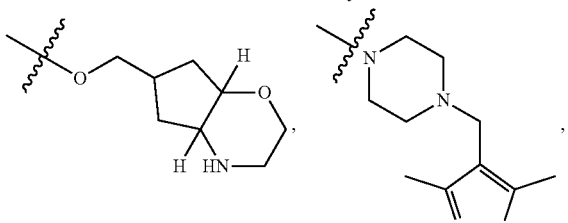

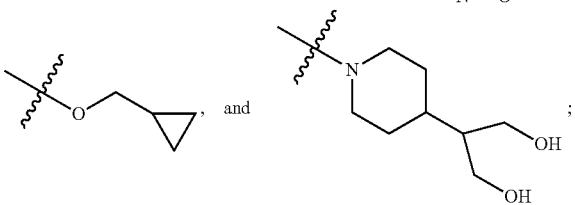

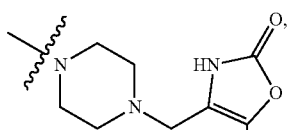 and

R[8] and R[9] are, independently at each occurrence, hydrogen, $C_{1-6}$alkyl optionally substituted with R[13], —C(O)R[13], $C_{3-6}$cycloalkyl group, or a 3-7 membered saturated or partially saturated heterocyclic group;

R[13] is, independently at each occurrence, $C_{1-6}$alkyl, —NH$_2$, or halogen;

R[16] is hydrogen, or $C_{1-3}$alkyl optionally substituted with —NH$_2$ or —OH;

R[17] is $C_{1-3}$alkyl optionally substituted with —NH$_2$ or —OH.

Yet another aspect of the invention includes a compound of Formula VIII:

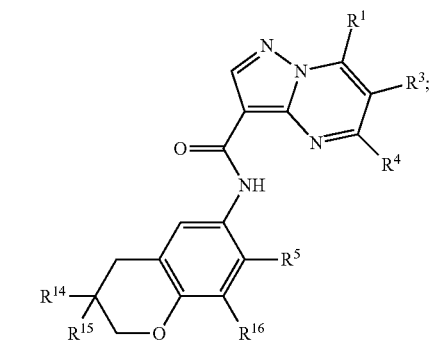

Formula VIII or a stereoisomer or a pharmaceutically acceptable salt thereof, wherein:

R[1] is hydrogen;

R[3] is hydrogen, halogen, —OH, or $C_{1-3}$alkyl;

R[4] is hydrogen, halogen, —NR[8]R[9], —C(O)NR[8]R[9], or a 3-7 membered monocyclic saturated or partially saturated heterocyclic group optionally substituted with one or more substituents selected from oxo, —NR[8]R[9], or R[13];

R[5] is selected from the group consisting of hydrogen, —NHCH$_3$, —N(CH$_3$)$_2$, —C(CH$_3$)$_2$OH, —OCH$_3$, —OCH(CH$_3$)$_2$, —OC(CH$_3$)$_3$, —OCH$_2$CH$_3$, —OCHF$_2$, —OCH$_2$CF$_3$, —OCH$_2$CHF$_2$, —CH$_2$OCHF$_2$, —CN, —CH$_2$NH$_2$,

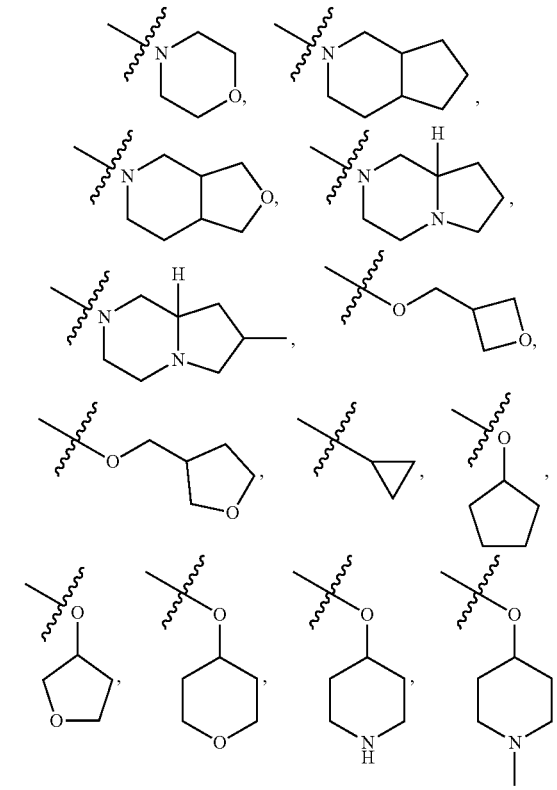

-continued
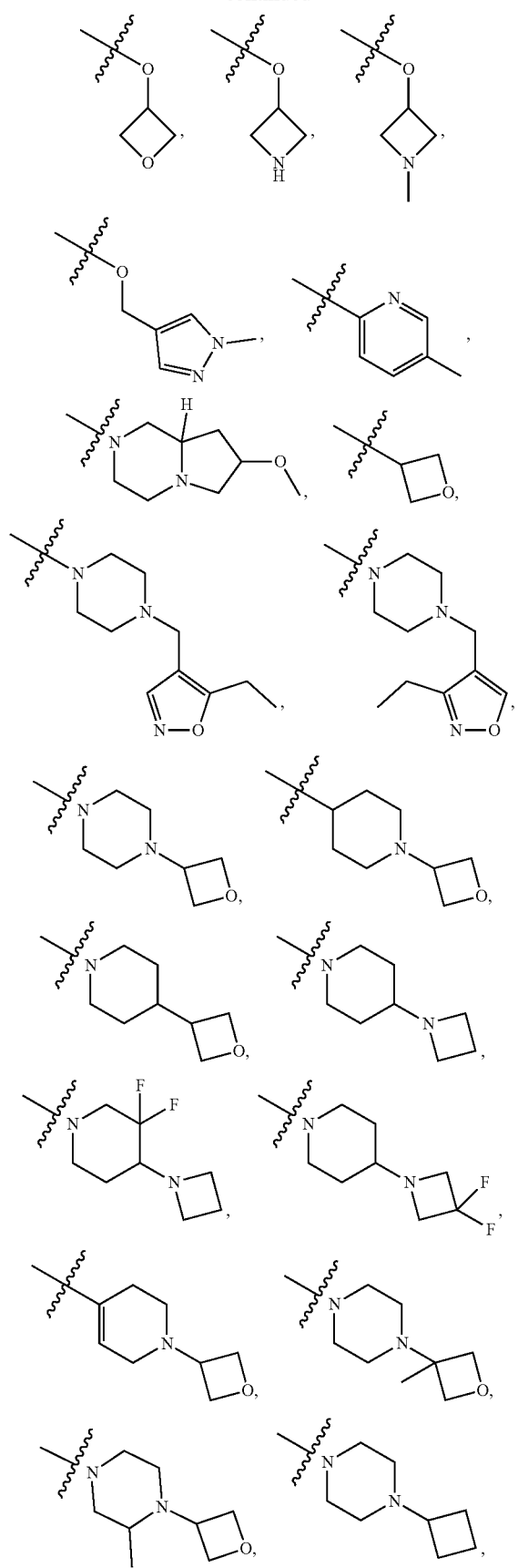
-continued
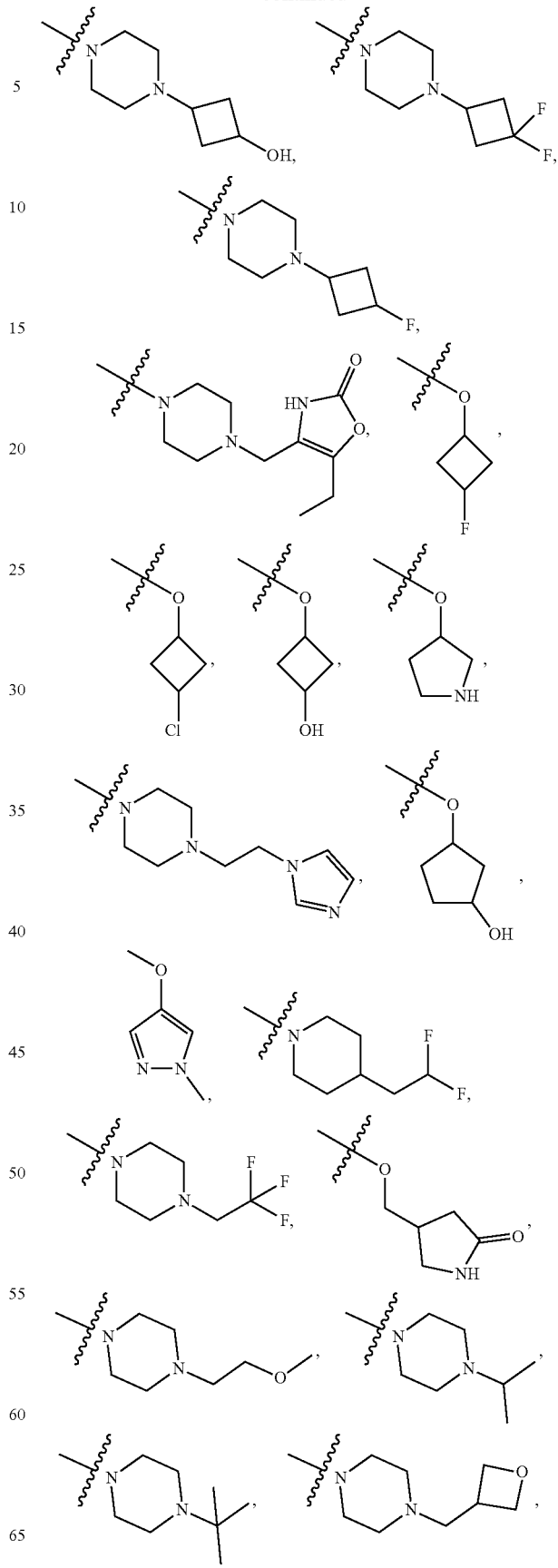

-continued
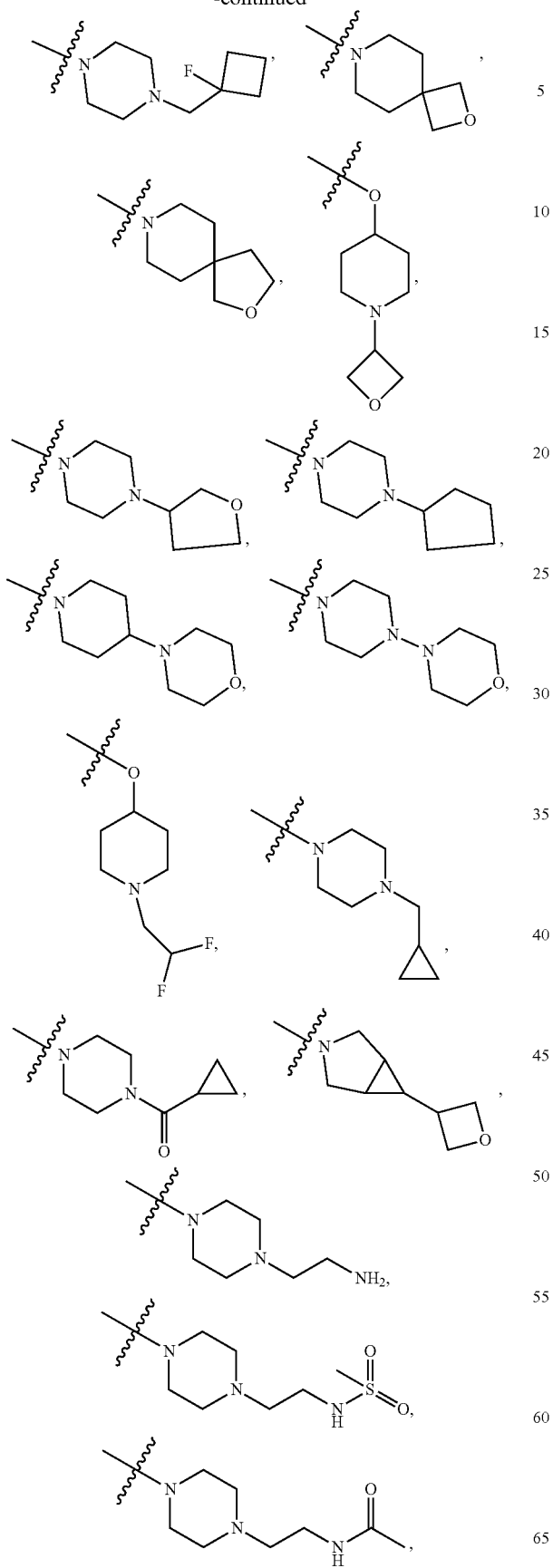
-continued
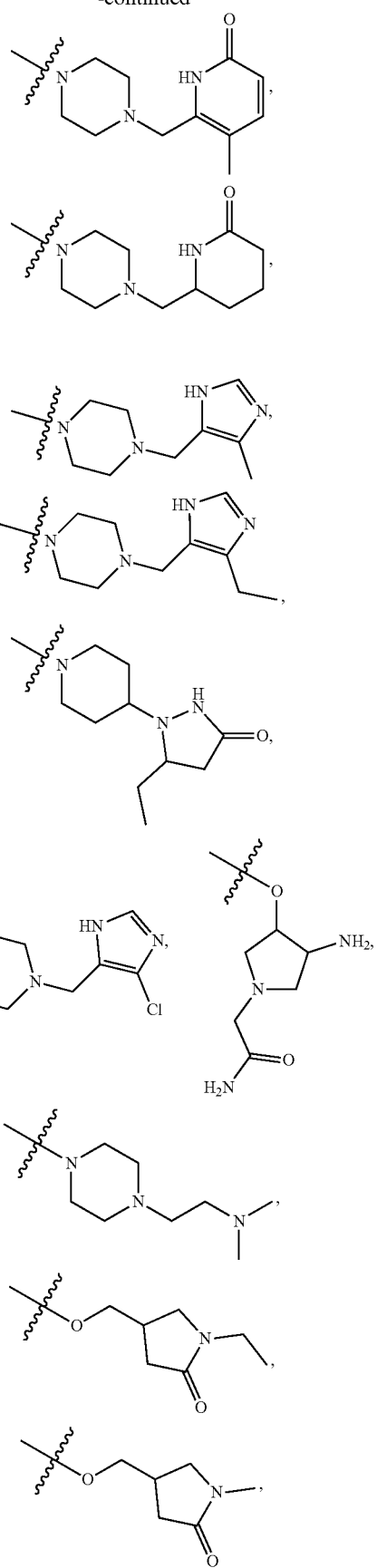

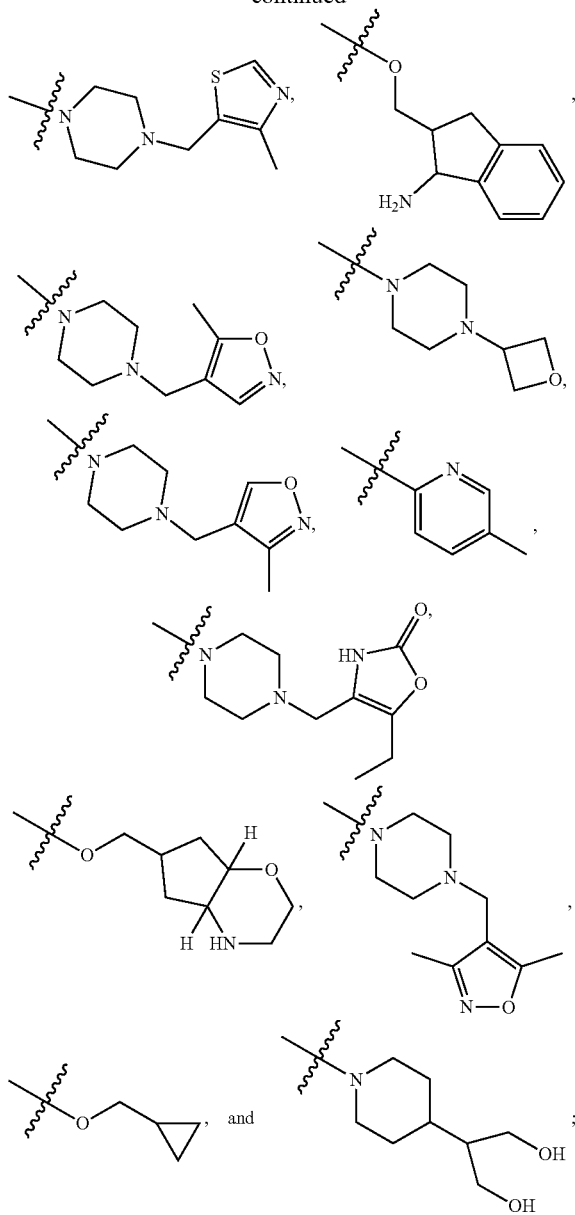

$R^8$ and $R^9$ are, independently at each occurrence, hydrogen, $C_{1-6}$alkyl optionally substituted with $R^{13}$, —C(O)$R^{13}$, $C_{3-6}$cycloalkyl group, or a 3-7 membered saturated or partially saturated heterocyclic group;

$R^{13}$ is, independently at each occurrence, $C_{1-6}$alkyl, —NH$_2$, or halogen;

$R^{14}$ and $R^{15}$ are selected from the group consisting of —OH, —CH$_3$, and —CH$_2$CH$_2$CN; and $R^{16}$ is hydrogen, or $C_{1-3}$alkyl optionally substituted with —NH$_2$ or —OH.

Also provided is a pharmaceutical composition that comprises a compound of the invention and a pharmaceutically acceptable carrier, diluent or excipient.

Another aspect includes a compound of the invention for use in therapy, such as the treatment of an inflammatory disease, an autoimmune disease or cancer.

Another aspect includes a method of preventing, treating or lessening the severity of a disease or condition responsive to the inhibition of IRAK4, in a patient. The method can comprise administering to the patient a therapeutically effective amount of a compound of the invention.

Another aspect includes the use of a compound of the invention in the manufacture of a medicament for the treatment of a disease responsive to the inhibition of IRAK4.

Another aspect includes a kit for treating a disease or disorder responsive to the inhibition of IRAK4. The kit can comprise a first pharmaceutical composition comprising a compound of the invention, and instructions for use.

DETAILED DESCRIPTION OF THE INVENTION

Definitions

"Halogen" or "halo" refers to F, Cl, Br or I. Additionally, terms such as "haloalkyl," are meant to include monohaloalkyl and polyhaloalkyl.

The term "alkyl" refers to a saturated linear or branched-chain monovalent hydrocarbon radical, wherein the alkyl radical may be optionally substituted. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. $C_0$ alkyl refers to a bond. Examples of alkyl groups include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl and 1-octyl. In some embodiments, substituents for "optionally substituted alkyls" include one to four instances of F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl and heterocyclic portions thereof may be optionally substituted, such as by one to four instances of substituents selected from this same list.

"Aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) 13$^{th}$ ed. Table 7-2 [1985]). A particular aryl is phenyl. Substituted phenyl or substituted aryl means a phenyl group or aryl group substituted with one, two, three, four or five substituents, for example, 1-2, 1-3 or 1-4 substituents, such as chosen from groups specified herein (see "optionally substituted" definition), such as F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 2,4-difluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, 2-chloro-5-difluoromethoxy and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino.

The terms "compound(s) of the invention," and "compound(s) of the present invention" and the like, unless otherwise indicated, include compounds of Formula I, Formula II, Formula III, Formula IV, Formula V, Formula VI, Formula VII, and Formula VIII and the compounds of Tables 1 and 2 herein, including stereoisomers (including atropisomers), geometric isomers, tautomers, solvates, metabolites, isotopes, salts (e.g., pharmaceutically acceptable salts), and prodrugs thereof. In some embodiments, solvates, metabolites, isotopes or prodrugs are excluded, or any combination thereof.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane. In some embodiments, substituents for "optionally substituted cycloalkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, isopropyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list.

"Heterocyclic group", "heterocyclic", "heterocycle", "heterocyclyl", or "heterocyclo" are used interchangeably and refer to any mono-, bi-, tricyclic or spiro, saturated, partially saturated or unsaturated, aromatic (heteroaryl) or non-aromatic (e.g., heterocycloalkyl), ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members") and includes monocycles, bicycles, tricycles and spiro ring systems, wherein the ring atoms are carbon, where at least one atom in the ring or ring system is a heteroatom selected from nitrogen, sulfur or oxygen. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles, e.g., 5-6 membered heteroaryl. In another example, heterocyclyl includes 3-11 membered heterocycloyalkyls, such as 4-11 membered heterocycloalkyls. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5] decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocycles are benzoxazol-2-yl, benzthiazol-2-yl and benzimidazol-2-yl. Example 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocycle groups. Heterocycles may be optionally substituted. For example, substituents for "optionally substituted heterocycles" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list.

"Heteroaryl" refers to any mono-, bi-, or tricyclic ring system where at least one ring is a 5- or 6-membered aromatic ring containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) 13$^{th}$ ed. Table 7-2 [1985]. Included in the definition are any bicyclic groups where any of the above heteroaryl rings are fused to an aryl ring, wherein the aryl ring or the heteroaryl ring is joined to the remainder of the molecule. In one embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b] pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl and indolyl. Heteroaryl groups can be optionally substituted. In some embodiments, substituents for "optionally substituted heteroaryls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

In particular embodiments, a heterocyclyl group is attached at a carbon atom of the heterocyclyl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "alkoxy" refers to a linear or branched monovalent radical represented by the formula —OR in which R is alkyl, as defined herein. Alkoxy groups include methoxy, ethoxy, propoxy, isopropoxy, mono-, di- and tri-fluoromethoxy and cyclopropoxy. "Haloalkoxy" refers to a haloalkyl group, as that term is defined herein, as R.

The term "alkanoyl" refers to group (alkyl)-C(═O)—, wherein alkyl is as defined herein. For example, $C_1$-$C_6$alkanoyl refers to a group of formula ($C_1$-$C_5$alkyl)-C(═O)—. Alkanoyl groups include, formyl, acetyl, propanoyl, isopropanoyl, butanoyl, isobutanoyl, pentanoyl, 3-methylpentanoyl, and hexanoyl.

"Optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent.

In another embodiment an optionally substituted group has 2 substituents. In another embodiment an optionally substituted group has 3 substituents. In another embodiment an optionally substituted group has 4 substituents. In another embodiment an optionally substituted group has 5 substituents.

As used herein a wavy line ⌇ that intersects a bond in a chemical structure indicate the point of attachment of the atom to which the wavy bond is connected in the chemical structure to the remainder of a molecule, or to the remainder of a fragment of a molecule. In some embodiments, an arrow together with an asterisk is used in the manner of a wavy line to indicate a point of attachment.

In certain embodiments, divalent groups are described generically without specific bonding configurations. It is understood that the generic description is meant to include both bonding configurations, unless specified otherwise. For example, in the group $R^1$-$R^2$-$R^3$, if the group $R^2$ is described as —$CH_2C(O)$—, then it is understood that this group can be bonded both as $R^1$—$CH_2C(O)$—$R^3$, and as $R^1$—$C(O)CH_2$—$R^3$, unless specified otherwise.

The phrase "pharmaceutically acceptable" refers to molecular entities and compositions that do not produce an adverse, allergic or other untoward reaction when administered to an animal, such as, for example, a human, as appropriate.

Compounds of the invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isothionate (2-hydroxyethylsulfonate), 2-mesitylenesulphonate, 2-naphthalenesulphonate, 2,5-dichlorobenzenesulphonate, D-mandelate, L-mandelate, cinnamate, benzoate, adipate, esylate, malonate, mesitylate (2-mesitylenesulphonate), napsylate (2-naphthalenesulfonate), camsylate (camphor-10-sulphonate, for example (1S)-(+)-10-camphorsulfonic acid salt), glutamate, glutarate, hippurate (2-(benzoylamino)acetate), orotate, xylate (p-xylene-2-sulphonate), and pamoic (2,2'-dihydroxy-1,1'-dinaphthylmethane-3,3'-dicarboxylate).

A "sterile" formulation is aseptic or free from all living microorganisms and their spores.

"Stereoisomers" refer to compounds that have identical chemical constitution, but differ with regard to the arrangement of the atoms or groups in space. Stereoisomers include diastereomers, enantiomers, conformers and the like.

"Chiral" refers to molecules which have the property of non-superimposability of the mirror image partner, while the term "achiral" refers to molecules which are superimposable on their mirror image partner.

"Diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Certain compounds of the invention can exist in unsolvated forms as well as solvated forms, including hydrated forms. A "solvate" refers to an association or complex of one or more solvent molecules and a compound of the present invention. Examples of solvents that form solvates include water, isopropanol, ethanol, methanol, DMSO, ethyl acetate, acetic acid, and ethanolamine. Certain compounds of the invention can exist in multiple crystalline or amorphous forms. In general, all physical forms are intended to be within the scope of the present invention. The term "hydrate" refers to the complex where the solvent molecule is water.

A "metabolite" refers to a product produced through metabolism in the body of a specified compound or salt thereof. Such products can result, for example, from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are Pmb (p-Methoxybenzyl), Boc (tert-Butyloxycarbonyl), Fmoc (9-Fluorenylmethyloxycarbonyl) and Cbz (Carbobenzyloxy). Further examples of these groups are found in T. W. Greene and P. G. M. Wuts, "Protecting Groups in Organic Synthesis, $3^{rd}$ ed., John Wiley & Sons, Inc., 1999. The term "protected amino" refers to an amino group substituted with one of the above amino-protecting groups.

"Carboxy-protecting group" as used herein refers to those groups that are stable to the conditions of subsequent reaction(s) at other positions of the molecule, which may be removed at the appropriate point without disrupting the remainder of the molecule, to give the unprotected carboxy-group. Examples of carboxy protecting groups include, ester groups and heterocyclyl groups. Ester derivatives of the carboxylic acid group may be employed to block or protect the carboxylic acid group while reactions are carried out on other functional groups on the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl or substituted alkyl esters such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl) prop-1-en-3-yl, and like moieties. Another example of carboxy-protecting groups are heterocyclyl groups such as 1,3-oxazolinyl. Further examples of these groups are found in T. W. Greene and P. G. M. Wuts, "Protecting Groups in Organic Synthesis, $3^{rd}$ ed., John Wiley & Sons, Inc., 1999. The term "protected carboxy" refers to a carboxy group substituted with one of the above carboxy-protecting groups.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g., TBS, TBDPS) groups. Further examples of these groups are found in T. W. Greene and P. G. M. Wuts, "Protecting Groups in Organic Synthesis, $3^{rd}$ ed., John Wiley & Sons, Inc., 1999. The term "protected hydroxy" refers to a hydroxy group substituted with one of the above hydroxy-protecting groups.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

Another aspect includes prodrugs of the compounds of the invention including known amino-protecting and carboxy-protecting groups which are released, for example hydrolyzed, to yield the compound of the present invention under physiologic conditions.

The term "prodrug" refers to a precursor or derivative form of a pharmaceutically active substance that is less efficacious to the patient compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, and 5-fluorocytosine and 5-fluorouridine prodrugs.

A particular class of prodrugs are compounds in which a nitrogen atom in an amino, amidino, aminoalkyleneamino, iminoalkyleneamino or guanidino group is substituted with a hydroxy group, an alkylcarbonyl (—CO—R) group, an alkoxycarbonyl (—CO—OR), or an acyloxyalkyl-alkoxycarbonyl (—CO—O—R—O—CO—R) group where R is a monovalent or divalent group, for example alkyl, alkylene or aryl, or a group having the Formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group of the compounds of the invention. Prodrugs may be prepared by reacting a compound of the present invention with an activated group, such as acyl groups, to bond, for example, a nitrogen atom in the compound to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at reduced temperatures such as −78 to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Additional types of prodrugs are also encompassed. For instance, a free carboxyl group of a compound of the invention can be derivatized as an amide or alkyl ester. As another example, compounds of the invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, alpha-amino$(C_1-C_4)$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_1-C_6)$al-kyl$)_2$ or glycosyl (the radical resulting from the removal of a hydroxyl group of the hemiacetal form of a carbohydrate).

"Leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

A "subject," "individual," or "patient" is a vertebrate. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a compound of to a patient, the patient is typically in need thereof.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., IRAK4 activity) compared to normal.

In some embodiments, a compound of Formula I, Formula II, Formula III, Formula IV, Formula V, Formula VI, Formula VII, and Formula VIII, such as a compound of Tables 1 and 2, is selective for inhibition of IRAK4 over IRAK1. By "selective for inhibition" it is meant that the compound is at least a 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, better inhibitor of IRAK4 activity compared to IRAK1 activity, or is at least a 2-, 3-, 4-, 5-, 10-, 25-, 50-, 100-, 250-, or 500-fold better inhibitor of IRAK4 activity compared to IRAK1 activity.

A "therapeutically effective amount" means an amount of a compound of the present invention, such as a compound of Formula I, Formula II, Formula III, Formula IV, Formula V, Formula VI, Formula VII, and Formula VIII (e.g., a compound of Tables 1 and 2), that (i) treats or prevents the particular disease, condition or disorder, or (ii) attenuates, ameliorates or eliminates one or more symptoms of the particular disease, condition, or disorder, and optionally (iii) prevents or delays the onset of one or more symptoms of the particular disease, condition or disorder described herein. In some embodiments, the therapeutically effective amount is an amount sufficient to decrease or alleviate the symptoms of an autoimmune or inflammatory disease (e.g., lupus). In some embodiments, a therapeutically effective amount is an amount of a chemical entity described herein sufficient to significantly decrease the activity or number of B-cells. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; or relieve to some extent one or more of the symptoms associated with the cancer. To the extent the drug may prevent growth or kill existing cancer cells, it may be cytostatic or cytotoxic. For cancer therapy, efficacy can, for example, be measured by assessing the time to disease progression (TTP) or determining the response rate (RR).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention, are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

"Inflammatory disorder" refers to any disease, disorder or syndrome in which an excessive or unregulated inflammatory response leads to excessive inflammatory symptoms, host tissue damage, or loss of tissue function. "Inflammatory disorder" also refers to a pathological state mediated by influx of leukocytes or neutrophil chemotaxis.

"Inflammation" refers to a localized, protective response elicited by injury or destruction of tissues, which serves to destroy, dilute, or wall off (sequester) both the injurious agent and the injured tissue. Inflammation is notably associated with influx of leukocytes or neutrophil chemotaxis. Inflammation can result from infection with pathogenic organisms and viruses and from noninfectious means such as trauma or reperfusion following myocardial infarction or stroke, immune responses to foreign antigens, and autoimmune responses. Accordingly, inflammatory disorders amenable to treatment with a compound of the present invention, such as a compound of Formula I, Formula II, Formula III, Formula IV, Formula V, Formula VI, Formula VII, and Formula VIII (e.g., a compound of Tables 1 and 2), encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity responses mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" refers to any group of disorders in which tissue injury is associated with humoral or cell-mediated responses to the body's own constituents. Non-limiting examples of autoimmune diseases include rheumatoid arthritis, lupus and multiple sclerosis.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

In some embodiments, inflammatory disorders which can be treated according to the methods of this invention include, but are not limited to, asthma, rhinitis (e.g., allergic rhinitis), allergic airway syndrome, atopic dermatitis, bronchitis, rheumatoid arthritis, psoriasis, lupus, chronic obstructive pulmonary disease (COPD), contact dermatitis, chronic obstructive pulmonary disease and delayed hypersensitivity reactions.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, diffuse large B-Cell lymphoma (DLBCL), central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

Unless otherwise stated, structures depicted herein are also meant to include compounds that differ only in the presence of one or more isotopically enriched atoms. Exemplary isotopes that can be incorporated into compounds of the invention, include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds of the invention, one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

If any discrepancy exists between a structure and its name, the structure prevails.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

IRAK4 Inhibitors

As noted, one aspect of the invention includes a compound of Formula I:

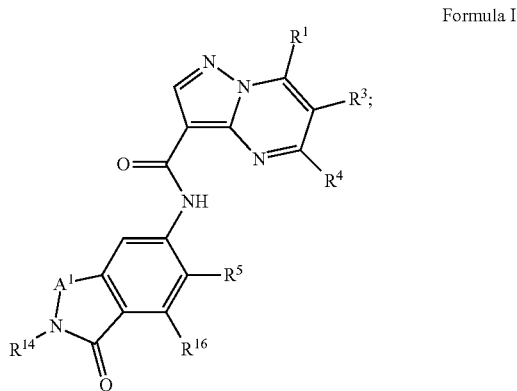

Formula I or a stereoisomer or a pharmaceutically acceptable salt thereof, wherein:
$A^1$ is $CH_2$ or NH;
$R^1$ is hydrogen;
$R^3$ is hydrogen, halogen, —OH, or $C_{1-3}$alkyl;
$R^4$ is hydrogen, halogen, —$NR^8R^9$, —$C(O)NR^8R^9$, or a 3-7 membered monocyclic saturated or partially saturated heterocyclic group optionally substituted with one or more substituents selected from oxo, —$NR^8R^9$, or $R^{13}$;
$R^5$ is selected from the group consisting of —$NHCH_3$, —$N(CH_3)_2$, —$C(CH_3)_2OH$, —$OCH_3$, —$OCH(CH_3)_2$, —$OC(CH_3)_3$, —$OCH_2CH_3$, —$OCHF_2$, —$OCH_2CF_3$, —$OCH_2CHF_2$, —$CH_2OCHF_2$, —CN,

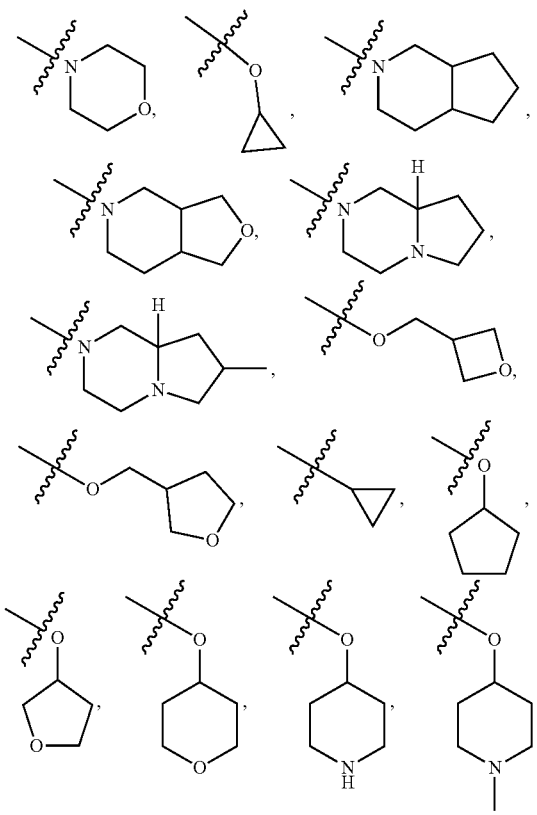

-continued
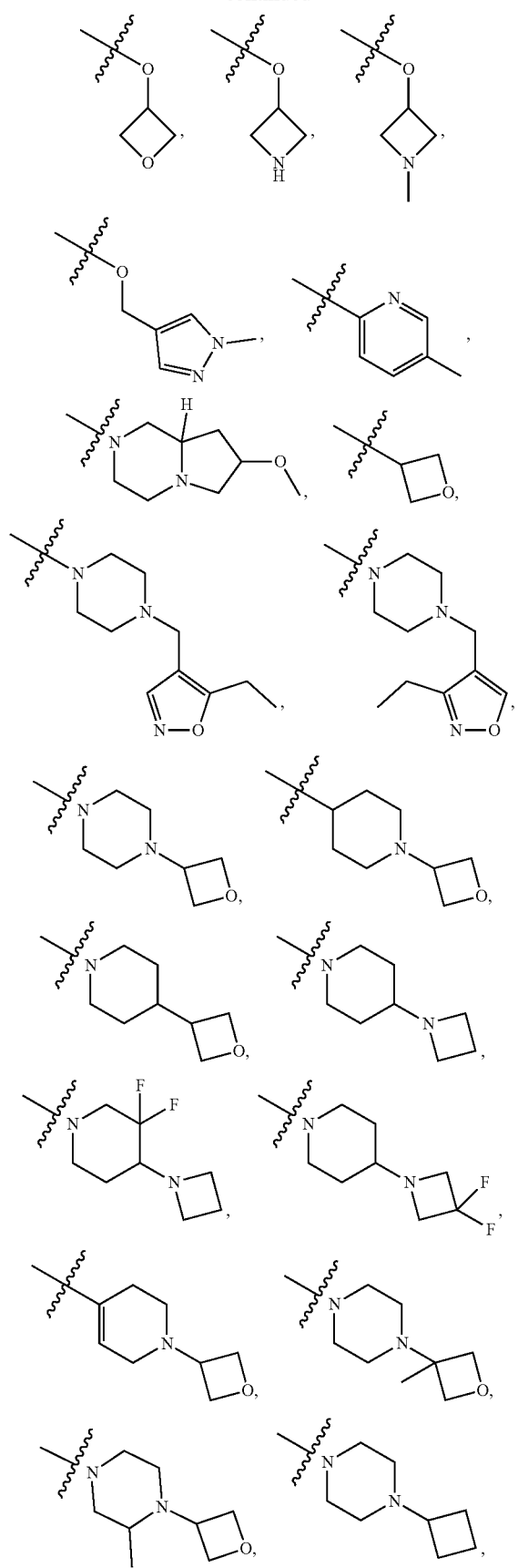
-continued
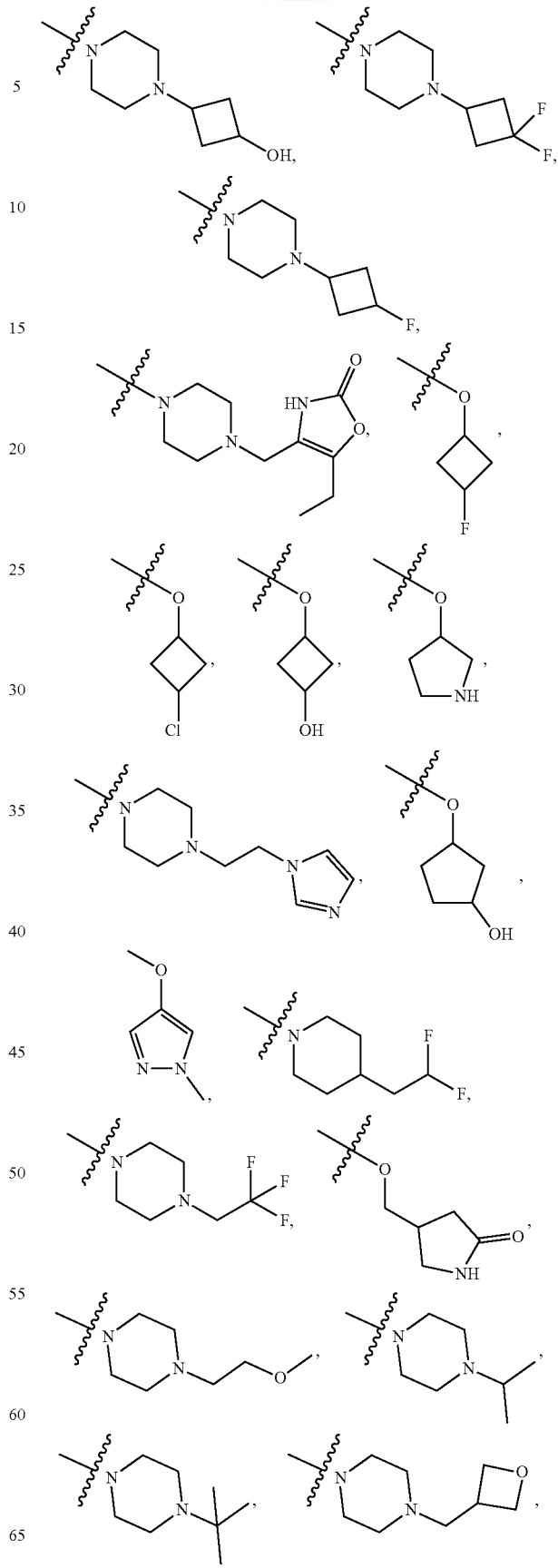

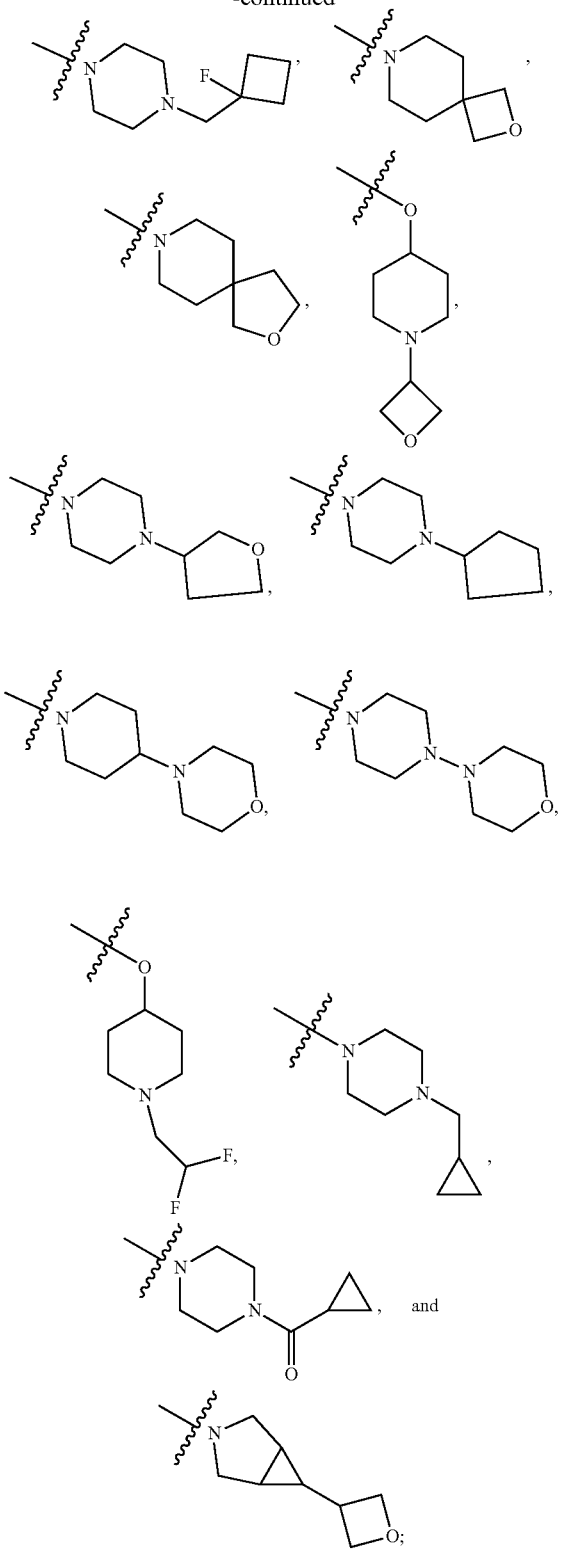

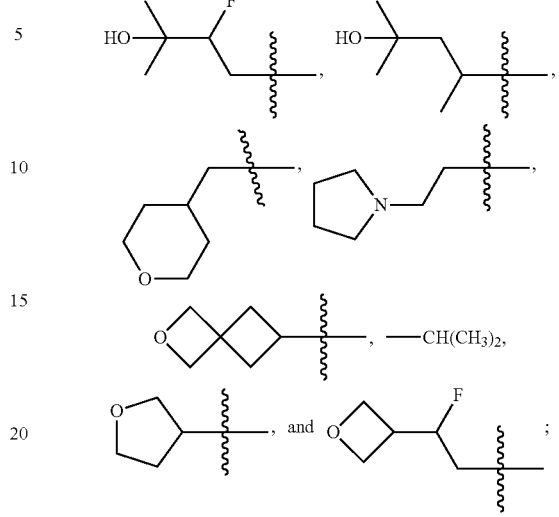

$R^8$ and $R^9$ are, independently at each occurrence, hydrogen, $C_{1-6}$alkyl optionally substituted with $R^{13}$, —C(O)$R^{13}$, $C_{3-6}$cycloalkyl group, or a 3-7 membered saturated or partially saturated heterocyclic group;

$R^{13}$ is, independently at each occurrence, $C_{1-6}$alkyl, —NH$_2$, or halogen;

$R^{14}$ is selected from the group consisting of $R^{16}$ is hydrogen, or $C_{1-3}$alkyl optionally substituted with —NH$_2$ or —OH.

According to some embodiments of the compound of Formula I or a stereoisomer or pharmaceutically acceptable salt thereof, $A^1$ is CH$_2$.

According to some embodiments of the compound of Formula I or a stereoisomer or pharmaceutically acceptable salt thereof, $A^1$ is NH.

According to some embodiments of the compound of Formula I or a stereoisomer or pharmaceutically acceptable salt thereof, $R^3$ is hydrogen.

According to some embodiments of the compound of Formula I or a stereoisomer or pharmaceutically acceptable salt thereof, $R^3$ is selected from the group consisting of —Cl, —OH, —CH$_3$. According to some embodiments of the compound of Formula I or a stereoisomer or pharmaceutically acceptable salt thereof, $R^3$ is —Cl. According to some embodiments of the compound of Formula I or a stereoisomer or pharmaceutically acceptable salt thereof, $R^3$ is —OH. According to some embodiments of the compound of Formula I or a stereoisomer or pharmaceutically acceptable salt thereof, $R^3$ is —CH$_3$.

According to some embodiments of the compound of Formula I or a stereoisomer or pharmaceutically acceptable salt thereof, $R^4$ is hydrogen.

According to some embodiments of the compound of Formula I or a stereoisomer or pharmaceutically acceptable salt thereof, $R^4$ is —Cl.

According to some embodiments of the compound of Formula I or a stereoisomer or pharmaceutically acceptable salt thereof, $R^4$ is —C(O)NR$^8$R$^9$, wherein $R^8$ is hydrogen and $R^9$ is cyclopropyl.

According to some embodiments of the compound of Formula I or a stereoisomer or pharmaceutically acceptable salt thereof, $R^4$ is —NR$^8$R$^9$, wherein $R^8$ is hydrogen and $R^9$ is —C(O)$R^{13}$, wherein $R^{13}$ is methyl.

According to some embodiments of the compound of Formula I or a stereoisomer or pharmaceutically acceptable salt thereof, $R^4$ is selected from the group consisting of —Cl,

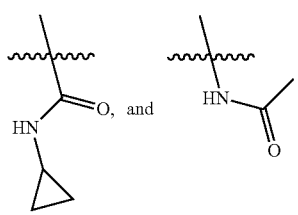
According to some embodiments of the compound of Formula I or a stereoisomer or pharmaceutically acceptable salt thereof, $R^5$ is selected from the group consisting of —NHCH$_3$, —N(CH$_3$)$_2$, —C(CH$_3$)$_2$OH, —OCH$_3$, —OCH(CH$_3$)$_2$, —OC(CH$_3$)$_3$, —OCH$_2$CH$_3$, —OCHF$_2$, —OCH$_2$CF$_3$, —OCH$_2$CHF$_2$, —CN,
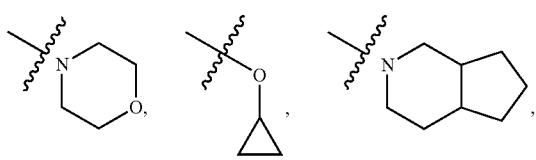
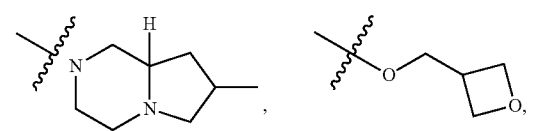
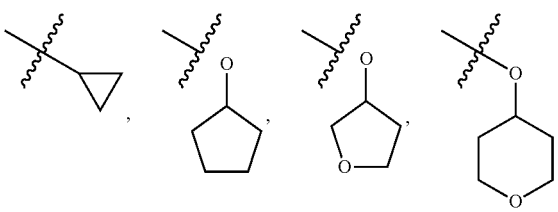
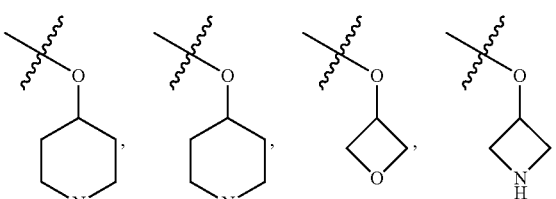
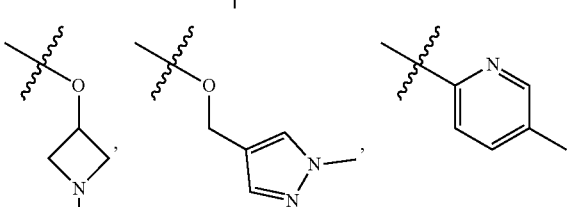
-continued
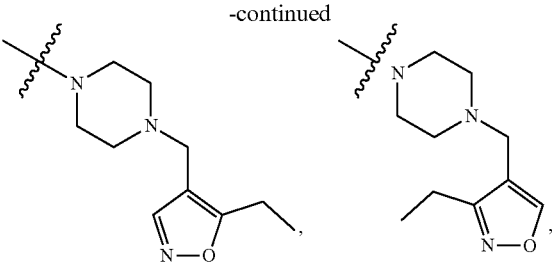
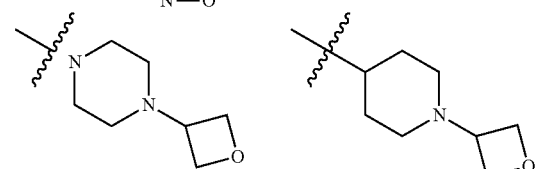
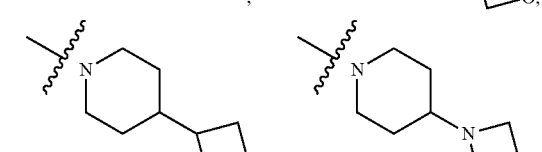
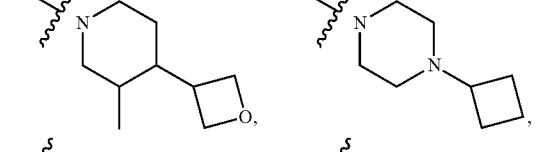
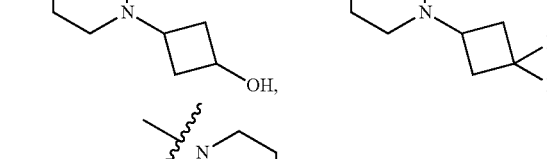
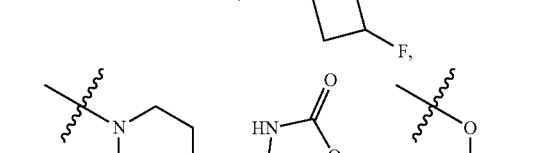

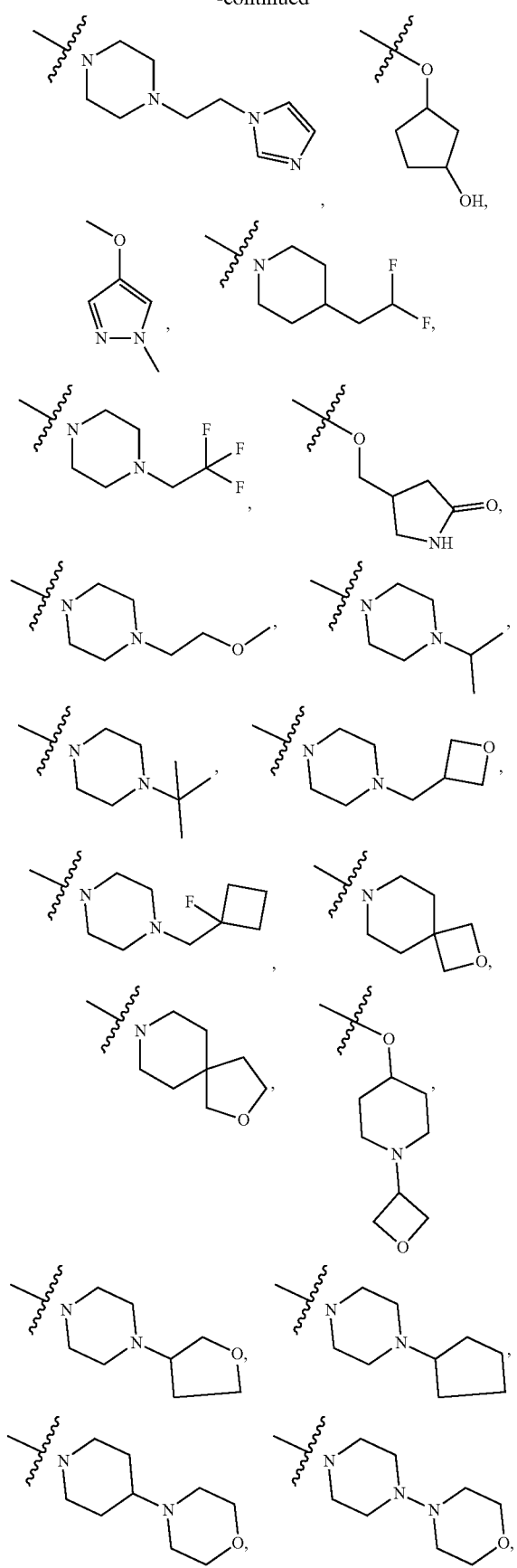
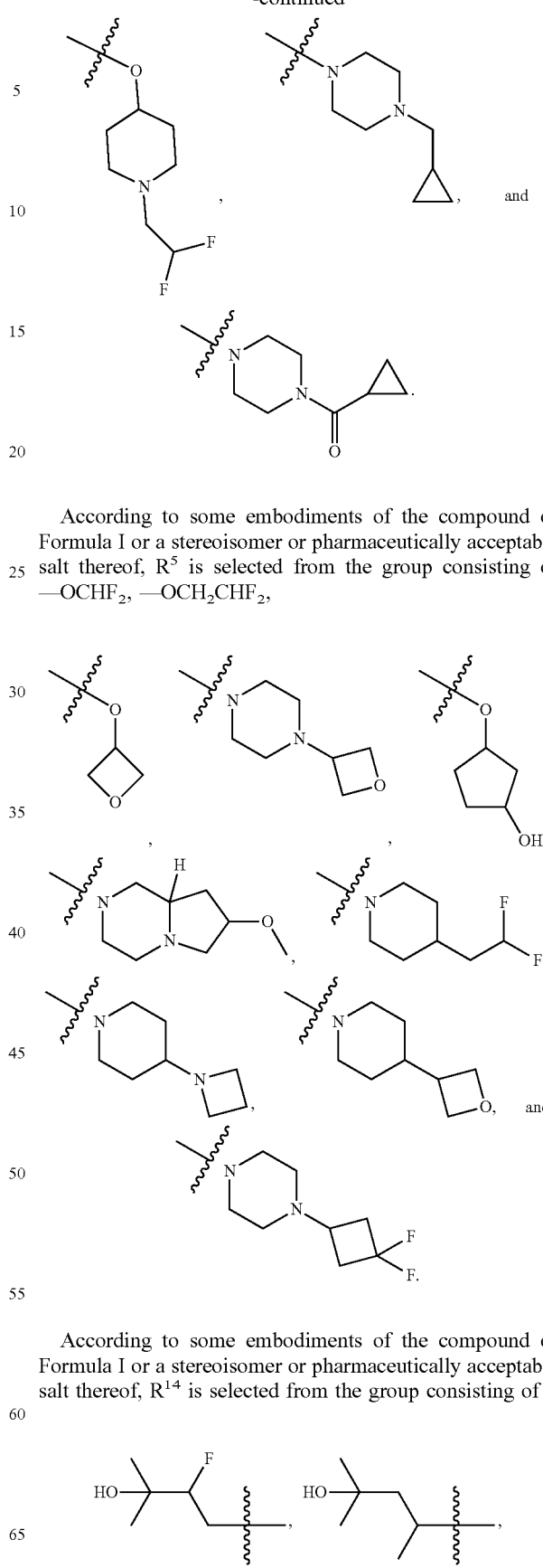
According to some embodiments of the compound of Formula I or a stereoisomer or pharmaceutically acceptable salt thereof, $R^5$ is selected from the group consisting of —OCHF$_2$, —OCH$_2$CHF$_2$,
According to some embodiments of the compound of Formula I or a stereoisomer or pharmaceutically acceptable salt thereof, $R^{14}$ is selected from the group consisting of -continued

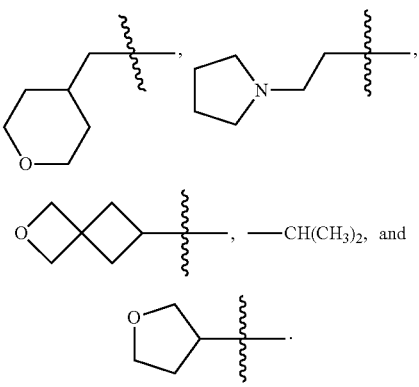

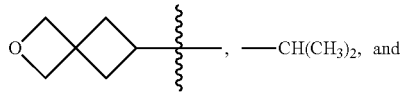, —CH(CH$_3$)$_2$, and

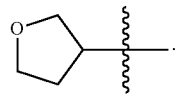

According to some embodiments of the compound of Formula I or a stereoisomer or pharmaceutically acceptable salt thereof, R$^{14}$ is

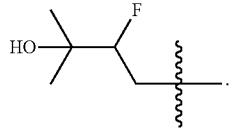 [SMILES: *CC(F)C(C)(C)O]

According to some embodiments of the compound of Formula I or a stereoisomer or pharmaceutically acceptable salt thereof, R$^{16}$ is hydrogen.

According to some embodiments of the compound of Formula I or a stereoisomer or pharmaceutically acceptable salt thereof, R$^{16}$ is —CH$_2$OH.

Another aspect of the invention includes a compound of Formula II:

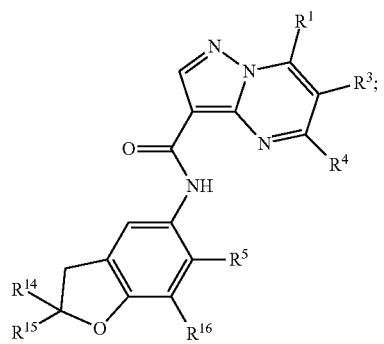

Formula II or a stereoisomer or a pharmaceutically acceptable salt thereof, wherein:

R$^1$ is hydrogen;

R$^3$ is hydrogen, halogen, —OH, or C$_{1-3}$alkyl;

R$^4$ is hydrogen, halogen, —NR$^8$R$^9$, —C(O)NR$^8$R$^9$, or a 3-7 membered monocyclic saturated or partially saturated heterocyclic group optionally substituted with one or more substituents selected from oxo, —NR$^8$R$^9$, or R$^{13}$;

R$^5$ is selected from the group consisting of hydrogen, —OCH$_3$, —CH$_2$NH$_2$,

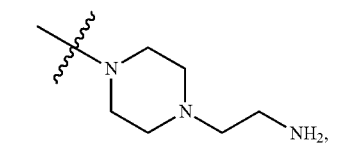

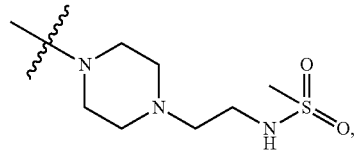

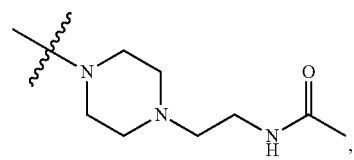

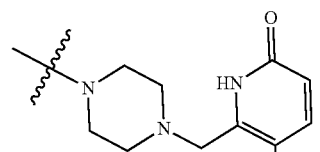

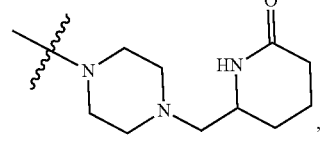

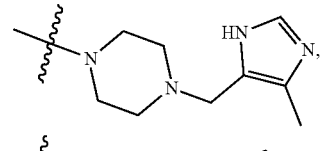

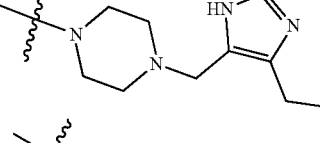

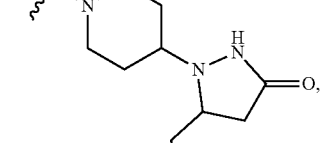

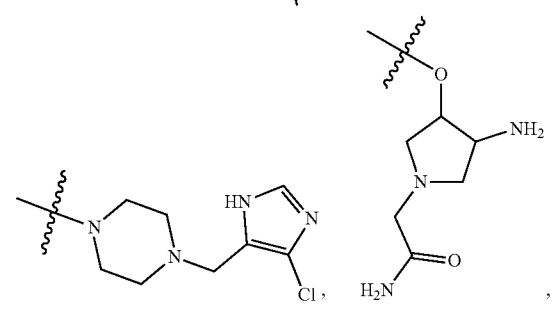

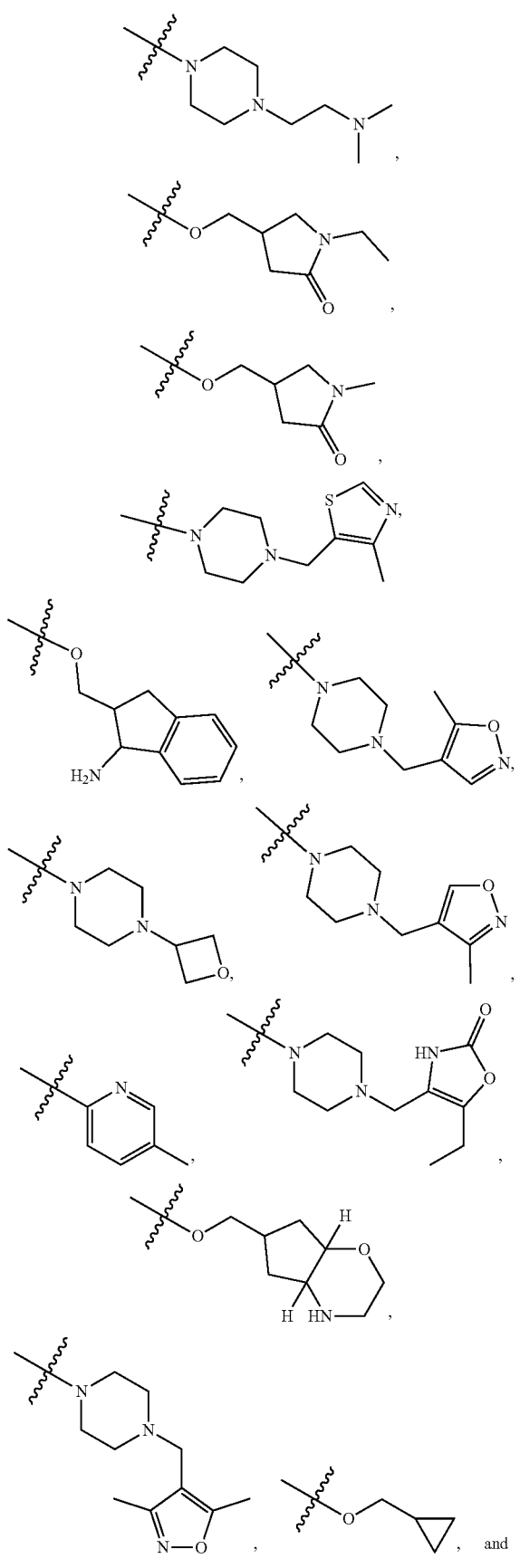

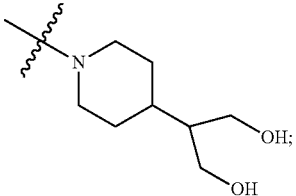 [SMILES: *N1CCC(C(CO)CO)CC1]

R[8] and R[9] are, independently at each occurrence, hydrogen, $C_{1-6}$alkyl optionally substituted with R[13], —C(O)R[3], $C_{3-6}$cycloalkyl group, or a 3-7 membered saturated or partially saturated heterocyclic group;

R[13] is, independently at each occurrence, $C_{1-6}$alkyl, —NH$_2$, or halogen;

R[14], R[15] are, independently at each occurrence, methyl or —CH$_2$OH, or taken together form a 6-membered, spiro bonded heterocyclic group with the carbon to which they are bonded; and R[16] is hydrogen, or $C_{1-3}$alkyl optionally substituted with —NH$_2$ or —OH, wherein no more than one of R[5] or R[16] can be hydrogen.

According to some embodiments of the compound of Formula II or a stereoisomer or pharmaceutically acceptable salt thereof, R[3] is hydrogen.

According to some embodiments of the compound of Formula II or a stereoisomer or pharmaceutically acceptable salt thereof, R[4] is hydrogen.

According to some embodiments of the compound of Formula II or a stereoisomer or pharmaceutically acceptable salt thereof, R[4] is —Cl.

According to some embodiments of the compound of Formula II or a stereoisomer or pharmaceutically acceptable salt thereof, R[4] is —NR[8]R[9], and further wherein each R[8] and R[9] are independently selected from the group consisting of hydrogen, methyl, cyclopropyl, piperidyl, and ethyl optionally substituted with R[13], and further wherein R[13] is —NH$_2$.

According to some embodiments of the compound of Formula II or a stereoisomer or pharmaceutically acceptable salt thereof, R[4] is a 3-7 membered monocyclic saturated or partially saturated heterocyclic group.

According to some embodiments of the compound of Formula II or a stereoisomer or pharmaceutically acceptable salt thereof, the 3-7 membered monocyclic saturated or partially saturated heterocyclic group is substituted with oxo.

According to some embodiments of the compound of Formula II or a stereoisomer or pharmaceutically acceptable salt thereof, the 3-7 membered monocyclic saturated or partially saturated heterocyclic group is substituted with —NR[8]R[9], and further wherein each R[8] and R[9] are each hydrogen.

According to some embodiments of the compound of Formula II or a stereoisomer or pharmaceutically acceptable salt thereof, the 3-7 membered monocyclic saturated or partially saturated heterocyclic group is substituted with one or more R[13], and further wherein each R[13] is —F.

According to some embodiments of the compound of Formula II or a stereoisomer or pharmaceutically acceptable salt thereof, R[4] is selected from the group consisting of —Cl, —NH$_2$, —N(CH$_3$)$_2$, —NHCH$_2$CH$_2$NH$_2$,

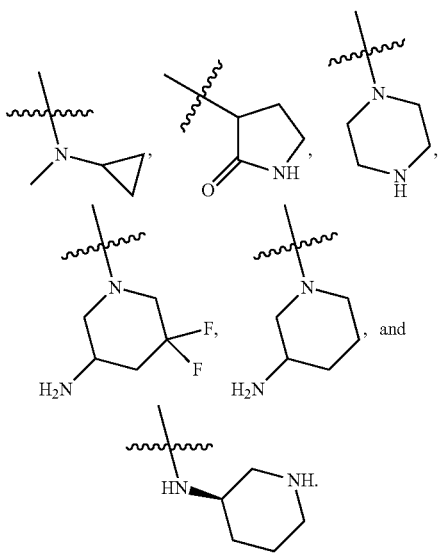

According to some embodiments of the compound of Formula II or a stereoisomer or pharmaceutically acceptable salt thereof, $R^{14}$ and $R^{15}$ are both methyl.

According to some embodiments of the compound of Formula II or a stereoisomer or pharmaceutically acceptable salt thereof, $R^{14}$ is methyl and $R^{15}$ is —CH$_2$OH.

According to some embodiments of the compound of Formula II or a stereoisomer or pharmaceutically acceptable salt thereof, $R^{14}$, $R^{15}$ are taken together form a 6-membered, spiro bonded heterocyclic group having the structure

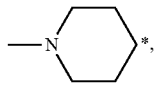

wherein * designates the spiro bonded carbon.

According to some embodiments of the compound of Formula II or a stereoisomer or pharmaceutically acceptable salt thereof, $R^{16}$ is hydrogen.

According to some embodiments of the compound of Formula II or a stereoisomer or pharmaceutically acceptable salt thereof, $R^{16}$ is —CH$_2$NH$_2$.

Yet another aspect of the invention includes a compound of Formula III:

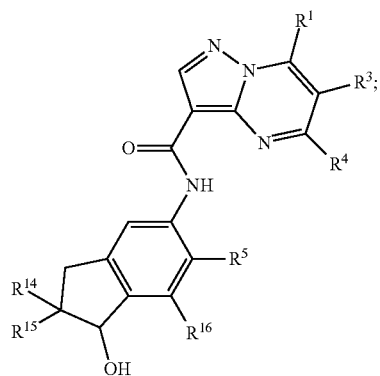

Formula III or a stereoisomer or a pharmaceutically acceptable salt thereof, wherein:

$R^1$ is hydrogen;

$R^3$ is hydrogen, halogen, —OH, or $C_{1-3}$alkyl;

$R^4$ is hydrogen, halogen, —NR$^8$R$^9$, —C(O)NR$^8$R$^9$, or a 3-7 membered monocyclic saturated or partially saturated heterocyclic group optionally substituted with one or more substituents selected from oxo, —NR$^8$R$^9$, or $R^{13}$;

$R^5$ is selected from the group consisting of hydrogen, —NHCH$_3$, —N(CH$_3$)$_2$, —C(CH$_3$)$_2$OH, —OCH$_3$, —OCH(CH$_3$)$_2$, —OC(CH$_3$)$_3$, —OCH$_2$CH$_3$, —OCHF$_2$, —OCH$_2$CF$_3$, —OCH$_2$CHF$_2$, —CH$_2$OCHF$_2$, —CN, —CH$_2$NH$_2$,

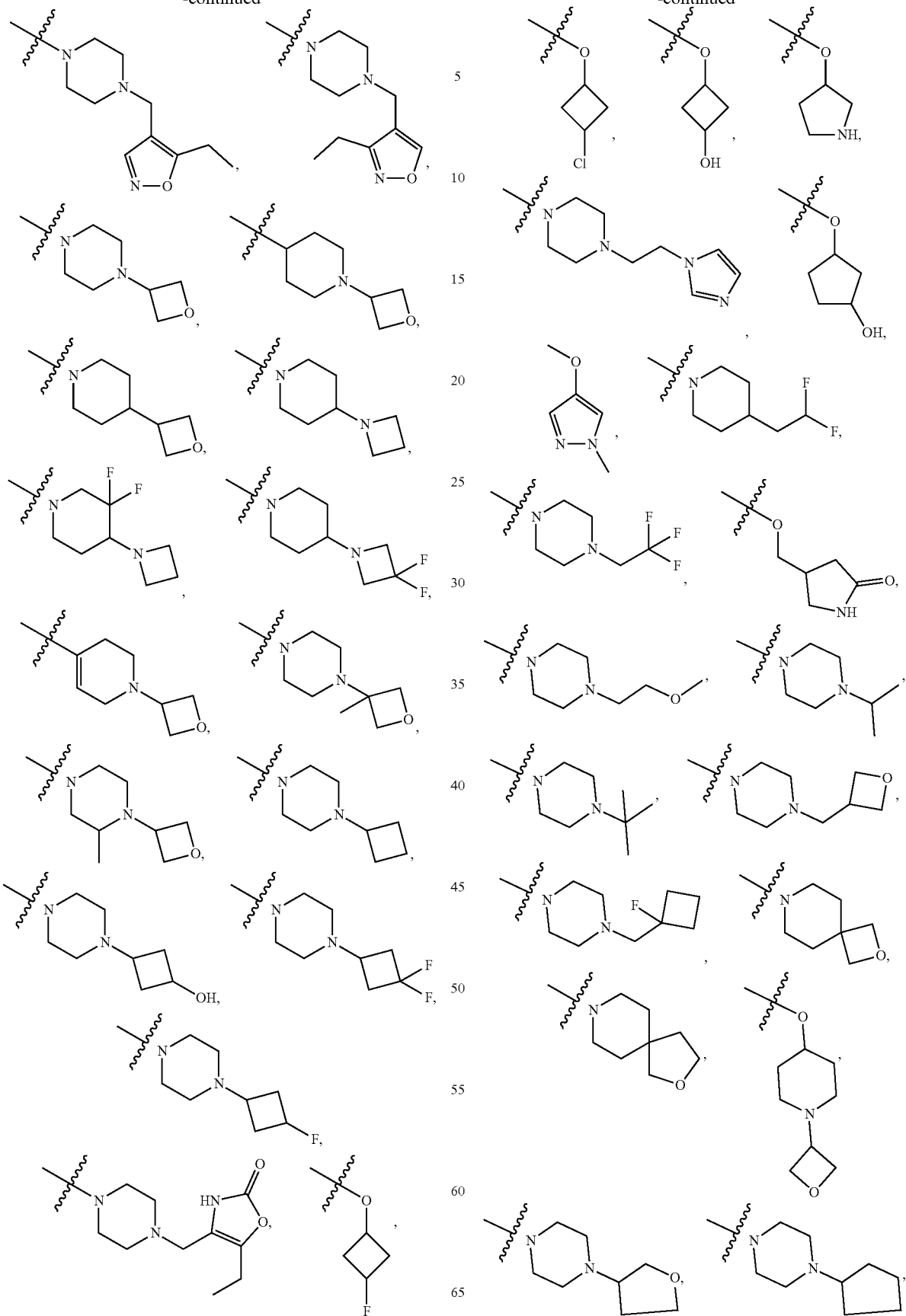

77
-continued
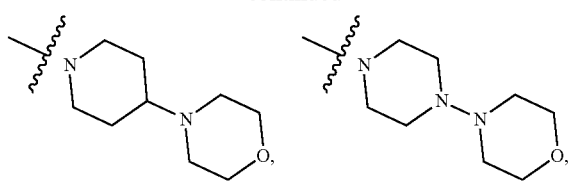
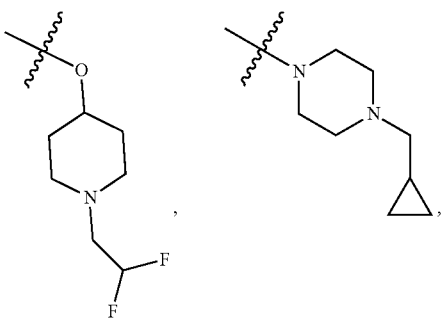
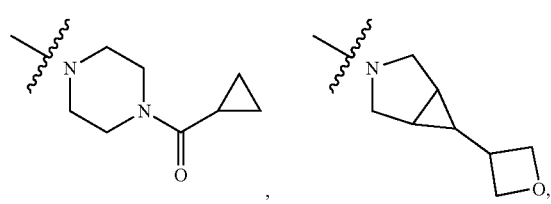
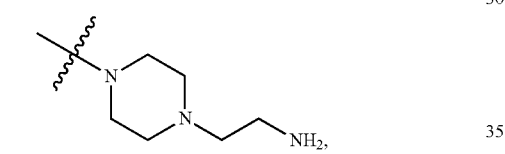
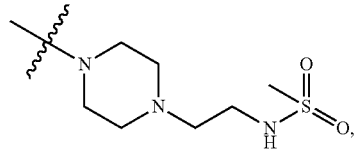
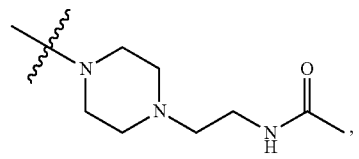
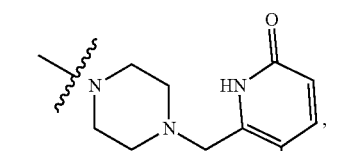
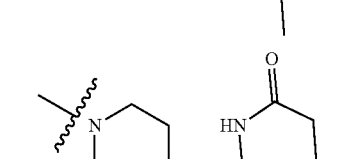
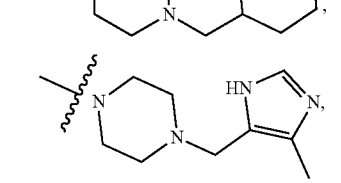
78
-continued
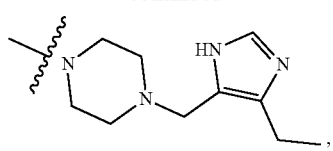
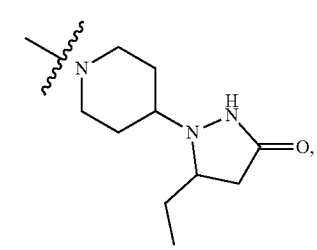
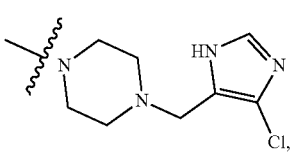
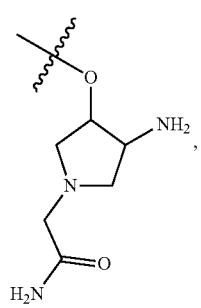
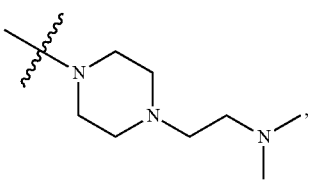
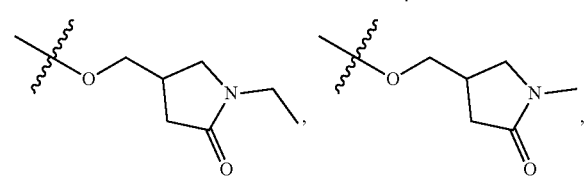
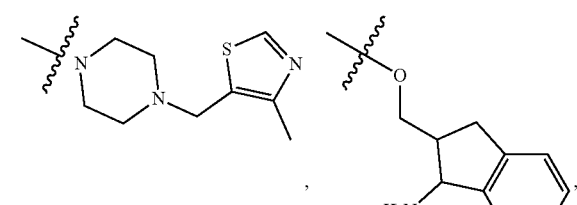
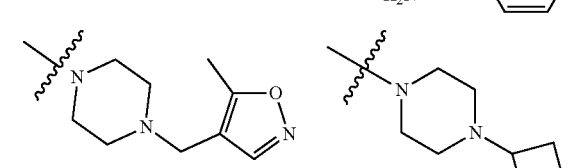
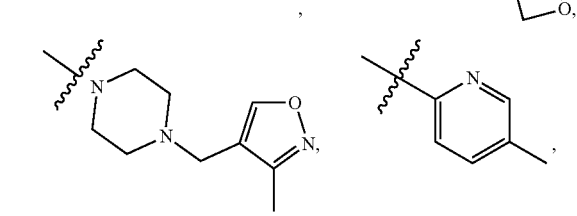

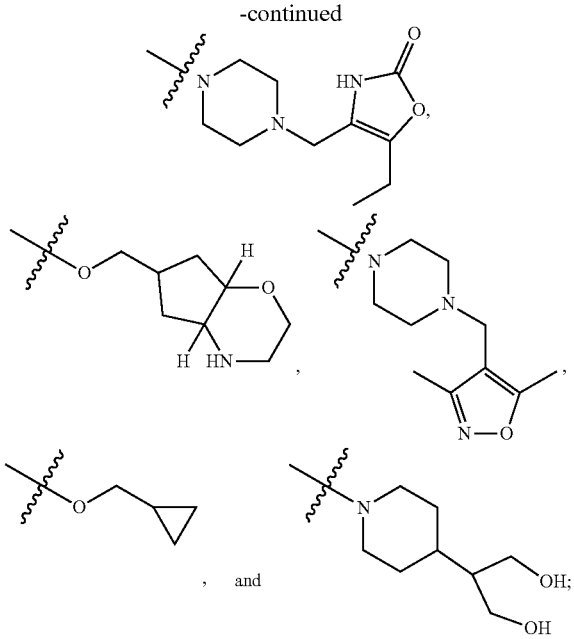

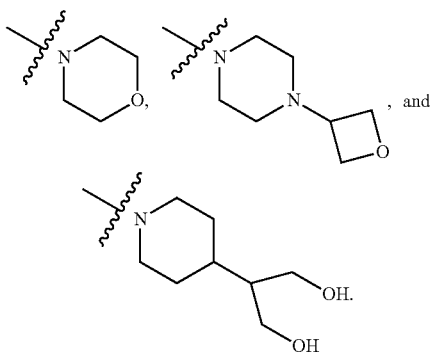

$R^8$ and $R^9$ are, independently at each occurrence, hydrogen, $C_{1-6}$alkyl optionally substituted with $R^{13}$, —C(O)$R^{13}$, $C_{3-6}$cycloalkyl group, or a 3-7 membered saturated or partially saturated heterocyclic group;

$R^{13}$ is, independently at each occurrence, $C_{1-6}$alkyl, —NH$_2$, or halogen;

$R^{14}$, $R^{15}$ are, independently at each occurrence, methyl or —CH$_2$OH, or taken together form a 6-membered, spiro bonded heterocyclic group with the carbon to which they are bonded; and $R^{16}$ is hydrogen, or $C_{1-3}$alkyl optionally substituted with —NH$_2$ or —OH.

According to some embodiments of the compound of Formula III or a stereoisomer or pharmaceutically acceptable salt thereof, $R^3$ is hydrogen.

According to some embodiments of the compound of Formula III or a stereoisomer or pharmaceutically acceptable salt thereof, $R^4$ is hydrogen.

According to some embodiments of the compound of Formula III or a stereoisomer or pharmaceutically acceptable salt thereof, $R^5$ is selected from the group consisting of —N(CH$_3$)$_2$, According to some embodiments of the compound of Formula III or a stereoisomer or pharmaceutically acceptable salt thereof, $R^5$ is —N(CH$_3$)$_2$.

According to some embodiments of the compound of Formula III or a stereoisomer or pharmaceutically acceptable salt thereof, $R^{14}$ and $R^{15}$ are both methyl.

According to some embodiments of the compound of Formula III or a stereoisomer or pharmaceutically acceptable salt thereof, $R^{16}$ is hydrogen.

Yet another aspect of the invention includes a compound of Formula IV:

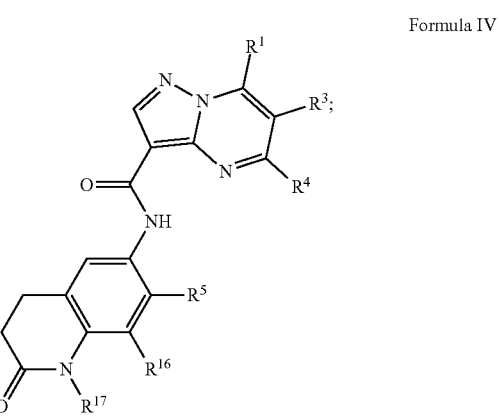

Formula IV or a stereoisomer or a pharmaceutically acceptable salt thereof, wherein:

$R^1$ is hydrogen;

$R^3$ is hydrogen, halogen, —OH, or $C_{1-3}$alkyl;

$R^4$ is hydrogen, halogen, —NR$^8$R$^9$, —C(O)NR$^8$R$^9$, or a 3-7 membered monocyclic saturated or partially saturated heterocyclic group optionally substituted with one or more substituents selected from oxo, —NR$^8$R$^9$, or $R^{13}$;

$R^5$ is selected from the group consisting of hydrogen, —NHCH$_3$, —N(CH$_3$)$_2$, —C(CH$_3$)$_2$OH, —OCH$_3$, —OCH(CH$_3$)$_2$, —OC(CH$_3$)$_3$, —OCH$_2$CH$_3$, —OCHF$_2$, —OCH$_2$CF$_3$, —OCH$_2$CHF$_2$, —CH$_2$OCHF$_2$, —CN, —CH$_2$NH$_2$,

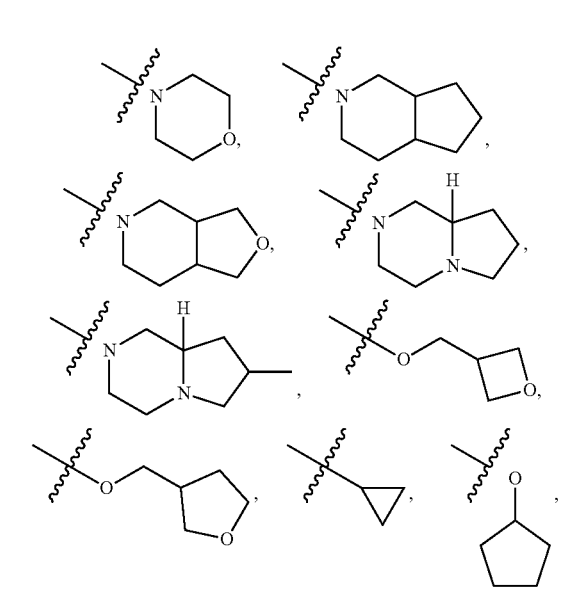

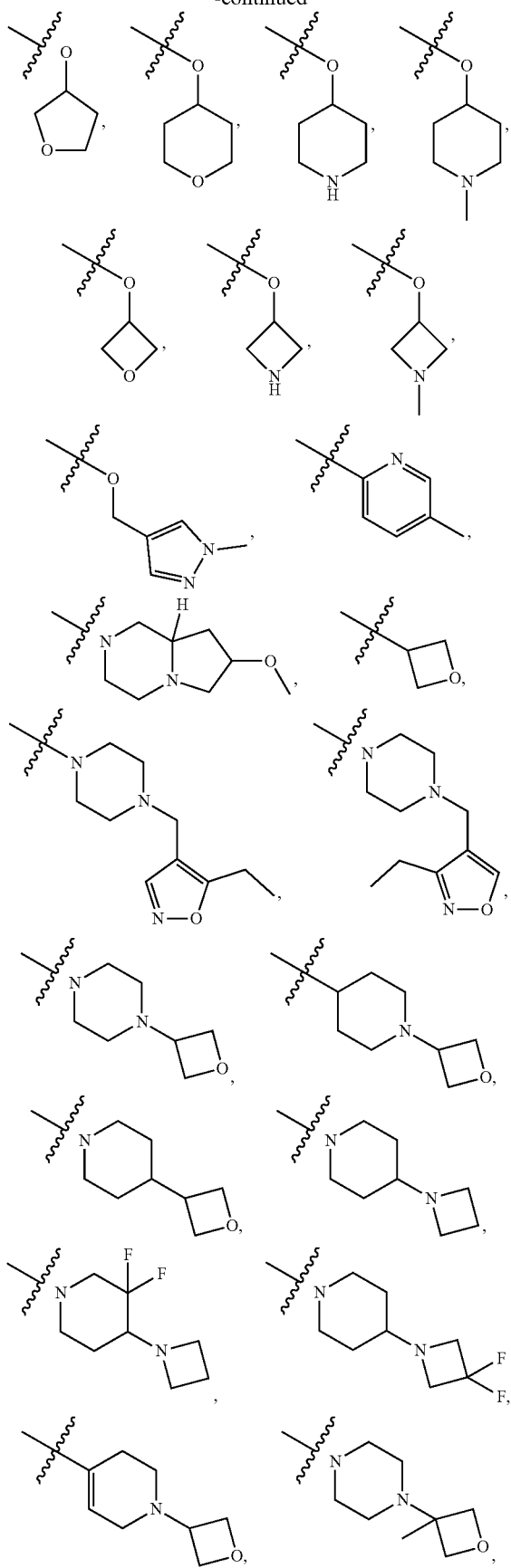
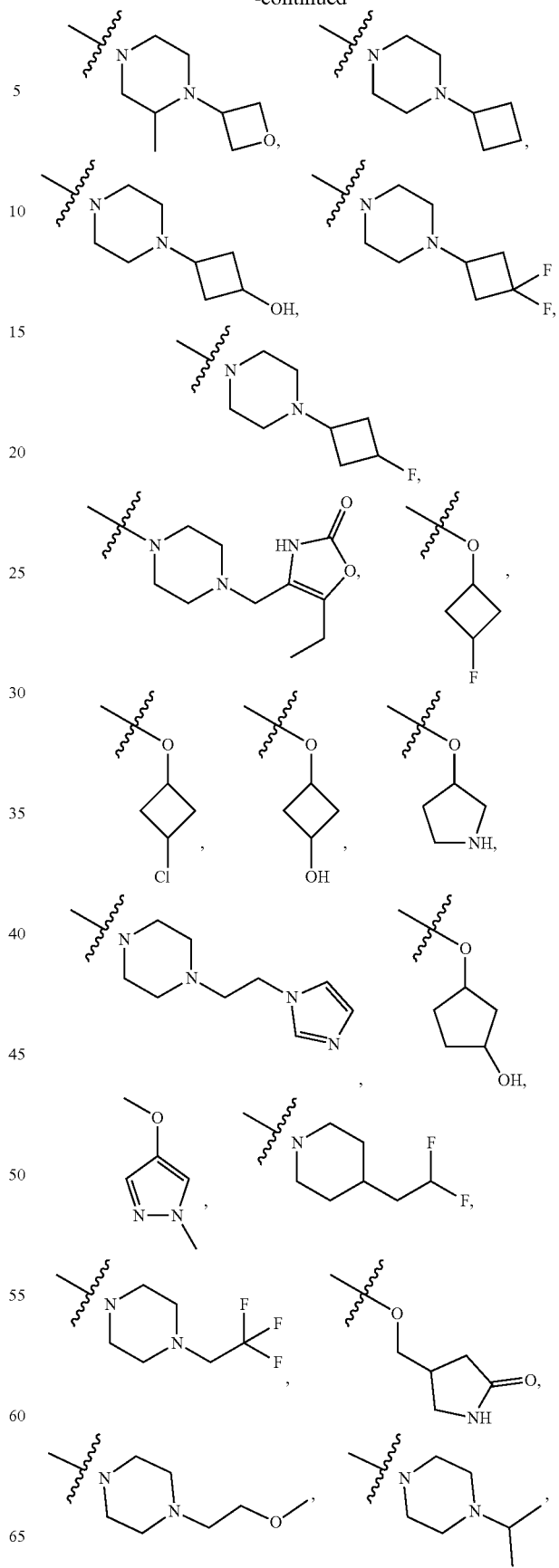

-continued
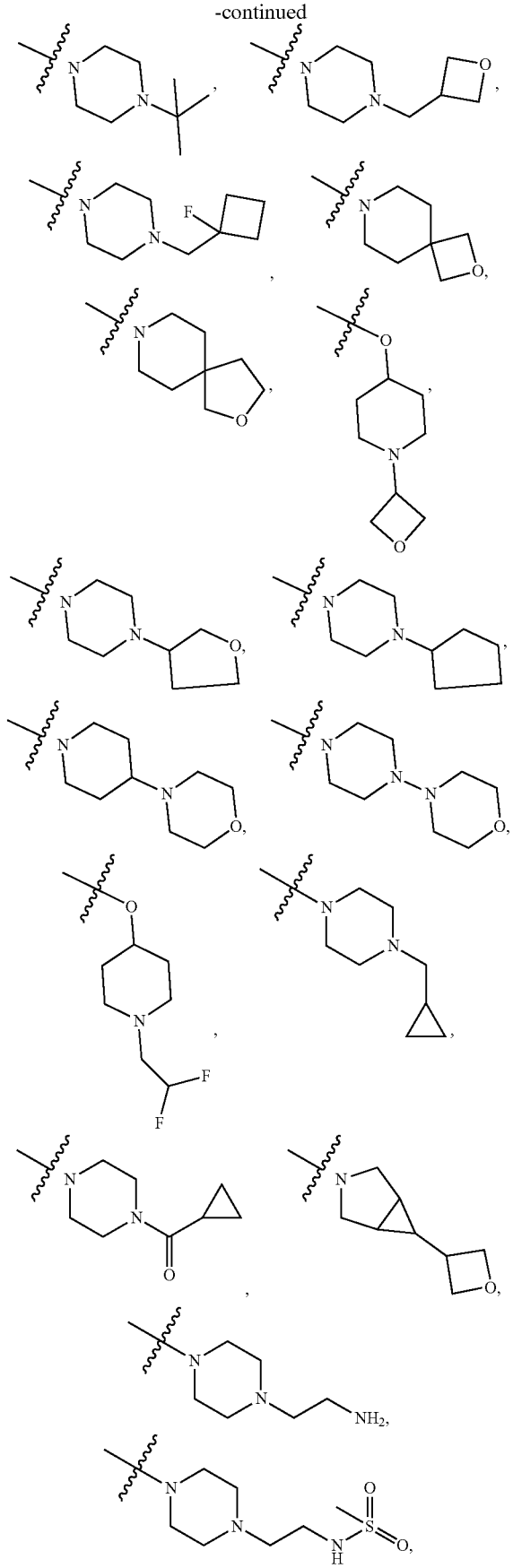
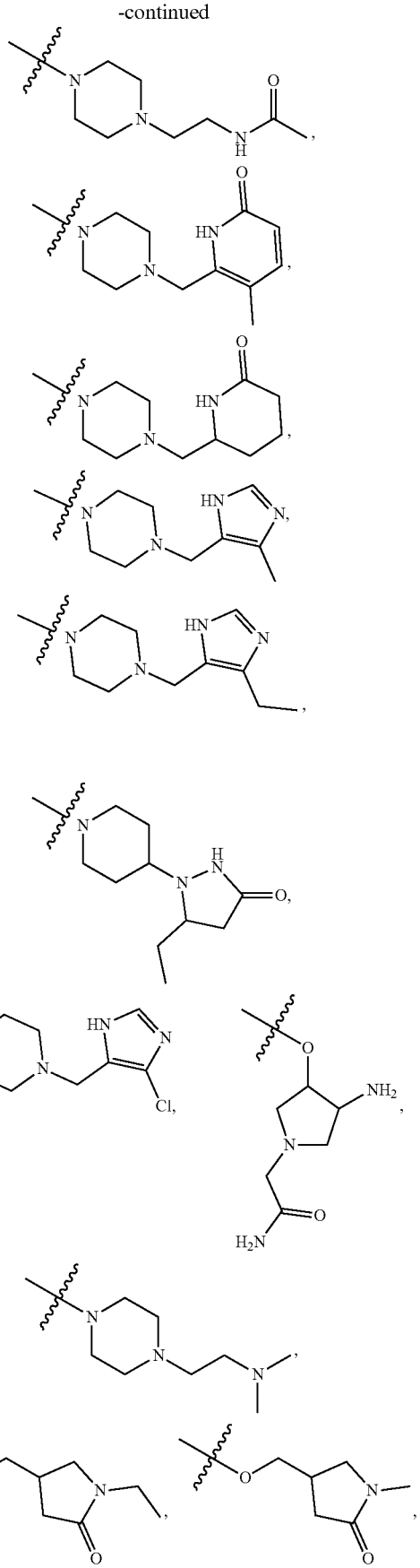

-continued

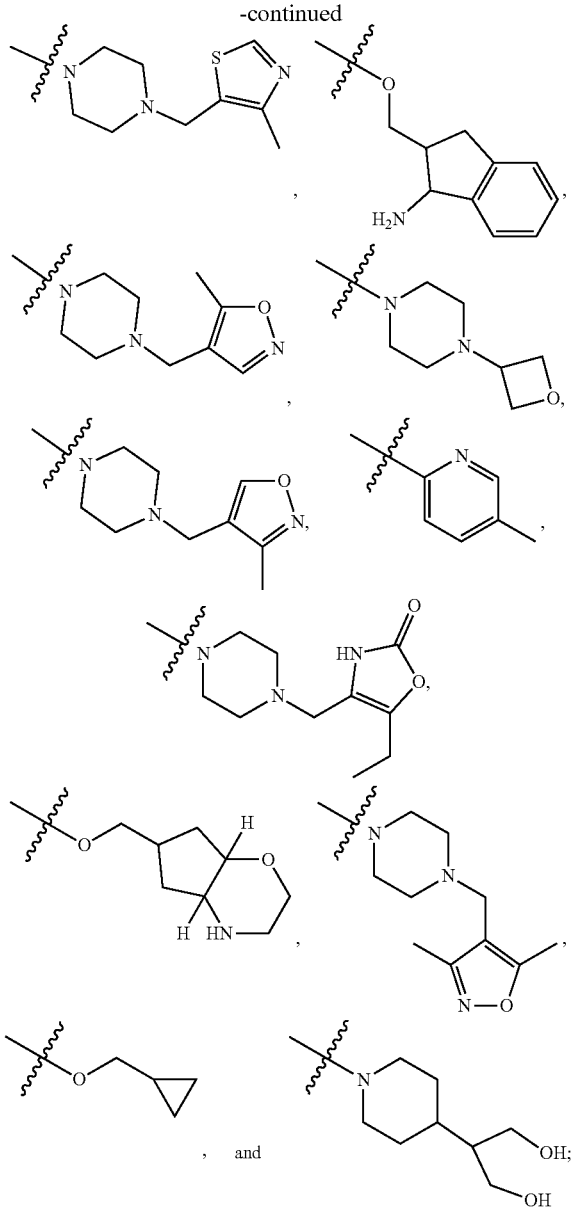

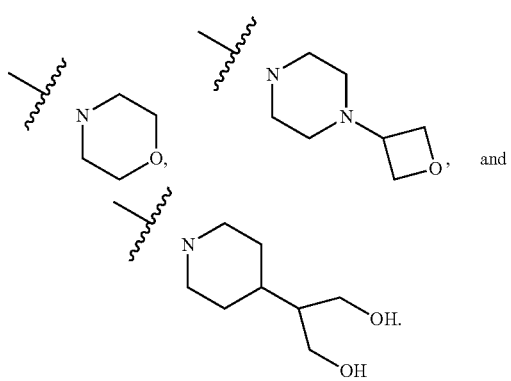

According to some embodiments of the compound of Formula IV or a stereoisomer or pharmaceutically acceptable salt thereof, $R^5$ is

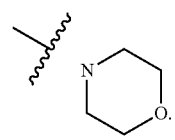

According to some embodiments of the compound of Formula IV or a stereoisomer or pharmaceutically acceptable salt thereof, $R^{16}$ is hydrogen.

According to some embodiments of the compound of Formula IV or a stereoisomer or pharmaceutically acceptable salt thereof, $R^{17}$ is selected from the group consisting of hydrogen, —CH$_2$CH$_2$OH, —CH$_2$CH$_2$CH$_2$OH.

Yet another aspect of the invention includes a compound of Formula V:

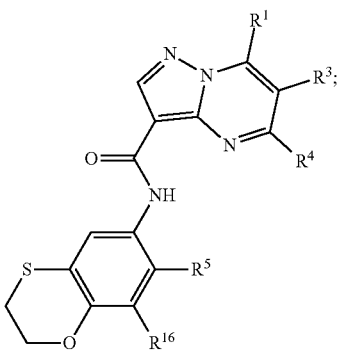

Formula V or a stereoisomer or a pharmaceutically acceptable salt thereof, wherein:

$R^1$ is hydrogen;

$R^3$ is hydrogen, halogen, —OH, or $C_{1-3}$alkyl;

$R^4$ is hydrogen, halogen, —NR$^8$R$^9$, —C(O)NR$^8$R$^9$, or a 3-7 membered monocyclic saturated or partially saturated heterocyclic group optionally substituted with one or more substituents selected from oxo, —NR$^8$R$^9$, or $R^{13}$;

$R^5$ is selected from the group consisting of hydrogen, —NHCH$_3$, —N(CH$_3$)$_2$, —C(CH$_3$)$_2$OH, —OCH$_3$, —OCH(CH$_3$)$_2$, —OC(CH$_3$)$_3$, —OCH$_2$CH$_3$, —OCHF$_2$, —OCH$_2$CF$_3$, —OCH$_2$CHF$_2$, —CH$_2$OCHF$_2$, —CN, —CH$_2$NH$_2$, $R^8$ and $R^9$ are, independently at each occurrence, hydrogen, $C_{1-6}$alkyl optionally substituted with $R^{13}$, —C(O)R$^{13}$, $C_{3-6}$cycloalkyl group, or a 3-7 membered saturated or partially saturated heterocyclic group;

$R^{13}$ is, independently at each occurrence, $C_{1-6}$alkyl, —NH$_2$, or halogen;

$R^{16}$ is hydrogen, or $C_{1-3}$alkyl optionally substituted with —NH$_2$ or —OH; and $R^{17}$ is hydrogen or $C_{1-3}$alkyl optionally substituted with —NH$_2$ or —OH.

According to some embodiments of the compound of Formula IV or a stereoisomer or pharmaceutically acceptable salt thereof, $R^3$ is hydrogen.

According to some embodiments of the compound of Formula IV or a stereoisomer or pharmaceutically acceptable salt thereof, $R^4$ is hydrogen.

According to some embodiments of the compound of Formula IV or a stereoisomer or pharmaceutically acceptable salt thereof, $R^5$ is selected from the group consisting of —N(CH$_3$)$_2$,

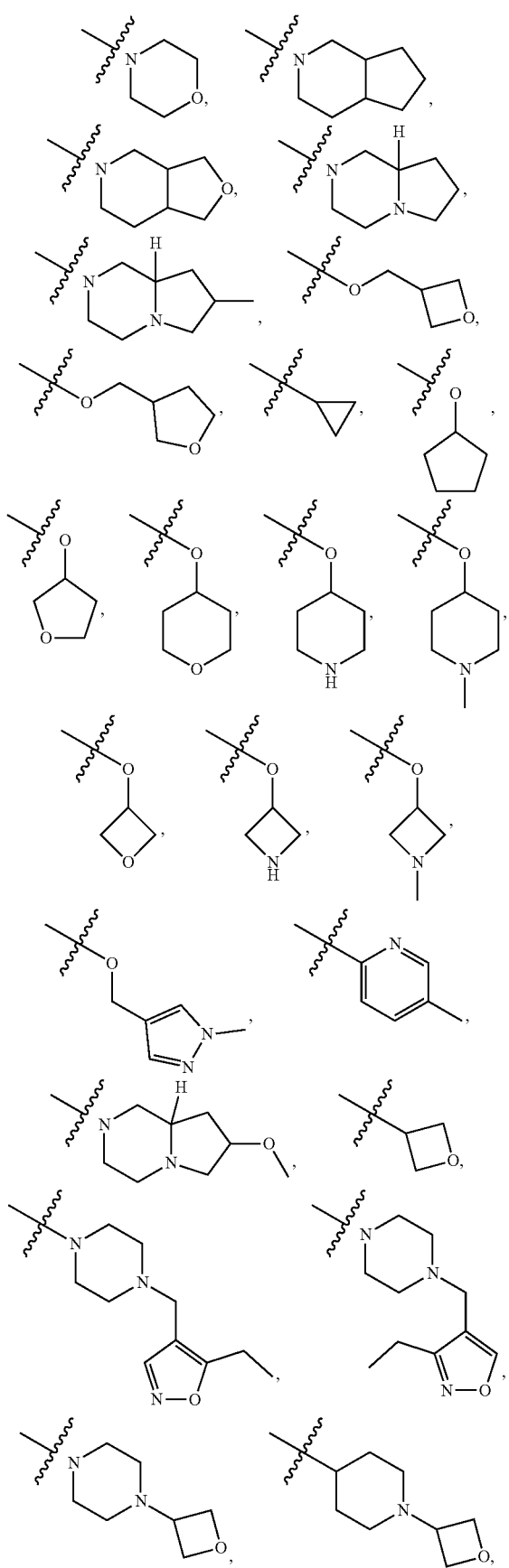
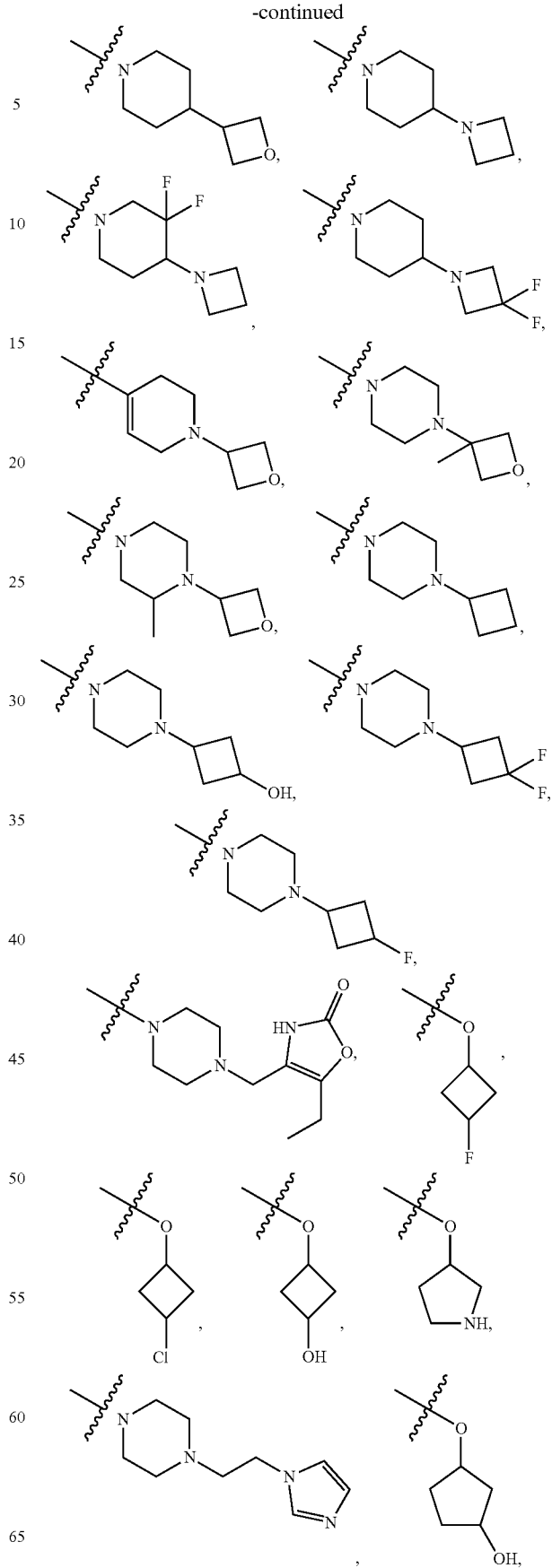

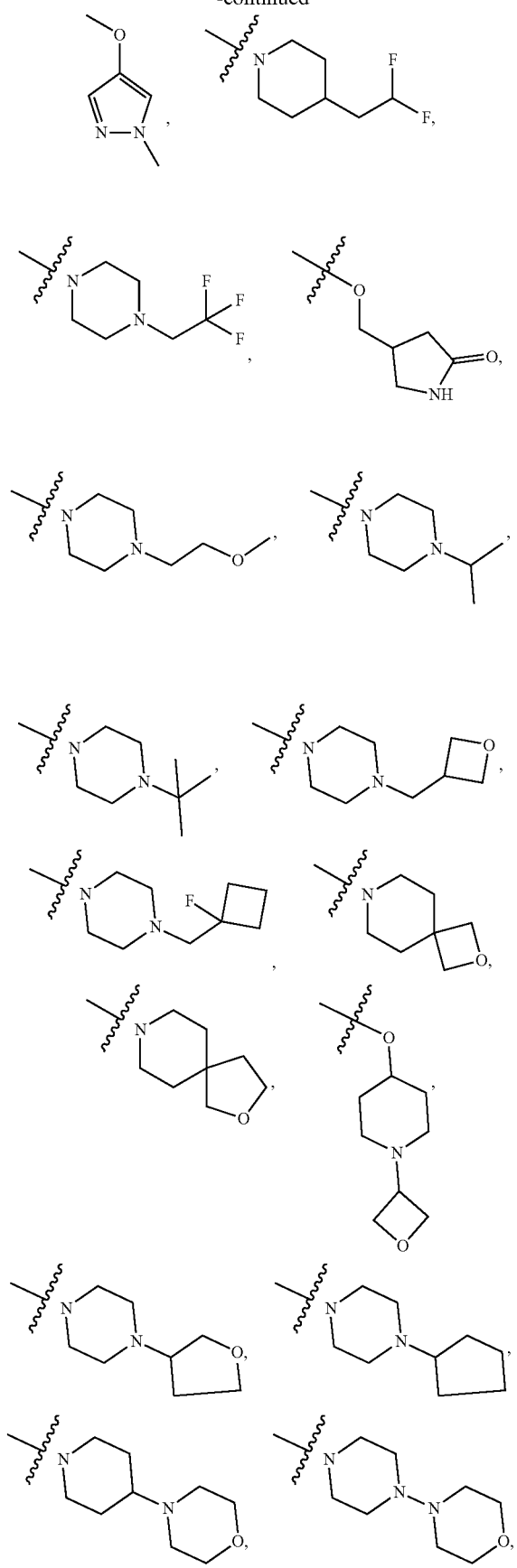
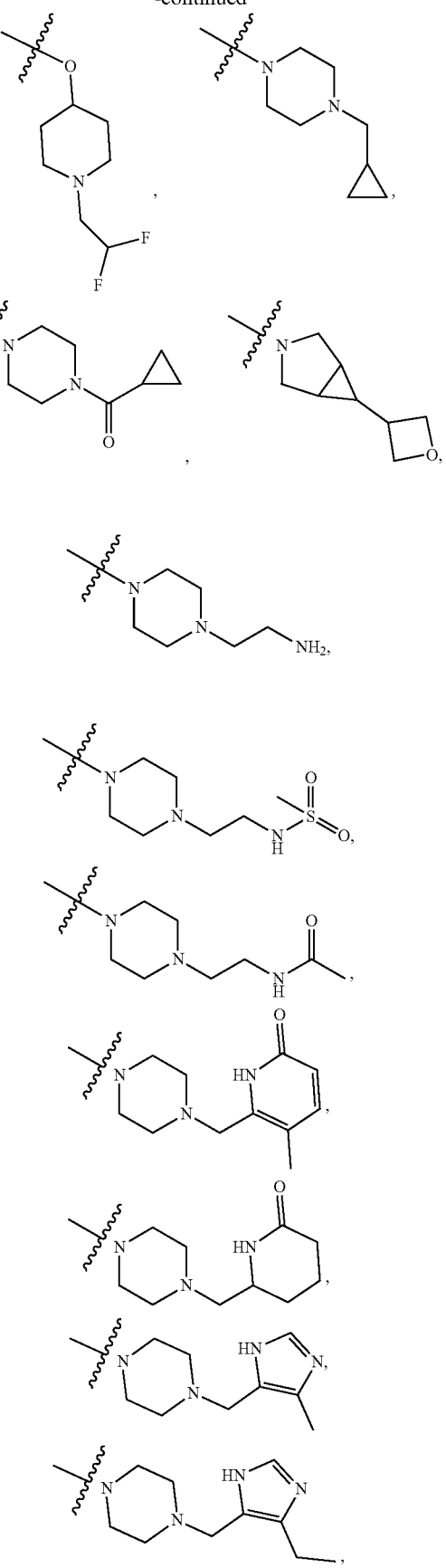

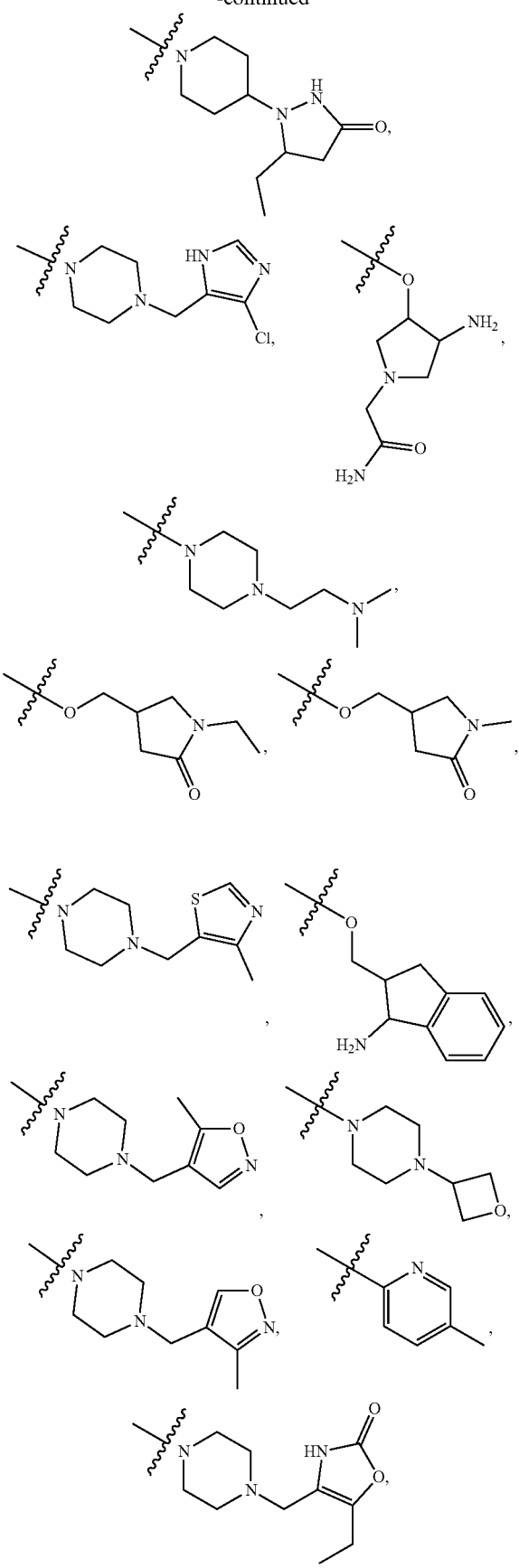

$R^8$ and $R^9$ are, independently at each occurrence, hydrogen, $C_{1-6}$alkyl optionally substituted with $R^{13}$, —C(O)$R^3$, $C_{3-6}$cycloalkyl group, or a 3-7 membered saturated or partially saturated heterocyclic group;

$R^{13}$ is, independently at each occurrence, $C_{1-6}$alkyl, —NH$_2$, or halogen; and $R^{16}$ is hydrogen, or $C_{1-3}$alkyl optionally substituted with —NH$_2$ or —OH.

According to some embodiments of the compound of Formula V or a stereoisomer or pharmaceutically acceptable salt thereof, $R^3$ is hydrogen.

According to some embodiments of the compound of Formula V or a stereoisomer or pharmaceutically acceptable salt thereof, in $R^4$ is hydrogen.

According to some embodiments of the compound of Formula V or a stereoisomer or pharmaceutically acceptable salt thereof, $R^5$ is selected from the group consisting of —N(CH$_3$)$_2$, According to some embodiments of the compound of Formula V or a stereoisomer or pharmaceutically acceptable salt thereof, $R^5$ is According to some embodiments of the compound of Formula V or a stereoisomer or pharmaceutically acceptable salt thereof, $R^{16}$ is hydrogen.

Yet another aspect of the invention includes a compound of Formula VI:

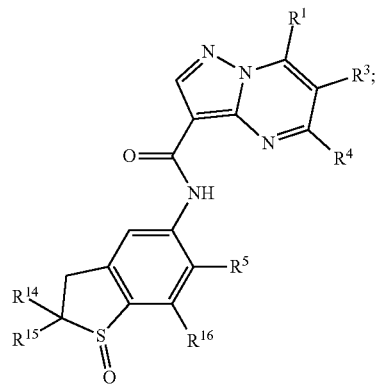

Formula V or a stereoisomer or a pharmaceutically acceptable salt thereof, wherein:

$R^1$ is hydrogen;

$R^3$ is hydrogen, halogen, —OH, or $C_{1-3}$alkyl;

$R^4$ is hydrogen, halogen, —NR$^8$R$^9$, —C(O)NR$^8$R$^9$, or a 3-7 membered monocyclic saturated or partially saturated heterocyclic group optionally substituted with one or more substituents selected from oxo, —NR$^8$R$^9$, or $R^{13}$.

$R^5$ is selected from the group consisting of hydrogen, —NHCH$_3$, —N(CH$_3$)$_2$, —C(CH$_3$)$_2$OH, —OCH$_3$, —OCH(CH$_3$)$_2$, —OC(CH$_3$)$_3$, —OCH$_2$CH$_3$, —OCHF$_2$, —OCH$_2$CF$_3$, —OCH$_2$CHF$_2$, —CH$_2$OCHF$_2$, —CN, —CH$_2$NH$_2$,

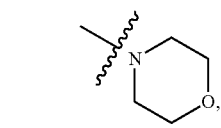
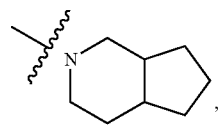

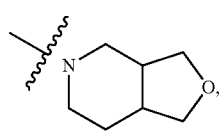
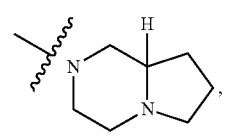

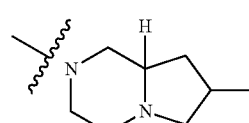
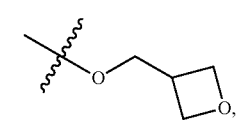

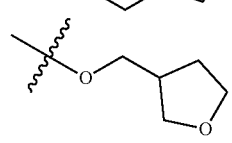
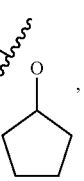

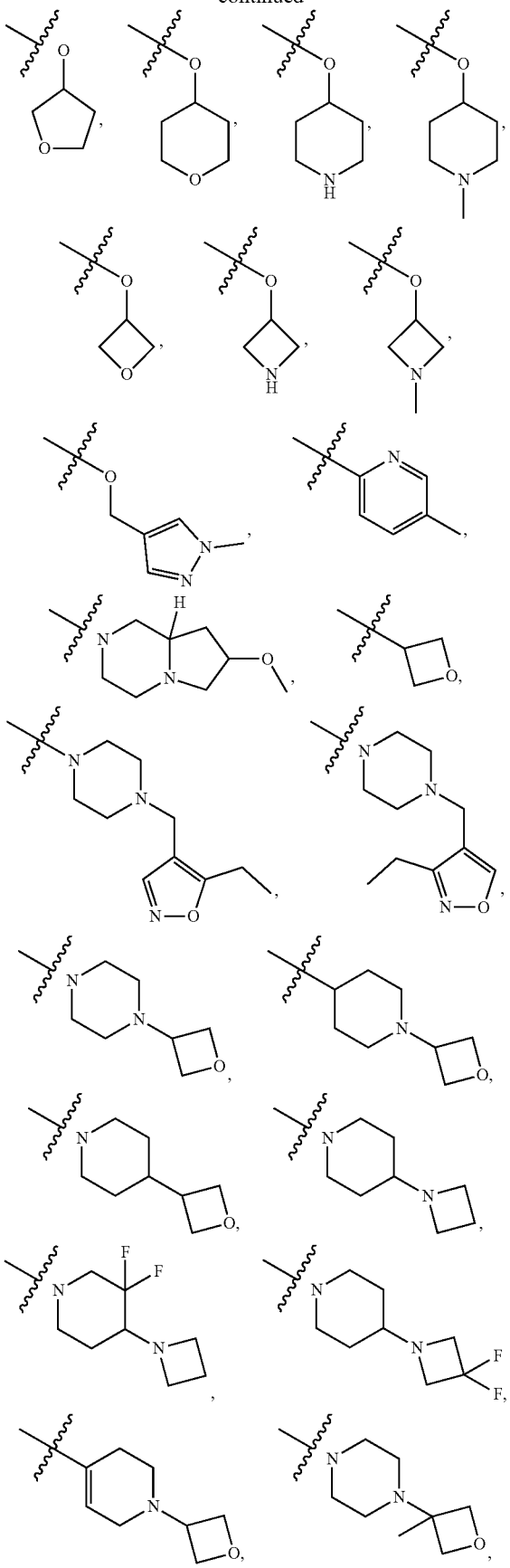

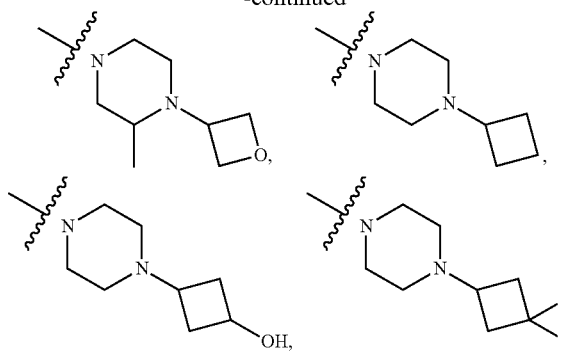
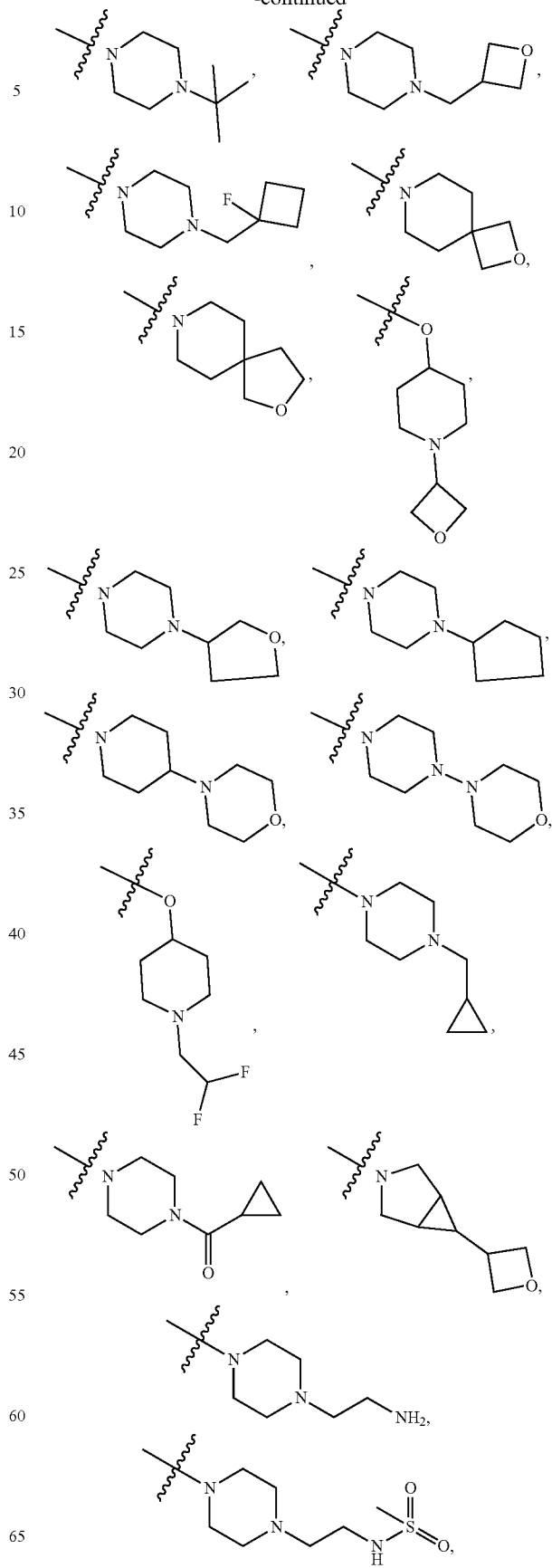

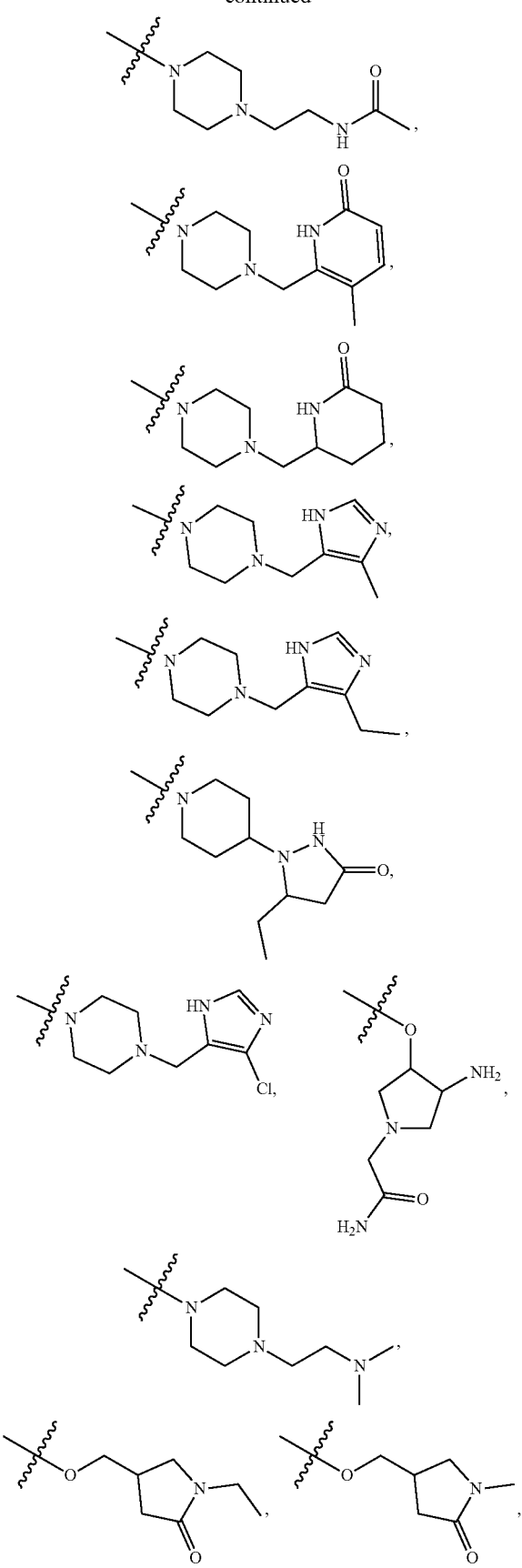
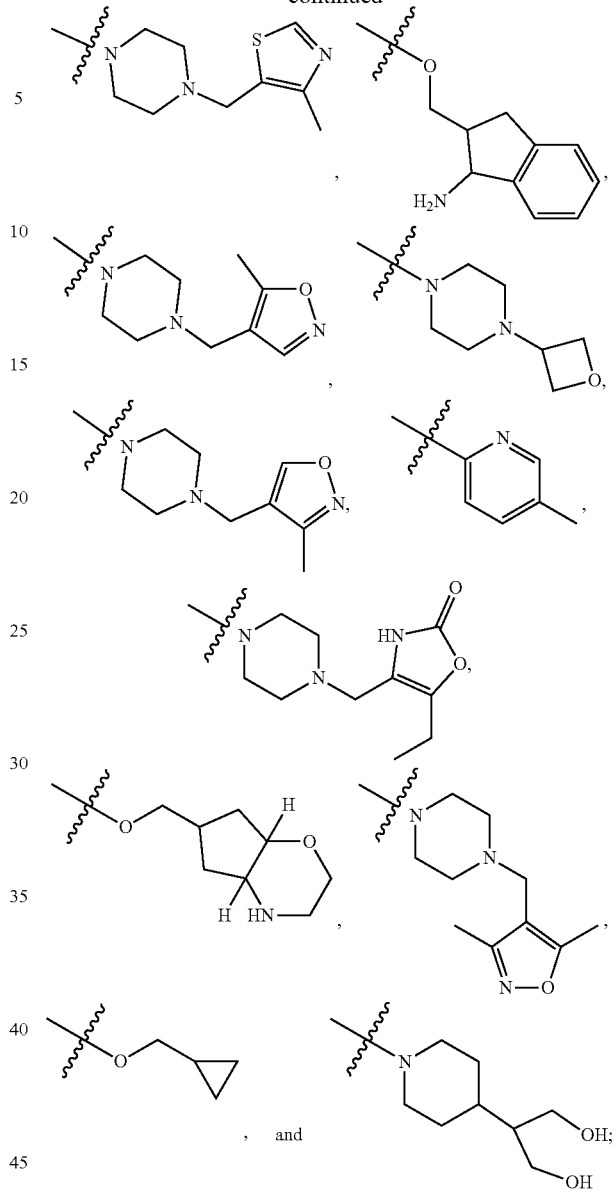

R[8] and R[9] are, independently at each occurrence, hydrogen, $C_{1-6}$alkyl optionally substituted with R[13], —C(O)R[13], $C_{3-6}$cycloalkyl group, or a 3-7 membered saturated or partially saturated heterocyclic group;

R[13] is, independently at each occurrence, $C_{1-6}$alkyl, —NH$_2$, or halogen;

R[14], R[15] are, independently at each occurrence, methyl or —CH$_2$OH, or taken together form a 6-membered, spiro bonded heterocyclic group with the carbon to which they are bonded; and R[16] is hydrogen, or $C_{1-3}$alkyl optionally substituted with —NH$_2$ or —OH.

According to some embodiments of the compound of Formula VI or a stereoisomer or pharmaceutically acceptable salt thereof, R[3] is hydrogen.

According to some embodiments of the compound of Formula VI or a stereoisomer or pharmaceutically acceptable salt thereof, R[4] is hydrogen.

According to some embodiments of the compound of Formula VI or a stereoisomer or pharmaceutically acceptable salt thereof, R⁵ is selected from the group consisting of —N(CH₃)₂,

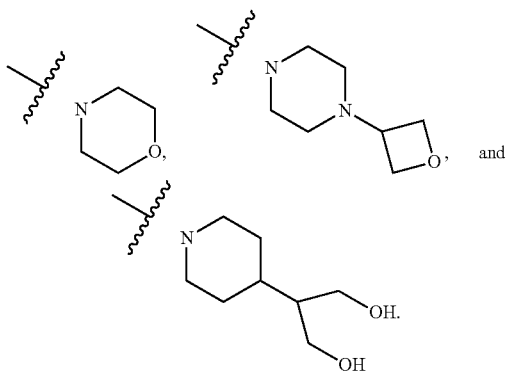

According to some embodiments of the compound of Formula VI or a stereoisomer or pharmaceutically acceptable salt thereof, R⁵ is

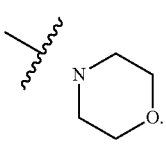

According to some embodiments of the compound of Formula VI or a stereoisomer or pharmaceutically acceptable salt thereof, R¹⁴ and R¹⁵ are methyl.

According to some embodiments of the compound of Formula VI or a stereoisomer or pharmaceutically acceptable salt thereof, R¹⁶ is hydrogen.

Yet another aspect of the invention includes a compound of Formula VII:

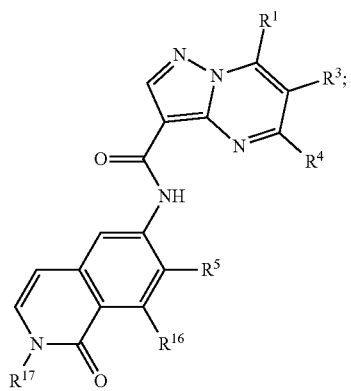

Formula VII or a stereoisomer or a pharmaceutically acceptable salt thereof, wherein:
R¹ is hydrogen;
R³ is hydrogen, halogen, —OH, or C₁₋₃alkyl;
R⁴ is hydrogen, halogen, —NR⁸R⁹, —C(O)NR⁸R⁹, or a 3-7 membered monocyclic saturated or partially saturated heterocyclic group optionally substituted with one or more substituents selected from oxo, —NR⁸R⁹, or R¹³;

R⁵ is selected from the group consisting of hydrogen, —NHCH₃, —N(CH₃)₂, —C(CH₃)₂OH, —OCH₃, —OCH(CH₃)₂, —OC(CH₃)₃, —OCH₂CH₃, —OCHF₂, —OCH₂CF₃, —OCH₂CHF₂, —CH₂OCHF₂, —CN, —CH₂NH₂,

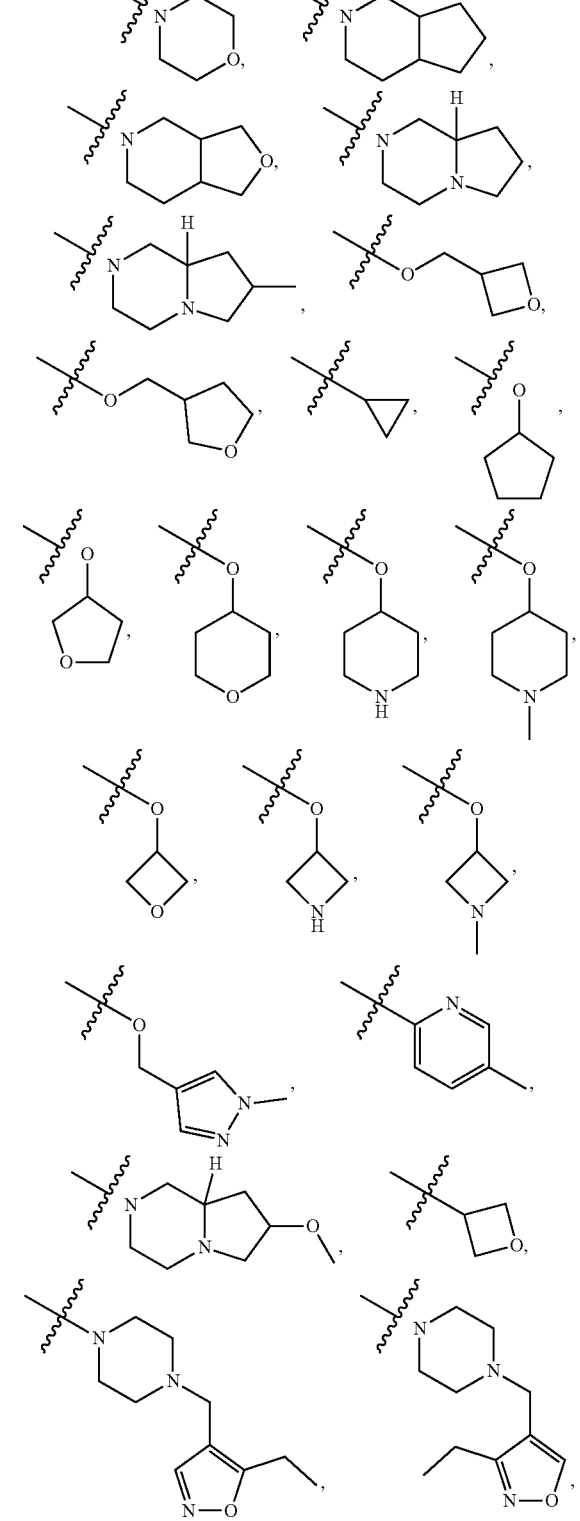

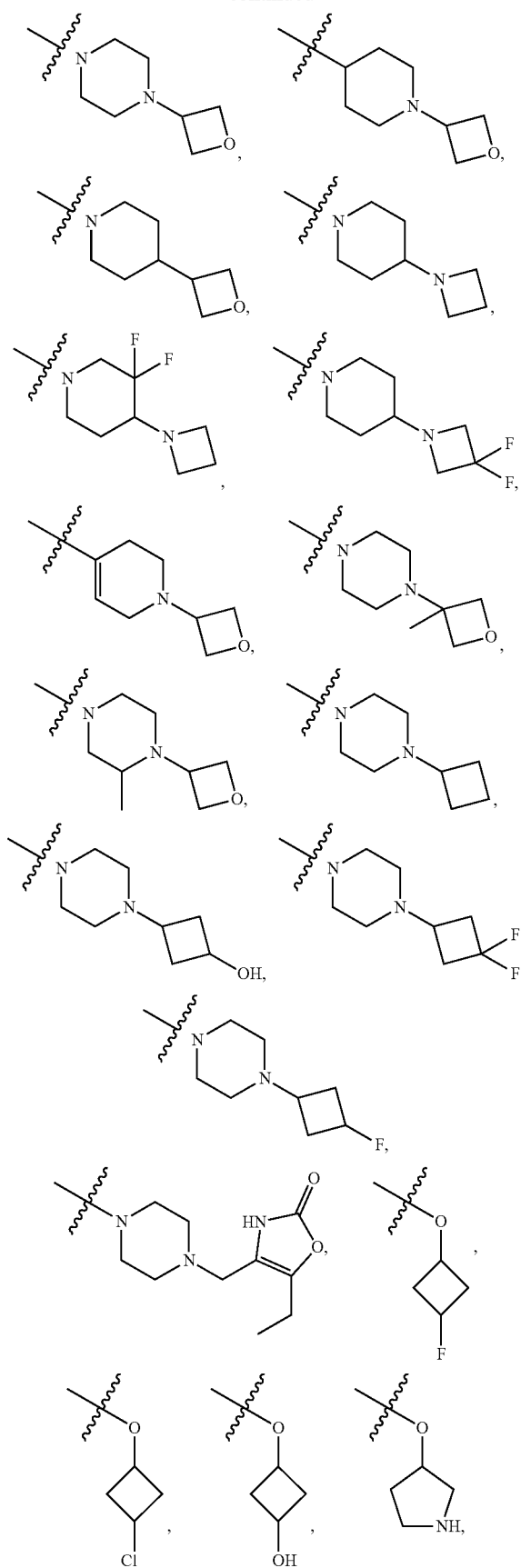
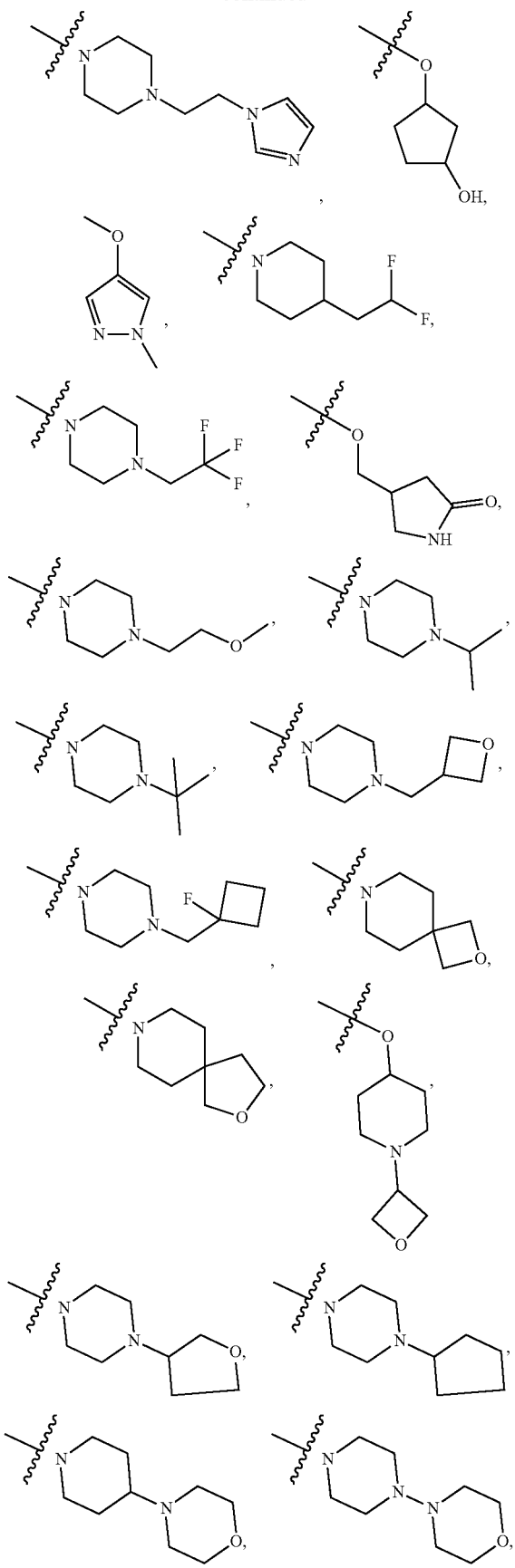

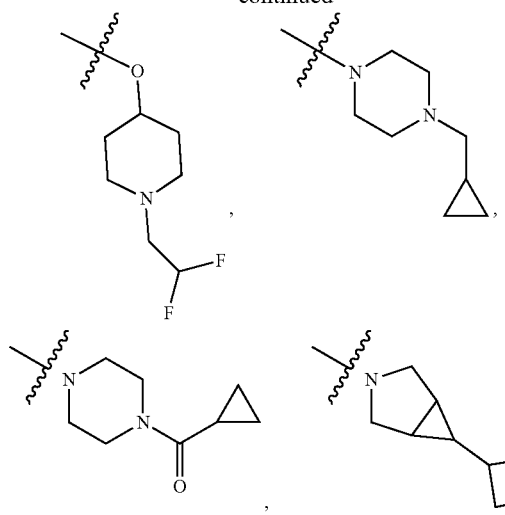
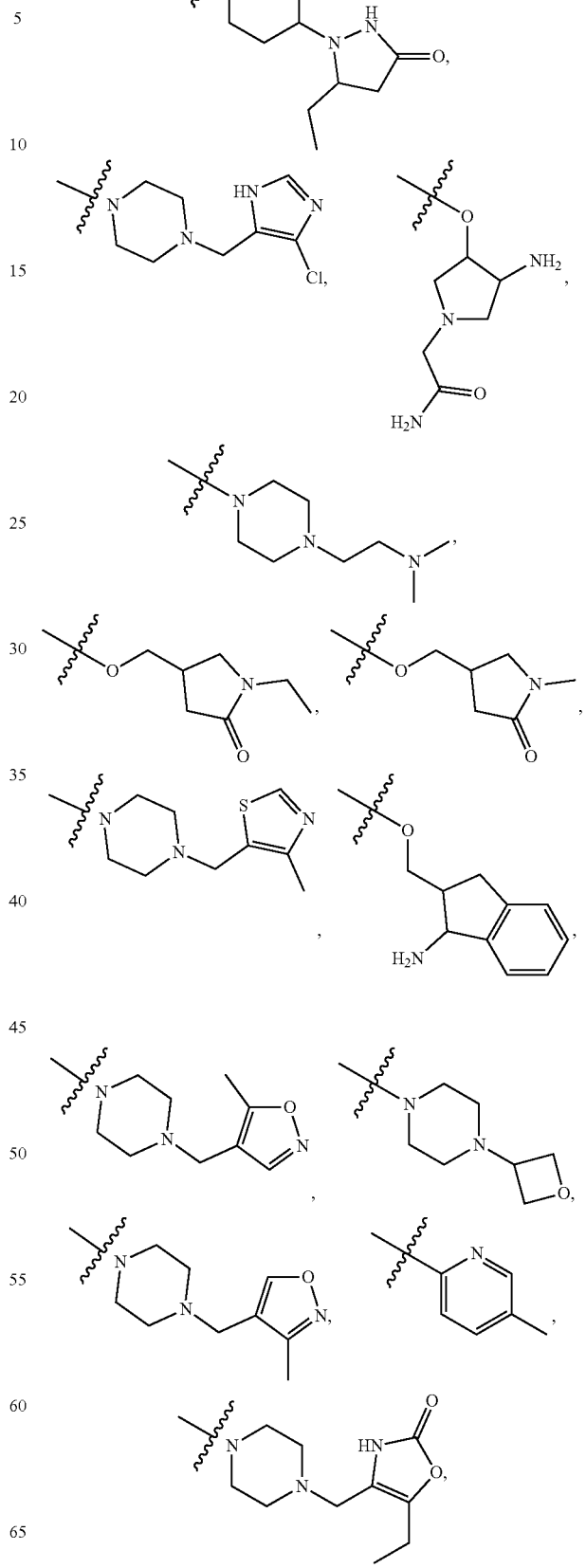

105

-continued

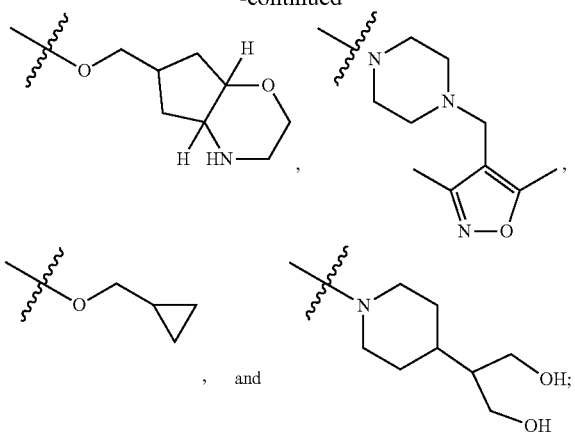

, and $R^8$ and $R^9$ are, independently at each occurrence, hydrogen, $C_{1-6}$alkyl optionally substituted with $R^{13}$, —C(O)$R^{13}$, $C_{3-6}$cycloalkyl group, or a 3-7 membered saturated or partially saturated heterocyclic group;

$R^{13}$ is, independently at each occurrence, $C_{1-6}$alkyl, —NH$_2$, or halogen;

$R^{16}$ is hydrogen, or $C_{1-3}$alkyl optionally substituted with —NH$_2$ or —OH;

$R^{17}$ is $C_{1-3}$alkyl optionally substituted with —NH$_2$ or —OH.

According to some embodiments of the compound of Formula VII or a stereoisomer or pharmaceutically acceptable salt thereof, $R^3$ is hydrogen.

According to some embodiments of the compound of Formula VII or a stereoisomer or pharmaceutically acceptable salt thereof, $R^4$ is hydrogen.

According to some embodiments of the compound of Formula VII or a stereoisomer or pharmaceutically acceptable salt thereof, $R^5$ is selected from the group consisting of —N(CH$_3$)$_2$,

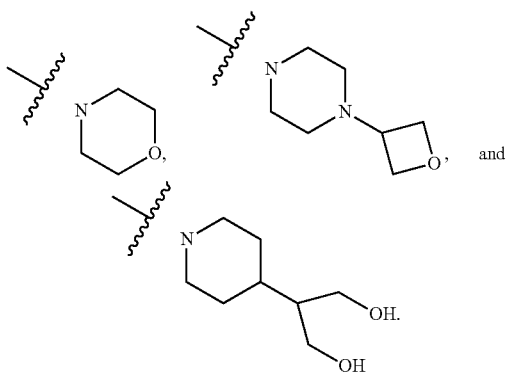

According to some embodiments of the compound of Formula VII or a stereoisomer or pharmaceutically acceptable salt thereof, $R^5$ is

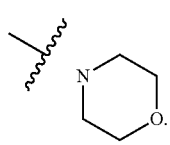

106

According to some embodiments of the compound of Formula VII or a stereoisomer or pharmaceutically acceptable salt thereof, $R^{16}$ is hydrogen.

According to some embodiments of the compound of Formula VII or a stereoisomer or pharmaceutically acceptable salt thereof, $R^{17}$ is methyl.

Yet another aspect of the invention includes a compound of Formula VIII:

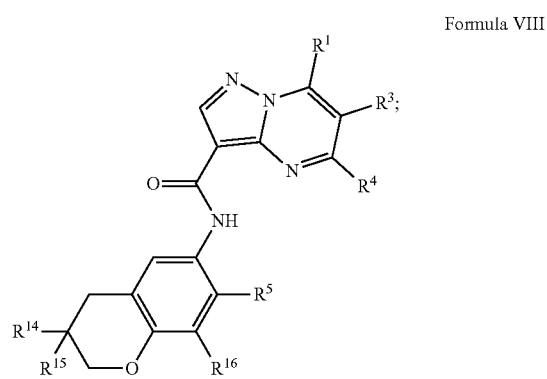

Formula VIII or a stereoisomer or a pharmaceutically acceptable salt thereof, wherein:

$R^1$ is hydrogen;

$R^3$ is hydrogen, halogen, —OH, or $C_{1-3}$alkyl;

$R^4$ is hydrogen, halogen, —NR$^8$R$^9$, —C(O)NR$^8$R$^9$, or a 3-7 membered monocyclic saturated or partially saturated heterocyclic group optionally substituted with one or more substituents selected from oxo, —NR$^8$R$^9$, or $R^{13}$;

$R^5$ is selected from the group consisting of hydrogen, —NHCH$_3$, —N(CH$_3$)$_2$, —C(CH$_3$)$_2$OH, —OCH$_3$, —OCH(CH$_3$)$_2$, —OC(CH$_3$)$_3$, —OCH$_2$CH$_3$, —OCHF$_2$, —OCH$_2$CF$_3$, —OCH$_2$CHF$_2$, —CH$_2$OCHF$_2$, —CN, —CH$_2$NH$_2$,

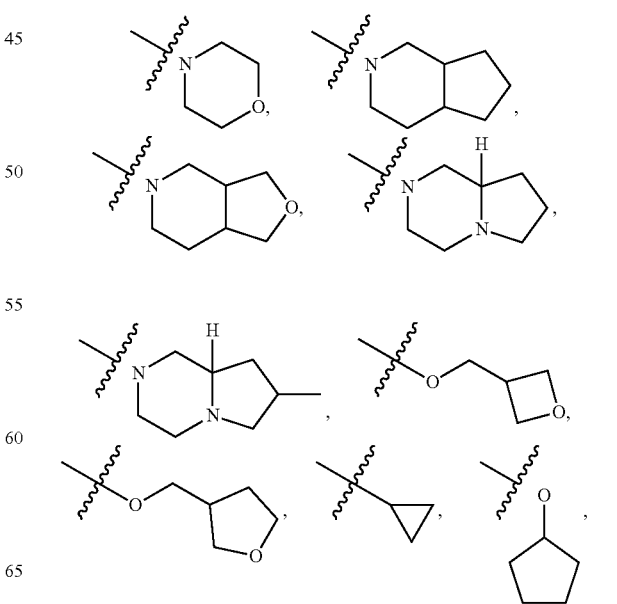

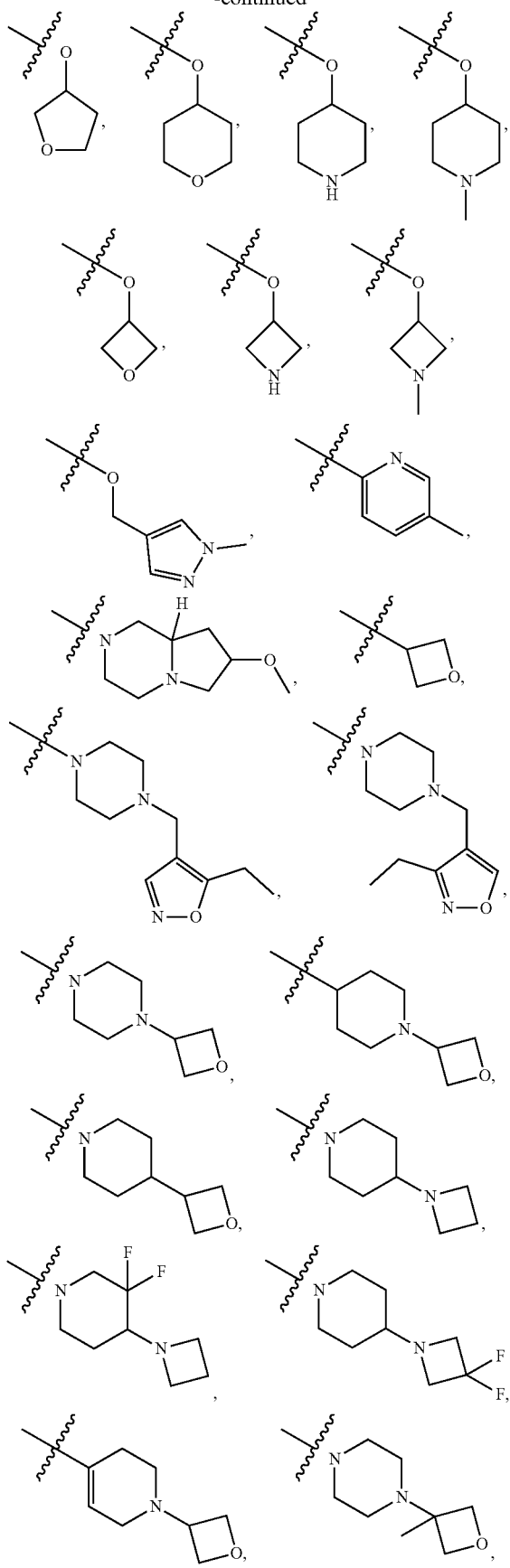
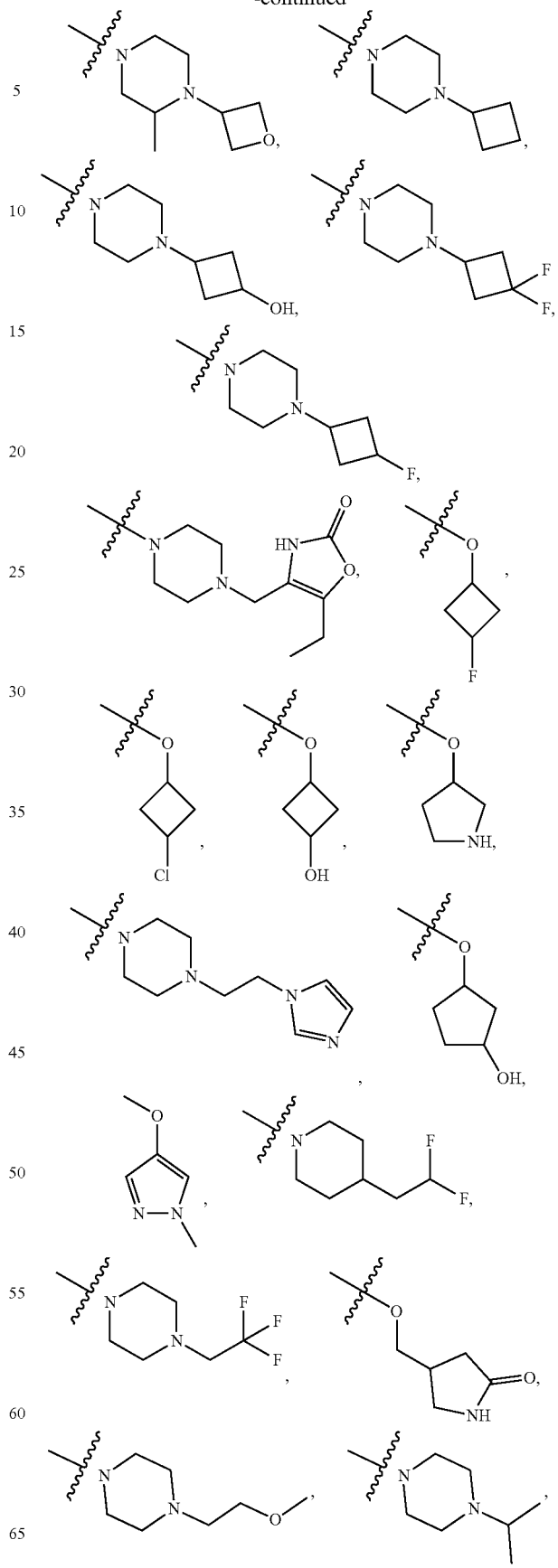

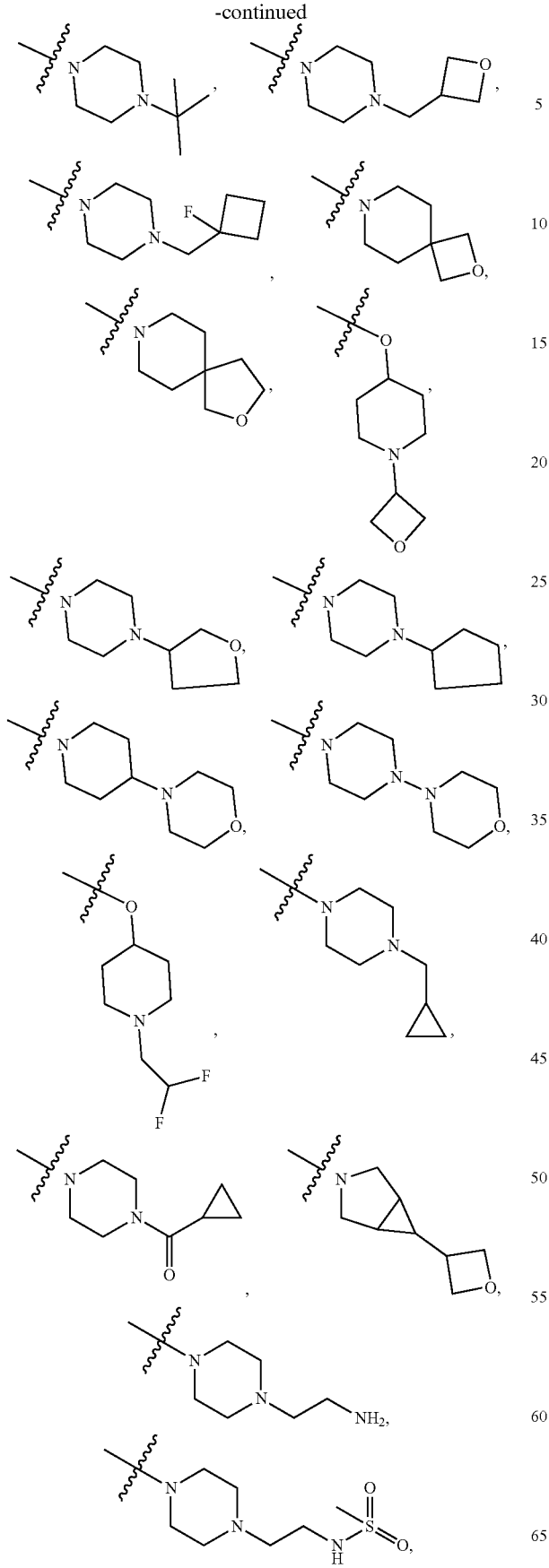
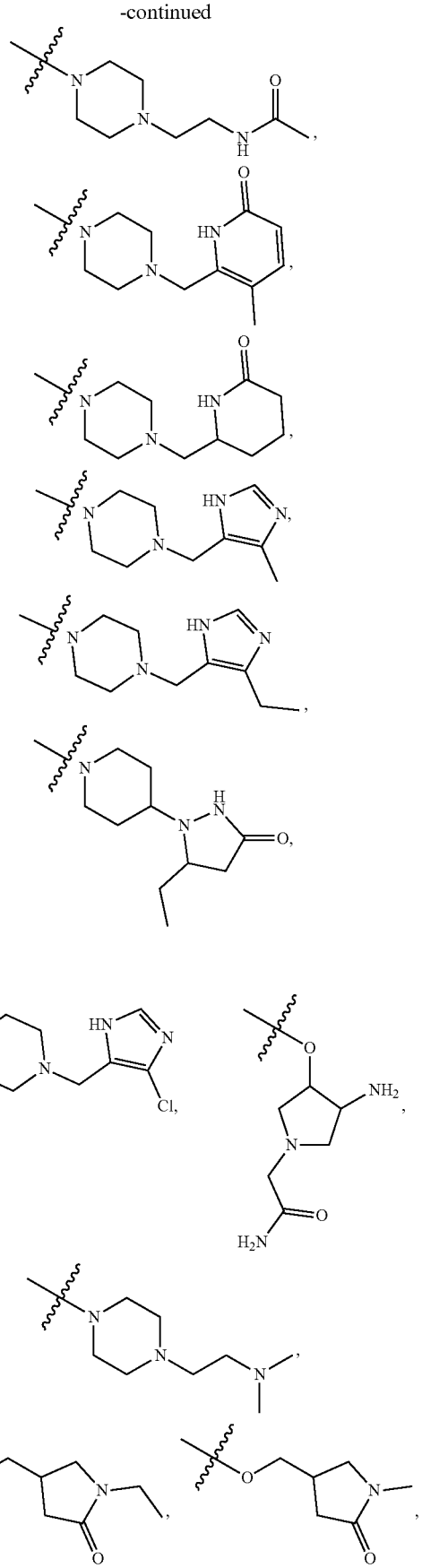

-continued

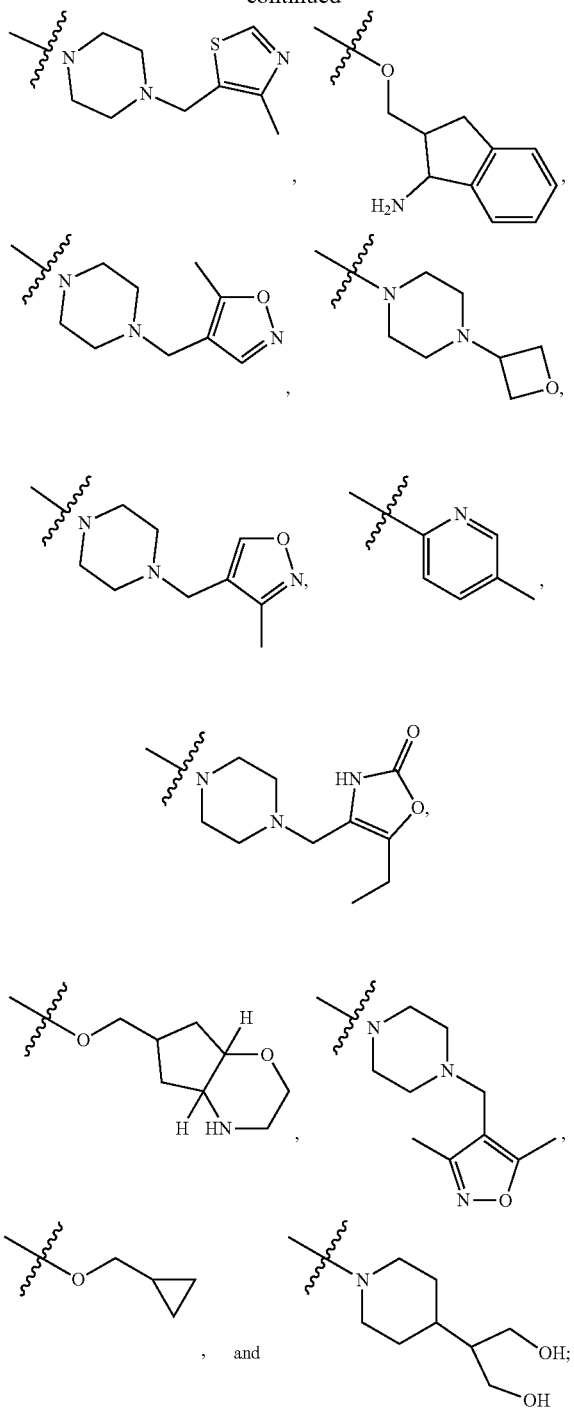

, and

R[8] and R[9] are, independently at each occurrence, hydrogen, $C_{1-6}$alkyl optionally substituted with R[13], —C(O)R[3], $C_{3-6}$cycloalkyl group, or a 3-7 membered saturated or partially saturated heterocyclic group;

R[13] is, independently at each occurrence, $C_{1-6}$alkyl, —NH$_2$, or halogen;

R[14] and R[15] are selected from the group consisting of —OH, —CH$_3$, and —CH$_2$CH$_2$CN; and R[16] is hydrogen, or $C_{1-3}$alkyl optionally substituted with —NH$_2$ or —OH.

According to some embodiments of the compound of Formula VIII or a stereoisomer or pharmaceutically acceptable salt thereof, R[3] is hydrogen.

According to some embodiments of the compound of Formula VIII or a stereoisomer or pharmaceutically acceptable salt thereof, R[4] is hydrogen.

According to some embodiments of the compound of Formula VIII or a stereoisomer or pharmaceutically acceptable salt thereof, R[5] is selected from the group consisting of —N(CH$_3$)$_2$,

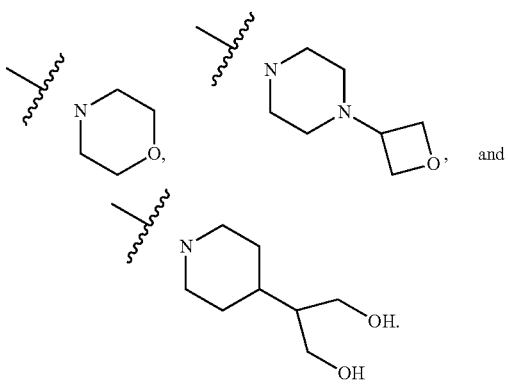

According to some embodiments of the compound of Formula VIII or a stereoisomer or pharmaceutically acceptable salt thereof, R[5] is selected from the group consisting of

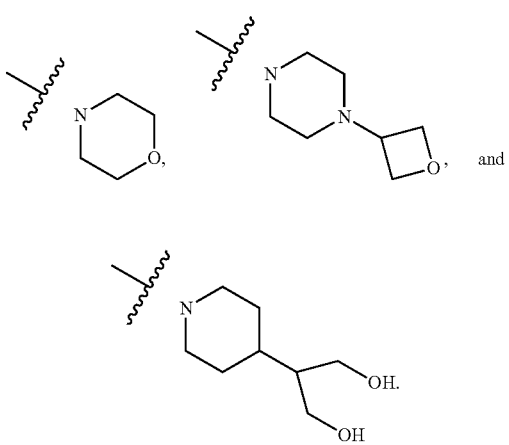

According to some embodiments of the compound of Formula VIII or a stereoisomer or pharmaceutically acceptable salt thereof, R[14] is —CH$_3$ and R[15] is —CH$_2$CH$_2$CN.

According to some embodiments of the compound of Formula VIII or a stereoisomer or pharmaceutically acceptable salt thereof, R[14] is —CH$_3$ and R[15] is —OH.

According to some embodiments of the compound of Formula VIII or a stereoisomer or pharmaceutically acceptable salt thereof, R[16] is hydrogen.

In some embodiments, a compound is selected from the group consisting of the compounds of Tables 1 and 2, shown below, or a stereoisomer or pharmaceutically acceptable salt thereof.

TABLE 1

Exemplary compounds of the present invention. Salts of such compounds are also contemplated.
See the Examples section for preparation of such compounds.

| Example | Structure | Name |
|---|---|---|
| 1 | 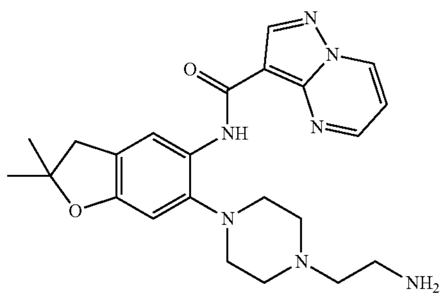 [SMILES: CC1(C)Cc2cc(NC(=O)c3cnn4cccnc34)c(N3CCN(CCN)CC3)cc2O1] | N-[6-[4-(2-aminoethyl)piperazin-1-yl]-2,2-dimethyl-3H-benzofuran-5-yl]pyrazolo[1,5-a]pyrimidine-3-carboxamide |
| 2 | 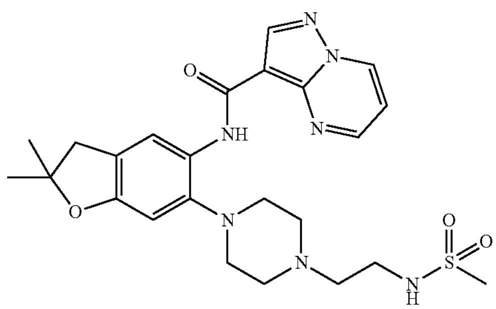 [SMILES: CC1(C)Cc2cc(NC(=O)c3cnn4cccnc34)c(N3CCN(CCNS(C)(=O)=O)CC3)cc2O1] | N-(2,2-Dimethyl-6-(4-(2-(methylsulfonamido)ethyl)piperazin-1-yl)-2,3-dihydrobenzofuran-5-yl)pyrazolo[1,5-a]pyrimidine-3-carboxamide |
| 3 | 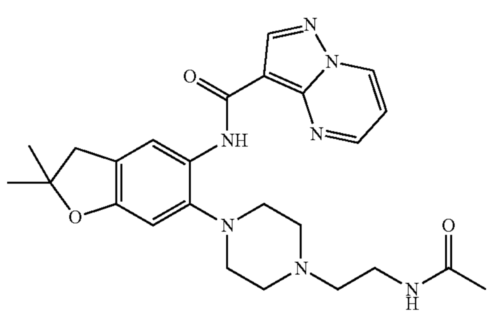 [SMILES: CC(=O)NCCN1CCN(c2cc3c(cc2NC(=O)c2cnn4cccnc24)CC(C)(C)O3)CC1] | N-[6-[4-(2-acetamidoethyl)piperazin-1-yl]-2,2-dimethyl-3H-benzofuran-5-yl]pyrazolo[1,5-a]pyrimidine-3-carboxamide |
| 4 | 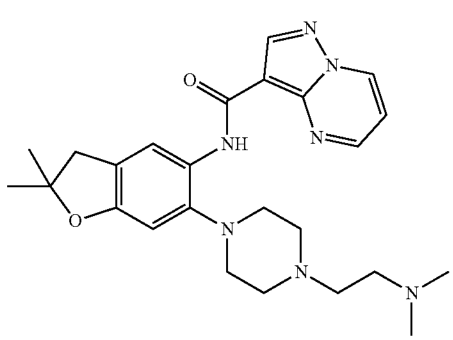 | N-[6-[4-[2-(dimethylamino)ethyl]piperazin-1-yl]-2,2-dimethyl-3H-benzofuran-5-yl]pyrazolo[1,5-a]pyrimidine]-3-carboxamide |

TABLE 1-continued

Exemplary compounds of the present invention. Salts of such compounds are also contemplated.
See the Examples section for preparation of such compounds.

| Example | Structure | Name |
|---|---|---|
| 5 | 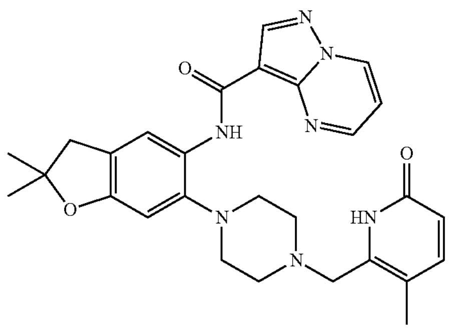 [SMILES: Cc1ccc(=O)[nH]c1CN1CCN(c2cc3c(cc2NC(=O)c2cnn4cccnc24)CC(C)(C)O3)CC1] | N-[2,2-dimethyl-6-[4-[(3-methyl-6-oxo-1H-pyridin-2-yl)methyl]piperazin-1-yl]-3H-benzofuran-5-yl]pyrazolo[1,5-a]pyrimidine-3-carboxamide |
| 6 & 7 | 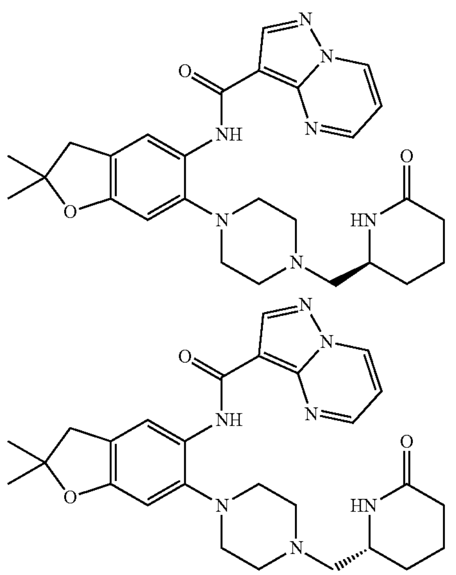 | (S)-N-(2,2-dimethyl-6-(4-((6-oxopiperidin-2-yl)methyl)piperazin-1-yl)-2,3-dihydrobenzofuran-5-yl)pyrazolo[1,5-a]pyrimidine-3-carboxamide & (R)-N-(2,2-dimethyl-6-(4-((6-oxopiperidin-2-yl)methyl)piperazin-1-yl)-2,3-dihydrobenzofuran-5-yl)pyrazolo[1,5-a]pyrimidine-3-carboxamide (absolute stereochemistry assigned arbitrarily) |
| 8 | 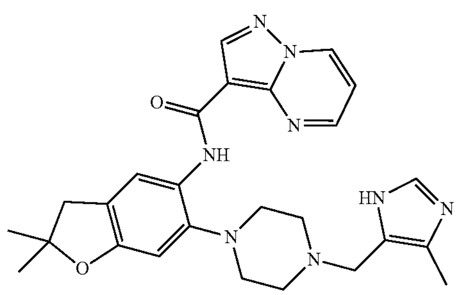 | N-[2,2-dimethyl-6-[4-[(4-methyl-1H-imidazol-5-yl)methyl]piperazin-1-yl]-3H-benzofuran-5-yl]pyrazolo[1,5-a]pyrimidine-3-carboxamide |
| 9 | 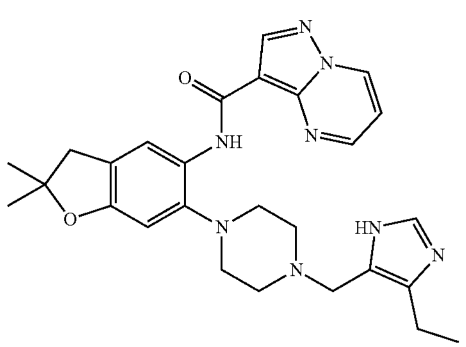 [SMILES: CCc1nc[nH]c1CN1CCN(c2cc3c(cc2NC(=O)c2cnn4cccnc24)CC(C)(C)O3)CC1] | N-[6-[4-[(4-ethyl-1H-imidazol-5-yl)methyl]piperazin-1-yl]-2,2-dimethyl-3H-benzofuran-5-yl]pyrazolo[1,5-a]pyrimidine-3 carboxamide |

TABLE 1-continued

Exemplary compounds of the present invention. Salts of such compounds are also contemplated.
See the Examples section for preparation of such compounds.

| Example | Structure | Name |
|---|---|---|
| 10 | 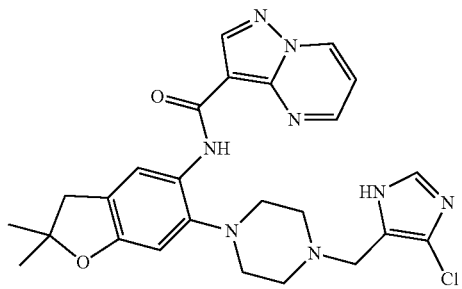 [SMILES: CC1(C)Cc2cc(NC(=O)c3cnn4cccnc34)c(N3CCN(Cc4[nH]cnc4Cl)CC3)cc2O1] | N-(6-(4-((4-Chloro-1H-imidazol-5-yl)methyl)piperazin-1-yl)-2,2-dimethyl-2,3-dihydrobenzofuran-5-yl)pyrazolo[1,5-a]pyrimidine-3 carboxamide |
| 11 | 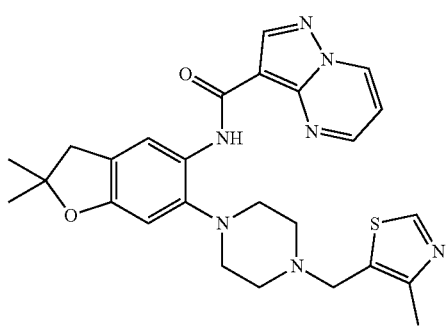 [SMILES: Cc1ncsc1CN1CCN(c2cc3c(cc2NC(=O)c2cnn4cccnc24)CC(C)(C)O3)CC1] | N-(2,2-Dimethyl-6-(4-((4-methylthiazol-5-yl)methyl)piperazin-1-yl)-2,3-dihydrobenzofuran-5-yl)pyrazolo[1,5-a]pyrimidine-3-carboxamide |
| 12 | 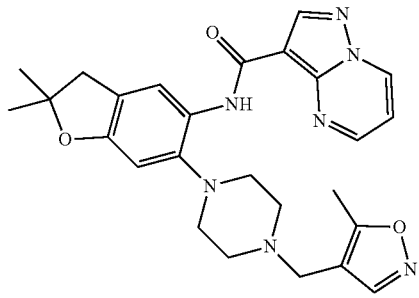 [SMILES: Cc1oncc1CN1CCN(c2cc3c(cc2NC(=O)c2cnn4cccnc24)CC(C)(C)O3)CC1] | N-(2,2-Dimethyl-6-(4-((5-methylisoxazol-4-yl)methyl)piperazin-1-yl)-2,3-dihydrobenzofuran-5-yl)pyrazolo[1,5-a]pyrimidine-3-carboxamide |
| 13 | 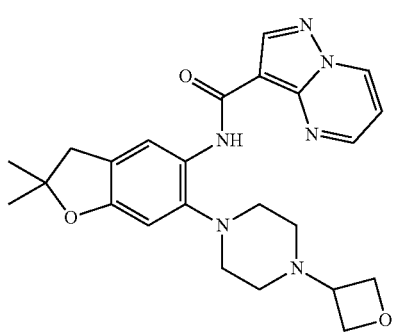 [SMILES: CC1(C)Cc2cc(NC(=O)c3cnn4cccnc34)c(N3CCN(C4COC4)CC3)cc2O1] | N-(2,2-Dimethyl-6-(4-(oxetan-3-yl)piperazin-1-yl)-2,3-dihydrobenzofuran-5-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 14 | 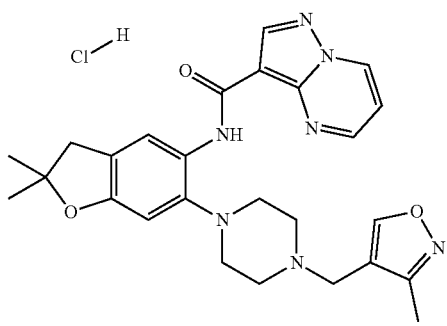 [SMILES: Cc1nocc1CN1CCN(c2cc3c(cc2NC(=O)c2cnn4cccnc24)CC(C)(C)O3)CC1 ; Cl] | N-(2,2-Dimethyl-6-(4-((3-methylisoxazol-4-yl)methyl)piperazin-1-yl)-2,3-dihydrobenzofuran-5-yl)pyrazolo[1,5-a]pyrimidine-3-carboxamide hydrochloride |
| 15 | 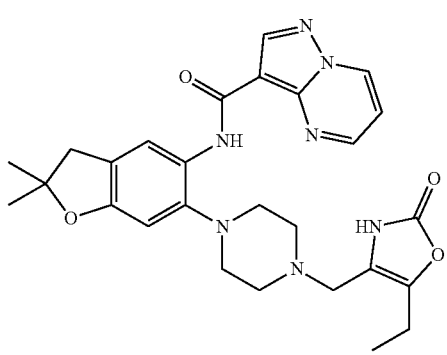 [SMILES: CCc1oc(=O)[nH]c1CN1CCN(c2cc3c(cc2NC(=O)c2cnn4cccnc24)CC(C)(C)O3)CC1] | N-(6-(4-((5-Ethyl-2-oxo-2,3-dihydrooxazol-4-yl)methyl)piperazin-1-yl)-2,2-dimethyl-2,3-dihydrobenzofuran-5-yl)pyrazolo[1,5-a]pyrimidine-3-carboxamide |
| 16 | 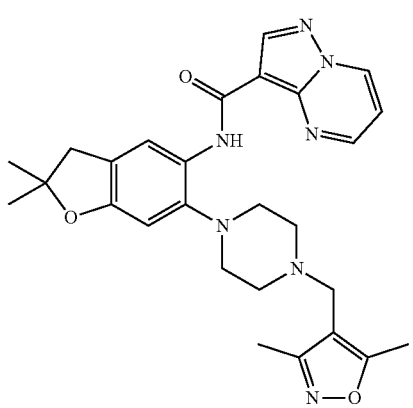 | N-(6-(4-((3,5-Dimethylisoxazol-4-yl)methyl)piperazin-1-yl)-2,2-dimethyl-2,3-dihydrobenzofuran-5-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 17 & 18 | 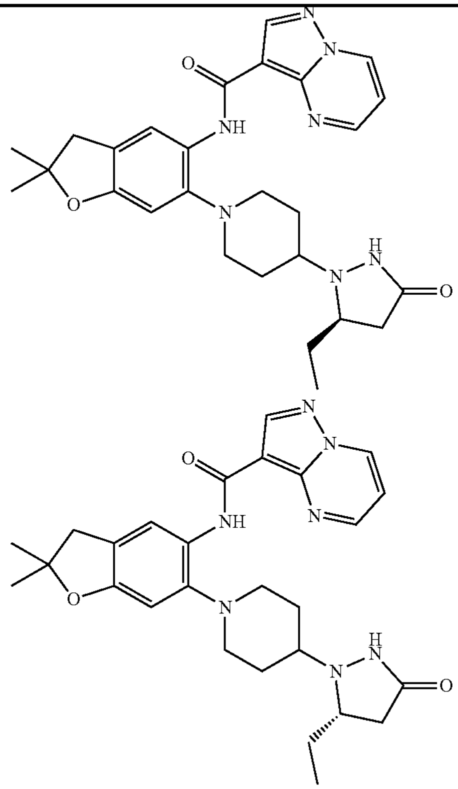 | (R)-N-(6-(4-(5-Ethyl-3-oxopyrazolidin-1-yl)piperidin-1-yl)-2,2-dimethyl-2,3-dihydrobenzofuran-5-yl)pyrazolo[1,5-a]pyrimidine-3-carboxamide and (S)-N-(6-(4-(5-Ethyl-3-oxopyrazolidin-1-yl)piperidin-1-yl)-2,2-dimethyl-2,3-dihydrobenzofuran-5-yl)pyrazolo[1,5-a]pyrimidine-3-carboxamide (absolute stereochemistry assigned arbitrarily) |
| 19 & 20 | 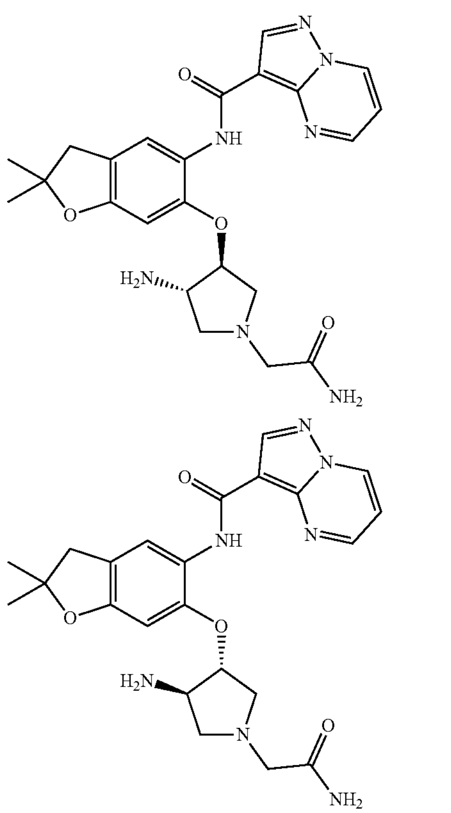 | N-(6-(((3S,4S)-4-Amino-1-(2-amino-2-oxoethyl)pyrrolidin-3-yl)oxy)-2,2-dimethyl-2,3-dihydrobenzofuran-5-yl)pyrazolo[1,5-a]pyrimidine-3-carboxamide & N-(6-(((3R,4R)-4-Amino-1-(2-amino-2-oxoethyl)pyrrolidin-3-yl)oxy)-2,2-dimethyl-2,3-dihydrobenzofuran-5-yl)pyrazolo[1,5-a]pyrimidine-3-carboxamide (absolute stereochemistry assigned arbitrarily) |

TABLE 1-continued

Exemplary compounds of the present invention. Salts of such compounds are also contemplated.
See the Examples section for preparation of such compounds.

| Example | Structure | Name |
|---|---|---|
| 21 | 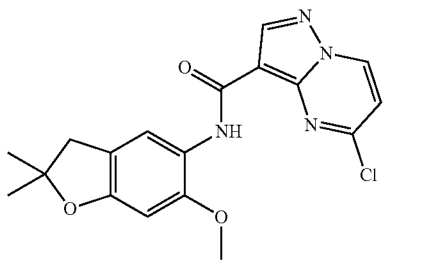 [SMILES: COc1cc2c(cc1NC(=O)c1cnn3ccc(Cl)nc13)CC(C)(C)O2] | 5-Chloro-N-(6-methoxy-2,2-dimethyl-2,3-dihydrobenzofuran-5-yl)pyrazolo[1,5-a]pyrimidine-3-carboxamide |
| 22 & 23 | | (R)-N-(6-((1-Ethyl-5-oxopyrrolidin-3-yl)methoxy)-2,2-dimethyl-2,3-dihydrobenzofuran-5-yl)pyrazolo[1,5-a]pyrimidine-3-carboxamide & (S)-N-(6-((1-Ethyl-5-oxopyrrolidin-3-yl)methoxy)-2,2-dimethyl-2,3-dihydrobenzofuran-5-yl)pyrazolo[1,5-a]pyrimidine-3-carboxamide (absolute stereochemistry assigned arbitrarily) |
| 24 & 25 | | (R)-N-(2,2-Dimethyl-6-((1-methyl-5-oxopyrrolidin-3-yl)methoxy)-2,3-dihydrobenzofuran-5-yl)pyrazolo[1,5-a]pyrimidine-3-carboxamide & (S)-N-(2,2-Dimethyl-6-((1-methyl-5-oxopyrrolidin-3-yl)methoxy)-2,3-dihydrobenzofuran-5-yl)pyrazolo[1,5-a]pyrimidine-3-carboxamide (absolute stereochemistry assigned arbitrarily) |

125 126

TABLE 1-continued

Exemplary compounds of the present invention. Salts of such compounds are also contemplated.
See the Examples section for preparation of such compounds.

| Example | Structure | Name |
|---|---|---|
| 26 & 27 & 28 & 29 | 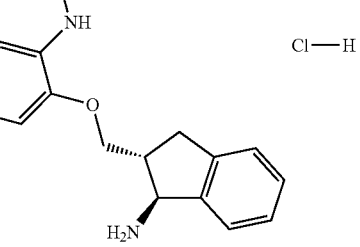 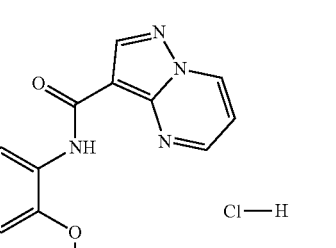 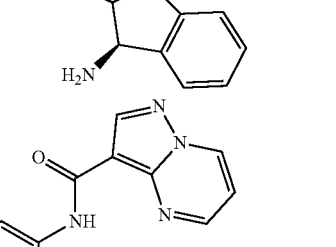 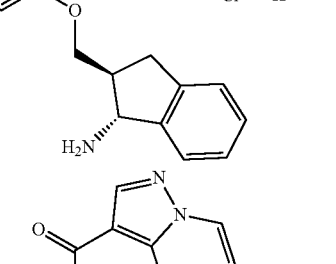 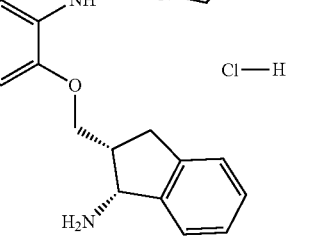 | N-[6-[[(1S,2R)-1-Aminoindan-2-yl]methoxy]-2,2-dimethyl-3H-benzofuran-5-yl]pyrazolo[1,5-a]pyrimidine-3-carboxamide & N-[6-[[(1S,2S)-1-Aminoindan-2-yl]methoxy]-2,2-dimethyl-3H-benzofuran-5-yl]pyrazolo[1,5-a]pyrimidine-3-carboxamide & N-[6-[[(1R,2S)-1-Aminoindan-2-yl]methoxy]-2,2-dimethyl-3H-benzofuran-5-yl]pyrazolo[1,5-a]pyrimidine-3-carboxamide & N-[6-[[(1R,2R)-1-Aminoindan-2-yl]methoxy]-2,2-dimethyl-3H-benzofuran-5-yl]pyrazolo[1,5-a]pyrimidine-3-carboxamide (absolute stereochemistry assigned arbitrarily) |

TABLE 1-continued

Exemplary compounds of the present invention. Salts of such compounds are also contemplated.
See the Examples section for preparation of such compounds.

| Example | Structure | Name |
|---|---|---|
| 30 & 31 & 32 & 33 | | N-(2,2-Dimethyl-6-(((4aS,6S,7aS)-octahydrocyclopenta[b][1,4]oxazin-6-yl)methoxy)-2,3-dihydrobenzofuran-5-yl)pyrazolo[1,5-a]pyrimidine-3-carboxamide & N-(2,2-Dimethyl-6-(((4aS,6R,7aS)-octahydrocyclopenta[b][1,4]oxazin-6-yl)methoxy)-2,3-dihydrobenzofuran-5-yl)pyrazolo[1,5-a]pyrimidine-3-carboxamide & N-(2,2-Dimethyl-6-(((4aR,6R,7aR)-octahydrocyclopenta[b][1,4]oxazin-6-yl)methoxy)-2,3-dihydrobenzofuran-5-yl)pyrazolo[1,5-a]pyrimidine-3-carboxamide & N-(2,2-Dimethyl-6-(((4aR,6S,7aR)-octahydrocyclopenta[b][1,4]oxazin-6-yl)methoxy)-2,3-dihydrobenzofuran-5-yl)pyrazolo[1,5-a]pyrimidine-3-carboxamide (absolute stereochemistry assigned arbitrarily) |
| 34 | 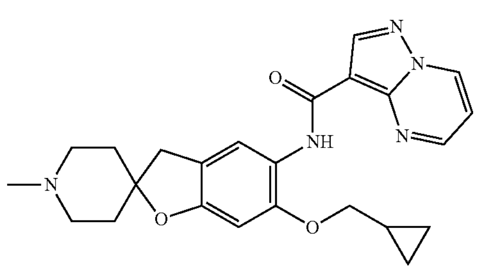 [SMILES: CN1CCC2(CC1)Cc1cc(NC(=O)c3cnn4cccnc34)c(OCC3CC3)cc1O2] | N-(6-(Cyclopropylmethoxy)-1'-methyl-3H-spiro[benzofuran-2,4'-piperidin]-5-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 35 | 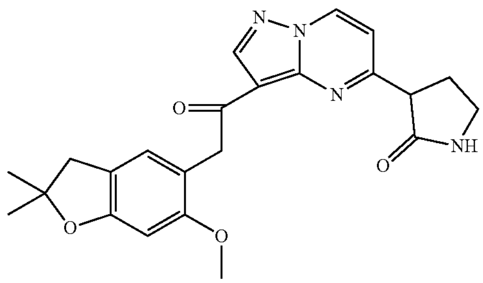 [SMILES: COc1cc2c(cc1CC(=O)c1cnn3ccc(C4CCNC4=O)nc13)CC(C)(C)O2] | N-(6-Methoxy-2,2-dimethyl-2,3-dihydrobenzofuran-5-yl)-5-(2-oxopyrrolidin-3-yl)pyrazolo[1,5-a]pyrimidine-3-carboxamide |
| 36 & 37 | | (S)-5-(5-Amino-3,3-difluoropiperidin-1-yl)-N-(6-methoxy-2,2-dimethyl-2,3-dihydrobenzofuran-5-yl)pyrazolo[1,5-a]pyrimidine-3-carboxamide & (R)-5-(5-Amino-3,3-difluoropiperidin-1-yl)-N-(6-methoxy-2,2-dimethyl-2,3-dihydrobenzofuran-5-yl)pyrazolo[1,5-a]pyrimidine-3-carboxamide (absolute stereochemistry assigned arbitrarily) |
| 38 | 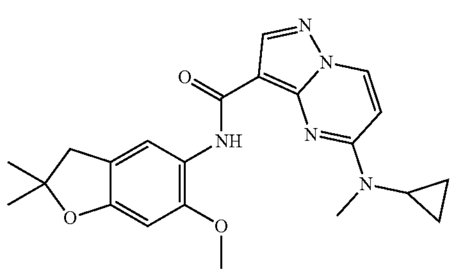 [SMILES: COc1cc2c(cc1NC(=O)c1cnn3ccc(N(C)C4CC4)nc13)CC(C)(C)O2] | 5-(Cyclopropyl(methyl)amino)-N-(6-methoxy-2,2-dimethyl-2,3-dihydrobenzofuran-5-yl)pyrazolo[1,5-a]pyrimidine-3-carboxamide |
| 39 | 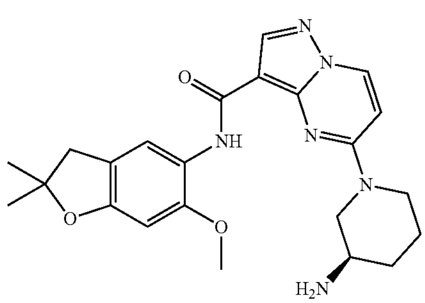 [SMILES: COc1cc2c(cc1NC(=O)c1cnn3ccc(N4CCC[C@@H](N)C4)nc13)CC(C)(C)O2] | (R)-5-(3-Aminopiperidin-1-yl)-N-(6-methoxy-2,2-dimethyl-2,3-dihydrobenzofuran-5-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 40 | 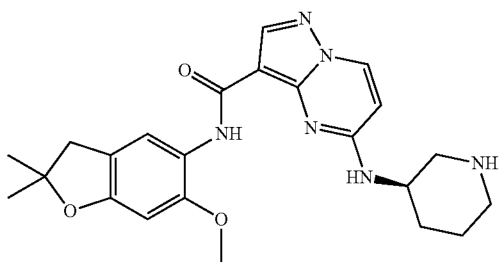 [SMILES: COc1cc2c(cc1NC(=O)c1cnn3ccc(N[C@@H]4CCCNC4)nc13)CC(C)(C)O2] | (R)-N-(6-Methoxy-2,2-dimethyl-2,3-dihydrobenzofuran-5-yl)-5-(piperidin-3-ylamino)pyrazolo[1,5-a]pyrimidine-3-carboxamide |
| 41 | 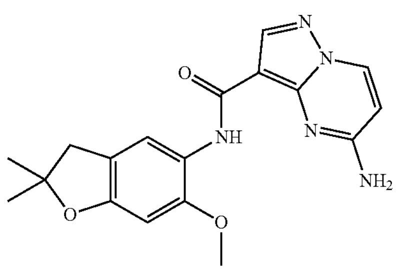 [SMILES: COc1cc2c(cc1NC(=O)c1cnn3ccc(N)nc13)CC(C)(C)O2] | 5-amino-N-(6-Methoxy-2,2-dimethyl-2,3-dihydrobenzofuran-5-yl)pyrazolo[1,5-a]pyrimidine-3-carboxamide |
| 42 | 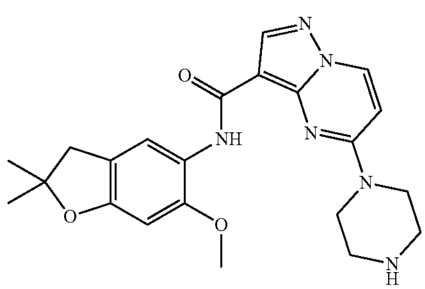 [SMILES: COc1cc2c(cc1NC(=O)c1cnn3ccc(N4CCNCC4)nc13)CC(C)(C)O2] | N-(6-Methoxy-2,2-dimethyl-2,3-dihydrobenzofuran-5-yl)-5-(piperazin-1-yl)pyrazolo[1,5-a]pyrimidine-3-carboxamide |
| 43 | 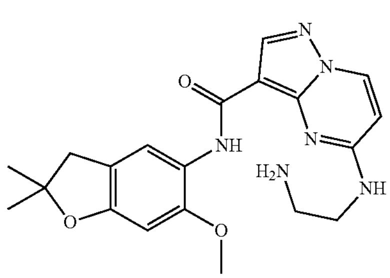 [SMILES: COc1cc2c(cc1NC(=O)c1cnn3ccc(NCCN)nc13)CC(C)(C)O2] | 5-((2-Aminoethyl)amino)-N-(6-methoxy-2,2-dimethyl-2,3-dihydrobenzofuran-5-yl)pyrazolo[1,5-a]pyrimidine-3-carboxamide |
| 44 | 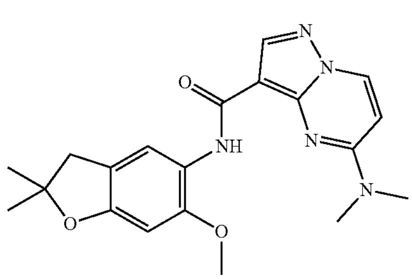 | 5-(Dimethylamino)-N-(6-methoxy-2,2-dimethyl-2,3-dihydrobenzofuran-5-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 45 | 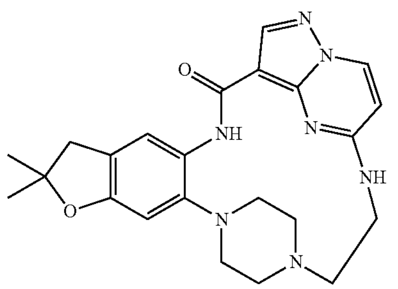 [SMILES: CC1(C)Cc2cc3c(cc2O1)N1CCN(CCNc2ccn4ncc(c4n2)C(=O)N3)CC1] | ($5^3$E,$5^4$E)-$2^2$,$2^2$-Dimethyl-$2^2$,$2^3$-dihydro-3,6-diaza-5(3,5)-pyrazolo[1,5-a]pyrimidina-1(1,4)-piperazina-2(6,5)-benzofuranacyclooctaphan-4-one |
| 46 | 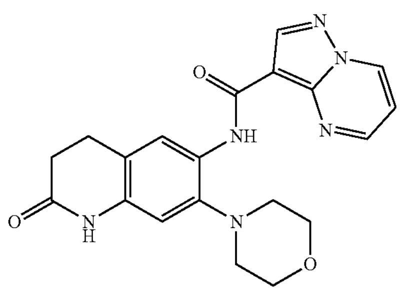 [SMILES: O=C1CCc2cc(NC(=O)c3cnn4cccnc34)c(N3CCOCC3)cc2N1] | N-(7-Morpholino-2-oxo-1,2,3,4-tetrahydroquinolin-6-yl)pyrazolo[1,5-a]pyrimidine-3-carboxamide |
| 47 | 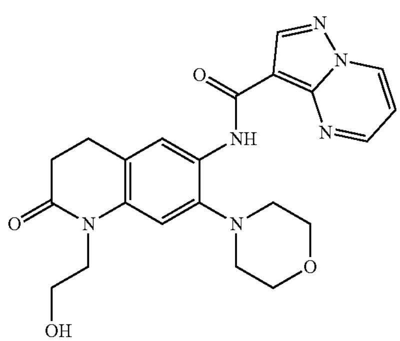 [SMILES: O=C(Nc1cc2c(cc1N1CCOCC1)N(CCO)C(=O)CC2)c1cnn2cccnc12] | N-(1-(2-Hydroxyethyl)-7-morpholino-2-oxo-1,2,3,4-tetrahydroquinolin-6-yl)pyrazolo[1,5-a]pyrimidine-3-carboxamide |
| 48 | 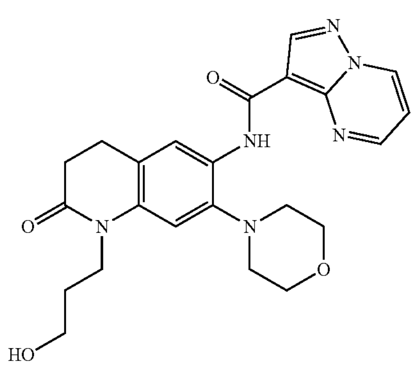 [SMILES: O=C(Nc1cc2c(cc1N1CCOCC1)N(CCCO)C(=O)CC2)c1cnn2cccnc12] | N-(1-(3-Hydroxypropyl)-7-morpholino-2-oxo-1,2,3,4-tetrahydroquinolin-6-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 49 | 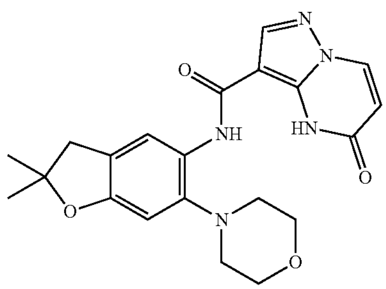 [SMILES: CC1(C)Cc2cc(NC(=O)c3cnn4ccc(=O)[nH]c34)c(N3CCOCC3)cc2O1] | N-(2,2-Dimethyl-6-morpholino-2,3-dihydrobenzofuran-5-yl)-5-oxo-4,5-dihydropyrazolo[1,5-a]pyrimidine-3-carboxamide |
| 50 & 51 | | (R)-N-(2-(Hydroxymethyl)-2-methyl-6-(4-(oxetan-3-yl)piperazin-1-yl)-2,3-dihydrobenzofuran-5-yl)pyrazolo[1,5-a]pyrimidine-3-carboxamide & (S)-N-(2-(Hydroxymethyl)-2-methyl-6-(4-(oxetan-3-yl)piperazin-1-yl)-2,3-dihydrobenzofuran-5-yl)pyrazolo[1,5-a]pyrimidine-3-carboxamide (absolute stereochemistry assigned arbitrarily) |

TABLE 1-continued

Exemplary compounds of the present invention. Salts of such compounds are also contemplated.
See the Examples section for preparation of such compounds.

| Example | Structure | Name |
|---|---|---|
| 52 & 53 | | (R)-N-(6-(4-(1,3-Dihydroxypropan-2-yl)piperidin-1-yl)-2-(hydroxymethyl)-2-methyl-2,3-dihydrobenzofuran-5-yl)pyrazolo[1,5-a]pyrimidine-3-carboxamide & (S)-N-(6-(4-(1,3-Dihydroxypropan-2-yl)piperidin-1-yl)-2-(hydroxymethyl)-2-methyl-2,3-dihydrobenzofuran-5-yl)pyrazolo[1,5-a]pyrimidine-3-carboxamide (absolute stereochemistry assigned arbitrarily) |
| 54 & 55 | | (R)-N-(3-Hydroxy-3-methyl-7-(4-(oxetan-3-yl)piperazin-1-yl)chroman-6-yl)pyrazolo[1,5-a]pyrimidine-3-carboxamide & (S)-N-(3-Hydroxy-3-methyl-7-(4-(oxetan-3-yl)piperazin-1-yl)chroman-6-yl)pyrazolo[1,5-a]pyrimidine-3-carboxamide (absolute stereochemistry assigned arbitrarily) |

TABLE 1-continued

Exemplary compounds of the present invention. Salts of such compounds are also contemplated.
See the Examples section for preparation of such compounds.

| Example | Structure | Name |
|---|---|---|
| 56 & 57 | 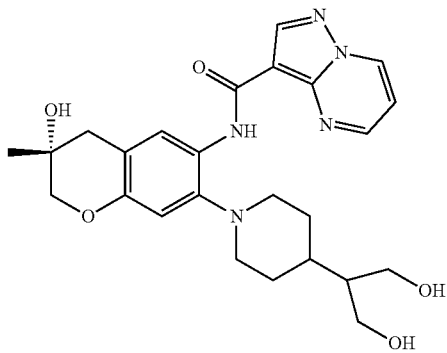 [SMILES: C[C@]1(O)COc2cc(N3CCC(C(CO)CO)CC3)c(NC(=O)c3cnn4cccnc34)cc2C1] 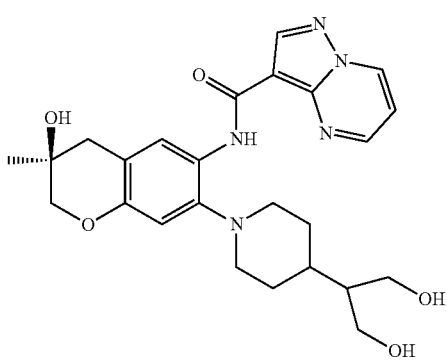 [SMILES: C[C@@]1(O)COc2cc(N3CCC(C(CO)CO)CC3)c(NC(=O)c3cnn4cccnc34)cc2C1] | (R)-N-(7-(4-(1,3-Dihydroxypropan-2-yl)piperazin-1-yl)-3-hydroxy-3-methylchroman-6-yl)pyrazolo[1,5-a]pyrimidine-3-carboxamide & (S)-N-(7-(4-(1,3-Dihydroxypropan-2-yl)piperazin-1-yl)-3-hydroxy-3-methylchroman-6-yl)pyrazolo[1,5-a]pyrimidine-3-carboxamide (absolute stereochemistry assigned arbitrarily) |
| 58 & 59 | 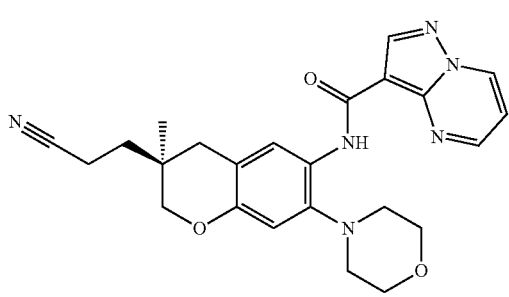 [SMILES: C[C@@]1(CCC#N)COc2cc(N3CCOCC3)c(NC(=O)c3cnn4cccnc34)cc2C1] 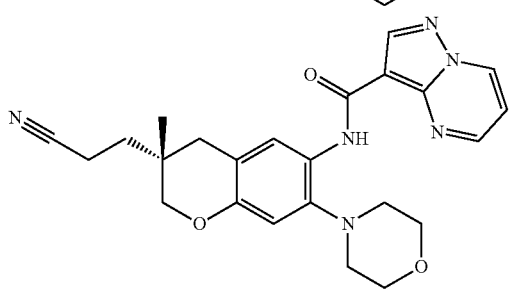 | (S)-N-(3-(2-Cyanoethyl)-3-methyl-7-morpholinochroman-6-yl)pyrazolo[1,5-a]pyrimidine-3-carboxamide & (R)-N-(3-(2-Cyanoethyl)-3-methyl-7-morpholinochroman-6-yl)pyrazolo[1,5-a]pyrimidine-3-carboxamide (absolute stereochemistry assigned arbitrarily) |

TABLE 1-continued

Exemplary compounds of the present invention. Salts of such compounds are also contemplated.
See the Examples section for preparation of such compounds.

| Example | Structure | Name |
|---|---|---|
| 60 | 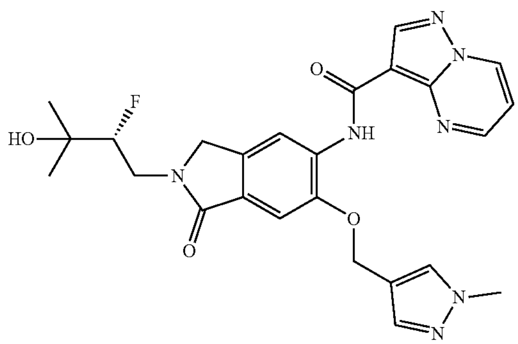 [SMILES: Cn1cc(COc2cc3c(cc2NC(=O)c2cnn4cccnc24)CN(C[C@@H](F)C(C)(C)O)C3=O)cn1] | (R)-N-(2-(2-Fluoro-3-hydroxy-3-methylbutyl)-6-((1-methyl-1H-pyrazol-4-yl)methoxy)-1-oxoisoindolin-5-yl)pyrazolo[1,5-a]pyrimidine-3-carboxamide |
| 61 | 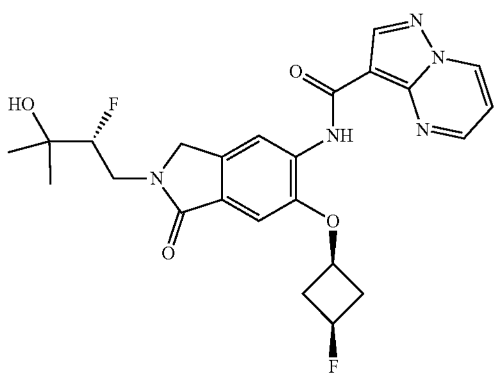 [SMILES: CC(C)(O)[C@H](F)CN1Cc2cc(NC(=O)c3cnn4cccnc34)c(O[C@H]3C[C@@H](F)C3)cc2C1=O] | N-[6-(3-Fluorocyclobutoxy)-2-[(2R)-2-fluoro-3-hydroxy-3-methyl-butyl]-1-oxo-isoindolin-5-yl]pyrazolo[1,5-a]pyrimidine-3-carboxamide |
| 62 & 63 | | N-[2-[(2R)-2-Fluoro-3-hydroxy-3-methyl-butyl]-1-oxo-6-[(3S)-pyrrolidin-3-yl]oxy-isoindolin-5-yl]pyrazolo[1,5-a]pyrimidine-3-carboxamide & N-[2-[(2R)-2-Fluoro-3-hydroxy-3-methyl-butyl]-1-oxo-6-[(3R)-pyrrolidin-3-yl]oxy-isoindolin-5-yl]pyrazolo[1,5-a]pyrimidine-3-carboxamide (absolute stereochemistry assigned arbitrarily) |

TABLE 1-continued

Exemplary compounds of the present invention. Salts of such compounds are also contemplated.
See the Examples section for preparation of such compounds.

| Example | Structure | Name |
| --- | --- | --- |
| 64 | 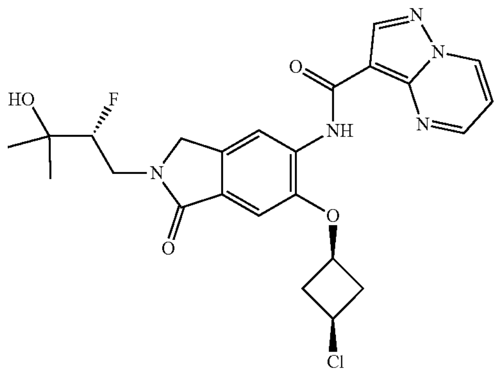 [SMILES: CC(C)(O)[C@H](F)CN1Cc2cc(NC(=O)c3cnn4cccnc34)c(O[C@H]3C[C@@H](Cl)C3)cc2C1=O] | N-[6-(3-Chlorocyclobutoxy)-2-[(2R)-2-fluoro-3-hydroxy-3-methyl-butyl]-1-oxo-isoindolin-5-yl]pyrazolo[1,5-a]pyrimidine-3-carboxamide |
| 65 | 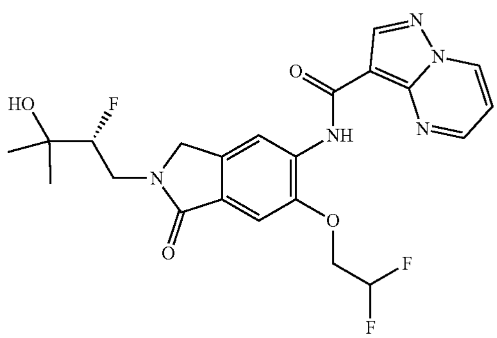 [SMILES: CC(C)(O)[C@H](F)CN1Cc2cc(NC(=O)c3cnn4cccnc34)c(OCC(F)F)cc2C1=O] | (R)-N-(6-(2,2-Difluoroethoxy)-2-(2-fluoro-3-hydroxy-3-methylbutyl)-1-oxoisoindolin-5-yl)pyrazolo[1,5-a]pyrimidine-3-carboxamide |
| 66 & 67 | | N-(2-((R)-2-Fluoro-3-hydroxy-3-methylbutyl)-6-(((1S,3R)-3-hydroxycyclopentyl)oxy)-1-oxoisoindolin-5-yl)pyrazolo[1,5-a]pyrimidine-3-carboxamide & N-(2-((R)-2-Fluoro-3-hydroxy-3-methylbutyl)-6-(((1R,3R)-3-hydroxycyclopentyl)oxy)-1-oxoisoindolin-5-yl)pyrazolo[1,5-a]pyrimidine-3-carboxamide (absolute stereochemistry assigned arbitrarily) |

TABLE 1-continued

Exemplary compounds of the present invention. Salts of such compounds are also contemplated.
See the Examples section for preparation of such compounds.

| Example | Structure | Name |
|---|---|---|
| 68 & 69 | 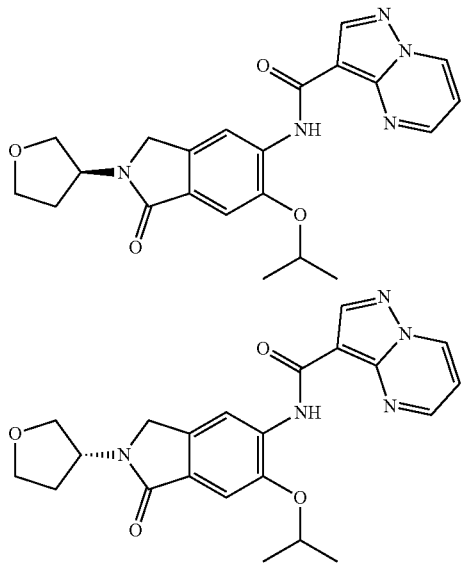 | (S)-N-(6-Isopropoxy-1-oxo-2-(tetrahydrofuran-3-yl)isoindolin-5-yl)pyrazolo[1,5-a]pyrimidine-3-carboxamide & (R)-N-(6-Isopropoxy-1-oxo-2-(tetrahydrofuran-3-yl)isoindolin-5-yl)pyrazolo[1,5-a]pyrimidine-3-carboxamide (absolute stereochemistry assigned arbitrarily) |
| 70 | 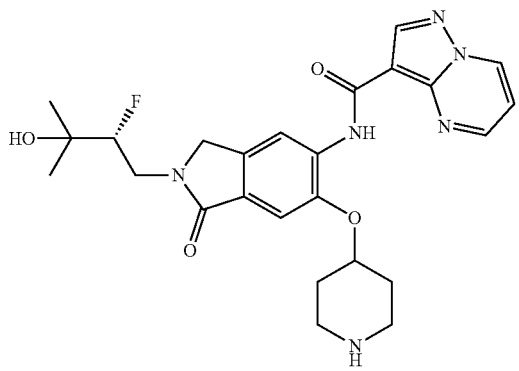 [SMILES: CC(C)(O)[C@H](F)CN1Cc2cc(NC(=O)c3cnn4cccnc34)c(OC3CCNCC3)cc2C1=O] | (R)-N-(2-(2-Fluoro-3-hydroxy-3-methylbutyl)-1-oxo-6-(piperidin-4-yloxy)isoindolin-5-yl)pyrazolo[1,5-a]pyrimidine-3-carboxamide |
| 71 & 72 | 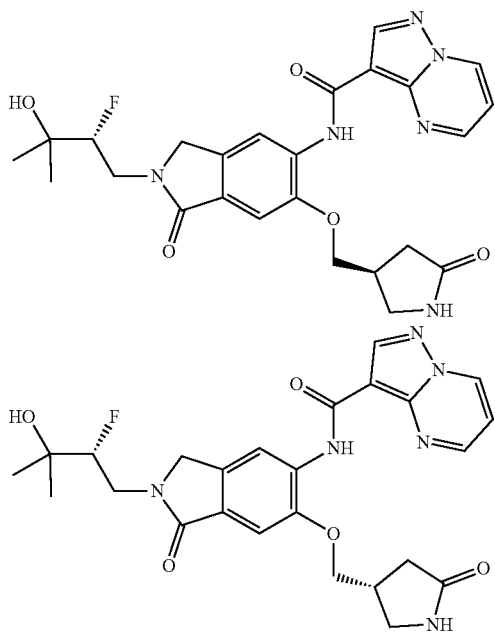 | N-[2-[(2R)-2-Fluoro-3-hydroxy-3-methyl-butyl]-1-oxo-6-[[(3S)-5-oxopyrrolidin-3-yl]methoxy]isoindolin-5-yl]pyrazolo[1,5-a]pyrimidine-3-carboxamide & N-[2-[(2R)-2-Fluoro-3-hydroxy-3-methyl-butyl]-1-oxo-6-[[(3R)-5-oxopyrrolidin-3-yl]methoxy]isoindolin-5-yl]pyrazolo[1,5-a]pyrimidine-3-carboxamide (absolute stereochemistry assigned arbitrarily) |

TABLE 1-continued

Exemplary compounds of the present invention. Salts of such compounds are also contemplated.
See the Examples section for preparation of such compounds.

| Example | Structure | Name |
|---|---|---|
| 73 | 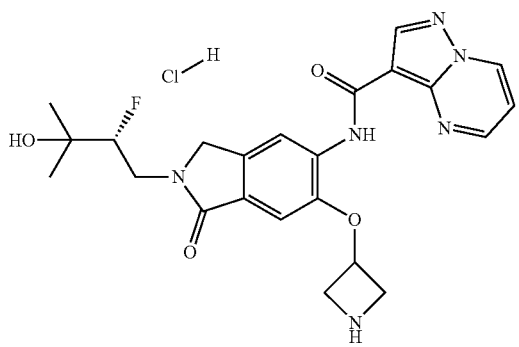 | N-[6-(Azetidin-3-yloxy)-2-[(2R)-2-fluoro-3-hydroxy-3-methyl-butyl]-1-oxo-isoindolin-5-yl]pyrazolo[1,5-a]pyrimidine-3-carboxamide hydrochloride |
| 74 | 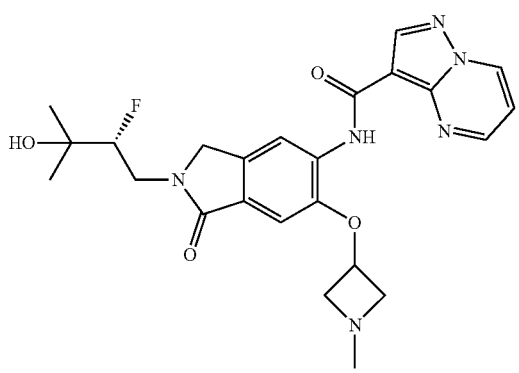 [SMILES: CN1CC(Oc2cc3c(cc2NC(=O)c2cnn4cccnc24)CN(C[C@@H](F)C(C)(C)O)C3=O)C1] | N-[6-(Azetidin-3-yloxy)-2-[(2R)-2-fluoro-3-hydroxy-3-methyl-butyl]-1-oxo-isoindolin-5-yl]pyrazolo[1,5-a]pyrimidine-3-carboxamide |
| 75 | 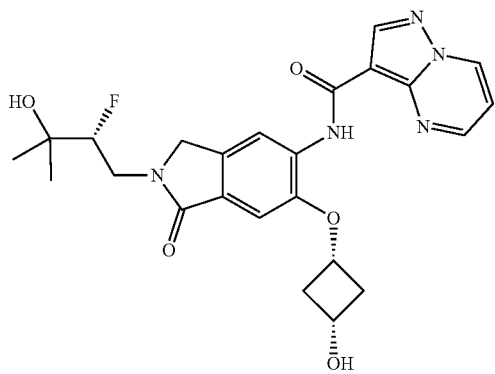 [SMILES: CC(C)(O)[C@H](F)CN1Cc2cc(NC(=O)c3cnn4cccnc34)c(O[C@H]3C[C@@H](O)C3)cc2C1=O] | N-[2-[(2R)-2-Fluoro-3-hydroxy-3-methyl-butyl]-6-(3-hydroxycyclobutoxy)-1-oxo-isoindolin-5-yl]pyrazolo[1,5-a]pyrimidine-3-carboxamide |
| 76 | 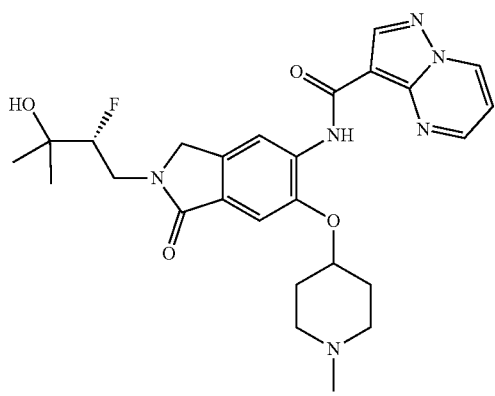 [SMILES: CN1CCC(Oc2cc3c(cc2NC(=O)c2cnn4cccnc24)CN(C[C@@H](F)C(C)(C)O)C3=O)CC1] | (R)-N-(2-(2-Fluoro-3-hydroxy-3-methylbutyl)-6-((1-methylpiperidin-4-yl)oxy)-1-oxoisoindolin-5-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 77 | 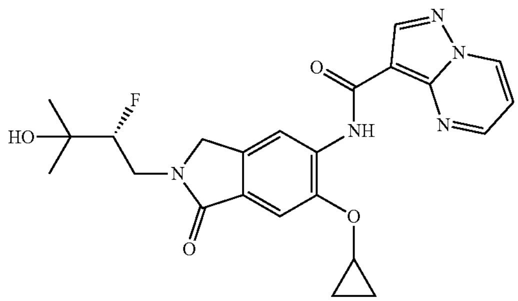 [SMILES: CC(C)(O)[C@H](F)CN1Cc2cc(NC(=O)c3cnn4cccnc34)c(OC3CC3)cc2C1=O] | (R)-N-(6-Cyclopropoxy-2-(2-fluoro-3-hydroxy-3-methylbutyl)-1-oxoisoindolin-5-yl)pyrazolo[1,5-a]pyrimidine-3-carboxamide |
| 78 | 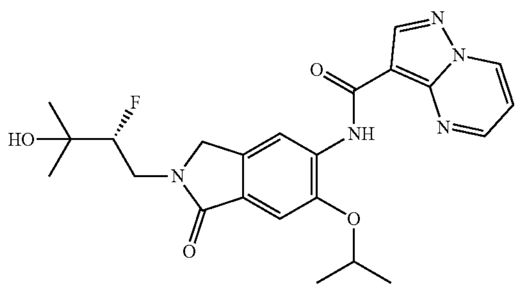 [SMILES: CC(C)Oc1cc2c(cc1NC(=O)c1cnn3cccnc13)CN(C[C@@H](F)C(C)(C)O)C2=O] | N-[2-[(2R)-2-Fluoro-3-hydroxy-3-methyl-butyl]-6-isopropoxy-1-oxo-isoindolin-5-yl]pyrazolo[1,5-a]pyrimidine-3-carboxamide |
| 79 | 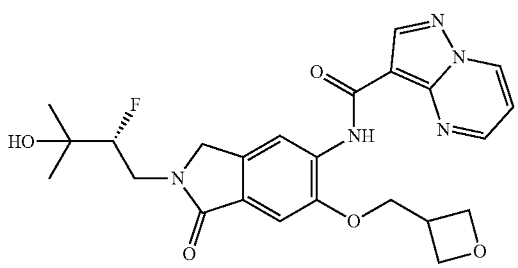 [SMILES: CC(C)(O)[C@H](F)CN1Cc2cc(NC(=O)c3cnn4cccnc34)c(OCC3COC3)cc2C1=O] | (R)-N-(2-(2-Fluoro-3-hydroxy-3-methylbutyl)-6-(oxetan-3-ylmethoxy)-1-oxoisoindolin-5-yl)pyrazolo[1,5-a]pyrimidine-3-carboxamide |
| 80 | 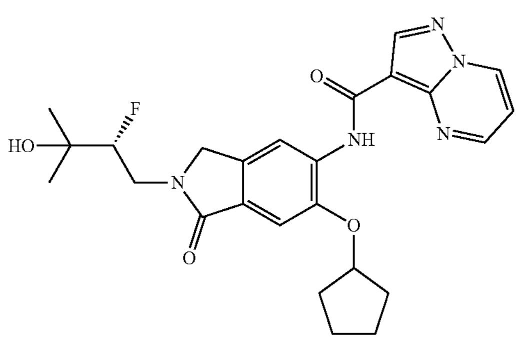 [SMILES: CC(C)(O)[C@H](F)CN1Cc2cc(NC(=O)c3cnn4cccnc34)c(OC3CCCC3)cc2C1=O] | (R)-N-(6-(Cyclopentyloxy)-2-(2-fluoro-3-hydroxy-3-methylbutyl)-1-oxoisoindolin-5-yl)pyrazolo[1,5-a]pyrimidine-3-carboxamide |
| 81 | 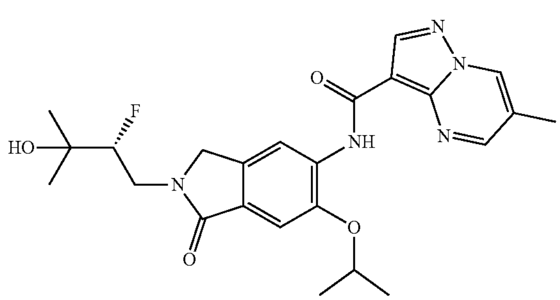 [SMILES: Cc1cnc2c(C(=O)Nc3cc4c(cc3OC(C)C)C(=O)N(C[C@@H](F)C(C)(C)O)C4)cnn2c1] | (R)-N-(2-(2-Fluoro-3-hydroxy-3-methylbutyl)-6-isopropoxy-1-oxoisoindolin-5-yl)-6-methylpyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 82 | 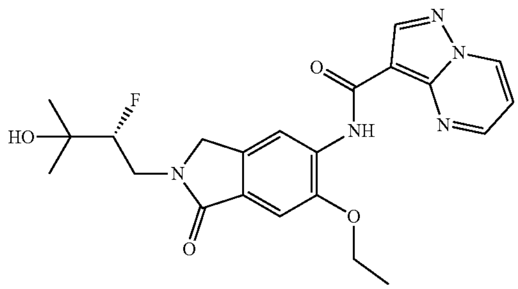 [SMILES: CCOc1cc2c(cc1NC(=O)c1cnn3cccnc13)CN(C[C@@H](F)C(C)(C)O)C2=O] | (R)-N-(6-Ethoxy-2-(2-fluoro-3-hydroxy-3-methylbutyl)-1-oxoisoindolin-5-yl)pyrazolo[1,5-a]pyrimidine-3-carboxamide |
| 83 & 84 | 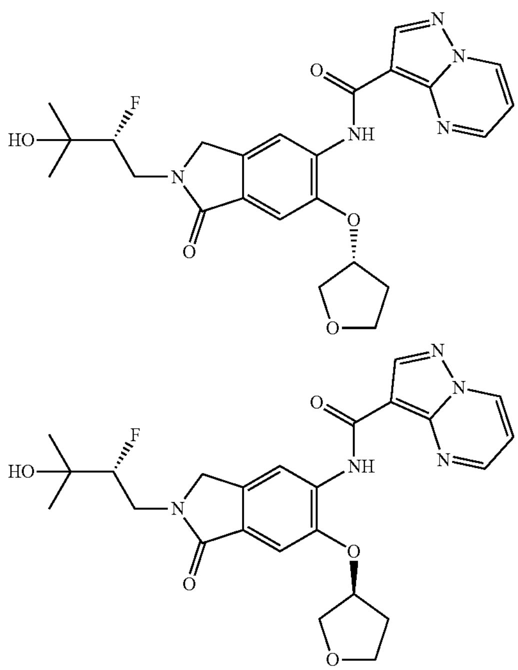 | N-(2-((R)-2-Fluoro-3-hydroxy-3-methylbutyl)-1-oxo-6-(((R)-tetrahydrofuran-3-yl)oxy)isoindolin-5-yl)pyrazolo[1,5-a]pyrimidine-3-carboxamide & N-(2-((R)-2-Fluoro-3-hydroxy-3-methylbutyl)-1-oxo-6-(((S)-tetrahydrofuran-3-yl)oxy)isoindolin-5-yl)pyrazolo[1,5-a]pyrimidine-3-carboxamide (absolute stereochemistry assigned arbitrarily) |
| 85 | 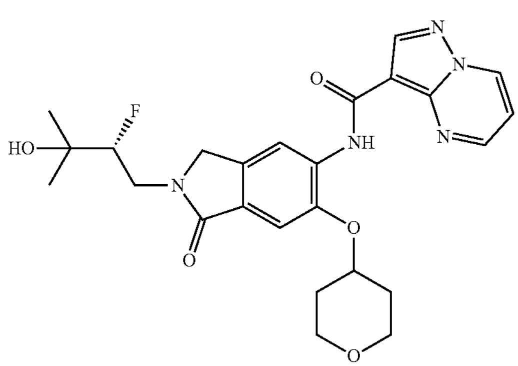 [SMILES: CC(C)(O)[C@H](F)CN1Cc2cc(NC(=O)c3cnn4cccnc34)c(OC3CCOCC3)cc2C1=O] | (R)-N-(2-(2-Fluoro-3-hydroxy-3-methylbutyl)-1-oxo-6-((tetrahydro-2H-pyran-4-yl)oxy)isoindolin-5-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 86 | 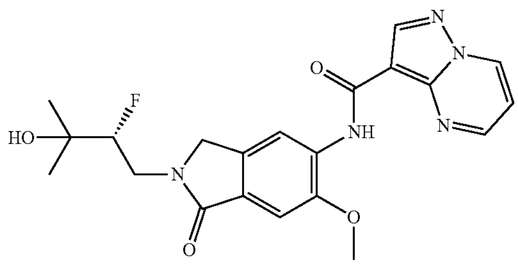 [SMILES: COc1cc2c(cc1NC(=O)c1cnn3cccnc13)CN(C[C@@H](F)C(C)(C)O)C2=O] | (R)-N-(2-(2-Fluoro-3-hydroxy-3-methylbutyl)-6-methoxy-1-oxoisoindolin-5-yl)pyrazolo[1,5-a]pyrimidine-3-carboxamide |
| 87 | 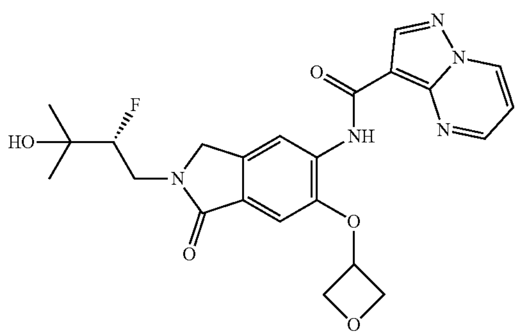 [SMILES: CC(C)(O)[C@H](F)CN1Cc2cc(NC(=O)c3cnn4cccnc34)c(OC3COC3)cc2C1=O] | (R)-N-(2-(2-Fluoro-3-hydroxy-3-methylbutyl)-6-(oxetan-3-yloxy)-1-oxoisoindolin-5-yl)pyrazolo[1,5-a]pyrimidine-3-carboxamide |
| 88 | 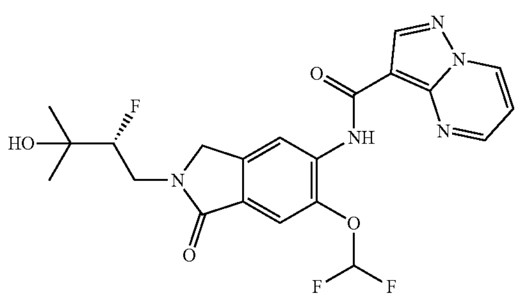 [SMILES: CC(C)(O)[C@H](F)CN1Cc2cc(NC(=O)c3cnn4cccnc34)c(OC(F)F)cc2C1=O] | (R)-N-(6-(Difluoromethoxy)-2-(2-fluoro-3-hydroxy-3-methylbutyl)-1-oxoisoindolin-5-yl)pyrazolo[1,5-a]pyrimidine-3-carboxamide |
| 89 | 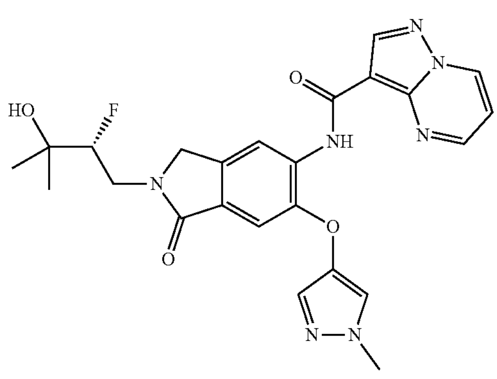 [SMILES: Cn1cc(Oc2cc3c(cc2NC(=O)c2cnn4cccnc24)CN(C[C@@H](F)C(C)(C)O)C3=O)cn1] | (R)-N-(2-(2-Fluoro-3-hydroxy-3-methylbutyl)-6-((1-methyl-1H-pyrazol-4-yl)oxy)-1-oxoisoindolin-5-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 90 | 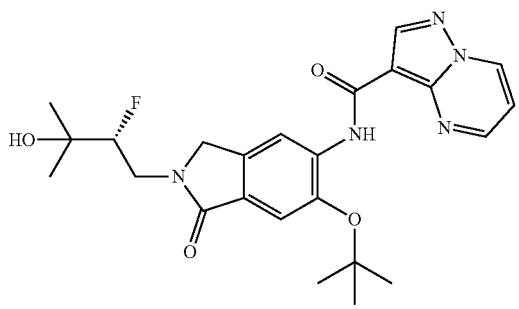 [SMILES: CC(C)(C)Oc1cc2c(cc1NC(=O)c1cnn3cccnc13)CN(C[C@@H](F)C(C)(C)O)C2=O] | (R)-N-(6-(tert-Butoxy)-2-(2-fluoro-3-hydroxy-3-methylbutyl)-1-oxoisoindolin-5-yl)pyrazolo[1,5-a]pyrimidine-3-carboxamide |
| 91 | 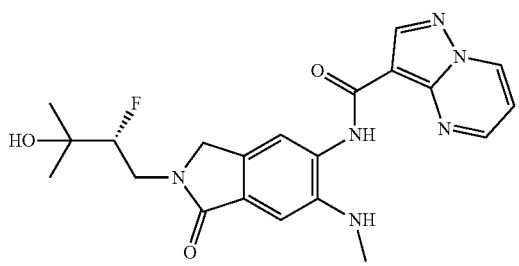 [SMILES: CNc1cc2c(cc1NC(=O)c1cnn3cccnc13)CN(C[C@@H](F)C(C)(C)O)C2=O] | N-[2-[(2R)-2-Fluoro-3-hydroxy-3-methyl-butyl]-6-(methylamino)-1-oxo-isoindolin-5-yl]pyrazolo[1,5-a]pyrimidine-3-carboxamide |
| 92 | 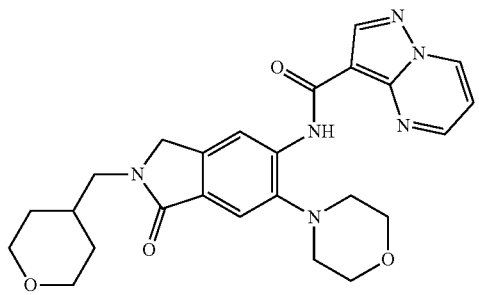 [SMILES: O=C(Nc1cc2c(cc1N1CCOCC1)C(=O)N(CC1CCOCC1)C2)c1cnn2cccnc12] | N-[6-Morpholino-1-oxo-2-(tetrahydropyran-4-ylmethyl)isoindolin-5-yl]pyrazolo[1,5-a]pyrimidine-3-carboxamide |
| 93 | 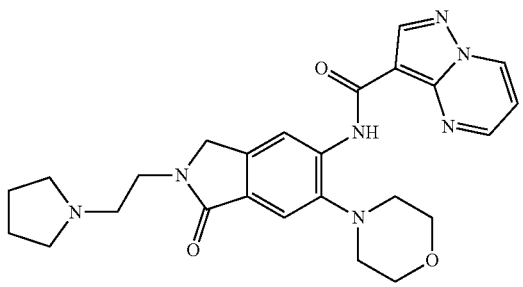 [SMILES: O=C(Nc1cc2c(cc1N1CCOCC1)C(=O)N(CCN1CCCC1)C2)c1cnn2cccnc12] | N-[6-Morpholino-1-oxo-2-(2-pyrrolidin-1-ylethyl)isoindolin-5-yl]pyrazolo[1,5-a]pyrimidine-3-carboxamide |
| 94 | 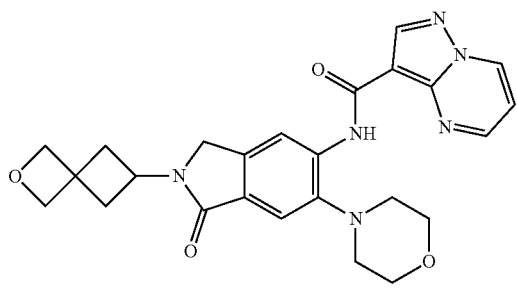 [SMILES: O=C(Nc1cc2c(cc1N1CCOCC1)C(=O)N(C1CC3(COC3)C1)C2)c1cnn2cccnc12] | N-[6-Morpholino-2-(2-oxaspiro[3,3]heptan-6-yl)-1-oxo-isoindolin-5-yl]pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 95 | 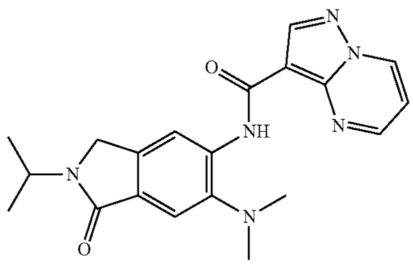 [SMILES: CC(C)N1Cc2cc(NC(=O)c3cnn4cccnc34)c(N(C)C)cc2C1=O] | N-[6-(Dimethylamino)-2-isopropyl-1-oxo-isoindolin-5-yl]pyrazolo[1,5-a]pyrimidine-3-carboxamide |
| 96 | 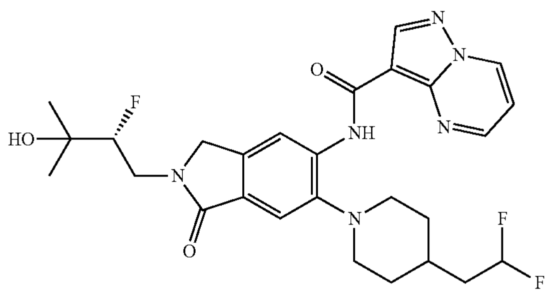 [SMILES: CC(C)(O)[C@H](F)CN1Cc2cc(NC(=O)c3cnn4cccnc34)c(N3CCC(CC(F)F)CC3)cc2C1=O] | (R)-N-(6-(4-(2,2-Difluoroethyl)piperidin-1-yl)-2-(2-fluoro-3-hydroxy-3-methylbutyl)-1-oxoisoindolin-5-yl)pyrazolo[1,5-a]pyrimidine-3-carboxamide |
| 97 | 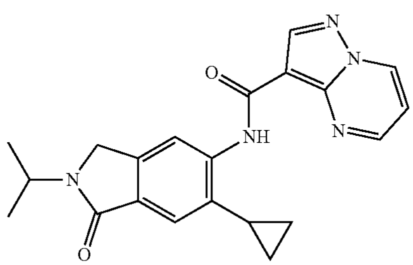 [SMILES: CC(C)N1Cc2cc(NC(=O)c3cnn4cccnc34)c(C3CC3)cc2C1=O] | N-(6-Cyclopropyl-2-isopropyl-1-oxoisoindolin-5-yl)pyrazolo[1,5-a]pyrimidine-3-carboxamide |
| 98 | 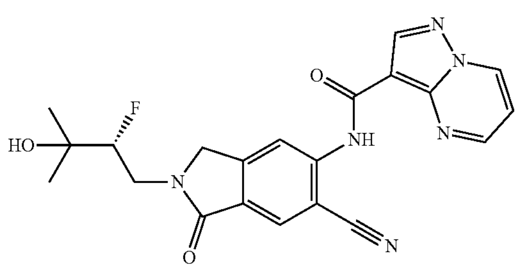 [SMILES: CC(C)(O)[C@H](F)CN1Cc2cc(NC(=O)c3cnn4cccnc34)c(C#N)cc2C1=O] | (R)-N-(6-Cyano-2-(2-fluoro-3-hydroxy-3-methylbutyl)-1-oxoisoindolin-5-yl)pyrazolo[1,5-a]pyrimidine-3-carboxamide |
| 99 | 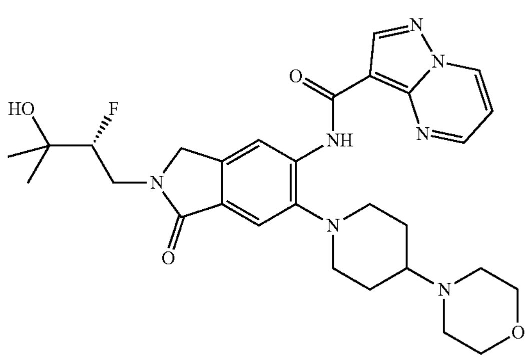 [SMILES: CC(C)(O)[C@H](F)CN1Cc2cc(NC(=O)c3cnn4cccnc34)c(N3CCC(N4CCOCC4)CC3)cc2C1=O] | (R)-N-(2-(2-Fluoro-3-hydroxy-3-methylbutyl)-6-(4-morpholinopiperidin-1-yl)-1-oxoisoindolin-5-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 100 | 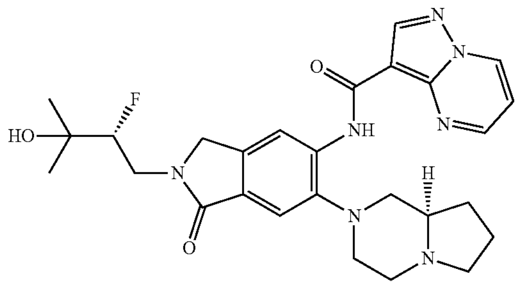 [SMILES: CC(C)(O)[C@H](F)CN1Cc2cc(NC(=O)c3cnn4cccnc34)c(N3CCN4CCC[C@@H]4C3)cc2C1=O] | N-(2-((R)-2-Fluoro-3-hydroxy-3-methylbutyl)-6-((R)-hexahydropyrrolo[1,2-a]pyrazin-2(1H)-yl)-1-oxoisoindolin-5-yl)pyrazolo[1,5-a]pyrimidine-3-carboxamide |
| 101 | 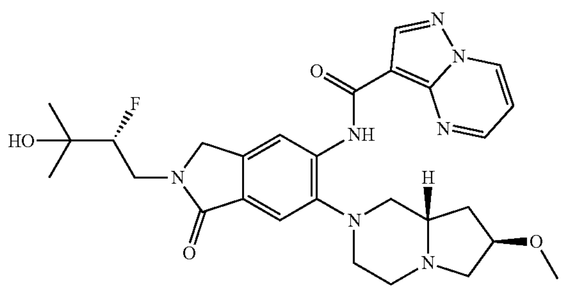 [SMILES: CO[C@@H]1C[C@H]2CN(c3cc4c(cc3NC(=O)c3cnn5cccnc35)CN(C[C@@H](F)C(C)(C)O)C4=O)CCN2C1] | N-(2-((R)-2-Fluoro-3-hydroxy-3-methylbutyl)-6-((7R,8aS)-7-methoxyhexahydropyrrolo[1,2-a]pyrazin-2(1H)-yl)-1-oxoisoindolin-5-yl)pyrazolo[1,5-a]pyrimidine-3-carboxamide |
| 102 | 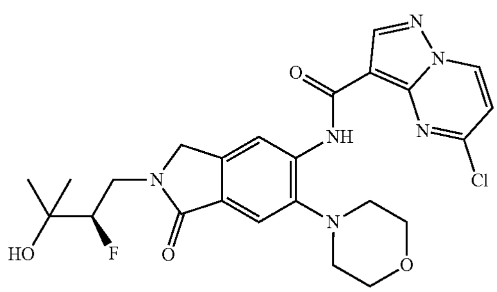 [SMILES: CC(C)(O)[C@H](F)CN1Cc2cc(NC(=O)c3cnn4ccc(Cl)nc34)c(N3CCOCC3)cc2C1=O] | (R)-5-Chloro-N-(2-(2-fluoro-3-hydroxy-3-methylbutyl)-6-morpholino-1-oxoisoindolin-5-yl)pyrazolo[1,5-a]pyrimidine-3-carboxamide |
| 103 | 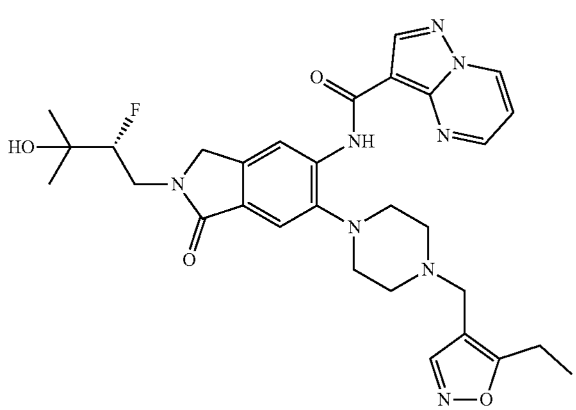 [SMILES: CCc1oncc1CN1CCN(c2cc3c(cc2NC(=O)c2cnn4cccnc24)CN(C[C@@H](F)C(C)(C)O)C3=O)CC1] | (R)-N-(6-(4-((5-Ethylisoxazol-4-yl)methyl)piperazin-1-yl)-2-(2-fluoro-3-hydroxy-3-methylbutyl)-1-oxoisoindolin-5-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 104 | 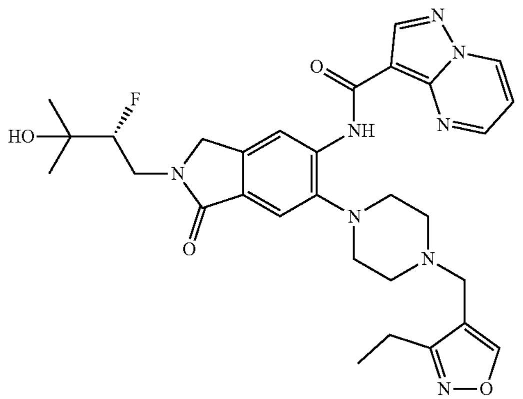 [SMILES: CCc1nocc1CN1CCN(c2cc3c(cc2NC(=O)c2cnn4cccnc24)CN(C[C@@H](F)C(C)(C)O)C3=O)CC1] | (R)-N-(6-(4-((3-Ethylisoxazol-4-yl)methyl)piperazin-1-yl)-2-(2-fluoro-3-hydroxy-3-methylbutyl)-1-oxoisoindolin-5-yl)pyrazolo[1,5-a]pyrimidine-3-carboxamide |
| 105 | 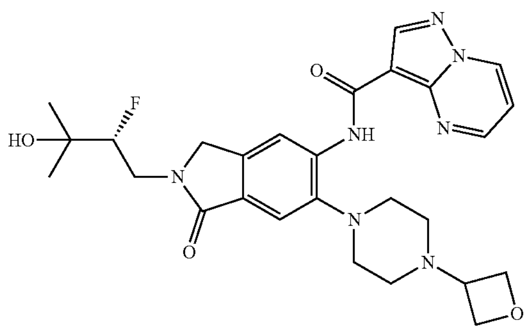 | (R)-N-(2-(2-Fluoro-3-hydroxy-3-methylbutyl)-6-(4-(oxetan-3-yl)piperazin-1-yl)-1-oxoisoindolin-5-yl)pyrazolo[1,5-a]pyrimidine-3-carboxamide |
| 106 | 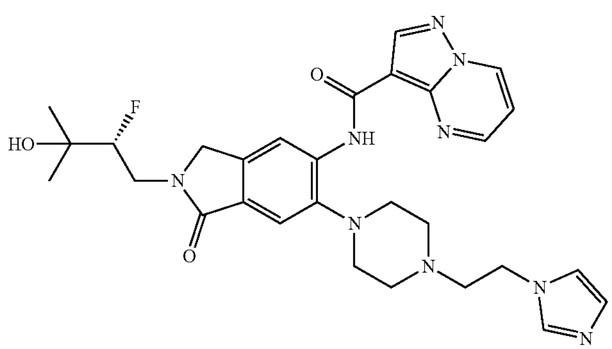 [SMILES: CC(C)(O)[C@H](F)CN1Cc2cc(NC(=O)c3cnn4cccnc34)c(N3CCN(CCn4ccnc4)CC3)cc2C1=O] | (R)-N-(6-(4-(2-(1H-Imidazol-1-yl)ethyl)piperazin-1-yl)-2-(2-fluoro-3-hydroxy-3-methylbutyl)-1-oxoisoindolin-5-yl)pyrazolo[1,5-a]pyrimidine-3-carboxamide |
| 107 | 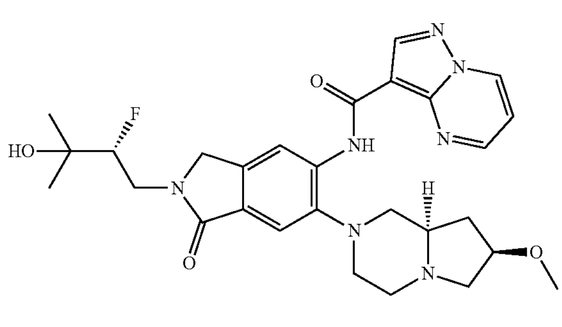 [SMILES: CO[C@@H]1C[C@@H]2CN(c3cc4c(cc3NC(=O)c3cnn5cccnc35)CN(C[C@@H](F)C(C)(C)O)C4=O)CCN2C1] | N-(2-((R)-2-Fluoro-3-hydroxy-3-methylbutyl)-6-((7R,8aR)-7-methoxyhexahydropyrrolo[1,2-a]pyrazin-2(1H)-yl)-1-oxoisoindolin-5-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 108 | 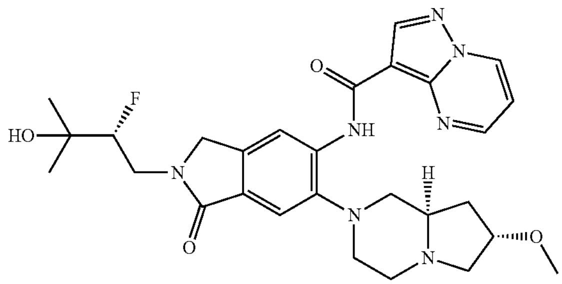 [SMILES: CO[C@H]1C[C@@H]2CN(c3cc4c(cc3NC(=O)c3cnn5cccnc35)CN(C[C@@H](F)C(C)(C)O)C4=O)CCN2C1] | N-(2-((R)-2-Fluoro-3-hydroxy-3-methylbutyl)-6-((7S,8aR)-7-methoxyhexahydropyrrolo[1,2-a]pyrazin-2(1H)-yl)-1-oxoisoindolin-5-yl)pyrazolo[1,5-a]pyrimidine-3-carboxamide |
| 109 | 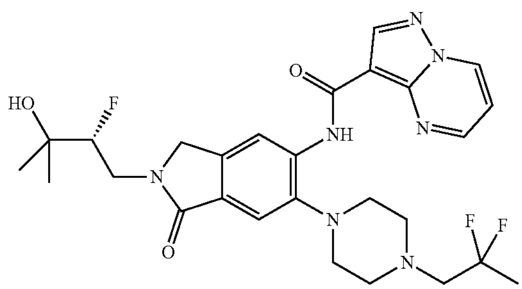 [SMILES: CC(F)(F)CN1CCN(c2cc3c(cc2NC(=O)c2cnn4cccnc24)CN(C[C@@H](F)C(C)(C)O)C3=O)CC1] | (R)-N-(2-(2-Fluoro-3-hydroxy-3-methylbutyl)-1-oxo-6-(4-(2,2,2-trifluoroethyl)piperazin-1-yl)isoindolin-5-yl)pyrazolo[1,5-a]pyrimidine-3-carboxamide |
| 110 & 111 | 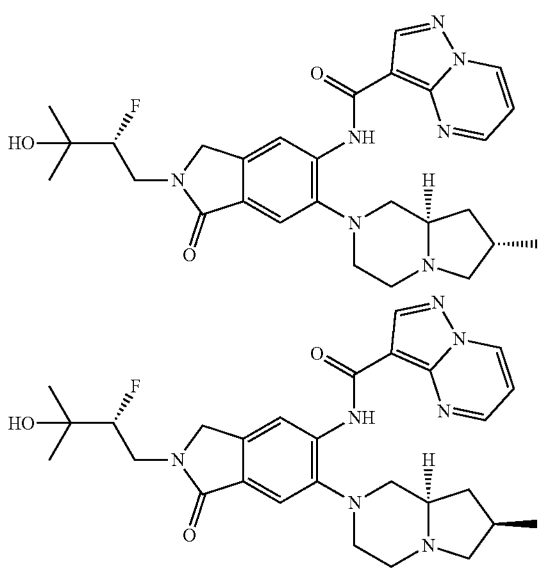 | N-[6-[(7S,8aR)-7-Methyl-3,4,6,7,8,8a-hexahydro-1H-pyrrolo[1,2-a]pyrazin-2-yl]-2-[(2R)-2-fluoro-3-hydroxy-3-methyl-butyl]-1-oxo-isoindolin-5-yl]pyrazolo[1,5-a]pyrimidine-3-carboxamide & N-[6-[(7R,8aR)-7-Methyl-3,4,6,7,8,8a-hexahydro-1H-pyrrolo[1,2-a]pyrazin-2-yl]-2-[(2R)-2-fluoro-3-hydroxy-3-methyl-butyl]-1-oxo-isoindolin-5-yl]pyrazolo[1,5-a]pyrimidine-3-carboxamide (absolute stereochemistry assigned arbitrarily) |
| 112 | 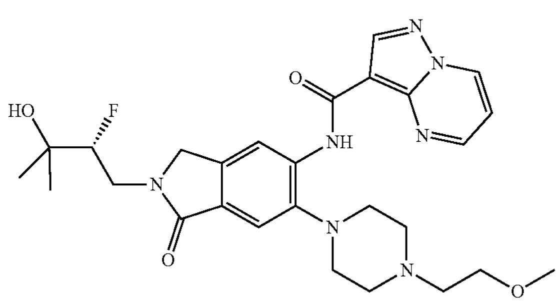 [SMILES: COCCN1CCN(c2cc3c(cc2NC(=O)c2cnn4cccnc24)CN(C[C@@H](F)C(C)(C)O)C3=O)CC1] | (R)-N-(2-(2-Fluoro-3-hydroxy-3-methylbutyl)-6-(4-(2-methoxyethyl)piperazin-1-yl)-1-oxoisoindolin-5-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 113 | 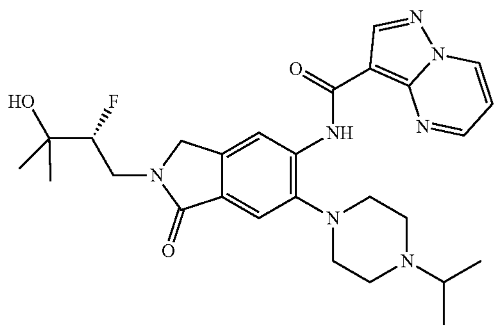 [SMILES: CC(C)N1CCN(c2cc3c(cc2NC(=O)c2cnn4cccnc24)CN(C[C@@H](F)C(C)(C)O)C3=O)CC1] | (R)-N-(2-(2-Fluoro-3-hydroxy-3-methylbutyl)-6-(4-isopropylpiperazin-1-yl)-1-oxoisoindolin-5-yl)pyrazolo[1,5-a]pyrimidine-3-carboxamide |
| 114 | 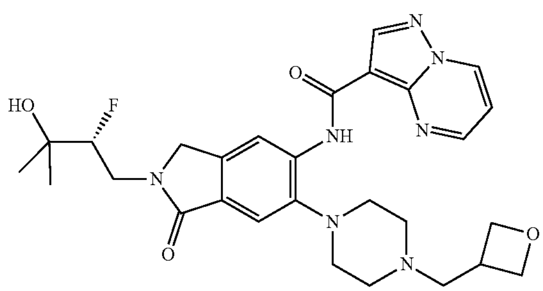 [SMILES: CC(C)(O)[C@H](F)CN1Cc2cc(NC(=O)c3cnn4cccnc34)c(N3CCN(CC4COC4)CC3)cc2C1=O] | (R)-N-(2-(2-Fluoro-3-hydroxy-3-methylbutyl)-6-(4-(oxetan-3-ylmethyl)piperazin-1-yl)-1-oxoisoindolin-5-yl)pyrazolo[1,5-a]pyrimidine-3-carboxamide |
| 115 | 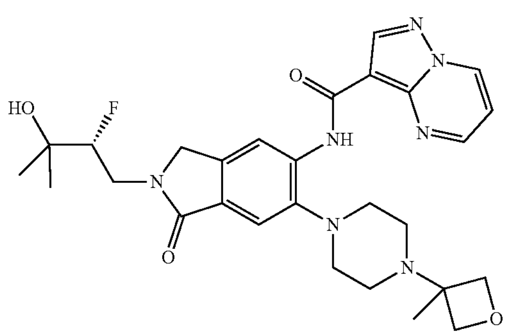 [SMILES: CC(C)(O)[C@H](F)CN1Cc2cc(NC(=O)c3cnn4cccnc34)c(N3CCN(C4(C)COC4)CC3)cc2C1=O] | (R)-N-(2-(2-Fluoro-3-hydroxy-3-methylbutyl)-6-(4-(3-methyloxetan-3-yl)piperazin-1-yl)-1-oxoisoindolin-5-yl)pyrazolo[1,5-a]pyrimidine-3-carboxamide |
| 116 | 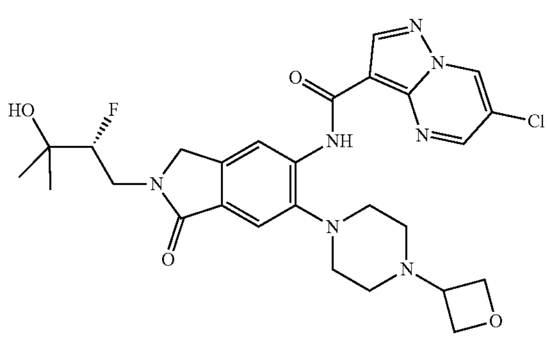 [SMILES: CC(C)(O)[C@H](F)CN1Cc2cc(NC(=O)c3cnn4cc(Cl)cnc34)c(N3CCN(C4COC4)CC3)cc2C1=O] | (R)-6-Chloro-N-(2-(2-fluoro-3-hydroxy-3-methylbutyl)-6-(4-(oxetan-3-yl)piperazin-1-yl)-1-oxoisoindolin-5-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 117 | 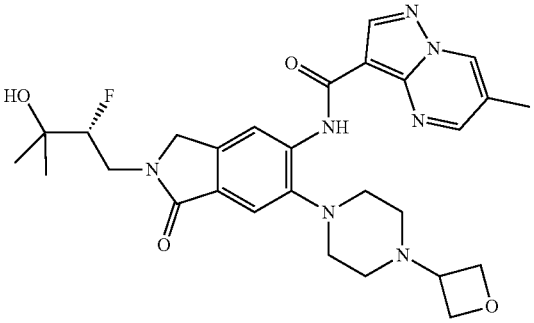 [SMILES: Cc1cnc2c(C(=O)Nc3cc4c(cc3N3CCN(C5COC5)CC3)C(=O)N(C[C@@H](F)C(C)(C)O)C4)cnn2c1] | ((R)-N-(2-(2-Fluoro-3-hydroxy-3-methylbutyl)-6-(4-(oxetan-3-yl)piperazin-1-yl)-1-oxoisoindolin-5-yl)-6-methylpyrazolo[1,5-a]pyrimidine-3-carboxamide |
| 118 | 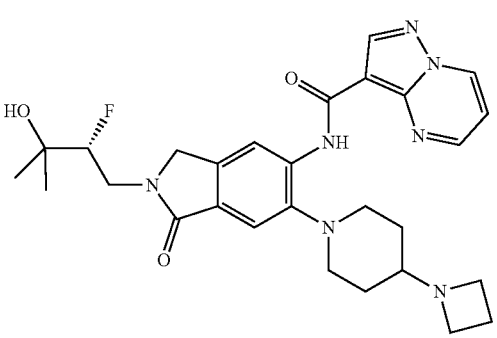 [SMILES: CC(C)(O)[C@H](F)CN1Cc2cc(NC(=O)c3cnn4cccnc34)c(N3CCC(N4CCC4)CC3)cc2C1=O] | (R)-N-(6-(4-(Azetidin-1-yl)piperidin-1-yl)-2-(2-fluoro-3-hydroxy-3-methylbutyl)-1-oxoisoindolin-5-yl)pyrazolo[1,5-a]pyrimidine-3-carboxamide |
| 119 | 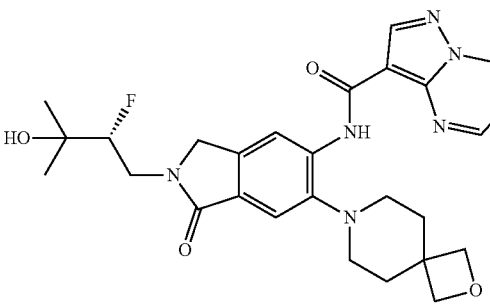 | (R)-N-(2-(2-Fluoro-3-hydroxy-3-methylbutyl)-1-oxo-6-(2-oxa-7-azaspiro[3.5]nonan-7-yl)isoindolin-5-yl)pyrazolo[1,5-a]pyrimidine-3-carboxamide |
| 120 | 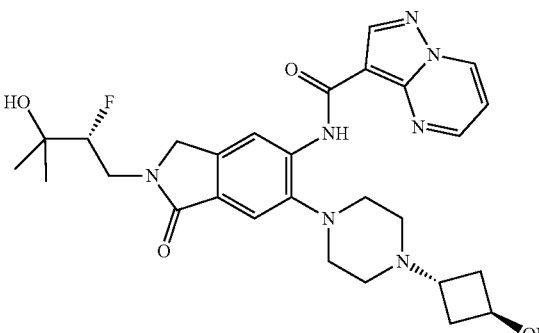 | N-[2-[2R)-2-Fluoro-3-hydroxy-3-methyl-butyl]-6-[4-(3-hydroxycyclobutyl)piperazin-1-yl]-1-oxo-isoindolin-5-yl]pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 121 | 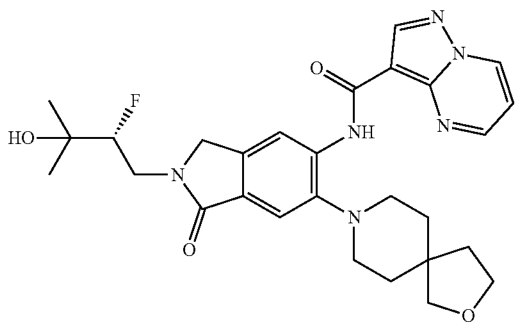 [SMILES: CC(C)(O)[C@H](F)CN1Cc2cc(NC(=O)c3cnn4cccnc34)c(N3CCC4(CCOC4)CC3)cc2C1=O] | (R)-N-(2-(2-Fluoro-3-hydroxy-3-methylbutyl)-1-oxo-6-(2-oxa-8-azaspiro[4.5]decan-8-yl)isoindolin-5-yl)pyrazolo[1,5-a]pyrimidine-3-carboxamide |
| 122 | 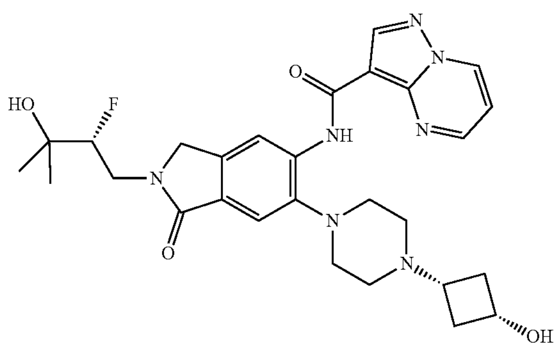 [SMILES: CC(C)(O)[C@H](F)CN1Cc2cc(NC(=O)c3cnn4cccnc34)c(N3CCN([C@H]4C[C@@H](O)C4)CC3)cc2C1=O] | N-[2-[(2R)-2-Fluoro-3-hydroxy-3-methyl-butyl]-6-[4-(3-hydroxycyclobutyl)piperazin-1-yl]-1-oxo-isoindolin-5-yl]pyrazolo[1,5-a]pyrimidine-3-carboxamide |
| 123 | 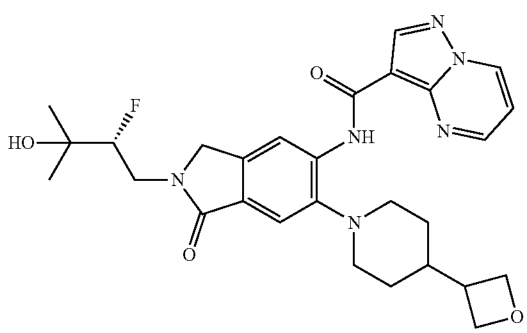 | (R)-N-(2-(2-Fluoro-3-hydroxy-3-methylbutyl)-6-(4-(oxetan-3-yl)piperidin-1-yl)-1-oxoisoindolin-5-yl)pyrazolo[1,5-a]pyrimidine-3-carboxamide |
| 124 | 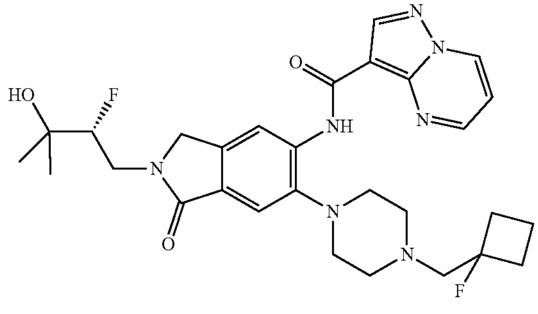 [SMILES: CC(C)(O)[C@H](F)CN1Cc2cc(NC(=O)c3cnn4cccnc34)c(N3CCN(CC4(F)CCC4)CC3)cc2C1=O] | N-[6-[4-[(1-Fluorocyclobutyl)methyl]piperazin-1-yl]-2-[(2R)-2-fluoro-3-hydroxy-3-methyl-butyl]-1-oxo-isoindolin-5-yl]pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 125 & 126 | | (S)-N-(2-(4-Hydroxy-4-methylpentan-2-yl)-6-(4-(oxetan-3-yl)piperazin-1-yl)-1-oxoisoindolin-5-yl)pyrazolo[1,5-a]pyrimidine-3-carboxamide & (R)-N-(2-(4-Hydroxy-4-methylpentan-2-yl)-6-(4-(oxetan-3-yl)piperazin-1-yl)-1-oxoisoindolin-5-yl)pyrazolo[1,5-a]pyrimidine-3-carboxamide (absolute stereochemistry assigned arbitrarily) |
| 127 | 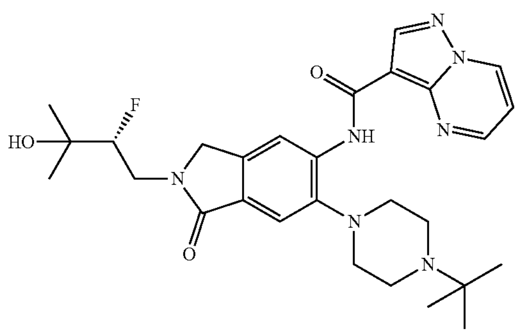 [SMILES: CC(C)(O)[C@H](F)CN1Cc2cc(NC(=O)c3cnn4cccnc34)c(N3CCN(C(C)(C)C)CC3)cc2C1=O] | (R)-N-(6-(4-(tert-Butyl)piperazin-1-yl)-2-(2-fluoro-3-hydroxy-3-methylbutyl)-1-oxoisoindolin-5-yl)pyrazolo[1,5-a]pyrimidine-3-carboxamide |
| 128 | 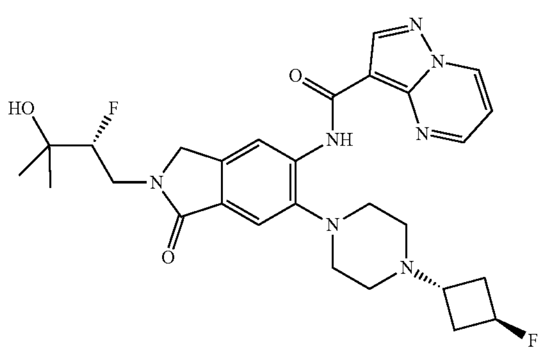 [SMILES: CC(C)(O)[C@H](F)CN1Cc2cc(NC(=O)c3cnn4cccnc34)c(N3CCN([C@H]4C[C@H](F)C4)CC3)cc2C1=O] | N-(2-((R)-2-Fluoro-3-hydroxy-3-methylbutyl)-6-(4-((1r,3R)-3-fluorocyclobutyl)piperazin-1-yl)-1-oxoisoindolin-5-yl)pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 129 & 130 | | N-(2-((R)-2-Fluoro-3-hydroxy-3-methylbutyl)-6-((S)-3-methyl-4-(oxetan-3-yl)piperazin-1-yl)-1-oxoisoindolin-5-yl)pyrazolo[1,5-a]pyrimidine-3-carboxamide & N-(2-((R)-2-Fluoro-3-hydroxy-3-methylbutyl)-6-((R)-3-methyl-4-(oxetan-3-yl)piperazin-1-yl)-1-oxoisoindolin-5-yl)pyrazolo[1,5-a]pyrimidine-3-carboxamide (absolute stereochemistry assigned arbitrarily) |
| 131 | 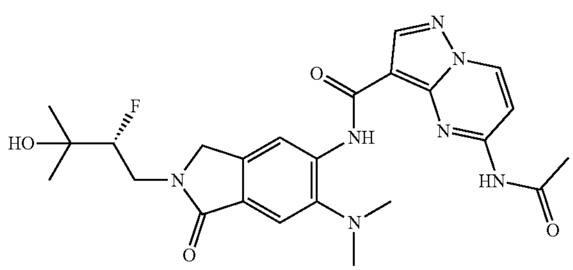 [SMILES: CC(=O)Nc1ccn2ncc(C(=O)Nc3cc4c(cc3N(C)C)C(=O)N(C[C@@H](F)C(C)(C)O)C4)c2n1] | (R)-5-Acetamido-N-(6-(dimethylamino)-2-(2-fluoro-3-hydroxy-3-methylbutyl)-1-oxoisoindolin-5-yl)pyrazolo[1,5-a]pyrimidine-3-carboxamide |
| 132 | 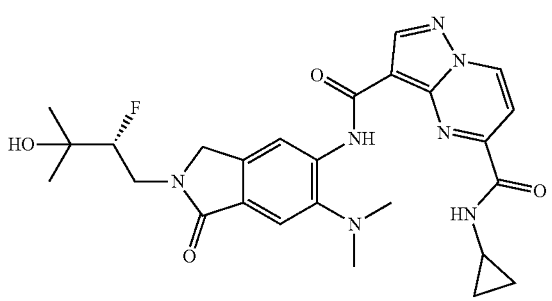 [SMILES: CN(C)c1cc2c(cc1NC(=O)c1cnn3ccc(C(=O)NC4CC4)nc13)CN(C[C@@H](F)C(C)(C)O)C2=O] | (R)-$N^5$-Cyclopropyl-$N^3$-(6-(dimethylamino)-2-(2-fluoro-3-hydroxy-3-methylbutyl)-1-oxoisoindolin-5-yl)pyrazolo[1,5-a]pyrimidine-3,5-dicarboxamide |
| 133 | 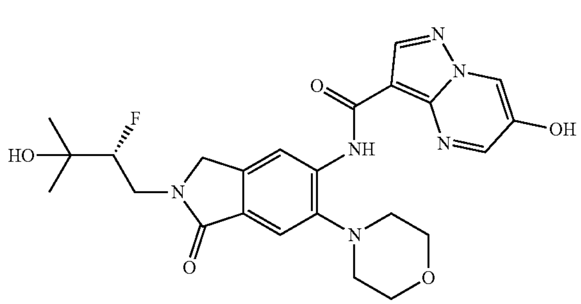 [SMILES: CC(C)(O)[C@H](F)CN1Cc2cc(NC(=O)c3cnn4cc(O)cnc34)c(N3CCOCC3)cc2C1=O] | (R)-N-(2-(2-Fluoro-3-hydroxy-3-methylbutyl)-6-morpholino-1-oxoisoindolin-5-yl)-6-hydroxypyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 134 | 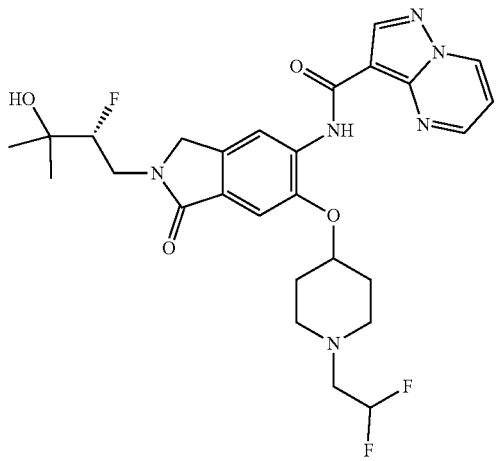 [SMILES: CC(C)(O)[C@H](F)CN1Cc2cc(NC(=O)c3cnn4cccnc34)c(OC3CCN(CC(F)F)CC3)cc2C1=O] | (R)-N-(6-((1-(2,2-Difluoroethyl)piperidin-4-yl)oxy)-2-(2-fluoro-3-hydroxy-3-methylbutyl)-1-oxoisoindolin-5-yl)pyrazolo[1,5-a]pyrimidine-3-carboxamide |
| 135 | 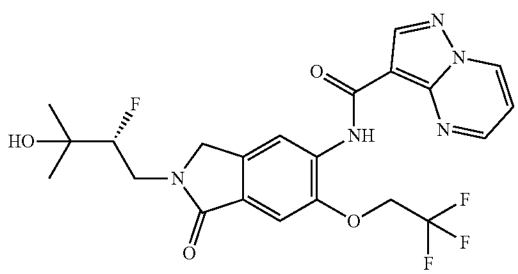 [SMILES: CC(C)(O)[C@H](F)CN1Cc2cc(NC(=O)c3cnn4cccnc34)c(OCC(F)(F)F)cc2C1=O] | (R)-N-(2-(2-Fluoro-3-hydroxy-3-methylbutyl)-1-oxo-6-(2,2,2-trifluoroethoxy)isoindolin-5-yl)pyrazolo[1,5-a]pyrimidine-3-carboxamide |
| 136 | 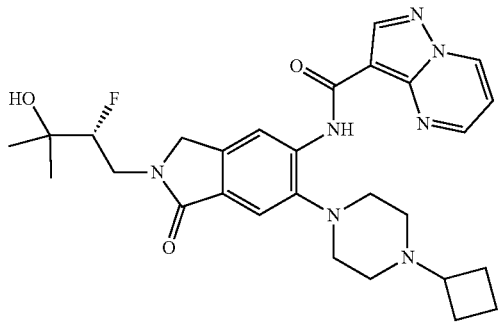 [SMILES: CC(C)(O)[C@H](F)CN1Cc2cc(NC(=O)c3cnn4cccnc34)c(N3CCN(C4CCC4)CC3)cc2C1=O] | (R)-N-(6-(4-Cyclobutylpiperazin-1-yl)-2-(2-fluoro-3-hydroxy-3-methylbutyl)-1-oxoisoindolin-5-yl)pyrazolo[1,5-a]pyrimidine-3-carboxamide |
| 137 | 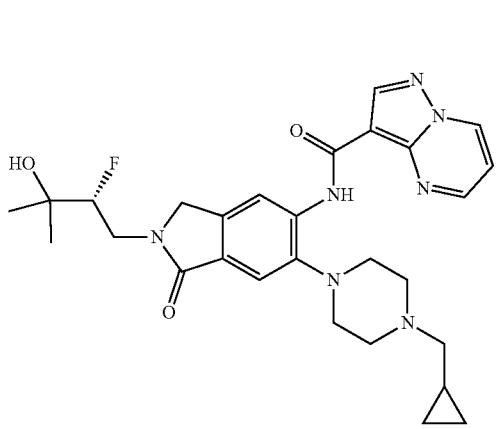 [SMILES: CC(C)(O)[C@H](F)CN1Cc2cc(NC(=O)c3cnn4cccnc34)c(N3CCN(CC4CC4)CC3)cc2C1=O] | N-[6-[4-(Cyclopropylmethyl)piperazin-1-yl]-2-[(2R)-2-fluoro-3-hydroxy-3-methyl-butyl]-1-oxo-isoindolin-5-yl]pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 138 | 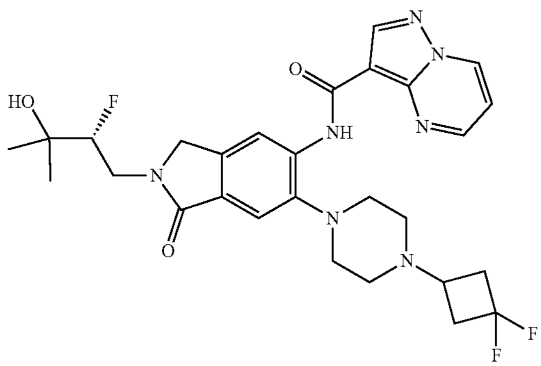 [SMILES: CC(C)(O)[C@H](F)CN1Cc2cc(NC(=O)c3cnn4cccnc34)c(N3CCN(C4CC(F)(F)C4)CC3)cc2C1=O] | (R)-N-(6-(4-(3,3-difluorocyclobutyl)piperazin-1-yl)-2-(2-fluoro-3-hydroxy-3-methylbutyl)-1-oxoisoindolin-5-yl)pyrazolo[1,5-a]pyrimidine-3-carboxamide |
| 139 | 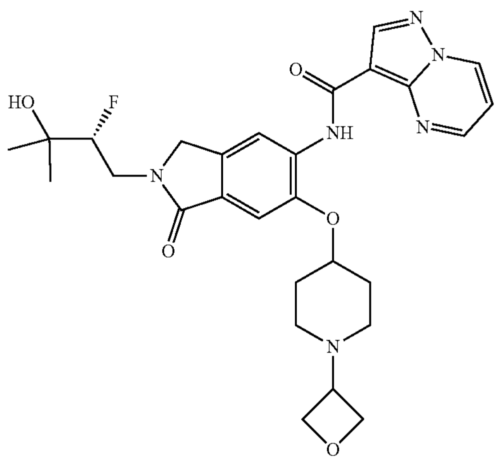 [SMILES: CC(C)(O)[C@H](F)CN1Cc2cc(NC(=O)c3cnn4cccnc34)c(OC3CCN(C4COC4)CC3)cc2C1=O] | (R)-N-(2-(2-Fluoro-3-hydroxy-3-methylbutyl)-6-((1-(oxetan-3-yl)piperidin-4-yl)oxy)-1-oxoisoindolin-5-yl)pyrazolo[1,5-a]pyrimidine-3-carboxamide |
| 140 & 141 | | N-[2-[(2R)-2-fluoro-3-hydroxy-3-methyl-butyl]-1-oxo-6-[4-[(3S)-tetrahydrofuran-3-yl]piperazin-1-yl]isoindolin-5-yl]pyrazolo[1,5-a]pyrimidine-3-carboxamide & N-[2-[(2R)-2-fluoro-3-hydroxy-3-methyl-butyl]-1-oxo-6-[4-[(3R)-tetrahydrofuran-3-yl]piperazin-1-yl]isoindolin-5-yl]pyrazolo[1,5-a]pyrimidine-3-carboxamide (absolute stereochemistry assigned arbitrarily) |

TABLE 1-continued

Exemplary compounds of the present invention. Salts of such compounds are also contemplated.
See the Examples section for preparation of such compounds.

| Example | Structure | Name |
|---|---|---|
| 142 | 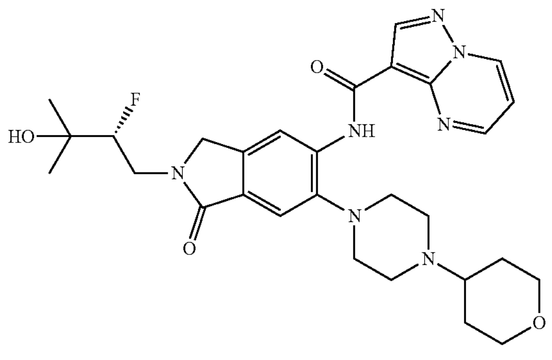 [SMILES: CC(C)(O)[C@H](F)CN1Cc2cc(NC(=O)c3cnn4cccnc34)c(N3CCN(C4CCOCC4)CC3)cc2C1=O] | N-[2-[(2R)-2-Fluoro-3-hydroxy-3-methyl-butyl]-1-oxo-6-(4-tetrahydropyran-4-ylpiperazin-1-yl)isoindolin-5-yl]pyrazolo[1,5-a]pyrimidine-3-carboxamide |
| 143 | 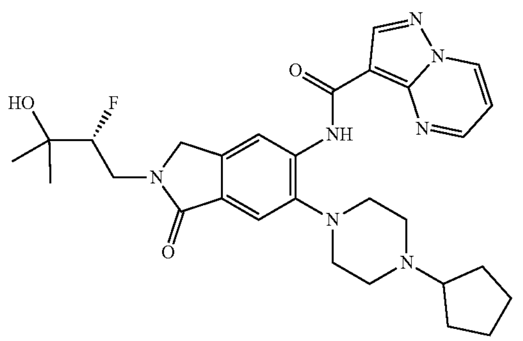 [SMILES: CC(C)(O)[C@H](F)CN1Cc2cc(NC(=O)c3cnn4cccnc34)c(N3CCN(C4CCCC4)CC3)cc2C1=O] | N-[6-(4-Cyclopentylpiperazin-1-yl)-2-[(2R)-2-fluoro-3-hydroxy-3-methyl-butyl]-1-oxo-isoindolin-5-yl]pyrazolo[1,5-a]pyrimidine-3-carboxamide |
| 144 | 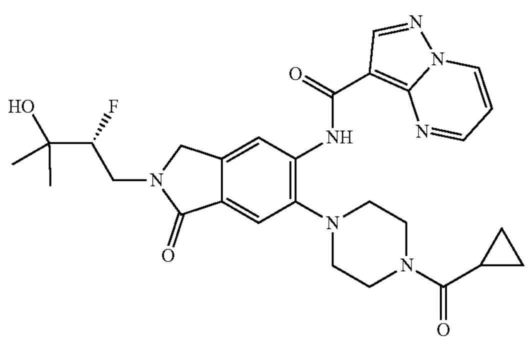 [SMILES: CC(C)(O)[C@H](F)CN1Cc2cc(NC(=O)c3cnn4cccnc34)c(N3CCN(C(=O)C4CC4)CC3)cc2C1=O] | N-[6-[4-(Cyclopropanecarbonyl)piperazin-1-yl]-2-[(2R)-2-fluoro-3-hydroxy-3-methyl-butyl]-1-oxo-isoindolin-5-yl]pyrazolo[1,5-a]pyrimidine-3-carboxamide |
| 145 | 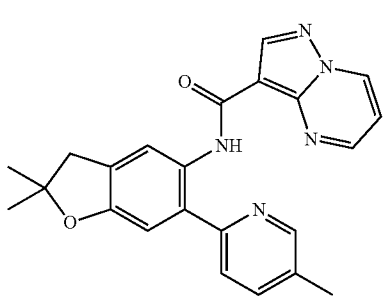 [SMILES: Cc1ccc(-c2cc3c(cc2NC(=O)c2cnn4cccnc24)CC(C)(C)O3)nc1] | N-[2,2-Dimethyl-6-(5-methyl-2-pyridyl)-3H-benzofuran-5-yl]pyrazolo[1,5-a]pyrimidine-3 carboxamide |

TABLE 1-continued

Exemplary compounds of the present invention. Salts of such compounds are also contemplated.
See the Examples section for preparation of such compounds.

| Example | Structure | Name |
|---|---|---|
| 146 | 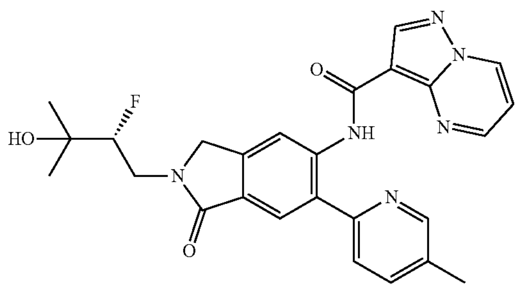 [SMILES: Cc1ccc(-c2cc3c(cc2NC(=O)c2cnn4cccnc24)CN(C[C@@H](F)C(C)(C)O)C3=O)nc1] | (R)-N-(2-(2-Fluoro-3-hydroxy-3-methylbutyl)-6-(5-methylpyridin-2-yl)-1-oxoisoindolin-5-yl)pyrazolo[1,5-a]pyrimidine-3-carboxamide |
| 147 | 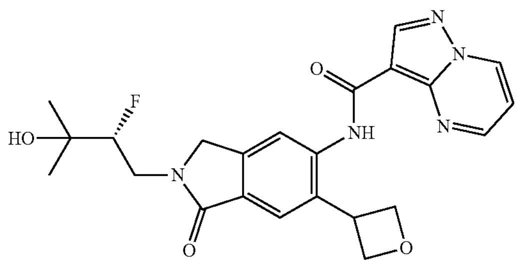 [SMILES: CC(C)(O)[C@H](F)CN1Cc2cc(NC(=O)c3cnn4cccnc34)c(C3COC3)cc2C1=O] | N-[2-[(2R)-2-Fluoro-3-hydroxy-3-methyl-butyl]-6-(oxetan-3-yl)-1-oxo-isoindolin-5-yl]pyrazolo[1,5-a]pyrimidine-3-carboxamide |
| 148 | 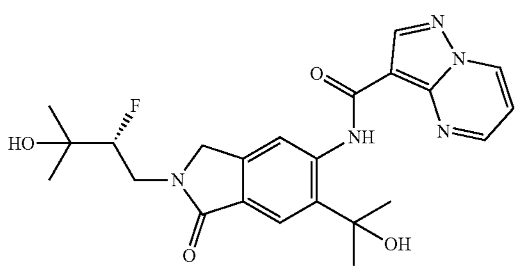 [SMILES: CC(C)(O)c1cc2c(cc1NC(=O)c1cnn3cccnc13)CN(C[C@@H](F)C(C)(C)O)C2=O] | (R)-N-(2-(2-Fluoro-3-hydroxy-3-methylbutyl)-6-(2-hydroxypropan-2-yl)-1-oxoisoindolin-5-yl)pyrazolo[1,5-a]pyrimidine-3-carboxamide |
| 149 | 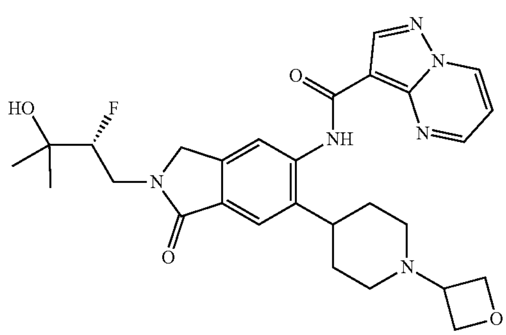 [SMILES: CC(C)(O)[C@H](F)CN1Cc2cc(NC(=O)c3cnn4cccnc34)c(C3CCN(C4COC4)CC3)cc2C1=O] | N-[2-[(2R)-2-Fluoro-3-hydroxy-3-methyl-butyl]-6-[1-(oxetan-3-yl)-4-piperidyl]-1-oxo-isoindolin-5-yl]pyrazolo[1,5-a]pyrimidine-3-carboxamide |
| 150 | 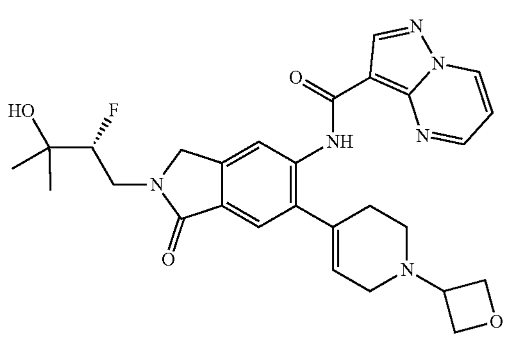 [SMILES: CC(C)(O)[C@H](F)CN1Cc2cc(NC(=O)c3cnn4cccnc34)c(C3=CCN(C4COC4)CC3)cc2C1=O] | N-[2-[(2R)-2-Fluoro-3-hydroxy-3-methyl-butyl]-6-[1-(oxetan-3-yl)-3,6-dihydro-2H-pyridin-4-yl]-1-oxo-isoindolin-5-yl]pyrazolo[1,5-a]pyrimidine-3-carboxamide |

TABLE 1-continued

Exemplary compounds of the present invention. Salts of such compounds are also contemplated.
See the Examples section for preparation of such compounds.

| Example | Structure | Name |
|---|---|---|
| 151 | 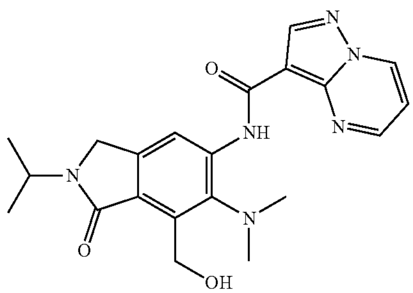 [SMILES: CC(C)N1Cc2cc(NC(=O)c3cnn4cccnc34)c(N(C)C)c(CO)c2C1=O] | N-(6-(Dimethylamino)-7-(hydroxymethyl)-2-isopropyl-1-oxoisoindolin-5-yl)pyrazolo[1,5-a]pyrimidine-3-carboxamide |
| 152 | 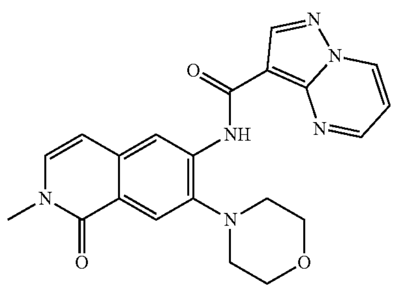 [SMILES: Cn1ccc2cc(NC(=O)c3cnn4cccnc34)c(N3CCOCC3)cc2c1=O] | N-(2-Methyl-7-morpholino-1-oxo-1,2-dihydroisoquinolin-6-yl)pyrazolo[1,5-a]pyrimidine-3-carboxamide |
| 153 | 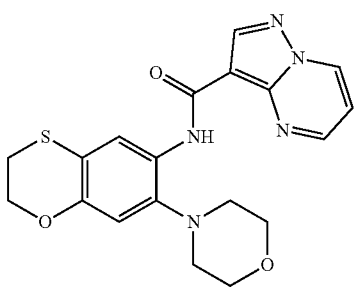 [SMILES: O=C(Nc1cc2c(cc1N1CCOCC1)OCCS2)c1cnn2cccnc12] | N-(7-Morpholino-2,3-dihydro-1,4-benzoxathiin-6-yl)pyrazolo[1,5-a]pyrimidine-3-carboxamide |
| 154 & 155 | | (S)-N-(2,2-Dimethyl-6-morpholino-1-oxido-2,3-dihydrobenzo[b]thiophen-5-yl)pyrazolo[1,5-a]pyrimidine-3-carboxamide & (R)-N-(2,2-Dimethyl-6-morpholino-1-oxido-2,3-dihydrobenzo[b]thiophen-5-yl)pyrazolo[1,5-a]pyrimidine-3-carboxamide (absolute stereochemistry assigned arbitrarily) |

TABLE 1-continued

Exemplary compounds of the present invention. Salts of such compounds are also contemplated.
See the Examples section for preparation of such compounds.

| Example | Structure | Name |
|---|---|---|
| 156 & 157 | 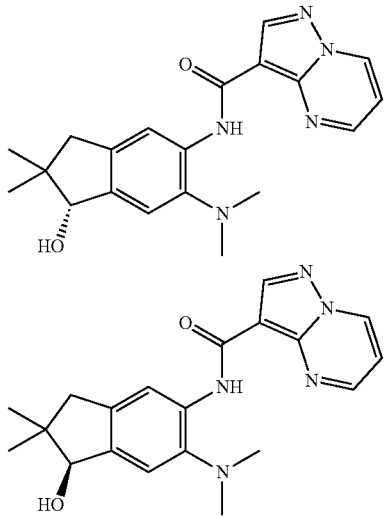 | N-[(1R)-6-(Dimethylamino)-1-hydroxy-2,2-dimethyl-indan-5-yl]pyrazolo[1,5-a]pyrimidine-3-carboxamide & N-[(1R)-6-(Dimethylamino)-1-hydroxy-2,2-dimethyl-indan-5-yl]pyrazolo[1,5-a]pyrimidine-3-carboxamide (absolute stereochemistry assigned arbitrarily) |

TABLE 2

Additional compounds of the present invention that are contemplated. Salts of such compounds are also contemplated.

| Example | Structure | Name |
|---|---|---|
| 158 | 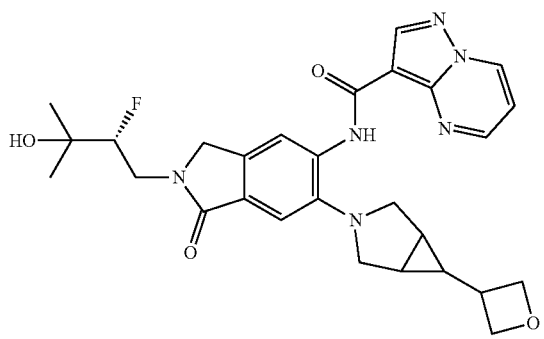 [SMILES: CC(C)(O)[C@H](F)CN1Cc2cc(NC(=O)c3cnn4cccnc34)c(N3CC4C(C3)C4C3COC3)cc2C1=O] | N-(2-((R)-2-fluoro-3-hydroxy-3-methylbutyl)-6-(6-(oxetan-3-yl)-3-azabicyclo[3.1.0]hexan-3-yl)-1-oxoisoindolin-5-yl)pyrazolo[1,5-a]pyrimidine-3-carboxamide |
| 159 | 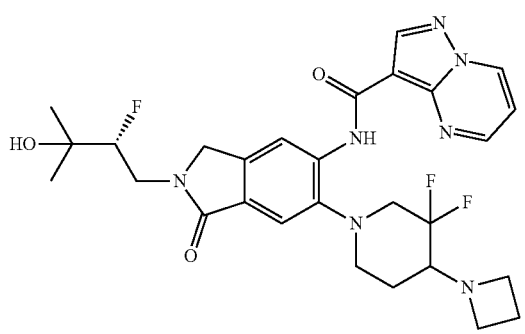 [SMILES: CC(C)(O)[C@H](F)CN1Cc2cc(NC(=O)c3cnn4cccnc34)c(N3CCC(N4CCC4)C(F)(F)C3)cc2C1=O] | N-(6-(4-(azetidin-1-yl)-3,3-difluoropiperidin-1-yl)-2-((R)-2-fluoro-3-hydroxy-3-methylbutyl)-1-oxoisoindolin-5-yl)pyrazolo[1,5-a]pyrimidine-3-carboxamide |

TABLE 2-continued

Additional compounds of the present invention that are contemplated. Salts of such compounds are also contemplated.

| Example | Structure | Name |
|---|---|---|
| 160 | 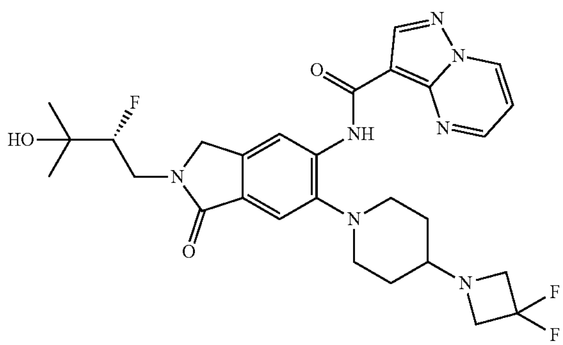 [SMILES: CC(C)(O)[C@H](F)CN1Cc2cc(NC(=O)c3cnn4cccnc34)c(N3CCC(N4CC(F)(F)C4)CC3)cc2C1=O] | (R)-N-(6-(4-(3,3-difluoroazetidin-1-yl)piperidin-1-yl)-2-(2-fluoro-3-hydroxy-3-methylbutyl)-1-oxoisoindolin-5-yl)pyrazolo[1,5-a]pyrimidine-3-carboxamide |
| 161 | 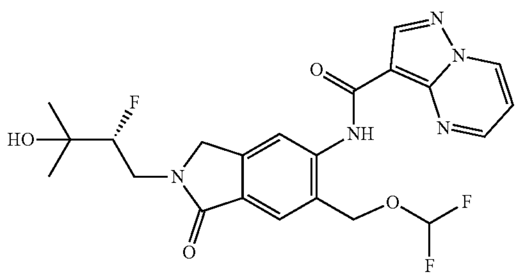 [SMILES: CC(C)(O)[C@H](F)CN1Cc2cc(NC(=O)c3cnn4cccnc34)c(COC(F)F)cc2C1=O] | (R)-N-(6-((difluoromethoxy)methyl)-2-(2-fluoro-3-hydroxy-3-methylbutyl)-1-oxoisoindolin-5-yl)pyrazolo[1,5-a]pyrimidine-3-carboxamide |
| 162 | 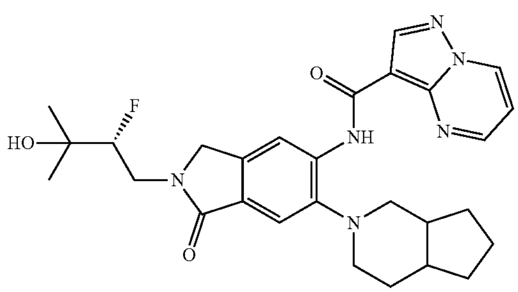 [SMILES: CC(C)(O)[C@H](F)CN1Cc2cc(NC(=O)c3cnn4cccnc34)c(N3CCC4CCCC4C3)cc2C1=O] | N-(2-((R)-2-fluoro-3-hydroxy-3-methylbutyl)-6-(octahydro-2H-cyclopenta[c]pyridin-2-yl)-1-oxoisoindolin-5-yl)pyrazolo[1,5-a]pyrimidine-3-carboxamide |
| 163 | 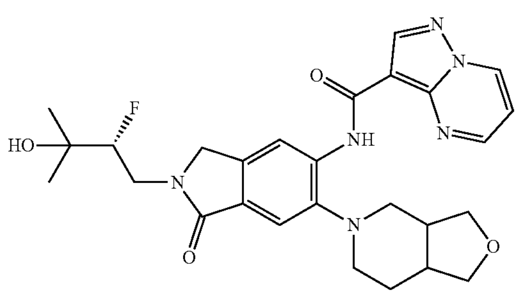 | N-(2-((R)-2-fluoro-3-hydroxy-3-methylbutyl)-6-(hexahydrofuro[3,4-c]pyridin-5(3H)-yl)-1-oxoisoindolin-5-yl)pyrazolo[1,5-a]pyrimidine-3-carboxamide |
| 164 | 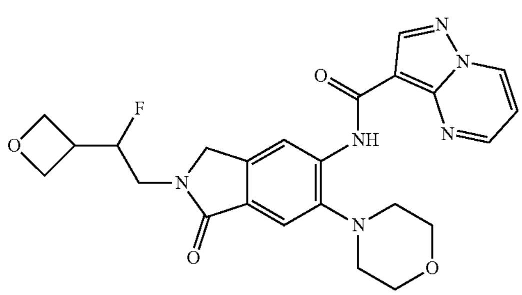 [SMILES: O=C(Nc1cc2c(cc1N1CCOCC1)C(=O)N(CC(F)C1COC1)C2)c1cnn2cccnc12] | N-(2-(2-fluoro-2-(oxetan-3-yl)ethyl)-6-morpholino-1-oxoisoindolin-5-yl)pyrazolo[1,5-a]pyrimidine-3-carboxamide |

TABLE 2-continued

Additional compounds of the present invention that are contemplated. Salts of such compounds are also contemplated.

| Example | Structure | Name |
| --- | --- | --- |
| 165 | 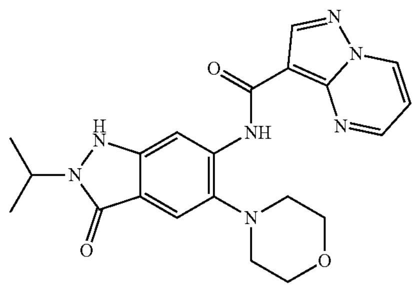 [SMILES: CC(C)n1[nH]c2cc(NC(=O)c3cnn4cccnc34)c(N3CCOCC3)cc2c1=O] | N-(2-isopropyl-5-morpholino-3-oxo-2,3-dihydro-1H-indazol-6-yl)pyrazolo[1,5-a]pyrimidine-3-carboxamide |

Synthesis of IRAK4 Inhibitors

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, vol. 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds.) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, vol. 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

For illustrative purposes, reaction Schemes below provide routes for synthesizing the compounds of the invention as well as key intermediates. For a more detailed description of the individual reaction steps, see the Examples section below. Those skilled in the art will appreciate that other synthetic routes may be used. Although some specific starting materials and reagents are depicted in the Schemes and discussed below, other starting materials and reagents can be substituted to provide a variety of derivatives or reaction conditions. In addition, many of the compounds prepared by the methods described below can be further modified in light of this disclosure using conventional chemistry well known to those skilled in the art.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, or, about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

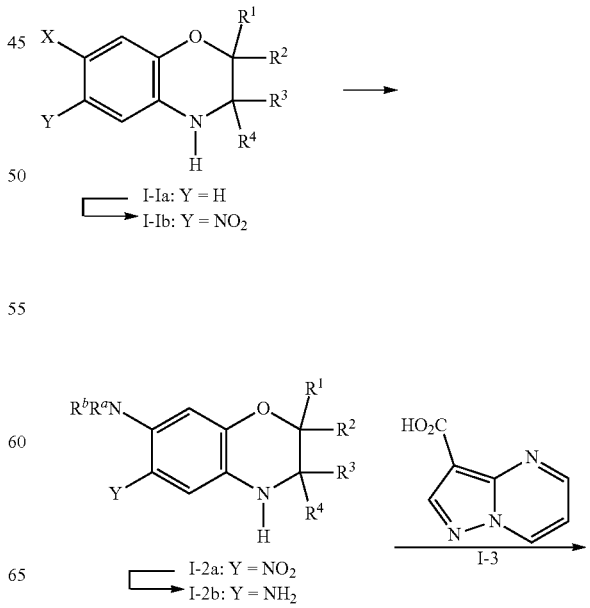

SCHEME I

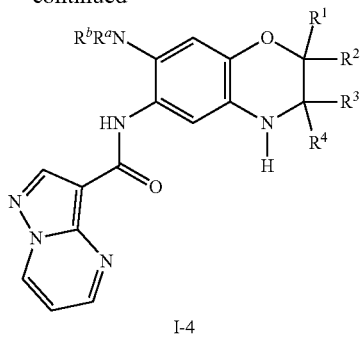

X = Cl or F; R¹, R², R³, R⁴ = H or Me, or R¹ and R² together are oxo

Regarding Scheme I, requisite 3,4-dihydro-2H-benzo[b][1,4]oxazin-6-yl derivatives can be prepared by nitration of 7-halo-3,4-dihydro-2H-benzo[b][1,4]oxazin-6-yl derivatives I-1a to afford I-1b followed by displacement of the halogen with an amine to afford I-2a. Typical amines include morpholine and 3-hydroxymethyl piperidine. Reduction of the nitro group and condensation with pyrazolo[1,5-a]pyrimidine-3-carboxylic acid (1-3), or an activated derivative thereof, affords the desired amides. The requisite precursors are commercially available or are prepared as described herein.

Aromatic nitration is well known and can be conducted under a variety of conditions known in the art. Nitration can be carried out, for example, by exposing an aromatic compound to concentrated nitric acid and sulfuric acid. Active substrates can be nitrated with $HNO_3$ alone or in $H_2O$, HOAc and acetic anhydride and active compounds may be oxidized by mixtures of $HNO_3$ and $H_2SO_4$. Other nitrating reagents include $NaNO_3$/TFA, $Cu(NO_3)_2$/HOAc/$Ac_2O$, $N_2O_4$, $NO_2^+BF_4^-$, $NO_2^+PF6^-$ and $NO_2^+CF_3SO^{4-}$. See, e.g., J. March, *Advanced Organic Chemistry*, John Wiley & Sons: New York, N.Y., 1992, pp. 522-23.

Reduction of the nitro group can be carried out with a variety of well-known reducing agents. For example, the nitro can be reduced under a hydrogen atmosphere in the presence of an inert solvent and in the presence of a metal effective to catalyze hydrogenation reactions such as platinum or palladium. The reduction can also be carried out with an activated metal such as activated iron, zinc or tin (produced for example by washing iron powder with a dilute acid solution such as dilute hydrochloric acid).

Coupling of the amine 2b intermediate with 3 is achieved with commonly used coupling reagents or, alternatively, 3 can be converted to the corresponding acid chloride and condensed with 2b.

Acylation of a primary amine with an acid chloride is typically carried out in an inert solvent such as DMF, DCM, THF, pyridine with or without water as a co-solvent, at temperatures between 0° C. and 60° C. generally in the presence of a base such as $Na_2CO_3$, $NaHCO_3$, $K_2CO_3$, DIPEA, TEA or pyridine and the like to afford the corresponding amide. Carboxylic acids can be converted into their acid chlorides using standard reagents well known to someone skilled in the art, such as thionyl chloride, oxalyl chloride, phosphoryl chloride and the like. Those reagents can be used in presence of bases such as DIPEA, TEA or pyridine.

Alternatively a carboxylic acid can be converted in situ into activated derivatives by utilizing reagents developed for peptide synthesis which are well known to those skilled in the art. These activated acids were reacted directly with the amines as described to afford the corresponding amide. Common coupling reagents include EDC, DCC, benzotriazol-1-yloxy-tris(dimethylamino)-phosphonium hexafluorophosphate (BOP), bromo-tris-pyrrolidinophosphonium hexafluorophosphate (PyBrOP), 2-fluoro-1-methylpyridinium p-toluenesulphonate (Mukaiyama's reagent), O-(7-azabenzotriazol-1-yl)-N,N,N',N'-tetramethyluronium hexafluorophosphate (HATU), 1-hydroxy-7-azabenzotriazole (HOAt) or (3-hydroxy-3H-1,2,3-triazolo[4,5-b]pyridinato-O)tri-1-pyrrolidinylphosphonium hexafluorophosphate (PyAOP) optionally in the presence of modifiers such as HOBt, with or without a base such NMM, TEA or DIPEA in an inert solvent such as DMF or DCM at temperatures between 0° C. and 60° C. Acylation of amines (see, e.g., J. March, supra pp. 417-425; H. G. Benz, *Synthesis of Amides and Related Compounds in Comprehensive Organic Synthesis*, E. Winterfeldt, ed., vol. 6, Pergamon Press, Oxford 1991 pp. 381-411; R. C. Larock, *Comprehensive Organic Transformations—A Guide to Functional Group Preparations*, 1989, VCH Publishers Inc., New York; pp. 972-976) has been reviewed.

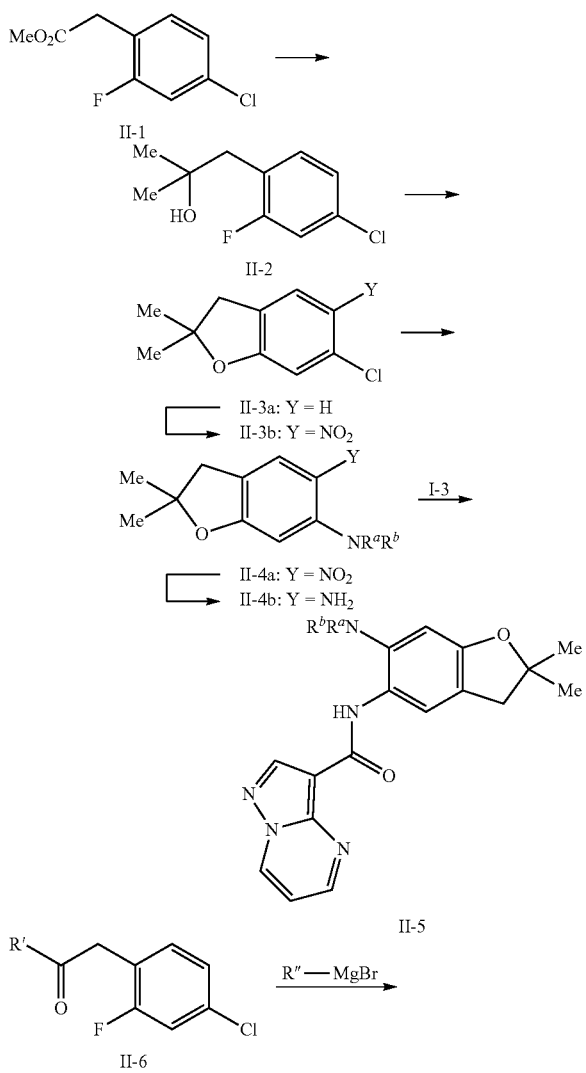

SCHEME II

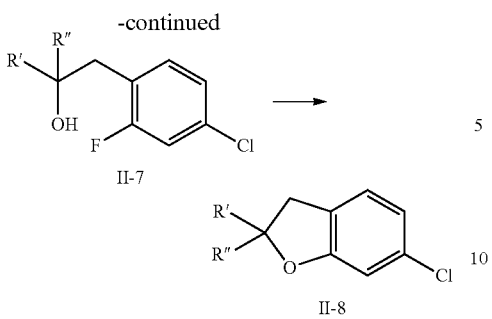

5,6-Diamino-2,2-dimethyl-3H-benzofuran derivatives exemplified herein can be prepared utilizing a 2,2-dimethyl-5-nitro-6-halo-3H-benzofuran II-3b as the key intermediate as depicted in Scheme II. Addition of a methyl Grignard to methyl 5-chloro-2-fluorophenylacetate affords the tertiary alcohol II-2 which undergoes an intra-molecular cyclization to afford the II-3a. Nitration and displacement of the chloride with an amine followed by reduction of the nitro and acylation with 1-3 is carried out in analogy with Scheme I. One skilled in the art will appreciate that the corresponding 5-fluoro and 5-bromo derivatives are readily available from methyl 2,5-difluorophenylacetate and methyl 5-bromo-2-fluorophenylacetate, respectively.

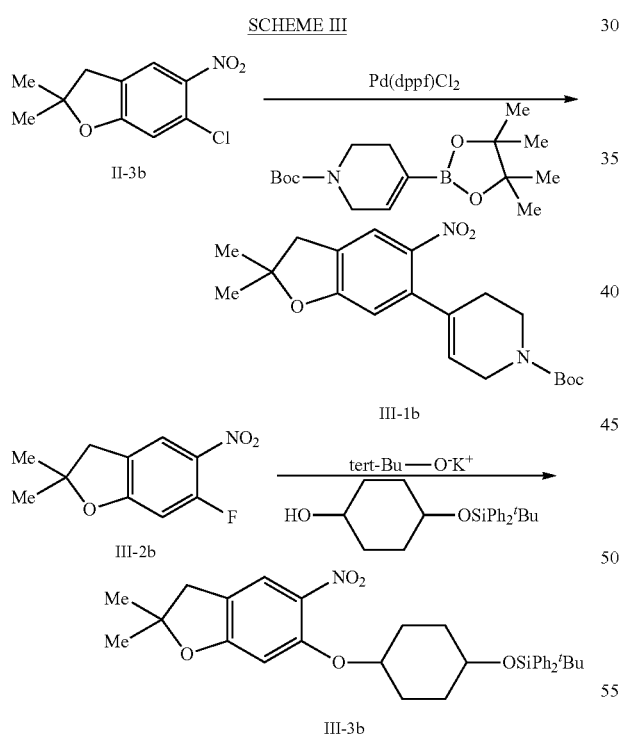

With respect to Scheme III, introduction of substituents other than amines at the 2-position can be easily accomplished by addition of an organometallic to 1-(4-chloro-2-fluorophenyl)propan-2-one, or a derivative thereof, and carry on further transformations as described herein. Compounds wherein the 5-amino-2,2-dimethyl-3H-benzofuran-6-yl moiety is linked to a substituent by a carbon-carbon bond were prepared by a palladium-catalyzed coupling of II-3b with a boric acid derivative or a boronic ester. Similarly ether substituents can be readily prepared by reacting 5-amino-2,2-dimethyl-6-fluoro-3H-benzofuran (III-2b) with a alcohol in the presence of potassium tert-butoxide or other suitable strong base. Subsequent reduction of the nitro group, acylation of the resulting amine and any subsequent deprotection which may be required are carried out using standard methodology.

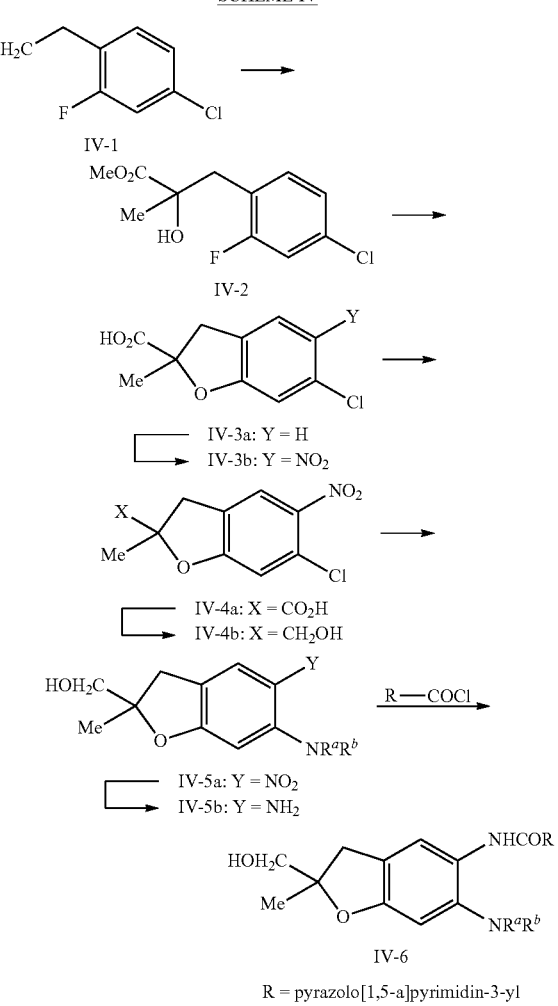

Compounds with a hydroxymethyl substituent attached to the dihydrofuran ring are accessible by condensation of 5-chloro-2-fluorobenzyl magnesium bromide with methyl pyruvate which afforded IV-2. (Scheme IV) Intramolecular cyclization and reduction of the pendant carboxylic acid affords IV-b which is transformed to the final compounds using protocols analogous to those previously described.

SCHEME V

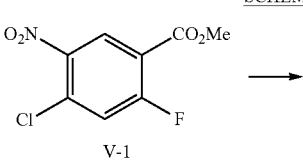

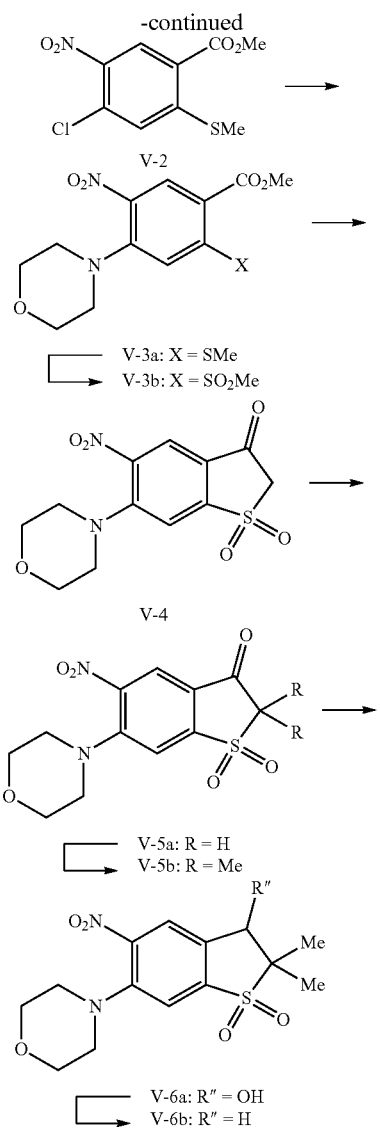

With respect to Scheme V, 3H-benzothiophene-1,1-dioxide derivatives can be prepared by intramolecular cyclization methyl 2-methylsulfonyl-4-morpholino-5-nitro-benzoate (V-3b) to afford morpholino-5-nitro-1,1-dioxobenzothiophen-3-one (V-4) which is subsequently reduced to V-6b utilizing a two-step sequence comprising sodium borohydride reduction followed by triethylsilane/TFA reduction that is carried on as previously described. Reduction of the nitro group and acylation of the resulting amine is carried out as described previously.

Methods of Treatment with and Uses of IRAK4 Inhibitors

Compounds of the present invention are useful as IRAK4 inhibitors. Accordingly, in one embodiment is provided a method of contacting a cell, such as an ex vivo cell, with a compound of the present invention to inhibit IRAK4 activity in the cell.

Also provided is a pharmaceutical composition comprising a compound of Formula I, Formula II, Formula III, Formula IV, Formula V, Formula VI, Formula VII, Formula VIII, or a stereoisomer or pharmaceutically acceptable salt thereof, and a pharmaceutically acceptable excipient, carrier or diluent. Compounds of the invention, including pharmaceutical compositions comprising such compounds, may be used in the methods described herein.

Further provided is a method of preventing, treating, or lessening the severity of a disease or condition responsive to the inhibition of IRAK4 in a patient, comprising administering to the patient a therapeutically effective amount of a compound of the present invention, or a stereoisomer or pharmaceutically acceptable salt thereof.

Also provided is a method for treating cancer in a patient, comprising administering to the patient a therapeutically effective amount of a compound of the present invention, or a stereoisomer or pharmaceutically acceptable salt thereof.

Further provided is a method for treating an inflammatory or autoimmune disease in a patient, comprising administering to the patient a therapeutically effective amount of a compound of the present invention, or a stereoisomer or pharmaceutically acceptable salt thereof. In some embodiments, the disease is selected from the group consisting of Crohn's disease, ulcerative colitis, inflammatory bowel disease (IBD), asthma, graft versus host disease, allograft rejection, chronic obstructive pulmonary disease (COPD), rheumatoid arthritis, systemic lupus erythematosus, lupus nephritis, cutaneous lupus, psoriasis, systemic onset juvenile idiopathic arthritis, multiple sclerosis, neuropathic pain, gout, and gouty arthritis.

In some embodiments, other diseases and conditions responsive to the inhibition of IRAK4 that can be treated using a compound of the present invention include metabolic syndromes, atherosclerosis, and neurodegeneration.

Further provided is the use of a compound of the present invention, or a stereoisomer or pharmaceutically acceptable salt thereof, in therapy. In some embodiments, use of a compound of the present invention, or a stereoisomer or pharmaceutically acceptable salt thereof, is provided in the treatment of an inflammatory disease. In some embodiments, use of a compound of the present invention, or a stereoisomer or pharmaceutically acceptable salt thereof, is provided for the preparation of a medicament for the treatment of an inflammatory disease. Furthermore, in some embodiments, a compound of the present invention, or a stereoisomer or pharmaceutically acceptable salt thereof, is provided for use in the treatment of an inflammatory disease.

In some embodiments, a disease or condition that may be treated is selected from the group consisting of acute kidney injury, acute respiratory distress syndrome, acute lung injury, adult onset Still's disease, allergic airway syndrome, allergic rhinitis, allograft rejection, asthma, atherosclerosis, atopic dermatitis, bronchitis, calcium pyrophosphate deposition disease (CPPD) also known as pseudo gout, cerebrovascular accident (e.g., stroke), chronic kidney disease, chronic obstructive pulmonary disease (COPD), contact dermatitis, Crohn's disease, cryopyrin-associated periodic syndromes (CAPS), cutaneous lupus, delayed hypersensitivity, diabetes, endometriosis, gout, gouty arthritis, graft vs host disease, graft rejection, inflammatory bowel disease (IBD), inflammatory myositis (e.g., polymyositis, dermatomyositis), interstitial lung disease, lupus, lupus nephritis, metabolic syndrome, multiple sclerosis, neurodegeneration, neuropathic pain, non-alcoholic fatty liver disease, obesity, psoriasis, rheumatoid arthritis, rhinitis, scleroderma, sepsis, Sjogren's syndrome, systemic lupus erythematosus, systemic onset juvenile idiopathic arthritis, systemic sclerosis and ulcerative colitis.

Also provided is a method of inhibiting IRAK4 in a patient in need of therapy, comprising administering to the patient a compound of the present invention.

Dosage & Administration

The present invention provides pharmaceutical compositions or medicaments containing the compounds of the invention and at least one therapeutically inert carrier, diluent or excipient, as well as methods of using the compounds of the invention to prepare such compositions and medicaments. In one example, compounds of Formula I, Formula II, Formula III, Formula IV, Formula V, Formula VI, Formula VII, Formula VIII, or a stereoisomer or pharmaceutically acceptable salt thereof, with the desired degree of purity may be formulated by mixing with physiologically acceptable carriers, i.e., carriers that are non-toxic to recipients at the dosages and concentrations employed into a dosage form at ambient temperature and at the appropriate pH. The pH of the formulation depends mainly on the particular use and the concentration of compound, but typically ranges anywhere from about 3 to about 8. In one example, a compound of Formula I, Formula II, Formula III, Formula IV, Formula V, Formula VI, Formula VII, Formula VIII is formulated in an acetate buffer, at pH 5. In another embodiment, the compounds of Formula I, Formula II, Formula III, Formula IV, Formula V, Formula VI, Formula VII, Formula VIII are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the severity of the disorder, the particular patient being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit IRAK4 activity. Typically such amount may be below the amount that is toxic to normal cells, or the patient as a whole.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Sustained-release preparations may be prepared. Suitable examples of sustained-release preparations include semipermeable matrices of solid hydrophobic polymers containing a compound of Formula I, Formula II, Formula III, Formula IV, Formula V, Formula VI, Formula VII, Formula VIII, or a stereoisomer or pharmaceutically acceptable salt thereof, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

A dose to treat human patients may range from about 0.1 mg to about 1000 mg of a compound of Formula I, Formula II, Formula III, Formula IV, Formula V, Formula VI, Formula VII, Formula VIII, or a stereoisomer or pharmaceutically acceptable salt thereof. A typical dose may be about 1 mg to about 300 mg of the compound. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal, epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, H. C., et al., Ansel's *Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, R. C., *Handbook of Pharmaceutical Excipients*, Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

For oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

An example of a suitable oral dosage form is a tablet containing about 25 mg, 50 mg, 100 mg, 250 mg or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such as sodium chloride, if desired. The solution may be filtered, e.g., using a 0.2 micron filter, to remove impurities and contaminants.

In one embodiment, the pharmaceutical composition also includes at least one additional anti-proliferative agent.

An embodiment, therefore, includes a pharmaceutical composition comprising a compound of Formula I, Formula II, Formula III, Formula IV, Formula V, Formula VI, Formula VII, Formula VIII, or a stereoisomer or pharmaceutically acceptable salt thereof. A further embodiment includes a pharmaceutical composition comprising a compound of Formula I, Formula II, Formula III, Formula IV, Formula V, Formula VI, Formula VII, Formula VIII, or a stereoisomer or pharmaceutically acceptable salt thereof, together with a pharmaceutically acceptable carrier or excipient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I, Formula II, Formula III, Formula IV, Formula V, Formula VI, Formula VII, Formula VIII may be employed alone or in combination with other therapeutic agents for the treatment of a disease or disorder described herein. The second compound of the pharmaceutical combination formulation or dosing regimen preferably has complementary activities to the compound of Formula I, Formula II, Formula III, Formula IV, Formula V, Formula VI, Formula VII, Formula VIII such that they do not adversely affect each other. The combination therapy may provide "synergy" and prove "synergistic", i.e., the effect achieved when the active ingredients used together is greater than the sum of the effects that results from using the compounds separately.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Combination therapies according to the present invention thus comprise the administration of at least one compound of Formula I, Formula II, Formula III, Formula IV, Formula V, Formula VI, Formula VII, Formula VIII, or a stereoisomer or pharmaceutically acceptable salt thereof, and the use of at least one other treatment method. The amounts of the compound(s) of Formula I, Formula II, Formula III, Formula IV, Formula V, Formula VI, Formula VII, Formula VIII and the other pharmaceutically active agent(s) and the relative timings of administration will be selected in order to achieve the desired combined therapeutic effect.

In some embodiments, a second agent that may be employed in combination therapy with a compound described herein may be an inhibitor of Bruton's tyrosine kinase (BTK), such as a small molecule BTK inhibitor. In some embodiments, the second agent may be prednisone.

Articles of Manufacture

In another embodiment of the invention, an article of manufacture, or "kit", containing materials useful for the treatment of the diseases and disorders described above is provided. In one embodiment, the kit comprises a container comprising a compound of Formula I, Formula II, Formula III, Formula IV, Formula V, Formula VI, Formula VII, Formula VIII, or a stereoisomer or pharmaceutically acceptable salt thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I, Formula II, Formula III, Formula IV, Formula V, Formula VI, Formula VII, Formula VIII or a formulation thereof which is effective for treating the condition and may have a sterile access port (for example, the container may be an intravenous solution bag or a vial having a stopper pierceable by a hypodermic injection needle). At least one active agent in the composition is a compound of Formula I, Formula II, Formula III, Formula IV, Formula V, Formula VI, Formula VII, Formula VIII. Alternatively, or additionally, the article of manufacture may further comprise a second container comprising a pharmaceutical diluent, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, the kits are suitable for the delivery of solid oral forms of a compound of Formula I, Formula II, Formula III, Formula IV, Formula V, Formula VI, Formula VII, Formula VIII, such as tablets or capsules. Such a kit can include a number of unit dosages. An example of such a kit is a "blister pack". Blister packs are well known in the packaging industry and are widely used for packaging pharmaceutical unit dosage forms.

Examples

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

The following non-limiting group of intermediates are useful for preparing compounds according to the present invention.

Intermediate A. 6-Chloro-2,2-dimethyl-5-nitro-3H-benzofuran

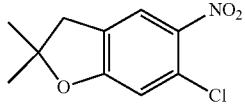

Step A. Methyl 2-(4-chloro-2-fluoro-phenyl)acetate

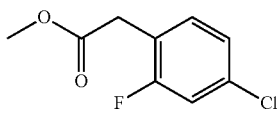

A mixture of 2-(4-chloro-2-fluoro-phenyl)acetic acid (8.4 g, 44.5 mmol) and concentrated sulfuric acid (3.0 mL) in methanol (50 mL) was stirred at reflux for 18 h. After concentration under reduced pressure, the residue was dissolved in dichloromethane (200 mL). The organic phase was washed with a saturated sodium bicarbonate solution and brine and dried over sodium sulfate. After filtration and concentration under reduced pressure, crude methyl 2-(4-chloro-2-fluoro-phenyl)acetate (7.6 g) was afforded as a yellow oil, which was used without further purification. MS (ESI): m/z=203.1 [M+1]$^+$.

Step B. 1-(4-Chloro-2-fluoro-phenyl)-2-methyl-propan-2-ol

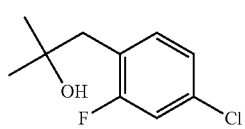

To a solution of methyl 2-(4-chloro-2-fluoro-phenyl)acetate (7.6 g, 37.5 mmol) in anhydrous tetrahydrofuran (70 mL) was added methyl magnesium bromide (3M in ethyl ether, 37.5 mL, 113 mmol) drop wise at −78° C. The reaction was warmed to room temperature, stirred for 30 min and quenched with a saturated ammonium chloride solution. The aqueous phase was extracted with ethyl acetate (2×200 mL). The combined organic phases were washed with brine, dried over sodium sulfate, filtered and concentrated under reduced pressure to afford 1-(4-chloro-2-fluoro-phenyl)-2-methyl-propan-2-ol (6.9 g) as a yellow oil, which was used without further purification. MS (ESI): m/z=185.1 [M-OH]$^+$.

Step C. 6-Chloro-2,2-dimethyl-3H-benzofuran

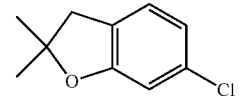

A mixture of 1-(4-chloro-2-fluoro-phenyl)-2-methyl-propan-2-ol (6.9 g, 34.05 mmol) and potassium tert-butanolate (9.55 g, 85.12 mmol) in tetrahydrofuran (170 mL) was stirred at 65° C. for 18 h. The reaction was acidified to pH 3 with a 1 N hydrochloric acid solution. Ethyl acetate (200 mL) was added and the organic phase was separated and dried over sodium sulfate. After filtration and concentration under reduced pressure, the residue was purified by silica gel chromatography (eluting gradient: 1:20 to 1:10 ethyl acetate: petroleum ether) to afford 6-chloro-2,2-dimethyl-3H-benzofuran (4.3 g, 69%) as a colorless oil. $^1$H NMR (400 MHz, CDCl$_3$): δ 6.99 (d, J=8.0 Hz, 1H), 6.75 (d, J=8.0 Hz, 1H), 6.88 (s, 1H), 2.93 (s, 2H), 1.44 (s, 6H).

Step D. 6-Chloro-2,2-dimethyl-5-nitro-3H-benzofuran

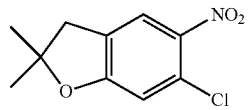

To a solution of 6-chloro-2,2-dimethyl-3H-benzofuran (4.3 g, 23.54 mmol) in dichloromethane (45 mL) at 25° C. was slowly added fuming nitric acid (4.5 mL). Upon consumption of starting material, water and ethyl acetate (100 mL) were added. The organic phase was separated and dried over sodium sulfate. After filtration and concentration under reduced pressure, 6-chloro-2,2-dimethyl-5-nitro-3H-benzofuran (5.0 g) was afforded as an orange solid, which was used without further purification. $^1$H NMR (400 MHz, CDCl$_3$): δ 7.84 (s, 1H), 6.83 (s, 1H), 3.04 (s, 2H), 1.52 (s, 6H).

Intermediate B. (6-Chloro-2-methyl-5-nitro-2,3-dihydrobenzofuran-2-yl)methanol

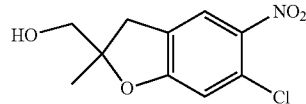

Step A. Methyl 3-(4-chloro-2-fluoro-phenyl)-2-hydroxy-2-methyl-propanoate

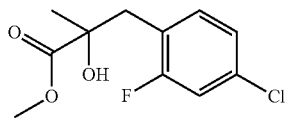 [SMILES: COC(=O)C(C)(O)Cc1ccc(Cl)cc1F]

To a solution of magnesium (1.35 g, 56.3 mmol) and iodine (100 mg, 0.39 mmol) in diethyl ether (50 mL) heated at reflux was added 1-(bromomethyl)-4-chloro-2-fluoro-benzene (5.0 g, 22.4 mmol) dropwise. The reaction was stirred for 30 min. The solution was then added to a solution of methyl pyruvate (2.3 g, 22.5 mmol) in diethyl ether (50 mL) at −78° C. and stirred for 30 min followed by warming to room temperature for 2 h. Saturated aqueous ammonium chloride and ethyl acetate (200 mL) were added, and the organic phase was separated and dried over sodium sulfate. The mixture was filtered, and the filtrate was concentrated under reduced pressure. The residue was purified by silica gel chromatography (eluting gradient 1:20 to 1:10 ethyl acetate:petroleum ether) to afford methyl 3-(4-chloro-2-fluoro-phenyl)-2-hydroxy-2-methyl-propanoate (2.8 g, 51%) as a yellow oil. $^1$H NMR (400 MHz, CDCl$_3$): δ 7.33-7.25 (m, 1H), 7.18-7.09 (m, 2H), 3.73 (s, 3H), 3.03 (s, 2H), 1.39 (s, 3H).

Step B.
6-Chloro-2-methyl-3H-benzofuran-2-carboxylic acid

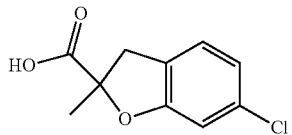

A mixture of methyl 3-(4-chloro-2-fluoro-phenyl)-2-hydroxy-2-methyl-propanoate (493 mg, 2 mmol) and potassium tert-butanolate (561 mg, 5 mmol) in tetrahydrofuran (10 mL) was stirred at 60° C. for 18 h. After cooling to room temperature, water and a 1 N hydrochloric acid solution were added until pH=3. Ethyl acetate (20 mL) was added, and the organic phase was separated and dried over sodium sulfate. The reaction was filtered and the filtrate was concentrated under reduced pressure. The residue was purified by silica gel chromatography (eluting gradient 1:1 to 2:1 ethyl acetate:petroleum ether) to afford 6-chloro-2-methyl-3H-benzofuran-2-carboxylic acid (271 mg, 64%) as a yellow solid. $^1$H NMR (400 MHz, CDCl$_3$) δ 10.95-10.24 (m, 1H), 7.04 (d, J=8.0 Hz, 1H), 6.87 (dd, J=1.6, 9.2 Hz, 1H), 6.85 (s, 1H), 3.59 (d, J=16 Hz, 1H), 3.13 (d, J=16 Hz, 1H), 1.73, (s, 3H).

Step C. 6-Chloro-2-methyl-5-nitro-3H-benzofuran-2-carboxylic acid

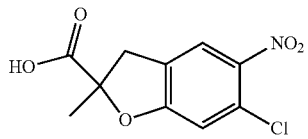 [SMILES: CC1(C(=O)O)Cc2cc([N+](=O)[O-])c(Cl)cc2O1]

To a solution of 6-chloro-2-methyl-3H-benzofuran-2-carboxylic acid (230 mg, 1.08 mmol) in dichloromethane (10 mL) at 25° C. was slowly added fuming nitric acid (0.5 mL). The resulting solution was stirred for 5 min. Water and ethyl acetate (20 mL) were added, and the organic phase was separated and dried over sodium sulfate. The mixture was filtered, and the filtrate was concentrated under reduced pressure. The residue was purified by silica gel chromatography (eluting gradient 1:4 to 1:3 ethyl acetate:petroleum ether) to afford 6-chloro-2-methyl-5-nitro-3H-benzofuran-2-carboxylic acid (150 mg, 54%) as an orange solid. $^1$H NMR (400 MHz, CDCl$_3$) δ 7.84 (s, 1H), 6.99 (s, 1H), 3.68 (d, J=16.8 Hz, 1H), 3.23 (d, J=16.8 Hz, 1H), 1.80 (s, 3H).

Step D. (6-Chloro-2-methyl-5-nitro-3H-benzofuran-2-yl)methanol

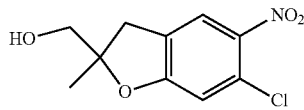

A mixture of 6-chloro-2-methyl-5-nitro-3H-benzofuran-2-carboxylic acid (1.93 g, 7.5 mmol) and borane (1 M in tetrahydrofuran, 14.0 ml, 14 mmol) in tetrahydrofuran (75 mL) was stirred at 25° C. for 2 h. Methanol (10 mL) was slowly added, and the reaction was concentrated under reduced pressure. The residue was purified by silica gel chromatography (eluting 1:1 ethyl acetate:petroleum ether) to afford (6-chloro-2-methyl-5-nitro-3H-benzofuran-2-yl)methanol (580 mg, 32%) as a yellow oil. $^1$H NMR (400 MHz, dimethyl sulfoxide-d$_6$): δ 7.84 (s, 1H), 6.99 (s, 1H), 6.60-5.80 (m, 1H), 3.68 (d, J=16.8 Hz, 1H), 3.23 (d, J=16.8 Hz, 1H), 1.80 (s, 3H). MS (ESI): m/z=244.1 [M+1]$^+$.

Intermediate C. tert-Butyl 6-fluoro-5-nitro-spiro[3H-benzofuran-2,4'-piperidine]-1'-carboxylate

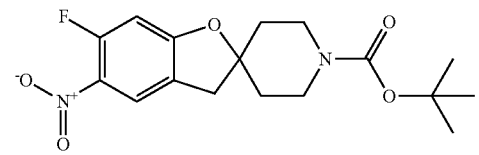

Step A. tert-Butyl 4-[(2,4-difluorophenyl)methyl]-4-hydroxy-piperidine-1-carboxylate

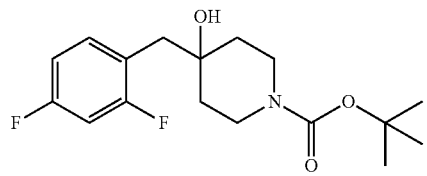 [SMILES: CC(C)(C)OC(=O)N1CCC(O)(Cc2ccc(F)cc2F)CC1]

To magnesium (2.40 g, 100 mmol) and iodine (180 mg, 0.71 mmol) in diethyl ether (25 mL) at reflux was added 1-(bromomethyl)-2,4-difluorobenzene (8.20 g, 39.6 mmol) slowly and the mixture was stirred for 30 min. The mixture was then added to a solution of tert-butyl 4-oxopiperidine-1-carboxylate (6.50 g, 32.6 mmol) in diethyl ether (200 mL) at −78° C. and the reaction was stirred room temperature for 2 h. Water and ethyl acetate (200 mL) were added and the organic layer was separated and dried over sodium sulfate. After concentration under reduced pressure, the residue was purified by silica gel chromatography (eluting gradient 1:4 to 1:2 ethyl acetate:petroleum ether) to afford tert-butyl 4-[(2,4-difluorophenyl)methyl]-4-hydroxy-piperidine-1-carboxylate (9.50 g, 73%) as a white solid. MS (ESI): m/z=350.1 [M+23]$^+$.

Step B. tert-Butyl 6-fluorospiro[3H-benzofuran-2,4'-piperidine]-1'-carboxylate

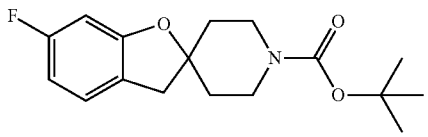 [SMILES: CC(C)(C)OC(=O)N1CCC2(CC1)Cc1ccc(F)cc1O2]

A mixture of tert-butyl 4-[(2,4-difluorophenyl)methyl]-4-hydroxy-piperidine-1-carboxylate (491 mg, 1.5 mmol) and potassium tert-butanolate (420 mg, 3.75 mmol) in tetrahydrofuran (30 mL) was stirred at 65° C. for 3 h. Water was added and the reaction was extracted with ethyl acetate (60 mL). The organic phase was isolated, dried over sodium sulfate and concentrated to afford tert-butyl 6-fluorospiro[3H-benzofuran-2,4'-piperidine]-1'-carboxylate (409 mg) as a yellow solid, which was used without further purification. MS (ESI): m/z=252.2 [M-55]$^+$.

Step C. 6-Fluorospiro[3H-benzofuran-2,4'-piperidine]

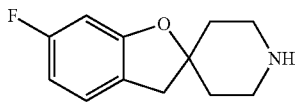 [SMILES: Fc1ccc2c(c1)OC1(CCNCC1)C2]

To a solution of tert-butyl 6-fluorospiro[3H-benzofuran-2,4'-piperidine]-1'-carboxylate (270 mg, 0.88 mmol) in dichloromethane (9 mL), was added trifluoroacetic acid (1 mL). The reaction was stirred for 2 h at room temperature. Saturated sodium bicarbonate solution was added to neutralize the reaction to pH 7 and the mixture was extracted with dichloromethane (20 mL×2). The combined organic phases were washed with saturated brine and dried over anhydrous magnesium sulfate. After removal of the solvent, it was afforded 6-fluorospiro[3H-benzofuran-2,4'-piperidine] (189 mg) as a yellow solid, which was used without further purification. MS (ESI): m/z=208.2 [M+1]$^+$.

Step D. 6-Fluoro-5-nitro-spiro[3H-benzofuran-2,4'-piperidine]

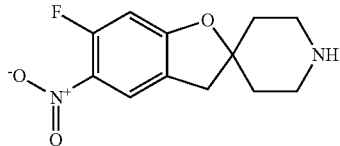

To a solution of 6-fluorospiro[3H-benzofuran-2,4'-piperidine] (171 mg, 0.83 mmol) in dichloromethane (10 mL) was added concentrated nitric acid (0.5 mL, 8 mmol). The reaction was stirred at 25° C. for 1 h. Water was added followed by saturated sodium bicarbonate to neutralize the reaction. The mixture was extracted with dichloromethane (50 mL), the organic phase was dried over sodium sulfate and concentrated in vacuo to afford 6-fluoro-5-nitro-spiro[3H-benzofuran-2,4'-piperidine] (135 mg) as a yellow solid, which was used without further purification. MS (ESI): m/z=253.2 [M+1]$^+$.

Step E. tert-Butyl 6-fluoro-5-nitro-spiro[3H-benzofuran-2,4'-piperidine]-1'-carboxylate

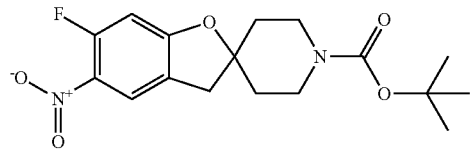

A mixture of 6-fluoro-5-nitro-spiro[3H-benzofuran-2,4'-piperidine] (135 mg, 0.54 mmol), triethylamine (108 mg, 1.07 mmol) and di-tert-butyl dicarbonate (80.3 mg, 0.80 mmol) was stirred at room temperature for 2 h. The reaction was then concentrated in vacuo to obtained tert-butyl 6-fluoro-5-nitro-spiro[3H-benzofuran-2,4'-piperidine]-1'-carboxylate (270 mg) as a yellow solid, which was used without further purification. MS (ESI): m/z=297.1 [M-55]$^+$.

Intermediate D. N-(2,2-Dimethyl-6-(piperazin-1-yl)-2,3-dihydrobenzofuran-5-yl)pyrazolo[1,5-a]pyrimidine-3-carboxamide

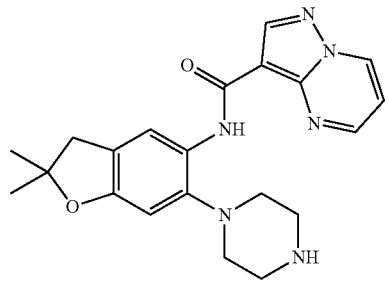 [SMILES: CC1(C)Cc2cc(NC(=O)c3cnn4cccnc34)c(N3CCNCC3)cc2O1]

Step A. tert-Butyl 4-(2,2-dimethyl-5-nitro-2,3-dihydrobenzofuran-6-yl)piperazine-1-carboxylate

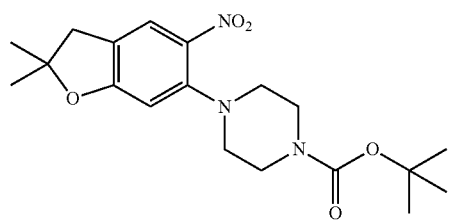

To a solution of tert-butyl 1-piperazinecarboxylate (2.70 g, 14.5 mmol) and 6-chloro-2,2-dimethyl-5-nitro-3H-benzofuran (Intermediate A, 3.00 g, 13.2 mmol) in acetonitrile (30 mL) was added potassium carbonate (5.5 g, 39.5 mmol). The mixture was stirred at 100° C. for 2 h.

The reaction mixture was diluted with water (50 mL) and extracted with dichloromethane (50 mL×3). The organics were washed with brine (50 mL×2), dried over sodium sulfate, filtered and concentrated. The residue was purified by flash chromatography (solvent gradient: 0-30% ethyl acetate in petroleum ether) to afford tert-butyl 4-(2,2-dimethyl-5-nitro-3H-benzofuran-6-yl)piperazine-1-carboxylate (4.2 g, 11.1 mmol, 84.4% yield) as a white solid. MS (ESI): m/z=378.2 [M+H]⁺.

Step B. tert-Butyl 4-(5-amino-2,2-dimethyl-2,3-dihydrobenzofuran-6-yl)piperazine-1-carboxylate

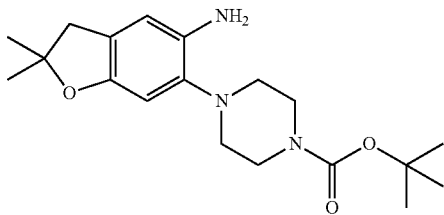 [SMILES: CC(C)(C)OC(=O)N1CCN(c2cc3c(cc2N)CC(C)(C)O3)CC1]

To a solution of tert-butyl 4-(2,2-dimethyl-5-nitro-3H-benzofuran-6-yl)piperazine-1-carboxylate (3.40 g, 9.79 mmol) in methanol (30 mL) was added 10% palladium on carbon (1.04 g, 0.98 mmol). The mixture was hydrogenated at 15 psi at 20° C. for 3 h. The reaction mixture was filtered and concentrated to afford tert-butyl 4-(5-amino-2,2-dimethyl-3H-benzofuran-6-yl)piperazine-1-carboxylate (3.10 g, 8.92 mmol, 91.2% yield) as a yellow solid. MS (ESI): m/z=348.2 [M+H]⁺.

Step C. tert-Butyl 4-(2,2-dimethyl-5-(pyrazolo[1,5-a]pyrimidine-3-carboxamido)-2,3-dihydrobenzofuran-6-yl)piperazine-1-carboxylate

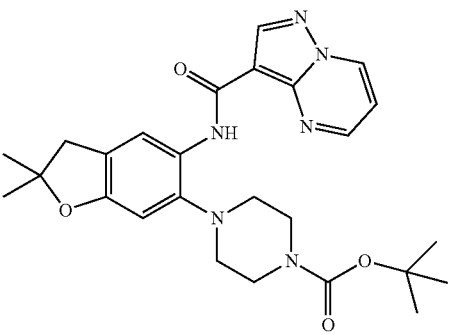 [SMILES: CC(C)(C)OC(=O)N1CCN(c2cc3c(cc2NC(=O)c2cnn4cccnc24)CC(C)(C)O3)CC1]

To a solution of tert-butyl 4-(5-amino-2,2-dimethyl-3H-benzofuran-6-yl)piperazine-1-carboxylate (4.1 g, 11.8 mmol) in pyridine (50 mL) was added pyrazolo[1,5-a]pyrimidine-3-carbonyl chloride (2.57 g, 14.2 mmol). The reaction was stirred at 60° C. for 4 h. The reaction mixture was diluted with water (20 mL) and extracted with dichloromethane (100 mL×3). The organics were washed with brine (100 mL×2), dried over sodium sulfate, filtered and concentrated. The residue was purified by flash chromatography (solvent gradient: 0-10% methanol in dichloromethane) to afford tert-butyl 4-[2,2-dimethyl-5-(pyrazolo[1,5-a]pyrimidine-3-carbonylamino)-3H-benzofuran-6-yl]piperazine-1-carboxylate (4.4 g, 8.93 mmol, 75.7% yield) as a brown solid. The product was used without further purification.

Step D. N-(2,2-Dimethyl-6-(piperazin-1-yl)-2,3-dihydrobenzofuran-5-yl)pyrazolo[1,5-a]pyrimidine-3-carboxamide

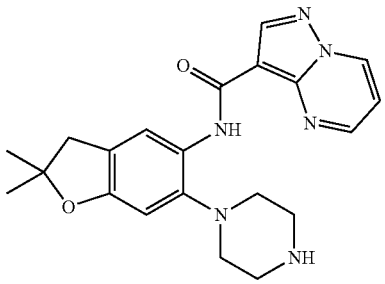 [SMILES: CC1(C)Cc2cc(NC(=O)c3cnn4cccnc34)c(N3CCNCC3)cc2O1]

To a solution of tert-butyl 4-[2,2-dimethyl-5-(pyrazolo[1,5-a]pyrimidine-3-carbonylamino)-3H-benzofuran-6-yl]piperazine-1-carboxylate (4.4 g, 8.92 mmol) in dichloromethane (50 mL) was added trifluroacetic acid (10 mL, 8.93 mmol). The reaction mixture was stirred at 25° C. for 4 h. The reaction was concentrated to afford N-(2,2-dimethyl-6-piperazin-1-yl-3H-benzofuran-5-yl)pyrazolo[1,5-a]pyrimidine-3-carboxamide (3.2 g, 8.15 mmol, 91.3% yield) as a yellow solid. ¹H NMR (400 MHz, DMSO-d₆) δ 10.34 (s, 1H), 9.39 (dd, J=6.8 Hz, 1.6 Hz, 1H), 9.02 (dd, J=4.0 Hz, 1.2 Hz, 1H), 8.70 (s, 1H), 8.34 (s, 1H), 7.39 (dd, J=6.8 Hz, 4.4 Hz, 1H), 6.70 (s, 1H), 4.17-4.13 (m, 1H), 3.32-3.28 (m, 2H), 3.16 (d, J=5.6 Hz, 2H), 3.07-3.00 (m, 6H), 1.41 (s, 6H). LCMS (ESI): m/z=393.0 [M+H]⁺.

Intermediate E.
5-Ethyl-1-(piperidin-4-yl)pyrazolidin-3-one hydrochloride

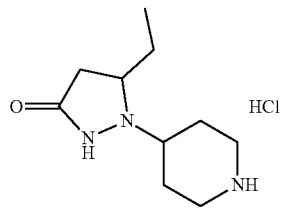

Step A. 5-Ethylpyrazolidin-3-one

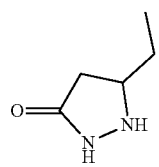

To a solution of hydrazine hydrate (1.03 g, 17.5 mmol) in ethanol (50 mL) was added dropwise methyl 2-pentenoate (2.00 g, 17.5 mmol) in ethanol (5 mL). The mixture was stirred at 25° C. for 1 h and then heated at 80° C. for 12 h. The reaction was concentrated to afford the title compound as a yellow oil (2.00 g, 99%).

Step B. tert-Butyl 4-(5-ethyl-3-oxopyrazolidin-1-yl)piperidine-1-carboxylate

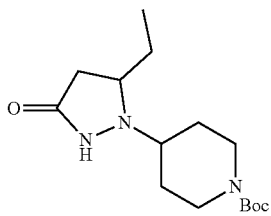

To a solution of N-(tert-butoxycarbonyl)-4-piperidone (4.19 g, 21.0 mmol) and 5-ethylpyrazolidin-3-one (2.00 g, 17.5 mmol) in chloroform (50 mL) was added sodium triacetoxyborohydride (4.22 g, 19.8 mmol) at 0° C. The reaction was stirred at 25° C. for 2 h followed by 50° C. for 2 h and quenched with water (25 mL) at 0° C. The organic layer was concentrated and purified by chromatography on silica (eluting gradient: 0-10% methanol in dichloromethane) to afford the desired product as a colorless oil (4.00 g, 77%). LCMS (ESI): m/z=298 [M+H]⁺.

Step C. 5-Ethyl-1-(piperidin-4-yl)pyrazolidin-3-one hydrochloride

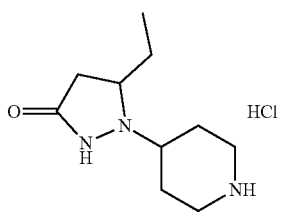

A mixture of tert-butyl 4-(5-ethyl-3-oxo-pyrazolidin-1-yl)piperidine-1-carboxylate (3.50 g, 11.8 mmol) in 4 M hydrogen chloride in ethyl acetate (43.8 mL, 175 mmol) was stirred at 25° C. for 10 min. The solution was concentrated to afford the desired product as a white solid (2.70 g, 99%).

Intermediate F. 3-Fluorocyclobutanol

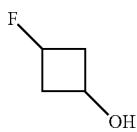

Step A. 3-Benzyloxycyclobutanol

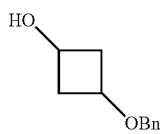

To a solution of 3-(benzyloxy)cyclobutanone (5.0 g, 28.4 mmol) in methanol (20 mL) was added sodium borohydride (1.18 g, 31.2 mmol). The mixture was stirred at 0° C. for 1 h. The reaction was quenched with water (20 mL) and concentrated. The residue was diluted with ethyl acetate (200 mL), washed with water (100 mL) and brine (100 mL), dried over sodium sulfate, and concentrated to give 3-benzyloxycyclobutanol (5 g, 99%) as a colorless oil.

Step B. (3-Fluorocyclobutoxy)methylbenzene

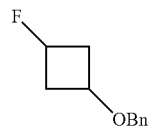

To a solution of 3-benzyloxycyclobutanol (5.0 g, 28.0 mmol) in dichloromethane (40 mL) was added dropwise diethylaminosulfur trifluoride (7.41 mL, 56.1 mmol) at 0° C. The reaction was stirred at 15° C. for 16 h and quenched with ice water (50 mL). Saturated aqueous sodium bicarbonate was added (100 mL), and the mixture was extracted with dichloromethane (200 mL). The organic phase was washed with brine (100 mL), dried over sodium sulfate and concentrated. The crude product was purified by flash column chromatography (eluting gradient: 10% ethyl acetate in petroleum ether) to give (3-fluorocyclobutoxy)methylbenzene (1.30 g, 26%) as a yellow oil.

Step C. 3-Fluorocyclobutanol

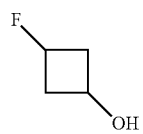

To a solution of (3-fluorocyclobutoxy)methylbenzene (1.00 g, 5.55 mmol) in methanol (150 mL) was added 10% palladium on carbon (29.5 g, 27.7 mmol) and palladium hydroxide on carbon (3.90 g, 27.7 mmol). The reaction mixture was stirred at 50° C. for 16 h under hydrogen (45 psi), filtered and concentrated at a low temperature to give 3-fluorocyclobutanol (350 mg, 70% yield) as a colorless oil.

Intermediate G. Methyl 5-(difluoromethoxy)-2-methyl-4-nitrobenzoate

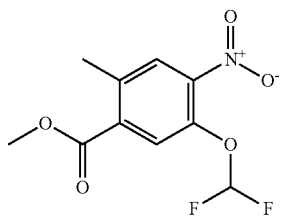 [SMILES: COC(=O)c1cc(OC(F)F)c([N+](=O)[O-])cc1C]

211

Step A. Methyl 5-hydroxy-2-methyl-4-nitrobenzoate

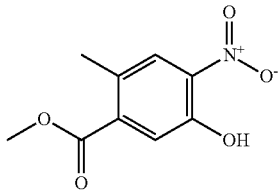

To a stirred solution of methyl 5-hydroxy-2-methylbenzoate (3.00 g, 18.0 mmol) in acetic acid (30 mL) was added dinitrooxycopper (5.08 g, 27.1 mmol) at 25° C. The mixture was stirred at 25° C. for 30 min, poured into ice water and extracted with ethyl acetate (50 mL×3). The combined organic phase was washed with saturated aqueous sodium bicarbonate (50 mL×2), dried over sodium sulfate and concentrated. The residue was purified by column chromatography (silica gel: 100-200 mesh, eluting gradient: 0-20% ethyl acetate in petroleum ether) to give methyl 5-hydroxy-2-methyl-4-nitro-benzoate (1.35 g, 35%) as a yellow solid. $^1$H NMR (400 MHz, CDCl$_3$): δ 10.24 (s, 1H), 7.97 (s, 1H), 7.66 (s, 1H), 3.94 (s, 3H), 2.54 (s, 3H).

Step B. Methyl 5-(difluoromethoxy)-2-methyl-4-nitrobenzoate

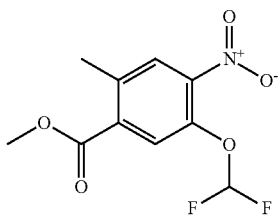 [SMILES: COC(=O)c1cc(OC(F)F)c([N+](=O)[O-])cc1C]

To a solution of methyl 5-hydroxy-2-methyl-4-nitro-benzoate (1.11 g, 5.26 mmol) in N,N-dimethylformamide (10 mL) was added methyl chlorodifluoroacetate (1.14 g, 7.89 mmol) and potassium carbonate (1.09 g, 7.89 mmol). The mixture was stirred at 100° C. for 2 h under nitrogen and concentrated. The residue was purified by column chromatography (silica gel: 100-200 mesh, eluting gradient: 0-5% ethyl acetate in petroleum ether) to give methyl 5-(difluoromethoxy)-2-methyl-4-nitro-benzoate (800 mg, 58% yield) as a yellow oil. $^1$H NMR (400 MHz, CDCl$_3$): δ 7.91 (s, 1H), 7.79 (s, 1H), 6.62 (t, J=72.8 Hz, 1H), 3.96 (s, 3H), 2.66 (s, 3H).

212

Intermediate H. N-[2-[(2R)-2-Fluoro-3-hydroxy-3-methyl-butyl]-1-oxo-6-piperazin-1-yl-isoindolin-5-yl]pyrazolo[1,5-a]pyrimidine-3-carboxamide

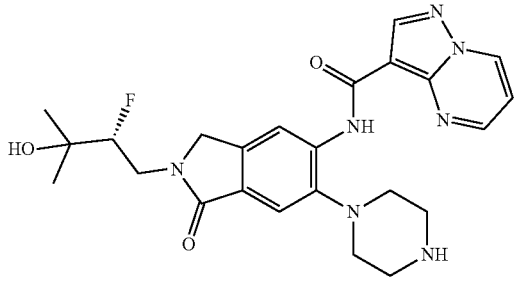 [SMILES: CC(C)(O)[C@H](F)CN1Cc2cc(NC(=O)c3cnn4cccnc34)c(N3CCNCC3)cc2C1=O]

Step A. 6-Chloro-2-[(2R)-2-fluoro-3-hydroxy-3-methyl-butyl]-5-nitro-isoindolin-1-one

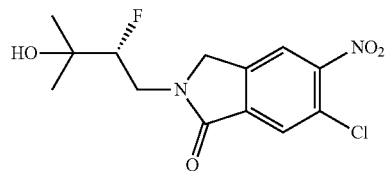

To a stirred solution of methyl 2-(bromomethyl)-5-chloro-4-nitro-benzoate (WO2013/079505, 4.5 g, 14.6 mmol) in methanol (90 mL) was added trimethylamine (2.95 g, 29.2 mmol) and (3R)-4-amino-3-fluoro-2-methyl-butan-2-ol (WO2014/074675, 3.5 g, 29.2 mmol). The mixture was stirred at 70° C. for 2 h under nitrogen. The reaction mixture was concentrated and purified by flash chromatography (40-63% ethyl acetate in petroleum ether) to afford 6-chloro-2-[(2R)-2-fluoro-3-hydroxy-3-methyl-butyl]-5-nitro-isoindolin-1-one (quant. yield) as a yellow solid. $^1$H NMR (400 MHz, DMSO-d$_6$) δ 8.36 (s, 1H), 8.03 (s, 1H), 4.91 (d, J=2.6 Hz, 1H), 4.75-4.58 (m, 2H), 4.47 (ddd, J=49.2, 9.4, 1.9 Hz, 1H), 4.00 (ddd, J=38.6, 14.9, 1.9 Hz, 1H), 3.74 (ddd, J=16.2, 14.9, 9.4 Hz, 1H), 3.34-3.23 (m, 1H), 1.18 (dd, J=4.9, 1.7 Hz, 6H). LCMS (ESI): m/z=317.1 [M+H]$^+$.

Step B. 4-[2-[(2R)-2-Fluoro-3-hydroxy-3-methyl-butyl]-6-nitro-3-oxo-isoindolin-5-yl]piperazine-1-carboxylate

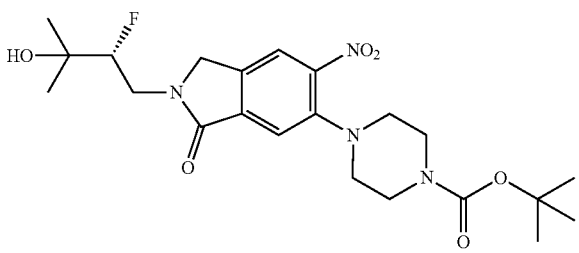 [SMILES: CC(C)(C)OC(=O)N1CCN(c2cc3c(cc2[N+](=O)[O-])CN(C[C@@H](F)C(C)(C)O)C3=O)CC1]

A mixture of 6-chloro-2-[(2R)-2-fluoro-3-hydroxy-3-methyl-butyl]-5-nitro-isoindolin-1-one (500 mg, 1.58 mmol), tert-butyl 1-piperazinecarboxylate (588 mg, 3.16 mmol) and N,N-diisopropylethylamine (612 mg, 4.74 mmol) in dimethyl sulfoxide (15 mL) was stirred at 90° C. for 2 h under nitrogen. The reaction mixture was concentrated, and the residue was purified by column chromatography (silica gel: 100-200 mesh, eluting gradient: 30-65% ethyl acetate in petroleum ether) to give tert-butyl 4-[2-[(2R)-2-fluoro-3-hydroxy-3-methyl-butyl]-6-nitro-3-oxo-isoindolin-5-yl]piperazine-1-carboxylate (460 mg, 0.986 mmol, 62.5% yield) as a yellow solid. LCMS (ESI): m/z=489.2 [M+Na]+.

Step C. tert-butyl 4-[6-Amino-2-[(2R)-2-fluoro-3-hydroxy-3-methyl-butyl]-3-oxo-isoindolin-5-yl]piperazine-1-carboxylate

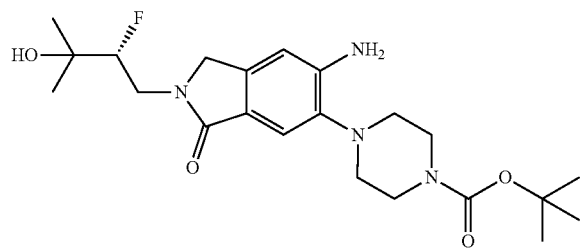

The title compound was made in a manner analogous to Example 60 (Step F) to afford tert-butyl 4-[6-amino-2-[(2R)-2-fluoro-3-hydroxy-3-methyl-butyl]-3-oxo-isoindolin-5-yl]piperazine-1-carboxylate (1.4 g, 3.14 mmol, 99.6% yield) as a white solid.

Step D. tert-Butyl (R)-4-(2-(2-fluoro-3-hydroxy-3-methylbutyl)-3-oxo-6-(pyrazolo[1,5-a]pyrimidine-3-carboxamido)isoindolin-5-yl)piperazine-1-carboxylate

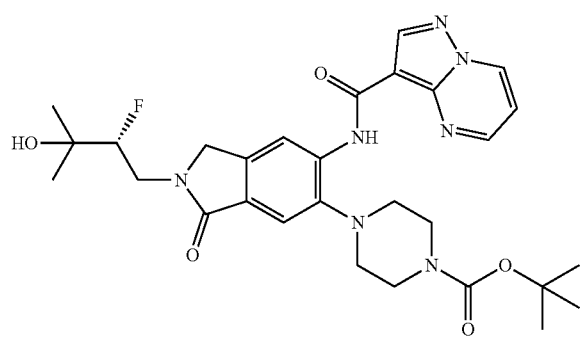 [SMILES: CC(C)(C)OC(=O)N1CCN(c2cc3c(cc2NC(=O)c2cnn4cccnc24)CN(C[C@@H](F)C(C)(C)O)C3=O)CC1]

The title compound was made in a manner analogous to Example 60 (Step G) to afford tert-butyl 4-[2-[(2R)-2-fluoro-3-hydroxy-3-methyl-butyl]-3-oxo-6-(pyrazolo[1,5-a]pyrimidine-3-carbonylamino)isoindolin-5-yl]piperazine-1-carboxylate (1.80 g, 3.10 mmol, 98.6% yield) as a white solid. LCMS (ESI): m/z=582.4 [M+H]+.

Step E. N-[2-[(2R)-2-Fluoro-3-hydroxy-3-methyl-butyl]-1-oxo-6-piperazin-1-yl-isoindolin-5-yl]pyrazolo[1,5-a]pyrimidine-3-carboxamide

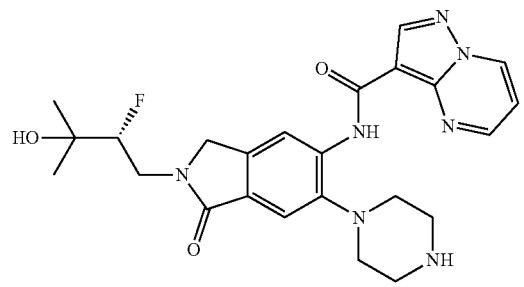 [SMILES: CC(C)(O)[C@H](F)CN1Cc2cc(NC(=O)c3cnn4cccnc34)c(N3CCNCC3)cc2C1=O]

To a stirring solution of tert-butyl 4-[2-[(2R)-2-fluoro-3-hydroxy-3-methyl-butyl]-3-oxo-6-(pyrazolo[1,5-a]pyrimidine-3-carbonylamino)isoindolin-5-yl]piperazine-1-carboxylate (1.50 g, 2.58 mmol) in ethyl acetate (10 mL) was added hydrogen chloride (4 M in ethyl acetate, 20 mL, 80 mmol). The mixture was stirred at 25° C. for 3 h. The reaction mixture was concentrated to afford N-[2-[(2R)-2-fluoro-3-hydroxy-3-methyl-butyl]-1-oxo-6-piperazin-1-yl-isoindolin-5-yl]pyrazolo[1,5-a]pyrimidine-3-carboxamide hydrochloride (1.20 g, 2.32 mmol, 89.8% yield) as a white solid. LCMS (ESI): m/z=482.2 [M+H]+.

Intermediate I. 5-Ethylisoxazole-4-carbaldehyde

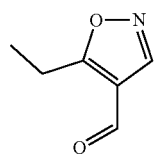

Step A. (E)-Ethyl 2-((dimethylamino)methylene)-3-oxopentanoate

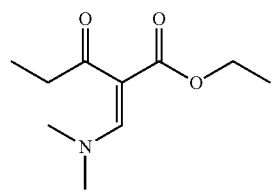

A solution of ethyl propionylacetate (1.48 mL, 10.40 mmol) in N,N-dimethylformamide dimethyl acetal (1.67 mL, 12.5 mmol) was stirred at 120° C. for 30 min under microwave irradiation. The reaction mixture was concentrated to afford ethyl (E)-ethyl 2-((dimethylamino)methylene)-3-oxopentanoate (2.0 g, 96%) as a yellow oil.

Step B. Ethyl 5-ethylisoxazole-4-carboxylate

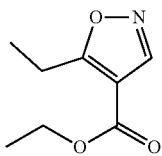

To a solution of ethyl (E)-ethyl 2-((dimethylamino)methylene)-3-oxopentanoate in ethanol (100 mL) was added hydroxylamine hydrochloride (1.22 g, 17.6 mmol). The reaction mixture was stirred at 80° C. for 1 h, after which it was concentrated. The resulting residue was purified by silica gel chromatography (eluting gradient: 0-10% ethyl acetate in petroleum ether) to afford ethyl 5-ethylisoxazole-4-carboxylate (2.3 g, 77%) as a colorless oil. $^1$H NMR (400 MHz, CDCl$_3$) δ 8.48 (s, 1H), 4.33 (q, J=7.2 Hz, 2H), 3.14 (q, J=7.6 Hz, 2H), 1.39-1.32 (m, 6H).

Step C. (5-Ethylisoxazol-4-yl)methanol

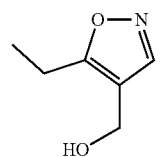

To a stirred solution of ethyl 5-ethylisoxazole-4-carboxylate (2.1 g, 12.4 mmol) in tetrahydrofuran (100 mL) was added dropwise diisobutyl aluminumhydride (1 M in toluene, 37.2 mL, 37.2 mmol) at −78° C. The mixture was stirred at 20° C. for 16 h under nitrogen and quenched with saturated aqueous ammonium chloride (4 mL). The mixture was concentrated and purified by silica gel chromatography (eluting gradient: 0-10% methanol in dichloromethane) to give (5-ethylisoxazol-4-yl)methanol (1.4 g, 89%) as a yellow oil. $^1$H NMR (400 MHz, CDCl$_3$) δ 8.22 (s, 1H), 4.53 (s, 2H), 2.82 (q, J=7.6 Hz, 2H), 1.31 (t, J=7.6 Hz, 3H).

Step D. 5-Ethylisoxazole-4-carbaldehyde

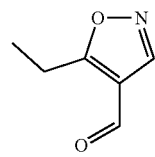

To a solution of (5-ethylisoxazol-4-yl)methanol (800 mg, 6.29 mmol) in dichloromethane (30 mL) was added manganese dioxide (5.5 g, 62.9 mmol). The reaction mixture was stirred at 20° C. for 16 h and filtered through a pad of Celite. The filtrate was concentrated and purified by silica gel chromatography (eluting gradient: 0-20% ethyl acetate in petroleum ether) to afford 5-ethylisoxazole-4-carbaldehyde (400 mg, 51%) as a yellow oil. $^1$H NMR (400 MHz, CDCl$_3$) δ 9.94 (s, 1H), 8.56 (s, 1H), 3.14 (q, J=7.6 Hz, 2H), 1.41 (t, J=7.6 Hz, 3H).

Intermediate J. 3-Ethylisoxazole-4-carbaldehyde

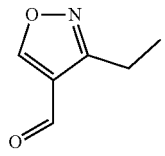

Step A. (E)-Ethyl 3-(pyrrolidin-1-yl)acrylate

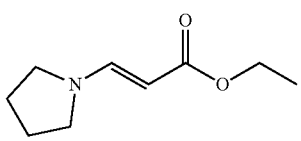

To a solution of ethyl propiolate (2.96 mL, 29.6 mmol) in toluene (20 mL) was added dropwise a solution of pyrrolidine (2.4 mL, 29.0 mmol) in toluene (5 mL). The mixture was stirred at 23° C. for 12 h and concentrated. The residue was purified by flash chromatography (eluting gradient: 0-10% ethyl acetate in petroleum ether) to give (E)-ethyl 3-(pyrrolidin-1-yl)acrylate as a yellow oil (4.2 g, 86%). $^1$H NMR (400 MHz, CDCl$_3$) δ 7.63 (d, J=12.8 Hz, 1H), 4.44 (d, J=12.8 Hz, 1H), 4.10 (q, J=7.2 Hz, 2H), 3.37-3.10 (m, 4H), 2.02-1.97 (m, 4H), 1.23 (t, J=7.2 Hz, 3H).

Step B. Ethyl 3-ethylisoxazole-4-carboxylate

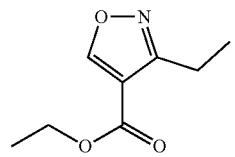

A solution of (E)-ethyl 3-(pyrrolidin-1-yl)acrylate (3.2 g, 18.9 mmol), 1-nitropropane (1.87 mL, 20.8 mmol), isocyanatobenzene (5.69 mL, 52.38 mmol) and triethylamine (0.39 mL, 2.84 mmol) in toluene (45 mL) was stirred at 20° C. for 2 h then heated at 60° C. for 12 h. The reaction mixture was cooled to 20° C., and the precipitate was filtered off and rinsed with toluene (30 mL×2). The filtrate was concentrated, and the residue was purified by flash chromatography (eluting gradient: 0-10% ethyl acetate in petroleum ether) to give ethyl 3-ethylisoxazole-4-carboxylate as a colorless oil (2.2 g, 69%). $^1$H NMR (400 MHz, CDCl$_3$) δ 8.84 (s, 1H), 4.33 (q, J=7.2 Hz, 2H), 2.95 (q, J=7.6 Hz, 2H), 1.38-1.28 (m, 6H).

Step C. (3-Ethylisoxazol-4-yl)methanol

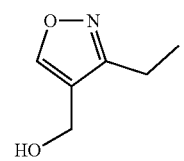

To a stirred solution of ethyl 3-ethylisoxazole-4-carboxylate (2.2 g, 13 mmol) in tetrahydrofuran (40 mL) was added dropwise diisobutyl aluminumhydride (1 M in toluene, 39.0 mL, 39.0 mmol) at 0° C. The mixture was stirred at 0° C. for 4 h under nitrogen. Methanol (20 mL) was added slowly into the reaction mixture at 0° C. The mixture was stirred at 20° C. for 1 h, and 2 M aqueous sodium potassium tartrate tetrahydrate (50 mL) was added, followed by stirring for an additional 1 h. The mixture was extracted with dichloromethane (50 mL×3), and the combined organic phase was dried over anhydrous sodium sulfate, concentrated and purified by flash chromatography (eluting gradient: 0-9% methanol in dichloromethane) to give (3-ethylisoxazol-4-yl)methanol as a colorless oil (1.4 g, 85%).

Step D. 3-Ethylisoxazole-4-carbaldehyde

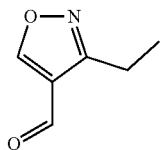

To a stirred solution of (3-ethylisoxazol-4-yl)methanol (1.4 g, 11.0 mmol) in dichloromethane (5 mL) was added manganese dioxide (9.6 g, 110 mmol). The mixture was stirred at 20° C. for 48 h, after which it was filtered. The filtrate was concentrated and purified by flash chromatography (eluting gradient: 0-9% methanol in dichloromethane) to give 3-ethylisoxazole-4-carbaldehyde as a colorless oil (1 g, 73%). $^1$H NMR (400 MHz, CDCl$_3$) δ 10.04 (s, 1H), 8.93 (s, 1H), 2.97 (q, J=7.6 Hz, 2H), 1.33 (t, J=7.6 Hz, 3H).

Intermediate K. (7R,8aR)-7-Methoxyoctahydropyrrolo[1,2-a]pyrazine

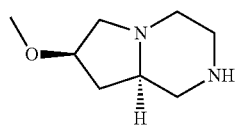

Step A. (2R,4R)-Methyl 1-(2-chloroacetyl)-4-hydroxypyrrolidine-2-carboxylate

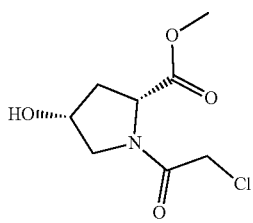

To a stirred solution of methyl (2R,4R)-4-hydroxypyrrolidine-2-carboxylate hydrochloride (10.0 g, 55.1 mmol) in dichloromethane (50 mL) was added triethylamine (16.8 mL, 121 mmol), followed by chloroacetyl chloride (4.56 mL, 60.6 mmol) in dichloromethane (25 mL) dropwise at 0° C. The mixture was stirred at 15° C. for 3 h and concentrated to afford crude methyl (2R,4R)-methyl 1-(2-chloroacetyl)-4-hydroxypyrrolidine-2-carboxylate (10.0 g, 82%) as a yellow solid.

Step B. (7R,8aR)-2-Benzyl-7-hydroxyhexahydropyrrolo[1,2-a]pyrazine-1,4-dione

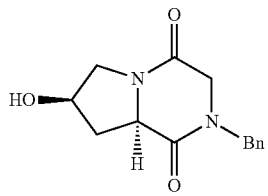 [SMILES: O=C1[C@H]2C[C@@H](O)CN2C(=O)CN1Cc1ccccc1]

To a solution of methyl (2R,4R)-methyl 1-(2-chloroacetyl)-4-hydroxypyrrolidine-2-carboxylate (10.0 g, 45.1 mmol) in 2-ethoxyethanol (100 mL) was added triethylamine (8.01 mL, 57.8 mmol) and benzylamine (6.0 mL, 54.9 mmol). The mixture was stirred at 140° C. for 16 h and concentrated. The residue was purified by silica gel chromatography (eluting gradient: 0-3% methanol in ethyl acetate) to afford (7R,8aR)-2-benzyl-7-hydroxyhexahydropyrrolo[1,2-a]pyrazine-1,4-dione (8.0 g, 68%) as a brown solid. $^1$H NMR (400 MHz, CDCl$_3$) δ 7.34-7.22 (m, 5H), 4.75 (d, J=14.8 Hz, 1H), 4.50-4.44 (m, 2H), 4.20-4.01 (m, 1H), 3.99 (d, J=16.4 Hz, 1H), 3.85 (d, J=12.0 Hz, 1H), 3.75 (d, J=16.8 Hz, 1H), 3.50-3.30 (m, 2H), 2.65-2.40 (m, 2H).

Step C. (7R,8aR)-2-Benzyloctahydropyrrolo[1,2-a]pyrazin-7-ol

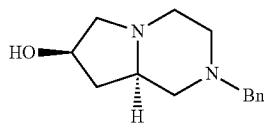 [SMILES: O[C@@H]1C[C@@H]2CN(Cc3ccccc3)CCN2C1]

To lithium aluminum hydride (4.6 g, 123 mmol) in tetrahydrofuran (300 mL) was added (7R,8aR)-2-benzyl-7-hydroxyhexahydropyrrolo[1,2-a]pyrazine-1,4-dione (8.0 g, 30.7 mmol) in tetrahydrofuran (100 mL) at 0° C. The reaction mixture was stirred at 65° C. for 16 h, after which it was cooled to 0-5° C. and quenched with sequential addition of ethyl acetate (40 mL), water (8 mL), 10% NaOH solution (16 mL), and water (24 mL). The mixture was stirred at 20-25° C. for 30 min, and the resulting suspension was filtered through a pad of Celite. The filtrate was concentrated, and the resulting residue was purified by silica gel chromatography (eluting gradient: 0-1% methanol in ethyl acetate) to afford (7R,8aR)-2-benzyloctahydropyrrolo[1,2-a]pyrazin-7-ol (7.0 g, 98%) as a yellow solid. $^1$H NMR (400 MHz, DMSO-d$_6$) δ 7.33-7.24 (m, 5H), 4.68 (d, J=5.2 Hz, 1H), 4.16-4.11 (m, 1H), 3.53-3.49 (m, 2H), 2.81-2.75 (m, 4H), 2.16-1.82 (m, 6H), 1.17-1.13 (m, 1H).

Step D. (7R,8aR)-2-Benzyl-7-methoxyoctahydropyrrolo[1,2-a]pyrazine

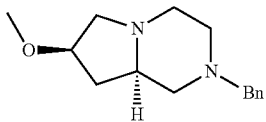 [SMILES: CO[C@@H]1C[C@@H]2CN(Cc3ccccc3)CCN2C1]

To a solution of (7R,8aR)-2-benzyloctahydropyrrolo[1,2-a]pyrazin-7-ol (500 mg, 2.15 mmol) in N,N-dimethylformamide (10 mL) was added sodium hydride (112 mg, 2.80 mmol) at 0° C., followed by iodomethane (268 uL, 4.30 mmol). The mixture was stirred at 25° C. for 1 h, quenched with saturated aqueous ammonium chloride (1 mL), and extracted with ethyl acetate (100 mL). The organic phase was washed with brine (10 mL) and concentrated. The residue was purified on silica gel chromatography (eluting gradient: 0-2% methanol in dichloromethane) to afford (7R,8aR)-2-benzyl-7-methoxyoctahydropyrrolo[1,2-a]pyrazine (200 mg, 38%) as a colorless oil. $^1$H NMR (400 MHz, CDCl$_3$) δ 7.30-7.22 (m, 5H), 3.85-3.84 (m, 1H), 3.60-3.49 (m, 2H), 3.25 (s, 3H), 3.12-3.09 (m, 1H), 2.94-2.87 (m, 2H), 2.78-2.72 (m, 1H), 2.35-1.97 (m, 6H), 1.40-1.35 (m, 1H).

Step E. (7R,8aR)-7-Methoxyoctahydropyrrolo[1,2-a]pyrazine

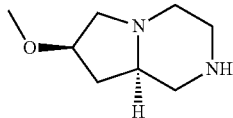

To wet palladium hydroxide on carbon (228 mg, 0.32 mmol) in methanol (20 mL) was added (7R,8aR)-2-benzyl-7-methoxyoctahydropyrrolo[1,2-a]pyrazine (400 mg, 1.62 mmol) and aqueous ammonium hydroxide (0.59 mL, 16.2 mmol). The mixture was stirred at 20° C. for 2 h under H$_2$ (15 psi) and filtered. The filtrate was concentrated and purified by silica gel chromatography (eluting gradient: 0-20% methanol in dichloromethane) to afford (7R,8aR)-7-methoxyoctahydropyrrolo[1,2-a]pyrazine (80 mg, 32%) as a white solid. $^1$H NMR (400 MHz, CDCl$_3$) δ 3.88-3.86 (m, 1H), 3.29 (s, 3H), 3.22-3.10 (m, 2H), 3.08-2.95 (m, 3H), 2.70-2.60 (m, 1H), 2.27-2.23 (m, 3H), 2.22-2.06 (m, 1H), 1.44-1.40 (m, 1H).

Intermediate L. (7S,8aR)-2-Benzyloctahydropyrrolo[1,2-a]pyrazin-7-ol

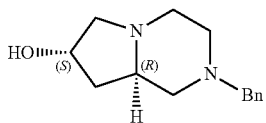

Step A. (7S,8aR)-2-Benzyloctahydropyrrolo[1,2-a]pyrazin-7-yl 4-nitrobenzoate

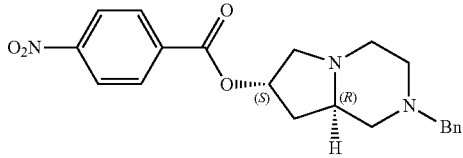

To a solution of (7R,8aR)-2-benzyl-3,4,6,7,8,8a-hexahydro-1H-pyrrolo[1,2-a]pyrazin-7-ol (2.0 g, 8.61 mmol), triphenylphosphine (3.3 g, 12.9 mmol) and 4-nitrobenzoic acid (2.10 g, 12.9 mmol) in tetrahydrofuran (50 mL) was added diisopropyl azodicarboxylate (3.41 mL, 17.2 mmol) dropwise at 0° C. under nitrogen. The reaction mixture was stirred at 20° C. for 16 h.

Dichloromethane (100 mL) was added, and the mixture was washed with water (50 mL×3), dried over sodium sulfate and concentrated. The residue was purified by flash chromatography on silica gel (eluting gradient: 0-2% methanol in dichloromethane) to afford (7S,8aR)-2-benzyloctahydropyrrolo[1,2-a]pyrazin-7-yl 4-nitrobenzoate (3.0 g, 91%) as a yellow oil.

Step B. (7S,8aR)-2-Benzyloctahydropyrrolo[1,2-a]pyrazin-7-ol

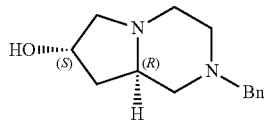

To a solution of (7S,8aR)-2-benzyloctahydropyrrolo[1,2-a]pyrazin-7-yl 4-nitrobenzoate (3.0 g, 7.87 mmol) in tetrahydrofuran (20 mL) and water (10 mL) was added lithium hydroxide hydrate (1.6 g, 39.37 mmol). The reaction mixture was stirred at 25° C. for 1 h, after which it was acidified with 1 M hydrochloric acid to pH=8 and extracted with ethyl acetate (30 mL×10). The combined organic phase was concentrated and purified by silica gel chromatography (eluting gradient: 0-2% methanol in dichloromethane) to afford (7S,8aR)-2-benzyloctahydropyrrolo[1,2-a]pyrazin-7-ol (800 mg, 44%) as a brown solid. $^1$H NMR (400 MHz, DMSO-d$_6$) δ 7.33-7.23 (m, 5H), 4.73 (d, J=4.4 Hz, 1H), 4.20-4.10 (m, 1H), 3.51-3.42 (m, 2H), 3.23 (dd, J=8.8, 6.8 Hz, 1H), 2.80-2.77 (m, 2H), 2.70-2.60 (m, 1H), 2.25-2.04 (m, 3H), 1.90 (dd, J=8.8, 5.6 Hz, 1H), 1.67 (t, J=10.0 Hz, 1H), 1.49-1.46 (m, 2H).

Intermediate M. (8aR)-7-Methyl-1,2,3,4,6,7,8,8a-octahydropyrrolo[1,2-a]pyrazine

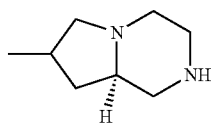

Step A. (8aS)-2-Benzyl-1,3,4,6,8,8a-hexahydropyrrolo[1,2-a]pyrazin-7-one

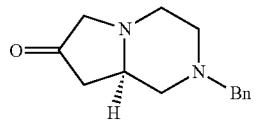 [SMILES: O=C1C[C@@H]2CN(Cc3ccccc3)CCN2C1]

To a solution of oxalyl chloride (1.20 g, 9.47 mmol) in dichloromethane (2 mL) was added dropwise dimethyl sulfoxide (1.03 g, 13.3 mmol) at −78° C. The reaction mixture was stirred at −78° C. for 10 minutes. (7R,8aS)-2-benzyl-3,4,6,7,8,8a-hexahydro-1H-pyrrolo[1,2-a]pyrazin-7-ol (1.10 g, 4.73 mmol) was added dropwise, and the mixture was stirred 20 min. Triethylamine (2.40 g, 23.7 mmol) was added dropwise, after which the reaction was warmed slowly to 20° C., quenched with water (30 mL), and extracted with dichloromethane (100 mL). The organic phase was washed with brine (80 mL), dried over sodium sulfate and concentrated. The residue was purified by flash column chromatography (eluting with ethyl acetate) to afford (8aS)-2-benzyl-1,3,4,6,8,8a-hexahydropyrrolo[1,2-a]pyrazin-7-one (550 mg, 50%) as a yellow oil. LCMS (ESI): m/z=231.2 [M+H]$^+$.

Step B. (8aS)-2-Benzyl-7-methylene-1,3,4,6,8,8a-hexahydropyrrolo[1,2-a]pyrazine

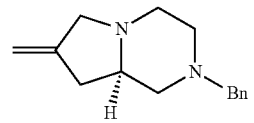 [SMILES: C=C1C[C@@H]2CN(Cc3ccccc3)CCN2C1]

To a mixture of methyltriphenylphosphonium bromide (2.32 g, 6.51 mmol) in tetrahydrofuran (8 mL) was added potassium tert-butoxide (1 M in tetrahydrofuran; 6.51 mL, 6.51 mmol) at 0° C. The reaction mixture was stirred for 2 h. (8aS)-2-benzyl-1,3,4,6,8,8a-hexahydropyrrolo[1,2-a]pyrazin-7-one (500 mg, 2.17 mmol) in tetrahydrofuran (2 mL) was added dropwise, and the mixture was stirred at 15° C. for 12 h. The reaction was diluted with water (35 mL) and extracted with ethyl acetate (60 mL). The organic phase was washed with brine (40 mL), dried over sodium sulfate and concentrated. The residue was purified by flash column chromatography (eluting with ethyl acetate) to give (8aS)-2-benzyl-7-methylene-1,3,4,6,8,8a-hexahydropyrrolo[1,2-a]pyrazine (300 mg, 60%) as a yellow oil.

Step C. (8aR)-7-Methyl-3,4,6,7,8,8a-hexahydro-1H-pyrrolo[1,2-a]pyrazine-2-carboxylate

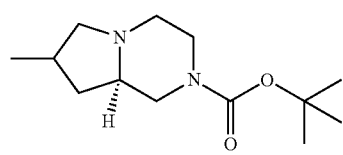 [SMILES: CC1C[C@@H]2CN(C(=O)OC(C)(C)C)CCN2C1]

A mixture of di-tert-butyldicarbonate (382 mg, 1.75 mmol), palladium on carbon (28.0 mg, 0.26 mmol) and (8aR)-2-benzyl-7-methylene-1,3,4,6,8,8a-hexahydropyrrolo[1,2-a]pyrazine (200 mg, 0.88 mmol) in methanol (5 mL) was stirred at 15° C. for 16 h under H$_2$ (15 psi). The mixture was filtered, and the filtrate was concentrated. The residue was purified by preparatory thin layer chromatography (eluting gradient: ethyl acetate) to afford tert-butyl (8aR)-7-methyl-3,4,6,7,8,8a-hexahydro-1H-pyrrolo[1,2-a]pyrazine-2-carboxylate (160 mg, 76%) as a colorless oil.

Step D. (8aR)-7-Methyl-1,2,3,4,6,7,8,8a-octahydropyrrolo[1,2-a]pyrazine

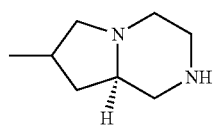

To a solution of tert-butyl (8aR)-7-methyl-3,4,6,7,8,8a-hexahydro-1H-pyrrolo[1,2-a]pyrazine-2-carboxylate (160 mg, 0.67 mmol) in methanol (5 mL) was added 4 M hydrogen chloride in methanol (5 mL, 19.97 mmol). The reaction was stirred at 15° C. for 1 h, after which it was concentrated to afford (8aR)-7-methyl-1,2,3,4,6,7,8,8a-octahydropyrrolo[1,2-a]pyrazine (90 mg, 96%) as a colorless oil.

Intermediate N. 1-(3-Methyloxetan-3-yl)piperazine

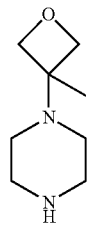

Step A. 3-((Phenylsulfonyl)methylene)oxetane

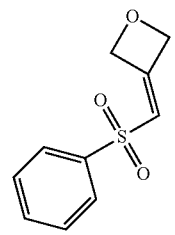

To a stirred solution of methylphenylsulfone (3 g, 19.2 mmol) in dry tetrahydrofuran (15 mL) was added n-butyllithium (2.5 M in tetrahydrofuran; 15.4 mL, 38.4 mmol) at 0° C. The reaction mixture was stirred for 30 min. Diethyl chlorophosphate (4 mL, 27.8 mmol) was added, and the mixture was stirred at 0° C. for an additional 30 min. It was then cooled to −78° C., and a solution of 3-oxetanone (1.38 g, 19.2 mmol) in dry tetrahydrofuran (3 mL) was added. The mixture was stirred at −78° C. for 1.5 h and filtered through a silica plug to give 3-((phenylsulfonyl)methylene)oxetane as a white solid (3 g, 74%). ¹H NMR (400 MHz, CDCl₃) δ 7.90-7.87 (m, 2H), 7.66-7.64 (m, 1H), 7.59-7.56 (m, 2H), 6.12 (s, 1H), 5.65 (d, J=6.0 Hz, 2H), 5.29 (d, J=5.6 Hz, 2H).

Step B. 1-Benzyl-4-(3-methyloxetan-3-yl)piperazine

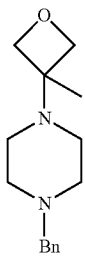

To a stirred solution of 3-((phenylsulfonyl)methylene) oxetane (1 g, 4.76 mmol) in methanol (25 mL) was added 1-benzylpiperazine (922 mg, 5.23 mmol). The reaction mixture was stirred at 50° C. for 24 h. Magnesium turnings (650 mg, 27.1 mmol) were added, and the mixture was stirred at 20° C. for 12 h. Petroleum ether (50 mL) was added, followed by sodium sulfate decahydrate (2 g). The mixture was stirred at 20° C. for 20 min and filtered. The filtrate was dried over anhydrous sodium sulfate, concentrated and purified by silica gel chromatography (eluting gradient: 0-5% methanol in dichloromethane) to give 1-benzyl-4-(3-methyloxetan-3-yl)piperazine (220 mg, 19% yield) as a white solid. ¹H NMR (400 MHz, CDCl₃) δ 7.73-7.26 (m, 5H), 4.59 (d, J=5.6 Hz, 2H), 4.22 (d, J=5.6 Hz, 2H), 3.54 (s, 2H), 2.60-2.45 (m, 4H), 2.41-2.38 (m, 4H), 1.38 (s, 3H).

Step C. 1-(3-Methyloxetan-3-yl)piperazine

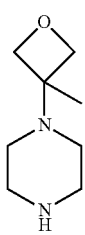

To a stirred solution of 1-benzyl-4-(3-methyloxetan-3-yl)piperazine (170 mg, 0.69 mmol) in ethanol (10 mL) was added 10% wet palladium on carbon (73 mg). The mixture was stirred at 25° C. for 1 h under H₂ (45 psi) and filtered. The filtrate was concentrated to give 1-(3-methyloxetan-3-yl)piperazine (98 mg, 91%) as a colorless oil. ¹H NMR (400 MHz, CDCl₃) δ 4.59 (d, J=5.6 Hz, 2H), 4.23 (d, J=5.6 Hz, 2H), 2.93-2.91 (m, 2H), 2.45-2.31 (m, 6H), 1.37 (s, 3H).

Intermediate O.
1-[(1-Fluorocyclobutyl)methyl]piperazine hydrochloride

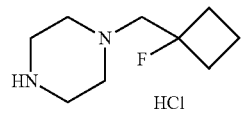 [SMILES: FC1(CN2CCNCC2)CCC1 ; Cl]

Step A. 1-Fluorocyclobutanecarbonyl chloride

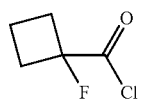

To a solution of 1-fluorocyclobutanecarboxylic acid (300 mg, 2.54 mmol) in dichloromethane (10 mL) was added ethanedioyl dichloride (0.26 mL, 3.05 mmol), followed by the addition of N,N-dimethylformamide (0.02 mL, 0.250 mmol). The mixture was stirred at 20° C. for 2 h. The reaction mixture was concentrated to afford 1-fluorocyclobutanecarbonyl chloride (346 mg, 2.53 mmol, 99.8% yield) as a colorless oil, which was used for next step directly without further purification.

Step B. (4-Benzylpiperazin-1-yl)-(1-fluorocyclobutyl)methanone

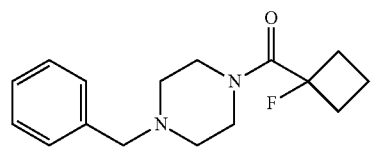 [SMILES: O=C(N1CCN(Cc2ccccc2)CC1)C1(F)CCC1]

To a solution of 1-benzylpiperazine hydrochloride (539 mg, 2.53 mmol) in dichloromethane (10 mL) was added N,N-diisopropylethylamine (327 mg, 2.53 mmol) followed by the addition of a solution of 1-fluorocyclobutanecarbonyl chloride (346 mg, 2.53 mmol) in dichloromethane (10 mL). The resulting mixture was stirred at 20° C. for 16 h. The reaction mixture was concentrated, and the residue was purified by flash chromatography (10-30% of ethyl acetate in petroleum ether) to afford (4-benzylpiperazin-1-yl)-(1-fluorocyclobutyl) methanone (640 mg, 2.32 mmol, 91.4% yield) as a colorless oil.

Step C. 1-Benzyl-4-[(1-fluorocyclobutyl)methyl]piperazine

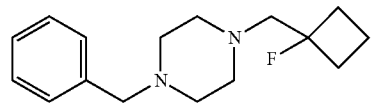 [SMILES: FC1(CN2CCN(Cc3ccccc3)CC2)CCC1]

To a solution of lithium aluminum hydride (181 mg, 4.78 mmol) in diethyl ether (20 mL) was added a solution of (4-benzylpiperazin-1-yl)-(1-fluorocyclobutyl) methanone (440 mg, 1.59 mmol) in diethyl ether (2 mL) dropwise. The mixture was stirred at 20° C. for 16 h. The reaction mixture was quenched with sodium sulfate decahydrate (10 g) and stirred for 30 min, filtered and concentrated. The residue was purified by preparatory thin layer chromatography (10-30% of ethyl acetate in petroleum ether) to afford 1-benzyl-4-[(1-fluorocyclobutyl) methyl]piperazine (270 mg, 1.03 mmol, 64.6% yield) as a colorless oil.

Step D. 1-[(1-Fluorocyclobutyl)methyl]piperazine hydrochloride

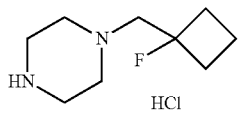

To a solution of 1-benzyl-4-[(1-fluorocyclobutyl)methyl] piperazine (200 mg, 0.760 mmol) in methanol (10 mL) was added palladium (10% on activated carbon, 81.1 mg, 0.1 mmol) and palladium hydroxide (20% on carbon, 53.5 mg, 0.100 mmol), followed by hydrochloric acid (0.01 mL). The mixture was stirred at 25° C. for 16 h under hydrogen (15 psi). The mixture was filtered and concentrated to afford 1-[(1-fluorocyclobutyl) methyl]piperazine hydrochloride (130 mg, 0.623 mmol, 81.7% yield) as a white solid. $^1$H NMR (400 MHz, CD$_3$OD) δ 3.66-3.77 (m, 10H), 2.44-2.53 (m, 4H), 1.91-2.03 (m, 1H), 1.70-1.82 (m, 1H).

Intermediate P. trans-3-Piperazin-1-ylcyclobutanol hydrochloride

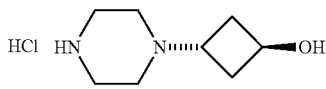

Step A. tert-Butyl 4-[3-(4-nitrobenzoyl)oxycyclobutyl]piperazine-1-carboxylate

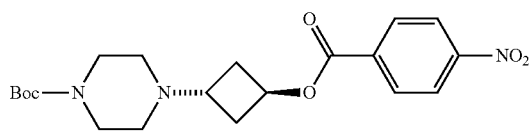

To a mixture of 4-nitrobenzoic acid (978 mg, 5.85 mmol), triphenylphosphine (1.5 g, 5.85 mmol) and tert-butyl 4-(3-hydroxycyclobutyl)piperazine-1-carboxylate (500 mg, 1.95 mmol) in toluene (10 mL) was added diisopropyl azodicarboxylate (1.17 mL, 5.85 mmol) at 0° C. under nitrogen. After the addition, the mixture was heated at 100° C. for 2 h. The reaction was diluted with water (10 mL) and extracted with ethyl acetate (20 mL×3). The organics were washed with brine (10 mL×3), dried over sodium sulfate, filtered and concentrated. The crude product was purified by reverse phase chromatography (acetonitrile 50-80/0.05% ammonia hydroxide in water) to afford tert-butyl 4-[3-(4-nitrobenzoyl)oxycyclobutyl]piperazine-1-carboxylate (420 mg, 53% yield) as a white solid. $^1$H NMR (400 MHz, CDCl$_3$) δ 8.32-8.29 (m, 2H), 8.23-8.22 (m, 2H), 5.37-5.32 (m, 1H), 3.48-3.45 (m, 4H), 3.10-3.03 (m, 1H), 2.52-2.45 (m, 2H), 2.39-2.36 (m, 2H), 2.35-2.32 (m, 4H), 1.47 (s, 9H).

Step B. trans-tert-Butyl 4-(3-hydroxycyclobutyl)piperazine-1-carboxylate

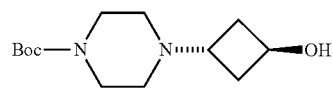

To a mixture of tert-butyl 4-[3-(4-nitrobenzoyl)oxycyclobutyl]piperazine-1-carboxylate (320 mg, 0.79 mmol) in methanol (2 mL) was added potassium carbonate (218 mg, 1.58 mmol) at 0° C. The reaction was stirred at 25° C. for 2 h. The reaction mixture was diluted with water (10 mL) and extracted with dichloromethane (10 mL×3). The organics were washed with brine (10 mL×3), dried over sodium sulfate, filtered and concentrated. The residue was purified by flash chromatography (solvent gradient: 0-10% methanol in dichloromethane) to afford tert-butyl 4-(3-hydroxycyclobutyl)piperazine-1-carboxylate (150 mg, 74.1% yield) as a white solid.

Step C. trans-3-Piperazin-1-ylcyclobutanol hydrochloride

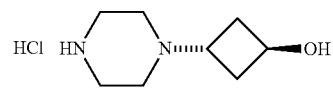

To a solution of tert-butyl 4-(3-hydroxycyclobutyl)piperazine-1-carboxylate (150 mg, 0.59 mmol) in methanol (5 mL) was added hydrogen chloride (0.15 mL, 0.59 mmol, 4 M) at 0° C. The reaction was stirred at 20° C. for 2 h. The reaction was concentrated to afford 3-piperazin-1-ylcyclobutanol hydrochloride (100 mg, 89% yield) as a white solid, which was used directly without purification.

Intermediate Q. cis-3-Piperazin-1-ylcyclobutanol hydrochloride

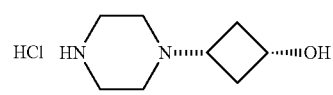

Step A. 1-Benzyl-4-(3-benzyloxycyclobutyl)piperazine

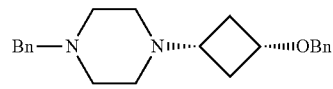 [SMILES: c1ccc(CO[C@H]2C[C@@H](N3CCN(Cc4ccccc4)CC3)C2)cc1]

To a solution of 3-(benzyloxy)cyclobutanone (11.0 g, 62.4 mmol), 1-benzylpiperazine (5.0 g, 28.3 mmol) in methanol (15 mL) was added sodium cyanoborohydride (3.9 g, 62.4 mmol). The reaction mixture was stirred at 18° C. for 16 h. The reaction was diluted with water (10 mL) and extracted with dichloromethane (20 mL×3). The organics were washed with brine (10 mL×3), dried over sodium sulfate, filtered and concentrated. The crude product was purified by reverse phase chromatography (acetonitrile 30-35/0.05% ammonia hydroxide in water) to afford 1-benzyl-4-(3-benzyloxycyclobutyl)piperazine (4.0 g, 42% yield) as a yellow oil. $^1$H NMR (400 MHz, CDCl$_3$) δ 7.31-7.22 (m, 10H), 4.39 (s, 2H), 3.79-3.72 (m, 1H), 3.50 (s, 2H), 2.47-2.13 (m, 11H), 1.88-1.82 (m, 2H).

Step B. cis-tert-Butyl 4-(3-hydroxycyclobutyl)piperazine-1-carboxylate

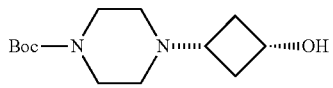

To a solution of 1-benzyl-4-(3-benzyloxycyclobutyl)piperazine (3.9 g, 11.6 mmol) and di-tert-butyldicarbonate (3.8 g, 17.4 mmol) in methanol (50 mL) was added 20% palladium hydroxide on carbon (2.0 g, 1.44 mmol) on carbon and 10% palladium (1.6 g, 1.44 mmol) on carbon. The reaction mixture was stirred at 50° C. for 1 h under hydrogen (50 psi). The reaction was filtered and concentrated to give cis-tert-butyl 4-(3-hydroxycyclobutyl)piperazine-1-carboxylate (2.3 g, 77% yield) as a colorless oil. $^1$H NMR (400 MHz, CD$_3$OD) δ 3.99-3.92 (m, 1H), 3.45 (s, 4H), 2.53-2.49 (m, 2H), 2.49-2.36 (m, 5H), 1.82-1.75 (m, 2H), 1.45 (s, 9H).

Step C. cis-3-Piperazin-1-ylcyclobutanol hydrochloride

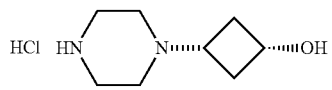

To a solution of tert-butyl 4-(3-hydroxycyclobutyl)piperazine-1-carboxylate (150 mg, 0.59 mmol) in methanol (5 mL) was added hydrogen chloride (0.15 mL, 0.59 mmol, 4 M) at 0° C. The reaction was stirred at 20° C. for 2 h, after which it was concentrated to afford cis-3-piperazin-1-ylcyclobutanol hydrochloride (100 mg, 89% yield) as a white solid, which was used directly without purification.

Intermediate R. 4-(Azetidin-1-yl)piperidine

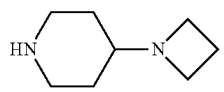

Step A. tert-Butyl 4-(azetidin-1-yl)piperidine-1-carboxylate

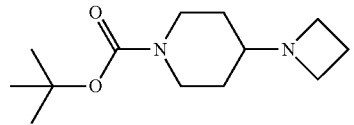

To a solution of azetidine hydrochloride (1.0 g, 10.7 mmol) in methyl alcohol (10 mL), dichloromethane (10 mL) and acetic acid (0.50 mL) was added 1-boc-4-piperidone (4.2 g, 21.4 mmol). The reaction mixture was stirred at 30° C. for 1 h. Sodium cyanoborohydride (1.3 g, 21.4 mmol) was added. Stirring was continued at room temperature for 16 h, after which the reaction was quenched with saturated aqueous sodium carbonate, adjusting to pH=7. The mixture was concentrated and purified by flash chromatography on silica (eluting gradient: 0-20% methanol in dichloromethane) to afford tert-butyl 4-(azetidin-1-yl)piperidine-1-carboxylate (2.5 g, 97%) as a white solid.

Step B. 4-(Azetidin-1-yl)piperidine

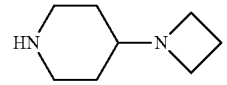

To a solution of tert-butyl 4-(azetidin-1-yl)piperidine-1-carboxylate (3.0 g, 12.5 mmol) in dichloromethane (20 mL) was added trifluoroacetic acid (6 mL, 80.5 mmol) at 0° C. The reaction mixture was stirred at 15° C. for 2 h and concentrated to afford crude 4-(azetidin-1-yl)piperidine (1.5 g) as a white solid, which was used directly without further purification.

Intermediate S. tert-Butyl (2-(hydroxymethyl)-2,3-dihydro-1H-inden-1-yl)carbamate

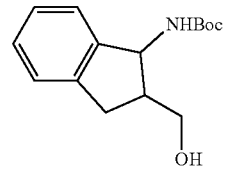 [SMILES: CC(C)(C)OC(=O)NC1c2ccccc2CC1CO]

Step A. cis-2a,3-Dihydro-1H-indeno[1,2-b]azet-2(7bH)-one

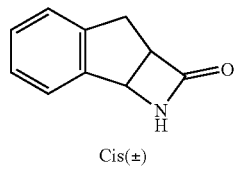 [SMILES: O=C1NC2c3ccccc3CC12]

To a solution of indene (5.5 g, 47.4 mmol) in diethyl ether (30 mL) was added chlorosulfonyl isocyanate (4.5 mL, 52.1 mmol). The reaction mixture was stirred at 25° C. for 2 h. n-Hexane (50 mL) was added. The resulting crystalline N-chlorosulfonyl derivative was filtered, re-dissolved in diethyl ether (100 mL), and added dropwise to a mixture of sodium sulfite (5 g) in water (25 mL) and diethyl ether (25 mL). The aqueous phase was separated and slightly basified by addition of 10% aqueous potassium hydroxide. The resulting precipitate was filtered to afford cis-2a,3-dihydro-1H-indeno[1,2-b]azet-2(7bH)-one (5 g, 66%) as a white solid. $^1$H NMR (400 MHz, CDCl3): 7.36-7.22 (m, 4H), 6.22 (br s, 1H), 5.05 (d, J=4.0 Hz, 1H), 4.05 (dd, J=10.4, 2.0 Hz, 1H), 3.37 (d, J=17.2 Hz, 1H), 3.09 (dd, J=17.6, 10.8 Hz, 1H).

Step B. cis-tert-Butyl 2-oxo-2,2a,3,7b-tetrahydro-1H-indeno[1,2-b]azete-1-carboxylate

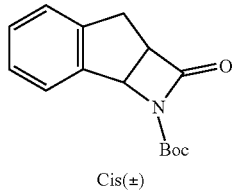 [SMILES: CC(C)(C)OC(=O)N1C(=O)C2Cc3ccccc3C21]

Cis(±)

To a solution of cis-2a,3-dihydro-1H-indeno[1,2-b]azet-2(7bH)-one (1.5 g, 9.42 mmol) in acetonitrile (10 mL) was added 4-dimethylaminopyridine (288 mg, 2.36 mmol), followed by di-tert-butyldicarbonate (4.11 g, 18.9 mmol). The reaction was stirred at 25° C. for 2 h, diluted with water (100 mL) and extracted with ethyl acetate (200 mL×3). The combined organic phase was washed with brine (200 mL×2), dried over sodium sulfate, and concentrated. The residue was purified by flash chromatography (eluting gradient: 0-50% ethyl acetate in petroleum ether) to afford cis-tert-butyl 2-oxo-3,7b-dihydro-2aH-indeno[1,2-b]azete-1-carboxylate (1.5 g, 61%) as a white solid.

Step C. tert-Butyl (2-(hydroxymethyl)-2,3-dihydro-1H-inden-1-yl)carbamate

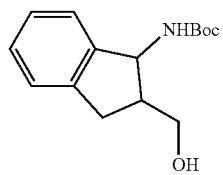 [SMILES: CC(C)(C)OC(=O)NC1c2ccccc2CC1CO]

To a solution of tert-butyl 2-oxo-3,7b-dihydro-2aH-indeno[1,2-b]azete-1-carboxylate (1.2 g, 4.63 mmol) in tetrahydrofuran (5 mL) was added lithium aluminum hydride (329 mg, 8.68 mmol). The reaction was stirred at 15° C. for 2 h and quenched with sequential addition of water (0.33 mL), 15% aqueous sodium hydroxide (0.33 mL) and water (1.0 mL). The mixture was filtered and concentrated. The residue was purified by flash chromatography (eluting gradient: 0-60% ethyl acetate in petroleum ether) to afford tert-butyl N-[2-(hydroxymethyl)indan-1-yl]carbamate (1.2 g, 79%) as a white solid.

Intermediate T. N-[2,2-Dimethyl-6-(1-methylimidazol-4-yl)-3H-benzofuran-5-yl]pyrazolo[1,5-a]pyrimidine-3-carboxamide

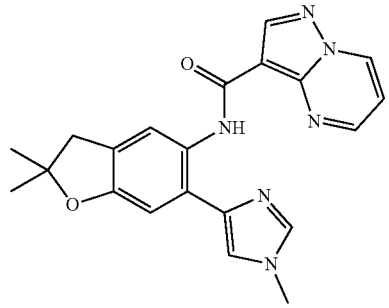 [SMILES: Cn1cnc(-c2cc3c(cc2NC(=O)c2cnn4cccnc24)CC(C)(C)O3)c1]

Step A: 4-(2,2-Dimethyl-5-nitro-3H-benzofuran-6-yl)-1-methyl-imidazole

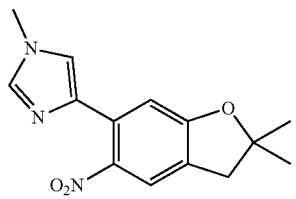 [SMILES: Cn1cnc(-c2cc3c(cc2[N+](=O)[O-])CC(C)(C)O3)c1]

To a solution of 6-bromo-2,2-dimethyl-5-nitro-3H-benzofuran (200 mg, 0.74 mmol) bis(triphenylphosphine)palladium(II) dichloride (103 mg, 0.15 mmol) in N,N-dimethylformamide (5 ml) was added tributyl-(1-methylimidazol-4-yl)stannane (382 mg, 1.03 mmol) under nitrogen. The mixture was stirred at 100° C. for 16 h. The reaction mixture was filtered, diluted with water (20 ml) and extracted with ethyl acetate (20 ml×2). The organic phase was washed with brine (10 ml×2), dried over sodium sulfate, filtered and concentrated. The residue was purified by flash chromatography (5-10% ethyl acetate in petroleum ether) to afford 4-(2,2-dimethyl-5-nitro-3H-benzofuran-6-yl)-1-methyl-imidazole (113 mg, 56%) as a yellow solid. $^1$H NMR (400 MHz, CDCl$_3$) δ 7.62 (s, 1H), 7.47 (s, 1H), 7.13 (s, 1H), 7.07 (s, 1H), 3.73 (s, 3H), 3.06 (s, 2H), 1.52 (s, 6H). LCMS (ESI): m/z=274.0 [M+H]$^+$.

Step B: 2,2-Dimethyl-6-(1-methylimidazol-4-yl)-3H-benzofuran-5-amine

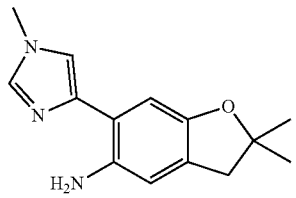 [SMILES: Cn1cnc(-c2cc3c(cc2N)CC(C)(C)O3)c1]

To a solution of 4-(2,2-dimethyl-5-nitro-3H-benzofuran-6-yl)-1-methyl-imidazole (120 mg, 0.44 mmol) in methanol (4 ml) was added 10% palladium on carbon (46 mg, 0.22 mmol). The reaction mixture was stirred under hydrogen atmosphere (15 psi) at 25° C. for 2 h. The reaction was filtered, and the filtrate was concentrated. The residue was purified by prep-TLC (5% methanol in dichloromethane) to afford 2,2-dimethyl-6-(1-methylimidazol-4-yl)-3H-benzofuran-5-amine (85 mg, 80%) as a yellow solid. LCMS (ESI): m/z=243.9 [M+H]$^+$.

Step C: N-[2,2-Dimethyl-6-(1-methylimidazol-4-yl)-3H-benzofuran-5-yl]pyrazolo[1,5-a]pyrimidine-3-carboxamide

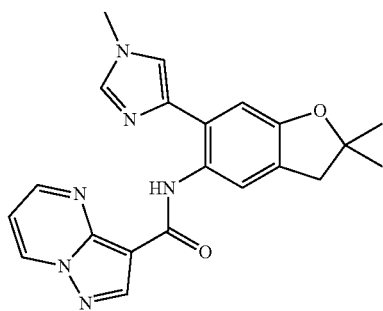 [SMILES: Cn1cnc(-c2cc3c(cc2NC(=O)c2cnn4cccnc24)CC(C)(C)O3)c1]

To a solution of 2,2-dimethyl-6-(1-methylimidazol-4-yl)-3H-benzofuran-5-amine (85 mg, 0.35 mmol) in pyridine (2 ml) was added pyrazolo[1,5-a]pyrimidine-3-carbonyl chloride (95 mg, 0.52 mmol). The reaction mixture was stirred at 25° C. for 2 h. The reaction was concentrated and the residue was purified by prep-TLC (10% ethyl acetate in petroleum ether) to give N-[2,2-dimethyl-6-(1-methylimidazol-4-yl)-3H-benzofuran-5-yl]pyrazolo[1,5-a]pyrimidine-3-carboxamide (45 mg, 33.2%) as a yellow solid. $^1$H NMR (400 MHz, CDCl$_3$) δ 11.45 (s, 1H), 8.78-8.76 (m, 2H), 8.67-8.65 (m, 1H), 8.28 (s, 1H), 7.48 (s, 1H), 7.11 (s, 1H), 6.98 (dd, J=7.2, 4.0 Hz, 1H), 6.92 (s, 1H), 3.71 (s, 3H), 3.08 (s, 2H), 1.51 (s, 6H). LCMS (ESI): m/z=389.0 [M+H]$^+$.

The following provides non-limiting examples of compounds according to the present invention.

Example 1. N-[6-[4-(2-aminoethyl)piperazin-1-yl]-2,2-dimethyl-3H-benzofuran-5-yl]pyrazolo[1,5-a]pyrimidine-3-carboxamide

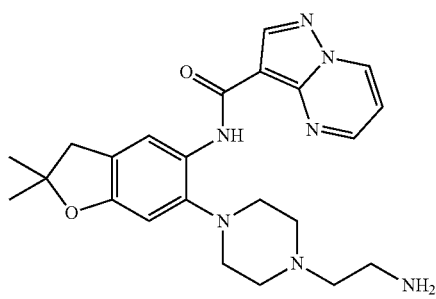 [SMILES: CC1(C)Cc2cc(NC(=O)c3cnn4cccnc34)c(N3CCN(CCN)CC3)cc2O1]

Step A. Benzyl (2-(4-(2,2-dimethyl-5-(pyrazolo[1,5-a]pyrimidine-3-carboxamido)-2,3-dihydrobenzofuran-6-yl)piperazin-1-yl)ethyl)carbamate

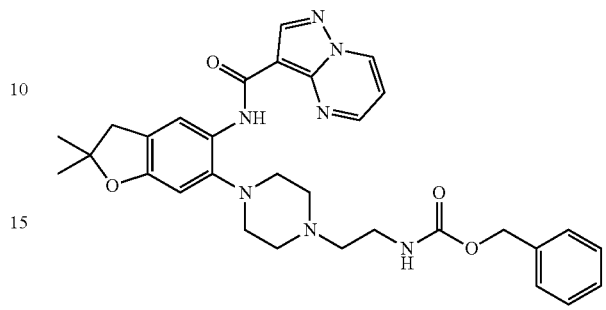

N-(2,2-Dimethyl-6-piperazin-1-yl-3H-benzofuran-5-yl)pyrazolo[1,5-a]pyrimidine-3-carboxamide (Intermediate D) (188 mg, 0.478 mmol) and benzyl (2-bromoethyl)carbamate (136 mg, 0.526 mmol) were dissolved in 1,4-dioxane (16 mL) and treated with N,N-diisopropylethylamine (0.250 mL, 1.43 mmol). The reaction mixture was stirred for 16 h at 90° C., concentrated under reduced pressure and the crude residue was purified by flash column chromatography (0-100% isopropyl acetate/heptane) to give benzyl (2-(4-(2,2-dimethyl-5-(pyrazolo[1,5-a]pyrimidine-3-carboxamido)-2,3-dihydrobenzofuran-6-yl)piperazin-1-yl)ethyl)carbamate (228 mg, 0.400 mmol, 84% yield) as a solid. $^1$H NMR (400 MHz, Chloroform-d) δ 10.35 (s, 1H), 8.81 (dd, J=7.0, 1.7 Hz, 1H), 8.78 (s, 1H), 8.72 (s, 1H), 8.40 (s, 1H), 7.42-7.28 (m, 5H), 7.05 (s, 1H), 6.64 (s, 1H), 5.30 (s, 1H), 5.12 (s, 2H), 3.36 (s, 2H), 3.05-3.01 (m, 2H), 2.93 (s, 4H), 2.69 (s, 3H), 2.58 (s, 2H), 1.48 (s, 6H).

Step B. N-(6-(4-(2-Aminoethyl)piperazin-1-yl)-2,2-dimethyl-2,3-dihydrobenzofuran-5-yl)pyrazolo[1,5-a]pyrimidine-3-carboxamide

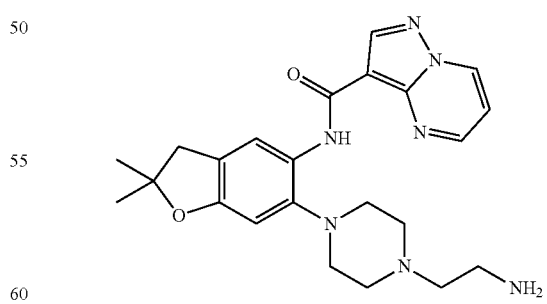

Benzyl (2-(4-(2,2-dimethyl-5-(pyrazolo[1,5-a]pyrimidine-3-carboxamido)-2,3-dihydrobenzofuran-6-yl)piperazin-1-yl)ethyl)carbamate (228 mg, 0.400 mmol) was suspended in concentrated hydrochloric acid (1.0 mL, 32 mmol) and stirred for 3 h at room temperature. The reaction mixture was absorbed onto celite under reduced pressure. The crude residue was purified by silica gel chromatography (eluting gradient 0-20% methanol in dichloromethane) to afford the title compound (118 mg, 0.271 mmol, 68% yield) as a solid. A sample of N-(6-(4-(2-aminoethyl)piperazin-1-yl)-2,2-dimethyl-2,3-dihydrobenzofuran-5-yl)pyrazolo[1,5-a]pyrimidine-3-carboxamide (30 mg, 0.0689 mmol) was removed for further purification by preparative HPLC ((Gemini NX, 5*3 cm c18, 5 um; A: acetonitrile 20-60%; B: 0.1% ammonium hydroxide in water) to afford the title compound (8.23 mg, 0.0189 mmol) as a white solid. $^1$H NMR (400 MHz, DMSO-$d_6$) δ 10.39 (s, 1H), 9.37 (dd, J=7.0, 1.6 Hz, 1H), 8.90 (dd, J=4.2, 1.6 Hz, 1H), 8.68 (s, 1H), 8.45 (s, 1H), 8.30 (s, 1H), 7.35 (dd, J=7.0, 4.2 Hz, 1H), 6.68 (s, 1H), 6.62 (s, 1H), 3.00 (s, 2H), 2.83 (t, J=4.4 Hz, 4H), 2.75 (t, J=6.3 Hz, 2H), 2.70-2.57 (m, 4H), 2.46 (s, 2H), 1.41 (s, 6H). MS (ESI): m/z=436.2 [M+1]$^+$.

Example 2. N-(2,2-Dimethyl-6-(4-(2-(methylsulfonamido)ethyl)piperazin-1-yl)-2,3-dihydrobenzofuran-5-yl)pyrazolo[1,5-a]pyrimidine-3-carboxamide

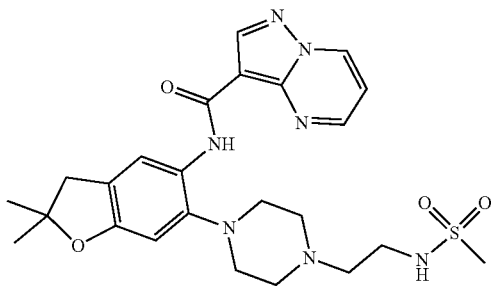

N-(6-(4-(2-Acetamidoethyl)piperazin-1-yl)-2,2-dimethyl-2,3-dihydrobenzofuran-5-yl)pyrazolo[1,5-a]pyrimidine-3-carboxamide (Example 1) (44 mg, 0.10 mmol) and 4-dimethylaminopyridine (2.5 mg, 0.020 mmol) were dissolved in dimethyl sulfoxide (3.4 mL) and treated with triethylamine (0.042 mL, 0.30 mmol) followed by methanesulfonyl chloride (0.0082 mL, 0.11 mmol). The reaction mixture was stirred for 4 h at room temperature and concentrated under reduced pressure. The crude residue was purified by preparative HPLC ((Gemini NX, 5*3 cm c18, 5 um; A: acetonitrile 20-60%; B: 0.1% ammonium hydroxide in water) to afford N-(2,2-dimethyl-6-(4-(2-(methylsulfonamido)ethyl)piperazin-1-yl)-2,3-dihydrobenzofuran-5-yl)pyrazolo[1,5-a]pyrimidine-3-carboxamide (23 mg, 0.043 mmol, 42% yield) as a solid. $^1$H NMR (400 MHz, DMSO-$d_6$) δ 10.39 (s, 1H), 9.36 (dd, J=7.0, 1.6 Hz, 1H), 8.90 (dd, J=4.2, 1.6 Hz, 1H), 8.68 (s, 1H), 8.30 (s, 1H), 7.35 (dd, J=7.0, 4.2 Hz, 1H), 6.88 (s, 1H), 6.69 (s, 1H), 3.17-3.05 (m, 2H), 3.00 (s, 2H), 2.94 (s, 3H), 2.82 (t, J=4.5 Hz, 4H), 2.72-2.60 (m, 4H), 2.54 (t, J=6.9 Hz, 2H), 1.41 (s, 6H). MS (ESI): m/z=478.2 [M+1]$^+$.

Example 3

N-(6-(4-(2-Acetamidoethyl)piperazin-1-yl)-2,2-dimethyl-2,3-dihydrobenzofuran-5-yl)pyrazolo[1,5-a]pyrimidine-3-carboxamide

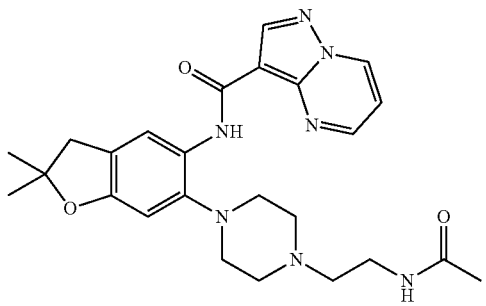 [SMILES: CC(=O)NCCN1CCN(c2cc3c(cc2NC(=O)c2cnn4cccnc24)CC(C)(C)O3)CC1]

N-(6-(4-(2-Acetamidoethyl)piperazin-1-yl)-2,2-dimethyl-2,3-dihydrobenzofuran-5-yl)pyrazolo[1,5-a]pyrimidine-3-carboxamide (Example 1) (44 mg, 0.10 mmol) and 4-dimethylaminopyridine (2.5 mg, 0.020 mmol) were dissolved in dimethyl sulfoxide (3.4 mL) and treated with triethylamine (0.042 mL, 0.30 mmol) followed by acetyl chloride (0.0076 mL, 0.11 mmol). The reaction mixture was stirred for 4 h at room temperature, concentrated under reduced pressure and the crude residue was purified by preparative HPLC ((Gemini NX, 5*3 cm c18, 5 um; A: acetonitrile 20-60%; B: 0.1% ammonium hydroxide in water) to afford N-(6-(4-(2-acetamidoethyl)piperazin-1-yl)-2,2-dimethyl-2,3-dihydrobenzofuran-5-yl)pyrazolo[1,5-a]pyrimidine-3-carboxamide (22 mg, 0.047 mmol, 46% yield) as a solid. $^1$H NMR (400 MHz, DMSO-$d_6$) δ 10.38 (s, 1H), 9.36 (dd, J=7.0, 1.6 Hz, 1H), 8.89 (dd, J=4.2, 1.6 Hz, 1H), 8.67 (s, 1H), 8.30 (s, 1H), 7.78 (t, J=5.4 Hz, 1H), 7.35 (dd, J=7.0, 4.2 Hz, 1H), 6.68 (s, 1H), 3.19 (q, J=6.6 Hz, 2H), 3.00 (s, 2H), 2.82 (t, J=4.5 Hz, 4H), 2.74-2.58 (m, 4H), 2.45 (t, J=6.8 Hz, 2H), 1.81 (s, 3H), 1.41 (s, 6H). MS (ESI): m/z=478.2 [M+1]$^+$.

Example 4

N-(6-(4-(2-(Dimethylamino)ethyl)piperazin-1-yl)-2,2-dimethyl-2,3-dihydrobenzofuran-5-yl)pyrazolo[1,5-a]pyrimidine-3-carboxamide

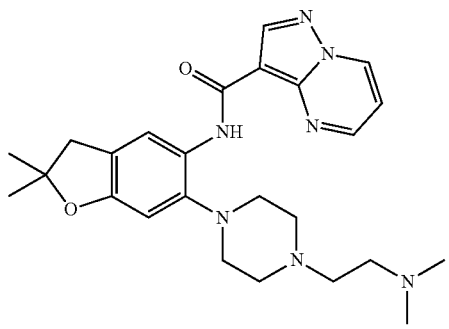

N-(2,2-Dimethyl-6-piperazin-1-yl-3H-benzofuran-5-yl)pyrazolo[1,5-a]pyrimidine-3-carboxamide (Intermediate D) (107 mg, 0.273 mmol), 4-dimethylaminopyridine (6.74 mg, 0.0546 mmol), and 2-bromo-N,N-dimethyl-ethanamine hydrobromide (76.4 mg, 0.328 mmol) were dissolved in dimethyl sulfoxide (9.1 mL) and treated with triethylamine (0.11 mL, 0.820 mmol). The reaction mixture was stirred for 16 h at 60° C. The reaction was cooled to ambient temperature. 2-bromo-N,N-dimethyl-ethanamine hydrobromide (76.4 mg, 0.328 mmol) and triethylamine (0.11 mL, 0.820 mmol) were added and the reaction mixture was stirred for 6 h at 120° C. The mixture was concentrated under reduced pressure, and the crude residue was purified by preparative HPLC ((Gemini NX, 5*3 cm c18, 5 um; A: acetonitrile 20-60%; B: 0.1% ammonium hydroxide in water) to afford N-(6-(4-(2-(dimethylamino)ethyl)piperazin-1-yl)-2,2-dimethyl-2,3-dihydrobenzofuran-5-yl)pyrazolo[1,5-a]pyrimidine-3-carboxamide (73 mg, 0.158 mmol, 58% yield) as a solid. $^1$H NMR (400 MHz, DMSO-d$_6$) δ 10.40 (s, 1H), 9.36 (dd, J=7.0, 1.6 Hz, 1H), 8.91 (dd, J=4.2, 1.6 Hz, 1H), 8.67 (s, 1H), 8.30 (s, 1H), 7.36 (dd, J=7.0, 4.2 Hz, 1H), 6.69 (s, 1H), 2.99 (s, 2H), 2.80 (t, J=4.6 Hz, 4H), 2.66 (d, J=7.3 Hz, 4H), 2.48 (s, 2H), 2.37 (dd, J=7.9, 5.7 Hz, 2H), 2.15 (s, 6H), 1.41 (s, 6H). MS (ESI): m/z=464.2 [M+1]$^+$.

TABLE 3

The following examples were made in a manner similar to that for Example 4:

| Ex. | Name | Structure | NMR, MS |
|---|---|---|---|
| 5 | N-(2,2-Dimethyl-6-(4-((3-methyl-6-oxo-1,6-dihydropyridin-2-yl)methyl)piperazin-1-yl)-2,3-dihydrobenzofuran-5-yl)pyrazolo[1,5-a]pyrimidine-3-carboxamide | 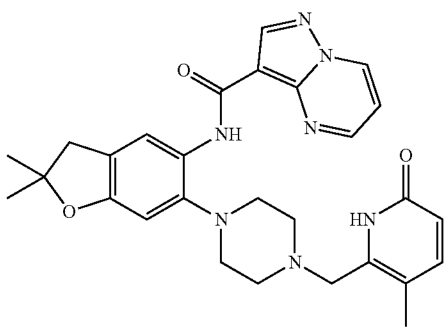 [SMILES: Cc1ccc(=O)[nH]c1CN1CCN(c2cc3c(cc2NC(=O)c2cnn4cccnc24)CC(C)(C)O3)CC1] | $^1$H NMR (400 MHz, CDCl$_3$) δ 10.32 (s, 1H), 10.02 (br s, 1H), 8.86-8.84 (m, 1H), 8.80 (s, 1H), 8.77-8.76 (m, 1H), 8.37 (s, 1H), 7.23 (d, J = 9.6 Hz, 1H), 7.09 (dd, J = 6.8, 4.0 Hz, 1H), 6.66 (s, 1H), 6.41 (d, J = 9.2 Hz, 1H), 3.49 (s, 2H), 3.04 (s, 2H), 2.99 (t, J = 4.4 Hz, 4H), 2.78 (t, J = 4.4 Hz, 4H), 2.06 (s, 3H), 1.50 (s, 6H). LCMS (ESI): m/z = 514.2 [M + H]$^+$. |
| 6 & 7 | (S)-N-(2,2-Dimethyl-6-(4-((6-oxopiperidin-2-yl)methyl)piperazin-1-yl)-2,3-dihydrobenzofuran-5-yl)pyrazolo[1,5-a]pyrimidine-3-carboxamide and (R)-N-(2,2-Dimethyl-6-(4-((6-oxopiperidin-2-yl)methyl)piperazin-1-yl)-2,3-dihydrobenzofuran-5-yl)pyrazolo[1,5-a]pyrimidine-3-carboxamide (absolute stereochemistry assigned arbitrarily) | | Example 6, Peak 1: $^1$H NMR (400 MHz, CDCl$_3$) δ 10.38 (s, 1H), 8.84-8.82 (m, 1H), 8.79 (s, 1H), 8.71-8.70 (m, 1H), 8.39 (s, 1H), 7.07-7.05 (m, 1H), 6.65 (s, 1H), 6.61 (s, 1H), 3.58-3.53 (m, 1H), 3.04 (s, 2H), 2.94-2.90 (m, 3H), 2.85-2.83 (m, 2H), 2.58 (br s, 1H), 2.51-2.42 (m, 2H), 2.41-2.25 (m, 2H), 2.00-1.92 (m, 1H), 1.92-1.82 (m, 1H), 1.87-1.85 (m, 2H), 1.78-1.71 (m, 2H), 1.50 (s, 6H), 1.30-1.29 (m, 1H). LCMS (ESI): m/z = 504.2 [M + H]$^+$. Example 7, Peak 2: $^1$H NMR (400 MHz, CDCl$_3$) δ 10.37 (s, 1H), 8.84-8.82 (m, 1H), 8.78 (s, 1H), 8.71-8.70 (m, 1H), 8.39 (s, 1H), 7.07-7.04 (m, 1H), 6.64 (s, 1H), 6.60 (s, 1H), 3.55-3.52 (m, 1H), 3.03 (s, 2H), 2.95-2.89 (m, 3H), 2.88-2.85 (m, 2H), 2.57 (s, 1H), 2.47-2.31 (m, 4H), 2.00-1.96 (m, 1H), 1.87-1.86 (m, 2H), 1.80-1.68 (m, 2H), 1.49 (s, 6H), 1.31-1.21 (m, 1H). LCMS (ESI): m/z = 504.2 [M + H]$^+$. |
| 8 | N-(2,2-Dimethyl-6-(4-((4-methyl-1H-imidazol-5-yl)methyl)piperazin-1-yl)-2,3-dihydrobenzofuran-5-yl)pyrazolo[1,5-a]pyrimidine-3-carboxamide | 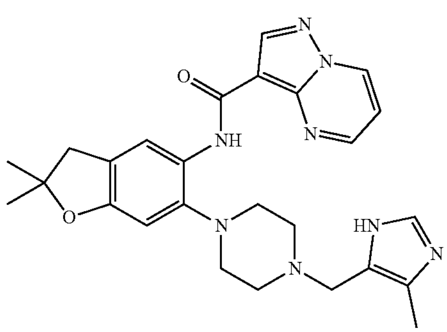 [SMILES: Cc1nc[nH]c1CN1CCN(c2cc3c(cc2NC(=O)c2cnn4cccnc24)CC(C)(C)O3)CC1] | $^1$H NMR (400 MHz. CDCl$_3$) δ 10.40 (s, 1H), 8.84-8.81 (m, 1H), 8.78 (s, 1H). 8.60-8.55 (m, 1H), 8.40 (s, 1H), 7.56 (s, 1H), 7.09 (dd, J = 6.8, 4.0 Hz, 1H), 6.65 (s, 1H), 3.66 (s, 2H), 3.03 (s, 2H), 3.00-2.92 (m, 4H), 2.83-2.73 (m, 4H), 2.25 (s, 3H), 1.49 (s, 6H). LCMS (ESI): m/z = 487.2 [M + H]$^+$. |

TABLE 3-continued

*The following examples were made in a manner similar to that for Example 4:*

| Ex. | Name | Structure | NMR, MS |
|---|---|---|---|
| 9 | N-[6-[4-[(4-Ethyl-1H-imidazol-5-yl)methyl]piperazin-1-yl]-2,2-dimethyl-3H-benzofuran-5-yl]pyrazolo[1,5-a]pyrimidine-3-carboxamide | 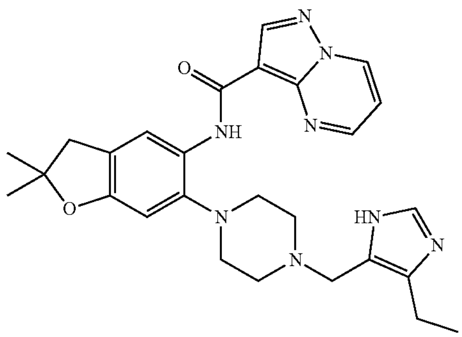 [SMILES: CCc1nc[nH]c1CN1CCN(c2cc3c(cc2NC(=O)c2cnn4cccnc24)CC(C)(C)O3)CC1] | $^1$H NMR (400 MHz, CDCl$_3$) δ 10.42 (s, 1H), 8.81 (dd, J = 7.2, 1.2 Hz, 1H), 8.75 (s, 1H), 8.50-8.45 (m, 1H), 8.38 (s, 1H), 7.55 (s, 1H), 7.07 (dd, J = 7.2, 4.0 Hz, 1H), 6.63 (s, 1H), 3.64 (s, 2H), 3.02 (s, 2H), 2.91 (br s, 4H), 2.72 (br s, 4H), 2.61 (q, J = 7.6 Hz, 2H), 1.48 (s, 6H), 1.21 (t, J = 7.6 Hz, 3H). LCMS (ESI): m/z = 501.3 [M + H]$^+$. |
| 10 | N-(6-(4-((4-Chloro-1H-imidazol-5-yl)methyl)piperazin-1-yl)-2,2-dimethyl-2,3-dihydrobenzofuran-5-yl)pyrazolo[1,5-a]pyrimidine-3-carboxamide | 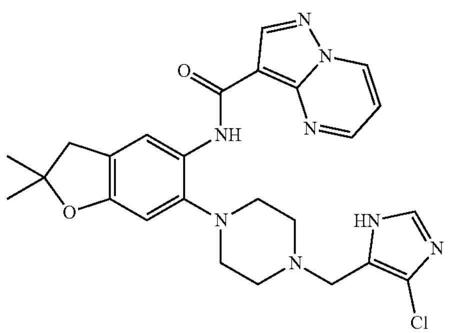 [SMILES: CC1(C)Cc2cc(NC(=O)c3cnn4cccnc34)c(N3CCN(Cc4[nH]cnc4Cl)CC3)cc2O1] | $^1$H NMR (400 MHz, CDCl$_3$) δ 10.33 (s, 1H), 8.85-8.83 (m, 1H), 8.77 (s, 1H), 8.64-8.63 (m, 1H), 8.38 (s, 1H), 7.51 (s, 1H), 7.11 (dd, J = 7.2, 4.0 Hz, 1H), 6.61 (s, 1H), 3.67 (s, 2H), 3.04 (s, 2H), 2.97-2.86 (m, 4H), 2.81-2.66 (m, 4H), 1.49 (s, 6H). MS (ESI): m/z = 507 [M + H]$^+$. |
| 11 | N-(2,2-Dimethyl-6-(4-((4-methylthiazol-5-yl)methyl)piperazin-1-yl)-2,3-dihydrobenzofuran-5-yl)pyrazolo[1,5-a]pyrimidine-3-carboxamide | 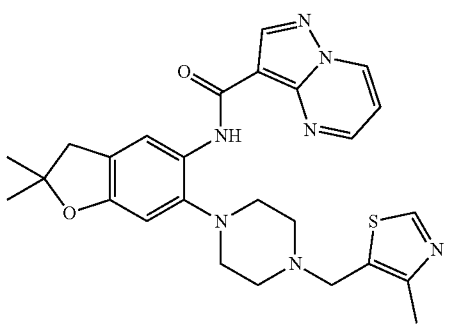 [SMILES: Cc1ncsc1CN1CCN(c2cc3c(cc2NC(=O)c2cnn4cccnc24)CC(C)(C)O3)CC1] | $^1$H NMR (400 MHz, CDCl$_3$) δ 10.37 (s, 1H), 8.82 (d, J = 6.8 Hz, 1H), 8.77 (s, 1H), 8.71 (s, 1H), 8.38 (s, 1H), 8.31 (d, J = 4.0 Hz, 1H), 7.03 (dd, J = 6.8, 4.4 Hz, 1H), 6.65 (s, 1H), 3.84 (s, 2H), 3.02 (s, 2H), 2.94 (t, J = 4.4 Hz, 4H), 2.74 (br s, 4H), 2.44 (s, 3H), 1.48 (s, 6H). LCMS (ESI): m/z = 504.2 [M + H]$^+$. |
| 12 | N-(2,2-Dimethyl-6-(4-((5-methylisoxazol-4-yl)methyl)piperazin-1-yl)-2,3-dihydrobenzofuran-5-yl)pyrazolo[1,5-a]pyrimidine-3-carboxamide | 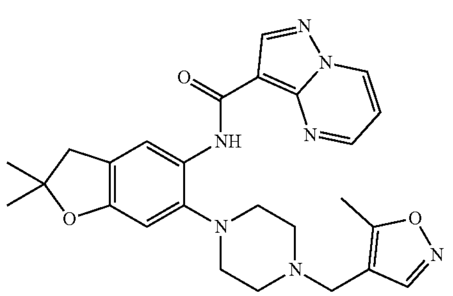 [SMILES: Cc1oncc1CN1CCN(c2cc3c(cc2NC(=O)c2cnn4cccnc24)CC(C)(C)O3)CC1] | $^1$H NMR (400 MHz, CDCl$_3$) δ 10.36 (s, 1H), 8.87-8.80 (m, 1H), 8.77 (s, 1H), 8.37 (s, 1H), 8.23-8.21 (m, 1H), 8.16 (s, 1H), 7.08 (dd, J = 7.2, 4.0 Hz, 1H), 6.65 (s, 1H), 3.56 (s, 2H), 3.03 (s, 2H), 2.94 (t, J = 4.4 Hz, 4H), 2.67-2.60 (m, 4H), 2.40 (s, 3H), 1.49 (s, 6H). LCMS (ESI): m/z = 488.2 [M + H]$^+$. |

TABLE 3-continued

The following examples were made in a manner similar to that for Example 4:

| Ex. | Name | Structure | NMR, MS |
|---|---|---|---|
| 13 | N-(2,2-Dimethyl-6-(4-(oxetan-3-yl)piperazin-1-yl)-2,3-dihydrobenzofuran-5-yl)pyrazolo[1,5-a]pyrimidine-3-carboxamide | 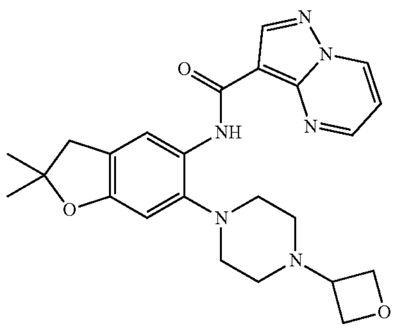 [SMILES: CC1(C)Cc2cc(NC(=O)c3cnn4cccnc34)c(N3CCN(C4COC4)CC3)cc2O1] | $^1$H NMR (400 MHz. CDCl$_3$) δ 10.37 (s, 1H), 8.85-8.83 (m, 1H), 8.79 (s, 1H), 8.75-8.70 (m, 1H), 8.39 (s, 1H), 7.08 (dd, J = 6.8, 4.0 Hz, 1H), 6.68 (s, 1H), 4.72-4.66 (m, 4H), 3.58-3.53 (m, 1H), 3.04 (s, 2H), 2.99-2.92 (m, 4H), 2.57 (br s, 4H), 1.49 (s, 6H). LCMS (ESI): m/z = 449.2 [M + H]$^+$. |
| 14 | N-(2,2-Dimethyl-6-(4-((3-methylisoxazol-4-yl)methyl)piperazin-1-yl)-2,3-dihydrobenzofuran-5-yl)pyrazolo[1,5-a]pyrimidine-3-carboxamide hydrochloride | 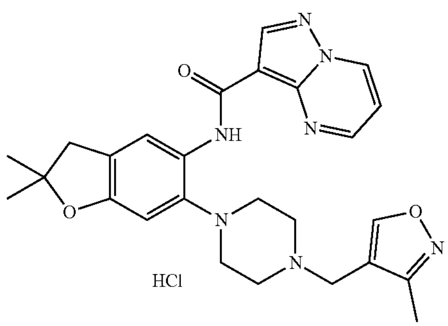 [SMILES: Cc1nocc1CN1CCN(c2cc3c(cc2NC(=O)c2cnn4cccnc24)CC(C)(C)O3)CC1 ; Cl] | $^1$H NMR (400 MHz, CD$_3$OD) δ 10.30 (s, 1H), 9.15 (d, J = 7.2 Hz, 1H), 8.92 (s, 1H), 8.66 (s, 1H), 8.59-8.63 (m, 1H), 8.12 (s, 1H), 7.27 (dd, J = 6.8, 4.4 Hz, 1H), 6.67 (s, 1H), 4.41 (s, 2H), 3.70-3.60 (m, 2H), 3.35-3.30 (m, 4H), 3.16-3.10 (m, 2H), 3.03 (s, 2H), 2.36 (s, 3H), 1.44 (s, 6H). LCMS (ESI): m/z = 488.2 [M + H]$^+$. |
| 15 | N-(6-(4-((5-Ethyl-2-oxo-2,3-dihydrooxazol-4-yl)methyl)piperazin-1-yl)-2,2-dimethyl-2,3-dihydrobenzofuran-5-yl)pyrazolo[1,5-a]pyrimidine-3-carboxamide | 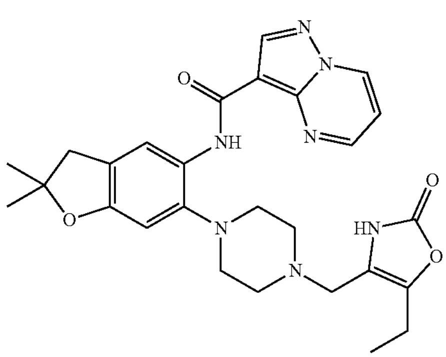 [SMILES: CCc1oc(=O)[nH]c1CN1CCN(c2cc3c(cc2NC(=O)c2cnn4cccnc24)CC(C)(C)O3)CC1] | $^1$H NMR (400 MHz, CDCl$_3$) δ 10.32 (s, 1H), 8.85-8.83 (m, 1H), 8.79 (s, 1H), 8.65-8.60 (m, 1H), 8.36 (s, 1H), 7.61 (br s, 1H), 7.10 (dd, J = 6.8, 4.0 Hz, 1H), 6.64 (s, 1H), 3.35 (s, 2H), 3.04 (s, 2H), 2.93 (br s, 4H), 2.69 (br s, 4H), 2.42 (q, J = 7.6 Hz, 2H), 1.49 (s, 6H), 1.17 (t, J = 7.6 Hz, 3H). LCMS (ESI): m/z = 518.1 [M + H]$^+$. |

TABLE 3-continued

The following examples were made in a manner similar to that for Example 4:

| Ex. | Name | Structure | NMR, MS |
|---|---|---|---|
| 16 | N-(6-(4-((3,5-Dimethylisoxazol-4-yl)methyl)piperazin-1-yl)-2,2-dimethyl-2,3-dihydrobenzofuran-5-yl)pyrazolo[1,5-a]pyrimidine-3-carboxamide | 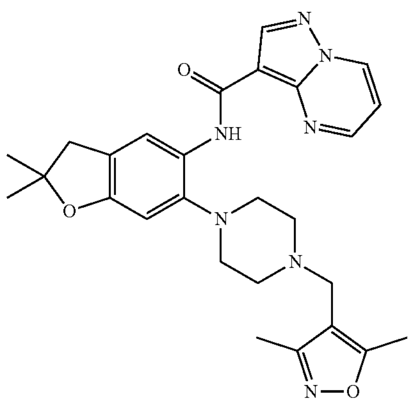 | $^1$H NMR (400 MHz, CDCl$_3$) δ 10.34 (s, 1H), 8.83 (d, J = 7.2 Hz, 1H), 8.79 (s, 1H), 8.45-8.40 (m, 2H), 7.08 (dd, J = 6.8, 4.4 Hz, 1H), 6.66 (s, 1H), 3.45 (s, 2H), 3.05 (s, 2H), 2.95 (br s, 4H), 2.67 (br s, 4H), 2.37 (s, 3H), 2.29 (s, 3H), 1.50 (s, 6H). LCMS (ESI): m/z = 502.2 [M + H]$^+$. |

TABLE 4

The following examples were made in a manner similar to that for Intermediate D, and using Intermediate E

| Ex. | Name | Structure | NMR, MS |
|---|---|---|---|
| 17 & 18 | (R)-N-(6-(4-(5-Ethyl-3-oxopyrazolidin-1-yl)piperidin-1-yl)-2,2-dimethyl-2,3-dihydrobenzofuran-5-yl)pyrazolo[1,5-a]pyrimidine-3-carboxamide and (S)-N-(6-(4-(5-Ethyl-3-oxopyrazolidin-1-yl)piperidin-1-yl)-2,2-dimethyl-2,3-dihydrobenzofuran-5-yl)pyrazolo[1,5-a]pyrimidine-3-carboxamide (absolute stereochemistry assigned arbitrarily) | | Example 17, Peak 2: $^1$H NMR (400 MHz, CDCl$_3$) δ 10.50 (s, 1H), 8.81-8.78 (m, 3H), 8.44 (s, 1H), 7.13-6.98 (m, 2H), 6.62 (s, 1H), 3.38-3.36 (m, 1H), 3.14-3.11 (m, 2H), 3.04 (s, 2H), 2.93-2.88 (m, 1H), 2.74-2.69 (m, 3H), 2.04-1.94 (m, 5H), 1.68-1.62 (m, 2H), 1.49 (s, 6H), 0.97 (t, J = 7.2 Hz, 3H). MS (ESI): m/z = 504.2 [M + H]$^+$. Example 18, Peak 1: $^1$H NMR (400 MHz, CDCl$_3$) δ 10.50 (s, 1H), 8.81-8.78 (m, 3H), 8.44 (s, 1H), 7.09-7.06 (m, 1H), 6.94 (br s, 1H), 6.62 (s, 1H), 3.38-3.36 (m, 2H), 3.14-3.10 (m, 2H), 3.04 (s, 2H), 2.89 (dd, J = 16.8, 8.0 Hz, 1H), 2.74-2.68 (m, 3H), 1.98-1.94 (m, 5H), 1.70-1.60 (m, 2H), 1.49 (s, 6H), 0.97 (t, J = 7.2 Hz, 3H). LCMS (ESI): m/z = 504.2 [M + H]$^+$. |

Examples 19 and 20

N-(6-(((3S,4S)-4-Amino-1-(2-amino-2-oxoethyl)pyrrolidin-3-yl)oxy)-2,2-dimethyl-2,3-dihydrobenzofuran-5-yl)pyrazolo[1,5-a]pyrimidine-3-carboxamide and N-(6-(((3R,4R)-4-Amino-1-(2-amino-2-oxoethyl)pyrrolidin-3-yl)oxy)-2,2-dimethyl-2,3-dihydrobenzofuran-5-yl)pyrazolo[1,5-a]pyrimidine-3-carboxamide

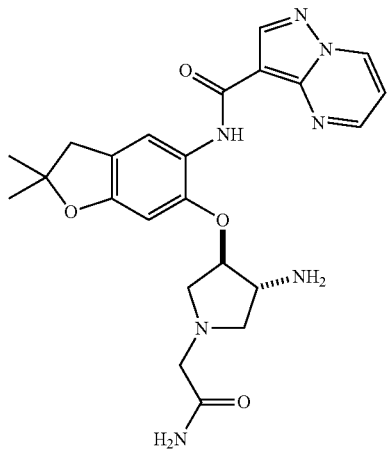

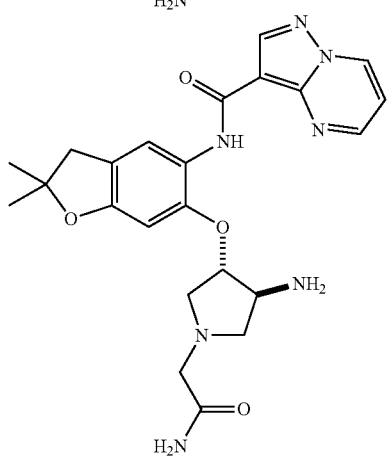

Step A. trans-tert-Butyl-3-amino-4-((2,2-dimethyl-5-nitro-2,3-dihydrobenzofuran-6-yl)oxy)pyrrolidine-1-carboxylate

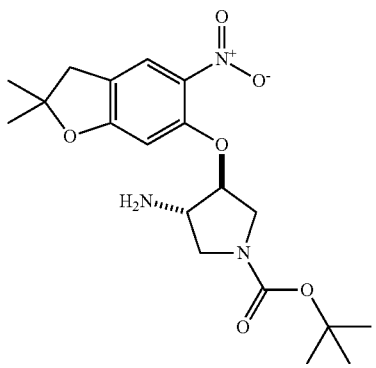

A mixture of 6-chloro-2,2-dimethyl-5-nitro-2,3-dihydrobenzofuran (Intermediate A) (200 mg, 0.88 mmol) and trans-tert-butyl-3-amino-4-hydroxy-pyrrolidine-1-carboxylate (355 mg, 1.76 mmol) were dissolved in dimethylsulfoxide (6.8 mL) and treated with sodium hydride (60% wt in mineral oil, 70.3 mg, 1.76 mmol) at room temperature. After 16 h, the reaction mixture was diluted with isopropyl acetate and washed with water. The layers were separated and the aqueous layer was extracted with isopropyl acetate (3×). The combined organic phases were dried over sodium sulfate and concentrated under reduced pressure. The residue was purified by silica gel chromatography (eluting gradient 0-100% isopropyl acetate in heptane) to afford trans-tert-butyl-3-amino-4-((2,2-dimethyl-5-nitro-2,3-dihydrobenzofuran-6-yl)oxy)pyrrolidine-1-carboxylate (244 mg, 0.620 mmol, 70% yield) as a solid. $^1$H NMR (400 MHz, DMSO-$d_6$) δ 7.82 (s, 1H), 6.85 (s, 1H), 4.67 (d, J=3.9 Hz, 1H), 3.77-3.64 (m, 1H), 3.49-3.40 (m, 2H), 3.40-3.31 (m, 2H), 3.15-3.08 (m, 1H), 3.01 (s, 2H), 1.46 (s, 6H), 1.40 (s, 9H).

Step B. trans-tert-Butyl-3-(((benzyloxy)carbonyl)amino)-4-((2,2-dimethyl-5-nitro-2,3-dihydrobenzofuran-6-yl)oxy)pyrrolidine-1-carboxylate

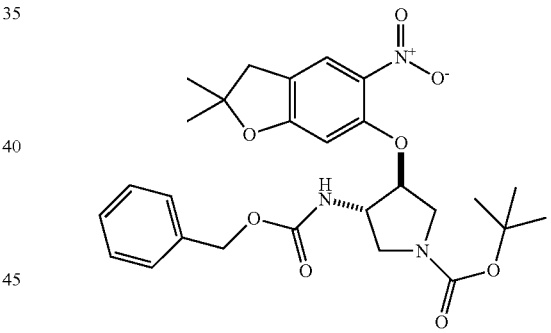

To a solution of trans-tert-butyl-3-amino-4-((2,2-dimethyl-5-nitro-2,3-dihydrobenzofuran-6-yl)oxy)pyrrolidine-1-carboxylate (243 mg, 0.62 mmol) in dichloromethane (1.5 mL) at room temperature was added N,N-diisopropylethylamine (0.16 mL, 0.93 mmol) followed by the addition of benzyl chloroformate (0.11 mL, 0.74 mmol). The reaction mixture was stirred for 15 min at room temperature, diluted with dichloromethane and washed with water. The layers were separated, and the aqueous layer was extracted with dichloromethane (3×). The combined organic phases were dried over sodium sulfate and concentrated under reduced pressure. The residue was purified by silica gel chromatography (eluting gradient 0-100% isopropyl acetate in heptane) to afford trans-tert-butyl-3-(((benzyloxy)carbonyl)amino)-4-((2,2-dimethyl-5-nitro-2,3-dihydrobenzofuran-6-yl)oxy)pyrrolidine-1-carboxylate (302 mg, 0.57 mmol, 93% yield) as a solid.

Step C. trans-Benzyl (4-((2,2-dimethyl-5-nitro-2,3-dihydrobenzofuran-6-yl)oxy)pyrrolidin-3-yl)carbamate

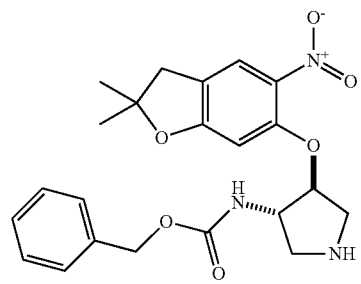

trans-tert-butyl-3-(((benzyloxy)carbonyl)amino)-4-((2,2-dimethyl-5-nitro-2,3-dihydrobenzofuran-6-yl)oxy)pyrrolidine-1-carboxylate (302 mg, 0.57 mmol) was dissolved in dichloromethane (6 mL) and treated with trifluoroacetic acid (0.5 mL) at room temperature. After 30 min, the solvent was removed under reduced pressure and the crude residue was purified by silica gel chromatography (eluting gradient 0-20% methanol in dichloromethane) to afford trans-benzyl (4-((2,2-dimethyl-5-nitro-2,3-dihydrobenzofuran-6-yl)oxy)pyrrolidin-3-yl)carbamate (290 mg, 0.678 mmol, quant) as a solid. $^1$H NMR (400 MHz, DMSO-$d_6$) δ 7.89 (s, 1H), 7.80 (s, 1H), 7.37 (s, 5H), 6.98 (s, 1H), 5.10 (m, 3H), 4.29 (s, 1H), 3.65 (dd, J=13.4, 4.5 Hz, 1H), 3.55 (dd, J=12.7, 6.1 Hz, 1H), 3.45 (d, J=13.5 Hz, 1H), 3.03 (s, 2H), 1.46 (s, 6H).

Step D. trans-Benzyl (1-(2-amino-2-oxoethyl)-4-((2,2-dimethyl-5-nitro-2,3-dihydrobenzofuran-6-yl)oxy)pyrrolidin-3-yl)carbamate

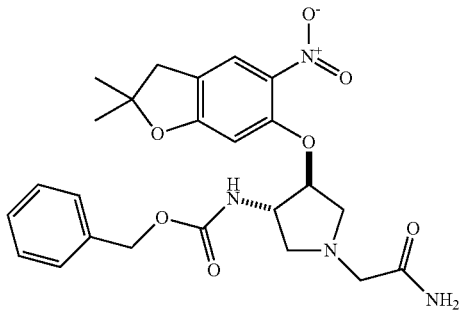

A solution of trans-benzyl (4-((2,2-dimethyl-5-nitro-2,3-dihydrobenzofuran-6-yl)oxy)pyrrolidin-3-yl)carbamate (290 mg, 0.678 mmol) in dioxane (11 mL) was treated with N,N-diisopropylethylamine (0.18 mL, 1.01 mmol) followed by 2-bromoacetamide (106 mg, 0.742 mmol). The reaction mixture was stirred at 60° C. for 16 h, diluted with dichloromethane and washed with water. The layers were separated and the aqueous layer was extracted with dichloromethane (3×). The combined organic phases were dried over sodium sulfate and concentrated under reduced pressure to afford the crude residue trans-benzyl (1-(2-amino-2-oxoethyl)-4-((2,2-dimethyl-5-nitro-2,3-dihydrobenzofuran-6-yl)oxy)pyrrolidin-3-yl)carbamate (380 mg, crude) as a viscous orange oil, which was carried on without further purification (assume quant, 330 mg, 0.67 mmol)

Step E. trans-Benzyl (-4-((5-amino-2,2-dimethyl-2,3-dihydrobenzofuran-6-yl)oxy)-1-(2-amino-2-oxoethyl)pyrrolidin-3-yl)carbamate

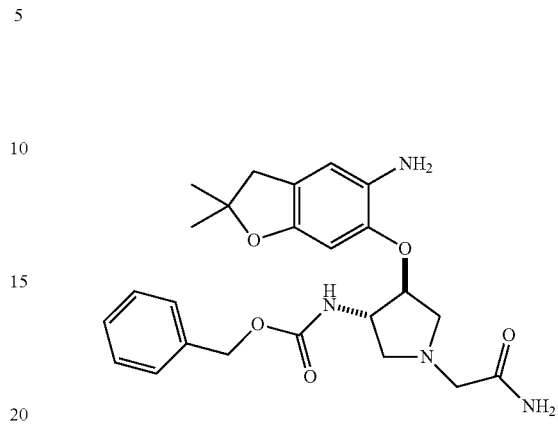

The title compound was made in a manner analogous to Example 46 (step C) to give trans-benzyl (-4-((5-amino-2,2-dimethyl-2,3-dihydrobenzofuran-6-yl)oxy)-1-(2-amino-2-oxoethyl)pyrrolidin-3-yl)carbamate (220 mg, 0.49 mmol, 72% yield) as a solid, which was used without further purification.

Step F. trans-Benzyl (1-(2-amino-2-oxoethyl)-4-((2,2-dimethyl-5-(pyrazolo[1,5-a]pyrimidine-3-carboxamido)-2,3-dihydrobenzofuran-6-yl)oxy)pyrrolidin-3-yl)carbamate

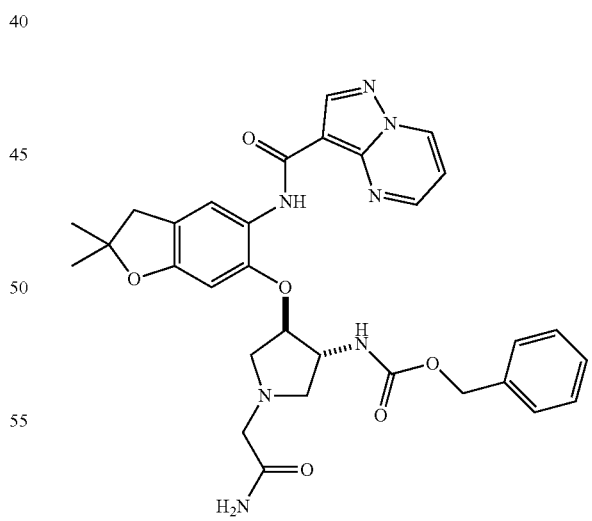

The title compound was made in a manner analogous to Example 46 (step D) to give crude trans-benzyl (1-(2-amino-2-oxoethyl)-4-((2,2-dimethyl-5-(pyrazolo[1,5-a]pyrimidine-3-carboxamido)-2,3-dihydrobenzofuran-6-yl)oxy)pyrrolidin-3-yl)carbamate (assume quant, 294 mg, 0.49 mmol) as a dark residue, which was used without further purification.

Step G. N-(6-(((3S,4S)-4-Amino-1-(2-amino-2-oxo-ethyl)pyrrolidin-3-yl)oxy)-2,2-dimethyl-2,3-dihydrobenzofuran-5-yl)pyrazolo[1,5-a]pyrimidine-3-carboxamide and N-(6-(((3R,4R)-4-Amino-1-(2-amino-2-oxoethyl)pyrrolidin-3-yl)oxy)-2,2-dimethyl-2,3-dihydrobenzofuran-5-yl)pyrazolo[1,5-a]pyrimidine-3-carboxamide

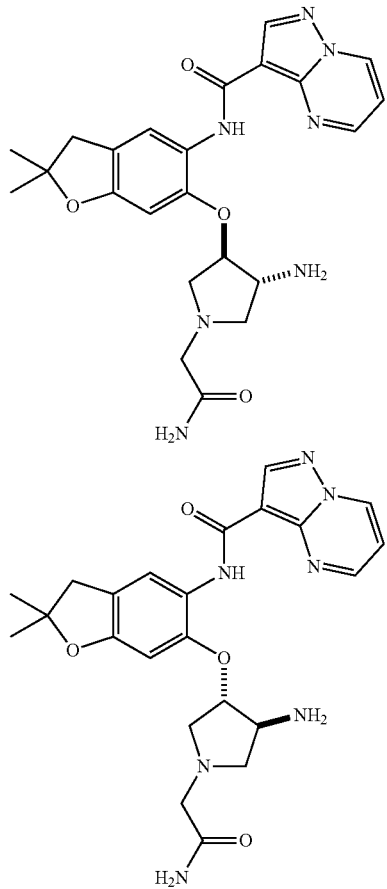

trans-Benzyl (1-(2-amino-2-oxoethyl)-4-((2,2-dimethyl-5-(pyrazolo[1,5-a]pyrimidine-3-carboxamido)-2,3-dihydrobenzofuran-6-yl)oxy)pyrrolidin-3-yl)carbamate (0.484 mmol) was treated with concentrated hydrochloric acid and allowed to stir for 6 h at room temperature. The reaction mixture was concentrated under reduced pressure and the crude residue was purified by preparative HPLC ((Gemini NX, 5*3 cm c18, 5 um; A: acetonitrile 20-60%; B: 0.1% ammonium hydroxide in water) to afford (+) trans-N-(6-(2-(4-acetylpiperazin-1-yl)ethyl)-2,2-dimethyl-2,3-dihydrobenzofuran-5-yl)pyrazolo[1,5-a]pyrimidine-3-carboxamide (76 mg, 0.163 mmol, 34% yield) as a yellow solid. This material was resolved by chiral SFC (Pyridyl Amide 15*3 cm, 5 um (Thar), A=CO$_2$, B=methanol{0.1% ammonium hydroxide} 30% isocratic) to obtain N-(6-(((3R,4R)-4-amino-1-(2-amino-2-oxoethyl)pyrrolidin-3-yl)oxy)-2,2-dimethyl-2,3-dihydrobenzofuran-5-yl)pyrazolo[1,5-a]pyrimidine-3-carboxamide and N-(6-(((3S,4S)-4-amino-1-(2-amino-2-oxoethyl)pyrrolidin-3-yl)oxy)-2,2-dimethyl-2,3-dihydrobenzofuran-5-yl)pyrazolo[1,5-a]pyrimidine-3-carboxamide (31 mg, 38%) (32 mg, 38%) as yellow solids with absolute stereochemistry assigned arbitrarily.

Example 19, Peak 1: $^1$H NMR (400 MHz, DMSO-d$_6$) δ 10.18 (s, 1H), 9.37 (dd, J=7.0, 1.6 Hz, 1H), 8.84 (dd, J=4.2, 1.6 Hz, 1H), 8.66 (s, 1H), 8.29 (s, 1H), 7.33 (dd, J=7.0, 4.2 Hz, 1H), 7.28 (s, 1H), 7.07 (s, 1H), 6.68 (s, 1H), 4.50-4.42 (m, 1H), 3.46 (m, 1H), 3.37-3.33 (m, 1H), 3.04 (s, 2H), 2.97 (s, 2H), 2.93 (dd, J=9.0, 5.9 Hz, 1H), 2.70 (td, J=10.2, 2.6 Hz, 1H), 2.48 (m, 1H), 2.09 (m, 2H), 1.42 (s, 6H). MS (ESI): m/z=466.2 [M+1]$^+$.

Example 20, Peak 2: $^1$H NMR (400 MHz, DMSO-d$_6$) δ 10.18 (s, 1H), 9.37 (dd, J=7.0, 1.6 Hz, 1H), 8.84 (dd, J=4.2, 1.6 Hz, 1H), 8.66 (s, 1H), 8.29 (s, 1H), 7.33 (dd, J=7.0, 4.2 Hz, 1H), 7.28 (s, 1H), 7.07 (s, 1H), 6.68 (s, 1H), 4.50-4.42 (m, 1H), 3.46 (m, 1H), 3.37-3.33 (m, 1H), 3.04 (s, 2H), 2.97 (s, 2H), 2.93 (dd, J=9.0, 5.9 Hz, 1H), 2.70 (td, J=10.2, 2.6 Hz, 1H), 2.48 (m, 1H), 2.09 (m, 2H), 1.42 (s, 6H). MS (ESI): m/z=466.2 [M+1]$^+$.

TABLE 5

The following examples were made in a manner similar to that for Example 19:

| Ex. | Name | Structure | NMR, MS |
|---|---|---|---|
| 21 | 5-Chloro-N-(6-methoxy-2,2-dimethyl-2,3-dihydrobenzofuran-5-yl)pyrazolo[1,5-a]pyrimidine-3-carboxamide | 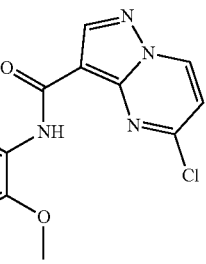 | $^1$H NMR (400 MHz, CDCl$_3$) δ 9.95 (s, 1H), 8.74 (s, 1H), 8.68 (d, J = 7.2 Hz, 1H), 8.35 (s, 1H), 6.99 (d, J = 7.2 Hz, 1H), 6.44 (s, 1H), 3.96 (s, 3H), 3.02 (s, 2H), 1.49 (s, 6H). LCMS (ESI): m/z = 373.0 [M + H]$^+$. |

TABLE 5-continued

The following examples were made in a manner similar to that for Example 19:

| Ex. | Name | Structure | NMR, MS |
|---|---|---|---|
| 22 & 23 | (R)-N-(6-((1-Ethyl-5-oxopyrrolidin-3-yl)methoxy)-2,2-dimethyl-2,3-dihydrobenzofuran-5-yl)pyrazolo[1,5-a]pyrimidine-3-carboxamide and (S)-N-(6-((1-Ethyl-5-oxopyrrolidin-3-yl)methoxy)-2,2-dimethyl-2,3-dihydrobenzofuran-5-yl)pyrazolo[1,5-a]pyrimidine-3-carboxamide (absolute stereochemistry assigned arbitrarily) | | Example 22, Peak 1: $^1$H NMR (400 MHz, CDCl$_3$) δ 9.86 (s, 1H), 8.82-8.80 (m, 1H), 8.77 (s, 1H), 8.72-8.70 (m, 1H), 8.30 (s, 1H), 7.05 (dd, J = 7.2, 4.0 Hz, 1H), 6.40 (s, 1H), 4.13-4.06 (m, 1H), 4.04-3.96 (m, 1H), 3.59-3.54 (m, 1H), 3.39-3.24 (m, 3H), 3.03 (s, 2H), 3.00-2.90 (m, 1H), 2.68-2.60 (m, 2H), 1.49 (s, 6H), 1.03 (t,. J = 7.2 Hz, 3H). LCMS (ESI): m/z = 472.3 [M + Na]$^+$. Example 23, Peak 2: $^1$H NMR (400 MHz, CDCl$_3$) δ 9.87 (s, 1H), 8.82-8.80 (m, 1H), 8.77 (s, 1H), 8.72-8.71 (m, 1H), 8.31 (s, 1H), 7.05 (dd, J = 7.2, 4.0 Hz, 1H), 6.40 (s, 1H), 4.13-4.05 (m, 1H), 4.04-3.95 (m, 1H), 3.59-3.54 (m, 1H), 3.39-3.25 (m, 3H), 3.03 (s, 2H), 3.00-2.90 (m, 1H), 2.70-2.59 (m, 2H), 1.49 (s, 6H), 1.04 (t, J = 7.2 Hz, 3H). LCMS (ESI): m/z = 472.2 [M + Na]$^+$. |
| 24 & 25 | (R)-N-(2,2-Dimethyl-6-((1-methyl-5-oxopyrrolidin-3-yl)methoxy)-2,3-dihydrobenzofuran-5-yl)pyrazolo[1,5-a]pyrimidine-3-carboxamide and (S)-N-(2,2-Dimethyl-6-((1-methyl-5-oxopyrrolidin-3-yl)methoxy)-2,3-dihydrobenzofuran-5-yl)pyrazolo[1,5-a]pyrimidine-3-carboxamide (absolute stereochemistry assigned arbitrarily) | | Example 24, Peak 1: $^1$H NMR (400 MHz, CDCl$_3$) δ 9.85 (s, 1H), 8.82-8.80 (m, 1H), 8.77 (s, 1H), 8.71-8.69 (m, 1H), 8.30 (s, 1H), 7.05 (dd, J = 7.2, 4.0 Hz, 1H), 6.40 (s, 1H), 4.12-4.05 (m, 1H), 4.04-3.97 (m, 1H), 3.58-3.53 (m, 1H), 3.38-3.34 (m, 1H), 3.02 (s, 2H), 3.00-2.90 (m, 1H), 2.80 (s, 3H), 2.72-2.54 (m, 2H), 1.49 (s, 6H). LCMS (ESI): m/z = 436.2 [M + H]$^+$. Example 25, Peak 2: $^1$H NMR (400 MHz, CDCl$_3$) δ 9.85 (s, 1H), 8.83-8.80 (m, 1H), 8.77 (s, 1H), 8.72-8.70 (m, 1H), 8.30 (s, 1H), 7.05 (dd, J = 7.2, 4.0 Hz, 1H), 6.40 (s, 1H), 4.11-4.05 (m, 1H), 4.04-3.97 (m, 1H), 3.58-3.54 (m, 1H), 3.39-3.35 (m, 1H), 3.03 (s, 2H), 3.00-2.90 (m, 1H), 2.80 (s, 3H), 2.72-2.55 (m, 2H), 1.49 (s, 6H). LCMS (ESI): m/z = 436.3 [M + H]$^+$. |

US 11,034,698 B2

251 252

TABLE 5-continued

The following examples were made in a manner similar to that for Example 19:

| Ex. | Name | Structure | NMR, MS |
|---|---|---|---|
| 26 & 27 & 28 & 29 | N-[6-[[(1S,2R)-1-Aminoindan-2-yl]methoxy]-2,2-dimethyl-3H-benzofuran-5-yl]pyrazolo[1,5-a]pyrimidine-3-carboxamide and N-[6-[[(1S,2S)-1-Aminoindan-2-yl]methoxy]-2,2-dimethyl-3H-benzofuran-5-yl]pyrazolo[1,5-a]pyrimidine-3-carboxamide and N-[6-[[(1R,2S)-1-Aminoindan-2-yl]methoxy]-2,2-dimethyl-3H-benzofuran-5-yl]pyrazolo[1,5-a]pyrimidine-3-carboxamide and N-[6-[[(1R,2R)-1-Aminoindan-2-yl]methoxy]-2,2-dimethyl-3H-benzofuran-5-yl]pyrazolo[1,5-a]pyrimidine-3-carboxamide (absolute stereochemistry assigned arbitrarily) | | Example 26, Peak 1: $^1$H NMR (400 MHz, CDCl$_3$) δ 9.67 (s, 1H), 9.06 (br s, 2H), 8.63(br s, 1H), 8.46 (br s, 1H), 8.22(br s, 1H), 8.06 (br s, 1H), 7.69(br s, 1H), 7.11 (br s, 2H), 7.03(br s, 1H), 6.66 (br s, 1H), 6.29(br s, 1H), 4.79 (br s, 1H), 4.17(d, J = 18.0 Hz, 2H), 3.09-3.35 (m, 2H), 2.86-3.03 (m, 3H), 1.43 (br s, 3H), 1.41 (br s, 3H). LCMS (ESI): m/z = 470.3 [M + H]$^+$. Example 27, Peak 2: $^1$H NMR (400 MHz, CDCl$_3$) δ 9.32 (s, 1H), 8.77 (br s, 2H), 8.62-8.51 (m, 2H), 7.98 (br s, 1H), 7.66-7.77 (m, 2H), 6.99 (br s, 2H), 6.90 (d, J = 6.0 Hz, 1H), 6.64 (br s, 1H), 6.46 (s, 1H), 4.87-4.66 (m, 2H), 4.26 (d, J = 4.8 Hz, 1H), 3.30 (dd, J = 15.8, 8.8 Hz, 1H), 3.08 (br s, 1H), 2.91 (dd, J = 16.0, 8.0 Hz, 1H), 2.83 (d, J = 15.0 Hz, 1H), 2.65 (d, J = 15.0 Hz, 1H), 1.37 (s, 3H), 1.29 (s, 3H). LCMS (ESI): m/z = 470.2 [M + H]$^+$. Example 28, Peak 3: $^1$H NMR (400 MHz, CDCl$_3$) δ 9.64 (br s, 1H), 8.57 (br s, 1H), 8.42 (br s, 1H), 8.00-8.13 (m, 2H), 7.52-7.61 (m, 1H), 7.06 (br s, 2H), 6.99 (br s, 1H), 6.60 (br s, 1H), 6.26 (s, 1H), 4.69 (brs, 1H), 4.12 (d, J = 19.4 Hz, 2H), 3.19 (d, J = 9.6 Hz, 1H), 3.02 (br s, 1H), 2.82-2.95 (m, 3H), 1.38 (s, 3H), 1.35 (s, 3H). LCMS (ESI): m/z = 470.2 [M + H]$^+$. Example 29, Peak 4: $^1$H NMR (400 MHz, CDCl$_3$) δ 9.32 (s, 1H), 8.55-8.46 (m, 2H), 7.94 (br s, 1H), 7.74 (s, 1H), 7.62 (d, J = 6.6 Hz, 1H), 6.91-7.00 (m, 2H), 6.87 (d, J = 6.6 Hz, 1H), 6.60 (dd, J = 6.6, 4.4 Hz, 1H), 6.40 (s, 1H), 4.67 (d, J = 7.6 Hz, 2H), 4.21 (dd, J = 9.6, 5.4 Hz, 1H), 3.22 (dd, J = 15.8, 8.8 Hz, 1H), 3.02 (d, J = 7.6 Hz, 1H), 2.87 (dd, J = 16.0, 8.2 Hz, 1H), 2.78 (d, J = 15.0 Hz, 1H), 2.57-2.67 (m, 1H), 1.31 (s, 3H), 1.24 (s, 3H). LCMS (ESI): m/z = 470.1 [M + H]$^+$. |

TABLE 5-continued

The following examples were made in a manner similar to that for Example 19:

| Ex. | Name | Structure | NMR, MS |
|---|---|---|---|
| 30 & 31 & 32 & 33 | N-(2,2-Dimethyl-6-(((4aS,6S,7aS)-octahydrocyclopenta[b][1,4]oxazin-6-yl)methoxy)-2,3-dihydrobenzofuran-5-yl)pyrazolo[1,5-a]pyrimidine-3-carboxamide and N-(2,2-Dimethyl-6-(((4aS,6R,7aS)-octahydrocyclopenta[b][1,4]oxazin-6-yl)methoxy)-2,3-dihydrobenzofuran-5-yl)pyrazolo[1,5-a]pyrimidine-3-carboxamide and N-(2,2-Dimethyl-6-(((4aR,6R,7aR)-octahydrocyclopenta[b][1,4]oxazin-6-yl)methoxy)-2,3-dihydrobenzofuran-5-yl)pyrazolo[1,5-a]pyrimidine-3-carboxamide and N-(2,2-Dimethyl-6-(((4aR,6S,7aR)-octahydrocyclopenta[b][1,4]oxazin-6-yl)methoxy)-2,3-dihydrobenzofuran-5-yl)pyrazolo[1,5-a]pyrimidine-3-carboxamide (absolute stereochemistry assigned arbitrarily) | 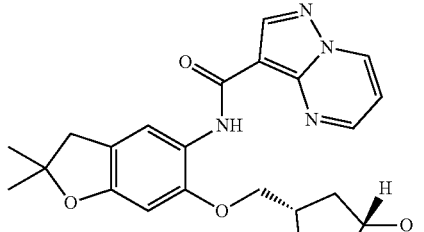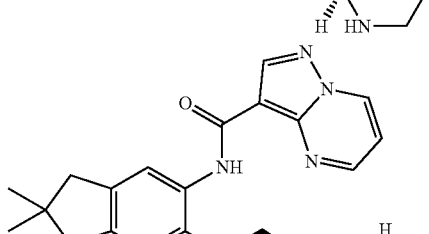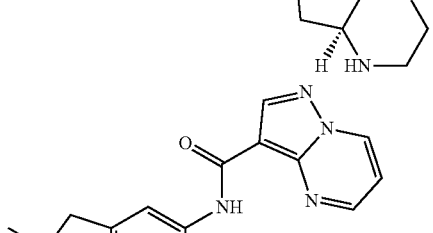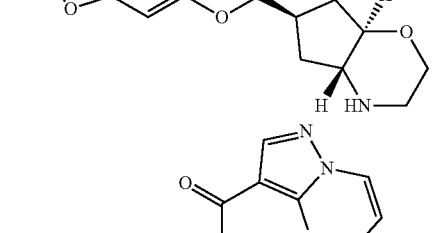 | Example 30: $^1$H NMR (400 MHz, CD$_3$OD) δ 9.10 (d, J = 6.8 Hz, 1H), 8.85-8.80 (m, 1H), 8.63 (s, 1H), 8.01 (s, 1H), 7.24 (dd, J = 6.8, 4.0 Hz, 1H), 6.47 (s, 1H), 4.00-3.95 (m, 2H), 3.86-3.85 (m, 1H), 3.66-3.65 (m, 1H), 3.45-3.38 (m, 1H), 3.00 (s, 2H), 2.97-2.93 (m, 1H), 2.71-2.67 (m, 3H), 2.21-2.19 (m, 1H), 1.93-1.87 (m, 1H), 1.70-1.67 (m, 1H), 1.57-1.55 (m, 1H), 1.46 (s, 6H). LCMS (ESI): m/z = 464.1 [M + H]$^+$. Example 31: $^1$H NMR (400 MHz, CD$_3$OD) δ 9.09 (d, J = 6.8 Hz, 1H), 8.82-8.78 (m, 1H), 8.62 (s, 1H), 8.04 (s, 1H), 7.23 (dd, J = 6.8, 4.4 Hz, 1H), 6.46 (s, 1H), 3.97-3.84 (m, 3H), 3.44-3.39 (m, 2H), 3.00 (s, 2H), 2.95-2.93 (m, 2H), 2.75-2.72 (m, 2H), 2.21-2.18 (m, 1H), 2.04-2.03 (m, 1H), 1.80-1.77 (m, 1H), 1.46 (s, 6H), 1.32-1.30 (m, 1H). LCMS (ESI): m/z = 464.0 [M + H]$^+$. Example 32: $^1$H NMR (400 MHz, CD$_3$OD) δ 9.15-9.12 (m, 1H), 8.89-8.85 (m, 1H), 8.65 (s, 1H), 8.00 (s, 1H), 7.27 (dd, J = 6.8, 4.4 Hz, 1H), 6.50 (s, 1H), 4.04-3.89 (m, 3H), 3.70-3.69 (m, 1H), 3.46-3.45 (m, 1H), 3.01 (s, 2H), 2.77-2.73 (m, 2H), 2.27-2.17 (m, 1H), 1.97-1.92 (m, 1H), 1.75-1.72 (m, 1H), 1.61-1.58 (m, 2H), 1.46 (s, 6H), 1.36-1.34 (m, 1H). LCMS (ESI): m/z = 464.2 [M + H]$^+$. Example 33: $^1$H NMR (400 MHz. CD$_3$OD) δ 9.12-9.10 (m, 1H), 8.84-8.80 (m, 1H), 8.63 (s, 1H), 8.02 (s, 1H), 7.24 (dd, J = 7.2, 4.4 Hz, 1H), 6.47 (s, 1H), 4.00-3.93 (m, 3H), 3.49 - 3.46 (m, 2H), 3.08-3.07 (m, 2H), 3.00 (s, 2H), 2.96-2.89 (m, 1H), 2.78-2.73 (m, 1H), 2.28-2.25 (m, 1H), 2.10-2.09 (m, 1H), 1.83-1.80 (m, 1H), 1.46 (s, 6H), 1.40-1.35 (m, 1H). LCMS (ESI): m/z = 464.2 [M + H]$^+$. |
| 34 | N-(6-(Cyclopropylmethoxy)-1'-methyl-3H-spiro[benzofuran-2,4'-piperidin]-5-yl)pyrazolo[1,5-a]pyrimidine-3-carboxamide | 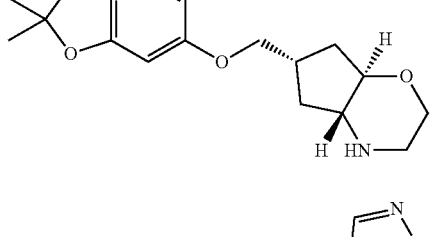 | $^1$H NMR (400 MHz, CDCl$_3$) δ 10.23 (s, 1H), 8.82 (dd, J = 6.8, 1.6 Hz, 1H), 8.77 (s, 1H), 8.68 (dd, J = 4.0, 1.6 Hz, 1H), 8.42 (s, 1H), 7.03 (dd, J = 6.8, 4.0 Hz, 1H), 6.41 (s, 1H), 3.91 (d, J = 6.8 Hz, 2H), 3.05 (s, 2H), 3.00-2.85 (m, 3H), 2.61 (s, 3H), 2.30-2.15 (s, 3H), 2.10-2.06 (m, 2H), 1.43-1.40 (m, 1H), 0.68-0.65 (m, 2H), 0.49-0.45 (m, 2H). LCMS (ESI): m/z = 434.2 [M + H]$^+$. |

Example 35. N-(6-Methoxy-2,2-dimethyl-2,3-dihydrobenzofuran-5-yl)-5-(2-oxopyrrolidin-3-yl)pyrazolo[1,5-a]pyrimidine-3-carboxamide

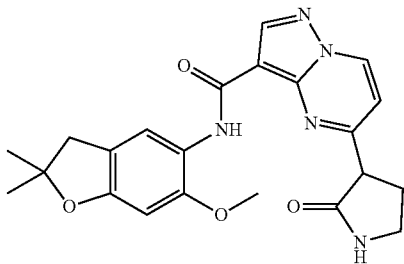 [SMILES: COc1cc2c(cc1NC(=O)c1cnn3ccc(C4CCNC4=O)nc13)CC(C)(C)O2]

Step A. Di-tert-butyl 2-oxopyrrolidine-1,3-dicarboxylate

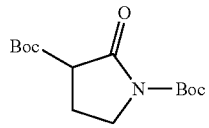

Sodium bis(trimethylsilyl)amide (1 M in tetrahydrofuran, 28.3 mL, 28.3 mmol) was added dropwise to a solution of 1-(tert-butoxycarbonyl)-2-pyrrolidinone (5.0 g, 27.0 mmol) in tetrahydrofuran (60 mL) at −78° C. under nitrogen. After stirring for 1 h, a solution of di-tert-butyldicarbonate (2.95 g, 13.5 mmol) in tetrahydrofuran (20 mL) was added dropwise over 10 min. After being further stirred at −78° C. for 30 min, the reaction was quenched with saturated aqueous ammonium chloride (20 mL) and extracted with ethyl acetate (100 mL×2). The organic phase was washed with brine (20 mL), dried over sodium sulfate, and concentrated. The residue was purified by flash chromatography (eluting gradient: 5-10% ethyl acetate in petroleum ether) to afford di-tert-butyl 2-oxopyrrolidine-1,3-dicarboxylate (3.0 g, 39%) as a light yellow oil. $^1$H NMR (400 MHz, CDCl$_3$) δ 3.89-3.83 (m, 1H), 3.71-3.63 (m, 1H), 3.42 (dd, J=9.2, 8.0 Hz, 1H), 2.38-2.27 (m, 1H), 2.24-2.14 (m, 1H), 1.53 (s, 9H), 1.49 (s, 9H).

Step B. Di-tert-butyl 3-[3-[(6-methoxy-2,2-dimethyl-3H-benzofuran-5-yl)carbamoyl]pyrazolo[1,5-a]pyrimidin-5-yl]-2-oxo-pyrrolidine-1,3-dicarboxylate

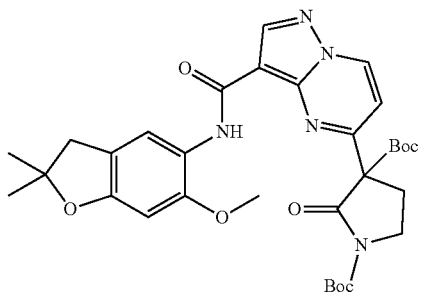 [SMILES: COc1cc2c(cc1NC(=O)c1cnn3ccc(C4(C(=O)OC(C)(C)C)CCN(C(=O)OC(C)(C)C)C4=O)nc13)CC(C)(C)O2]

To a solution of 5-chloro-N-(6-methoxy-2,2-dimethyl-3H-benzofuran-5-yl)pyrazolo[1,5-a]pyrimidine-3-carboxamide (Example 21; 150 mg, 0.40 mmol) and di-tert-butyl 2-oxopyrrolidine-1,3-dicarboxylate (126 mg, 0.44 mmol) in acetonitrile (10 mL) was added potassium carbonate (167 mg, 1.21 mmol). The mixture was stirred at 80° C. for 16 h under nitrogen, after which it was filtered through a pad of Celite rinsing with ethyl acetate (100 mL). The filtrate was concentrated, and the residue was purified by preparatory thin layer chromatography (eluting gradient: 33% ethyl acetate in 20:1 petroleum ether/dichloromethane) to afford di-tert-butyl 3-[3-[(6-methoxy-2,2-dimethyl-3H-benzofuran-5-yl)carbamoyl]pyrazolo[1,5-a]pyrimidin-5-yl]-2-oxo-pyrrolidine-1,3-dicarboxylate (170 mg, 68%) as a light yellow solid. LCMS (ESI): m/z=622.1 [M+H]$^+$.

Step C. N-(6-Methoxy-2,2-dimethyl-3H-benzofuran-5-yl)-5-(2-oxopyrrolidin-3-yl)pyrazolo[1,5-a]pyrimidine-3-carboxamide

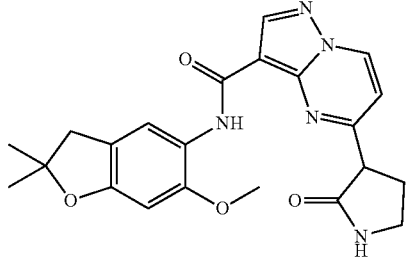 [SMILES: COc1cc2c(cc1NC(=O)c1cnn3ccc(C4CCNC4=O)nc13)CC(C)(C)O2]

A solution of di-tert-butyl 3-[3-[(6-methoxy-2,2-dimethyl-3H-benzofuran-5-yl)carbamoyl]pyrazolo[1,5-a]pyrimidin-5-yl]-2-oxo-pyrrolidine-1,3-dicarboxylate (150 mg, 0.24 mmol) and anisole (2 mL, 2.41 mmol) in 2,2,2-trifluoroacetic acid (3 mL) was stirred at 25° C. for 1 h. The reaction was concentrated, basified with saturated aqueous sodium bicarbonate, and extracted with ethyl acetate (100 mL×3). The organic phase was washed with brine (10 mL), dried over sodium sulfate, filtered and concentrated. The residue was purified by preparatory thin layer chromatography (eluting gradient: 5% methanol in dichloromethane) to afford N-(6-methoxy-2,2-dimethyl-3H-benzofuran-5-yl)-5-(2-oxopyrrolidin-3-yl)pyrazolo[1,5-a]pyrimidine-3-carboxamide (35 mg, 34%) as a light yellow solid. $^1$H NMR (400 MHz, CDCl$_3$) δ: 9.76 (s, 1H), 8.76-8.67 (m, 2H), 8.25 (s, 1H), 7.28-7.26 (m, 1H), 6.44 (s, 1H), 6.08 (br s, 1H), 3.94 (t, J=8.4 Hz, 1H), 3.85 (s, 3H), 3.68-3.49 (m, 2H), 3.23-3.11 (m, 1H), 3.02 (s, 2H), 2.69-2.61 (m, 1H), 1.48 (s, 6H). LCMS (ESI): m/z=422.1 [M+H]$^+$.

Examples 36 and 37

(S)-5-(5-Amino-3,3-difluoropiperidin-1-yl)-N-(6-methoxy-2,2-dimethyl-2,3-dihydrobenzofuran-5-yl)pyrazolo[1,5-a]pyrimidine-3-carboxamide and (R)-5-(5-Amino-3,3-difluoropiperidin-1-yl)-N-(6-methoxy-2,2-dimethyl-2,3-dihydrobenzofuran-5-yl)pyrazolo[1,5-a]pyrimidine-3-carboxamide

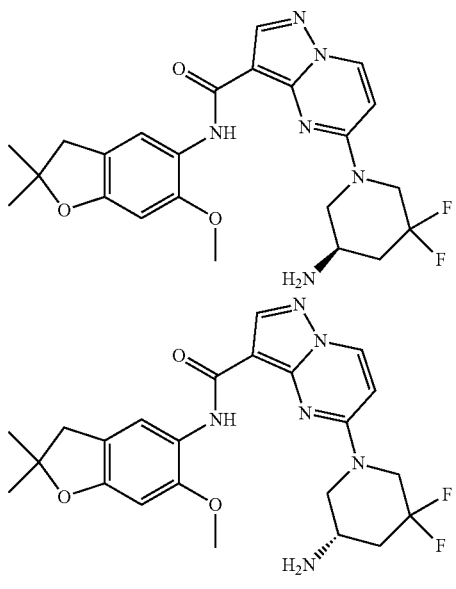

Step A. tert-Butyl (5,5-difluoro-1-(3-((6-methoxy-2,2-dimethyl-2,3-dihydrobenzofuran-5-yl)carbamoyl)pyrazolo[1,5-a]pyrimidin-5-yl)piperidin-3-yl)carbamate

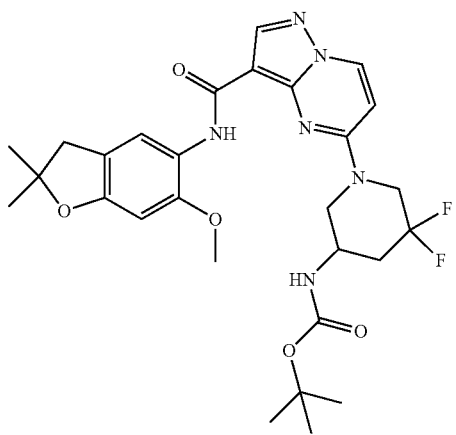 [SMILES: COc1cc2c(cc1NC(=O)c1cnn3ccc(N4CC(NC(=O)OC(C)(C)C)CC(F)(F)C4)nc13)CC(C)(C)O2]

5-Chloro-N-(6-methoxy-2,2-dimethyl-3H-benzofuran-5-yl)pyrazolo[1,5-a]pyrimidine-3-carboxamide (Example 21) (100 mg, 0.268 mmol), ethanol (2.7 mL), tert-butyl N-(5,5-difluoro-3-piperidyl)carbamate (127 mg, 0.537 mmol), and N,N-diisopropylethylamine (69.3 mg, 0.094 mL, 0.537 mmol) were combined in a microwave vial with stirbar. The vial was sealed and the contents were stirred in the microwave at 120° C. for 20 min. The reaction mixture was concentrated, and the resulting residue was partitioned between dichloromethane and deionized water. The aqueous phase was extracted with dichloromethane (2×). The combined organic phase was dried over sodium sulfate, filtered, and concentrated in vacuo to afford the title compound, which was used without purification. MS: m/z=573.3 [M+1]$^+$.

Step B. (R)-5-(5-Amino-3,3-difluoropiperidin-1-yl)-N-(6-methoxy-2,2-dimethyl-2,3-dihydrobenzofuran-5-yl)pyrazolo[1,5-a]pyrimidine-3-carboxamide and (S)-5-(5-Amino-3,3-difluoropiperidin-1-yl)-N-(6-methoxy-2,2-dimethyl-2,3-dihydrobenzofuran-5-yl)pyrazolo[1,5-a]pyrimidine-3-carboxamide

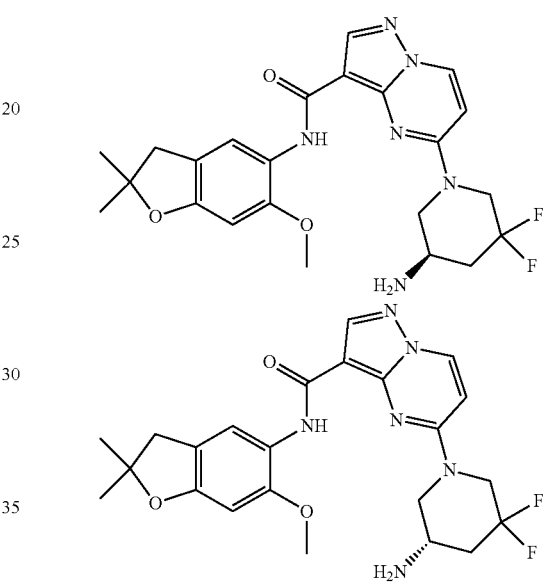

Trifluoroacetic acid (0.670 mL, 8.869 mmol) was added to a stirred solution of tert-butyl N-[5,5-difluoro-1-[3-[(6-methoxy-2,2-dimethyl-3H-benzofuran-5-yl)carbamoyl]pyrazolo[1,5-a]pyrimidin-5-yl]-3-piperidyl]carbamate in dichloromethane (2.7 mL). The reaction mixture was stirred overnight and then concentrated to afford a bright yellow solid. The resulting residue was purified by chiral SFC to afford (R)-5-(5-amino-3,3-difluoropiperidin-1-yl)-N-(6-methoxy-2,2-dimethyl-2,3-dihydrobenzofuran-5-yl)pyrazolo[1,5-a]pyrimidine-3-carboxamide (44.1 mg, 0.0933 mmol) and (S)-5-(5-amino-3,3-difluoropiperidin-1-yl)-N-(6-methoxy-2,2-dimethyl-2,3-dihydrobenzofuran-5-yl)pyrazolo[1,5-a]pyrimidine-3-carboxamide (43.2 mg, 0.0914 mmol) as yellow solids. Absolute stereochemistry was assigned arbitrarily.

Example 36, Peak 1: $^1$H NMR (400 MHz, DMSO-d$_6$) δ 9.50 (s, 1H), 8.87 (d, J=7.9 Hz, 1H), 8.28 (s, 1H), 8.17 (s, 1H), 7.00 (d, J=8.0 Hz, 1H), 6.58 (s, 1H), 4.89 (s, 1H), 4.36 (s, 1H), 3.85 (s, 3H), 3.72 (dd, J=28.9, 13.7 Hz, 1H), 3.13-3.02 (m, 1H), 2.96 (s, 2H), 2.38 (d, J=11.1 Hz, 1H), 2.00-1.85 (m, 1H), 1.41 (s, 6H). MS (ESI): m/z=473.2 [M+1]$^+$.

Example 37, Peak 2: $^1$H NMR (400 MHz, DMSO-d$_6$) δ 9.50 (s, 1H), 8.86 (d, J=8.0 Hz, 1H), 8.27 (s, 1H), 8.16 (s, 1H), 6.99 (d, J=7.9 Hz, 1H), 6.58 (s, 1H), 4.88 (s, 1H), 4.35 (s, 1H), 3.84 (s, 3H), 3.71 (dd, J=29.0, 13.6 Hz, 1H), 3.12-2.95 (m, 2H), 2.96 (s, 2H), 2.37 (d, J=10.9 Hz, 1H), 2.26-1.64 (m, 1H), 1.41 (s, 6H). MS (ESI): m/z=473.2 [M+1]$^+$.

TABLE 6

The following examples were made in a manner similar to that for Example 37:

| Ex. | Name | Structure | NMR, MS |
|---|---|---|---|
| 38 | 5-(Cyclopropyl(methyl)amino)-N-(6-methoxy-2,2-dimethyl-2,3-dihydrobenzofuran-5-yl)pyrazolo[1,5-a]pyrimidine-3-carboxamide | 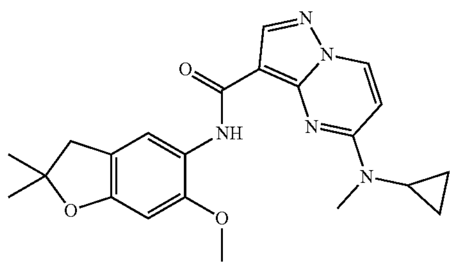 [SMILES: COc1cc2c(cc1NC(=O)c1cnn3ccc(N(C)C4CC4)nc13)CC(C)(C)O2] | $^1$H NMR (400 MHz, CDCl$_3$): δ 9.73 (s, 1H), 8.46 (s, 1H), 8.35-8.32 (m, 2H), 6.85 (d, J = 8.0 Hz, 1H), 6.42 (s, 1H), 3.81 (s, 3H), 3.37 (s, 3H), 3.02 (s, 2H), 2.84-2.79 (m, 1H), 1.48 (s, 6H), 1.08-1.03 (m, 2H), 0.87-0.84 (m, 2H). LCMS (ESI): m/z = 408 [M + H]$^+$. |
| 39 | (R)-5-(3-Aminopiperidin-1-yl)-N-(6-methoxy-2,2-dimethyl-2,3-dihydrobenzofuran-5-yl)pyrazolo[1,5-a]pyrimidine-3-carboxamide | 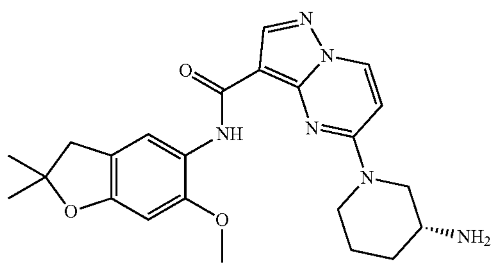 [SMILES: COc1cc2c(cc1NC(=O)c1cnn3ccc(N4CCC[C@@H](N)C4)nc13)CC(C)(C)O2] | $^1$H NMR (400 MHz, DMSO-d$_6$) δ 9.58 (s, 1H), 8.75 (d, J = 8.0 Hz, 1H), 8.22 (s, 1H), 8.17 (s, 1H), 6.87 (d, J = 8.0 Hz, 1H), 6.56 (s, 1H), 4.38 (s, 1H), 4.21 (s, 1H), 3.82 (s, 3H), 3.13-3.03 (m, 1H), 2.96 (s, 2H), 2.87-2.75 (m, 1H), 1.96-1.87 (m, 1H), 1.86-1.74 (m, 1H), 1.59-1.33 (m, 2H), 1.41 (s, 6H). MS (ESI): m/z = 437.2 [M + H]$^+$. |
| 40 | (R)-N-(6-Methoxy-2,2-dimethyl-2,3-dihydrobenzofuran-5-yl)-5-(piperidin-3-ylamino)pyrazolo[1,5-a]pyrimidine-3-carboxamide | 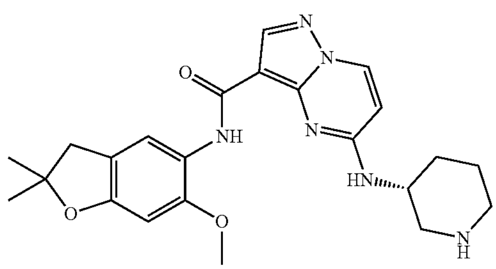 [SMILES: COc1cc2c(cc1NC(=O)c1cnn3ccc(N[C@@H]4CCCNC4)nc13)CC(C)(C)O2] | $^1$H NMR (400 MHz, DMSO-d$_6$) δ 9.62 (s, 1H), 8.57 (d, J = 7.6 Hz, 1H), 8.16 (s, 1H), 8.05 (d, J = 7.7 Hz, 1H), 7.99 (s, 1H), 6.56 (s, 1H), 6.47 (d, J = 7.7 Hz, 1H), 4.20-4.09 (m, 1H), 3.86 (s, 3H), 3.09-3.00 (m, 1H), 2.96 (s, 2H), 2.81-2.71 (m, 2H), 2.67-2.52 (m, 3H), 1.97-1.87 (m, 1H), 1.72-1.59 (m, 1H), 1.58-1.35 (m, 2H), 1.41 (s, 6H). MS (ESI): m/z = 437.2 [M + H]$^+$. |
| 41 | 5-amino-N-(6-Methoxy-2,2-dimethyl-2,3-dihydrobenzofuran-5-yl)pyrazolo[1,5-a]pyrimidine-3-carboxamide | 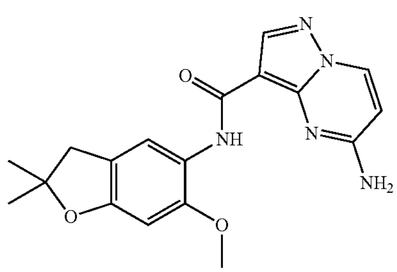 [SMILES: COc1cc2c(cc1NC(=O)c1cnn3ccc(N)nc13)CC(C)(C)O2] | $^1$H NMR (400 MHz, DMSO-d$_6$) δ 9.79 (s, 1H), 8.64 (d, J = 7.5 Hz, 1H), 8.17 (s, 1H), 8.10 (d, J = 1.1 Hz, 1H), 7.17 (s, 2H), 6.54 (s, 1H), 6.41 (d, J = 7.5 Hz, 1H), 3.88 (s, 3H), 2.98-2.93 (m, 2H), 1.41 (s, 6H). MS (ESI): m/z = 354.1 [M + H]$^+$. |
| 42 | N-(6-Methoxy-2,2-dimethyl-2,3-dihydrobenzofuran-5-yl)-5-(piperazin-1-yl)pyrazolo[1,5-a]pyrimidine-3-carboxamide | 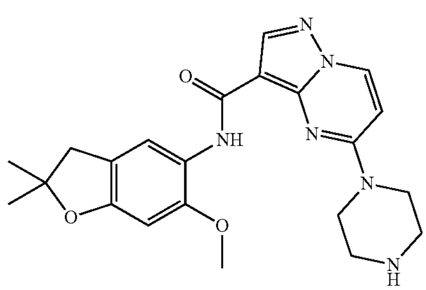 [SMILES: COc1cc2c(cc1NC(=O)c1cnn3ccc(N4CCNCC4)nc13)CC(C)(C)O2] | $^1$H NMR (400 MHz, DMSO-d$_6$) δ 9.57 (s, 1H), 8.75 (d, J = 7.9 Hz, 1H), 8.23 (s, 1H), 8.18 (s, 1H), 6.87 (d, J = 8.0 Hz, 1H), 6.55 (s, 1H), 3.80 (s, 3H), 3.76 (s, 4H), 2.96 (s, 2H), 2.88-2.78 (m, 4H), 1.41 (s, 6H). MS (ESI): m/z = 423.2 [M + H]$^+$. |

TABLE 6-continued

The following examples were made in a manner similar to that for Example 37:

| Ex. | Name | Structure | NMR, MS |
|---|---|---|---|
| 43 | 5-((2-Aminoethyl)amino)-N-(6-methoxy-2,2-dimethyl-2,3-dihydrobenzofuran-5-yl)pyrazolo[1,5-a]pyrimidine-3-carboxamide | 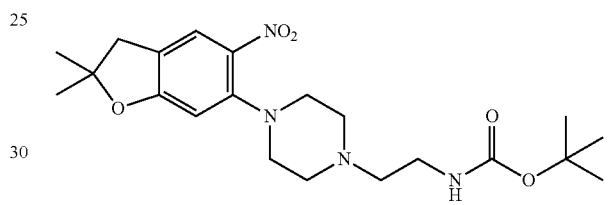 | $^1$H NMR (400 MHz, DMSO-$d_6$) δ 9.72 (s, 1H), 8.56 (d, J = 7.6 Hz, 1H), 8.17 (d, J =5.3 Hz, 2H), 8.09 (s, 1H), 6.55 (s, 1H), 6.44 (d, J = 7.6 Hz, 1H), 3.83 (s, 3H), 3.54 (t, J = 6.2 Hz, 2H), 2.96 (s, 2H), 2.83 (t, J = 6.1 Hz, 2H), 1.41 (s, 6H). MS (ESI): m/z = 397.1 [M + H]$^+$. |

Example 44. 5-(Dimethylamino)-N-(6-methoxy-2,2-dimethyl-2,3-dihydrobenzofuran-5-yl)pyrazolo[1,5-a]pyrimidine-3-carboxamide

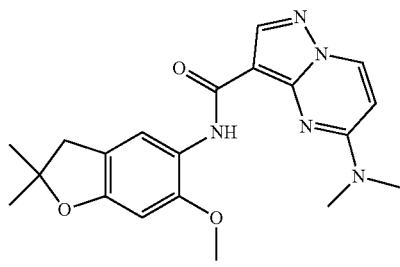

To a mixture of 5-chloro-N-(6-methoxy-2,2-dimethyl-3H-benzofuro[1,5-a]pyrimidine-3-carboxamide (Example 21; 50 mg, 0.13 mmol) in acetonitrile (2 mL) was added N,N-diethylpropan-2-amine (52 mg, 0.40 mmol) and N,N-dimethylamine hydrochloride (32 mg, 0.40 mmol). The mixture was stirred at 80° C. for 2 h and concentrated. The residue was purified by preparatory thin layer chromatography (eluting gradient: 20% ethyl acetate in petroleum ether) to give 5-(Dimethylamino)-N-(6-methoxy-2,2-dimethyl-3H-benzofuran-5-yl)pyrazolo[1,5-a]pyrimidine-3-carboxamide (25 mg, 46%) as a white solid. $^1$H NMR (400 MHz, CDCl$_3$): δ 9.75 (s, 1H), 8.45 (s, 1H), 8.33-8.31 (m, 2H), 6.43 (s, 1H), 6.37 (d, J=8.0 Hz, 1H), 3.82 (s, 3H), 3.32 (br s, 6H), 3.02 (s, 2H), 1.48 (s, 6H). LCMS (ESI): m/z=382 [M+H]$^+$.

Example 45. (5$^3$E,5$^4$E)-2$^2$,2$^2$-Dimethyl-2$^2$,2$^3$-dihydro-3,6-diaza-5(3,5)-pyrazolo[1,5-a]pyrimidina-1(1,4)-piperazina-2(6,5)-benzofuranacyclooctaphan-4-one

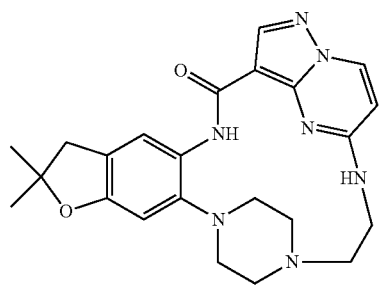 [SMILES: CC1(C)Cc2cc3c(cc2O1)N1CCN(CCNc2ccn4ncc(c4n2)C(=O)N3)CC1]

Step A. tert-Butyl (2-(4-(2,2-dimethyl-5-nitro-2,3-dihydrobenzofuran-6-yl)piperazin-1-yl)ethyl)carbamate

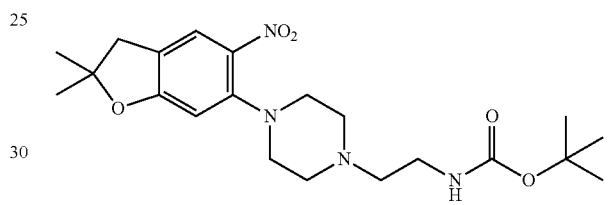

The title compound was made in a manner analogous to Intermediate D with 6-chloro-2,2-dimethyl-5-nitro-3H-benzofuran (Intermediate A, 500 mg, 2.20 mmol) and tert-butyl N-(2-piperazin-1-ylethyl)carbamate (604 mg, 2.64 mmol). Tert-butyl N-[2-[4-(2,2-dimethyl-5-nitro-3H-benzofuran-6-yl)piperazin-1-yl]ethyl]carbamate (386 mg, 0.92 mmol, 42% yield) was obtained as a yellow residue. MS (ESI): m/z=421.3 [M+H]$^+$.

Step B. tert-Butyl (2-(4-(5-amino-2,2-dimethyl-2,3-dihydrobenzofuran-6-yl)piperazin-1-yl)ethyl)carbamate

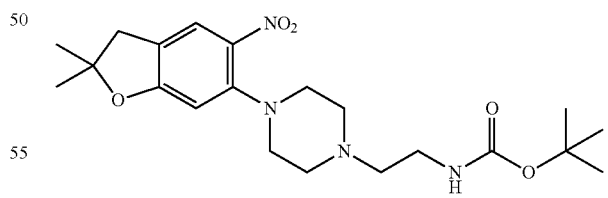

The title compound was made in a manner analogous to Example 149, step D, with tert-butyl N-[2-[4-(2,2-dimethyl-5-nitro-3H-benzofuran-6-yl)piperazin-1-yl]ethyl]carbamate (386 mg, 0.92 mmol). Tert-butyl (2-(4-(5-amino-2,2-dimethyl-2,3-dihydrobenzofuran-6-yl)piperazin-1-yl)ethyl)carbamate (340 mg, 0.87 mmol, 95% yield) was obtained as a clear oil and used without purification. MS (ESI): m/z=391.3 [M+H]$^+$.

Step C. tert-Butyl (2-(4-(5-(5-chloropyrazolo[1,5-a]pyrimidine-3-carboxamido)-2,2-dimethyl-2,3-dihydrobenzofuran-6-yl)piperazin-1-yl)ethyl)carbamate

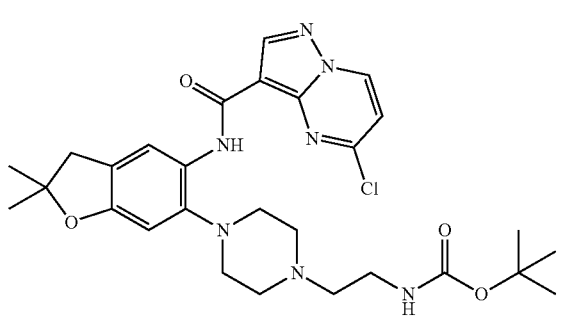 [SMILES: CC(C)(C)OC(=O)NCCN1CCN(c2cc3c(cc2NC(=O)c2cnn4ccc(Cl)nc24)CC(C)(C)O3)CC1]

The title compound was made in a manner analogous to Example 50, Step G, with tert-butyl (2-(4-(5-amino-2,2-dimethyl-2,3-dihydrobenzofuran-6-yl)piperazin-1-yl)ethyl)carbamate (126 mg, 0.323 mmol) and 5-chloropyrazolo[1,5-a]pyrimidine-3-carbonyl chloride (83.64 mg, 0.387 mmol). Tert-butyl (2-(4-(5-(5-chloropyrazolo[1,5-a]pyrimidine-3-carboxamido)-2,2-dimethyl-2,3-dihydrobenzofuran-6-yl)piperazin-1-yl)ethyl)carbamate (202 mg, 0.355 mmol) was obtained and used without purification. MS (ESI): m/z=570.4 [M+H]$^+$.

Step D. N-(6-(4-(2-Aminoethyl)piperazin-1-yl)-2,2-dimethyl-2,3-dihydrobenzofuran-5-yl)-5-chloropyrazolo[1,5-a]pyrimidine-3-carboxamide

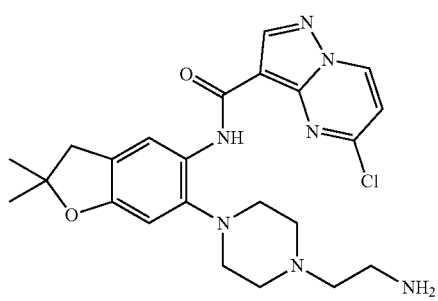 [SMILES: CC1(C)Cc2cc(NC(=O)c3cnn4ccc(Cl)nc34)c(N3CCN(CCN)CC3)cc2O1]

Trifluoroacetic acid (1.22 g, 0.81 mL, 10.7 mmol) was added to a solution of tert-butyl N-[2-[4-[5-[(5-chloropyrazolo[1,5-a]pyrimidine-3-carbonyl)amino]-2,2-dimethyl-3H-benzofuran-6-yl]piperazin-1-yl]ethyl]carbamate (184.0 mg, 0.3227 mmol) in dichloromethane (3.2 mL). After 30 min, the reaction mixture was concentrated to afford N-(6-(4-(2-aminoethyl)piperazin-1-yl)-2,2-dimethyl-2,3-dihydrobenzofuran-5-yl)-5-chloropyrazolo[1,5-a]pyrimidine-3-carboxamide as a sticky orange oil that was used without further purification. MS (ESI): m/z=470.3 [M+H]$^+$.

Step E. ($5^3$E,$5^4$E)-$2^2$,$2^2$-Dimethyl-$2^2$,$2^3$-dihydro-3,6-diaza-5(3,5)-pyrazolo[1,5-a]pyrimidina-1(1,4)-piperazina-2(6,5)-benzofuranacyclooctaphan-4-one

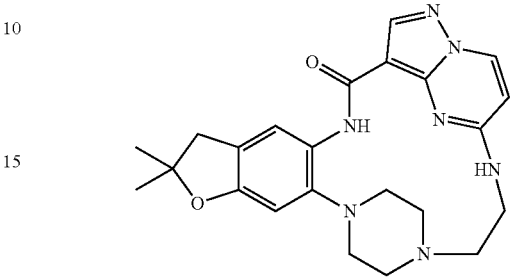

Two microwave vials were each charged with N-[6-[4-(2-aminoethyl)piperazin-1-yl]-2,2-dimethyl-3H-benzofuran-5-yl]-5-chloro-pyrazolo[1,5-a]pyrimidine-3-carboxamide (100 mg, 0.213 mmol) (crude from previous step), dimethyl sulfoxide (10.6 mL) and N,N-diisopropylethylamine (275 mg, 0.371 mL, 2.13 mmol). The vials were sealed, and the reaction mixture was stirred in the microwave at 120° C. for 30 min. The crude reaction mixtures were combined and partitioned between deionized water and dichloromethane. The aqueous phase was extracted with dichloromethane (2×). The combined organic layer was washed with water (2×), dried over sodium sulfate, filtered, and concentrated to afford a dark red solid. The product was purified by HPLC to afford ($5^3$E,$5^4$E)-$2^2$,$2^2$-dimethyl-$2^2$,$2^3$-dihydro-3,6-diaza-5(3,5)-pyrazolo[1,5-a]pyrimidina-1(1,4)-piperazina-2(6,5)-benzofuranacyclooctaphan-4-one (6.5 mg, 0.0148 mmol, 3.5% yield) as an off-white solid.

$^1$H NMR (400 MHz, DMSO-d$_6$) δ 9.17 (s, 1H), 8.54 (s, 1H), 8.53 (d, J=7.5 Hz, 1H), 8.24 (s, 1H), 8.20 (t, J=6.9 Hz, 1H), 6.54 (s, 1H), 6.36 (d, J=7.6 Hz, 1H), 3.76-3.67 (m, 2H), 3.53-3.43 (m, 3H), 3.05-2.97 (m, 2H), 3.00-2.87 (m, 4H), 2.86-2.75 (m, 2H), 2.70-2.58 (m, 2H), 1.41 (s, 6H). MS (ESI): m/z=434.2 [M+H]$^+$.

Example 46. N-(7-Morpholino-2-oxo-1,2,3,4-tetrahydroquinolin-6-yl)pyrazolo[1,5-a]pyrimidine-3-carboxamide

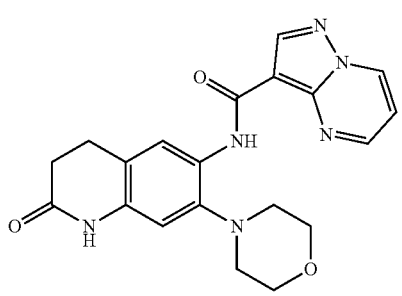 [SMILES: O=C1CCc2cc(NC(=O)c3cnn4cccnc34)c(N3CCOCC3)cc2N1]

Step A.
7-Bromo-6-nitro-3,4-dihydroquinolin-2(1H)-one

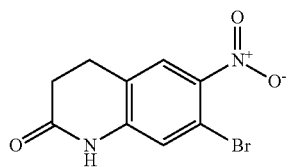 [SMILES: O=C1CCc2cc([N+](=O)[O-])c(Br)cc2N1]

Potassium nitrate (134 mg, 1.33 mmol) was added portion-wise to a mixture of 7-bromo-3,4-dihydro-1H-quinolin-2-one (250 mg, 1.11 mmol) in sulfuric acid (7 mL). The mixture was stirred at 0° C. to ambient temperature for 1 h. The reaction mixture was poured onto ice and extracted with isopropyl acetate. The solids that would not dissolve were first filtered off and dried under hi-vacuum. The organic extracts were washed with water, saturated sodium bicarbonate solution, and brine. The combined organics were dried over sodium sulfate and concentrated under reduce pressure to afford 7-bromo-6-nitro-3,4-dihydroquinolin-2(1H)-one (300 mg, quant.) as a yellow solid, which was carried on without further purification. $^1$H NMR (400 MHz, DMSO-$d_6$) δ 10.60 (s, 1H), 8.02 (s, 1H), 7.23 (s, 1H), 2.96 (t, J=7.7 Hz, 2H), 2.57-2.51 (m, 2H).

Step B.
7-Morpholino-6-nitro-3,4-dihydroquinolin-2(1H)-one

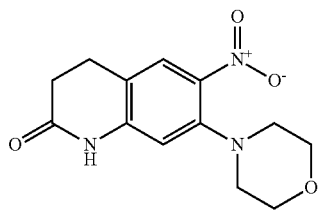 [SMILES: O=C1CCc2cc([N+](=O)[O-])c(N3CCOCC3)cc2N1]

A mixture of 7-bromo-6-nitro-3,4-dihydroquinolin-2(1H)-one (250 mg, 0.91 mmol) and morpholine (0.40 mL, 4.5 mmol) in dimethyl sulfoxide (7.0 mL) was stirred at 60° C. for 18 h. The reaction mixture was cooled to room temperature, and then diluted with dichloromethane and washed with water. The layers were separated and the aqueous layer was extracted with dichloromethane (3×). The combined organic phases were dried over sodium sulfate and concentrated under reduced pressure. The residue was purified by silica gel chromatography (eluting gradient 0-20% methanol in dichloromethane) to afford 7-morpholino-6-nitro-3,4-dihydroquinolin-2(1H)-one (222 mg, 0.80 mmol, 88%) as a bright yellow solid. $^1$H NMR (400 MHz, DMSO-d6) δ 10.42 (s, 1H), 7.85 (s, 1H), 6.70 (s, 1H), 3.76-3.66 (m, 4H), 2.97-2.84 (m, 6H), 2.47 (s, 2H).

Step C.
6-Amino-7-morpholino-3,4-dihydroquinolin-2(1H)-one

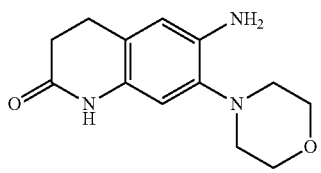 [SMILES: Nc1cc2c(cc1N1CCOCC1)NC(=O)CC2]

A mixture of 7-morpholino-6-nitro-3,4-dihydroquinolin-2(1H)-one (100 mg, 0.36 mmol), iron powder (101 mg, 1.8 mmol) and ammonium chloride (96 mg, 1.8 mmol) in ethanol (2.4 mL) and water (0.40 mL) was stirred at 60° C. for 2 h. The reaction was filtered and the filtrate was dried over sodium sulfate and concentrated. The residue was purified by silica gel chromatography (eluting gradient 0-20% methanol in dichloromethane) to afford 6-amino-7-morpholino-3,4-dihydroquinolin-2(1H)-one (71 mg, 0.29 mmol, 89%) as an oil.

Step D. N-(7-Morpholino-2-oxo-1,2,3,4-tetrahydroquinolin-6-yl)pyrazolo[1,5-a]pyrimidine-3-carboxamide A mixture of pyrazolo[1,5-a]pyrimidine-3-carboxylic acid (52 mg, 0.32 mmol), (7-azabenzotriazol-1-yloxy)tripyrrolidinophosphonium hexafluorophosphate (172 mg, 0.32 mmol), 2,4,6-trimethylpyridine (0.042 mL, 0.32 mmol), and 6-amino-7-morpholino-3,4-dihydroquinolin-2(1H)-one (71 mg, 0.29 mmol) in N,N-dimethylformamide (1.0 mL) was stirred at room temperature overnight. After concentration, the residue was purified by preparative HPLC ((Gemini NX, 5*3 cm c18, 5 um; A: acetonitrile 20-60%; B: 0.1% ammonium hydroxide in water) to afford N-(7-morpholino-2-oxo-1,2,3,4-tetrahydroquinolin-6-yl)pyrazolo[1,5-a]pyrimidine-3-carboxamide (39 mg, 34%) as a yellow solid. $^1$H NMR (400 MHz, DMSO-$d_6$) δ 10.45 (s, 1H), 10.01 (s, 1H), 9.39 (dd, J=7.0, 1.6 Hz, 1H), 8.97 (dd, J=4.2, 1.6 Hz, 1H), 8.70 (s, 1H), 8.32 (s, 1H), 7.36 (dd, J=7.0, 4.2 Hz, 1H), 6.80 (s, 1H), 3.90-3.81 (m, 4H), 2.86 (t, J=7.5 Hz, 2H), 2.83-2.78 (m, 4H), 2.45 (m, 2H). MS (ESI): m/z=393.1 [M+1]$^+$.

Example 47. N-(1-(2-Hydroxyethyl)-7-morpholino-2-oxo-1,2,3,4-tetrahydroquinolin-6-yl)pyrazolo[1,5-a]pyrimidine-3-carboxamide

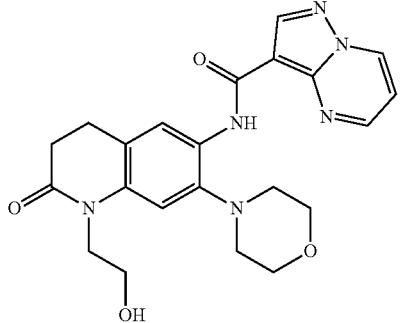 [SMILES: O=C(Nc1cc2c(cc1N1CCOCC1)N(CCO)C(=O)CC2)c1cnn2cccnc12]

Step A. 1-(2-Hydroxyethyl)-7-morpholino-6-nitro-3,4-dihydroquinolin-2(1H)-one

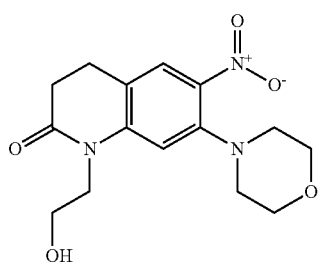 [SMILES: O=C1CCc2cc([N+](=O)[O-])c(N3CCOCC3)cc2N1CCO]

Sodium hydride (60 mass % in oil, 15 mg, 0.37 mmol) was added to a solution of 7-morpholino-6-nitro-3,4-dihydroquinolin-2(1H)-one (Example 46, step B) (85 mg, 0.31 mmol) in N,N-dimethylformamide (1.5 mL). The mixture was heated at 60° C. for 30 min. A solution of ethylene oxide was added and the reaction mixture was heated at 60° C. for 18 h. The mixture was cooled to ambient temperature and diluted with isopropyl acetate and washed with water. The layers were separated and the aqueous layer was extracted with isopropyl acetate (2×). The combined organic phases were dried over sodium sulfate and concentrated under reduced pressure to afford 1-(2-hydroxyethyl)-7-morpholino-6-nitro-3,4-dihydroquinolin-2(1H)-one (98 mg, quant).

Step B. 6-Amino-1-(2-hydroxyethyl)-7-morpholino-3,4-dihydroquinolin-2(1H)-one

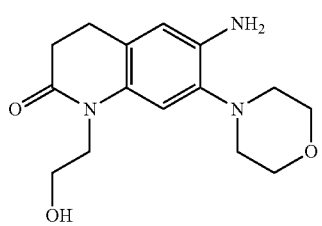 [SMILES: Nc1cc2c(cc1N1CCOCC1)N(CCO)C(=O)CC2]

The title compound was made in a manner analogous to Example 46 (step C) to give 6-amino-1-(2-hydroxyethyl)-7-morpholino-3,4-dihydroquinolin-2(1H)-one (18 mg, 0.062 mmol, 18%) as an oil.

Step C. N-(1-(2-Hydroxyethyl)-7-morpholino-2-oxo-1,2,3,4-tetrahydroquinolin-6-yl)pyrazolo[1,5-a]pyrimidine-3-carboxamide

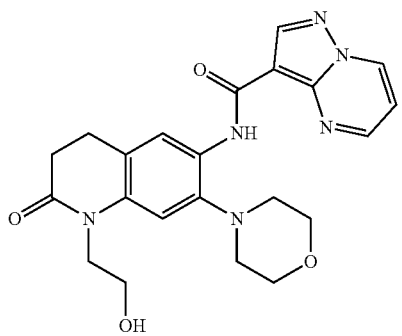 [SMILES: O=C(Nc1cc2c(cc1N1CCOCC1)N(CCO)C(=O)CC2)c1cnn2cccnc12]

The title compound was made in a manner analogous to Example 46 (step D) to give N-(1-(2-hydroxyethyl)-7-morpholino-2-oxo-1,2,3,4-tetrahydroquinolin-6-yl)pyrazolo[1,5-a]pyrimidine-3-carboxamide (6.1 mg, 0.014 mmol, 23%) as a solid. $^1$H NMR (400 MHz, DMSO-$d_6$) δ 10.56 (s, 1H), 9.38 (dd, J=7.0, 1.6 Hz, 1H), 8.97 (dd, J=4.2, 1.6 Hz, 1H), 8.70 (s, 1H), 8.37 (s, 1H), 7.36 (dd, J=7.0, 4.2 Hz, 1H), 7.21 (s, 1H), 4.88 (s, 1H), 3.95 (t, J=6.3 Hz, 2H), 3.92-3.85 (m, 4H), 3.59 (q, J=6.1 Hz, 2H), 2.93-2.87 (m, 4H), 2.87-2.79 (m, 2H), 2.57-2.52 (m, 2H). MS (ESI): m/z=437.2 [M+1]$^+$.

Example 48. N-(1-(3-Hydroxypropyl)-7-morpholino-2-oxo-1,2,3,4-tetrahydroquinolin-6-yl)pyrazolo[1,5-a]pyrimidine-3-carboxamide

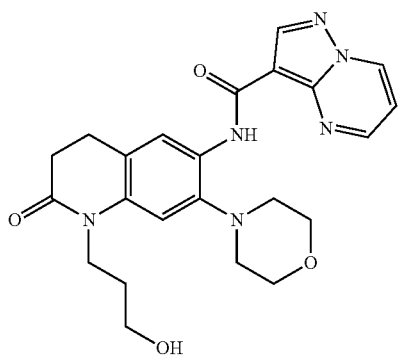 [SMILES: O=C(Nc1cc2c(cc1N1CCOCC1)N(CCCO)C(=O)CC2)c1cnn2cccnc12]

The title compound was made in a manner analogous to Example 36 to give N-(1-(3-hydroxypropyl)-7-morpholino-2-oxo-1,2,3,4-tetrahydroquinolin-6-yl)pyrazolo[1,5-a]pyrimidine-3-carboxamide (16 mg, 0.035 mmol, 15%) as a solid. $^1$H NMR (400 MHz, DMSO-$d_6$) δ 10.55 (s, 1H), 9.39 (dd, J=7.0, 1.6 Hz, 1H), 8.97 (dd, J=4.2, 1.6 Hz, 1H), 8.70 (s, 1H), 8.37 (s, 1H), 7.36 (dd, J=7.0, 4.2 Hz, 1H), 7.14 (s, 1H), 4.62 (t, J=5.1 Hz, 1H), 3.96 (t, J=7.2 Hz, 2H), 3.92-3.83 (m, 4H), 3.47 (q, J=5.9 Hz, 2H), 2.93-2.87 (m, 4H), 2.87-2.78 (m, 2H), 2.59-2.52 (m, 2H), 1.72 (p, J=6.1 Hz, 2H). MS (ESI): m/z=451.1 [M+1]$^+$.

Example 49. N-(2,2-Dimethyl-6-morpholino-2,3-dihydrobenzofuran-5-yl)-5-oxo-4,5-dihydropyrazolo[1,5-a]pyrimidine-3-carboxamide

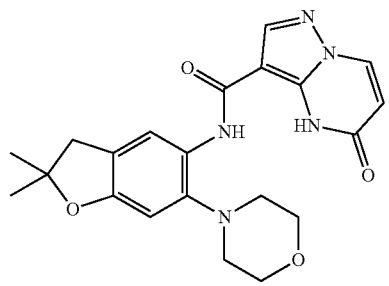 [SMILES: CC1(C)Cc2cc(NC(=O)c3cnn4ccc(=O)[nH]c34)c(N3CCOCC3)cc2O1]

The title compound was made in a manner analogous to Example 46 (step D), to afford N-(2,2-dimethyl-6-morpholino-2,3-dihydrobenzofuran-5-yl)-5-oxo-4,5-dihydropyrazolo[1,5-a]pyrimidine-3-carboxamide (10.4 mg, 0.025 mmol, 13% yield) as a white solid. $^1$H NMR (400 MHz, DMSO-$d_6$) δ 8.74 (s, 1H), 8.36 (s, 1H), 7.87 (s, 1H), 6.59 (s, 1H), 6.35 (s, 1H), 3.79 (t, J=4.6 Hz, 4H), 2.98 (s, 2H), 2.77 (t, J=4.6 Hz, 4H), 1.41 (s, 6H). MS (ESI): m/z=410.2 [M+H]$^+$.

Examples 50 and 51. (R)—N-(2-(Hydroxymethyl)-2-methyl-6-(4-(oxetan-3-yl)piperazin-1-yl)-2,3-dihydrobenzofuran-5-yl)pyrazolo[1,5-a]pyrimidine-3-carboxamide and (S)—N-(2-(Hydroxymethyl)-2-methyl-6-(4-(oxetan-3-yl)piperazin-1-yl)-2,3-dihydrobenzofuran-5-yl)pyrazolo[1,5-a]pyrimidine-3-carboxamide

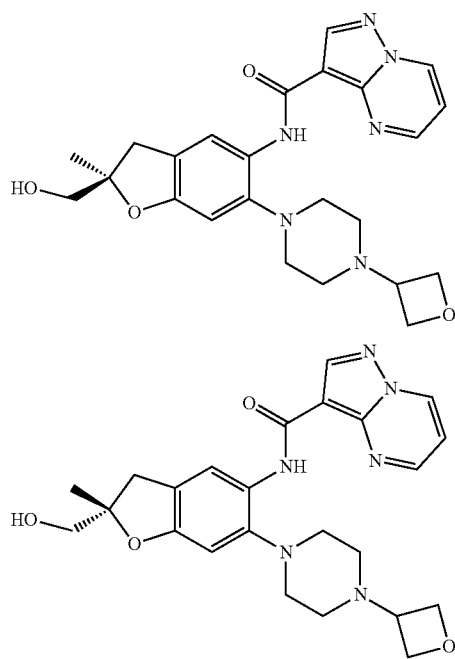

Step A. (2-Methyl-5-nitro-6-(4-(oxetan-3-yl)piperazin-1-yl)-2,3-dihydrobenzofuran-2-yl)methanol

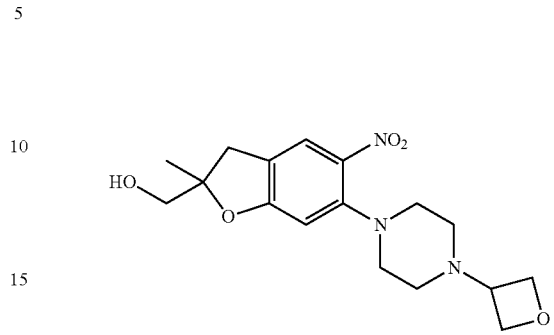

A mixture of (6-chloro-2-methyl-5-nitro-2,3-dihydrobenzofuran-2-yl)methanol (Intermediate B) (100 mg, 0.44 mmol), 1-(oxetan-3-yl)piperazine (94 mg, 0.66 mmol) and N,N-diisopropylethylamine (0.11 mL, 0.66 mmol) in dimethyl sulfoxide (2.2 mL) was stirred at 45° C. for 18 h. The reaction was filtered and concentrated, and the residue was purified by silica gel chromatography (eluent 1:2 ethyl acetate:petroleum ether) to afford (2-methyl-5-nitro-6-(4-(oxetan-3-yl)piperazin-1-yl)-2,3-dihydrobenzofuran-2-yl)methanol (154 mg, quant) as an orange foam. $^1$H NMR (400 MHz, DMSO-$d_6$) δ 7.81 (t, J=1.2 Hz, 1H), 6.58 (s, 1H), 5.11 (t, J=5.7 Hz, 1H), 4.55 (t, J=6.6 Hz, 2H), 4.44 (t, J=6.1 Hz, 2H), 3.54-3.39 (m, 3H), 3.23-3.14 (m, 1H), 2.98 (t, J=4.8 Hz, 5H), 2.83 (dd, J=16.1, 1.4 Hz, 1H), 2.42-2.35 (m, 4H), 1.36 (s, 3H).

Step B. (5-Amino-2-methyl-6-(4-(oxetan-3-yl)piperazin-1-yl)-2,3-dihydrobenzofuran-2-yl)methanol

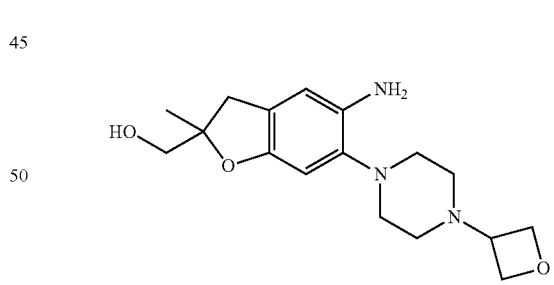

A mixture of (2-methyl-5-nitro-6-(4-(oxetan-3-yl)piperazin-1-yl)-2,3-dihydrobenzofuran-2-yl)methanol (154 mg, 0.44 mmol), iron powder (123 mg, 2.2 mmol) and ammonium chloride (118 mg, 2.2 mmol) in ethanol (3.3 mL) and water (0.7 mL) was stirred at 50° C. for 30 min. The reaction was filtered, and the filtrate was dried over sodium sulfate and concentrated. The residue was purified by silica gel chromatography (eluting gradient: 0-20% methanol in dichloromethane) to afford (5-amino-2-methyl-6-(4-(oxetan-3-yl)piperazin-1-yl)-2,3-dihydrobenzofuran-2-yl)methanol (171 mg, 0.53 mmol, quant.) as an oil.

Step C. (R)—N-(2-(Hydroxymethyl)-2-methyl-6-(4-(oxetan-3-yl)piperazin-1-yl)-2,3-dihydrobenzofuran-5-yl)pyrazolo[1,5-a]pyrimidine-3-carboxamide and (S)—N-(2-(Hydroxymethyl)-2-methyl-6-(4-(oxetan-3-yl)piperazin-1-yl)-2,3-dihydrobenzofuran-5-yl)pyrazolo[1,5-a]pyrimidine-3-carboxamide Examples 52 and 53. (R)—N-(6-(4-(1,3-Dihydroxypropan-2-yl)piperidin-1-yl)-2-(hydroxymethyl)-2-methyl-2,3-dihydrobenzofuran-5-yl)pyrazolo[1,5-a]pyrimidine-3-carboxamide and (S)—N-(6-(4-(1,3-Dihydroxypropan-2-yl)piperidin-1-yl)-2-(hydroxymethyl)-2-methyl-2,3-dihydrobenzofuran-5-yl)pyrazolo[1,5-a]pyrimidine-3-carboxamide

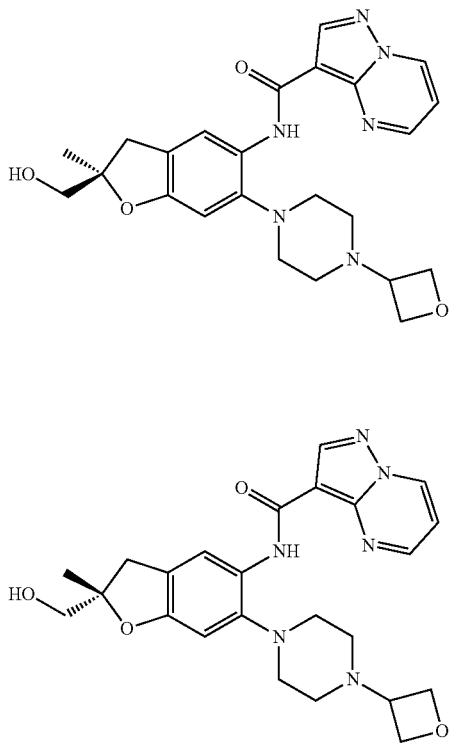

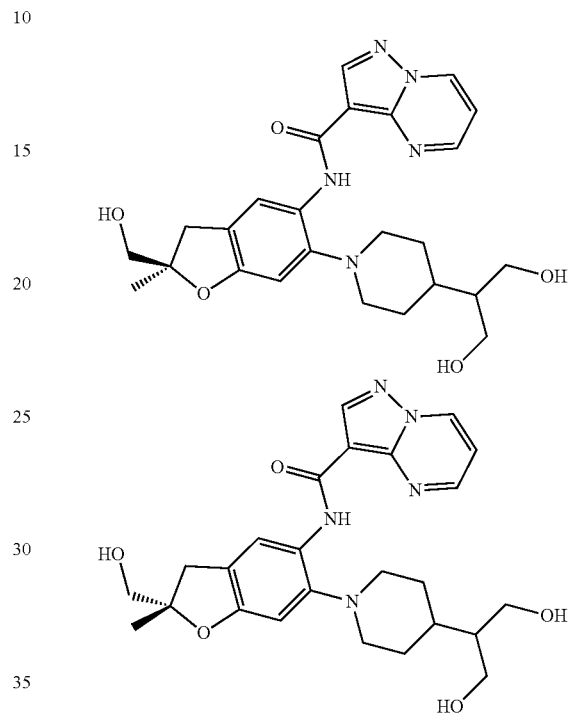

The title compounds were made in a manner analogous to Example 46, step D. The product was resolved by chiral preparatory SFC to afford (R)—N-(2-(hydroxymethyl)-2-methyl-6-(4-(oxetan-3-yl)piperazin-1-yl)-2,3-dihydrobenzofuran-5-yl)pyrazolo[1,5-a]pyrimidine-3-carboxamide and (S)—N-(2-(hydroxymethyl)-2-methyl-6-(4-(oxetan-3-yl)piperazin-1-yl)-2,3-dihydrobenzofuran-5-yl)pyrazolo[1,5-a]pyrimidine-3-carboxamide as yellow solids with absolute stereochemistry assigned arbitrarily (28.3 mg, 0.061 mmol, 11%) (28.8 mg, 0.062 mmol, 12%).

Example 50, Peak 1: $^1$H NMR (400 MHz, DMSO-$d_6$) δ 10.39 (s, 1H), 9.36 (dd, J=7.0, 1.6 Hz, 1H), 8.91 (dd, J=4.2, 1.7 Hz, 1H), 8.67 (s, 1H), 8.30 (d, J=1.0 Hz, 1H), 7.35 (dd, J=7.0, 4.2 Hz, 1H), 6.71 (s, 1H), 5.04 (t, J=5.8 Hz, 1H), 4.57 (t, J=6.5 Hz, 2H), 4.46 (t, J=6.1 Hz, 2H), 3.56 (m, 1H), 3.48-3.39 (m, 3H), 3.38-3.34 (m, 1H), 3.30-3.26 (m, 1H), 3.25-3.16 (m, 1H), 2.89-2.77 (m, 5H), 1.34 (s, 3H). MS (ESI): m/z=465.2[M+1]$^+$.

Example 51, Peak 2: $^1$H NMR (400 MHz, DMSO-$d_6$) δ 10.39 (s, 1H), 9.36 (dd, J=7.0, 1.6 Hz, 1H), 8.91 (dd, J=4.2, 1.6 Hz, 1H), 8.67 (s, 1H), 8.30 (d, J=1.1 Hz, 1H), 7.35 (dd, J=7.0, 4.2 Hz, 1H), 6.71 (s, 1H), 5.04 (t, J=5.8 Hz, 1H), 4.57 (t, J=6.5 Hz, 2H), 4.46 (t, J=6.1 Hz, 2H), 3.56 (t, J=6.3 Hz, 1H), 3.44 (h, J=5.7 Hz, 2H), 3.40-3.34 (m, 1H), 3.30-3.25 (m, 2H), 3.19 (dd, J=15.6, 1.2 Hz, 1H), 2.88-2.78 (m, 5H), 1.34 (s, 3H). MS (ESI): m/z=465.2[M+1]$^+$.

The title compounds were made in a manner analogous to Examples 50 and 51. The product was resolved by chiral preparatory SFC to afford (R)—N-(6-(4-(1,3-dihydroxypropan-2-yl)piperidin-1-yl)-2-(hydroxymethyl)-2-methyl-2,3-dihydrobenzofuran-5-yl)pyrazolo[1,5-a]pyrimidine-3-carboxamide and (S)—N-(6-(4-(1,3-dihydroxypropan-2-yl)piperidin-1-yl)-2-(hydroxymethyl)-2-methyl-2,3-dihydrobenzofuran-5-yl)pyrazolo[1,5-a]pyrimidine-3-carboxamide (4.3 mg, 0.009 mmol) (4.9 mg, 0.010 mmol) as yellow solids with absolute stereochemistry assigned arbitrarily.

Example 52, Peak 2: $^1$H NMR (400 MHz, DMSO-$d_6$) δ 10.37 (s, 1H), 9.35 (dd, J=7.0, 1.6 Hz, 1H), 8.87 (dd, J=4.2, 1.7 Hz, 1H), 8.67 (s, 1H), 8.26 (d, J=1.0 Hz, 1H), 7.33 (dd, J=7.0, 4.2 Hz, 1H), 6.65 (s, 1H), 5.02 (t, J=5.8 Hz, 1H), 4.34 (t, J=5.0 Hz, 2H), 3.59-3.36 (m, 5H), 3.29 (m, 1H), 3.18 (dd, J=15.6, 1.2 Hz, 1H), 2.94 (d, J=11.2 Hz, 2H), 2.86-2.76 (dd, J=15.6, 1.2 Hz, 1H), 2.64-2.51 (m, 2H), 1.73 (m, 2H), 1.67-1.50 (m, 3H), 1.41 (q, J=5.6 Hz, 1H), 1.34 (s, 3H). MS (ESI): m/z=482.3[M+1]$^+$.

Example 53, Peak 1: $^1$H NMR (400 MHz, DMSO-$d_6$) δ 10.37 (s, 1H), 9.35 (dd, J=7.0, 1.6 Hz, 1H), 8.87 (dd, J=4.2, 1.7 Hz, 1H), 8.67 (s, 1H), 8.26 (d, J=1.0 Hz, 1H), 7.33 (dd, J=7.0, 4.2 Hz, 1H), 6.65 (s, 1H), 5.02 (t, J=5.8 Hz, 1H), 4.34 (t, J=5.0 Hz, 2H), 3.59-3.36 (m, 5H), 3.29 (m, 1H), 3.18 (dd, J=15.6, 1.2 Hz, 1H), 2.94 (d, J=11.2 Hz, 2H), 2.86-2.76 (dd, J=15.6, 1.2 Hz, 1H), 2.64-2.51 (m, 2H), 1.73 (m, 2H), 1.67-1.50 (m, 3H), 1.41 (q, J=5.6 Hz, 1H), 1.34 (s, 3H). MS (ESI): m/z=482.3[M+1]$^+$.

TABLE 7

The following examples were made in the process of generating Examples 50, 51, 52, and 53, step A and isolated during the corresponding Step C.

| Ex. | Name | Structure | NMR, MS |
|---|---|---|---|
| 54 & 55 | (R)-N-(3-Hydroxy-3-methyl-7-(4-(oxetan-3-yl)piperazin-1-yl)chroman-6-yl)pyrazolo[1,5-a]pyrimidine-3-carboxamide and (S)-N-(3-Hydroxy-3-methyl-7-(4-(oxetan-3-yl)piperazin-1-yl)chroman-6-yl)pyrazolo[1,5-a]pyrimidine-3-carboxamide (absolute stereochemistry assigned arbitrarily) | 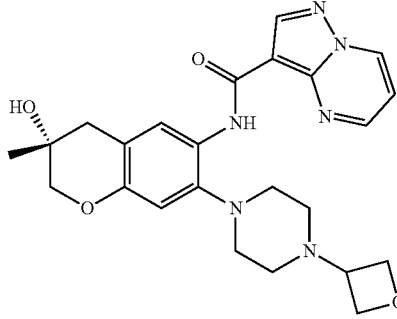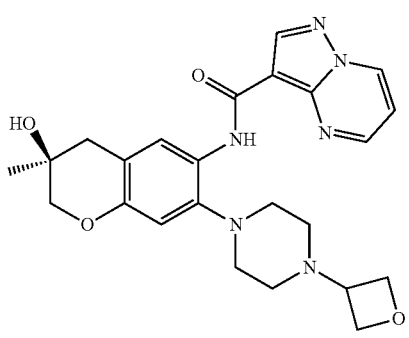 | Example 54, Peak 1: $^1$H NMR (400 MHz, DMSO-$d_6$) δ 10.34 (s, 1H), 9.36 (dd, J = 7.0, 1.6 Hz, 1H), 8.91 (dd, J = 4.2, 1.7 Hz, 1H), 8.67 (s, 1H), 8.16 (s, 1H), 7.35 (dd, J = 7.0, 4.2 Hz, 1H), 6.70 (s, 1H), 4.83 (s, 1H), 4.58 (t, J = 6.5 Hz, 2H), 4.47 (t, J = 6.0 Hz, 2H), 3.75 (s, 2H), 3.57 (p, J = 6.3 Hz, 1H), 3.38-3.34 (m, 4H), 2.85 (t, J = 4.8 Hz, 4H), 2.77-2.61 (m, 2H), 1.20 (s, 3H). MS (ESI): m/z = 465.2 [M + 1]$^+$. Example 55, Peak 2: $^1$H NMR (400 MHz, DMSO-$d_6$) δ 10.34 (s, 1H), 9.36 (dd, J = 7.0, 1.6 Hz, 1H), 8.91 (dd, J = 4.2, 1.7 Hz, 1H), 8.67 (s, 1H), 8.16 (s, 1H), 7.35 (dd, J = 7.0, 4.2 Hz, 1H), 6.70 (s, 1H), 4.83 (s, 1H), 4.58 (t, J = 6.5 Hz, 2H), 4.47 (t, J = 6.0 Hz, 2H), 3.75 (s, 2H), 3.57 (p, J = 6.3 Hz, 1H), 3.38-3.34 (m, 4H), 2.85 (t, J = 4.8 Hz, 4H), 2.77-2.61 (m, 2H), 1.20 (s, 3H). MS (ESI): m/z = 465.2 [M + 1]$^+$. |
| 56 & 57 | (R)-N-(7-(4-(1,3-Dihydroxypropan-2-yl)piperazin-1-yl)-3-hydroxy-3-methylchroman-6-yl)pyrazolo[1,5-a]pyrimidine-3-carboxamide and (S)-N-(7-(4-(1,3-Dihydroxypropan-2-yl)piperazin-1-yl)-3-hydroxy-3-methylchroman-6-yl)pyrazolo[1,5-a]pyrimidine-3-carboxamide (absolute stereochemistry assigned arbitrarily) | 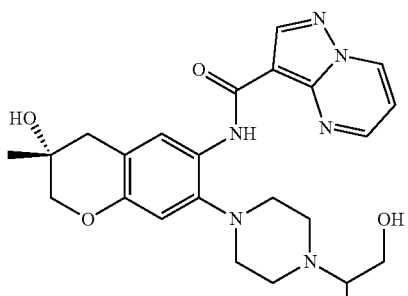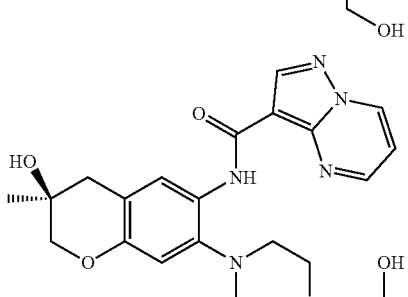 | Example 56, Peak 1: $^1$H NMR (400 MHz, DMSO-$d_6$) δ 10.33 (s, 1H), 9.36 (dd, J = 7.0, 1.6 Hz, 1H), 8.88 (dd, J = 4.2, 1.7 Hz, 1H), 8.67 (s, 1H) 8.14 (s, 1H) 7.33 (dd, J = 7.0, 4.2 Hz, 1H), 6.65 (s, 1H), 4.82 (s, 1H), 4.35 (t, J = 5.0 Hz, 2H), 3.74 (s, 2H), 3.52 (m, 4H), 2.97 (d, J = 11.2 Hz, 2H), 2.76-2.51 (m, 4H), 1.78-1.51 (m, 4H), 1.41 (m, 1H), 1.19 (s, 3H). MS (ESI): m/z = 482.3 [M + 1]$^+$. Example 57, Peak 2: $^1$H NMR (400 MHz, DMSO-$d_6$) δ 10.33 (s, 1H), 9.36 (dd, J = 7.0, 1.6 Hz, 1H), 8.88 (dd, J = 4.2, 1.7 Hz, 1H), 8.67 (s, 1H), 8.14 (s, 1H), 7.33 (dd, J = 7.0, 4.2 Hz, 1H), 6.65 (s, 1H), 4.82 (s, 1H), 4.35 (t, J = 5.0 Hz, 2H), 3.74 (s, 2H), 3.52 (m, 4H), 2.97 (d, J = 11.2 Hz, 2H), 2.76-2.51 (m, 4H), 1.78-1.51 (m, 4H), 1.41 (m, 1H), 1.19 (s, 3H). MS (ESI): m/z = 482.3 [M + 1]$^+$. |

Examples 58 and 59. (S)—N-(3-(2-Cyanoethyl)-3-methyl-7-morpholinochroman-6-yl)pyrazolo[1,5-a]pyrimidine-3-carboxamide and (R)—N-(3-(2-Cyanoethyl)-3-methyl-7-morpholinochroman-6-yl)pyrazolo[1,5-a]pyrimidine-3-carboxamide

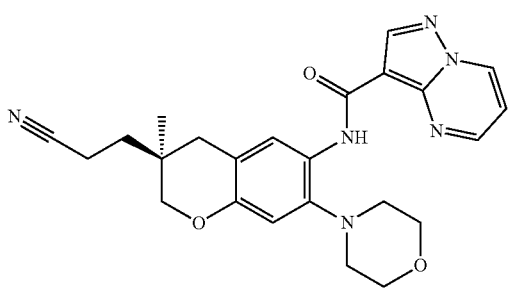

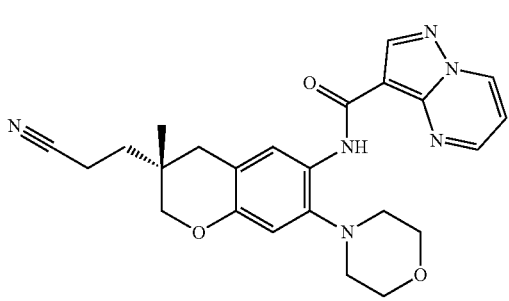

Step A. Diethyl 2-(2,4-difluorobenzyl)-2-methylmalonate

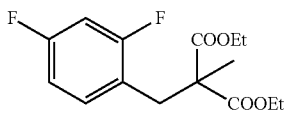 [SMILES: CCOC(=O)C(C)(Cc1ccc(F)cc1F)C(=O)OCC]

To a suspension of 60% sodium hydride (1.4 g, 34.5 mmol) in N,N-dimethylformamide (100 mL) was added diethyl methyl malonate (5.0 g, 28.7 mmol) dropwise at 0° C. The mixture was stirred at 0° C. for 30 min, then 2,4-difluorobenzyl bromide (6.5 g, 31.6 mmol) in N, N-dimethylformamide (6 mL) was added dropwise. The mixture was stirred from 0° C. to 28° C. for 2.5 h. The reaction was quenched with saturated ammonium chloride solution (10 mL) and extracted with ethyl acetate (100 mL×3). The combined organic phase was dried over sodium sulfate, filtered and concentrated. The residue was purified by flash column chromatography (eluting gradient: 3-7% ethyl acetate in petroleum ether) to give diethyl 2-[(2,4-difluorophenyl)methyl]-2-methyl-propanedioate (8.4 g, 97%) as a colorless oil. $^1$H NMR (400 MHz, CDCl$_3$): δ 7.14-7.09 (m, 1H), 6.80-6.74 (m, 2H), 4.23-4.17 (m, 4H), 3.25 (s, 2H), 1.34 (s, 3H), 1.26 (t, J=7.2 Hz 6H).

Step B. 2-(2,4-Difluorobenzyl)-2-methylpropane-1,3-diol

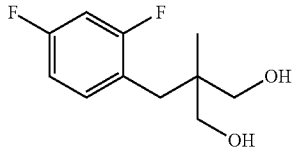

To a stirred solution of diethyl 2-[(2,4-difluorophenyl)methyl]-2-methyl-propanedioate (6.4 g, 21.2 mmol) in tetrahydrofuran (70 mL) was added lithium aluminum hydride (2.0 g, 53.0 mmol) in batches at −10° C. The mixture was stirred from −10° C. to 25° C. for 3.5 h. The reaction was quenched with water (30 mL) and extracted with ethyl acetate (100 mL×3). The combined organic phase was dried over sodium sulfate, filtered and concentrated. The residue was purified by flash column chromatography (eluting gradient: 20-60% ethyl acetate in petroleum ether) to give 2-[(2,4-difluorophenyl)methyl]-2-methyl-propane-1,3-diol (4.5 g, 97%) as a colorless oil. $^1$H NMR (400 MHz, CDCl$_3$) δ 7.31-7.25 (m, 1H), 6.87-6.80 (m, 2H), 3.61-3.54 (m, 4H), 2.77 (s, 2H), 2.56 (s, 2H), 0.77 (s, 3H).

Step C. (7-Fluoro-3-methylchroman-3-yl)methanol

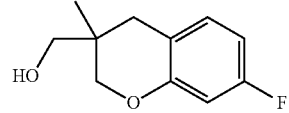

To a stirred solution of 2-[(2,4-difluorophenyl)methyl]-2-methyl-propane-1,3-diol (4.7 g, 21.6 mmol) in N,N-dimethylformamide (20 mL) and toluene (80 mL) was added 60% sodium hydride in mineral oil (1.9 g, 47.6 mmol) at 0° C. The reaction was heated at 100° C. for 2 h under nitrogen. The reaction was quenched with a saturated ammonium chloride solution (25 mL) and extracted with dichloromethane (100 mL×3). The combined organic phase was dried over sodium sulfate, filtered and concentrated. The residue was purified by flash column chromatography (eluting gradient: 0-15% ethyl acetate in petroleum ether) to afford (7-fluoro-3-methyl-chroman-3-yl)methanol (3.9 g, 92%) as a light yellow solid. $^1$H NMR (400 MHz, CDCl$_3$) δ 6.98-6.94 (m, 1H), 6.61-6.53 (m, 2H), 4.06-4.03 (m, 1H), 3.80-3.77 (m, 1H), 3.55 (d, J=10.8 Hz, 1H), 3.46 (d, J=10.8 Hz, 1H), 2.64 (d, J=16.8 Hz, 1H), 2.48 (d, J=16.0 Hz, 1H), 1.65 (s, 1H), 1.05 (s, 3H).

Step D. 7-Fluoro-3-methylchroman-3-carbaldehyde

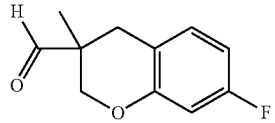

To a stirred solution of oxalyl dichloride (3.8 mL, 44.9 mmol) in anhydrous dichloromethane (80 mL) was added dropwise dimethyl sulfoxide (3.9 g, 49.3 mmol) at −70° C. The mixture was stirred at −70° C. for 45 min under nitrogen. A solution of (7-fluoro-3-methyl-chroman-3-yl)methanol (4.4 g, 22.4 mmol) in anhydrous dichloromethane (10 mL) was added dropwise and stirred at −70° C. for 1 h under a nitrogen atmosphere. Triethylamine (11.3 g, 112 mmol) was added dropwise and stirred at −70° C. for another 1.5 h under nitrogen. The reaction was quenched with saturated aqueous ammonium chloride (10 mL) and extracted with dichloromethane (50 mL×3). The combined organic phase was dried over sodium sulfate, concentrated, and purified by column chromatography (silica gel: 100-200 mesh, eluting gradient: 0-6% ethyl acetate in petroleum ether) to give 7-fluoro-3-methyl-chromane-3-carbaldehyde (4.3 g, 99%) as a white solid. $^1$H NMR (400 MHz, CDCl$_3$): δ 9.62 (s, 1H), 7.06-7.02 (m, 1H), 6.65-6.60 (m, 1H), 6.56-6.53 (m, 1H), 4.36-4.33 (m, 1H), 3.90 (d, J=10.8 Hz, 1H), 3.12 (d, J=16.4 Hz, 1H), 2.62 (d, J=16.0 Hz, 1H), 1.17 (s, 3H).

Step E. (E)-3-(7-Fluoro-3-methyl-chroman-3-yl)prop-2-enenitrile

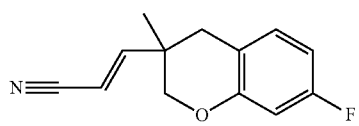 [SMILES: CC1(/C=C/C#N)COc2cc(F)ccc2C1]

A mixture of (triphenylphosphoranylidene)acetonitrile (17.3 g, 57.3 mmol) and 7-fluoro-3-methyl-chromane-3-carbaldehyde (4.5 g, 22.9 mmol) in toluene (100 mL) was stirred at 100° C. for 15 h under nitrogen and concentrated. To the residue was added water (60 mL), and the mixture was extracted with dichloromethane (100 mL×3). The combined organic phase was dried over sodium sulfate, concentrated and purified by column chromatography (silica gel: 100-200 mesh, eluting gradient: 0-16% ethyl acetate in petroleum ether) to give (E)-3-(7-fluoro-3-methyl-chroman-3-yl)prop-2-enenitrile (4.7 g, 95%) as a colorless oil. $^1$H NMR (400 MHz, CD$_3$OD): δ 7.06 (t, J=7.6 Hz, 1H), 6.79 (d, J=16.8 Hz, 1H), 6.64-6.59 (m, 1H), 6.54-6.51 (m, 1H), 5.62 (d, J=16.8 Hz, 1H), 4.05 (d, J=10.8 Hz, 1H), 3.87 (d, J=10.8 Hz, 1H), 2.84 (d, J=16.0 Hz, 1H), 2.70 (d, J=16.4 Hz, 1H), 1.16 (s, 3H).

Step F. 3-(7-Fluoro-3-methylchroman-3-yl)propanenitrile

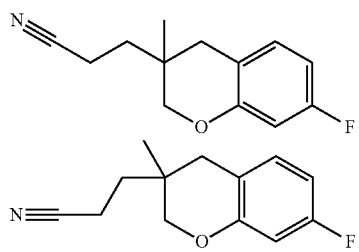

To a stirred solution of (E)-3-(7-fluoro-3-methyl-chroman-3-yl)prop-2-enenitrile (4.7 g, 21.8 mmol) in ethyl acetate (50 mL) was added 10% palladium on carbon (2.3 g, 2.2 mmol). The mixture was stirred at 25° C. for 1.2 h under H$_2$ (15 psi), filtered over a pad of Celite, and concentrated to give crude 3-(7-fluoro-3-methyl-chroman-3-yl)propanenitrile (4.0 g, 84%) as a colorless oil. $^1$H NMR (400 MHz, CD$_3$OD): δ 7.04-7.00 (m, 1H), 6.61-6.56 (m, 1H), 6.52-6.49 (m, 1H), 3.85 (d, J=11.2 Hz, 1H), 3.77 (d, J=11.2 Hz, 1H), 2.63-2.49 (m, 4H), 1.72-1.67 (m, 2H), 1.01 (s, 3H).

Step G. 3-(7-Fluoro-3-methyl-6-nitro-chroman-3-yl)propanenitrile

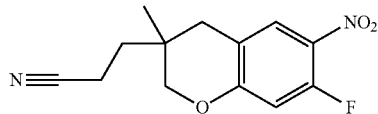

To a stirred solution of 3-(7-fluoro-3-methyl-chroman-3-yl)propanenitrile (1.0 g, 4.56 mmol) in the mixture of acetic acid (5 mL) and acetic anhydride (10 mL) was added dinitrooxycopper (2.57 g, 13.7 mmol) at 0° C. The mixture was stirred at 0° C. to 28° C. for 25 min. Water was added (100 ml), and the mixture was extracted with ethyl acetate (100 mL×3). The combined organic phase was washed with saturated aqueous sodium bicarbonate (100 mL×3), dried over sodium sulfate, and concentrated. The residue was purified by column chromatography (silica gel: 100-200 mesh, eluting gradient: 15-30% ethyl acetate in petroleum ether) to give 3-(7-fluoro-3-methyl-6-nitro-chroman-3-yl)propanenitrile (1.67 g, 6.32 mmol) as light yellow oil, which was unpure. The material was taken forward without further purification.

Step H. N-[(3S)-3-(Cyanoethyl)-3-methyl-7-morpholino-chroman-$^6$-yl]pyrazolo[1,5-a]pyrimidine-3-carboxamide and N-[(3R)-3-(Cyanoethyl)-3-methyl-7-morpholino-chroman-6-yl]pyrazolo[1,5-a]pyrimidine-3-carboxamide

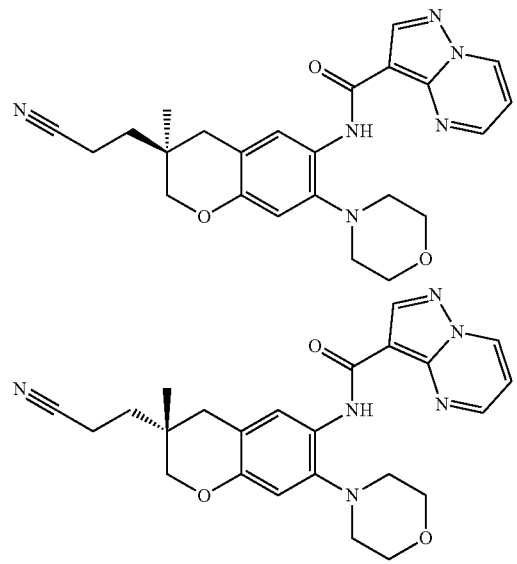

Following the procedures described for Example 46, steps B-D, N-[3-(cyanoethyl)-3-methyl-7-morpholino-chroman- 6-yl]pyrazolo[1,5-a]pyrimidine-3-carboxamide (300 mg, 0.7 mmol) was obtained and resolved by chiral preparatory SFC to afford N-[(3S)-3-(cyanoethyl)-3-methyl-7-morpholino-chroman-6-yl]pyrazolo[1,5-a]pyrimidine-3-carboxamide (113 mg, 37%; RT=2.041 min) and N-[(3R)-3-(cyanoethyl)-3-methyl-7-morpholino-chroman-6-yl]pyrazolo[1,5-a]pyrimidine-3-carboxamide (116 mg, 38%; RT=2.472 min) as light yellow solids. Absolute stereochemistry was assigned arbitrarily.

Example 58, Peak 1: $^1$H NMR (400 MHz, CDCl$_3$) δ 10.44 (s, 1H), 8.84 (dd, J=7.2, 1.6 Hz, 1H), 8.79-8.77 (m, 2H), 8.33 (s, 1H), 7.08 (dd, J=7.2, 4.0 Hz, 1H), 6.69 (s, 1H), 3.96 (t, J=4.4 Hz, 4H), 3.84 (d, J=10.8 Hz, 1H), 3.76 (d, J=10.8 Hz, 1H), 2.94 (t, J=4.4 Hz, 4H), 2.67-2.57 (m, 2H), 2.42-2.38 (m, 2H), 1.85-1.71 (m, 2H), 1.06 (s, 3H). LCMS (ESI): m/z=447.2 [M+H]$^+$.

Example 59, Peak 2: $^1$H NMR (400 MHz, CDCl$_3$) δ 10.44 (s, 1H), 8.84 (dd, J=7.2, 1.6 Hz, 1H), 8.79-8.77 (m, 2H), 8.33 (s, 1H), 7.08 (dd, J=7.2, 4.0 Hz, 1H), 6.69 (s, 1H), 3.96 (t, J=4.4 Hz, 4H), 3.84 (d, J=11.2 Hz, 1H), 3.75 (d, J=10.8 Hz, 1H), 2.93 (t, J=4.4 Hz, 4H), 2.67-2.57 (m, 2H), 2.42-2.38 (m, 2H), 1.85-1.71 (m, 2H), 1.06 (s, 3H). LCMS (ESI): m/z=447.2 [M+H]$^+$.

Example 60. (R)—N-(2-(2-Fluoro-3-hydroxy-3-methylbutyl)-6-((1-methyl-1H-pyrazol-4-yl)methoxy)-1-oxoisoindolin-5-yl)pyrazolo[1,5-a]pyrimidine-3-carboxamide

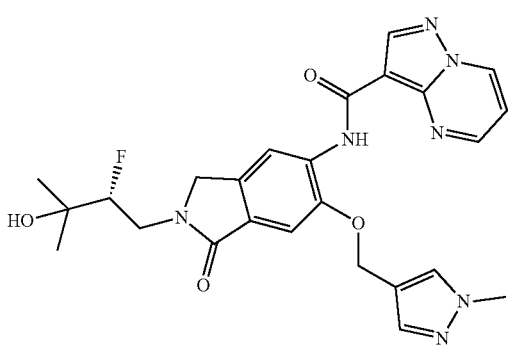 [SMILES: Cn1cc(COc2cc3c(cc2NC(=O)c2cnn4cccnc24)CN(C[C@@H](F)C(C)(C)O)C3=O)cn1]

Step A. Methyl 5-hydroxy-2-methylbenzoate

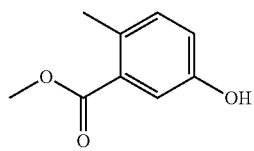

To a solution of 5-hydroxy-2-methylbenzoic acid (50.0 g, 329 mmol) in methanol (500 mL) was added sulfuric acid (3.29 g, 32.9 mmol). The mixture was stirred at 70° C. for 16 h under nitrogen and concentrated. The residue was diluted with water (50 mL) and extracted with dichloromethane (50 mL×3). The combined organic phase was washed with saturated aqueous sodium bicarbonate (100 mL×2), dried over sodium sulfate and concentrated to give crude methyl 5-hydroxy-2-methyl-benzoate (52.0 g, 95%) as a white solid.

Step B. Methyl 5-acetoxy-2-methyl-4-nitrobenzoate

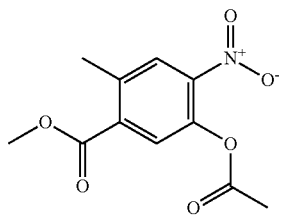 [SMILES: COC(=O)c1cc(OC(C)=O)c([N+](=O)[O-])cc1C]

To a stirred solution of methyl 5-hydroxy-2-methylbenzoate (1.0 g, 6.0 mmol) in acetic acid (10 mL) and acetic anhydride (20 mL) was added dinitrooxycopper (1.7 g, 9.0 mmol) at 0° C. The mixture was stirred at 0° C. for 1 h, poured into ice water and extracted with ethyl acetate (50 mL×3). The combined organic phase was washed with saturated aqueous sodium bicarbonate (50 mL×2), dried over sodium sulfate, concentrated and purified by column chromatography (silica gel: 100-200 mesh, eluting gradient: 0-20% ethyl acetate in petroleum ether) to give methyl 5-acetoxy-2-methyl-4-nitro-benzoate (400 mg, 26%) as a yellow solid. $^1$H NMR (400 MHz, CDCl$_3$): δ 7.96 (s, 1H), 7.79 (s, 1H), 3.94 (s, 3H), 2.67 (s, 3H), 2.38 (s, 3H).

Step C. Methyl 5-acetoxy-2-(bromomethyl)-4-nitrobenzoate

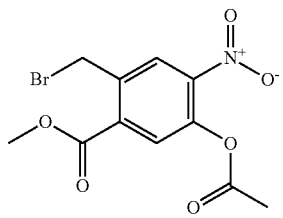 [SMILES: COC(=O)c1cc(OC(C)=O)c([N+](=O)[O-])cc1CBr]

To a stirred solution of methyl 5-acetoxy-2-methyl-4-nitro-benzoate (279 mg, 1.1 mmol) in carbon tetrachloride (10 mL) was added 1-bromo-2,5-pyrrolidinedione (235 mg, 1.3 mmol) and benzoylperoxide (26.7 mg, 0.1 mmol). The mixture was stirred at 95° C. for 16 h under nitrogen and concentrated. The residue was purified by column chromatography (silica gel:eluting gradient: 0-10% ethyl acetate in petroleum ether) to give methyl 5-acetoxy-2-(bromomethyl)-4-nitro-benzoate (270 mg, 74%) as a light yellow oil.

Step D. (R)-2-(2-Fluoro-3-hydroxy-3-methylbutyl)-6-hydroxy-5-nitroisoindolin-1-one

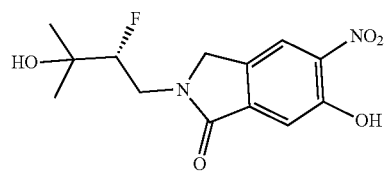 [SMILES: CC(C)(O)[C@H](F)CN1Cc2cc([N+](=O)[O-])c(O)cc2C1=O]

To a stirred solution of methyl 5-acetoxy-2-(bromomethyl)-4-nitro-benzoate (270 mg, 0.8 mmol) in methanol (10 mL) was added triethylamine (165 mg, 1.6 mmol) and (3R)-4-amino-3-fluoro-2-methyl-butan-2-ol (WO2014/074675, 197 mg, 1.6 mmol). The mixture was stirred at 75° C. for 2 h under nitrogen and concentrated. The residue was purified by column chromatography (silica gel: 100-200 mesh, eluting gradient: 0-3% methanol in dichloromethane) to give (R)-2-(2-fluoro-3-hydroxy-3-methylbutyl)-6-hydroxy-5-nitroisoindolin-1-one (180 mg, 74%) as an orange solid.

Step E. (R)-2-(2-Fluoro-3-hydroxy-3-methylbutyl)-6-((1-methyl-1H-pyrazol-4-yl)methoxy)-5-nitroisoindolin-1-one

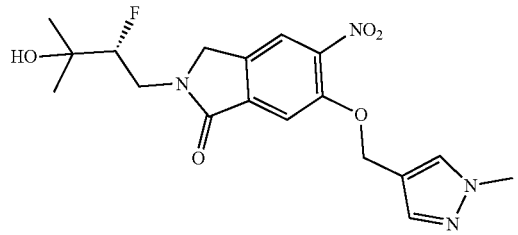 [SMILES: Cn1cc(COc2cc3c(cc2[N+](=O)[O-])CN(C[C@@H](F)C(C)(C)O)C3=O)cn1]

To a solution of (R)-2-(2-fluoro-3-hydroxy-3-methylbutyl)-6-hydroxy-5-nitroisoindolin-1-one (130 mg, 0.4 mmol), (1-methyl-1H-pyrazol-4-yl)methanol (122 mg, 1.1 mmol) and triphenylphosphine (343 mg, 1.3 mmol) in toluene (25 mL) was added diisopropyl azodicarboxylate (264 mg, 1.3 mmol) at 0° C. under nitrogen. The mixture was stirred at 0° C. for 20 min, heated to 110° C. and stirred for 16 h. The mixture was concentrated and purified by column chromatography (silica gel: 100-200 mesh, eluting gradient: 0-10% methanol in dichloromethane) to give (R)-2-(2-fluoro-3-hydroxy-3-methylbutyl)-6-((1-methyl-1H-pyrazol-4-yl)methoxy)-5-nitroisoindolin-1-one (100 mg, 59%) as a light yellow oil. LCMS (ESI): m/z=393.1 [M+H]$^+$.

Step F. (R)-5-Amino-2-(2-fluoro-3-hydroxy-3-methylbutyl)-6-((1-methyl-1H-pyrazol-4-yl)methoxy)isoindolin-1-one

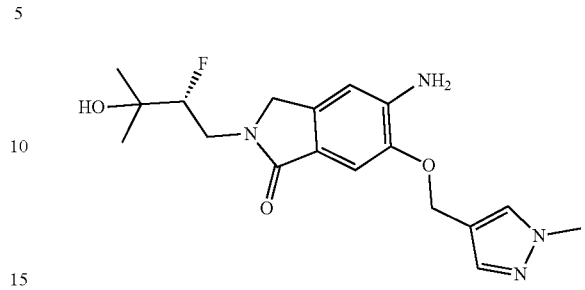

To a stirred solution of (R)-2-(2-fluoro-3-hydroxy-3-methylbutyl)-6-((1-methyl-1H-pyrazol-4-yl)methoxy)-5-nitroisoindolin-1-one (100 mg, 0.3 mmol) in ethanol (5 mL) and water (1 mL) was added iron (71.2 mg, 1.3 mmol) and ammonium chloride (68.2 mg, 1.3 mmol). The mixture was stirred at 80° C. for 2 h under nitrogen, filtered and concentrated. The residue was taken up in dichloromethane (30 mL), filtered again and concentrated to give crude (R)-5-amino-2-(2-fluoro-3-hydroxy-3-methylbutyl)-6-((1-methyl-1H-pyrazol-4-yl)methoxy)isoindolin-1-one (90 mg, 97%) as light yellow oil. LCMS (ESI): m/z=363.1 [M+H]$^+$.

Step G. (R)—N-(2-(2-Fluoro-3-hydroxy-3-methylbutyl)-6-((1-methyl-1H-pyrazol-4-yl)methoxy)-1-oxoisoindolin-5-yl)pyrazolo[1,5-a]pyrimidine-3-carboxamide

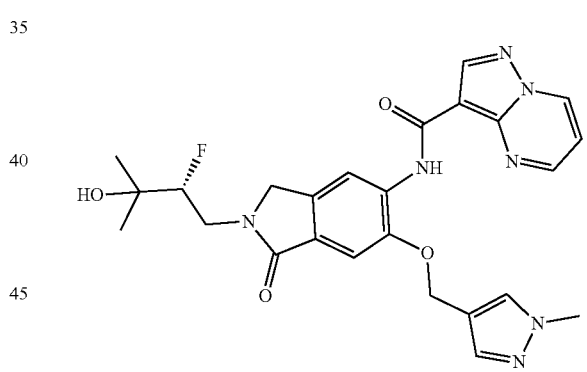

A mixture of (R)-5-amino-2-(2-fluoro-3-hydroxy-3-methylbutyl)-6-((1-methyl-1H-pyrazol-4-yl)methoxy)isoindolin-1-one (90 mg, 0.3 mmol) and pyrazolo[1,5-a]pyrimidine-3-carbonyl chloride (67.6 mg, 0.4 mmol) in pyridine (5 mL) was stirred at 16° C. for 16 h and concentrated. The residue was purified first by column chromatography (silica gel: 100-200 mesh, eluting gradient: 0-5% methanol in dichloromethane), then by preparatory thin layer chromatography (7% methanol in dichloromethane) to give (R)—N-(2-(2-fluoro-3-hydroxy-3-methylbutyl)-6-((1-methyl-1H-pyrazol-4-yl)methoxy)-1-oxoisoindolin-5-yl)pyrazolo[1,5-a]pyrimidine-3-carboxamide (79.0 mg, 61%) as a white solid. $^1$H NMR (400 MHz, DMSO-d$_6$) δ 10.66 (s, 1H), 9.40-9.35 (m, 1H), 8.72 (s, 1H), 8.71 (s, 1H), 8.20-8.15 (m, 1H), 7.89 (s, 1H), 7.68 (s, 1H), 7.46 (s, 1H), 7.36 (dd, J=7.2, 4.4 Hz, 1H), 5.20 (s, 2H), 4.94 (s, 1H), 4.56-4.38 (m, 3H), 4.01-3.89 (m, 4H; including a (s, 3H) at 3.89), 3.75-3.65 (m, 1H), 1.19, 1.18 (s, 3H each). LCMS (ESI): m/z=508.2 [M+H]$^+$.

TABLE 8

*The following examples were made in a manner similar to that for Example 60:*

| Ex. | Name | Structure | NMR, MS |
|---|---|---|---|
| 61 | N-[6-(3-Fluorocyclo-butoxy)-2-[(2R)-2-fluoro-3-hydroxy-3-methyl-butyl]-1-oxo-isoindolin-5-yl]pyrazolo[1,5-a]pyrimidine-3-carboxamide | 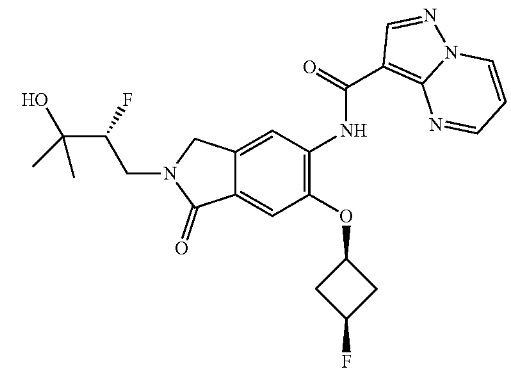 [SMILES: CC(C)(O)[C@H](F)CN1Cc2cc(NC(=O)c3cnn4cccnc34)c(O[C@H]3C[C@@H](F)C3)cc2C1=O] | $^1$H NMR (400 MHz, CDCl$_3$) δ 10.71 (s, 1H), 8.88-8.78 (m, 4H), 7.19 (s, 1H), 7.11 (dd, J = 6.8, 4.0 Hz, 1H), 5.05-4.89 (m, 1H), 4.62-4.43 (m, 4H), 4.21-4.12 (m, 1H), 3.70-3.68 (m, 1H), 3.22-3.18 (m, 2H), 2.70-2.63 (m, 2H), 2.40 (s, 1H), 1.34 (s, 3H), 1.33 (s, 3H). LCMS (ESI): m/z = 486.1 [M+ H]$^+$. |
| 62 & 63 | N-[2-[(2R)-2-Fluoro-3-hydroxy-3-methyl-butyl]-1-oxo-6-[(3S)-pyrrolidin-3-yl]oxy-isoindolin-5-yl]pyrazolo[1,5-a]pyrimidine-3-carboxamide and N-[2-[(2R)-2-Fluoro-3-hydroxy-3-methyl-butyl]-1-oxo-6-[(3R)-pyrrolidin-3-yl]oxy-isoindolin-5-yl]pyrazolo[1,5-a]pyrimidine-3-carboxamide (absolute stereochemistry assigned arbitrarily) | | Example 62, Peak 1: $^1$H NMR (400 MHz, CD$_3$OD) δ 10.59 (s, 1H), 9.18 (dd, J = 7.2, 1.6 Hz, 1H), 8.88-8.87 (m, 1H), 8.80 (s, 1H), 8.70 (s, 1H), 7.39 (s, 1H), 7.31 (dd, J = 7.2, 4.4 Hz, 1H), 5.44 (s, 1H) ,4.66-4.47 (m, 4H), 4.27-4.06 (m, 1H), 3.84-3.67 (m, 6H), 2.68-2.58 (m, 2H), 1.31 (s, 6H). LCMS (ESI): m/z = 483.1 [M + H]$^+$. Example 63, Peak 2: $^1$H NMR (400 MHz, CD$_3$OD) δ 9.17-9.15 (m, 1H), 8.87-8.86 (m, 1H), 8.79 (s, 1H), 8.70 (s, 1H), 7.38 (s, 1H), 7.30 (dd, J = 7.2, 4.4 Hz, 1H), 5.43 (s, 1H), 4.63-4.45 (m, 4H), 4.27-4.06 (m, 1H), 3.80-3.66 (m, 6H), 2.65-2.51 (m, 2H), 1.31 (s, 6H). LCMS (ESI): m/z = 483.1 [M + H]$^+$. |
| 64 | N-[6-(3-Chlorocyclo-butoxy)-2-[(2R)-2-fluoro-3-hydroxy-3-methyl-butyl]-1-oxo-isoindolin-5-yl]pyrazolo[1,5-a]pyrimidine-3-carboxamide | 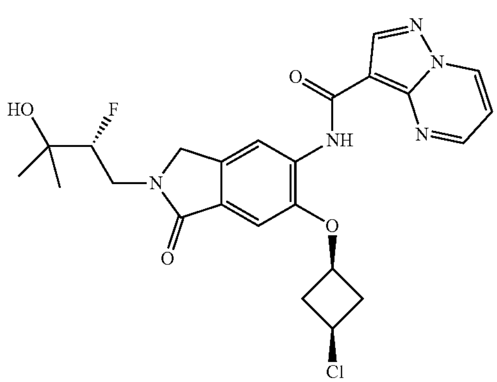 [SMILES: CC(C)(O)[C@H](F)CN1Cc2cc(NC(=O)c3cnn4cccnc34)c(O[C@H]3C[C@@H](Cl)C3)cc2C1=O] | $^1$H NMR (400 MHz, CDCl$_3$) δ 10.69 (s, 1H), 8.88-8.80 (m, 4H), 7.16 (s, 1H), 7.13 (dd, J = 7.2, 4.0 Hz, 1H), 4.71-4.43 (m, 4H), 4.26-4.07 (m, 2H), 3.73-3.63 (m, 1H), 3.39-3.34 (m, 2H), 2.74-2.72 (m, 2H), 2.43 (s, 1H), 1.34 (s, 3H), 1.32 (s, 3H). LCMS (ESI): m/z = 502.1 [M + H]$^+$. |

TABLE 8-continued

The following examples were made in a manner similar to that for Example 60:

| Ex. | Name | Structure | NMR, MS |
|---|---|---|---|
| 65 | (R)-N-(6-(2,2-Difluoroethoxy)-2-(2-fluoro-3-hydroxy-3-methylbutyl)-1-oxoisoindolin-5-yl)pyrazolo[1,5-a]pyrimidine-3-carboxamide | 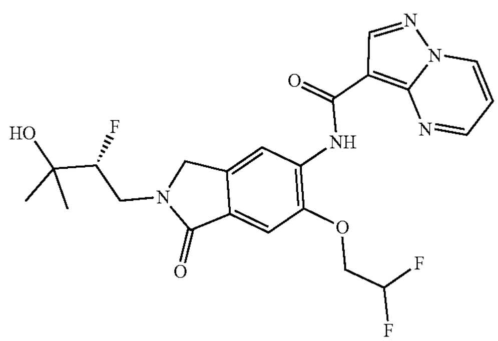 [SMILES: CC(C)(O)[C@H](F)CN1Cc2cc(NC(=O)c3cnn4cccnc34)c(OCC(F)F)cc2C1=O] | $^1$H NMR (400 MHz, CDCl$_3$) δ 10.74 (s, 1H), 8.88 (s, 1H), 8.85-8.83 (m, 1H), 8.78 (m, 1H), 8.76-8.75 (m, 1H), 7.33 (s, 1H), 7.10 (dd, J = 7.2, 4.4 Hz, 1H), 6.32 (tt, J = 54.4, 4.0 Hz, 1H), 4.64-4.38 (m, 5H), 4.26-4.12 (m, 1H), 3.74-3.68 (m, 1H), 2.37 (s, 1H), 1.34 (s, 3H), 1.32 (s, 3H). LCMS (ESI): m/z = 478.2 [M + H]$^+$. |
| 66 & 67 | N-(2-((R)-2-Fluoro-3-hydroxy-3-methylbutyl)-6-(((1S,3R)-3-hydroxycyclopentyl)oxy)-1-oxoisoindolin-5-yl)pyrazolo[1,5-a]pyrimidine-3-carboxamide and N-(2-((R)-2-Fluoro-3-hydroxy-3-methylbutyl)-6-(((1R,3S)-3-hydroxycyclopentyl)oxy)-1-oxoisoindolin-5-yl)pyrazolo[1,5-a]pyrimidine-3-carboxamide (absolute stereochemistry assigned arbitrarily) | | Example 66, Peak 1: $^1$H NMR (400 MHz, DMSO-d$_6$) δ 10.77 (s, 1H), 9.42-9.40 (m, 1H), 8.97-8.96 (m, 1H), 8.74 (s, 2H), 7.40 (dd, J = 6.8, 4.4 Hz, 1H), 7.22 (s, 1H), 5.08-4.93 (m, 3H), 4.56-4.35 (m, 3H), 4.20-4.17 (m, 1H), 4.05-3.82 (m, 1H), 3.71-3.68 (m, 1H), 2.57-2.53 (m, 1H), 2.08-2.04 (m, 2H), 1.85-1.78 (m, 3H), 1.18 (s, 6H) LCMS (ESI): m/z = 498.3 [M + H]$^+$. Example 67, Peak 2: $^1$H NMR (400 MHz, DMSO-d$_6$) δ 10.76 (s, 1H), 9.41-9.40 (m, 1H), 8.96-8.95 (m, 1H), 8.74 (s, 2H), 7.39 (dd, J = 6.8, 4.4 Hz, 1H), 7.21 (s, 1H), 5.01-4.99 (m, 1H), 4.92 (s, 1H), 4.82 (d, J = 4.0 Hz, 1H), 4.56-4.36 (m, 3H), 4.19-4.18 (m, 1H), 4.03-3.85 (m, 1H), 3.70-3.68 (m, 1H), 2.54-2.52 (m, 1H), 2.08-2.04 (m, 2H), 1.87-1.78 (m, 3H), 1.18 (s, 6H). LCMS (ESI): m/z = 498.2 [M + H]$^+$. |

TABLE 8-continued

The following examples were made in a manner similar to that for Example 60:

| Ex. | Name | Structure | NMR, MS |
|---|---|---|---|
| 68 & 69 | (S)-N-(6-Isopropoxy-1-oxo-2-(tetrahydrofuran-3-yl)isoindolin-5-yl)pyrazolo[1,5-a]pyrimidine-3-carboxamide and (R)-N-(6-Isopropoxy-1-oxo-2-(tetrahydrofuran-3-yl)isoindolin-5-yl)pyrazolo[1,5-a]pyrimidine-3-carboxamide (absolute stereochemistry assigned arbitrarily) | | Example 68, Peak 1: $^1$H NMR (400 MHz, CDCl$_3$) δ 10.72 (s, 1H), 8.86-8.73 (m, 4H), 7.38 (s, 1H), 7.09 (dd, J = 6.8, 4.4 Hz, 1H), 5.16-5.15 (m, 1H), 4.82-4.80 (m, 1H), 4.43-4.40 (m, 2H), 4.15-4.13 (m, 1H), 3.91-3.85 (m, 3H), 2.41-2.37 (m, 1H), 2.07-2.05 (m, 1H), 1.52 (d, J = 6.0 Hz, 6H). LCMS (ESI): m/z = 422.0 [M + H]$^+$. Example 69, Peak 2: $^1$H NMR (400 MHz, CDCl$_3$) δ 10.71 (s, 1H), 8.85-8.72 (m, 4H), 7.37 (s, 1H), 7.08 (dd, J = 6.8, 4.0 Hz, 1H), 5.16-5.15 (m, 1H), 4.80-4.78 (m, 1H), 4.42-4.35 (m, 2H), 4.15-4.13 (m, 1H), 3.90-3.84 (m, 3H), 2.40-2.36 (m, 1H), 2.05-2.03 (m, 1H), 1.51 (d, J = 6.0 Hz, 6H). LCMS (ESI): m/z = 422.0 [M + H]$^+$. |
| 70 | (R)-N-(2-(2-Fluoro-3-hydroxy-3-methylbutyl)-1-oxo-6-(piperidin-4-yloxy)isoindolin-5-yl)pyrazolo[1,5-a]pyrimidine-3-carboxamide | 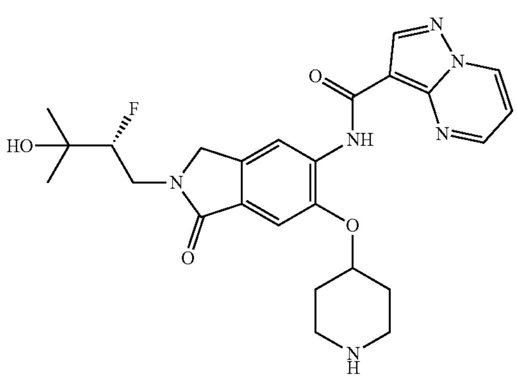 [SMILES: CC(C)(O)[C@H](F)CN1Cc2cc(NC(=O)c3cnn4cccnc34)c(OC3CCNCC3)cc2C1=O] | $^1$H NMR (400 MHz, DMSO-d$_6$) δ 10.60 (s, 1H), 9.45 (d, J = 7.2 Hz, 1H), 9.03-9.02 (m, 1H), 8.77 (s, 1H), 8.75 (s, 1H), 7.48 (s, 1H), 7.42 (dd, J = 7.2, 4.4 Hz, 1H), 4.98-4.93 (m, 2H), 4.58-4.40 (m, 3H), 3.97-3.87 (m, 1H), 3.73-3.71 (m, 1H), 3.32-3.10 (m, 4H), 2.21-2.19 (m, 2H), 2.02-2.00 (m, 2H), 1.19 (s, 3H), 1.18 (s, 3H). LCMS (ESI): m/z = 497.1 [M + H]$^+$. |

TABLE 8-continued

The following examples were made in a manner similar to that for Example 60:

| Ex. | Name | Structure | NMR, MS |
|---|---|---|---|
| 71 & 72 | N-[2-[(2R)-2-Fluoro-3-hydroxy-3-methyl-butyl]-1-oxo-6-[[(3S)-5-oxopyrrolidin-3-yl]methoxy]isoindolin-5-yl]pyrazolo[1,5-a]pyrimidine-3-carboxamide and N-[2-[(2R)-2-Fluoro-3-hydroxy-3-methyl-butyl]-1-oxo-6-[[(3R)-5-oxopyrrolidin-3-yl]methoxy]isoindolin-5-yl]pyrazolo[1,5-a]pyrimidine-3-carboxamide (absolute stereochemistry assigned arbitrarily) | | Example 71, Peak 1: $^1$H NMR (400 MHz, DMSO-$d_6$) δ 10.50 (s, 1H), 9.42 (dd, J = 7.2, 1.6 Hz, 1H), 8.91-8.89 (m, 1H), 8.75 (s, 1H), 8.73 (s, 1H), 7.63 (s, 1H), 7.38 (dd, J = 7.2, 4.4 Hz, 1H), 7.36 (s, 1H), 4.93 (s, 1H), 4.52-4.39 (m, 3H), 4.25-4.23 (m, 2H), 4.01-3.88 (m, 1H), 3.75-3.65 (m, 1H), 3.56-3.52 (m, 1H), 3.26-3.22 (m, 1H), 3.10-3.08 (m, 1H), 2.44-2.40 (m, 1H), 2.25-2.24 (m, 1H), 1.18 (s, 6H). LCMS (ESI): m/z = 511.1 [M + H]$^+$. Example 72, Peak 2: $^1$H NMR (400 MHz, DMSO-$d_6$) δ 10.48 (s, 1H), 9.40 (dd, J = 6.8, 1.6 Hz, 1H), 8.89-8.88 (m, 1H), 8.74 (s, 1H), 8.72 (s, 1H), 7.63 (s, 1H), 7.37 (dd, J = 6.8, 4.4 Hz, 1H), 7.34 (s, 1H), 4.93 (s, 1H), 4.51-4.38 (m, 3H), 4.24-4.21 (m, 2H), 4.00-3.87 (m, 1H), 3.74-3.64 (m, 1H), 3.56-3.52 (m, 1H), 3.26-3.22 (m, 1H), 3.11-3.06 (m, 1H), 2.47-2.40 (m, 1H), 2.25-2.24 (m, 1H), 1.18 (s, 6H). LCMS (ESI): m/z = 511.2 [M + H]$^+$. |
| 73 | N-[6-(Azetidin-3-yloxy)-2-[(2R)-2-fluoro-3-hydroxy-3-methyl-butyl]-1-oxo-isoindolin-5-yl]pyrazolo[1,5-a]pyrimidine-3-carboxamide hydrochloride | 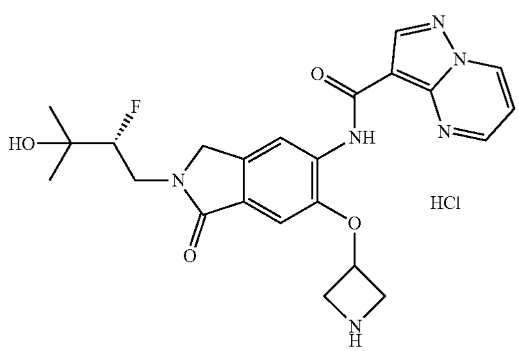 [SMILES: CC(C)(O)[C@H](F)CN1Cc2cc(NC(=O)c3cnn4cccnc34)c(OC3CNC3)cc2C1=O ; Cl] | $^1$H NMR (400 MHz, CD$_3$OD) δ 9.09 (dd, J = 7.2, 1.6 Hz, 1H), 8.84-8.83 (m, 1H), 8.72 (s, 1H), 8.67 (s, 1H), 7.23 (dd, J = 7.2, 4.4 Hz, 1H), 7.02 (s, 1H), 5.35-5.32 (m, 1H), 4.67-4.62 (m, 2H), 4.58-4.45 (m, 3H), 4.33-4.32 (m, 2H), 4.15-4.02 (m, 1H), 3.74-3.72 (m, 1H), 1.30 (s, 6H). LCMS (ESI): m/z = 469.1 [M + H]$^+$. |
| 74 | N-[6-(Azetidin-3-yloxy)-2-[(2R)-2-fluoro-3-hydroxy-3-methyl-butyl]-1-oxo-isoindolin-5-yl]pyrazolo[1,5-a]pyrimidine-3-carboxamide | 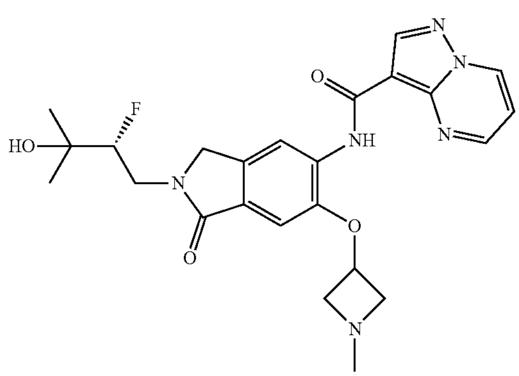 [SMILES: CN1CC(Oc2cc3c(cc2NC(=O)c2cnn4cccnc24)CN(C[C@@H](F)C(C)(C)O)C3=O)C1] | $^1$H NMR (400 MHz, DMSO-$d_6$) δ 10.72 (s, 1H) 9.45-9.40 (m, 1H) 9.00-8.95 (m, 1H), 8.76 (s, 1H), 8.74 (s, 2H), 7.39 (dd, J = 6.8, 4.4 Hz, 1H), 7.07 (s, 1H), 5.19-5.16 (m, 1H), 4.94 (s, 1H), 4.52-4.37 (m, 3H), 4.17-4.15 (m, 2H), 3.99-3.89 (m, 1H), 3.72-3.71 (m, 1H), 3.68-3.60 (m, 2H), 2.57 (s, 3H), 1.17 (s, 6H). LCMS (ESI): m/z = 483.2 [M + H]$^+$. |

TABLE 8-continued

The following examples were made in a manner similar to that for Example 60:

| Ex. | Name | Structure | NMR, MS |
|---|---|---|---|
| 75 | N-[2-[(2R)-2-Fluoro-3-hydroxy-3-methyl-butyl]-6-(3-hydroxycyclo-butoxy)-1-oxo-isoindolin-5-yl]pyrazolo[1,5-a]pyrimidine-3-carboxamide | 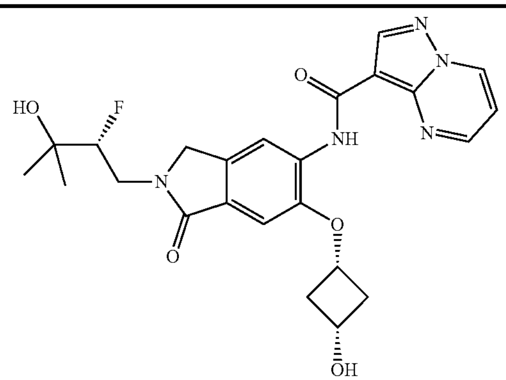 | $^1$H NMR (400 MHz, DMSO-$d_6$) δ 10.80 (s, 1H), 9.43 (d, J = 6.8 Hz, 1H), 8.92-8.91 (m, 1H), 8.76 (s, 1H), 8.72 (s, 1H), 7.41 (dd, J = 6.8, 4.4 Hz, 1H), 7.14 (s, 1H), 5.31 (d, J = 6.8 Hz, 1H), 4.93 (s, 1H), 4.60-4.35 (m, 4H), 3.96-3.87 (m, 2H), 3.71-3.68 (m, 1H), 2.98-2.95 (m, 2H), 2.14-2.12 (m, 2H), 1.18 (s, 6H). LCMS (ESI): m/z = 484.1 [M + H]$^+$. |
| 76 | (R)-N-(2-(2-Fluoro-3-hydroxy-3-methylbutyl)-6-((1-methylpiperidin-4-yl)oxy)-1-oxoisoindolin-5-yl)pyrazolo[1,5-a]pyrimidine-3-carboxamide | 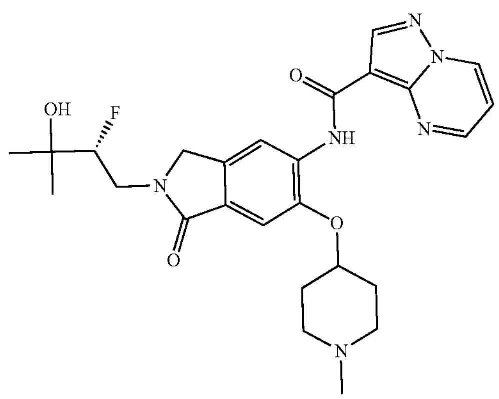 [SMILES: CN1CCC(Oc2cc3c(cc2NC(=O)c2cnn4cccnc24)CN(C[C@@H](F)C(C)(C)O)C3=O)CC1] | LCMS (ESI): m/z = 511.3 [M + H]$^+$. |

Example 77. (R)—N-(6-Cyclopropoxy-2-(2-fluoro-3-hydroxy-3-methylbutyl)-1-oxoisoindolin-5-yl)pyrazolo[1,5-a]pyrimidine-3-carboxamide

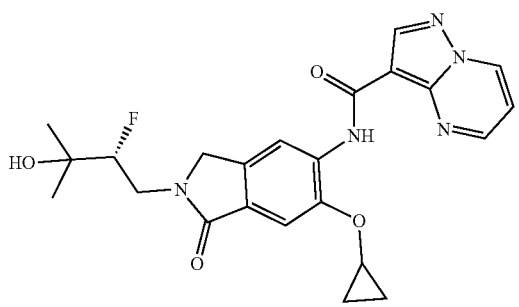 [SMILES: CC(C)(O)[C@H](F)CN1Cc2cc(NC(=O)c3cnn4cccnc34)c(OC3CC3)cc2C1=O]

Step A.
1-Bromo-5-cyclopropoxy-2-methyl-4-nitrobenzene

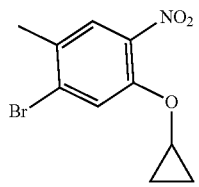

To a solution of cyclopropanol (1.3 mL, 26 mmol) and 1-bromo-5-fluoro-2-methyl-4-nitrobenzene (3.0 g, 13 mmol) in tetrahydrofuran (50 mL) was added sodium tert-butoxide (1.5 g, 15 mmol). The mixture was stirred at 60° C. for 16 h, after which it was filtered and concentrated. The crude product was purified by flash column chromatography (5% ethyl acetate in petroleum ether) to give 1-bromo-5-(cyclopropoxy)-2-methyl-4-nitro-benzene (3.2 g, 12 mmol, 92% yield) as a yellow solid.

Step B. Ethyl 5-cyclopropoxy-2-methyl-4-nitrobenzoate

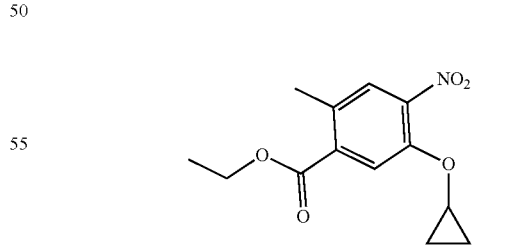

To a stirred solution of 1-bromo-5-(cyclopropoxy)-2-methyl-4-nitro-benzene (1.0 g, 3.68 mmol) in ethanol (20 mL) was added triethylamine (10 mL, 72.1 mmol) and bis(triphenylphosphine)palladium(II)dichloride (258 mg, 0.370 mmol). The mixture was stirred at 80° C. for 16 h under CO (50 psi). The reaction mixture was concentrated, and the residue was purified by column chromatography (silica gel: 100-200 mesh, eluting gradient: 0-5% ethyl acetate in petroleum ether) to give ethyl 5-(cyclopropoxy)-2-methyl-4-nitro-benzoate (400 mg, 1.51 mmol, 41% yield) as a yellow solid.

Step C. Ethyl 2-(bromomethyl)-5-cyclopropoxy-4-nitrobenzoate

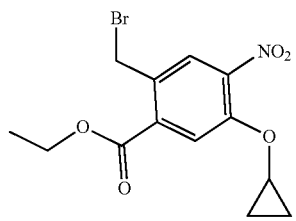 [SMILES: CCOC(=O)c1cc(OC2CC2)c([N+](=O)[O-])cc1CBr]

A mixture of ethyl 5-(cyclopropoxy)-2-methyl-4-nitro-benzoate (300 mg, 1.13 mmol), 1-bromo-2,5-pyrrolidinedione (242 mg, 1.36 mmol) and benzoyl peroxide (27.4 mg, 0.110 mmol) in carbon tetrachloride (15 mL) was stirred at 95° C. for 20 h under nitrogen. The reaction mixture was concentrated, and the residue was purified by column chromatography (silica gel: 100-200 mesh, eluting gradient: 2-5% ethyl acetate in petroleum ether) to give ethyl 2-(bromomethyl)-5-(cyclopropoxy)-4-nitro-benzoate (230 mg, 0.67 mmol, 59.1% yield) as light yellow solid.

Step D. (R)-6-Cyclopropoxy-2-(2-fluoro-3-hydroxy-3-methylbutyl)-5-nitroisoindolin-1-one

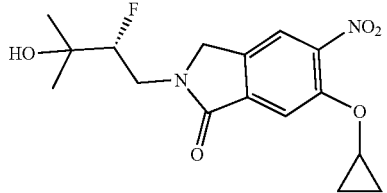 [SMILES: CC(C)(O)[C@H](F)CN1Cc2cc([N+](=O)[O-])c(OC3CC3)cc2C1=O]

The title compound was made in a manner analogous to Example 60 (Step D) to give (R)-6-cyclopropoxy-2-(2-fluoro-3-hydroxy-3-methylbutyl)-5-nitroisoindolin-1-one (120 mg, 0.355 mmol, 42.1% yield) as light yellow oil.

Step E. (R)-5-Amino-6-cyclopropoxy-2-(2-fluoro-3-hydroxy-3-methylbutyl)isoindolin-1-one

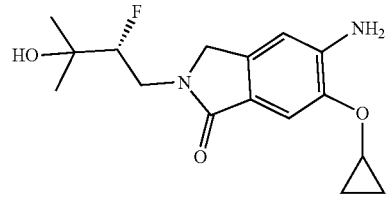 [SMILES: CC(C)(O)[C@H](F)CN1Cc2cc(N)c(OC3CC3)cc2C1=O]

The title compound was made in a manner analogous to Example 60 (Step F) to afford (R)-5-amino-6-cyclopropoxy-2-(2-fluoro-3-hydroxy-3-methylbutyl)isoindolin-1-one.

Step F. (R)—N-(6-Cyclopropoxy-2-(2-fluoro-3-hydroxy-3-methylbutyl)-1-oxoisoindolin-5-yl)pyrazolo[1,5-a]pyrimidine-3-carboxamide

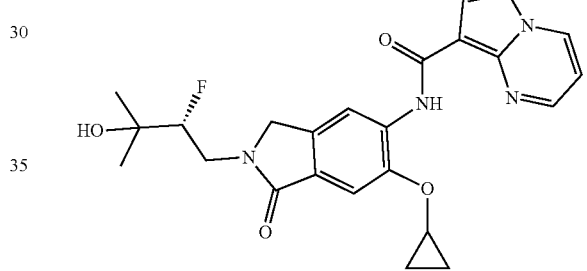

The title compound was made in a manner analogous to Example 60 (Step G) to afford (R)—N-(6-cyclopropoxy-2-(2-fluoro-3-hydroxy-3-methylbutyl)-1-oxoisoindolin-5-yl)pyrazolo[1,5-a]pyrimidine-3-carboxamide.

TABLE 9

The following examples were made in a manner similar to that for Example 77:

| Ex. | Name | Structure | NMR, MS |
|---|---|---|---|
| 78 | N-[2-[(2R)-2-Fluoro-3-hydroxy-3-methyl-butyl]-6-isopropoxy-1-oxo-isoindolin-5-yl]pyrazolo[1,5-a]pyrimidine-3-carboxamide | 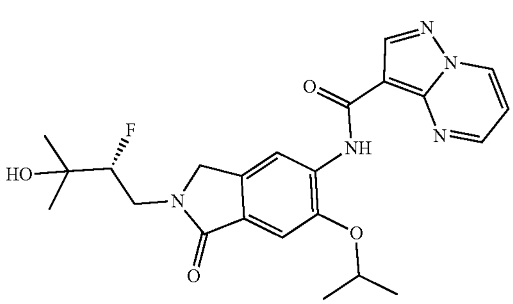 [SMILES: CC(C)Oc1cc2c(cc1NC(=O)c1cnn3cccnc13)CN(C[C@@H](F)C(C)(C)O)C2=O] | $^1$H NMR (400 MHz, CDCl$_3$) δ 10.70 (s, 1H), 8.85-8.82 (m, 2H), 8.77 (s, 1H), 8.72-8.71 (m, 1H), 7.36 (s, 1H), 7.08 (dd, J = 6.8, 4.4 Hz, 1H), 4.80-4.77 (m, 1H), 4.60-4.41 (m, 3H), 4.21-4.13 (m, 1H), 3.69-3.63 (m, 1H), 2.71 (br s, 1H), 1.51 (d, J = 6.4 Hz, 6H), 1.34 (s, 3H), 1.32 (s, 3H). LCMS (ESI): m/z = 456.2 [M + H]$^+$. |

TABLE 9-continued

The following examples were made in a manner similar to that for Example 77:

| Ex. | Name | Structure | NMR, MS |
|---|---|---|---|
| 79 | (R)-N-(2-(2-Fluoro-3-hydroxy-3-methylbutyl)-6-(oxetan-3-ylmethoxy)-1-oxoisoindolin-5-yl)pyrazolo[1,5-a]pyrimidine-3-carboxamide | 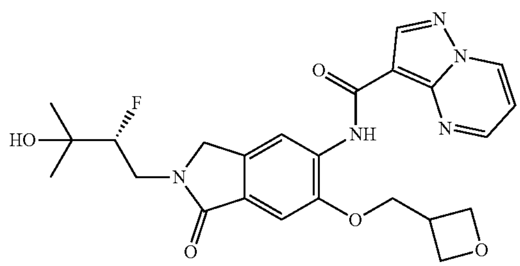 [SMILES: CC(C)(O)[C@H](F)CN1Cc2cc(NC(=O)c3cnn4cccnc34)c(OCC3COC3)cc2C1=O] | $^1$H NMR (400 MHz, CDCl$_3$) δ 10.45 (s, 1H), 8.88-8.80 (m, 4H), 7.40 (s, 1H), 7.11-7.08 (m, 1H), 4.92-4.86 (m, 4H), 4.63-4.44 (m, 3H), 4.39 (d, J = 6.0 Hz, 2H), 4.25-4.13 (m, 1H), 3.75-3.65 (m, 2H), 2.42 (s, 1H), 1.35 (s, 3H), 1.33 (s, 3H). LCMS (ESI): m/z = 484.2 [M + H]$^+$. |
| 80 | (R)-N-(6-(Cyclopentyloxy)-2-(2-fluoro-3-hydroxy-3-methylbutyl)-1-oxoisoindolin-5-yl)pyrazolo[1,5-a]pyrimidine-3-carboxamide | 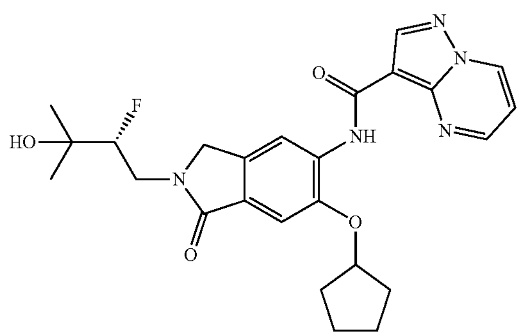 [SMILES: CC(C)(O)[C@H](F)CN1Cc2cc(NC(=O)c3cnn4cccnc34)c(OC3CCCC3)cc2C1=O] | $^1$H NMR (400 MHz, CDCl$_3$) δ 10.62 (s, 1H), 8.86-8.84 (m, 2H), 8.80 (s, 1H), 8.71-8.70 (m, 1H), 7.34 (s, 1H), 7.09 (dd, J = 6.8, 4.4 Hz, 1H), 5.04-5.00 (m, 1H), 4.61-4.43 (m, 3H), 4.24-4.11 (m, 1H), 3.76-3.66 (m, 1H), 2.45 (s, 1H), 2.13-2.03 (m, 4H), 1.95-1.90 (m, 2H), 1.79-1.71 (m, 2H), 1.35 (s, 3H), 1.32 (s, 3H). LCMS (ESI): m/z = 482.1 [M + H]$^+$. |
| 81 | (R)-N-(2-(2-Fluoro-3-hydroxy-3-methylbutyl)-6-isopropoxy-1-oxoisoindolin-5-yl)-6-methylpyrazolo[1,5-a]pyrimidine-3-carboxamide | 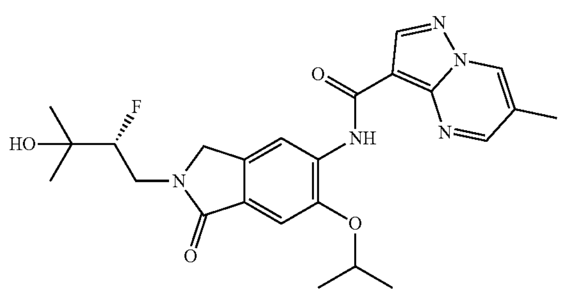 [SMILES: Cc1cnc2c(C(=O)Nc3cc4c(cc3OC(C)C)C(=O)N(C[C@@H](F)C(C)(C)O)C4)cnn2c1] | $^1$H NMR (400 MHz, CDCl$_3$) 10.68 (s, 1H), 8.84 (s, 1H), 8.71 (s, 1H), 8.64 (s, 1H), 8.59 (d, J = 2.0 Hz, 1H), 7.38 (s, 1H), 4.83-4.77 (m, 1H), 4.63-4.41 (m, 3H), 4.25-4.10 (m, 1H), 3.75-3.65 (m, 1H), 2.51 (s, 3H), 2.48 (s, 1H), 1.52 (d, J = 4.8 Hz, 6H), 1.34 (s, 3H), 1.32 (s, 3H). LCMS (ESI): m/z = 470.2 [M + H]$^+$. |
| 82 | (R)-N-(6-Ethoxy-2-(2-fluoro-3-hydroxy-3-methylbutyl)-1-oxoisoindolin-5-yl)pyrazolo[1,5-a]pyrimidine-3-carboxamide | 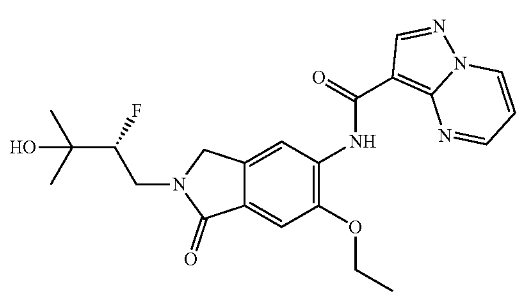 [SMILES: CCOc1cc2c(cc1NC(=O)c1cnn3cccnc13)CN(C[C@@H](F)C(C)(C)O)C2=O] | $^1$H NMR (400 MHz, DMSO-d$_6$) δ 10.79 (s, 1H), 9.39 (d, J = 6.8 Hz, 1H), 8.86 (d, J = 4.0 Hz, 1H), 8.73 (s, 1H), 8.71 (s, 1H), 7.35 (dd, J = 6.8, 4.0 Hz, 1H), 7.28 (s, 1H), 4.93 (s, 1H), 4.51-4.37 (m, 3H), 4.25 (q, J = 6.8 Hz, 2H), 3.97-3.87 (m, 1H), 3.70-3.68 (m, 1H), 1.58 (t, J = 6.8 Hz, 3H), 1.18 (s, 6H). LCMS (ESI): m/z = 442.0 [M + H]$^+$. |

TABLE 9-continued

The following examples were made in a manner similar to that for Example 77:

| Ex. | Name | Structure | NMR, MS |
|---|---|---|---|
| 83 & 84 | N-(2-((R)-2-Fluoro-3-hydroxy-3-methylbutyl)-1-oxo-6-(((R)-tetrahydrofuran-3-yl)oxy)isoindolin-5-yl)pyrazolo[1,5-a]pyrimidine-3-carboxamide and N-(2-((R)-2-Fluoro-3-hydroxy-3-methylbutyl)-1-oxo-6-(((S)-tetrahydrofuran-3-yl)oxy)isoindolin-5-yl)pyrazolo[1,5-a]pyrimidine-3-carboxamide (absolute stereochemistry assigned arbitrarily) | | Example 83, Peak 1: $^1$H NMR (400 MHz, DMSO-$d_6$) δ 10.75 (s, 1H), 9.40 (dd, J = 6.8, 1.6 Hz, 1H), 8.85-8.84 (m, 1H), 8.73 (s, 2H), 7.36 (dd, J = 7.2, 4.0 Hz, 1H), 7.29 (s, 1H), 5.40-5.35 (m, 1H), 4.92 (s, 1H), 4.51-4.39 (m, 3H), 4.06-3.87 (m, 5H), 3.70-3.68 (m, 1H), 2.33-2.30 (m, 1H), 2.19-2.18 (m, 1H), 1.18, 1.17 (s, 3H each). LCMS (ESI): m/z = 484.2 [M + H]$^+$. Example 84, Peak 2: $^1$H NMR (400 MHz, DMSO-$d_6$) δ 10.74 (s, 1H), 9.39 (d, J = 6.8 Hz, 1H), 8.84 (d, J = 4.0 Hz, 1H), 8.73 (s, 2H), 7.36 (dd, J = 6.8, 4.4 Hz, 1H), 7.29 (s, 1H), 5.40-5.35 (m, 1H), 4.93 (s, 1H), 4.51-4.38 (m, 3H), 4.06-3.86 (m, 5H), 3.71-3.61 (m, 1H), 2.33-2.18 (m, 2H), 1.18 (s, 6H). LCMS (ESI): m/z = 484.1 [M + H]$^+$. |
| 85 | (R)-N-(2-(2-Fluoro-3-hydroxy-3-methylbutyl)-1-oxo-6-((tetrahydro-2H-pyran-4-yl)oxy)isoindolin-5-yl)pyrazolo[1,5-a]pyrimidine-3-carboxamide | 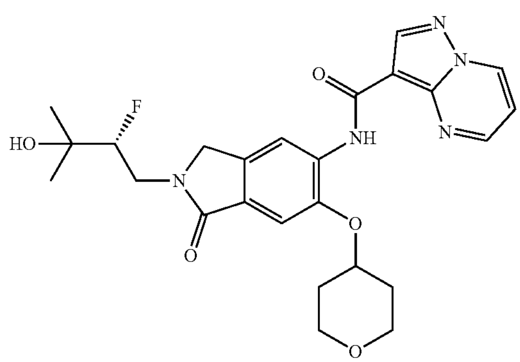 [SMILES: CC(C)(O)[C@H](F)CN1Cc2cc(NC(=O)c3cnn4cccnc34)c(OC3CCOCC3)cc2C1=O] | $^1$H NMR (400 MHz, CDCl$_3$) δ 10.59 (s, 1H), 8.88-8.86 (m, 2H), 8.81 (s, 1H), 8.76-8.75 (m, 1H), 7.41 (s, 1H), 7.11 (dd, J = 6.8, 4.4 Hz, 1H), 4.78-4.77 (m, 1H), 4.63-4.44 (m, 4H), 4.17-1.14 (m, 2H), 3.71-3.65 (m, 3H), 2.44 (br s, 1H), 2.22-2.19 (m, 2H), 2.01-1.96 (m, 2H), 1.34 (s, 3H), 1.33 (s, 3H). LCMS (ESI): m/z = 498.2 [M + H]$^+$. |
| 86 | (R)-N-(2-(2-Fluoro-3-hydroxy-3-methylbutyl)-6-methoxy-1-oxoisoindolin-5-yl)pyrazolo[1,5-a]pyrimidine-3-carboxamide | 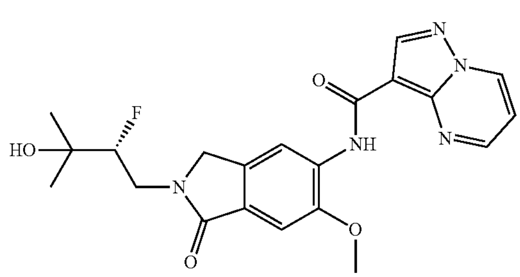 [SMILES: COc1cc2c(cc1NC(=O)c1cnn3cccnc13)CN(C[C@@H](F)C(C)(C)O)C2=O] | $^1$H NMR (400 MHz, CDCl$_3$) δ 10.67 (s, 1H), 9.36 (d, J = 6.8 Hz, 1H), 8.96- 8.92 (m, 1H), 8.71 (s, 1H), 8.66 (s, 1H), 7.35 (dd, J = 6.8, 4.4 Hz, 1H), 7.29 (s, 1H), 4.93 (s, 1H), 4.52-4.37 (m, 3H), 4.05 (s, 3H), 4.02-3.87 (m, 1H), 3.71-3.68 (m, 1H), 1.18 (s, 3H), 1.17 (s, 3H). LCMS (ESI): m/z = 428.1 [M + H]$^+$. |

TABLE 9-continued

The following examples were made in a manner similar to that for Example 77:

| Ex. | Name | Structure | NMR, MS |
|-----|------|-----------|---------|
| 87 | (R)-N-(2-(2-Fluoro-3-hydroxy-3-methylbutyl)-6-(oxetan-3-yloxy)-1-oxoisoindolin-5-yl)pyrazolo[1,5-a]pyrimidine-3-carboxamide | 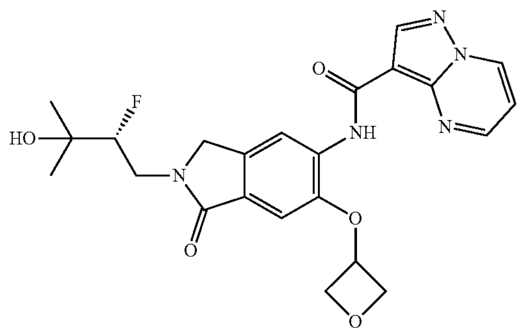 [SMILES: CC(C)(O)[C@H](F)CN1Cc2cc(NC(=O)c3cnn4cccnc34)c(OC3COC3)cc2C1=O] | $^1$H NMR (400 MHz, CDCl$_3$) δ 10.72 (s, 1H), 8.88-8.86 (m, 2H), 8.80 (s, 1H), 8.77-8.76 (m, 1H), 7.11 (dd, J = 6.8, 4.4 Hz, 1H), 6.95 (s, 1H), 5.43-5.41 (m, 1H), 5.18-5.15 (m, 2H), 4.96-4.92 (m, 2H), 4.62-4.43 (m, 3H), 4.20-4.12 (m, 1H), 3.69-3.68 (m, 1H), 2.43 (s, 1H), 1.34 (s, 3H), 1.32 (s, 3H). LCMS (ESI): m/z = 470.1 [M + H]$^+$. |
| 88 | (R)-N-(6-(Difluoromethoxy)-2-(2-fluoro-3-hydroxy-3-methylbutyl)-1-oxoisoindolin-5-yl)pyrazolo[1,5-a]pyrimidine-3-carboxamide | 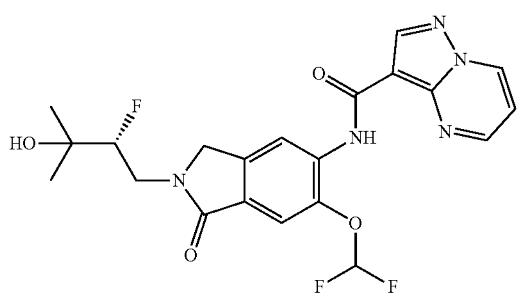 [SMILES: CC(C)(O)[C@H](F)CN1Cc2cc(NC(=O)c3cnn4cccnc34)c(OC(F)F)cc2C1=O] | $^1$H NMR (400 MHz, CDCl$_3$) δ 10.83 (s, 1H), 8.92 (s, 1H), 8.86 (dd, J = 6.8, 1.6 Hz, 1H), 8.78-8.77 (m, 2H), 7.65 (s, 1H), 7.12 (dd, J = 6.8, 4.4 Hz, 1H), 6.69 (t, J = 73.6 Hz, 1H), 4.68-4.47 (m, 3H), 4.23-4.15 (m, 1H), 3.74-3.67 (m, 1H), 2.29 (s, 1H), 1.35 (s, 3H), 1.33 (s, 3H). LCMS (ESI): m/z = 464.1 [M + H]$^+$. |
| 89 | (R)-N-(2-(2-Fluoro-3-hydroxy-3-methylbutyl)-6-((1-methyl-1H-pyrazol-4-yl)oxy)-1-oxoisoindolin-5-yl)pyrazolo[1,5-a]pyrimidine-3-carboxamide | 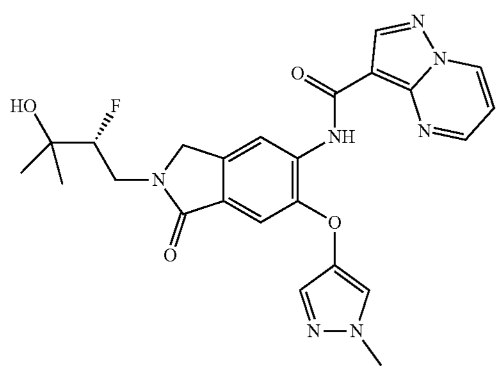 [SMILES: Cn1cc(Oc2cc3c(cc2NC(=O)c2cnn4cccnc24)CN(C[C@@H](F)C(C)(C)O)C3=O)cn1] | $^1$H NMR (400 MHz, DMSO-d$_6$) δ 10.81 (s, 1H), 9.40-9.38 (m, 1H), 8.82 (dd, J = 4.4, 1.6 Hz, 1H), 8.77, 8.76 (s, 1H each), 7.89 (s, 1H), 7.54 (s, 1H), 7.31 (dd, J = 6.8, 4.4 Hz, 1H), 7.21 (s, 1H), 4.92 (s, 1H), 4.60-4.36 (m, 3H), 3.99-3.95 (m, 1H), 3.85 (s, 3H), 3.70-3.63 (m, 1H), 1.17 (s, 6H). LCMS (ESI): m/z = 494.0 [M + H]$^+$. |
| 90 | (R)-N-(6-(tert-Butoxy)-2-(2-fluoro-3-hydroxy-3-methylbutyl)-1-oxoisoindolin-5-yl)pyrazolo[1,5-a]pyrimidine-3-carboxamide | 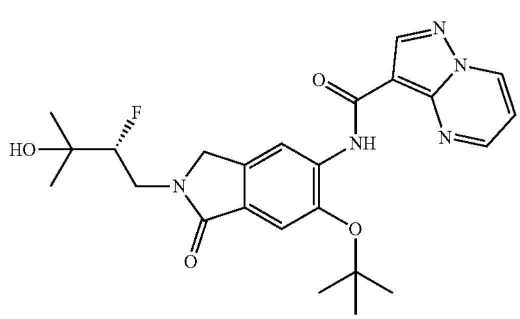 [SMILES: CC(C)(C)Oc1cc2c(cc1NC(=O)c1cnn3cccnc13)CN(C[C@@H](F)C(C)(C)O)C2=O] | $^1$H NMR (400 MHz, CDCl$_3$) δ 10.54 (s, 1H), 8.88-8.85 (m, 2H), 8.80 (s, 1H), 8.73 (d, J = 4.0 Hz, 1H), 7.57 (s, 1H), 7.10 (dd, J = 6.8, 4.4 Hz, 1H), 4.63-4.44 (m, 3H), 4.25-4.13 (m, 1H), 3.70-3.67 (m, 1H), 2.48 (s, 1H), 1.57 (s, 9H), 1.35, 1.33 (s, 3H each). LCMS (ESI): m/z = 470.2 [M + H]$^+$. |

TABLE 10

The following examples were made in a manner similar to Intermediate H:

| Ex. | Name | Structure | NMR, MS |
|---|---|---|---|
| 91 | N-[2-[(2R)-2-Fluoro-3-hydroxy-3-methyl-butyl]-6-(methylamino)-1-oxo-isoindolin-5-yl]pyrazolo[1,5-a]pyrimidine-3-carboxamide | | ¹H NMR (400 MHz, CDCl₃) δ 9.62 (s, 1H), 8.88 (d, J = 7.2 Hz, 1H), 8.79-8.76 (m, 2H), 7.93 (s, 1H), 7.25 (s, 1H), 7.12-7.10 (m, 1H), 4.60-4.42 (m, 3H), 4.25-4.13 (m, 2H), 3.76-3.65 (m, 1H), 2.99 (s, 3H), 2.52 (s, 1H), 1.34 (s, 3H), 1.32 (s, 3H). LCMS (ESI): m/z = 427.2 [M + H]⁺. |
| 92 | N-[6-Morpholino-1-oxo-2-(tetrahydropyran-4-ylmethyl)isoindolin-5-yl]pyrazolo[1,5-a]pyrimidine-3-carboxamide | | ¹H NMR (400 MHz, CDCl₃) δ 10.92 (s, 1 H), 8.87-8.81 (m, 4H), 7.73 (s, 1H), 7.12 (dd, J = 6.8, 4.4 Hz, 1H), 4.40 (s, 2H), 4.02-3.97 (m, 6H), 3.50 (d, J = 7.6 Hz, 2H), 3.40-3.35 (m, 2 H), 2.99 (t, J = 4.4 Hz, 4H), 2.04-2.01 (m, 1H), 1.49-1.41 (m, 4H). LCMS (ESI): m/z = 477.2 [M + H]⁺. |
| 93 | N-[6-Morpholino-1-oxo-2-(2-pyrrolidin-1-ylethyl)isoindolin-5-yl]pyrazolo[1,5-a]pyrimidine-3-carboxamide | | ¹H NMR (400 MHz, CDCl₃) δ 10.90 (s, 1H), 8.87-8.82 (m, 4H), 7.68 (s, 1H), 7.12 (dd, J = 6.8, 4.4 Hz, 1H), 4.56 (s, 2H), 4.12-4.08 (m, 2H), 4.00-3.99 (m, 4H), 3.45-3.30 (m, 2H), 2.99-2.97 (m, 4H), 2.12-2.11 (m, 4H), 1.30-1.20 (m, 4H). LCMS (ESI): m/z = 476.2 [M + H]⁺. |
| 94 | N-[6-Morpholino-2-(2-oxaspiro[3.3]heptan-6-yl)-1-oxo-isoindolin-5-yl]pyrazolo[1,5-a]pyrimidine-3-carboxamide | | ¹H NMR (400 MHz, CDCl₃) δ 10.94 (s, 1H), 8.88-8.82 (m, 4H), 7.71 (s, 1H), 7.14 (dd, J = 6.8, 4.4 Hz, 1H), 4.83 (s, 2H), 4.76-4.71 (m, 3H), 4.38 (s, 2H), 4.01 (t, J = 4.4 Hz, 4H), 2.99 (t, J = 4.4 Hz, 4H), 2.70-2.65 (m, 2H), 2.50-2.47 (m, 2H). LCMS (ESI): m/z = 475.0 [M + H]⁺. |
| 95 | N-[6-(Dimethylamino)-2-isopropyl-1-oxo-isoindolin-5-yl]pyrazolo[1,5-a]pyrimidine-3-carboxamide | | ¹H NMR (400 MHz, CDCl₃) δ 11.03 (s, 1H), 8.86-8.75 (m, 4H), 7.70 (s, 1H), 7.08 (dd, J = 6.8, 4.4 Hz, 1H), 4.69-4.64 (m, 1H), 4.33 (s, 2H), 2.80 (s, 6H), 1.31 (m, 6H). LCMS (ESI): m/z = 379.1 [M + H]⁺. |

TABLE 10-continued

The following examples were made in a manner similar to Intermediate H:

| Ex. | Name | Structure | NMR, MS |
|---|---|---|---|
| 96 | (R)-N-(6-(4-(2,2-Difluoroethyl)piperidin-1-yl)-2-(2-fluoro-3-hydroxy-3-methylbutyl)-1-oxoisoindolin-5-yl)pyrazolo[1,5-a]pyrimidine-3-carboxamide | 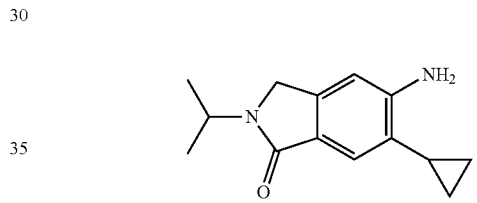 | $^1$H NMR (400 MHz, CDCl$_3$) δ 10.78 (s, 1H), 8.80-8.79 (m, 1H), 8.75 (s, 2H), 8.65-8.63 (m, 1H) 7.63 (s, 1H), 7.05 (dd, J = 6.8, 4.4 Hz, 1H), 5.89 (tt, J = 56.4, 4.4 Hz, 1H), 4.56-4.37 (m, 3H), 4.17-4.04 (m, 1H), 3.67-3.57 (m, 1H), 3.05-3.02 (m, 2H), 2.76-2.71 (m, 2H), 2.33 (s, 1H), 1.88-1.64 (m, 7H), 1.27, 1.25 (s, 3H each). LCMS (ESI): m/z = 545.2 [M + H]$^+$. |

Example 97. N-(6-Cyclopropyl-2-isopropyl-1-oxoisoindolin-5-yl)pyrazolo[1,5-a]pyrimidine-3-carboxamide

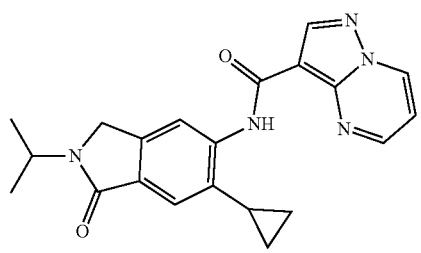 [SMILES: CC(C)N1Cc2cc(NC(=O)c3cnn4cccnc34)c(C3CC3)cc2C1=O]

Step A.
6-Chloro-2-isopropyl-5-nitroisoindolin-1-one

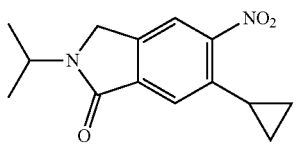

The title compound was made in a manner analogous to Intermediate H (Step A) to afford 6-chloro-2-isopropyl-5-nitro-isoindolin-1-one (1.16 g, 74%) as a yellow solid.

Step B.
6-Cyclopropyl-2-isopropyl-5-nitroisoindolin-1-one

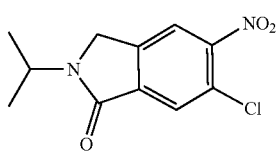 [SMILES: CC(C)N1Cc2cc([N+](=O)[O-])c(Cl)cc2C1=O]

A mixture of 6-chloro-2-isopropyl-5-nitro-isoindolin-1-one (500 mg, 1.96 mmol), cyclopropylboronic acid (506 mg, 5.89 mmol), triphenylphosphine (30.9 mg, 0.12 mmol), potassium phosphate tribasic (1.25 g, 5.89 mmol), and palladium(II) acetate (4.41 mg, 0.02 mmol) in toluene (15 mL) and water (5 mL) was stirred at 120° C. under microwave conditions under nitrogen for 30 min and filtered. The filtrate was concentrated and purified by preparatory TLC (eluting with 10% methanol in dichloromethane) to give 6-cyclopropyl-2-isopropyl-5-nitro-isoindolin-1-one (280 mg, 55%) as a yellow oil.

Step C.
5-Amino-6-cyclopropyl-2-isopropylisoindolin-1-one

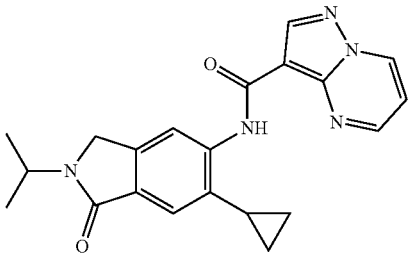

The title compound was made in a manner analogous to Example 60 (Step F) to afford 5-amino-6-cyclopropyl-2-isopropyl-isoindolin-1-one (80 mg, 90%) as a yellow solid.

Step D. N-(6-Cyclopropyl-2-isopropyl-1-oxoisoindolin-5-yl)pyrazolo[1,5-a]pyrimidine-3-carboxamide The title compound was made in a manner analogous to Example 60 (Step G) to afford N-(6-cyclopropyl-2-isopropyl-1-oxo-isoindolin-5-yl)pyrazolo[1,5-a]pyrimidine-3-carboxamide (50 mg, 35%) as a white solid. $^1$H NMR (400 MHz, CDCl$_3$) δ 10.48 (s, 1H), 8.88-8.86 (m, 1H), 8.83 (s, 1H), 8.74 (s, 1H), 8.71-8.69 (m, 1H), 7.68 (s, 1H), 7.09 (dd, J=6.8, 4.4 Hz, 1H), 4.71-4.64 (m, 1H), 4.35 (s, 2H), 2.09-2.02 (m, 1H), 1.30 (d, J=6.8 Hz, 6H), 1.20-1.17 (m, 2H), 0.84-0.82 (m, 2H). LCMS (ESI): m/z=376.4 [M+H]$^+$.

Example 98. (R)—N-(6-Cyano-2-(2-fluoro-3-hydroxy-3-methylbutyl)-1-oxoisoindolin-5-yl)pyrazolo[1,5-a]pyrimidine-3-carboxamide

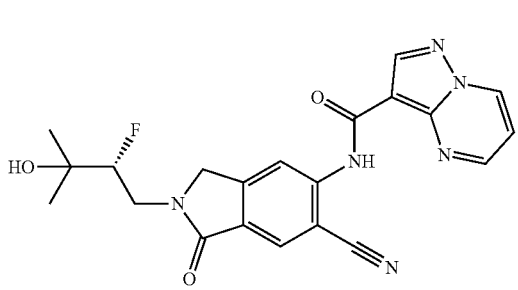 [SMILES: CC(C)(O)[C@H](F)CN1Cc2cc(NC(=O)c3cnn4cccnc34)c(C#N)cc2C1=O]

Step A. Methyl 4-amino-5-chloro-2-methylbenzoate

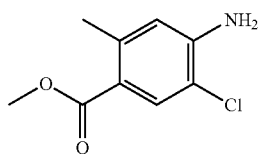

The title compound was made in a manner analogous to Example 60 (Step F) to afford methyl 4-amino-5-chloro-2-methylbenzoate (1.8 g, 98%) as a yellow solid. MS (ESI): m/z=200 [M+H]$^+$.

Step B. Methyl 5-chloro-2-methyl-4-(pyrazolo[1,5-a]pyrimidine-3-carboxamido)benzoate

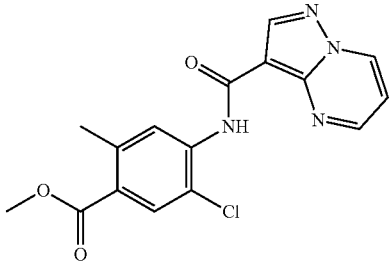 [SMILES: COC(=O)c1cc(Cl)c(NC(=O)c2cnn3cccnc23)cc1C]

The title compound was made in a manner analogous to Example 60 (Step G) to afford methyl 5-chloro-2-methyl-4-(pyrazolo[1,5-a]pyrimidine-3-carboxamido)benzoate (1.7 g, 98%) as a brown solid. MS (ESI): m/z=345 [M+H]$^+$.

Step C. Methyl 5-cyano-2-methyl-4-(pyrazolo[1,5-a]pyrimidine-3-carboxamido)benzoate

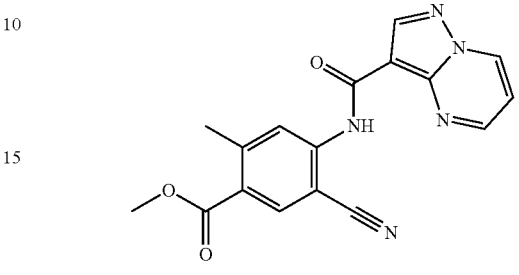

To a solution of methyl 5-chloro-2-methyl-4-(pyrazolo[1,5-a]pyrimidine-3-carboxamido)benzoate (500 mg, 1.45 mmol), potassium acetate (427 mg, 4.35 mmol), 2-di-tert-butylphosphino-2',4',6'-triisopropylbiphenyl (62 mg, 0.15 mmol) in 1,4-dioxane (6 mL) and water (6 mL) were added [2-(2-aminophenyl)phenyl]-methylsulfonyloxy-palladium; di-tert-butyl-[2-[2,4-diisopropyl-6-(1-methylethyl)phenyl]phenyl]phosphane (115 mg, 0.15 mmol) and potassium hexacyanoferrate (II) trihydrate (306 mg, 0.73 mmol). The reaction mixture was stirred under nitrogen at 130° C. under microwave conditions for 2 h and concentrated. The residue was purified by silica gel chromatography (eluting gradient: 0-10% methanol in dichloromethane) to afford methyl 5-cyano-2-methyl-4-(pyrazolo[1,5-a]pyrimidine-3-carboxamido)benzoate (400 mg, 82%) as a yellow solid. MS (ESI): m/z=336 [M+H]$^+$.

Step D. Methyl 2-(bromomethyl)-5-cyano-4-(pyrazolo[1,5-a]pyrimidine-3-carboxamido)benzoate

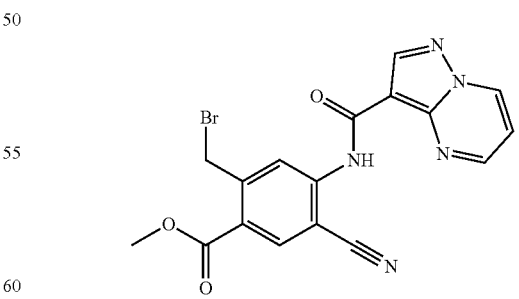

The title compound was made in a manner analogous to Example 60 (Step C) to afford methyl 2-(bromomethyl)-5-cyano-4-(pyrazolo[1,5-a]pyrimidine-3-carboxamido)benzoate (400 mg, 15%) as a yellow solid. MS (ESI): m/z=415 [M+H]$^+$.

307

Step E. (R)—N-(6-cyano-2-(2-fluoro-3-hydroxy-3-methylbutyl)-1-oxoisoindolin-5-yl)pyrazolo[1,5-a]pyrimidine-3-carboxamide

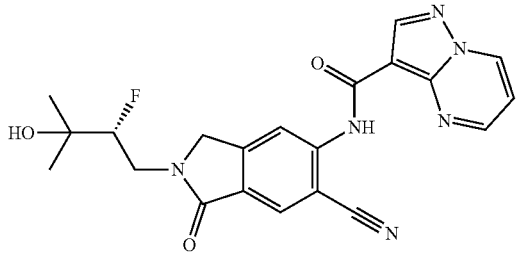 [SMILES: CC(C)(O)[C@H](F)CN1Cc2cc(NC(=O)c3cnn4cccnc34)c(C#N)cc2C1=O]

The title compound was made in a manner analogous to Intermediate H, Step A to afford (R)—N-(6-cyano-2-(2-fluoro-3-hydroxy-3-methylbutyl)-1-oxoisoindolin-5-yl)pyrazolo[1,5-a]pyrimidine-3-carboxamide (7 mg, 43%) as a white solid. $^1$H NMR (400 MHz, DMSO-$d_6$) δ 10.83 (s, 1H), 9.43 (d, J=6.8 Hz, 1H), 8.89-8.85 (m, 1H), 8.79 (s, 1H), 8.74 (s, 1H), 8.16 (s, 1H), 7.38 (dd, J=6.8, 4.8 Hz, 1H), 4.96 (s, 1H), 4.77-4.61 (m, 2H), 4.53-4.39 (m, 1H), 4.02-3.88 (m, 1H), 3.76-3.69 (m, 1H), 1.18 (s, 3H), 1.17 (s, 3H). LCMS (ESI): m/z=445.0 [M+Na]$^+$.

Example 99. (R)—N-(2-(2-Fluoro-3-hydroxy-3-methylbutyl)-6-(4-morpholinopiperidin-1-yl)-1-oxoisoindolin-5-yl)pyrazolo[1,5-a]pyrimidine-3-carboxamide

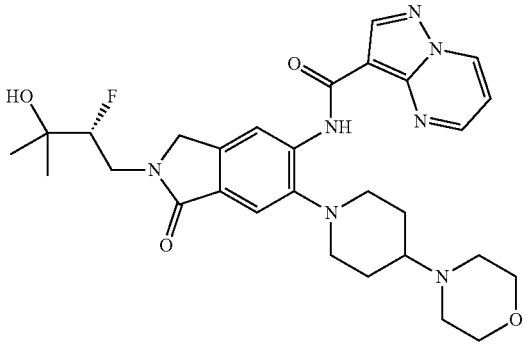 [SMILES: CC(C)(O)[C@H](F)CN1Cc2cc(NC(=O)c3cnn4cccnc34)c(N3CCC(N4CCOCC4)CC3)cc2C1=O]

Step A. Ethyl 5-fluoro-2-methyl-4-nitro-benzoate

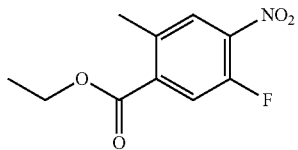 [SMILES: CCOC(=O)c1cc(F)c([N+](=O)[O-])cc1C]

308

To a solution of 1-bromo-5-fluoro-2-methyl-4-nitrobenzene (5.0 g, 21.4 mmol) and triethylamine (50 mL, 361 mmol) in ethanol (100 mL) was added bis(triphenylphosphine) palladium(II) dichloride (1.5 g, 2.14 mmol). The reaction was stirred at 70° C. for 16 h under carbon monoxide (50 psi). The reaction was filtered through celite and the filtrate was concentrated to dryness. The residue was purified by flash column chromatography (eluent 10% ethyl acetate:petroleum ether) to give ethyl 5-fluoro-2-methyl-4-nitro-benzoate (2.0 g, 41% yield) as a yellow solid. $^1$H NMR (400 MHz, CDCl$_3$) δ 7.92 (d, J=7.2 Hz, 1H), 7.82 (d, J=11.6 Hz, 1H), 4.42 (q, J=7.2 Hz, 2H), 2.63 (s, 3H), 1.42 (t, J=7.2 Hz, 3H).

Step B. Ethyl 2-(bromomethyl)-5-fluoro-4-nitro-benzoate

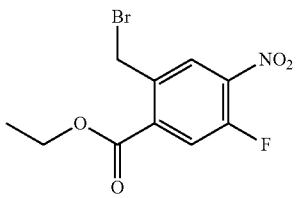 [SMILES: CCOC(=O)c1cc(F)c([N+](=O)[O-])cc1CBr]

To a solution of ethyl 5-fluoro-2-methyl-4-nitro-benzoate (200 mg, 0.88 mmol) in carbon tetrachloride (5 mL) was added benzoyl peroxide (43 mg, 0.18 mmol) and N-bromosuccinimide (313 mg, 1.76 mmol). The mixture was stirred at 100° C. for 16 h under nitrogen. The reaction was concentrated to dryness and the crude reaction was purified by flash column chromatography (eluent 20% ethyl acetate: petroleum ether) to afford ethyl 2-(bromomethyl)-5-fluoro-4-nitro-benzoate (110 mg, 41% yield) as a yellow oil. $^1$HNMR (400 MHz, CDCl$_3$) δ 8.18 (d, J=6.4 Hz, 1H), 7.90 (d, J=10.8 Hz, 1H), 4.92 (s, 2H), 4.50 (q, J=7.2 Hz, 2H), 1.49 (t, J=7.2 Hz, 3H).

Step C. (R)-6-Fluoro-2-(2-fluoro-3-hydroxy-3-methylbutyl)-5-nitroisoindolin-1-one

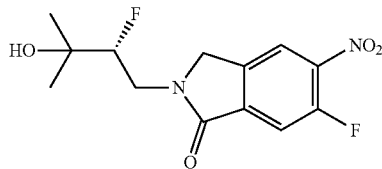 [SMILES: CC(C)(O)[C@H](F)CN1Cc2cc([N+](=O)[O-])c(F)cc2C1=O]

To a solution of triethylamine (0.43 mL, 3.14 mmol) in methanol (8 mL) was added ethyl 2-(bromomethyl)-5-fluoro-4-nitro-benzoate (480 mg, 1.57 mmol) and (3R)-4-amino-3-fluoro-2-methyl-butan-2-ol (WO2014/074675, 209 mg, 1.72 mmol). The mixture was stirred at 60° C. for 4 h. The mixture was concentrated and purified by flash column chromatography (eluting gradient: 50% ethyl acetate in petroleum ether) to afford 6-fluoro-2-[(2R)-2-fluoro-3-hydroxy-3-methyl-butyl]-5-nitro-isoindolin-1-one (300 mg, 1.0 mmol, 63.7% yield) as a yellow solid.

Step D. 2-[(2R)-2-Fluoro-3-hydroxy-3-methyl-butyl]-6-(4-morpholino-1-piperidyl)-5-nitro-isoindolin-1-one

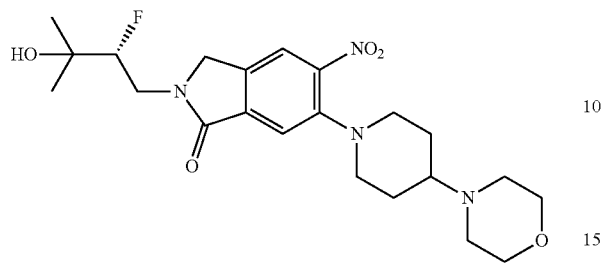

The title compound was made in a manner analogous to Intermediate H (Step B) to afford 2-[(2R)-2-fluoro-3-hydroxy-3-methyl-butyl]-6-(4-morpholino-1-piperidyl)-5-nitro-isoindolin-1-one (80 mg, 0.18 mmol, 89% yield) as a yellow solid.

Step E. 5-amino-2-[(2R)-2-Fluoro-3-hydroxy-3-methyl-butyl]-6-(4-morpholino-1-piperidyl)isoindolin-1-one

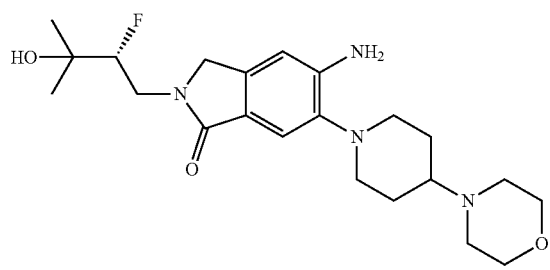 [SMILES: CC(C)(O)[C@H](F)CN1Cc2cc([N+](=O)[O-])c(N3CCC(N4CCOCC4)CC3)cc2C1=O]

The title compound was made in a manner analogous to Example 60 (Step F) to afford 5-amino-2-[(2R)-2-fluoro-3-hydroxy-3-methyl-butyl]-6-(4-morpholino-1-piperidyl) isoindolin-1-one (60 mg, 0.14 mol, 80% yield) as a white solid.

Step F. (R)—N-(2-(2-Fluoro-3-hydroxy-3-methyl-butyl)-6-(4-morpholinopiperidin-1-yl)-1-oxoisoindolin-5-yl)pyrazolo[1,5-a]pyrimidine-3-carboxamide

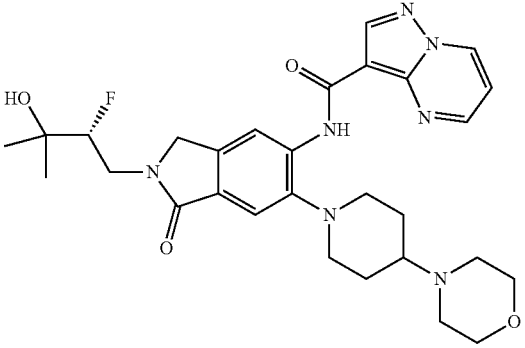 [SMILES: CC(C)(O)[C@H](F)CN1Cc2cc(NC(=O)c3cnn4cccnc34)c(N3CCC(N4CCOCC4)CC3)cc2C1=O]

The title compound was made in a manner analogous to Example 60 (Step G) to afford N-[2-[(2R)-2-fluoro-3-hydroxy-3-methyl-butyl]-6-(4-morpholino-1-piperidyl)-1-oxo-isoindolin-5-yl]pyrazolo[1,5-a]pyrimidine-3-carboxamide (55 mg, 0.097 mmol, 74% yield) as a white solid. $^1$HNMR (400 MHz, CDCl$_3$) δ 10.91 (s, 1H), 9.42-9.40 (m, 1H), 8.96 (s, 1H), 8.75 (s, 1H), 8.73 (s, 1H), 7.56 (s, 1H), 7.46-7.43 (m, 1H), 4.91 (s, 1H), 4.59-4.37 (m, 3H), 4.01-3.87 (m, 1H), 3.75-3.65 (m, 5H), 3.33-3.30 (m, 4H), 3.05-3.02 (m, 2H), 2.82-2.76 (m, 2H), 2.33 (m, 1H), 1.92-1.83 (m, 4H), 1.19-1.18 (m, 6H).

TABLE 11

The following examples were made in a manner similar to that for Example 99:

| Ex. | Name | Structure | NMR, MS |
|---|---|---|---|
| 100 | N-(2-((R)-2-Fluoro-3-hydroxy-3-methylbutyl)-6-((R)-hexahydropyrrolo[1,2-a]pyrazin-2(1H)-yl)-1-oxoisoindolin-5-yl)pyrazolo[1,5-a]pyrimidine-3-carboxamide | 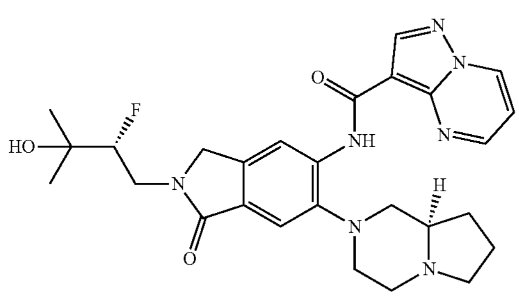 [SMILES: CC(C)(O)[C@H](F)CN1Cc2cc(NC(=O)c3cnn4cccnc34)c(N3CCN4CCC[C@@H]4C3)cc2C1=O] | $^1$H NMR (400 MHz, DMSO-d$_6$) δ 10.85 (s, 1H), 9.40-9.35 (m, 1H), 8.90-8.85 (m, 1H), 8.74, 8.72 (s, 1H each), 7.54 (s, 1H), 7.36 (dd, J = 6.8, 4.0 Hz, 1H), 4.89 (s, 1H), 4.56-4.34 (m, 3H), 3.97-3.83 (m, 1H), 3.70-3.66 (m, 1H), 3.04-2.83 (m, 5H), 2.73-2.63 (m, 3H), 2.31-2.20 (m, 1H), 1.78-1.65 (m, 3H), 1.40-1.32 (m, 1H), 1.15 (s, 3H), 1.14 (s, 3H). MS (ESI): m/z = 522.3 [M + 1]$^+$. |

TABLE 11-continued

The following examples were made in a manner similar to that for Example 99:

| Ex. | Name | Structure | NMR, MS |
|---|---|---|---|
| 101 | N-(2-((R)-2-Fluoro-3-hydroxy-3-methylbutyl)-6-((7R,8aS)-7-methoxyhexahydropyrrolo[1,2-a]pyrazin-2(1H)-yl)-1-oxoisoindolin-5-yl)pyrazolo[1,5-a]pyrimidine-3-carboxamide | 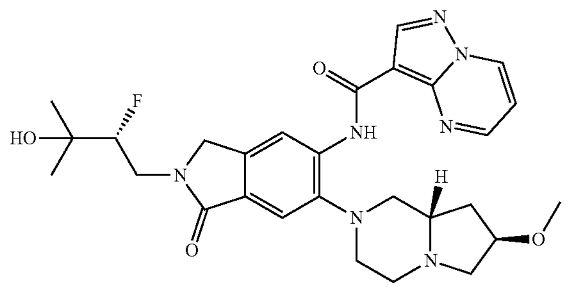 [SMILES: CO[C@@H]1C[C@H]2CN(c3cc4c(cc3NC(=O)c3cnn5cccnc35)CN(C[C@@H](F)C(C)(C)O)C4=O)CCN2C1] | $^1$H NMR (400 MHz, DMSO-d$_6$) δ 10.87 (s, 1H), 9.42 (d, J = 7.2 Hz, 1H), 8.88-8.86 (m, 1H), 8.79 (s, 1H), 8.76 (s, 1H), 7.57 (s, 1H), 7.44 (dd, J = 7.2, 4.4 Hz, 1H), 4.93 (s, 1H), 4.60-4.43 (m, 3H), 3.97-3.84 (m, 2H), 3.69-3.59 (m, 1H), 3.50-3.46 (m, 1H), 3.22 (s, 3H), 3.07-2.62 (m, 7H), 2.24-2.22 (m, 1H), 1.72-1.59 (m, 2H), 1.18 (s, 6H). MS (ESI): m/z = 552.2 [M + 1]$^+$. |
| 102 | (R)-5-Chloro-N-(2-(2-fluoro-3-hydroxy-3-methylbutyl)-6-morpholino-1-oxoisoindolin-5-yl)pyrazolo[1,5-a]pyrimidine-3-carboxamide | 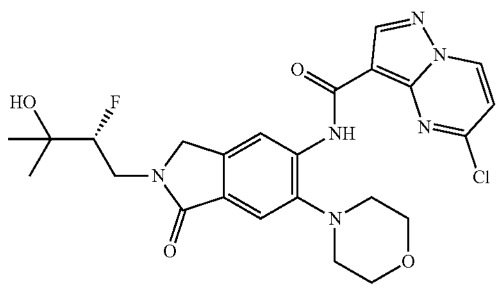 [SMILES: CC(C)(O)[C@H](F)CN1Cc2cc(NC(=O)c3cnn4ccc(Cl)nc34)c(N3CCOCC3)cc2C1=O] | $^1$H NMR (400 MHz, DMSO-d$_6$) δ 10.08 (s, 1H), 9.43 (d, J = 7.2 Hz, 1H), 8.78 (s, 1H), 8.65 (s, 1H), 7.54 (s, 1H), 7.49 (d, J = 7.2 Hz, 1H), 4.90 (s, 1H), 4.62-4.34 (m, 3H), 4.04-3.85 (m, 5H), 3.70 (td, J = 15.7, 9.4 Hz, 1H), 2.97-2.84 (m, 3H), 1.18 (dd, J = 4.4, 1.8 Hz, 6H). MS (ESI): m/z = 517.1 [M + H]$^+$. |
| 103 | (R)-N-(6-(4-((5-Ethylisoxazol-4-yl)methyl)piperazin-1-yl)-2-(2-fluoro-3-hydroxy-3-methylbutyl)-1-oxoisoindolin-5-yl)pyrazolo[1,5-a]pyrimidine-3-carboxamide | 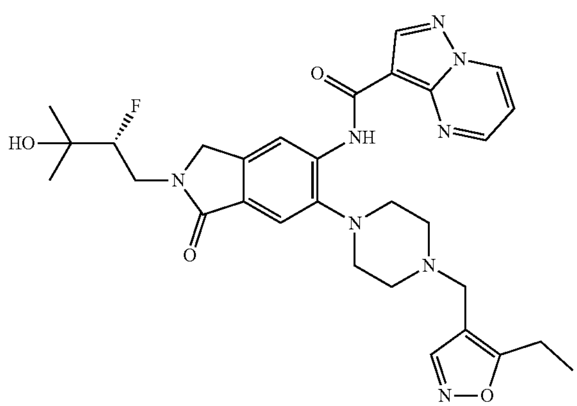 [SMILES: CCc1oncc1CN1CCN(c2cc3c(cc2NC(=O)c2cnn4cccnc24)CN(C[C@@H](F)C(C)(C)O)C3=O)CC1] | $^1$H NMR (400 MHz, CD$_3$OD) δ 9.15 (d, J = 6.8 Hz, 1H), 8.73 (s, 1H), 8.70 (s, 1H), 8.53-8.52 (m, 1H), 8.38 (s, 1H), 7.72 (s, 1H), 7.30 (dd, J = 7.2, 4.4 Hz, 1H), 4.62-4.45 (m, 3H), 4.15-4.01 (m, 1H), 3.78-3.75 (m, 1H), 3.64 (s, 2H), 3.03 (t, J = 4.4 Hz, 4H), 2.85-2.80 (m, 6H), 1.31 (s, 6H), 1.25 (t, J = 8.0 Hz, 3H). LCMS (ESI): m/z = 591.1 [M + H]$^+$. |
| 104 | (R)-N-(6-(4-((3-Ethylisoxazol-4-yl)methyl)piperazin-1-yl)-2-(2-fluoro-3-hydroxy-3-methylbutyl)-1-oxoisoindolin-5-yl)pyrazolo[1,5-a]pyrimidine-3-carboxamide | 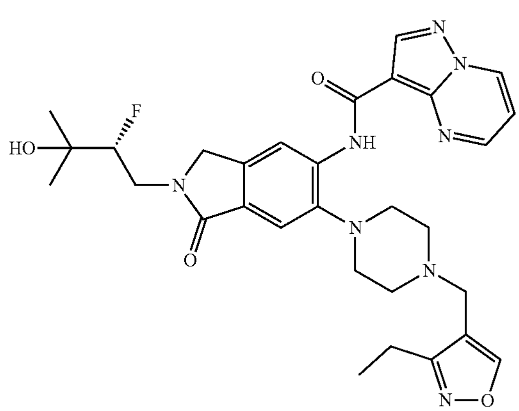 [SMILES: CCc1nocc1CN1CCN(c2cc3c(cc2NC(=O)c2cnn4cccnc24)CN(C[C@@H](F)C(C)(C)O)C3=O)CC1] | $^1$H NMR (400 MHz, CD$_3$OD) δ 9.14 (d, J = 7.2 Hz, 1H), 8.90-8.86 (m, 1H), 8.69 (s, 1H), 8.65 (s, 2H), 7.69 (s, 1H), 7.32-7.28 (m, 1H), 4.62-4.40 (m, 3H), 4.22 (br s, 2H), 4.16-4.12 (m, 1H), 3.77-3.73 (m, 1H), 3.32 (br s, 4H), 3.24 (br s, 4H), 2.83 (q, J = 7.6 Hz, 2H), 1.35 (t, J = 7.2 Hz, 2H), 1.30 (s, 6H). LCMS (ESI): m/z = 591.2 [M + H]$^+$. |

TABLE 11-continued

*The following examples were made in a manner similar to that for Example 99:*

| Ex. | Name | Structure | NMR, MS |
|---|---|---|---|
| 105 | (R)-N-(2-(2-Fluoro-3-hydroxy-3-methylbutyl)-6-(4-(oxetan-3-yl)piperazin-1-yl)-1-oxoisoindolin-5-yl)pyrazolo[1,5-a]pyrimidine-3-carboxamide | 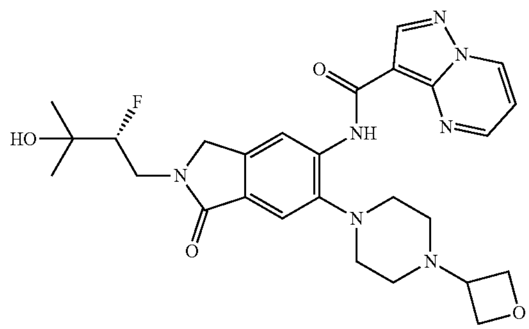 | $^1$H NMR (400 MHz, CD$_3$OD) δ 9.17-9.16 (m, 1H), 8.98-8.94 (m, 1H), 8.78 (s, 1H), 8.72 (s, 1H), 7.76 (s, 1H), 7.33 (dd, J = 7.2, 4.4 Hz, 1H), 4.77-4.74 (m, 2H) 4.68-4.45 (m, 5H), 4.17-4.0 7 (m, 1H), 3.78-3.69 (m, 2H), 3.06 (t, J = 4.4 Hz, 4H), 2.70 (br s, 4H), 1.30 (s, 6H). LCMS (ESI): m/z = 538.1 [M + H]$^+$. |
| 106 | (R)-N-(6-(4-(2-(1H-Imidazol-1-yl)ethyl)piperazin-1-yl)-2-(2-fluoro-3-hydroxy-3-methylbutyl)-1-oxoisoindolin-5-yl)pyrazolo[1,5-a]pyrimidine-3-carboxamide | 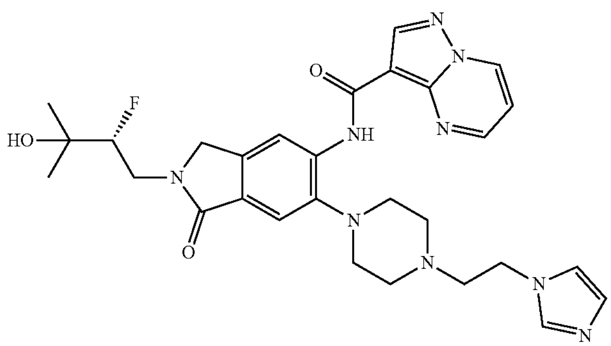 [SMILES: CC(C)(O)[C@H](F)CN1Cc2cc(NC(=O)c3cnn4cccnc34)c(N3CCN(CCn4ccnc4)CC3)cc2C1=O] | $^1$H NMR (400 MHz, CDCl$_3$) δ 10.83 (s, 1H), 8.88-8.86 (m, 1H), 8.83 (s, 1H), 8.82 (s, 1H), 8.76-8.74 (m, 1H), 7.74 (s, 1H), 7.58 (s, 1H), 7.14-7.10 (m, 2H), 7.04 (s, 1H), 4.64-4.45 (m, 3H), 4.26-4.22 (m, 1H), 4.12 (t, J = 6.8 Hz, 2H), 3.74-3.64 (m, 1H), 3.04-3.02 (m, 4H), 2.83-2.80 (m, 6H), 1.35 (s, 3H), 1.33 (s, 3H). LCMS (ESI): m/z = 576.1 [M + H]$^+$. |
| 107 | N-(2-((R)-2-Fluoro-3-hydroxy-3-methylbutyl)-6-((7R,8aR)-7-methoxyhexahydropyrrolo[1,2-a]pyrazin-2(1H)-yl)-1-oxoisoindolin-5-yl)pyrazolo[1,5-a]pyrimidine-3-carboxamide | 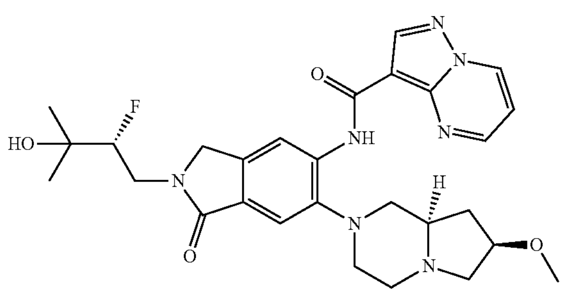 [SMILES: CO[C@@H]1C[C@@H]2CN(c3cc4c(cc3NC(=O)c3cnn5cccnc35)CN(C[C@@H](F)C(C)(C)O)C4=O)CCN2C1] | $^1$H NMR (400 MHz, DMSO-d$_6$) δ 10.87 (s, 1H), 9.41-9.39 (m, 1H), 8.92-8.88 (m, 1H), 8.77 (s, 1H), 8.75 (s, 1H), 7.58 (s, 1H), 7.37 (dd, J = 6.8, 4.4 Hz, 1H), 4.93 (s, 1H), 4.55-4.39 (m, 3H), 3.96-3.55 (m, 3H), 3.19 (s, 3H), 3.11-2.67 (m, 7H), 2.34-2.32 (m, 1H), 2.21-2.17 (m, 1H), 1.35-1.33 (m, 1H), 1.23-1.22 (m, 1H), 1.18 (s, 3H), 1.17 (s, 3H). LCMS (ESI): m/z = 552.1 [M + H]$^+$. |
| 108 | N-(2-((R)-2-Fluoro-3-hydroxy-3-methylbutyl)-6-((7S,8aR)-7-methoxyhexahydropyrrolo[1,2-a]pyrazin-2(1H)-yl)-1-oxoisoindolin-5-yl)pyrazolo[1,5-a]pyrimidine-3-carboxamide | 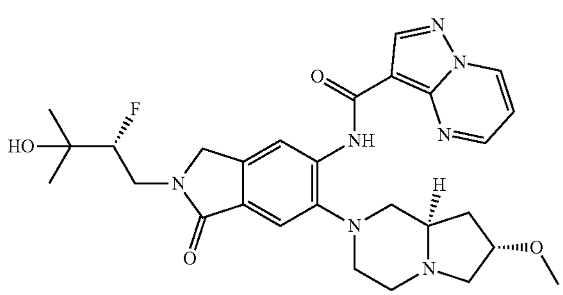 [SMILES: CO[C@H]1C[C@@H]2CN(c3cc4c(cc3NC(=O)c3cnn5cccnc35)CN(C[C@@H](F)C(C)(C)O)C4=O)CCN2C1] | $^1$H NMR (400 MHz, DMSO-d$_6$) δ 10.85 (s, 1H), 9.43-9.39 (m, 1H), 8.86-8.85 (m, 1H), 8.75 (s, 1H), 8.74 (s, 1H), 7.56 (s, 1H), 7.43 (dd, J = 6.8, 4.4 Hz, 1H), 4.92 (s, 1H), 4.54-4.48 (m, 3H), 3.95-3.86 (m, 2H), 3.75-3.65 (m, 1H), 3.49-3.46 (m, 1H), 3.21 (s, 3H), 3.06-3.03 (m, 1H), 2.99-2.86 (m, 4H), 2.63-2.50 (m, 2H), 2.22-2.19 (m, 1H), 1.72-1.70 (m, 1H), 1.58-1.58-1.56 (m, 1H), 1.18 (s, 3H), 1.17 (s, 3H). LCMS (ESI): m/z = 552.1 [M + H]$^+$. |

TABLE 11-continued

The following examples were made in a manner similar to that for Example 99:

| Ex. | Name | Structure | NMR, MS |
|---|---|---|---|
| 109 | (R)-N-(2-(2-Fluoro-3-hydroxy-3-methylbutyl)-1-oxo-6-(4-(2,2,2-trifluoroethyl)piperazin-1-yl)isoindolin-5-yl)pyrazolo[1,5-a]pyrimidine-3-carboxamide | 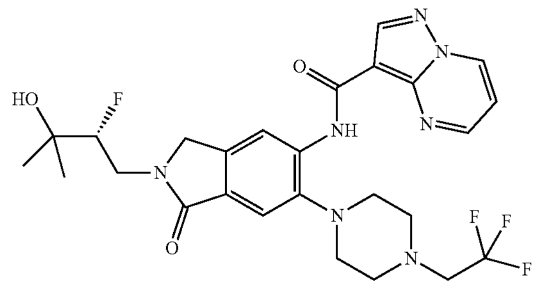 [SMILES: CC(C)(O)[C@H](F)CN1Cc2cc(NC(=O)c3cnn4cccnc34)c(N3CCN(CC(F)(F)F)CC3)cc2C1=O] | $^1$H NMR (400 MHz, DMSO-d$_6$) δ 10.83 (s, 1H), 9.42-9.40 (m, 1H), 9.00-8.99 (m, 1H), 8.75 (s, 2H), 7.57 (s, 1H), 7.39 (dd, J = 6.8, 4.4 Hz, 1H), 4.92 (s, 1H), 4.59-4.37 (m, 3H), 4.00-3.87 (m, 1H), 3.75-3.68 (m, 1H), 3.41-3.38 (m, 2H), 2.93 (br s, 8H), 1.18 (s, 3H), 1.17 (s, 3H). LCMS (ESI): m/z = 564.4 [M + H]$^+$. |
| 110 & 111 | N-[6-[(7S,8aR)-7-Methyl-3,4,6,7,8,8a-hexahydro-1H-pyrrolo[1,2-a]pyrazin-2-yl]-2-[(2R)-2-fluoro-3-hydroxy-3-methyl-butyl]-1-oxo-isoindolin-5-yl]pyrazolo[1,5-a]pyrimidine-3-carboxamide and N-[6-[(7R,8aR)-7-Methyl-3,4,6,7,8,8a-hexahydro-1H-pyrrolo[1,2-a]pyrazin-2-yl]-2-[(2R)-2-fluoro-3-hydroxy-3-methyl-butyl]-1-oxo-isoindolin-5-yl]pyrazolo[1,5-a]pyrimidine-3-carboxamide (absolute stereochemistry assigned arbitrarily) | | Example 110, Peak 1: $^1$H NMR (400 MHz, DMSO-d$_6$) δ 10.87 (s, 1H), 9.40-9.39 (m, 1H), 8.92-8.86 (m, 1H), 8.76-8.74 (m, 2H), 7.57 (s, 1H), 7.41-7.35 (m, 1H), 4.93 (s, 1H), 4.59-4.37 (m, 3H), 3.99-3.68 (m, 3H), 3.06-2.90 (m, 4H), 2.75-2.65 (m, 3H), 2.26-2.20 (m, 1H), 2.02-1.96 (m, 1H), 1.24-1.12 (m, 7H), 1.06 (d, J = 6.0 Hz, 3H), 1.00-0.94 (m, 1H). LCMS (ESI): m/z = 536.1 [M + H]$^+$.<br>Example 111, Peak 2: $^1$H NMR (400 MHz, DMSO-d$_6$) δ 10.84 (s, 1H), 9.41 (d, J = 7.2 Hz, 1H), 8.89-8.87 (m, 1H), 8.80-8.70 (m, 2H), 7.55 (s, 1H), 7.46-7.40 (m, 1H), 4.94 (s, 1H), 4.59- 4.37 (m, 3H), 3.99-3.69 (m, 3H), 3.02-2.82 (m, 4H), 2.70-2.64 (m, 1H), 2.33-2.26 (m, 2H), 1.91-1.85 (m, 1H), 1.69-1.63 (m, 1H), 1.23-1.17 (m, 8H), 1.05-0.98 (m, 3H). LCMS (ESI): m/z = 536.1 [M + H]$^+$. |
| 112 | (R)-N-(2-(2-Fluoro-3-hydroxy-3-methylbutyl)-6-(4-(2-methoxyethyl)piperazin-1-yl)-1-oxoisoindolin-5-yl)pyrazolo[1,5-a]pyrimidine-3-carboxamide | 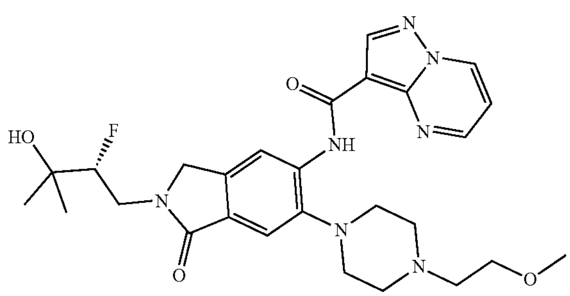 [SMILES: COCCN1CCN(c2cc3c(cc2NC(=O)c2cnn4cccnc24)CN(C[C@@H](F)C(C)(C)O)C3=O)CC1] | $^1$H NMR (400 MHz, DMSO-d$_6$) δ 10.85 (s, 1H), 9.41 (dd, J = 7.2, 1.6 Hz, 1H), 9.00-8.95 (m, 1H), 8.76 (s, 1H), 8.75 (s, 1H), 7.55 (s, 1H), 7.42 (dd, J = 7.2, 4.4 Hz, 1H), 4.93 (s, 1H), 4.59-4.38 (m, 3H), 3.98-3.87 (m, 1H), 3.75-3.65 (m, 1H), 3.55-3.45 (m, 2H), 3.27 (s, 3H), 2.91 (br s, 4H), 2.75 (br s, 4H), 2.67-2.65 (m, 2H), 1.19 (s, 3H), 1.18 (s, 3H). LCMS (ESI): m/z = 540.2 [M + H]$^+$. |
| 113 | (R)-N-(2-(2-Fluoro-3-hydroxy-3-methylbutyl)-6-(4-isopropylpiperazin-1-yl)-1-oxoisoindolin-5-yl)pyrazolo[1,5-a]pyrimidine-3-carboxamide | 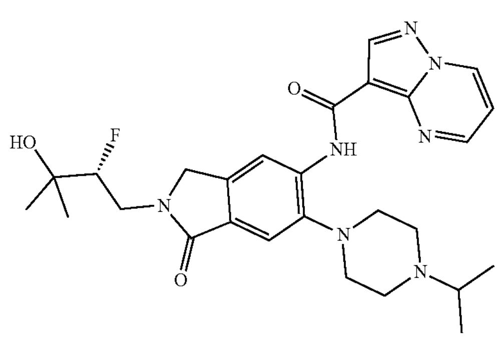 [SMILES: CC(C)N1CCN(c2cc3c(cc2NC(=O)c2cnn4cccnc24)CN(C[C@@H](F)C(C)(C)O)C3=O)CC1] | $^1$H NMR (400 MHz, DMSO-d$_6$) δ 10.73 (s, 1H), 9.41 (d, J = 6.8 Hz, 1H), 8.96-8.90 (m, 1H), 8.76 (s, 1H), 8.70 (s, 1H), 7.52 (s, 1H), 7.41 (dd, J = 7.2, 4.4 Hz, 1H), 4.93 (s, 1H), 4.54-4.37 (m, 3H), 4.00-3.87 (m, 1H), 3.75-3.64 (m, 1H), 3.32 (br s, 4H), 2.91-2.74 (m, 5H), 1.18 (s, 3H), 1.17 (s, 3H), 1.10-0.95 (m, 6H). LCMS (ESI): m/z = 524.3 [M + H]$^+$. |

TABLE 11-continued

The following examples were made in a manner similar to that for Example 99:

| Ex. | Name | Structure | NMR, MS |
|---|---|---|---|
| 114 | (R)-N-(2-(2-Fluoro-3-hydroxy-3-methylbutyl)-6-(4-(oxetan-3-ylmethyl)piperazin-1-yl)-1-oxoisoindolin-5-yl)pyrazolo[1,5-a]pyrimidine-3-carboxamide | 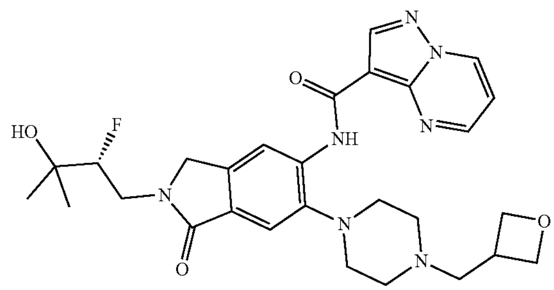 [SMILES: CC(C)(O)[C@H](F)CN1Cc2cc(NC(=O)c3cnn4cccnc34)c(N3CCN(CC4COC4)CC3)cc2C1=O] | $^1$H NMR (400 MHz, DMSO-$d_6$) δ 10.82 (s, 1H), 9.41 (dd, J = 6.8, 1.6 Hz, 1H), 8.99-8.98 (m, 1H), 8.75 (s, 1H), 8.74 (s, 1H), 7.53 (s, 1H), 7.42 (dd, J = 7.2, 4.4 Hz, 1H), 4.92 (s, 1H), 4.68-4.65 (m, 2H), 4.54-4.35 (m, 3H), 4.31 (t, J = 6.0 Hz, 2H), 3.98-3.86 (m, 1H), 3.70-3.68 (m, 1H), 3.25-3.23 (m, 1H), 2.88 (br s, 4H), 2.78 (d, J = 7.6 Hz, 2H), 2.67-2.64 (m, 4H), 1.18 (s, 3H), 1.17 (s, 3H). LCMS (ESI): m/z = 552.1 [M + H]$^+$. |
| 115 | (R)-N-(2-(2-Fluoro-3-hydroxy-3-methylbutyl)-6-(4-(3-methyloxetan-3-yl)piperazin-1-yl)-1-oxoisoindolin-5-yl)pyrazolo[1,5-a]pyrimidine-3-carboxamide | 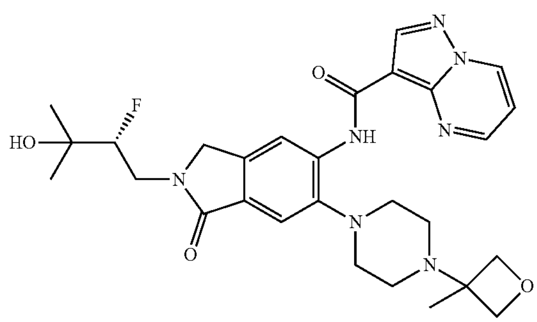 [SMILES: CC(C)(O)[C@H](F)CN1Cc2cc(NC(=O)c3cnn4cccnc34)c(N3CCN(C4(C)COC4)CC3)cc2C1=O] | $^1$H NMR (400 MHz, DMSO-$d_6$) δ 10.71 (s, 1H), 9.40 (d, J = 6.8 Hz, 1H), 8.90-8.85 (m, 1H), 8.74 (s, 1H), 8.67 (s, 1H), 7.52 (s, 1H), 7.41 (dd, J = 6.8, 4.4 Hz, 1H), 4.93 (s, 1H), 4.58-4.37 (m, 5H), 4.14 (d, J = 5.6 Hz, 2H), 4.00-3.87 (m, 1H), 3.74-3.64 (m, 1H), 2.92 (br s, 4H), 2.55 (br s, 4H), 1.38 (s, 3H), 1.18 (s, 3H), 1.17 (s, 3H). LCMS (ESI): m/z = 552.2 [M + H]$^+$. |
| 116 | (R)-6-Chloro-N-(2-(2-fluoro-3-hydroxy-3-methylbutyl)-6-(4-(oxetan-3-yl)piperazin-1-yl)-1-oxoisoindolin-5-yl)pyrazolo[1,5-a]pyrimidine-3-carboxamide | 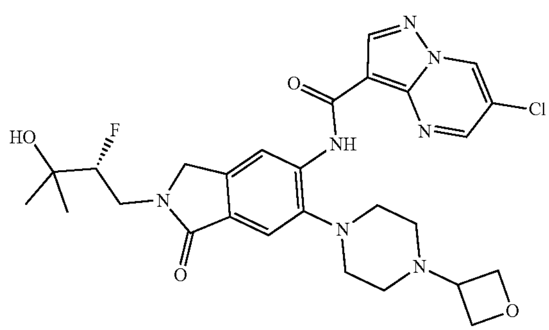 [SMILES: CC(C)(O)[C@H](F)CN1Cc2cc(NC(=O)c3cnn4cc(Cl)cnc34)c(N3CCN(C4COC4)CC3)cc2C1=O] | $^1$H NMR (400 MHz, DMSO-$d_6$) δ 10.62 (s, 1H), 9.87 (s, 1H), 8.96 (d, J = 2.4 Hz, 1H), 8.78 (s, 1H), 8.70 (s, 1H), 7.56 (s, 1H), 4.93 (s, 1H), 4.62-4.37 (m, 7H), 4.01-3.84 (m, 1H), 3.71-3.61 (m, 2H), 2.93 (br s, 4H), 2.59-2.53 (m, 4H), 1.18 (s, 3H), 1.17 (s, 3H). LCMS (ESI): m/z = 572.0 [M + H]$^+$. |
| 117 | ((R)-N-(2-(2-Fluoro-3-hydroxy-3-methylbutyl)-6-(4-(oxetan-3-yl)piperazin-1-yl)-1-oxoisoindolin-5-yl)-6-methylpyrazolo[1,5-a]pyrimidine-3-carboxamide | 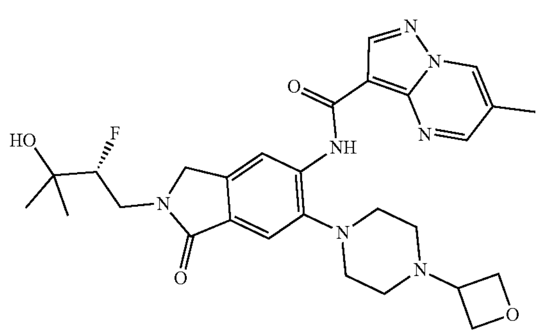 [SMILES: Cc1cnc2c(C(=O)Nc3cc4c(cc3N3CCN(C5COC5)CC3)C(=O)N(C[C@@H](F)C(C)(C)O)C4)cnn2c1] | $^1$H NMR (400 MHz, DMSO-$d_6$) δ 10.75 (s, 1H), 9.27 (s, 1H), 8.83 (s, 1H), 8.73 (s, 1H), 8.66 (s, 1H), 7.55 (s, 1H), 4.93 (s, 1H), 4.62-4.60 (m, 2H), 4.59-4.37 (m, 5H), 4.01-3.85 (m, 1H), 3.71-3.62 (m, 2H), 2.94-2.93 (m, 4H), 2.57 (br s, 4H), 2.47 (s, 3H), 1.18 (s, 3H), 1.17 (s, 3H). LCMS (ESI): m/z = 552.1 [M + H]$^+$. |

TABLE 11-continued

The following examples were made in a manner similar to that for Example 99:

| Ex. | Name | Structure | NMR, MS |
|---|---|---|---|
| 118 | (R)-N-(6-(4-(Azetidin-1-yl)piperidin-1-yl)-2-(2-fluoro-3-hydroxy-3-methylbutyl)-1-oxoisoindolin-5-yl)pyrazolo[1,5-a]pyrimidine-3-carboxamide | 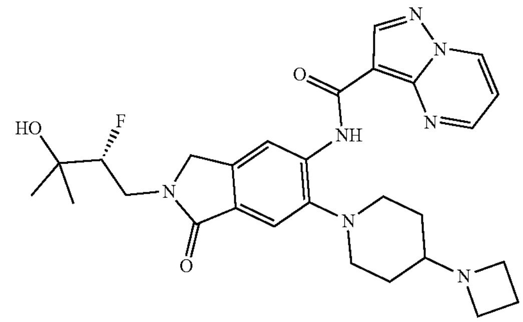 [SMILES: CC(C)(O)[C@H](F)CN1Cc2cc(NC(=O)c3cnn4cccnc34)c(N3CCC(N4CCC4)CC3)cc2C1=O] | $^1$H NMR (400 MHz, DMSO-d$_6$): δ 10.99 (s, 1H), 9.42-9.40 (m, 1H), 8.93-8.91 (m, 1H), 8.76 (s, 1H), 8.74 (s, 1H), 7.56 (s, 1H), 7.46 (dd, J = 6.8, 4.4 Hz, 1H), 4.90 (s, 1H), 4.58-4.37 (m, 3H), 4.00-3.87 (m, 1H), 3.70-3.68 (m, 1H), 3.13 (t, J = 6.8 Hz, 4H), 2.99-2.95 (m, 2H), 2.80-2.70 (m, 2H), 2.22-2.14 (m, 1H), 1.98 (quintet, J = 6.8 Hz, 2H), 1.84-1.74 (m, 2H), 1.67-1.52 (m, 2H), 1.18 (s, 3H), 1.17 (s, 3H). LCMS m/z = 536.2 [M + H]$^+$. |
| 119 | (R)-N-(2-(2-Fluoro-3-hydroxy-3-methylbutyl)-1-oxo-6-(2-oxa-7-azaspiro[3.5]nonan-7-yl)isoindolin-5-yl)pyrazolo[1,5-a]pyrimidine-3-carboxamide | 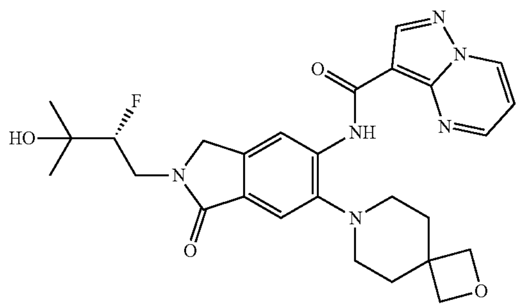 [SMILES: CC(C)(O)[C@H](F)CN1Cc2cc(NC(=O)c3cnn4cccnc34)c(N3CCC4(CC3)COC4)cc2C1=O] | $^1$H NMR (400MHz, DMSO-d$_6$) δ 10.95 (s, 1H), 9.40-9.38 (m, 1H), 8.78-8.75 (m, 3H), 7.57 (s, 1H), 7.37-7.34 (m, 1H), 4.91 (s, 1H), 4.53-4.37 (m, 7H), 4.00-3.87 (m, 1H), 3.74-3.63 (m, 1H), 2.80 (s, 4H), 2.08 (s, 4H), 1.18 (d, J = 4.4 Hz, 6H). MS (ESI): m/z = 523.2 [M + H]$^+$. |
| 120 | N-[2-[(2R)-2-Fluoro-3-hydroxy-3-methyl-butyl]-6-[4-(3-hydroxycyclobutyl)piperazin-1-yl]-1-oxo-isoindolin-5-yl]pyrazolo[1,5-a]pyrimidine-3-carboxamide | 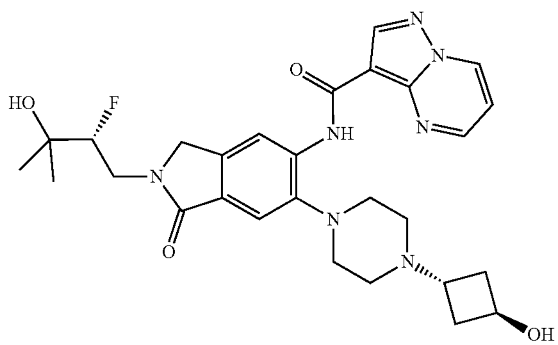 [SMILES: CC(C)(O)[C@H](F)CN1Cc2cc(NC(=O)c3cnn4cccnc34)c(N3CCN([C@H]4C[C@H](O)C4)CC3)cc2C1=O] | $^1$H NMR (400MHz, DMSO-d$_6$) δ 10.83 (s, 1H), 9.40 (d, J = 4.0 Hz, 1H), 9.15( d, J = 4.0 Hz, 1H), 8.74 (d, J = 4.0 Hz, 2H), 7.54 (s, 1H), 7.42-7.40 (m, 1H), 4.97 (d, J = 4.8 Hz, 1H), 4.92 (s, 1H), 4.58-4.37 (m, 3H), 4.20-4.19 (m, 1H), 4.00-3.87 (m, 1H), 3.74-3.64 (m, 1H), 2.99-2.95 (m, 1H), 2.90 (s, 4H), 2.64-2.52 (m, 4H), 2.16-2.11 (m, 2H), 1.94-1.91 (m, 2H), 1.18 (d, J = 4.4 Hz, 6H). MS (ESI): m/z = 552.1 [M + H]$^+$. |
| 121 | (R)-N-(2-(2-Fluoro-3-hydroxy-3-methylbutyl)-1-oxo-6-(2-oxa-8-azaspiro[4.5]decan-8-yl)isoindolin-5-yl)pyrazolo[1,5-a]pyrimidine-3-carboxamide | 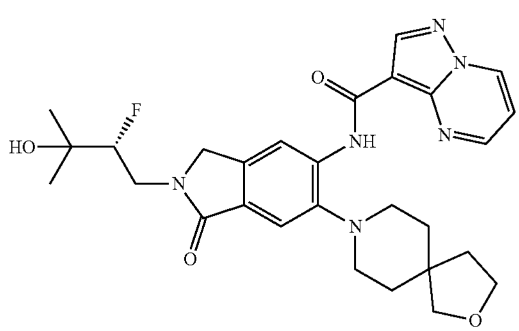 [SMILES: CC(C)(O)[C@H](F)CN1Cc2cc(NC(=O)c3cnn4cccnc34)c(N3CCC4(CCOC4)CC3)cc2C1=O] | $^1$H NMR (400MHz, DMSO-d$_6$) δ 10.96 (s, 1H), 9.42-9.40 (m, 1H), 8.88-8.86 (m, 1H), 8.75 (s, 2H), 7.64 (s, 1H), 7.40-7.37 (m, 1H), 4.92 (s, 1H), 4.54-4.32 (m, 3H), 4.00-3.87 (m, 1H), 3.79 (t, 2H), 3.76-3.67 (m, 1H), 3.62 (s, 2H), 2.89-2.86 (m, 4H), 1.88-1.82 (m, 6H), 1.18 (d, J = 3.6 Hz, 6H). MS (ESI): m/z = 537.3 [M + 1]$^+$. |

TABLE 11-continued

The following examples were made in a manner similar to that for Example 99:

| Ex. | Name | Structure | NMR, MS |
|---|---|---|---|
| 122 | N-[2-[(2R)-2-Fluoro-3-hydroxy-3-methyl-butyl]-6-[4-(3-hydroxycyclobutyl)piperazin-1-yl]-1-oxo-isoindolin-5-yl]pyrazolo[1,5-a]pyrimidine-3-carboxamide | 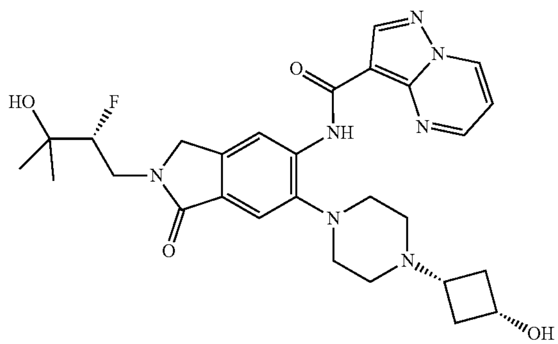 [SMILES: CC(C)(O)[C@H](F)CN1Cc2cc(NC(=O)c3cnn4cccnc34)c(N3CCN([C@H]4C[C@@H](O)C4)CC3)cc2C1=O] | $^1$H NMR (400MHz, DMSO-d$_6$) δ 10.82 (s, 1H), 9.41-9.39 (m, 1H), 8.92 (s, 1H), 8.74 (s, 2H), 7.54 (s, 1H), 7.42-7.39 (m, 1H), 5.01 (s, 1H), 4.91 (s, 1H), 4.58-4.37 (m, 3H), 4.00-3.89 (m, 1H), 3.84-3.75 (m, 1H), 3.72-3.65 (m, 1H), 2.91 (s, 4H), 2.64-2.52 (m, 5H), 2.40 (s, 2H), 1.68 (s, 2H), 1.18 (d, J = 3.6 Hz, 6H). MS (ESI): m/z = 552.1 [M + H]$^+$. |
| 123 | (R)-N-(2-(2-Fluoro-3-hydroxy-3-methylbutyl)-6-(4-(oxetan-3-yl)piperidin-1-yl)-1-oxoisoindolin-5-yl)pyrazolo[1,5-a]pyrimidine-3-carboxamide | 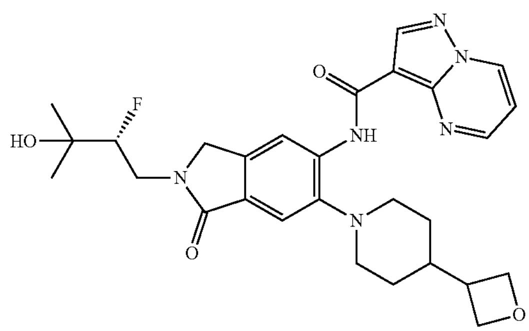 | $^1$H NMR (400 MHz, DMSO-d$_6$): δ 10.86 (s, 1H), 9.41-9.39 (m, 1H), 8.90-8.88 (m, 1H), 8.73 (d, J = 4.0 Hz, 2H), 7.56 (s, 1H), 7.40-7.38 (m, 1H), 4.93 (s, 1H), 4.69-4.65 (m, 2H), 4.58-4.38 (m, 5H), 4.00-3.87 (m, 1H), 3.74-3.64 (m, 1H), 3.00-2.97 (m, 2H), 2.93-2.87 (m, 1H), 2.79-2.74 (m, 2H), 1.88-1.83 (m, 1H), 1.73-1.70 (m, 2H), 1.47-1.42 (m, 2H), 1.18-1.17 (m, 6H). LCMS (ESI): m/z = 537.2 [M + H]$^+$. |
| 124 | N-[6-[4-[(1-Fluorocyclobutyl)methyl]piperazin-1-yl]-2-[(2R)-2-fluoro-3-hydroxy-3-methyl-butyl]-1-oxo-isoindolin-5-yl]pyrazolo[1,5-a]pyrimidine-3-carboxamide | 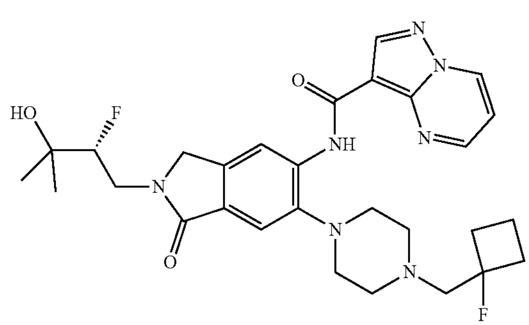 [SMILES: CC(C)(O)[C@H](F)CN1Cc2cc(NC(=O)c3cnn4cccnc34)c(N3CCN(CC4(F)CCC4)CC3)cc2C1=O] | $^1$H NMR (400 MHz, CDCl$_3$) δ 10.89 (s, 1H), 8.86-8.81 (m, 4H), 7.73 (s, 1H), 7.14-7.11 (m, 1H), 4.63-4.44 (m, 3H), 4.23-4.12 (m, 1H), 3.68-3.66 (m, 1H), 3.00 (s, 4H), 2.85-2.72 (m, 6H), 2.42 (s, 1H), 2.34-2.25 (m, 4H), 1.92-1.80 (m, 1H), 1.54-1.47 (m, 1H), 1.33 (s, 3H), 1.31 (s, 3H) |

TABLE 11-continued

The following examples were made in a manner similar to that for Example 99:

| Ex. | Name | Structure | NMR, MS |
|---|---|---|---|
| 125 & 126 | (S)-N-(2-(4-Hydroxy-4-methylpentan-2-yl)-6-(4-(oxetan-3-yl)piperazin-1-yl)-1-oxoisoindolin-5-yl)pyrazolo[1,5-a]pyrimidine-3-carboxamide and (R)-N-(2-(4-Hydroxy-4-methylpentan-2-yl)-6-(4-(oxetan-3-yl)piperazin-1-yl)-1-oxoisoindolin-5-yl)pyrazolo[1,5-a]pyrimidine-3-carboxamide (absolute stereochemistry assigned arbitrarily) | | Example 125, Peak 1: $^1$H NMR (400 MHz, DMSO-d$_6$) δ 10.79 (s, 1H), 9.37 (d, J = 7.2 Hz, 1H), 8.94 (d, J = 4.0 Hz, 1H), 8.73 (s, 1H), 8.71 (s, 1H), 7.50 (s, 1H), 7.37 (dd, J = 7.2, 4.0 Hz, 1H), 4.59-4.32 (m, 7H), 4.13 (s, 1H), 3.60-3.52 (m, 1H), 2.90 (br s, 4H), 2.53 (br s, 4H), 1.85 (dd, J = 14.4, 8.8 Hz, 1H), 1.52 (dd, J = 14.4, 3.6 Hz, 1H), 1.17 (d, J = 7.2 Hz, 3H), 1.05 (s, 3H), 1.04 (s, 3H). LCMS (ESI): m/z = 534.1 [M + H]$^+$. Example 126, Peak 2: $^1$H NMR (400 MHz, DMSO-d$_6$) δ 10.82 (s, 1H), 9.40 (d J = 7 .2 Hz, 1H), 8.96 (d, J = 3.2 Hz, 1H), 8.75 (s, 1H), 8.74 (s, 1H), 7.53 (s, 1H), 7.40 (dd, J = 6.8, 4.0 Hz, 1H), 4.62-4.35 (m, 7H), 4.16 (s, 1H), 3.65-3.57 (m, 1H), 2.93 (br s, 4H), 2.56 (br s, 4H), 1.92-1.84 (m, 1H), 1.60-1.52 (m, 1H), 1.19 (d, J = 6.8 Hz, 3H), 1.07 (s, 3H), 1.06 (s, 3H). LCMS (ESI): m/z = 534.1 [M + H]$^+$. |
| 127 | (R)-N-(6-(4-(tert-Butyl)piperazin-1-yl)-2-(2-fluoro-3-hydroxy-3-methylbutyl)-1-oxoisoindolin-5-yl)pyrazolo[1,5-a]pyrimidine-3-carboxamide | 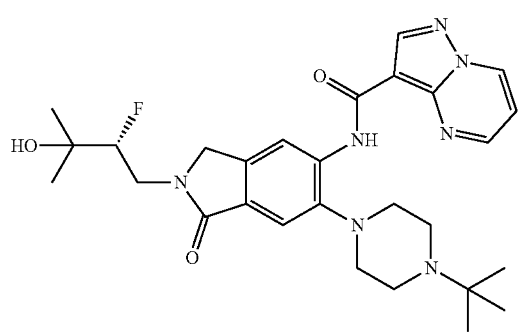 [SMILES: CC(C)(O)[C@H](F)CN1Cc2cc(NC(=O)c3cnn4cccnc34)c(N3CCN(C(C)(C)C)CC3)cc2C1=O] | $^1$H NMR (400 MHz, DMSO-d$_6$) δ 10.62 (s, 1H), 9.48-9.40 (m, 1H), 9.00-8.90 (m, 1H), 8.78 (s, 1H), 8.67 (s, 1H), 7.51 (s, 1H), 7.45-7.39 (m, 1H), 4.94 (s, 1H), 4.61-4.38 (m, 3H), 4.01-3.87 (m, 1H), 3.72-3.65 (m, 2H), 3.30-3.15 (m, 7H), 1.42 (s, 6H), 1.18 (s, 9H). LCMS (ESI): m/z = 538.2 [M + H]$^+$. |
| 128 | N-(2-((R)-2-Fluoro-3-hydroxy-3-methylbutyl)-6-(4-((1r,3R)-3-fluorocyclobutyl)piperazin-1-yl)-1-oxoisoindolin-5-yl)pyrazolo[1,5-a]pyrimidine-3-carboxamide | 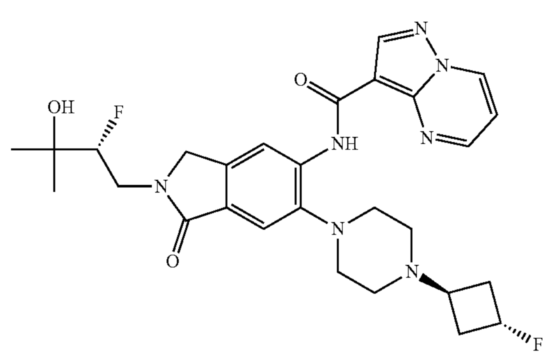 [SMILES: CC(C)(O)[C@H](F)CN1Cc2cc(NC(=O)c3cnn4cccnc34)c(N3CCN([C@H]4C[C@H](F)C4)CC3)cc2C1=O] | $^1$H NMR (400 MHz, DMSO-d$_6$) δ 10.81 (s, 1H), 9.39 (dd, J = 6.8, 1.6 Hz, 1H), 8.93 (dd, J = 4.0, 1.6 Hz, 1H), 8.74 (s, 2H), 7.53 (s, 1H), 7.41 (dd, J = 6.8, 4.0 Hz, 1H), 5.25-5.05 (m, 1H), 4.92 (s, 1H), 4.58-4.37 (m, 3H), 4.00-3.85 (m, 1H), 3.74-3.64 (m, 1H), 3.18-3.10 (m, 1H), 2.93-2.89 (m, 4H), 2.64-2.52 (m, 4H), 2.34-2.22 (m, 4H), 1.18 (s, 3H), 1.17 (s, 3H). MS (ESI): m/z = 554.2 [M + 1]$^+$. |

TABLE 11-continued

The following examples were made in a manner similar to that for Example 99:

| Ex. | Name | Structure | NMR, MS |
|---|---|---|---|
| 129 & 130 | N-(2-((R)-2-Fluoro-3-hydroxy-3-methylbutyl)-6-((S)-3-methyl-4-(oxetan-3-yl)piperazin-1-yl)-1-oxoisoindolin-5-yl)pyrazolo[1,5-a]pyrimidine-3-carboxamide and N-(2-((R)-2-Fluoro-3-hydroxy-3-methylbutyl)-6-((R)-3-methyl-4-(oxetan-3-yl)piperazin-1-yl)-1-oxoisoindolin-5-yl)pyrazolo[1,5-a]pyrimidine-3-carboxamide | | Example 128, Peak 1: $^1$H NMR (400 MHz, DMSO-$d_6$) δ 10.72 (s, 1H), 9.39 (dd, J = 6.8, 1.6 Hz, 1H), 8.94 (dd, J = 4.0, 1.6 Hz, 1H), 8.73 (s, 2H), 7.52 (s, 1H), 7.39 (dd, J = 6.8, 4.0 Hz, 1H), 4.93 (s, 1H), 4.65-4.35 (m, 7H), 4.00-3.80 (m, 2H), 3.75-3.60 (m, 1H), 2.93-2.83 (m, 3H), 2.75-2.60 (m, 3H), 2.43-2.33 (m, 1H), 1.18 (s, 3H), 1.17 (s, 3H), 0.89 (d, J = 5.2 Hz, 3H). MS (ESI): m/z = 555.2 [M + 1]$^+$. Example 129, Peak 2: $^1$H NMR (400 MHz, CDCl$_3$) δ 10.73 (s, 1H), 8.88 (d, J = 7.2 Hz, 1H), 8.83 (s, 2H), 8.77 (d, J = 4.4 Hz, 1H), 7.72 (s, 1H), 7.15 (dd, J = 7.2, 4.4 Hz, 1H), 4.82-4.46 (m, 7H), 4.27-4.12 (m, 1H), 3.85-3.60 (m, 2H), 3.08-2.93 (m, 3H), 2.78-2.68 (m, 3H), 2.55-2.45 (m, 1H), 2.40 (s, 1H), 1.34, 1.33 (s, 3H each), 0.98 (d, J = 6.8 Hz, 3H). MS (ESI): m/z = 555.2 [M + 1]$^+$. |

Example 131. (R)-5-Acetamido-N-(6-(dimethylamino)-2-(2-fluoro-3-hydroxy-3-methylbutyl)-1-oxoisoindolin-5-yl)pyrazolo[1,5-a]pyrimidine-3-carboxamide

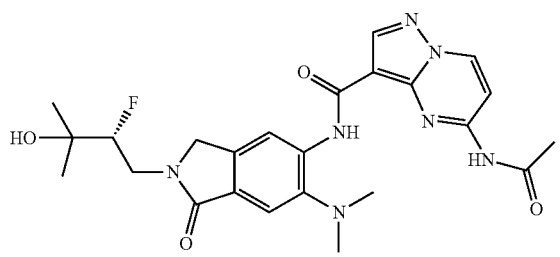 [SMILES: CC(=O)Nc1ccn2ncc(C(=O)Nc3cc4c(cc3N(C)C)C(=O)N(C[C@@H](F)C(C)(C)O)C4)c2n1]

Step A. (R)-5-Chloro-N-(6-(dimethylamino)-2-(2-fluoro-3-hydroxy-3-methylbutyl)-1-oxoisoindolin-5-yl)pyrazolo[1,5-a]pyrimidine-3-carboxamide

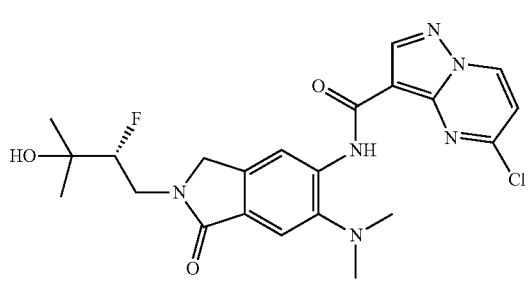 [SMILES: CN(C)c1cc2c(cc1NC(=O)c1cnn3ccc(Cl)nc13)CN(C[C@@H](F)C(C)(C)O)C2=O]

The title compound was prepared in an analogous manner to that for Intermediate H. 5-chloro-N-[6-(dimethylamino)-2-[(2R)-2-fluoro-3-hydroxy-3-methyl-butyl]-1-oxo-isoindolin-5-yl]pyrazolo[1,5-a]pyrimidine-3-carboxamide (160 mg, 77%) was obtained as a yellow solid.

Step B. (R)-5-Amino-N-(6-(dimethylamino)-2-(2-fluoro-3-hydroxy-3-methylbutyl)-1-oxoisoindolin-5-yl)pyrazolo[1,5-a]pyrimidine-3-carboxamide

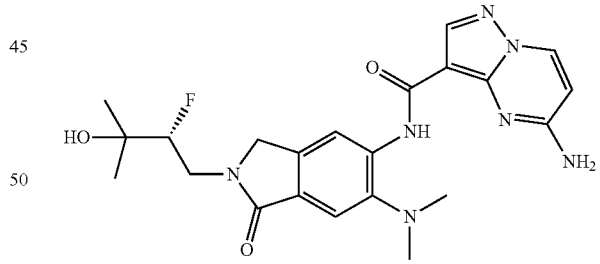

A sealed tube was charged with 5-chloro-N-[6-(dimethylamino)-2-[(2R)-2-fluoro-3-hydroxy-3-methyl-butyl]-1-oxo-isoindolin-5-yl]pyrazolo[1,5-a]pyrimidine-3-carboxamide (60.0 mg, 0.1 mmol) and ammonium hydroxide (5.0 mL, 138 mmol) in tetrahydrofuran (5 mL). The mixture was stirred at 50° C. for 10 h and concentrated. The residue was purified by preparatory thin layer chromatography (eluting gradient: 6% methanol in dichloromethane) to give 5-amino-N-[6-(dimethylamino)-2-[(2R)-2-fluoro-3-hydroxy-3-methyl-butyl]-1-oxo-isoindolin-5-yl]pyrazolo[1,5-a]pyrimidine-3-carboxamide (38.0 mg, 66%) as a white solid. LCMS (ESI): m/z=456.0 [M+H]$^+$.

Step C. (R)-5-Acetamido-N-(6-(dimethylamino)-2-(2-fluoro-3-hydroxy-3-methylbutyl)-1-oxoisoindolin-5-yl)pyrazolo[1,5-a]pyrimidine-3-carboxamide

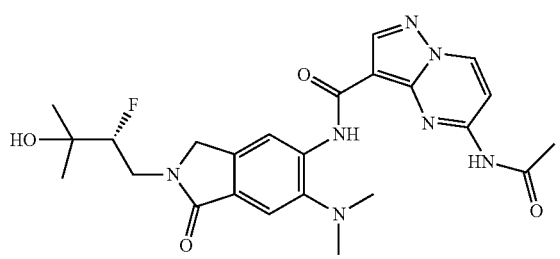 [SMILES: CC(=O)Nc1ccn2ncc(C(=O)Nc3cc4c(cc3N(C)C)C(=O)N(C[C@@H](F)C(C)(C)O)C4)c2n1]

A solution of 5-amino-N-[6-(dimethylamino)-2-[(2R)-2-fluoro-3-hydroxy-3-methyl-butyl]-1-oxo-isoindolin-5-yl]pyrazolo[1,5-a]pyrimidine-3-carboxamide (43.0 mg, 0.1 mmol) in acetic anhydride (5 mL) was stirred at 100° C. for 5.5 h under nitrogen and concentrated under reduced pressure. Saturated aqueous sodium bicarbonate (10 mL) was added, and the mixture was extracted with dichloromethane (30 mL×3). The organic phase was dried over sodium sulfate, concentrated and purified by preparatory thin layer chromatography (eluting gradient: 5% methanol in dichloromethane) to give 5-acetamido-N-[6-(dimethylamino)-2-[(2R)-2-fluoro-3-hydroxy-3-methyl-butyl]-1-oxo-isoindolin-5-yl]pyrazolo[1,5-a]pyrimidine-3-carboxamide (29.2 mg, 59%) as a white solid. $^1$H NMR (400 MHz, CDCl$_3$): δ 10.61 (s, 1H), 8.73 (d, J=7.6 Hz, 1H), 8.71 (s, 1H), 8.66 (s, 1H), 8.14 (s, 1H), 8.12 (d, J=7.6 Hz, 1H), 7.68 (s, 1H), 4.62-4.43 (m, 3H), 4.25-4.12 (m, 1H), 3.74-3.64 (m, 1H), 2.82 (s, 6H), 2.53 (s, 1H), 2.37 (s, 3H), 1.34-1.32 (m, 6H). LCMS (ESI): m/z=498.2 [M+H]$^+$.

Example 132. (R)—N$^5$-Cyclopropyl-N$^3$-(6-(dimethylamino)-2-(2-fluoro-3-hydroxy-3-methylbutyl)-1-oxoisoindolin-5-yl)pyrazolo[1,5-a]pyrimidine-3,5-dicarboxamide

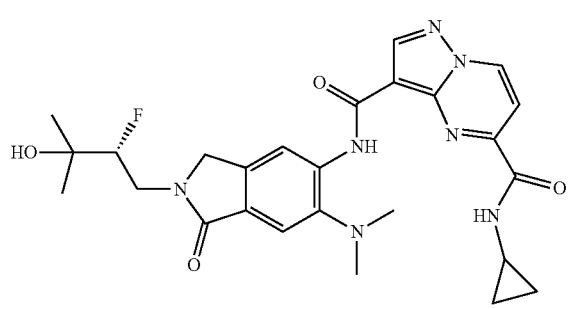 [SMILES: CN(C)c1cc2c(cc1NC(=O)c1cnn3ccc(C(=O)NC4CC4)nc13)CN(C[C@@H](F)C(C)(C)O)C2=O]

Step A. (R)-Methyl 3-((6-(dimethylamino)-2-(2-fluoro-3-hydroxy-3-methylbutyl)-1-oxoisoindolin-5-yl)carbamoyl)pyrazolo[1,5-a]pyrimidine-5-carboxylate

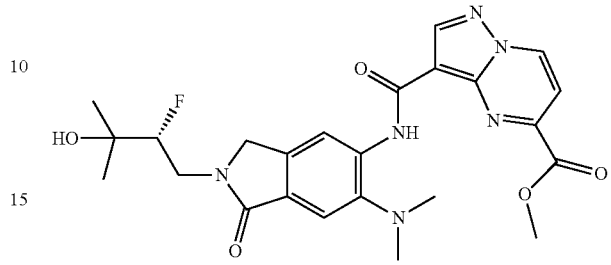

To a solution of 5-chloro-N-[6-(dimethylamino)-2-[(2R)-2-fluoro-3-hydroxy-3-methyl-butyl]-1-oxo-isoindolin-5-yl]pyrazolo[1,5-a]pyrimidine-3-carboxamide (100 mg, 0.2 mmol) in methanol (10 mL) was added triethylamine (63.9 mg, 0.6 mmol) and 1,1'-bis(diphenylphosphino)ferrocene palladium(II) dichloride (15.4 mg, 0.02 mmol). The mixture was stirred at 80° C. for 16 h under CO (40 psi) and concentrated. The residue was purified by preparatory thin layer chromatography (eluting gradient: 5% methanol in dichloromethane) to give methyl 3-[[6-(dimethylamino)-2-[(2R)-2-fluoro-3-hydroxy-3-methyl-butyl]-1-oxo-isoindolin-5-yl]carbamoyl]pyrazolo[1,5-a]pyrimidine-5-carboxylate (66.0 mg, 63%) as a yellow solid. LCMS (ESI): m/z=499.2 [M+H]$^+$.

Step B. (R)-N5-Cyclopropyl-N3-(6-(dimethylamino)-2-(2-fluoro-3-hydroxy-3-methylbutyl)-1-oxoisoindolin-5-yl)pyrazolo[1,5-a]pyrimidine-3,5-dicarboxamide

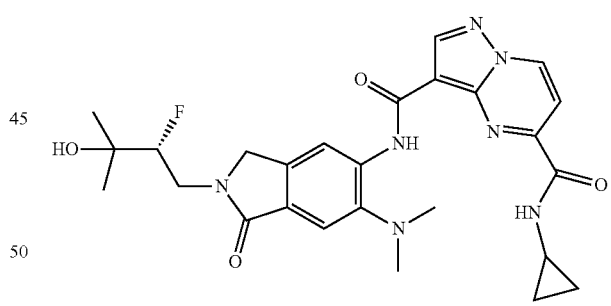

A sealed tube (8 mL) was charged with methyl 3-[[6-(dimethylamino)-2-[(2R)-2-fluoro-3-hydroxy-3-methyl-butyl]-1-oxo-isoindolin-5-yl]carbamoyl]pyrazolo[1,5-a]pyrimidine-5-carboxylate (76.0 mg, 0.2 mmol), cyclopropylamine (26.1 mg, 0.5 mmol) and methanol (5 mL). The mixture was stirred at 100° C. for 18 h and more cyclopropylamine (131 mg, 2.3 mmol) was added. After being stirred at 100° C. for another 7 h, the reaction mixture was concentrated and purified by preparatory thin layer chromatography (eluting gradient: 5% methanol in dichloromethane) to give N5-cyclopropyl-N3-[6-(dimethylamino)-2-[(2R)-2-fluoro-3-hydroxy-3-methyl-butyl]-1-oxo-isoindolin-5-yl]pyrazolo[1,5-a]pyrimidine-3,5-dicarboxamide (60.4 mg, 74%) as a yellow solid. $^1$H NMR (400 MHz, CDCl$_3$): δ 10.30 (s, 1H), 8.97 (d, J=7.2 Hz, 1H), 8.88 (s, 1H), 8.70 (s, 1H), 8.07 (s, 1H), 7.97 (d, J=7.2 Hz, 1H), 7.71 (s, 1H), 4.65-4.46 (m, 3H), 4.26-4.13 (m, 1H), 3.76-3.66 (m, 1H), 2.92-2.86 (m, 1H), 2.84 (s, 6H), 2.41 (s, 1H), 1.35-1.33 (m, 6H), 1.03-0.98 (m, 2H), 0.76-0.72 (m, 2H). LCMS (ESI): m/z=524.2 [M+H]$^+$.

Example 133. (R)—N-(2-(2-Fluoro-3-hydroxy-3-methylbutyl)-6-morpholino-1-oxoisoindolin-5-yl)-6-hydroxypyrazolo[1,5-a]pyrimidine-3-carboxamide

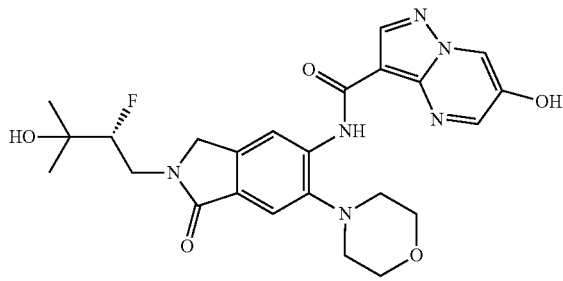 [SMILES: CC(C)(O)[C@H](F)CN1Cc2cc(NC(=O)c3cnn4cc(O)cnc34)c(N3CCOCC3)cc2C1=O]

Step A. (3-(Ethoxycarbonyl)pyrazolo[1,5-a]pyrimidin-6-yl)boronic acid

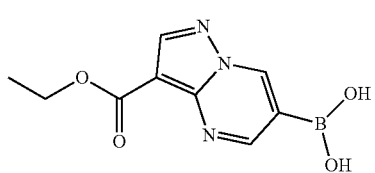 [SMILES: CCOC(=O)c1cnn2cc(B(O)O)cnc12]

To a solution of ethyl 6-bromopyrazolo[1,5-a]pyrimidine-3-carboxylate (2.0 g, 7.41 mmol) in 1,4-dioxane (20 mL) in a 50 mL three-neck flask was added bis(pinacolato)diboron (2.8 g, 11.1 mmol), 1,1'-bis(diphenylphosphino)ferrocene palladium dichloride (542 mg, 0.74 mmol) and potassium acetate (2.18 g, 22.2 mmol) under nitrogen, and stirred at 80° C. for 24 h. The reaction was cooled to 25° C., quenched with 2 M aqueous hydrochloric acid (20 mL) and extracted with ethyl acetate (30 mL×3). The combined organic phase was concentrated. The residue was dissolved in ethyl acetate (30 mL) and extracted with 2 M aqueous NaOH. The aqueous layer was acidified with hydrochloric acid and extracted twice with EtOAc. The combined organic phase was dried over magnesium sulfate and concentrated in vacuo to afford the desired product as a yellow solid (1.7 g, 98%). LCMS (ESI): m/z=236 [M+H]$^+$.

Step B. 6-Boronopyrazolo[1,5-a]pyrimidine-3-carboxylic acid

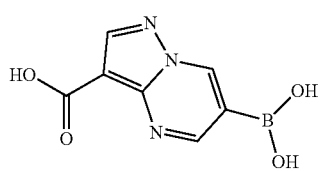 [SMILES: O=C(O)c1cnn2cc(B(O)O)cnc12]

To a solution of (3-ethoxycarbonylpyrazolo[1,5-a]pyrimidin-6-yl)boronic acid (1 g, 4.26 mmol) in water (12.8 mL) was added lithium hydroxide monohydrate (536 mg, 12.8 mmol). The mixture was stirred at 65° C. for 40 min and 2 M hydrochloric acid (2.55 mL) was added. The resulting precipitate was filtered and dried under vacuo to afford the desired product as a white solid (460 mg, 52% yield). LCMS (ESI): m/z=208 [M+H]$^+$.

Step C. (R)-(3-((2-(2-Fluoro-3-hydroxy-3-methylbutyl)-6-morpholino-1-oxoisoindolin-5-yl)carbamoyl)pyrazolo[1,5-a]pyrimidin-6-yl)boronic acid

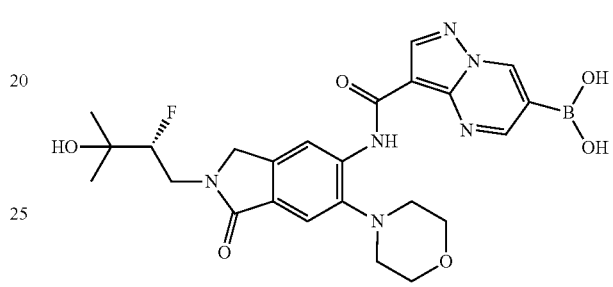

To a solution of 6-boronopyrazolo[1,5-a]pyrimidine-3-carboxylic acid (429 mg, 2.07 mmol) in dimethyl sulfoxide (30 mL) were added 5-amino-2-[(2R)-2-fluoro-3-hydroxy-3-methyl-butyl]-6-morpholino-isoindolin-1-one (500 mg, 1.48 mmol), 1-[bis(dimethylamino)methylene]-1H-1,2,3-triazolo[4,5-b]pyridinium 3-oxide hexafluorophosphate (676 mg, 1.78 mmol) and triethylamine (0.82 mL, 5.93 mmol). The mixture was stirred at 60° C. for 12 h and concentrated to give the crude product, which was used directly in the next step. LCMS (ESI): m/z=527 [M+H]$^+$.

Step D. (R)—N-(2-(2-Fluoro-3-hydroxy-3-methylbutyl)-6-morpholino-1-oxoisoindolin-5-yl)-6-hydroxypyrazolo[1,5-a]pyrimidine-3-carboxamide

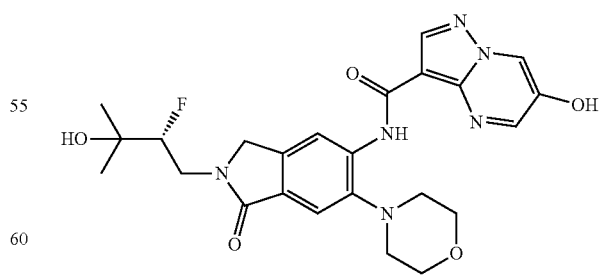

To a solution of (R)-(3-((2-(2-fluoro-3-hydroxy-3-methylbutyl)-6-morpholino-1-oxoisoindolin-5-yl)carbamoyl)pyrazolo[1,5-a]pyrimidin-6-yl)boronic acid (750 mg, 1.42 mmol) in dichloromethane (15 mL) and methanol (7.5 mL)

was added 3-chloroperoxybenzoic acid (289 mg, 1.42 mmol). The mixture was stirred at 25° C. for 2 h and concentrated. The residue was purified by reverse phase chromatography (acetonitrile 25-45/0.1% HCl in water) to afford the desired product as a white solid (230 mg, 32%). $^{1}$H NMR (400 MHz, DMSO-d$_{6}$) δ 10.81 (s, 1H), 10.72 (s, 1H), 8.83 (d, J=2.4 Hz, 1H), 8.77 (d, J=2.4 Hz, 1H), 8.75 (s, 1H), 8.59 (s, 1H), 7.58 (s, 1H), 4.93 (s, 1H), 4.61-4.46 (m, 3H), 4.38-3.98 (m, 1H), 3.91-3.87 (m, 4H), 3.70-3.60 (m, 1H), 2.95-2.90 (m, 4H), 1.19-1.18 (m, 6H). LCMS (ESI): m/z=499.2 [M+H]$^{+}$.

Example 134. (R)—N-(6-((1-(2,2-Difluoroethyl)piperidin-4-yl)oxy)-2-(2-fluoro-3-hydroxy-3-methylbutyl)-1-oxoisoindolin-5-yl)pyrazolo[1,5-a]pyrimidine-3-carboxamide

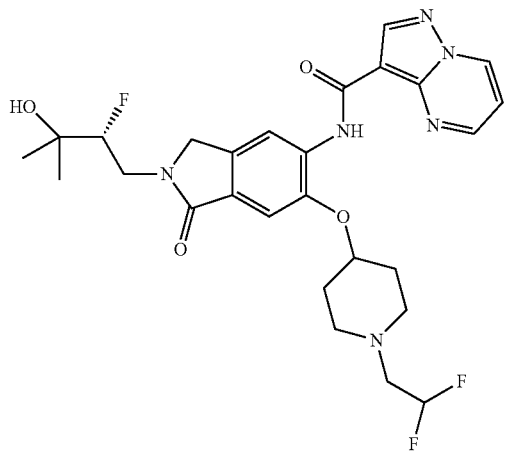 [SMILES: CC(C)(O)[C@H](F)CN1Cc2cc(NC(=O)c3cnn4cccnc34)c(OC3CCN(CC(F)F)CC3)cc2C1=O]

A mixture of N-[2-[(2R)-2-fluoro-3-hydroxy-3-methylbutyl]-1-oxo-6-(4-piperidyloxy)isoindolin-5-yl]pyrazolo[1,5-a]pyrimidine-3-carboxamide hydrochloride (64.0 mg, 0.12 mmol), 2,2-difluoroethyl trifluoromethanesulfonate (51.4 mg, 0.24 mmol) and N,N-diisopropylethylamine (46.6 mg, 0.36 mmol) in dimethyl sulfoxide (2 mL) was stirred at 80° C. for 2 h. The mixture was cooled to 15° C., diluted with ethyl acetate (200 mL), washed with water (100 mL×3), dried over sodium sulfate, filtered and concentrated to give a residue. The residue was purified by a column chromatography (2% methanol in dichloromethane) to give (R)—N-(6-((1-(2,2-difluoroethyl)piperidin-4-yl)oxy)-2-(2-fluoro-3-hydroxy-3-methylbutyl)-1-oxoisoindolin-5-yl)pyrazolo[1,5-a]pyrimidine-3-carboxamide (16.2 mg, 23.1%) as a white solid. $^{1}$H NMR (400 MHz, DMSO-d$_{6}$) δ 10.62 (s, 1H), 9.40 (d, J=4.0 Hz, 1H), 8.87 (d, J=4.0 Hz, 1H), 8.73 (s, 1H), 7.37 (s, 2H), 6.27-5.97 (m, 1H), 4.94 (s, 1H), 4.68 (s, 1H), 4.55-4.49 (m, 2H), 4.39-4.37 (m, 1H), 3.96-3.90 (m, 1H), 3.71-3.68 (m, 1H), 2.93-2.90 (m, 2H), 2.78-2.73 (m, 2H), 2.71 (s, 1H), 2.54 (s, 1H), 2.08-2.06 (m, 2H), 2.84-1.82 (m, 2H), 1.18 (d, J=4.0 Hz, 6H). MS (ESI): m/z=561.3 [M+1]$^{+}$.

Example 135. (R)—N-(2-(2-Fluoro-3-hydroxy-3-methylbutyl)-1-oxo-6-(2,2,2-trifluoroethoxy)isoindolin-5-yl)pyrazolo[1,5-a]pyrimidine-3-carboxamide

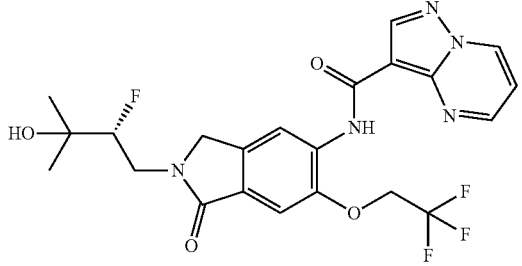 [SMILES: CC(C)(O)[C@H](F)CN1Cc2cc(NC(=O)c3cnn4cccnc34)c(OCC(F)(F)F)cc2C1=O]

Step A. (R)-2-(2-Fluoro-3-hydroxy-3-methylbutyl)-5-nitro-6-(2,2,2-trifluoroethoxy)isoindolin-1-one

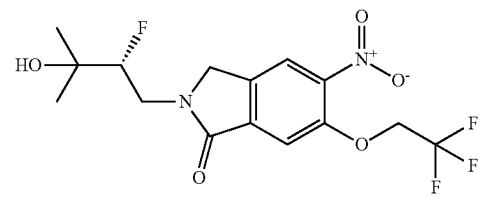 [SMILES: CC(C)(O)[C@H](F)CN1Cc2cc([N+](=O)[O-])c(OCC(F)(F)F)cc2C1=O]

To a stirred solution of 2-[(2R)-2-fluoro-3-hydroxy-3-methyl-butyl]-6-hydroxy-5-nitro-isoindolin-1-one (280 mg, 0.94 mmol) in N,N-dimethylformamide (5 mL) was added 2,2,2-trifluoroethyl trifluoromethanesulfonate (436 mg, 1.88 mmol) and potassium carbonate (260 mg, 1.88 mmol). The mixture was stirred at 50° C. for 16 h under nitrogen and concentrated. The residue was purified by column chromatography (silica gel: 100-200 mesh, eluting gradient: 0-1% methanol in dichloromethane) to give 2-[(2R)-2-fluoro-3-hydroxy-3-methyl-butyl]-5-nitro-6-(2,2,2-trifluoroethoxy)isoindolin-1-one (55.0 mg, 15% yield) as a yellow solid. LCMS (ESI): m/z=380.9 [M+H]$^{+}$.

Step B. (R)-5-Amino-2-(2-fluoro-3-hydroxy-3-methylbutyl)-6-(2,2,2-trifluoroethoxy)isoindolin-1-one

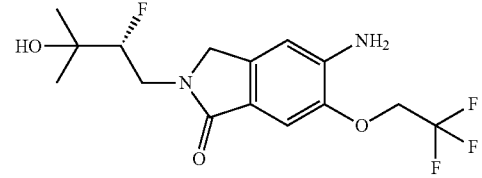 [SMILES: CC(C)(O)[C@H](F)CN1Cc2cc(N)c(OCC(F)(F)F)cc2C1=O]

To a solution of 2-[(2R)-2-fluoro-3-hydroxy-3-methylbutyl]-5-nitro-6-(2,2,2-trifluoroethoxy)isoindolin-1-one (55.0 mg, 0.14 mmol) in ethanol (5 mL) and water (1 mL) was added iron (40.4 mg, 0.72 mmol) and ammonium chloride (38.7 mg, 0.72 mmol). The mixture was stirred at 80° C. for 8 h under nitrogen, filtered and concentrated. The residue was taken up in dichloromethane (30 mL), filtered again and concentrated to give crude 5-amino-2-[(2R)-2-fluoro-3-hydroxy-3-methyl-butyl]-6-(2,2,2-trifluoroethoxy)isoindolin-1-one (43.0 mg, 85% yield) as a yellow solid. LCMS (ESI): m/z=351.2 [M+H]$^+$.

Step C. (R)—N-(2-(2-Fluoro-3-hydroxy-3-methyl-butyl)-1-oxo-6-(2,2,2-trifluoroethoxy)isoindolin-5-yl)pyrazolo[1,5-a]pyrimidine-3-carboxamide

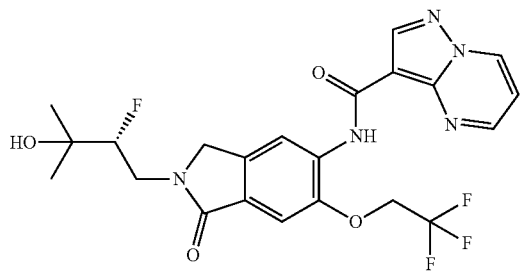 [SMILES: CC(C)(O)[C@H](F)CN1Cc2cc(NC(=O)c3cnn4cccnc34)c(OCC(F)(F)F)cc2C1=O]

To a stirred solution of 5-amino-2-[(2R)-2-fluoro-3-hydroxy-3-methyl-butyl]-6-(2,2,2-trifluoroethoxy)isoindolin-1-one (43 mg, 0.12 mmol) in pyridine (3 mL) was added pyrazolo[1,5-a]pyrimidine-3-carbonyl chloride (33 mg, 0.18 mmol). The mixture was stirred at 25° C. for 24 h and concentrated. The residue was purified by column chromatography (silica gel: 100-200 mesh, eluting gradient: 0-2% methanol in dichloromethane) to give N-[2-[(2R)-2-fluoro-3-hydroxy-3-methyl-butyl]-1-oxo-6-(2,2,2-trifluoroethoxy)isoindolin-5-yl]pyrazolo[1,5-a]pyrimidine-3-carboxamide (50 mg, 80% yield) as a white solid. $^1$H NMR (400 MHz, CDCl$_3$) δ 10.77 (s, 1H), 8.94 (s, 1H), 8.85 (dd, J=7.2, 1.6 Hz, 1H), 8.78 (s, 1H), 8.74 (dd, J=4.0, 1.2 Hz, 1H), 7.32 (s, 1H), 7.10 (dd, J=7.2, 4.0 Hz, 1H), 4.65-4.46 (m, 5H), 4.25-4.14 (m, 1H), 3.75-3.65 (m, 1H), 2.32 (s, 1H), 1.35 (s, 3H), 1.33 (s, 3H). LCMS (ESI): m/z=496.1 [M+H]$^+$.

Example 136. (R)—N-(6-(4-Cyclobutylpiperazin-1-yl)-2-(2-fluoro-3-hydroxy-3-methylbutyl)-1-oxoisoindolin-5-yl)pyrazolo[1,5-a]pyrimidine-3-carboxamide

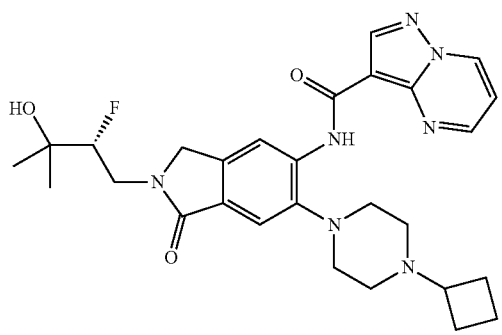 [SMILES: CC(C)(O)[C@H](F)CN1Cc2cc(NC(=O)c3cnn4cccnc34)c(N3CCN(C4CCC4)CC3)cc2C1=O]

A mixture of N-[2-[(2R)-2-fluoro-3-hydroxy-3-methyl-butyl]-1-oxo-6-piperazin-1-yl-isoindolin-5-yl]pyrazolo[1,5-a]pyrimidine-3-carboxamide (Intermediate H, 50.0 mg, 0.1 mmol), cyclobutanone (36.4 mg, 0.5 mmol) and zinc chloride (28.3 mg, 0.2 mmol) in methanol (10 mL) was stirred at 60° C. for 1 h. The reaction mixture was cooled to 16° C. and sodium cyanoborohydride (13.1 mg, 0.2 mmol) was added. The mixture was heated to 60° C. for another 3.5 h, after which it was quenched with water (2 mL) and concentrated. The residue was purified by column chromatography (silica gel: 100-200 mesh, eluting gradient: 0-20% methanol in dichloromethane) followed by further purification by SFC (column: AS (250 mm*30 mm, 5 um); condition: 0.1% NH$_3$/H$_2$O MeOH; Flow Rate: 50 mL/min) to give N-[6-(4-cyclobutylpiperazin-1-yl)-2-[(2R)-2-fluoro-3-hydroxy-3-methyl-butyl]-1-oxo-isoindolin-5-yl]pyrazolo[1,5-a]pyrimidine-3-carboxamide (28.5 mg, 51%) as a white solid. $^1$H NMR (400 MHz, DMSO-d$_6$): δ 10.83 (s, 1H), 9.41-9.39 (m, 1H), 8.93 (s, 1H), 8.74 (s, 1H), 7.54 (s, 1H), 7.43-7.40 (m, 1H), 4.92 (s, 1H), 4.58-4.37 (m, 3H), 4.00-3.87 (m, 1H), 3.72-3.68 (m, 1H), 3.00-2.80 (m, 5H), 2.70-2.52 (t, 4H), 2.10-1.95 (m, 2H), 1.84-1.81 (m, 2H), 1.68-1.67 (m, 2H), 1.20-1.10 (m, 6H). LCMS (ESI): m/z=536.1 [M+H]$^+$.

Example 137. N-[6-[4-(Cyclopropylmethyl)piperazin-1-yl]-2-[(2R)-2-fluoro-3-hydroxy-3-methyl-butyl]-1-oxo-isoindolin-5-yl]pyrazolo[1,5-a]pyrimidine-3-carboxamide

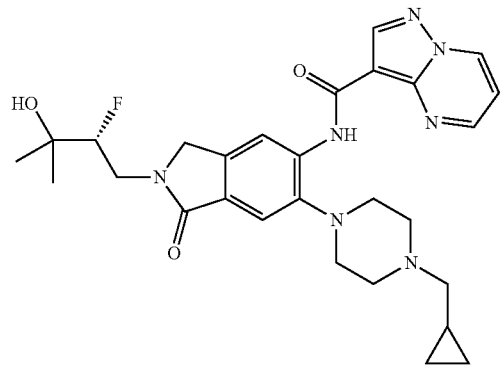 [SMILES: CC(C)(O)[C@H](F)CN1Cc2cc(NC(=O)c3cnn4cccnc34)c(N3CCN(CC4CC4)CC3)cc2C1=O]

To a stirred solution of N-[2-[(2R)-2-fluoro-3-hydroxy-3-methyl-butyl]-1-oxo-6-piperazin-1-yl-isoindolin-5-yl]pyrazolo[1,5-a]pyrimidine-3-carboxamide hydrochloride (Intermediate H, 50 mg, 0.10 mmol) and (iodomethyl)cyclopropane (35 mg, 0.19 mmol) in dimethyl sulfoxide (1 mL) was added N,N-diisopropylethylamine (0.05 mL, 0.29 mmol), and the mixture was stirred at 80° C. for 6 h. The mixture was concentrated, and the residue was purified by preparatory thin layer chromatography (9% methanol in dichloromethane) to give N-[6-[4-(cyclopropylmethyl)piperazin-1-yl]-2-[(2R)-2-fluoro-3-hydroxy-3-methyl-butyl]-1-oxo-isoindolin-5-yl]pyrazolo[1,5-a]pyrimidine-3-carboxamide (26 mg, 50% yield) as a white solid. $^1$H NMR (400 MHz, DMSO-d$_6$): δ 9.15 (d, J=5.6 Hz, 1H), 8.91 (d, J=2.8 Hz, 1H), 8.75 (s, 1H), 8.71 (s, 1H), 7.74 (s, 1H), 7.33-7.30 (m, 1H), 4.67-4.46 (m, 3H), 4.20-4.06 (m, 1H), 3.82-3.75 (m, 1H), 3.08-2.93 (m, 8H), 2.48-2.46 (m, 2H), 1.31 (s, 6H), 1.02-0.96 (m, 1H), 0.63-0.58 (m, 2H), 0.25-0.21 (m, 2H). LCMS (ESI): m/z=536.1 [M+H]$^+$.

TABLE 12

The following examples were made in a manner similar to that for Example 137:

| Ex. | Name | Structure | NMR, MS |
|---|---|---|---|
| 138 | (R)-N-(6-(4-(3,3-difluorocyclobutyl)piperazin-1-yl)-2-(2-fluoro-3-hydroxy-3-methylbutyl)-1-oxoisoindolin-5-yl)pyrazolo[1,5-a]pyrimidine-3-carboxamide | 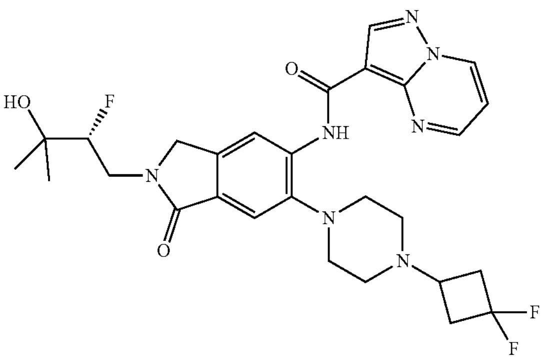 [SMILES: CC(C)(O)[C@H](F)CN1Cc2cc(NC(=O)c3cnn4cccnc34)c(N3CCN(C4CC(F)(F)C4)CC3)cc2C1=O] | $^1$H-NMR (400 MHz, CDCl$_3$) δ 10.82 (s, 1H), 8.89-8.87 (m, 1H), 8.84-8.82 (m, 2H), 8.80-8.77 (m, 1H), 7.73 (s, 1H), 7.17-7.14 (m, 1H), 4.64-4.45 (m, 3H), 4.25-4.13 (m, 1H), 3.69-3.67 (m, 1H), 3.06-3.00 (m, 4H), 2.98-2.93 (m, 1H), 2.80-2.60 (m, 6H), 2.58-2.45 (m, 2H), 2.38 (s, 1H), 1.34-1.33 (m, 6H). MS (ESI): m/z = 572 [M + 1]$^+$. |
| 139 | (R)-N-(2-(2-Fluoro-3-hydroxy-3-methylbutyl)-6-((1-(oxetan-3-yl)piperidin-4-yl)oxy)-1-oxoisoindolin-5-yl)pyrazolo[1,5-a]pyrimidine-3-carboxamide | 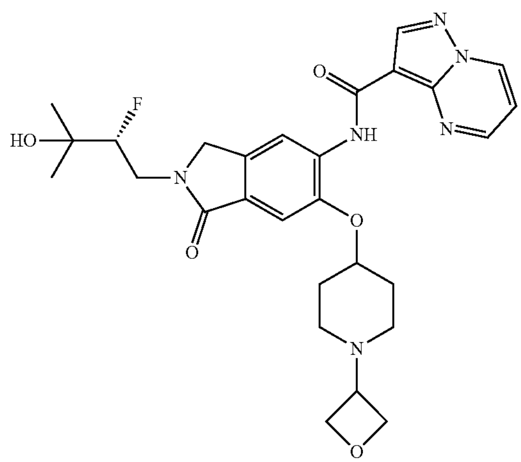 [SMILES: CC(C)(O)[C@H](F)CN1Cc2cc(NC(=O)c3cnn4cccnc34)c(OC3CCN(C4COC4)CC3)cc2C1=O] | $^1$H-NMR (400 MHz, CDCl$_3$) δ 10.62 (s, 1H) 8.87-8.77 (m, 3H) 7.38 (s, 1H), 7.26 (s, 1H), 7.13-7.10 (m, 1H), 4.71-4.68 (m, 2H), 4.63-4.62 (m, 2H), 4.58-4.43 (m, 1H), 4.48-4.47 (m, 1H), 4.19 (s, 1H), 4.16-4.10 (m, 1H), 3.72-3.70 (m, 1H), 3.50 (s, 1H), 2.79 (s, 2H), 2.63 (s, 1H), 2.40 (s, 2H), 2.25 (s, 2H), 2.03 (s, 2H), 1.33 (d, J = 8.0 Hz, 6H). MS (ESI): m/z = 553.3 [M + 1]$^+$. |
| 140 & 141 | N-[2-[(2R)-2-fluoro-3-hydroxy-3-methyl-butyl]-1-oxo-6-[4-[(3S)-tetrahydrofuran-3-yl]piperazin-1-yl]isoindolin-5-yl]pyrazolo[1,5-a]pyrimidine-3-carboxamide and N-[2-[(2R)-2-fluoro-3-hydroxy-3-methyl-butyl]-1-oxo-6-[4-[(3R)-tetrahydrofuran-3-yl]piperazin-1-yl]isoindolin-5-yl]pyrazolo[1,5-a]pyrimidine-3-carboxamide | | Example 140, Peak 2: $^1$H NMR (400 MHz, DMSO-d$_6$): δ 10.81 (s, 1H), 9.40 (d, J = 6.0 Hz, 1H), 8.99 (d, J = 2.8 Hz, 1H), 8.74 (d, J = 2.4 Hz, 2H), 7.53 (s, 1H), 7.43-7.40 (m, 1H), 4.92 (s, 1H), 4.58-4.37 (m, 3H), 4.00-3.80 (m, 3H), 3.74-3.64 (m, 2H), 3.55-3.48 (m, 1H), 3.06-2.99 (m, 1H), 2.91-2.84 (m, 4H), 2.78-2.72 (m, 2H), 2.67-2.60 (m, 2H), 2.07-1.99 (m, 1H), 1.81-1.72 (m, 1H), 1.19-1.15 (m, 6H). LCMS (ESI): m/z = 552.1 [M + H]$^+$. Example 141, Peak 1: $^1$H NMR (400 MHz, DMSO-d$_6$): δ 10.81 (s, 1H), 9.40 (d, J = 7.2 Hz, 1H), 8.98 (d, J = 2.8 Hz, 1H), 8.74 (d, J = 4.4 Hz, 2H), 7.53 (s, 1H), 7.43-7.40 (m, 1H), 4.92 (s, 1H), 4.58-4.37 (m, 3H), 4.00-3.80 (m, 3H), 3.74-3.64 (m, 2H), 3.50 (t, 1H), 3.05-2.98 (m, 1H), 2.92-2.82 (m, 4H), 2.82-2.70 (m, 2H), 2.68-2.60 (m, 2H), 2.07-2.01 (m, 1H), 1.81-1.72 (m, 1H), 1.22-1.13 (m, 6H). LCMS (ESI): m/z = 552.2 [M + H]$^+$. |

TABLE 12-continued

The following examples were made in a manner similar to that for Example 137:

| Ex. | Name | Structure | NMR, MS |
|---|---|---|---|
| 142 | N-[2-[(2R)-2-Fluoro-3-hydroxy-3-methyl-butyl]-1-oxo-6-(4-tetrahydropyran-4-ylpiperazin-1-yl)isoindolin-5-yl]pyrazolo[1,5-a]pyrimidine-3-carboxamide | 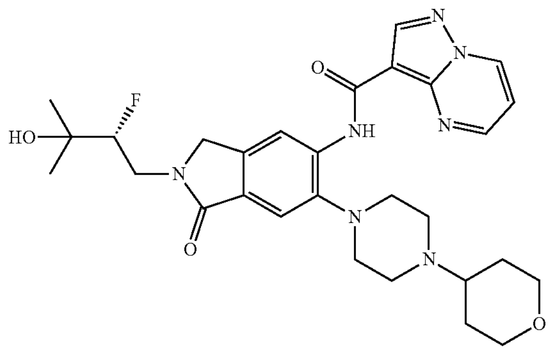 [SMILES: CC(C)(O)[C@H](F)CN1Cc2cc(NC(=O)c3cnn4cccnc34)c(N3CCN(C4CCOCC4)CC3)cc2C1=O] | $^1$H NMR (400MHz, CDCl$_3$) δ 10.81 (s, 1H), 8.88-8.82 (m, 4H), 7.73 (s, 1H), 7.15-7.12 (m, 1H), 4.64-4.45 (m, 3H), 4.25-4.21 (m, 1H), 4.17-4.09 (m, 2H), 3.70-3.69 (m, 1H), 3.48-3.42 (m, 2H), 3.07-2.89 (m, 8H), 2.57 (s, 1H), 2.43 (s, 1H), 1.86-1.64 (m, 4H), 1.34-1.32 (m, 6H). LCMS (ESI): m/z = 566.2 [M + H]$^+$. |
| 143 | N-[6-(4-Cyclopentylpiperazin-1-yl)-2-[(2R)-2-fluoro-3-hydroxy-3-methyl-butyl]-1-oxo-isoindolin-5-yl]pyrazolo[1,5-a]pyrimidine-3-carboxamide | 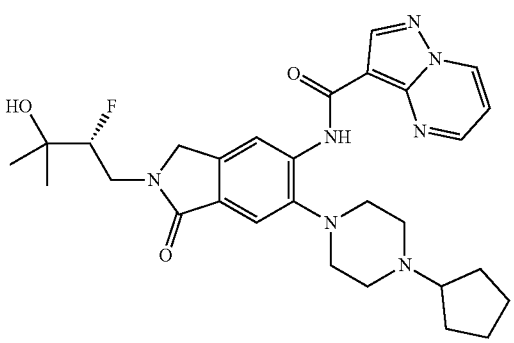 [SMILES: CC(C)(O)[C@H](F)CN1Cc2cc(NC(=O)c3cnn4cccnc34)c(N3CCN(C4CCCC4)CC3)cc2C1=O] | $^1$H NMR (400MHz, DMSO-d$_6$) δ 10.82 (s, 1H), 9.42-9.40 (m, 1H), 8.94 (s, 1H), 8.74 (m, 2H), 7.53 (s, 1H), 7.43-7.40 (m, 1H), 4.92 (s, 1H), 4.58-4.37 (m, 3H), 4.00-3.87 (m, 1H), 3.72-3.68 (m, 1H), 2.91-2.67 (m, 9H), 1.85 (m, 2H), 1.65 (m, 2H), 1.54-5.53 (m, 2H), 1.40-1.38 (m, 2H), 1.18 (s, 3H), 1.17 (s, 3H). LCMS (ESI): m/z = 550.2 [M + H]$^+$. |

Example 144. N-[6-[4-(Cyclopropanecarbonyl)piperazin-1-yl]-2-[(2R)-2-fluoro-3-hydroxy-3-methyl-butyl]-1-oxo-isoindolin-5-yl]pyrazolo[1,5-a]pyrimidine-3-carboxamide

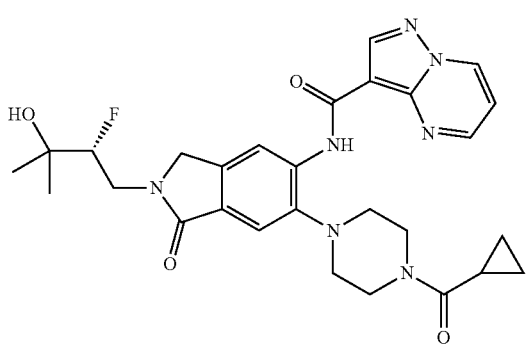 [SMILES: CC(C)(O)[C@H](F)CN1Cc2cc(NC(=O)c3cnn4cccnc34)c(N3CCN(C(=O)C4CC4)CC3)cc2C1=O]

To a solution of N-[2-[(2R)-2-fluoro-3-hydroxy-3-methyl-butyl]-1-oxo-6-piperazin-1-yl-isoindolin-5-yl]pyrazolo[1,5a]pyrimidine-3-carboxamide hydrochloride (Intermediate H, 70 mg, 0.14 mmol) in pyridine (3 mL) was added cyclopropanecarbonyl chloride (17 mg, 0.16 mmol). The mixture was stirred at 25° C. for 16 h. The mixture was concentrated, and the residue was purified by column chromatography (silica gel: 100-200 mesh, eluting gradient: 0-3% methanol in dichloromethane) to give N-[6-[4-(cyclopropanecarbonyl)piperazin-1-yl]-2-[(2R)-2-fluoro-3-hydroxy-3-methyl-butyl]-1-oxo-isoindolin-5-yl]pyrazolo[1,5-a]pyrimidine-3-carboxamide (66 mg, 88% yield) as a white solid. $^1$H NMR (400 MHz, chloroform-d) δ 10.95 (s, 1H), 8.89-8.83 (m, 3H), 8.73-8.72 (m, 1H), 7.70 (s, 1H), 7.12 (dd, J=4.0, 7.2 Hz, 1H), 4.65-4.46 (m, 3H), 4.25-4.00 (m, 5H), 3.74-3.63 (m, 1H), 3.02 (s, 4H), 2.39 (s, 1H), 1.84-1.79 (m, 1H), 1.34-1.33 (m, 6H), 1.09-1.06 (m, 2H), 0.87-0.82 (m, 2H). MS (ESI): m/z=550.1 [M+H]$^+$.

TABLE 13

The following examples were made in a manner similar to that for Intermediate T:

| Ex. | Name | Structure | NMR, MS |
|---|---|---|---|
| 145 | N-[2,2-Dimethyl-6-(5-methyl-2-pyridyl)-3H-benzofuran-5-yl]pyrazolo[1,5-a]pyrimidine-3-carboxamide | 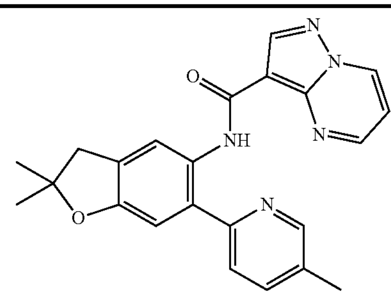 | $^1$H NMR (400 MHz, CDCl$_3$) δ 11.71 (s, 1H), 8.78-8.76 (m, 1H), 8.72 (s, 1H), 8.68 (dd, J = 4.0, 1.6 Hz, 1H), 8.51 (s, 1H), 8.23 (s, 1H), 7.59-7.57 (m, 1H), 7.46 (d, J = 7.6 Hz, 1H), 7.02 (dd, J = 7.2, 4.0 Hz, 1H), 6.89 (s, 1H), 3.12 (s, 2H), 2.38 (s, 3H), 1.52 (s, 6H). LCMS (ESI): m/z = 400.1 [M + H]$^+$. |
| 146 | (R)-N-(2-(2-Fluoro-3-hydroxy-3-methylbutyl)-6-(5-methylpyridin-2-yl)-1-oxoisoindolin-5-yl)pyrazolo[1,5-a]pyrimidine-3-carboxamide | 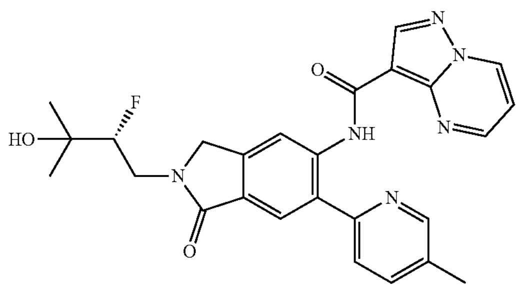 [SMILES: Cc1ccc(-c2cc3c(cc2NC(=O)c2cnn4cccnc24)CN(C[C@@H](F)C(C)(C)O)C3=O)nc1] | $^1$H NMR (400 MHz, CDCl$_3$) δ 12.40 (s, 1H), 8.83-8.80 (m, 2H), 8.76 (s, 1H), 8.70-8.66 (m, 1H), 8.56 (s, 1H), 8.04 (s, 1H), 7.70-7.64 (m, 2H), 7.08-7.05 (m, 1H), 4.74-4.50 (m, 3H), 4.29-4.16 (m, 1H), 3.78-3.71 (m, 1H), 2.44 (s, 3H), 2.38 (s, 1H), 1.36 (s, 3H), 1.34 (s, 3H). LCMS (ESI): m/z = 489.2 [M + H]$^+$. |

Example 147. N-[2-[(2R)-2-Fluoro-3-hydroxy-3-methyl-butyl]-6-(oxetan-3-yl)-1-oxo-isoindolin-5-yl]pyrazolo[1,5-a]pyrimidine-3-carboxamide

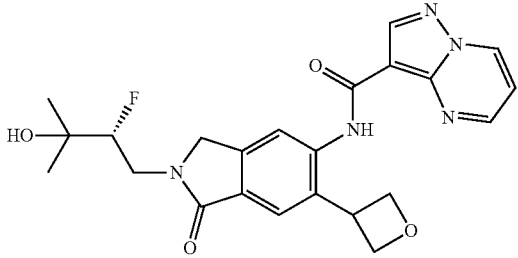 [SMILES: CC(C)(O)[C@H](F)CN1Cc2cc(NC(=O)c3cnn4cccnc34)c(C3COC3)cc2C1=O]

Step A. 5-Amino-6-bromo-2-[(2R)-2-fluoro-3-hydroxy-3-methyl-butyl]isoindolin-1-one

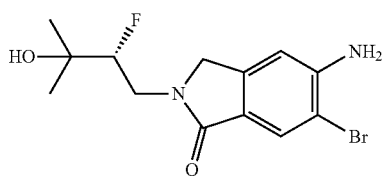 [SMILES: CC(C)(O)[C@H](F)CN1Cc2cc(N)c(Br)cc2C1=O]

To a solution of 6-bromo-2-[(2R)-2-fluoro-3-hydroxy-3-methyl-butyl]-5-nitro-isoindolin-1-one (200 mg, 0.55 mmol) in ethanol (5 mL) and water (1 mL) was added iron (155 mg, 2.77 mmol) and ammonium chloride (148 mg, 2.77 mmol). The reaction was stirred at 80° C. for 2 h, filtered and concentrated. The residue was taken up in ethyl acetate (100 mL), washed with brine (40 mL), dried over sodium sulfate and concentrated to give 5-amino-6-bromo-2-[(2R)-2-fluoro-3-hydroxy-3-methyl-butyl]isoindolin-1-one (170 mg, 92.7%) as a yellow solid.

Step B. 5-Amino-2-[(2R)-2-fluoro-3-hydroxy-3-methyl-butyl]-6-(oxetan-3-yl)isoindolin-1-one

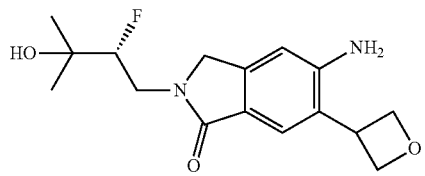 [SMILES: CC(C)(O)[C@H](F)CN1Cc2cc(N)c(C3COC3)cc2C1=O]

A vial was charged with 5-amino-6-bromo-2-[(2R)-2-fluoro-3-hydroxy-3-methyl-butyl]isoindolin-1-one (150 mg, 0.45 mmol), [4,4'-bis(1,1-dimethylethyl)-2,2'-bipyridine-N1,N1']bis[3,5-difluoro-2-[5-(trifluoromethyl)-2-pyridinyl-N]phenyl-C]iridium(III) hexafluorophosphate (50.8 mg, 0.05 mmol), dry molecular sieves (100 mg) and anhydrous sodium carbonate (48.0 mg, 0.45 mmol) and purged with nitrogen for 5 min. A solution of 3-bromooxetane (186 mg, 1.36 mmol) in anhydrous 1,2-dimethoxyethane (2 mL) was added, followed by tris(trimethylsilyl)silane (338 mg, 1.36 mmol). The resulting mixture was purged with nitrogen for 5 min. A second vial was charged with nickel(ii) chloride diglyme complex (16.7 mg, 0.09 mmol), 4,4'-di-tert-butyl-2,2'-dipyridyl (24.31 mg, 0.09 mmol) and 1,2-dimethoxyethane (2 mL) and purged with nitrogen for 5 min. This resulted in the formation of a green active Ni catalyst solution. The catalyst solution was transferred by syringe to the first vial. The resulting mixture was further purged with nitrogen for 2 min, stirred at 15° C. under nitrogen and a cooling fan, and irradiated with a 34 W blue LED for 16 h. The reaction was filtered and concentrated. The residue was purified by preparatory thin layer chromatography (eluting with ethyl acetate) to give 5-amino-2-[(2R)-2-fluoro-3-hydroxy-3-methyl-butyl]-6-(oxetan-3-yl)isoindolin-1-one (30 mg, 21.5%) as a white solid. LCMS (ESI): m/z=309.1 [M+H]$^+$.

Step C. N-[2-[(2R)-2-Fluoro-3-hydroxy-3-methyl-butyl]-6-(oxetan-3-yl)-1-oxo-isoindolin-5-yl]pyrazolo[1,5-a]pyrimidine-3-carboxamide

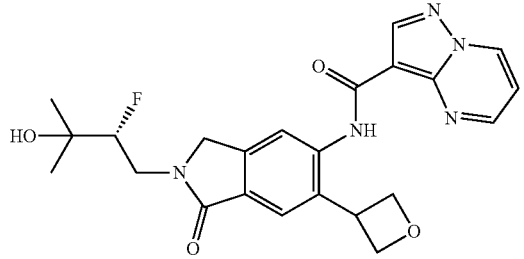 [SMILES: CC(C)(O)[C@H](F)CN1Cc2cc(NC(=O)c3cnn4cccnc34)c(C3COC3)cc2C1=O]

To a solution of pyrazolo[1,5-a]pyrimidine-3-carbonyl chloride (21.2 mg, 0.12 mmol) in pyridine (3 mL) was added 5-amino-2-[(2R)-2-fluoro-3-hydroxy-3-methyl-butyl]-6-(oxetan-3-yl)isoindolin-1-one (30.0 mg, 0.10 mmol). The reaction mixture was stirred at 50° C. for 16 h and concentrated. The residue was purified by flash column chromatography (eluting gradient: 3% methanol in dichloromethane) to give N-[2-[(2R)-2-fluoro-3-hydroxy-3-methyl-butyl]-6-(oxetan-3-yl)-1-oxo-isoindolin-5-yl]pyrazolo[1,5-a]pyrimidine-3-carboxamide (30.8 mg, 66%) as a yellow solid. $^1$H NMR (400 MHz, CDCl$_3$): δ 9.66 (s, 1H), 8.92-8.83 (m, 2H), 8.79 (s, 1H), 8.49 (s, 1H), 7.92 (s, 1H), 7.15 (dd, J=6.8, 4.4 Hz, 1H), 5.22-5.14 (m, 2H), 5.02-4.94 (m, 2H), 4.88-4.77 (m, 1H), 4.70-4.46 (m, 3H), 4.31-4.14 (m, 1H), 3.73-3.67 (m, 1H), 2.39 (s, 1H), 1.35 (s, 3H), 1.33 (s, 3H). LCMS (ESI): m/z=454.1 [M+H]$^+$.

Example 148. (R)—N-(2-(2-Fluoro-3-hydroxy-3-methylbutyl)-6-(2-hydroxypropan-2-yl)-1-oxoisoindolin-5-yl)pyrazolo[1,5-a]pyrimidine-3-carboxamide

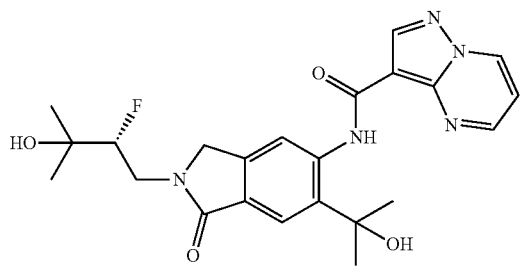 [SMILES: CC(C)(O)c1cc2c(cc1NC(=O)c1cnn3cccnc13)CN(C[C@@H](F)C(C)(C)O)C2=O]

Step A. Methyl 5-bromo-2-(bromomethyl)-4-nitrobenzoate

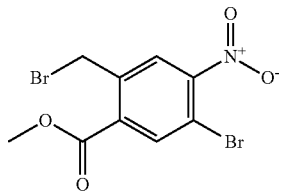 [SMILES: COC(=O)c1cc(Br)c([N+](=O)[O-])cc1CBr]

To a solution of methyl 5-bromo-2-methyl-4-nitro-benzoate (1.1 g, 4.0 mmol) in acetonitrile (20 mL) was added 1-bromo-2,5-pyrrolidinedione (857 mg, 4.8 mmol) and 2,2'-azobis(2-methylpropionitrile) (65.9 mg, 0.4 mmol). The mixture was stirred at 75° C. for 16 h under nitrogen and concentrated. The residue was purified by column chromatography (eluting gradient: 0-2% ethyl acetate in petroleum ether) to give methyl 5-bromo-2-(bromomethyl)-4-nitrobenzoate (730 mg, 52%) as a light yellow solid. $^1$H NMR (400 MHz, CDCl$_3$): 8.33 (s, 1H), 7.94 (s, 1H), 4.90 (s, 2H), 4.01 (s, 3H).

Step B. (R)-6-Bromo-2-(2-fluoro-3-hydroxy-3-methylbutyl)-5-nitroisoindolin-1-one

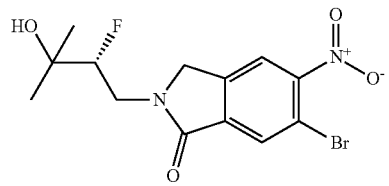 [SMILES: CC(C)(O)[C@H](F)CN1Cc2cc([N+](=O)[O-])c(Br)cc2C1=O]

To a stirred solution of methyl 5-bromo-2-(bromomethyl)-4-nitro-benzoate (730 mg, 2.1 mmol) in methanol (20 mL) was added triethylamine (419 mg, 4.1 mmol) and (3R)-4-amino-3-fluoro-2-methyl-butan-2-ol (WO2014/074675, 501 mg, 4.1 mmol). The mixture was stirred at 75° C. for 2 h under nitrogen and concentrated. The residue was purified by column chromatography (eluting gradient: 0-3% methanol in dichloromethane) to give 6-bromo-2-[(2R)-2-fluoro-3-hydroxy-3-methyl-butyl]-5-nitro-isoindolin-1-one (680 mg, 91%) as a light yellow solid.

Step C. (R)-Methyl 6-amino-2-(2-fluoro-3-hydroxy-3-methylbutyl)-3-oxoisoindoline-5-carboxylate

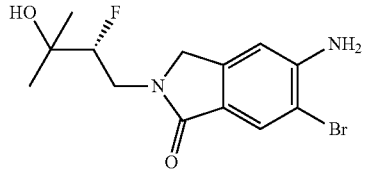 [SMILES: CC(C)(O)[C@H](F)CN1Cc2cc(N)c(Br)cc2C1=O]

A mixture of 1,1'-bis(diphenylphosphino)ferrocene palladium dichloride (118 mg, 0.2 mmol), triethylamine (488 mg, 4.8 mmol) and 6-bromo-2-[(2R)-2-fluoro-3-hydroxy-3-methyl-butyl]-5-nitro-isoindolin-1-one (580 mg, 1.6 mmol)

in methanol (25 mL) was stirred at 70° C. for 16 h under CO (15 psi) and concentrated. The residue was purified by column chromatography (eluting gradient: 0-2% methanol in dichloromethane) to give methyl 6-amino-2-[(2R)-2-fluoro-3-hydroxy-3-methyl-butyl]-3-oxo-isoindoline-5-carboxylate (120 mg, 24%) as a brown solid. LCMS (ESI): m/z=311.0 [M+H]+.

Step D. (R)-5-Amino-2-(2-fluoro-3-hydroxy-3-methylbutyl)-6-(2-hydroxypropan-2-yl)isoindolin-1-one

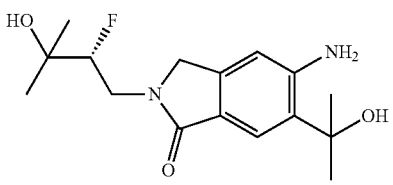 [SMILES: CC(C)(O)c1cc2c(cc1N)CN(C[C@@H](F)C(C)(C)O)C2=O]

To a stirred solution of methyl 6-amino-2-[(2R)-2-fluoro-3-hydroxy-3-methyl-butyl]-3-oxo-isoindoline-5-carboxylate (90 mg, 0.3 mmol) in anhydrous tetrahydrofuran (17 mL) was added dropwise methylmagnesium bromide (3 M in diethyl ether; 1.0 mL, 3.0 mmol) at 0° C. The mixture was stirred at 18° C. for 6 h under nitrogen atmosphere. The reaction was quenched with saturated aqueous ammonium chloride and extracted with dichloromethane (50 mL×3). The combined organic phase was dried over sodium sulfate, concentrated and purified by preparatory thin layer chromatography (eluting gradient: 9% methanol in dichloromethane) to give 5-amino-2-[(2R)-2-fluoro-3-hydroxy-3-methyl-butyl]-6-(1-hydroxy-1-methyl-ethyl)isoindolin-1-one (62 mg, 69%) as a light yellow oil. LCMS (ESI): m/z=311.1 [M+H]+.

Step E. (R)—N-(2-(2-Fluoro-3-hydroxy-3-methyl-butyl)-6-(2-hydroxypropan-2-yl)-1-oxoisoindolin-5-yl)pyrazolo[1,5-a]pyrimidine-3-carboxamide

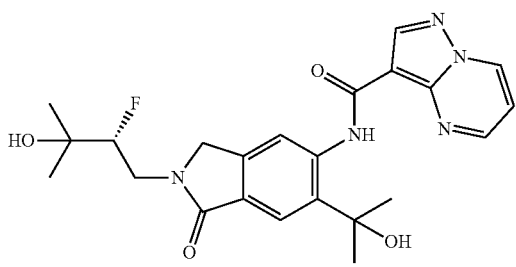 [SMILES: CC(C)(O)c1cc2c(cc1NC(=O)c1cnn3cccnc13)CN(C[C@@H](F)C(C)(C)O)C2=O]

To a stirred solution of 5-amino-2-[(2R)-2-fluoro-3-hydroxy-3-methyl-butyl]-6-(1-hydroxy-1-methyl-ethyl)isoindolin-1-one (62.0 mg, 0.2 mmol) in pyridine (5 mL) was added pyrazolo[1,5-a]pyrimidine-3-carbonyl chloride (54.4 mg, 0.3 mmol). The mixture was stirred at 18° C. for 2 h and concentrated. The residue was purified by column chromatography (eluting gradient: 0-6% methanol in dichloromethane) to give N-[2-[(2R)-2-fluoro-3-hydroxy-3-methyl-butyl]-6-(1-hydroxy-1-methyl-ethyl)-1-oxo-isoindolin-5-yl] pyrazolo[1,5-a]pyrimidine-3-carboxamide (68.3 mg, 74%) as a white solid. 1H NMR (400 MHz, CD3OD): δ 9.10 (dd, J=7.2, 1.6 Hz, 1H), 8.82 (dd, J=4.0, 1.6 Hz, 1H), 8.68 (s, 1H), 8.40 (s, 1H), 7.84 (s, 1H), 7.24 (dd, J=7.2, 4.0 Hz, 1H), 4.69-4.45 (m, 3H), 4.19-4.06 (m, 1H), 3.82-3.72 (m, 1H), 1.71 (s, 6H), 1.30 (s, 6H). LCMS (ESI): m/z=478.1 [M+Na]+.

Example 149. N-[2-[(2R)-2-Fluoro-3-hydroxy-3-methyl-butyl]-6-[1-(oxetan-3-yl)-4-piperidyl]-1-oxo-isoindolin-5-yl]pyrazolo[1,5-a]pyrimidine-3-carboxamide

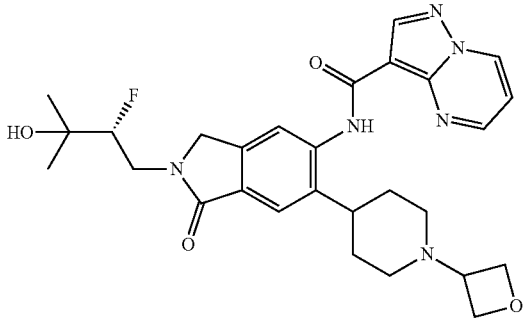 [SMILES: CC(C)(O)[C@H](F)CN1Cc2cc(NC(=O)c3cnn4cccnc34)c(C3CCN(C4COC4)CC3)cc2C1=O]

Step A. tert-Butyl 4-[2-[(2R)-2-fluoro-3-hydroxy-3-methyl-butyl]-6-nitro-3-oxo-isoindolin-5-yl]-3,6-dihydro-2H-pyridine-1-carboxylate

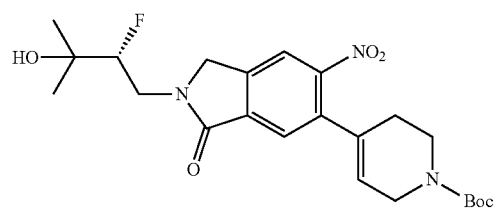 [SMILES: CC(C)(C)OC(=O)N1CC=C(c2cc3c(cc2[N+](=O)[O-])CN(C[C@@H](F)C(C)(C)O)C3=O)CC1]

N-boc-1,2,5,6-tetrahydropyridine-4-boronic acid pinacol ester (834 mg, 2.7 mmol), 6-bromo-2-[(2R)-2-fluoro-3-hydroxy-3-methyl-butyl]-5-nitro-isoindolin-1-one (650 mg, 1.8 mmol), sodium carbonate (476 mg, 4.5 mmol) and cyclopentyl(diphenyl)phosphane; dichloropalladium; iron (134 mg, 0.180 mmol) were combined in 1,4-dioxane (20 mL) and water (2 mL). The reaction mixture was stirred at 80° C. for 3 h under nitrogen. The mixture was diluted with water (20 mL) and extracted with ethyl acetate (50 mL×2). The organics were washed with brine (20 mL×2), dried over sodium sulfate, filtered and concentrated. The residue was purified by flash chromatography (solvent gradient: 0-50% ethyl acetate in petroleum ether) to afford tert-butyl 4-[2-[(2R)-2-fluoro-3-hydroxy-3-methyl-butyl]-6-nitro-3-oxo-isoindolin-5-yl]-3,6-dihydro-2H-pyridine-1-carboxylate (700 mg, 1.51 mmol, 83.9% yield) as a yellow solid. LCMS: m/z=486.1 [M+H]+.

Step B. 2-[(2R)-2-Fluoro-3-hydroxy-3-methyl-butyl]-5-nitro-6-(1,2,3,6-tetrahydropyridin-4-yl)isoindolin-1-one

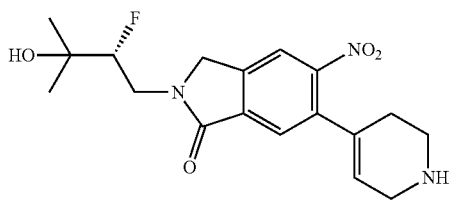 [SMILES: CC(C)(O)[C@H](F)CN1Cc2cc([N+](=O)[O-])c(C3=CCNCC3)cc2C1=O]

To a solution of tert-butyl 4-[2-[(2R)-2-fluoro-3-hydroxy-3-methyl-butyl]-6-nitro-3-oxo-isoindolin-5-yl]-3,6-dihydro-2H-pyridine-1-carboxylate (700 mg, 1.51 mmol) in dichloromethane (15 mL) was added trifluoroacetic acid (0.34 mL, 4.53 mmol). The reaction mixture was stirred at 25° C. for 2 h. The mixture was concentrated, diluted with water (30 mL), and extracted with ethyl acetate (40 mL×2). The organics were washed with saturated sodium bicarbonate (30 mL×2), dried over sodium sulfate, filtered and concentrated to give 2-[(2R)-2-fluoro-3-hydroxy-3-methyl-butyl]-5-nitro-6-(1,2,3,6-tetrahydropyridin-4-yl)isoindolin-1-one (540 mg, 1.48 mmol, 98.4% yield) as a brown solid.

Step C. 2-[(2R)-2-Fluoro-3-hydroxy-3-methyl-butyl]-5-nitro-6-[1-(oxetan-3-yl)-3,6-dihydro-2H-pyridin-4-yl]isoindolin-1-one

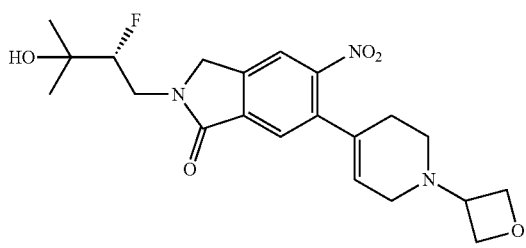 [SMILES: CC(C)(O)[C@H](F)CN1Cc2cc([N+](=O)[O-])c(C3=CCN(C4COC4)CC3)cc2C1=O]

A mixture of 2-[(2R)-2-fluoro-3-hydroxy-3-methyl-butyl]-5-nitro-6-(1,2,3,6-tetrahydropyridin-4-yl)isoindolin-1-one (200 mg, 0.55 mmol), acetic acid (0.09 mL, 1.65 mmol), and 3-oxetanone (79 mg, 1.1 mmol) in methanol (4 mL) was stirred at 60° C. for 2 h under nitrogen. Sodium cyanoborohydride (69.2 mg, 1.1 mmol) was added at 20° C., and the reaction mixture was stirred for 16 h. The mixture was concentrated, and the residue was purified by flash chromatography (solvent gradient: 0-10% methanol in dichloromethane) to afford 2-[(2R)-2-fluoro-3-hydroxy-3-methyl-butyl]-5-nitro-6-[1-(oxetan-3-yl)-3,6-dihydro-2H-pyridin-4-yl]isoindolin-1-one (200 mg, 0.48 mmol, 86.6% yield) as a brown solid. MS: m/z=420 [M+H]⁺.

Step D. 5-Amino-2-[(2R)-2-fluoro-3-hydroxy-3-methyl-butyl]-6-[1-(oxetan-3-yl)-4-piperidyl]isoindolin-1-one

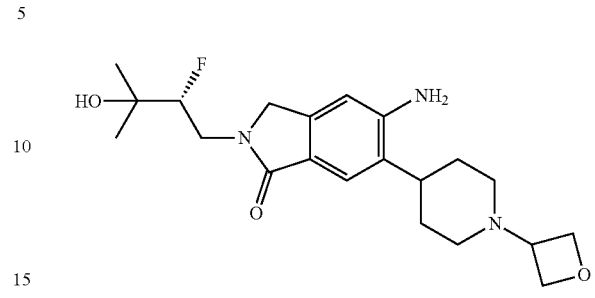

To a solution of 2-[(2R)-2-fluoro-3-hydroxy-3-methyl-butyl]-5-nitro-6-[1-(oxetan-3-yl)-3,6-dihydro-2H-pyridin-4-yl]isoindolin-1-one (100 mg, 0.24 mmol) in ethanol (10 mL) was added palladium on carbon (36 mg, 0.02 mmol). The resulting mixture was stirred at 60° C. under hydrogen (15 psi) for 16 h, after which it was filtered and concentrated. The residue was purified by preparatory thin layer chromatography (solvent gradient: 10% methanol in dichloromethane) to afford 5-amino-2-[(2R)-2-fluoro-3-hydroxy-3-methyl-butyl]-6-[1-(oxetan-3-yl)-4-piperidyl]isoindolin-1-one (60 mg, 0.15 mmol, 64.3% yield) as a white oil. LCMS: m/z=392.1 [M+H]⁺.

Step E. N-[2-[(2R)-2-Fluoro-3-hydroxy-3-methyl-butyl]-6-[1-(oxetan-3-yl)-4-piperidyl]-1-oxo-isoindolin-5-yl]pyrazolo[1,5-a]pyrimidine-3-carboxamide

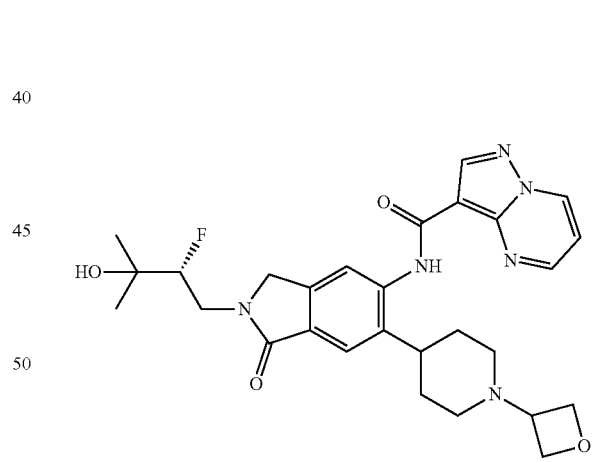

The title compound was made in a manner analogous to Example 60 (Step G) to afford N-[2-[(2R)-2-fluoro-3-hydroxy-3-methyl-butyl]-6-[1-(oxetan-3-yl)-4-piperidyl]-1-oxo-isoindolin-5-yl]pyrazolo[1,5-a]pyrimidine-3-carboxamide (40 mg, 0.07 mmol, 48.6% yield) as a white solid. $^1$H NMR (400 MHz, CDCl$_3$) δ 10.02 (s, 1H), 8.91 (d, J=6.8 Hz, 1H), 8.82 (s, 1H), 8.73 (d, J=4.2 Hz, 1H), 8.57 (s, 1H), 7.84 (s, 1H), 7.15 (dd, J=4.2, 6.8 Hz, 1H), 4.70 (d, J=6.4 Hz, 4H), 4.67-4.45 (m, 3H), 4.29-4.14 (m, 1H), 3.67 (m, 1H), 3.59-3.51 (m, 1H), 3.11-3.02 (m, 1H), 2.97 (m, 2H), 2.45 (s, 1H), 2.09-1.93 (m, 6H), 1.34 (d, J=7.6 Hz, 6H). LCMS (ESI): m/z=537.1 [M+H]⁺.

Example 150. N-[2-[(2R)-2-Fluoro-3-hydroxy-3-methyl-butyl]-6-[1-(oxetan-3-yl)-3,6-dihydro-2H-pyridin-4-yl]-1-oxo-isoindolin-5-yl]pyrazolo[1,5-a]pyrimidine-3-carboxamide

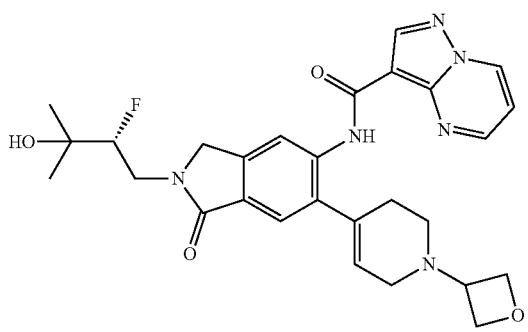 [SMILES: CC(C)(O)[C@H](F)CN1Cc2cc(NC(=O)c3cnn4cccnc34)c(C3=CCN(C4COC4)CC3)cc2C1=O]

Step A. 5-Amino-2-[(2R)-2-fluoro-3-hydroxy-3-methyl-butyl]-6-[1-(oxetan-3-yl)-3,6-dihydro-2H-pyridin-4-yl]isoindolin-1-one

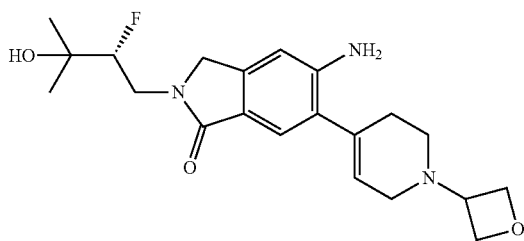 [SMILES: CC(C)(O)[C@H](F)CN1Cc2cc(N)c(C3=CCN(C4COC4)CC3)cc2C1=O]

The title compound was made in a manner analogous to Example 60 (Step F) to afford 5-amino-2-[(2R)-2-fluoro-3-hydroxy-3-methyl-butyl]-6-[1-(oxetan-3-yl)-3,6-dihydro-2H-pyridin-4-yl]isoindolin-1-one (60 mg, 0.15 mmol, 64.6% yield) as a white solid.

Step B. N-[2-[(2R)-2-Fluoro-3-hydroxy-3-methyl-butyl]-6-[1-(oxetan-3-yl)-3,6-dihydro-2H-pyridin-4-yl]-1-oxo-isoindolin-5-yl]pyrazolo[1,5-a]pyrimidine-3-carboxamide

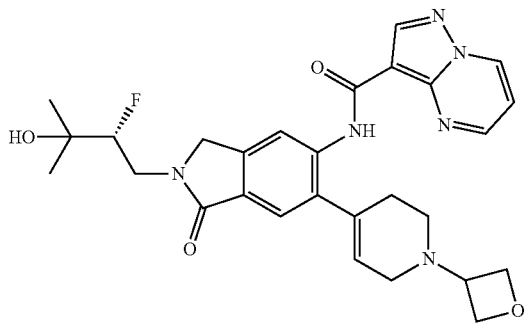 [SMILES: CC(C)(O)[C@H](F)CN1Cc2cc(NC(=O)c3cnn4cccnc34)c(C3=CCN(C4COC4)CC3)cc2C1=O]

The title compound was made in a manner analogous to Example 60 (Step G) to afford N-[2-[(2R)-2-fluoro-3-hydroxy-3-methyl-butyl]-6-[1-(oxetan-3-yl)-3,6-dihydro-2H-pyridin-4-yl]-1-oxo-isoindolin-5-yl]pyrazolo[1,5-a]pyrimidine-3-carboxamide (30 mg, 0.06 mmol, 48.6% yield) as a white solid. $^1$H NMR (400 MHz, DMSO-$d_6$) δ 10.23 (s, 1H), 9.40 (dd, J=1.6, 7.2 Hz, 1H), 9.02-8.97 (m, 1H), 8.73 (s, 1H), 8.71 (s, 1H), 7.44 (s, 1H), 7.37 (dd, J=4.2, 6.8 Hz, 1H), 5.86 (m, 1H), 5.75 (s, 1H), 4.93 (s, 1H), 4.66-4.35 (m, 7H), 4.02-3.86 (m, 1H), 3.76-3.62 (m, 2H), 3.06 (m, 2H), 2.68-2.58 (m, 2H), 2.32 (s, 1H), 1.18 (m, 6H). LCMS: m/z=535.1 [M+H]$^+$.

Example 151. N-(6-(Dimethylamino)-7-(hydroxymethyl)-2-isopropyl-1-oxoisoindolin-5-yl)pyrazolo[1,5-a]pyrimidine-3-carboxamide

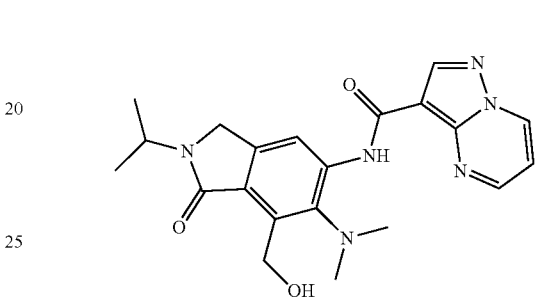

Step A. 7-Bromo-6-(dimethylamino)-2-isopropyl-5-nitroisoindolin-1-one

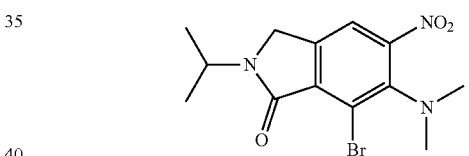

A mixture of 6-(dimethylamino)-2-isopropyl-5-nitro-isoindolin-1-one (500 mg, 1.9 mmol) and 1-bromo-2,5-pyrrolidinedione (372 mg, 2.09 mmol) in N,N-dimethylformamide (10 mL) was stirred at 20° C. for 12 h and concentrated. The residue was purified by column chromatography (eluting gradient: 12% ethyl acetate in petroleum ether) to give 7-bromo-6-(dimethylamino)-2-isopropyl-5-nitro-isoindolin-1-one (300 mg, 46.2%) as a yellow solid.

Step B. 6-(Dimethylamino)-7-(hydroxymethyl)-2-isopropyl-5-nitroisoindolin-1-one

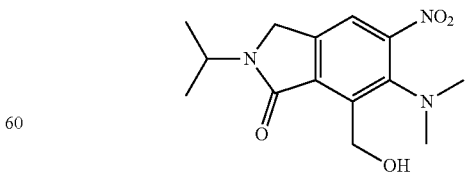

A mixture of potassium acetoxymethyl(trifluoro)boron (53 mg, 0.29 mmol), chloro(2-dicyclohexylphosphino-2',6'-diisopropoxy-1,1'-biphenyl)[2-(2'-amino-1,1'-biphenyl)]palladium(II) (11 mg, 0.01 mmol), sodium carbonate (31 mg, 0.29 mmol), 7-bromo-6-(dimethylamino)-2-isopropyl-5-nitro-isoindolin-1-one (50 mg, 0.15 mmol), and 2-dicyclohexylphosphino-2',6'-diisopropoxybiphenyl (14 mg, 0.03 mmol) in 1,4-dioxane (2 mL) and water (0.2 mL) was stirred at 120° C. in microwave under nitrogen for 50 min. Three batches of the same reaction were combined and filtered. The filtrate was concentrated and purified by preparatory thin layer chromatography (eluting gradient: 50% ethyl acetate in petroleum) to give 6-(dimethylamino)-7-(hydroxymethyl)-2-isopropyl-5-nitro-isoindolin-1-one (22 mg, 17%) as a yellow solid. $^1$H NMR (400 MHz, CDCl$_3$) δ 7.58 (s, 1H), 5.95-5.92 (m, 1H), 5.03 (d, J=8.0 Hz, 2H), 4.69-4.62 (m, 1H), 4.39 (s, 2H), 2.82 (s, 3H), 2.80 (s, 3H), 1.32 (d, J=6.8 Hz, 6H).

Step C. 5-Amino-6-(dimethylamino)-7-(hydroxymethyl)-2-isopropylisoindolin-1-one

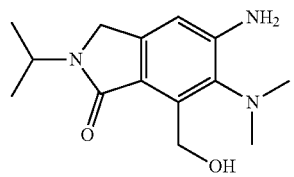 [SMILES: CC(C)N1Cc2cc([N+](=O)[O-])c(N(C)C)c(CO)c2C1=O]

A mixture of 6-(dimethylamino)-7-(hydroxymethyl)-2-isopropyl-5-nitro-isoindolin-1-one (30.0 mg, 0.09 mmol), ammonium chloride (27.3 mg, 0.51 mmol), and iron (28.5 mg, 0.51 mmol) in ethanol (3 mL) and water (0.6 mL) was stirred at 80° C. for 1 h and filtered. The filtrate was concentrated to give 5-amino-6-(dimethylamino)-7-(hydroxymethyl)-2-isopropyl-isoindolin-1-one (26 mg, 96%) as a white solid.

Step D. N-(6-(Dimethylamino)-7-(hydroxymethyl)-2-isopropyl-1-oxoisoindolin-5-yl)pyrazolo[1,5-a]pyrimidine-3-carboxamide

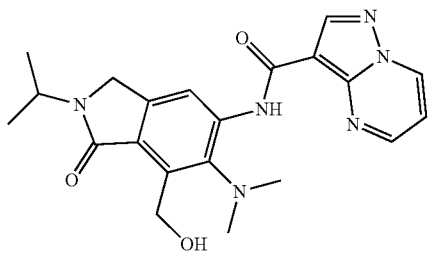 [SMILES: CC(C)N1Cc2cc(NC(=O)c3cnn4cccnc34)c(N(C)C)c(CO)c2C1=O]

A mixture of 5-amino-6-(dimethylamino)-7-(hydroxymethyl)-2-isopropyl-isoindolin-1-one (25.5 mg, 0.10 mmol) and pyrazolo[1,5-a]pyrimidine-3-carbonyl chloride (35.2 mg, 0.19 mmol) in pyridine (1 mL) was stirred at 30° C. for 12 h. The mixture was quenched with methanol (1 mL) and filtered. The filtrated was concentrated and purified by preparatory thin layer chromatography (eluting gradient: 10% methanol in dichloromethane) to give N-[6-(dimethylamino)-7-(hydroxymethyl)-2-isopropyl-1-oxo-isoindolin-5-yl]pyrazolo[1,5-a]pyrimidine-3-carboxamide (19 mg, 48%) as a white solid. $^1$H NMR (400 MHz, CDCl$_3$) δ 11.63 (s, 1H), 8.86-8.75 (m, 4H), 7.09 (dd, J=6.8, 4.0 Hz, 1H), 6.35 (t, J=7.6 Hz, 1H), 4.99 (d, J=7.6 Hz, 2H), 4.67-4.60 (m, 1H), 4.37 (s, 2H), 2.99 (s, 6H), 1.31 (d, J=6.8 Hz, 6H). LCMS (ESI): m/z=409.1 [M+H]$^+$.

Example 152. N-(2-Methyl-7-morpholino-1-oxo-1,2-dihydroisoquinolin-6-yl)pyrazolo[1,5-a]pyrimidine-3-carboxamide

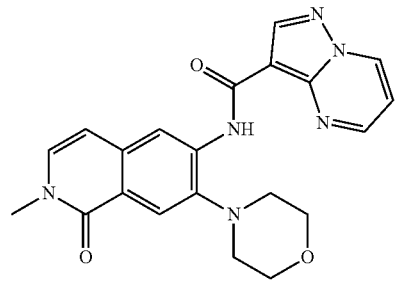 [SMILES: Cn1ccc2cc(NC(=O)c3cnn4cccnc34)c(N3CCOCC3)cc2c1=O]

Step A. Ethyl 2-methyl-5-morpholino-4-nitro-benzoate

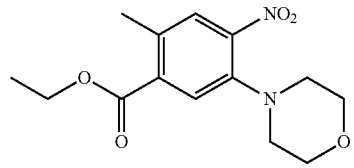 [SMILES: CCOC(=O)c1cc(N2CCOCC2)c([N+](=O)[O-])cc1C]

A mixture of ethyl 5-fluoro-2-methyl-4-nitro-benzoate (1.4 g, 6.16 mmol) and morpholine (2.15 g, 24.7 mmol) was stirred at 110° C. for 2 h. The reaction mixture was concentrated to dryness and purified by silica gel column chromatography (eluting gradient: 10-50% ethyl acetate: petroleum ether) to afford ethyl 2-methyl-5-morpholino-4-nitro-benzoate (1.6 g, 88% yield) as a red oil.

Step B. Ethyl 5-morpholino-4-nitro-2-(2-oxoethyl)benzoate

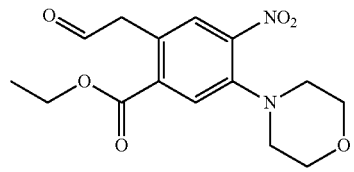 [SMILES: CCOC(=O)c1cc(N2CCOCC2)c([N+](=O)[O-])cc1CC=O]

To a solution of ethyl 2-methyl-5-morpholino-4-nitro-benzoate (0.5 g, 1.70 mmol) in N,N-dimethylformamide (5 mL) was added Bredereck's reagent (0.3 g, 1.70 mmol). The mixture was at 140° C. for 3 h, cooled to room temperature, concentrated to dryness and purified by silica gel column chromatography (eluting gradient: 10-50% ethyl acetate: petroleum ether) to afford ethyl 5-morpholino-4-nitro-2-(2-oxoethyl)benzoate (0.2 g, 36% yield) as a red oil. $^1$H NMR (400 MHz, CDCl$_3$) δ 9.80 (s, 1H), 7.80 (s, 1H), 7.61 (s, 1H), 4.37 (q, J=6.8 Hz, 2H), 4.08 (s, 2H), 3.85 (t, J=4.4 Hz, 4H), 3.10 (t, J=4.4 Hz, 4H), 1.40 (t, J=7.2 Hz, 3H).

Step C.
2-Methyl-7-morpholino-6-nitro-isoquinolin-1-one

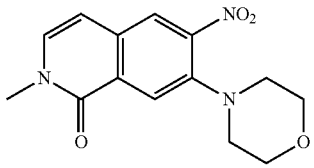 [SMILES: Cn1ccc2cc([N+](=O)[O-])c(N3CCOCC3)cc2c1=O]

To a solution of methylamine (135 mg, 4.34 mmol) in N,N-dimethylformamide (5 mL) was added ethyl 5-morpholino-4-nitro-2-(2-oxoethyl)benzoate (200 mg, 0.62 mmol) and the reaction was irradiated under microwave conditions at 140° C. for 30 min. The reaction mixture was concentrated to dryness and purified by preparatory thin layer chromatography (eluent 50% ethyl acetate:petroleum ether) to afford 2-methyl-7-morpholino-6-nitro-isoquinolin-1-one (60 mg, 33% yield) as a red oil. $^1$H NMR (400 MHz, CDCl$_3$) δ 8.15 (s, 1H), 7.83 (s, 1H), 7.09 (d, J=7.6 Hz, 1H), 6.47 (d, J=7.6 Hz, 1H), 3.86 (t, J=4.4 Hz, 4H), 3.63 (s, 3H), 3.12 (t, J 4.4 Hz, 4H).

Step D. N-(2-Methyl-7-morpholino-1-oxo-1,2-dihydroisoquinolin-6-yl)pyrazolo[1,5-a]pyrimidine-3-carboxamide

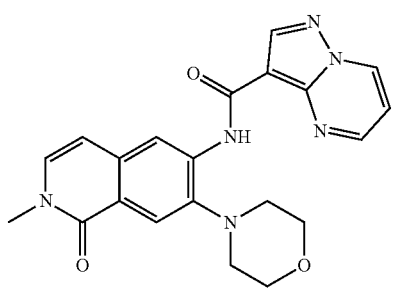 [SMILES: Cn1ccc2cc(NC(=O)c3cnn4cccnc34)c(N3CCOCC3)cc2c1=O]

Following analogous procedures to those described for Example 60 (Steps F and G), N-(2-methyl-7-morpholino-1-oxo-6-isoquinolyl)pyrazolo[1,5-a]pyrimidine-3-carboxamide (150 mg, 64%) was obtained as a white solid. $^1$H NMR (400 MHz, CDCl$_3$) δ 10.91 (s, 1H), 8.90-8.80 (m, 4H), 8.24 (s, 1H), 7.12 (dd, J=7.2, 4.0 Hz, 1H), 7.03 (d, J=7.6 Hz, 1H), 6.53 (d, J=7.2 Hz, 1H), 4.07-3.98 (m, 4H), 3.60 (s, 3H), 3.13-3.02 (m, 4H). LCMS (ESI): m/z=405.2 [M+H]$^+$.

Example 153. N-(7-Morpholino-2,3-dihydro-1,4-benzoxathiin-6-yl)pyrazolo[1,5-a]pyrimidine-3-carboxamide

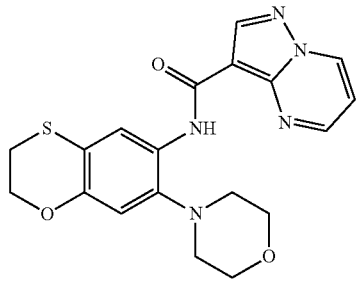 [SMILES: O=C(Nc1cc2c(cc1N1CCOCC1)OCCS2)c1cnn2cccnc12]

Step A. 3-Morpholino-4-nitro-phenol

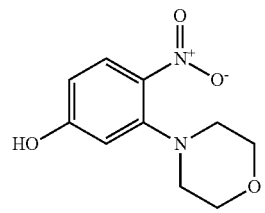

To a solution of 3-fluoro-4-nitrophenol (13.5 g, 85.87 mmol) and morpholine (15.0 mL, 172 mmol) in dimethyl sulfoxide (80 mL) was added N,N-diisopropylethylamine (29.9 mL, 172 mmol) and stirred at 90° C. for 2 h. The mixture was adjusted to pH=7 with 2 M hydrochloric acid, diluted with water (200 mL) and extracted with ethyl acetate (200 mL×3). The combined organic phase was washed with brine (200 mL×2), dried over sodium sulfate, filtered and concentrated. The residue was purified by flash chromatography (eluting gradient: 0-30% ethyl acetate in dichloromethane) to afford 3-morpholino-4-nitro-phenol (16.5 g, 86%) as a yellow solid. LCMS (ESI): m/z=225.0 [M+H]$^+$.

Step B. 2-Bromo-5-morpholino-4-nitro-phenol

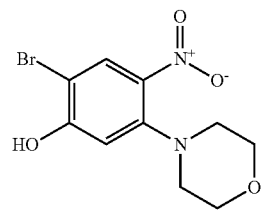

3-Morpholino-4-nitro-phenol (5.0 g, 22.30 mmol) was dissolved in chloroform (80 mL). A solution of bromine (0.69 mL, 13.38 mmol) in chloroform (80 mL) was slowly added over 1 h at 30° C. The reaction mixture was stirred for 16 h and filtered. The filtrate was evaporated, and the residue was partitioned between ethyl acetate and 1 M aqueous sodium carbonate. The organic phase was dried over sodium sulfate and concentrated. The residue purified by flash chromatography (silica gel, eluting gradient: 0-10% ethyl acetate in petroleum ether) to afford 2-bromo-5-morpholino-4-nitro-phenol (2.5 g, 37%) as a yellow solid. $^1$H NMR (400 MHz, CDCl$_3$) δ 8.19 (s, 1H), 6.72 (s, 1H), 5.99 (s, 1H), 3.88-3.86 (m, 4H), 3.07-3.05 (m, 4H).

Step C. 4-[4-Bromo-5-(2-bromoethoxy)-2-nitro-phenyl]morpholine

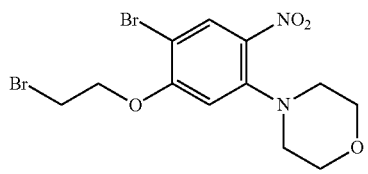 [SMILES: O=[N+]([O-])c1cc(Br)c(OCCBr)cc1N1CCOCC1]

To a solution of 2-bromo-5-morpholino-4-nitro-phenol (1.8 g, 5.94 mmol), triphenylphosphine (4.7 g, 17.82 mmol), 2-bromoethanol (1.9 g, 14.85 mmol) in toluene (30 mL) was added DIAD (3.6 g, 17.82 mmol) at 0° C. The mixture was stirred at 60° C. for 2 h under nitrogen and concentrated. The residue was purified by flash chromatography (eluting gradient: 0-50% ethyl acetate in petroleum ether) to afford 4-[4-bromo-5-(2-bromoethoxy)-2-nitro-phenyl]morpholine (1.6 g, 66%) as a yellow oil. LCMS (ESI): m/z=408.9 [M+H]$^+$.

Step D. S-[2-(2-Bromo-5-morpholino-4-nitro-phenoxy)ethyl]ethanethioate

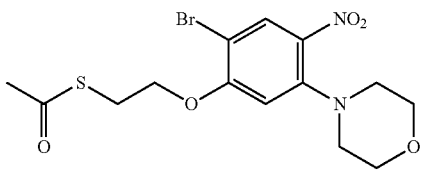 [SMILES: CC(=O)SCCOc1cc(N2CCOCC2)c([N+](=O)[O-])cc1Br]

To a solution of 4-[4-bromo-5-(2-bromoethoxy)-2-nitro-phenyl]morpholine (1.6 g, 3.90 mmol) in N,N-dimethylformamide (20 mL) was added potassium thioacetate (534.7 mg, 4.68 mmol). The reaction mixture was stirred at 35° C. for 2 h, diluted with water (50 mL) and extracted with ethyl acetate (50 mL×3). The combined organic phase was washed with brine (50 mL×3), dried over sodium sulfate, filtered and concentrated. The residue was purified by flash chromatography (eluting gradient: 0-40% ethyl acetate in petroleum ether) to afford S-[2-(2-bromo-5-morpholino-4-nitro-phenoxy)ethyl]ethanethioate (1.2 g, 76%) as a yellow solid. $^1$H NMR (400 MHz, CDCl$_3$) δ 8.23 (s, 1H), 6.67 (s, 1H), 4.22 (t, J=6.8 Hz, 2H), 3.89-3.87 (m, 4H), 3.31 (t, J=6.8 Hz, 2H), 3.13-3.11 (m, 4H), 2.41 (s, 3H).

Step E. 4-(6-Nitro-2,3-dihydro-1,4-benzoxathiin-7-yl)morpholine

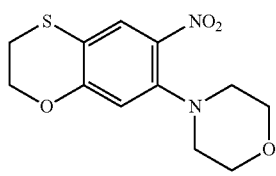 [SMILES: O=[N+]([O-])c1cc2c(cc1N1CCOCC1)OCCS2]

A mixture of tris(dibenzylideneacetone) dipalladium(0) (135.6 mg, 0.15 mmol), S-[2-(2-bromo-5-morpholino-4-nitro-phenoxy)ethyl]ethanethioate (600.0 mg, 1.48 mmol), potassium hydroxide (415 mg, 7.40 mmol) (dissolved in water) and 1,1'-bis(diphenylphosphino)ferrocene (164.2 mg, 0.30 mmol) in toluene (10 mL) was stirred at 90° C. for 16 h under nitrogen. The reaction mixture was diluted with water (5 mL) and extracted with dichloromethane (20 mL×3). The combined organic phase was washed with brine (20 mL×2), dried over sodium sulfate, filtered and concentrated. The residue was purified by flash chromatography (eluting gradient: 0-50% ethyl acetate in petroleum ether) to afford 4-(6-nitro-2,3-dihydro-1,4-benzoxathiin-7-yl)morpholine (200 mg, 48%) as a yellow solid. LCMS (ESI): m/z=282.8 [M+H]$^+$.

Step F. 7-Morpholino-2,3-dihydro-1,4-benzoxathiin-6-amine

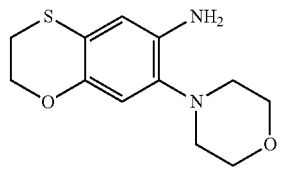

To a stirred solution of 4-(6-nitro-2,3-dihydro-1,4-benzoxathiin-7-yl)morpholine (200 mg, 0.71 mmol) in ethanol (5 mL) and water (1 mL) was added iron (198 mg, 3.54 mmol) and ammonium chloride (190 mg, 3.54 mmol). The mixture was stirred at 80° C. for 2 h under nitrogen and filtered. The filtrate was concentrated and purified by flash chromatography (eluting gradient: 0-10% methanol in dichloromethane) to afford 7-morpholino-2,3-dihydro-1,4-benzoxathiin-6-amine (135 mg, 76%) as a yellow solid. LCMS (ESI): m/z=252.9 [M+H]$^+$.

Step G. N-(7-Morpholino-2,3-dihydro-1,4-benzoxathiin-6-yl)pyrazolo[1,5-a]pyrimidine-3-carboxamide

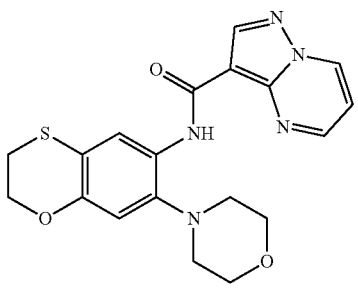 [SMILES: O=C(Nc1cc2c(cc1N1CCOCC1)OCCS2)c1cnn2cccnc12]

To a solution of 7-morpholino-2,3-dihydro-1,4-benzoxathiin-6-amine (135 mg, 0.54 mmol) in pyridine (3 mL) was added pyrazolo[1,5-a]pyrimidine-3-carbonyl chloride (107 mg, 0.59 mmol). The reaction mixture was stirred at 25° C. for 16 h and concentrated. The residue was purified by preparatory thin layer chromatography (eluting gradient: 10% methanol in dichloromethane) to afford N-(7-morpholino-2,3-dihydro-1,4-benzoxathiin-6-yl)pyrazolo[1,5-a]pyrimidine-3-carboxamide (50.0 mg, 23%) as a yellow solid. ¹H NMR (400 MHz, DMSO-d₆) δ 10.44 (s, 1H), 9.39-9.37 (m, 1H), 8.96-8.95 (m, 1H), 8.69 (s, 1H), 8.24 (s, 1H), 7.35 (dd, J=7.2, 4.0 Hz, 1H), 6.78 (s, 1H), 4.34 (d, J=4.8 Hz, 2H), 3.85-3.82 (m, 4H), 3.18 (d, J=4.8 Hz, 2H), 2.81 (t, J=4.4 Hz, 4H). LCMS (ESI): m/z=398.1 [M+H]⁺.

Examples 154 and 155

(S)—N-(2,2-Dimethyl-6-morpholino-1-oxido-2,3-dihydrobenzo[b]thiophen-5-yl)pyrazolo[1,5-a]pyrimidine-3-carboxamide and (R)—N-(2,2-Dimethyl-6-morpholino-1-oxido-2,3-dihydrobenzo[b]thiophen-5-yl)pyrazolo[1,5-a]pyrimidine-3-carboxamide

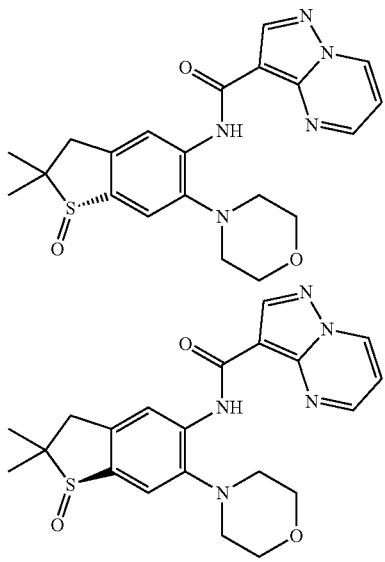

Step A. 1-(2,4-Difluorophenyl)-2-methylpropan-2-ol

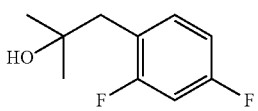

To a solution of methyl 2-(2,4-difluorophenyl)acetate (38.0 g, 204 mmol) in anhydrous tetrahydrofuran (300 mL) was added methylmagnesium bromide (3 M in ethyl ether; 204 mL, 612 mmol) dropwise at −78° C. The reaction was warmed to room temperature and stirred for 30 min. It was quenched with saturated aqueous ammonium chloride (200 mL) at 0° C. and extracted with ethyl acetate (300 mL×2). The combined organic phase was washed with brine (100 mL×2), dried over sodium sulfate and concentrated. The residue was purified by flash chromatography (eluting gradient: 0-10% ethyl acetate in petroleum ether) to afford 1-(2,4-difluorophenyl)-2-methyl-propan-2-ol (38 g, 100%) as a light yellow oil. ¹H NMR (400 MHz, CDCl₃) δ 7.25-7.17 (m, 1H), 6.85-6.75 (m, 2H), 2.77 (s, 2H), 1.23 (s, 6H).

Step B. 1-(2,4-Difluorophenyl)-2-methylpropan-2-yl carbamimidothioate

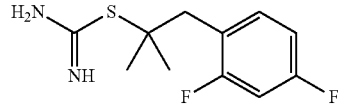 [SMILES: CC(C)(Cc1ccc(F)cc1F)SC(=N)N]

To a mixture of thiourea (6.13 g, 80.56 mmol) in trifluoroacetic acid (100 mL, 53.7 mmol) was added 1-(2,4-difluorophenyl)-2-methyl-propan-2-ol (10.0 g, 53.7 mmol) and stirred at 75° C. for 6 h under nitrogen. The mixture was taken up in ethyl acetate (150 mL×2) and washed with water (100 mL×2) and brine (80 mL×2), dried over sodium sulfate, and concentrated to afford crude 2-[2-(2,4-difluorophenyl)-1,1-dimethyl-ethyl]isothiourea (11.3 g, 86%) as a white solid. The crude product was used without further purification. LCMS (ESI): m/z=244.9 [M+H]⁺.

Step C. 6-Fluoro-2,2-dimethyl-3H-benzothiophene

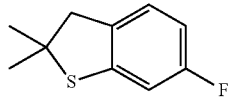

To a mixture of 2-[2-(2,4-difluorophenyl)-1,1-dimethyl-ethyl]isothiourea (6.32 g, 25.9 mmol) in dimethyl sulfoxide (50 mL) was added sodium hydroxide (4.14 g, 103 mmol) and stirred at 90° C. for 4 h. The reaction was diluted with water (80 mL) and extracted with ethyl acetate (150 mL×2). The combined organic phase was washed with water (80 mL×2) and brine (50 mL), dried over sodium sulfate, and concentrated. The residue was purified by flash chromatography (eluting gradient: 0-1% ethyl acetate in petroleum ether) to afford 6-fluoro-2,2-dimethyl-3H-benzothiophene (2.65 g, 56%) as a colorless oil. ¹H NMR (400 MHz, CDCl₃) δ 7.08-7.02 (m, 1H), 6.85 (dd, J=8.8, 2.4 Hz, 1H), 6.67 (dt, J=6.4, 2.4 Hz, 1H), 3.04 (s, 2H), 1.55 (s, 6H).

Step D. 6-Fluoro-2,2-dimethyl-5-nitro-2,3-dihydrobenzo[b]thiophene

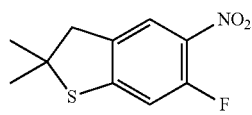

To a solution of 6-fluoro-2,2-dimethyl-3H-benzothiophene (2.0 g, 11.0 mmol) in acetic acid (20 mL) was added nitric acid (0.29 mL, 16.5 mmol) at 0° C. and stirred at 0 to 25° C. for 30 min. The reaction was diluted with water (30 mL) and extracted with dichloromethane (80 mL×2). The combined organic phase was washed with saturated aqueous sodium bicarbonate (30 mL×2), brine (30 mL), dried over sodium sulfate and concentrated. The residue was purified by preparatory thin layer chromatography (eluting gradient: 10% ethyl acetate in petroleum ether) to afford 6-fluoro-2,2-dimethyl-5-nitro-3H-benzothiophene (240 mg, 10%) as a light yellow oil. ¹H NMR (400 MHz, CDCl₃) δ 7.85 (d, J=7.6 Hz, 1H), 7.01 (d, J=10.8 Hz, 1H), 3.14 (s, 2H), 1.59 (s, 6H).

Step E. 4-(2,2-Dimethyl-5-nitro-3H-benzothiophen-6-yl)morpholine

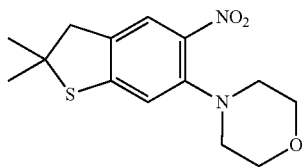 [SMILES: CC1(C)Cc2cc([N+](=O)[O-])c(N3CCOCC3)cc2S1]

To a mixture of 6-fluoro-2,2-dimethyl-5-nitro-3H-benzothiophene (240 mg, 1.06 mmol) in acetonitrile (10 mL) was added morpholine (920 mg, 10.6 mmol) and N,N-diisopropylethylamine (1.36 g, 10.56 mmol). The mixture was stirred at 75° C. for 3 h and concentrated. The residue was purified by preparatory thin layer chromatography (eluting gradient: 10% ethyl acetate in petroleum ether) to afford 4-(2,2-dimethyl-5-nitro-3H-benzothiophen-6-yl)morpholine (270 mg, 87%) as a yellow oil. ¹H NMR (400 MHz, CDCl₃) δ 7.71 (s, 1H), 6.89 (s, 1H), 3.86-3.83 (m, 4H), 3.09 (s, 2H), 3.04-3.01 (m, 4H), 1.58 (s, 6H). LCMS (ESI): m/z=294.9 [M+H]⁺.

Step F. 2,2-Dimethyl-6-morpholino-5-nitro-3H-benzothiophene 1-oxide

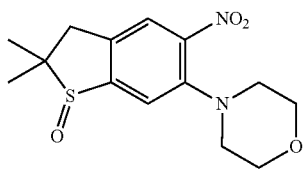 [SMILES: CC1(C)Cc2cc([N+](=O)[O-])c(N3CCOCC3)cc2S1=O]

To a mixture of 4-(2,2-dimethyl-5-nitro-3H-benzothiophen-6-yl)morpholine (270 mg, 0.92 mmol) in dichloromethane (8 mL) was added 3-chloroperoxybenzoic acid (186 mg, 0.92 mmol) and stirred at 25° C. for 2 h. The reaction was quenched with water (20 mL) and extracted with dichloromethane (30 mL×2). The combined organic phase was washed with water (20 mL×2) and brine (10 mL), dried over sodium sulfate and concentrated. The residue was purified by preparatory thin layer chromatography (eluting gradient: 50% ethyl acetate in petroleum ether) to afford 2,2-dimethyl-6-morpholino-5-nitro-3H-benzothiophene 1-oxide (75 mg, 26%) as a yellow oil. LCMS (ESI): m/z=310.9 [M+H]⁺.

Step G. 2,2-Dimethyl-6-morpholino-1-oxo-3H-benzothiophen-5-amine

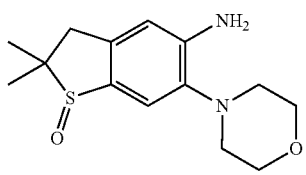 [SMILES: CC1(C)Cc2cc(N)c(N3CCOCC3)cc2S1=O]

To a solution of 2,2-dimethyl-6-morpholino-5-nitro-3H-benzothiophene 1-oxide (90 mg, 0.29 mmol) in water (2 mL) and ethanol (10 mL) was added ammonium chloride (77.6 mg, 1.45 mmol) and iron (81 mg, 1.45 mmol). The reaction was stirred at 80° C. for 2 h and filtered over Celite. The filtrate was concentrated, and the resulting residue was diluted with water (15 mL) and extracted with ethyl acetate (20 mL×2). The combined organic phase was washed with brine (15 mL×2), dried over sodium sulfate and concentrated. The residue was purified by flash chromatography (eluting gradient: 0-10% methanol in dichloromethane) to afford 2,2-dimethyl-6-morpholino-1-oxo-3H-benzothiophen-5-amine (70 mg, 86%) as a white solid. LCMS (ESI): m/z=280.9 [M+H]⁺.

Step H (S)—N-(2,2-Dimethyl-6-morpholino-1-oxido-2,3-dihydrobenzo[b]thiophen-5-yl)pyrazolo[1,5-a]pyrimidine-3-carboxamide and (R)—N-(2,2-Dimethyl-6-morpholino-1-oxido-2,3-dihydrobenzo[b]thiophen-5-yl)pyrazolo[1,5-a]pyrimidine-3-carboxamide

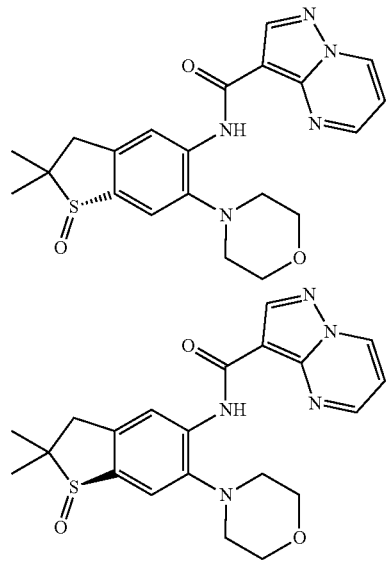

To a solution of 2,2-dimethyl-6-morpholino-1-oxo-3H-benzothiophen-5-amine (70 mg, 0.25 mmol) in pyridine (3 mL) was added pyrazolo[1,5-a]pyrimidine-3-carbonyl chloride (54.4 mg, 0.30 mmol) and stirred at 50° C. for 2 h. The reaction was concentrated and diluted with water (10 mL), and extracted with ethyl acetate (30 mL×2). The combined organic phase was washed with brine (10 mL×2), dried over sodium sulfate, filtered and concentrated. The residue was purified by flash chromatography (eluting gradient: 50% ethyl acetate in petroleum ether) to afford N-(2,2-dimethyl-6-morpholino-1-oxido-2,3-dihydrobenzo[b]thiophen-5-yl)pyrazolo[1,5-a]pyrimidine-3-carboxamide (50 mg, 47%) as a yellow solid. LCMS (ESI): m/z=426.0 [M+H]⁺. The mixture was resolved by chiral preparatory SFC to afford (R)—N-(2,2-dimethyl-6-morpholino-1-oxido-2,3-dihydrobenzo[b]thiophen-5-yl)pyrazolo[1,5-a]pyrimidine-3-carboxamide (20 mg, 40%; RT=3.916 min) and (S)—N-(2,2- dimethyl-6-morpholino-1-oxido-2,3-dihydrobenzo[b]thiophen-5-yl)pyrazolo[1,5-a]pyrimidine-3-carboxamide (19 mg, 38%; RT=4.990 min) as yellow solids. Absolute stereochemistry was assigned arbitrarily.

Example 154, Peak 1: $^1$H NMR (400 MHz, CDCl$_3$) δ 10.83 (s, 1H), 8.86 (dd, J=7.2, 2.0 Hz, 1H), 8.82 (dd, J=4.4, 1.6 Hz, 1H), 8.80 (s, 1H), 8.74 (s, 1H), 7.68 (s, 1H), 7.12 (dd, J=7.2, 4.4 Hz, 1H), 4.00 (t, J=4.4 Hz, 4H), 3.55 (d, J=16.0 Hz, 1H), 3.05-2.96 (m, 5H), 1.55 (s, 3H), 1.35 (s, 3H). LCMS (ESI): m/z=426.0 [M+H]$^+$.

Example 155, Peak 2: $^1$H NMR (400 MHz, CDCl$_3$) δ 10.83 (s, 1H), 8.85 (dd, J=6.8, 2.0 Hz, 1H), 8.81 (dd, J=4.0, 1.6 Hz, 1H), 8.79 (s, 1H), 8.73 (s, 1H), 7.67 (s, 1H), 7.12 (dd, J=6.8, 4.0 Hz, 1H), 3.99 (t, J=4.4 Hz, 4H), 3.55 (d, J=16.0 Hz, 1H), 3.03-2.94 (m, 5H), 1.54 (s, 3H), 1.34 (s, 3H). LCMS (ESI): m/z=426.0 [M+H]$^+$.

Examples 156 and 157. N-[(1R)-6-(Dimethylamino)-1-hydroxy-2,2-dimethyl-indan-5-yl]pyrazolo[1,5-a]pyrimidine-3-carboxamide and N-[(1S)-6-(Dimethylamino)-1-hydroxy-2,2-dimethyl-indan-5-yl]pyrazolo[1,5-a]pyrimidine-3-carboxamide

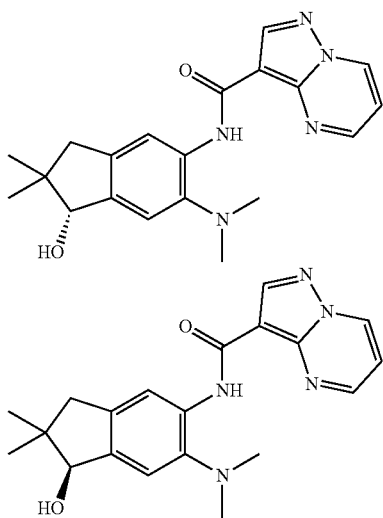

Step A. N-Indan-5-ylacetamide

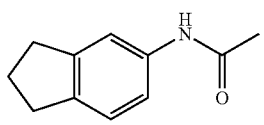

To a stirred solution of 2,3-dihydro-1H-inden-5-ylamine (2.80 g, 21.0 mmol) in dichloromethane (40 mL) was added triethylamine (3.19 g, 31.5 mmol) followed by dropwise addition of acetyl chloride (4.95 g, 63.1 mmol) at 0° C. The reaction mixture was stirred at 26° C. for 12 h. The reaction mixture was diluted with water (20 mL) and extracted with dichloromethane (40 mL×2). The combined organic phase was washed with brine (20 mL×2), dried over sodium sulfate, filtered and concentrated. The residue was purified by flash chromatography (eluting gradient: 50% ethyl acetate in petroleum ether) to afford N-indan-5-ylacetamide (3.40 g, 92%) as a white solid. $^1$H NMR (400 MHz, CDCl$_3$) δ 7.43 (s, 1H), 7.22 (br s, 1H), 7.14 (s, 2H), 2.90-2.83 (m, 4H), 2.15 (s, 3H), 2.06 (quintet, J=7.6 Hz, 2H).

Step B. N-(6-Bromoindan-5-yl)acetamide

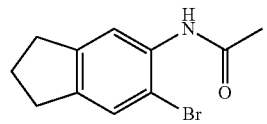

To a stirred solution of N-indan-5-ylacetamide (1.7 g, 9.7 mmol) in acetic acid (40 mL) was added dropwise bromine (0.21 mL, 4.19 mmol) in acetic acid (3 mL) at 0° C. over a period of 20 min. The mixture was stirred at 26° C. for 12 h under nitrogen, after which the reaction was quenched with addition of water until no more precipitate formed. The precipitate was collected, washed with water, and dried under vacuum to give N-(6-bromoindan-5-yl)acetamide (2.1 g, 85%) as a white solid. $^1$H NMR (400 MHz, CDCl$_3$) δ 8.10 (s, 1H), 7.50 (br s, 1H), 7.35 (s, 1H), 2.85 (q, J=7.6 Hz, 4H), 2.21 (s, 3H), 2.06 (quintet, J=7.6 Hz, 2H).

Step C. N-(6-Bromo-1-oxo-indan-5-yl)acetamide

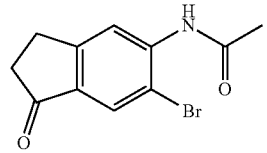

To a stirred solution of N-(6-bromoindan-5-yl)acetamide (1.0 g, 3.94 mmol) in acetic acid (20 mL) was added chromium trioxide (1.57 g, 15.7 mmol) in 50% aqueous acetic acid (10 mL). The reaction was stirred at 55° C. for 20 min, cooled to 0° C. and quenched with 2-propanol (10 mL). The solvent was removed in vacuo, water (30 mL) was added and extracted with ethyl acetate (100 mL×2). The combined organic phase was washed with brine (50 mL×2), dried over sodium sulfate, filtered and concentrated. The residue was purified by flash chromatography (eluting gradient: 0-5% ethyl acetate in dichloromethane) to afford N-(6-bromo-1-oxo-indan-5-yl)acetamide (400 mg, 38%) as a white solid. $^1$H NMR (400 MHz, CDCl$_3$) δ 8.60 (s, 1H), 7.94 (s, 1H), 7.91 (br s, 1H), 3.13-3.09 (m, 2H), 2.73-2.69 (m, 2H), 2.30 (s, 3H).

Step D. 5-Amino-6-bromo-indan-1-one

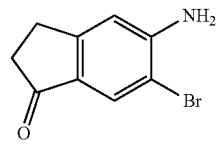 [SMILES: Nc1cc2c(cc1Br)C(=O)CC2]

A mixture of N-(6-bromo-1-oxo-indan-5-yl)acetamide (400 mg, 1.49 mmol) and 6 M aqueous hydrochloric acid (8.96 mL, 53.73 mmol) was stirred at 100° C. for 1 h under nitrogen. The solution was cooled to 0° C. and adjusted to pH 8 with 10 M aqueous sodium hydroxide. The precipitate formed was collected, washed with water, and dried under vacuum to afford 5-amino-6-bromo-indan-1-one (300 mg, 89%) as a light brown powder. ¹H NMR (400 MHz, CDCl₃) δ 7.87 (s, 1H), 6.74 (s, 1H), 4.67 (br s, 2H), 3.05-2.95 (m, 2H), 2.70-2.61 (m, 2H).

Step E. 6-Bromo-5-nitro-indan-1-one

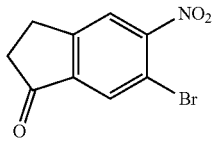 [SMILES: O=C1CCc2cc([N+](=O)[O-])c(Br)cc21]

To a solution of 5-amino-6-bromo-indan-1-one (1.0 g, 4.42 mmol) in 20% aqueous fluoroboric acid (5.0 mL, 8.85 mmol) at 0° C. was added dropwise 4 M aqueous sodium nitrite (0.6 g, 8.33 mmol) over a period of 5 min. The mixture was stirred for 30 min. The resulting foamy suspension was added portion-wise to a vigorously stirred mixture of copper (1.3 g, 21.0 mmol) and sodium nitrite (4.6 g, 66.4 mmol) in water (8 mL) at 26° C. over a period of 15 min. During the addition, excessive foaming was broken up by the addition of small amounts of diethyl ether. After being stirred for an additional 30 min, the reaction mixture was diluted with water (8 mL) and extracted with ethyl acetate (20 mL×4). The combined organic phase was washed with brine (8 mL×2), dried over sodium sulfate, filtered and concentrated. The residue was purified by flash chromatography (eluting gradient: 0-50% ethyl acetate in petroleum ether) to afford 6-bromo-5-nitro-indan-1-one (320 mg, 28%) as a yellow solid. ¹H NMR (400 MHz, CDCl₃) δ 8.00 (s, 1H), 7.78 (s, 1H), 3.16-3.11 (m, 2H), 2.78-2.73 (m, 2H).

Step F. 6-Bromo-2,2-dimethyl-5-nitro-indan-1-one

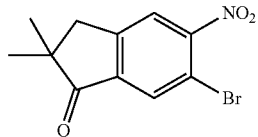 [SMILES: CC1(C)Cc2cc([N+](=O)[O-])c(Br)cc2C1=O]

To a mixture of 6-bromo-5-nitro-indan-1-one (1.0 g, 3.9 mmol) and iodomethane (2.2 g, 15.6 mmol) in N,N-dimethylformamide (10 mL) was added 60% sodium hydride (468 mg, 11.7 mmol) in batches at 0° C. The reaction mixture was stirred at 0° C. for 30 min, after which it was quenched with saturated aqueous ammonium chloride (10 mL) and water (10 mL). The mixture was extracted with ethyl acetate (30 mL×2), and the combined organic phase was washed with brine (10 mL×2), dried over sodium sulfate, filtered and concentrated. The residue was purified by preparatory thin layer chromatography (eluting gradient: 10% ethyl acetate in petroleum ether) to afford 6-bromo-2,2-dimethyl-5-nitro-indan-1-one (260 mg, 23%) as a yellow solid. ¹H NMR (400 MHz, CDCl₃) δ 8.08 (s, 1H), 7.80 (s, 1H), 3.04 (s, 2H), 1.28 (s, 6H).

Step G.
6-(Dimethylamino)-2,2-dimethyl-5-nitro-indan-1-one

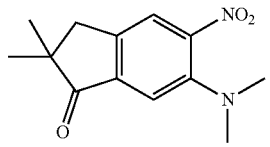

To a stirred solution of 6-bromo-2,2-dimethyl-5-nitro-indan-1-one (200 mg, 0.70 mmol) in dimethyl sulfoxide (8 mL) was added N,N-dimethylamine HCl salt (127 mg, 2.82 mmol) and N,N-diisopropylethylamine (273 mg, 2.11 mmol). The mixture was stirred at 110° C. for 16 h, after which it was diluted with water (20 mL) and extracted with ethyl acetate (40 mL×2). The combined organic phase was washed with brine (15 mL×2), dried over sodium sulfate, filtered and concentrated. The residue was purified by flash chromatography (eluting gradient: 0-10% ethyl acetate in petroleum ether) to afford 6-(dimethylamino)-2,2-dimethyl-5-nitro-indan-1-one (60 mg, 34%) as a yellow solid. LCMS (ESI): m/z=248.9 [M+H]⁺.

Step H.
5-Amino-6-(dimethylamino)-2,2-dimethyl-indan-1-one

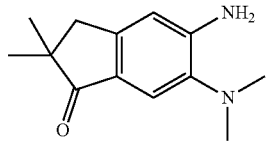

A mixture of 6-(dimethylamino)-2,2-dimethyl-5-nitro-indan-1-one (80 mg, 0.32 mmol), iron (90 mg, 1.61 mmol) and ammonium chloride (86 mg, 1.61 mmol) in ethanol (20 mL) and water (4 mL) was stirred at 80° C. for 2 h under nitrogen. The reaction mixture was filtered, and the filtrate was concentrated to afford 5-amino-6-(dimethylamino)-2,2-dimethyl-indan-1-one (65 mg, 92%) as a light yellow solid. LCMS (ESI): m/z=219.0 [M+H]⁺.

Step I. 5-Amino-6-(dimethylamino)-2,2-dimethyl-2,3-dihydro-1H-inden-1-ol

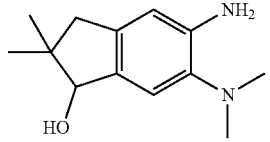

To a stirred solution of 5-amino-6-(dimethylamino)-2,2-dimethyl-indan-1-one (54 mg, 0.25 mmol) in tetrahydrofuran (6 mL) and methanol (1 mL) was added sodium borohydride (19 mg, 0.50 mmol) at 0° C. The reaction mixture was stirred at 0° C. for 10 min and 28° C. for 4.5 h under nitrogen, after which it was diluted with water (15 mL) and extracted with ethyl acetate (20 mL×2). The combined organic phase was washed with brine (10 mL×2), dried over sodium sulfate, filtered and concentrated to afford crude 5-amino-6-(dimethylamino)-2,2-dimethyl-indan-1-ol (50 mg, 91%) as a yellow solid. LCMS (ESI): m/z=221.0 [M+H]$^+$.

Step J. N-[(1R)-6-(Dimethylamino)-1-hydroxy-2,2-dimethyl-indan-5-yl]pyrazolo[1,5-a]pyrimidine-3-carboxamide and N-[(1S)-6-(Dimethylamino)-1-hydroxy-2,2-dimethyl-indan-5-yl]pyrazolo[1,5-a]pyrimidine-3-carboxamide

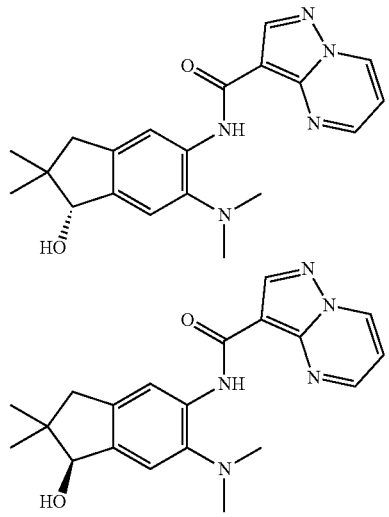

A mixture of 5-amino-6-(dimethylamino)-2,2-dimethyl-indan-1-ol (60 mg, 0.27 mmol) and pyrazolo[1,5-a]pyrimidine-3-carbonyl chloride (99 mg, 0.54 mmol) in pyridine (10 mL) was stirred at 28° C. for 18 h. The reaction mixture was concentrated, diluted with water (10 mL) and extracted with ethyl acetate (30 mL×2). The combined organic phase was washed with brine (10 mL×2), dried over sodium sulfate, filtered and concentrated. The residue was purified by preparatory thin layer chromatography (eluting gradient: 50% ethyl acetate in petroleum ether) to afford N-[6-(dimethylamino)-1-hydroxy-2,2-dimethyl-indan-5-yl]pyrazolo[1,5-a]pyrimidine-3-carboxamide (40 mg, 40%) as a light yellow solid. The mixture was resolved by chiral preparatory SFC to afford N-[(1R)-6-(dimethylamino)-1-hydroxy-2,2-dimethyl-indan-5-yl]pyrazolo[1,5-a]pyrimidine-3-carboxamide (18 mg, 45%; RT=5.208 min) and N-[(1S)-6-(dimethylamino)-1-hydroxy-2,2-dimethyl-indan-5-yl]pyrazolo[1,5-a]pyrimidine-3-carboxamide (19 mg, 48%; RT=6.678 min) as yellow solids with absolute stereochemistry assigned arbitrarily.

Example 156, Peak 1: $^1$H NMR (400 MHz, CDCl$_3$) δ 10.78 (s, 1H), 8.82 (dd, J=7.2, 1.6 Hz, 1H), 8.78 (s, 1H), 8.72 (dd, J=4.0, 1.6 Hz, 1H), 8.46 (s, 1H), 7.25 (s, 1H), 7.04 (dd, J=7.2, 4.0 Hz, 1H), 4.66 (d, J=5.2 Hz, 1H), 2.83-2.64 (m, 8H), 1.19 (s, 3H), 1.07 (s, 3H). LCMS (ESI): m/z=366.1 [M+H]$^+$.

Example 157, Peak 2: $^1$H NMR (400 MHz, CDCl$_3$) δ 10.78 (s, 1H), 8.82 (dd, J=6.8, 1.6 Hz, 1H), 8.78 (s, 1H), 8.72 (dd, J=4.4, 2.0 Hz, 1H), 8.46 (s, 1H), 7.25 (s, 1H), 7.04 (dd, J=7.2, 4.0 Hz, 1H), 4.66 (d, J=6.8 Hz, 1H), 2.82-2.66 (m, 8H), 1.20 (s, 3H), 1.07 (s, 3H). LCMS (ESI): m/z=366.0 [M+H]$^+$.

BIOLOGICAL EXAMPLES

Compounds were assayed for inhibition of human IRAK4 and IRAK1 catalytic activity using recombinant enzyme produced from insect cells. Full-length IRAK4 protein, carrying an N-terminal His6-Tag, was obtained from Life Technologies (Carlsbad, Calif., USA). The IRAK1 construct was produced internally and was comprised of IRAK1 residues Arg194 to Ser712, preceded by an NH2-terminal His6 tag and the coding sequence for glutathione-S-transferase.

Kinase activities were assayed using the Transcreener-Fluorecescence polarization platform (BelBrook Labs, Madison, Wis., USA) that measures amounts of the reaction product, ADP. The IRAK4 reaction conditions were optimized using an IRAK1-derived peptide (sequence H-KKARFSRFAGSSPSQSSMVAR) to provide a linear reaction rate over the course of a 90 min incubation, which resulted in 10-12% conversion of the starting ATP to ADP. Final IRAK4 assay conditions were 1.25 nM IRAK4; 125 uM ATP; 10 uM MgCl$_2$; 125 uM peptide in reaction buffer (25 mM HEPES (pH7.4); 2 mM Dithiothreitol; 0.015% Brij-35; and 0.5% dimethyl sulfoxide. The IRAK1 activity was optimized similarly, yielding final assay conditions of 1.5 nM IRAK1; 62.5 uM ATP; 5 uM MgCl$_2$, and 62.5 uM IRAK1 peptide in reaction buffer for 60 min.

Assays of compounds for kinase inhibition were performed using inhibitors serially-diluted in dimethyl sulfoxide, which was accomplished with a LabCyte Echo 555 liquid dispenser. 384 well assay plates spotted with compound received 4 ul of a 2× substrate (ATP+peptide) mix in reaction buffer, followed by 4 ul of 2× enzyme diluted in reaction buffer. Reactions were halted at 60 (IRAK1) or 90 (IRAK4) min by addition of 6 ul of detection buffer, containing EDTA (40 nM final concentration), 0.95 ug of the ADP-binding antibody ADP2, ADP tracer (3 nM final concentration), and 25 uM HEPES. Following a 1 hr incubation, fluorescence polarization of the ADP2-antibody::TRACER complex was read on a Tecan M1000 plate reader using a 635/20 excitation filter in combination with a 670/20 emission filter. Delta milli-P values were analyzed using Genedata software to fit dose-response curves and compute compound Ki values, using ATP Km values of 642 um and 83.2 uM for IRAK4 and IRAK1, respectively. Table 14 provides IRAK4 Ki values for representative compounds of the present invention.

TABLE 14

IRAK4 Ki values of representative compounds of the present invention.

| Example | IRAK4 Ki (uM) |
|---|---|
| 1 | 0.0074 |
| 2 | 0.0051 |
| 3 | 0.0037 |
| 4 | 0.041 |
| 5 | 0.018 |
| 6 | 0.0053 |
| 7 | 0.01 |
| 8 | 0.0038 |
| 9 | 0.0039 |
| 10 | 0.0023 |
| 11 | 0.0046 |
| 12 | 0.0052 |
| 13 | 0.0081 |
| 14 | 0.0052 |
| 15 | 0.0094 |
| 16 | 0.014 |

TABLE 14-continued

IRAK4 Ki values of representative compounds of the present invention.

| Example | IRAK4 Ki (uM) |
|---|---|
| 17 | 0.0084 |
| 18 | 0.0067 |
| 19 | 0.053 |
| 20 | 0.017 |
| 21 | 0.11 |
| 22 | 0.46 |
| 23 | 0.25 |
| 24 | 0.16 |
| 25 | 0.09 |
| 26 | 0.28 |
| 27 | 0.67 |
| 28 | 0.26 |
| 29 | 0.78 |
| 30 | 0.066 |
| 31 | 0.06 |
| 32 | 0.72 |
| 33 | 0.23 |
| 34 | |
| 35 | 0.1 |
| 36 | 0.014 |
| 37 | 0.0077 |
| 38 | 0.18 |
| 39 | 0.0041 |
| 40 | 0.00087 |
| 41 | 0.0046 |
| 42 | 0.022 |
| 43 | 0.0032 |
| 44 | 0.22 |
| 45 | 0.12 |
| 46 | 0.042 |
| 47 | 0.053 |
| 48 | 0.24 |
| 49 | 0.93 |
| 50 | |
| 51 | |
| 52 | |
| 53 | |
| 54 | |
| 55 | |
| 56 | |
| 57 | |
| 58 | 0.019 |
| 59 | 0.03 |
| 60 | 0.0011 |
| 61 | 0.00028 |
| 62 | 0.0092 |
| 63 | 0.0053 |
| 64 | 0.00051 |
| 65 | 0.00026 |
| 66 | 0.00067 |
| 67 | 0.0011 |
| 68 | 0.0025 |
| 69 | 0.0018 |
| 70 | 0.0007 |
| 71 | 0.0032 |
| 72 | 0.001 |
| 73 | 0.0037 |
| 74 | |
| 75 | |
| 76 | |
| 77 | 0.00063 |
| 78 | 0.00017 |
| 79 | 0.00097 |
| 80 | 0.00097 |
| 81 | 0.00042 |
| 82 | 0.00037 |
| 83 | 0.00071 |
| 84 | 0.00049 |
| 85 | 0.0018 |
| 86 | 0.0013 |
| 87 | 0.00059 |
| 88 | 0.0005 |
| 89 | 0.0013 |
| 90 | 0.00061 |
| 91 | 0.28 |
| 92 | 0.0037 |
| 93 | 0.022 |
| 94 | 0.0049 |
| 95 | 0.0019 |
| 96 | 0.0015 |
| 97 | 0.0052 |
| 98 | 0.0085 |
| 99 | |
| 100 | 0.0018 |
| 101 | 0.012 |
| 102 | 0.0065 |
| 103 | 0.0054 |
| 104 | 0.005 |
| 105 | 0.0034 |
| 106 | 0.0021 |
| 107 | 0.0065 |
| 108 | 0.0013 |
| 109 | 0.0026 |
| 110 | 0.0075 |
| 111 | 0.0099 |
| 112 | 0.0026 |
| 113 | 0.0075 |
| 114 | |
| 115 | |
| 116 | |
| 117 | |
| 118 | |
| 119 | |
| 120 | |
| 121 | |
| 122 | |
| 123 | |
| 124 | |
| 125 | |
| 126 | |
| 127 | |
| 128 | |
| 129 | |
| 130 | |
| 131 | 0.0064 |
| 132 | 0.019 |
| 133 | 0.0057 |
| 134 | |
| 135 | 0.00063 |
| 136 | |
| 137 | |
| 138 | |
| 139 | |
| 140 | |
| 141 | |
| 142 | |
| 143 | |
| 144 | |
| 145 | 0.06 |
| 146 | 0.0081 |
| 147 | 0.048 |
| 148 | 0.016 |
| 149 | |
| 150 | |
| 151 | 0.0082 |
| 152 | 0.21 |
| 153 | 0.28 |
| 154 | 0.022 |
| 155 | 0.56 |
| 156 | 0.016 |
| 157 | 0.31 |

Blank = not determined

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually.

What is claimed is:

1. A compound of Formula I:

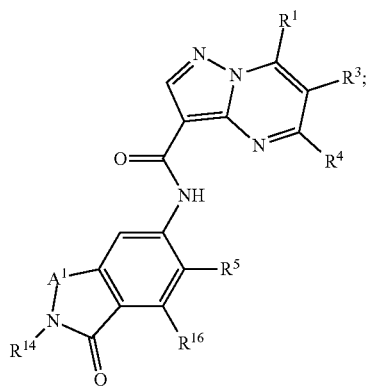

Formula I;

or a stereoisomer or a pharmaceutically acceptable salt thereof, wherein:

$A^1$ is $CH_2$ or NH;
$R^1$ is hydrogen;
$R^3$ is hydrogen, halogen, —OH, or $C_{1-3}$alkyl;
$R^4$ is hydrogen, halogen, —$NR^8R^9$, —$C(O)NR^8R^9$, or a 3-7 membered monocyclic saturated or partially saturated heterocyclic group optionally substituted with one or more substituents selected from oxo, —$NR^8R^9$, or $R^{13}$;
$R^5$ is selected from the group consisting of —$NHCH_3$, —$N(CH_3)_2$, —$C(CH_3)_2OH$, —$OCH_3$, —$OCH(CH_3)_2$, —$OC(CH_3)_3$, —$OCH_2CH_3$, —$OCHF_2$, —$OCH_2CF_3$, —$OCH_2CHF_2$, —$CH_2OCHF_2$, —CN,

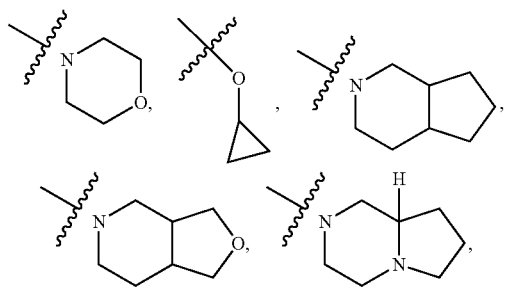

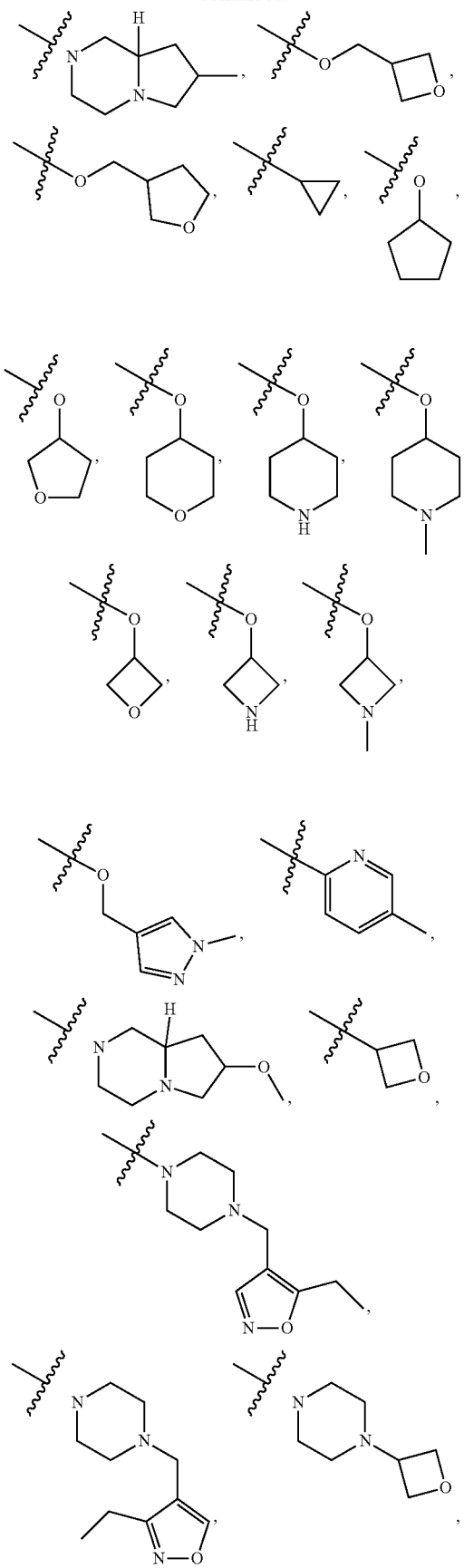

369
-continued
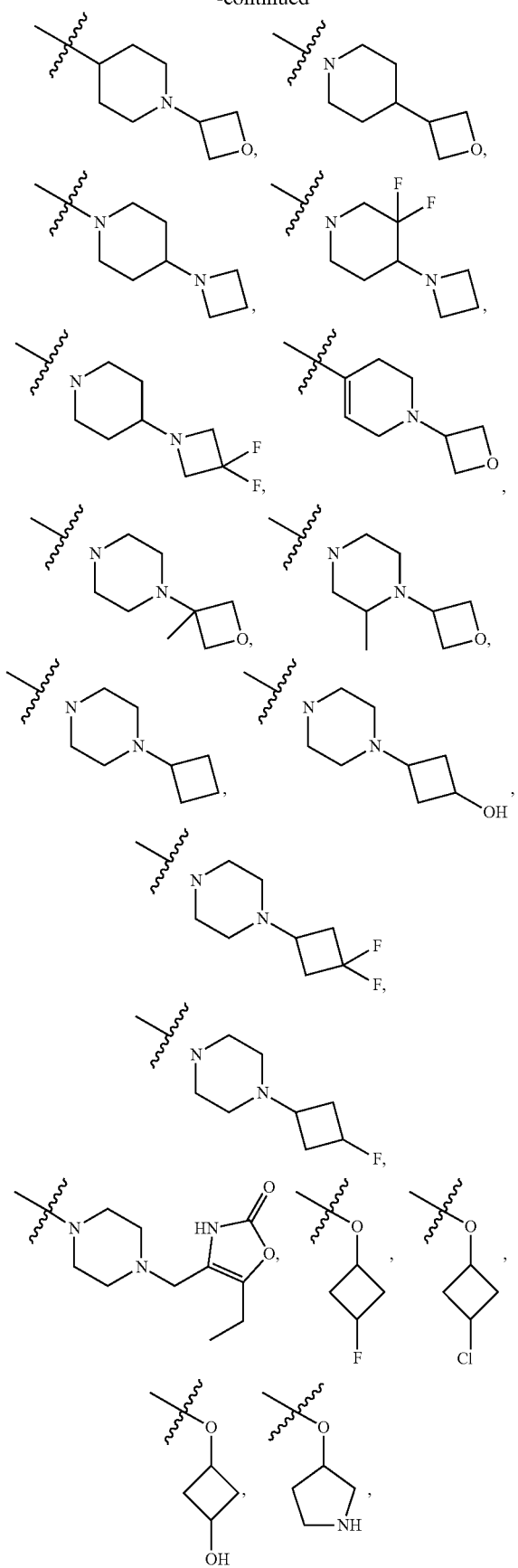
370
-continued
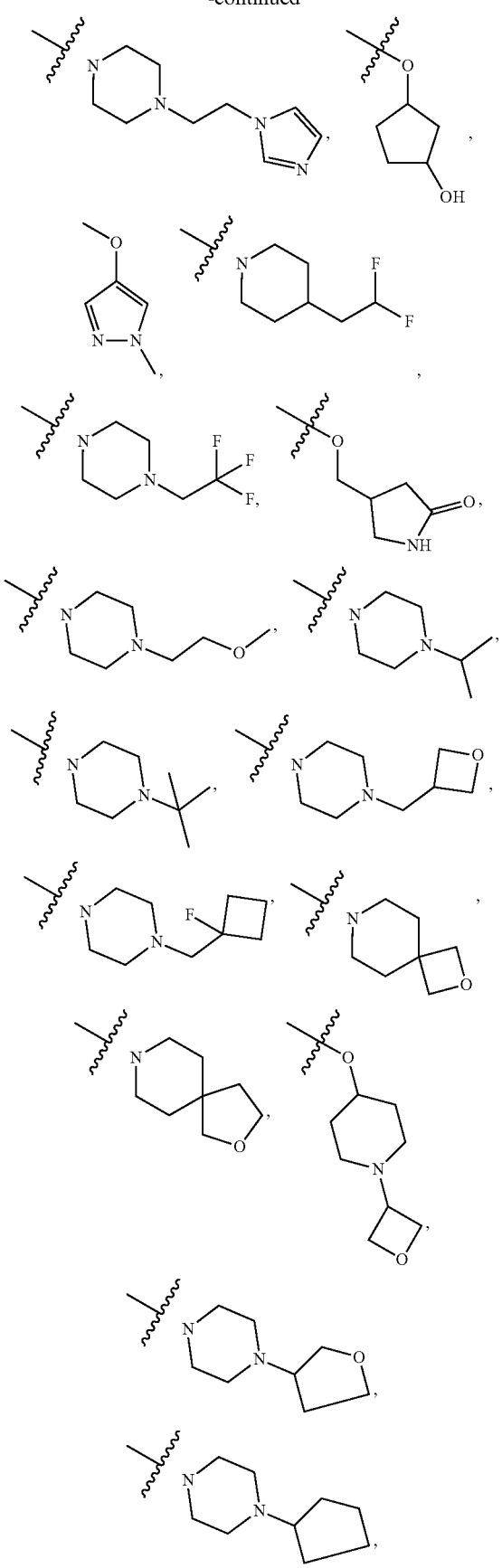

-continued

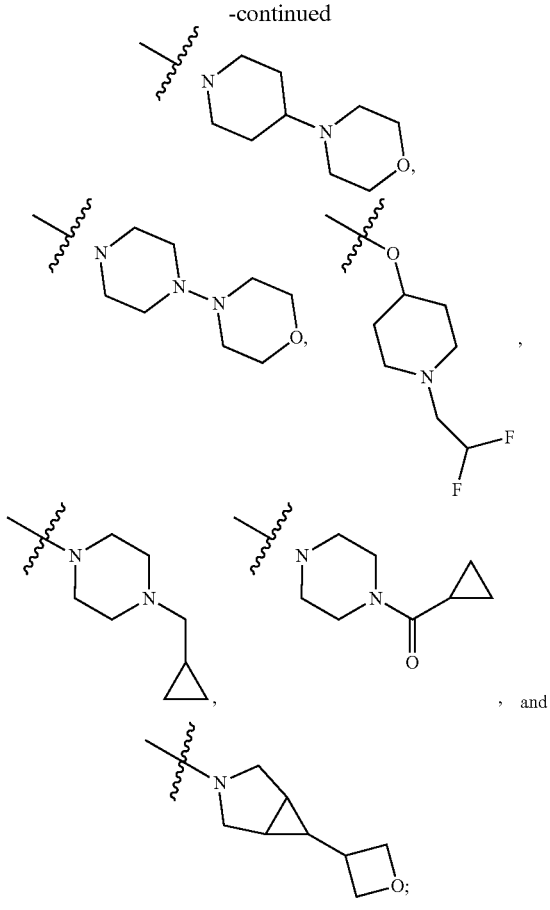

$R^8$ and $R^9$ are, independently at each occurrence, hydrogen, $C_{1-6}$alkyl optionally substituted with $R^{13}$, —C(O)$R^{13}$, $C_{3-6}$cycloalkyl group, or a 3-7 membered saturated or partially saturated heterocyclic group;

$R^{13}$ is, independently at each occurrence, $C_{1-6}$ alkyl, —NH$_2$, or halogen;

$R^{14}$ is selected from the group consisting of

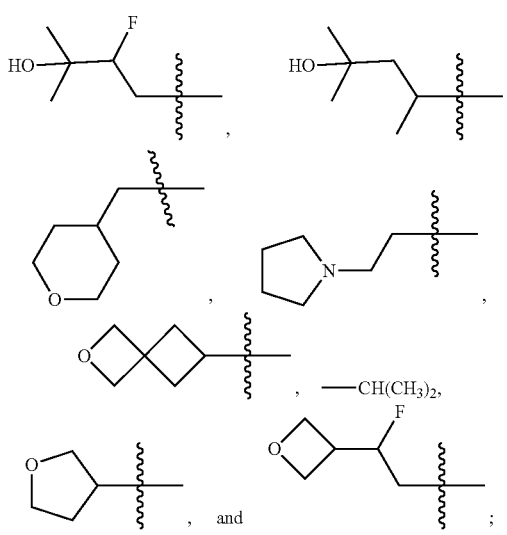

and $R^{16}$ is hydrogen, or $C_{1-3}$ alkyl optionally substituted with —NH$_2$ or —OH.

2. The compound of claim 1, or a stereoisomer or pharmaceutically acceptable salt thereof, wherein $R^3$ is hydrogen.

3. The compound of claim 1, or a stereoisomer or pharmaceutically acceptable salt thereof, wherein $R^3$ is selected from the group consisting of —Cl, —OH, —CH$_3$.

4. The compound of claim 1, or a stereoisomer or pharmaceutically acceptable salt thereof, wherein $R^4$ is hydrogen.

5. The compound of claim 1, or a stereoisomer or pharmaceutically acceptable salt thereof, wherein $R^4$ is —Cl.

6. The compound of claim 1, or a stereoisomer or pharmaceutically acceptable salt thereof, wherein $R^4$ is —C(O)NR$^8$R$^9$, wherein $R^8$ is hydrogen and $R^9$ is cyclopropyl.

7. The compound of claim 1, or a stereoisomer or pharmaceutically acceptable salt thereof, wherein $R^4$ is —NR$^8$R$^9$, wherein $R^8$ is hydrogen and $R^9$ is —C(O)R$^{13}$, wherein $R^{13}$ is methyl.

8. The compound of claim 1, or a stereoisomer or pharmaceutically acceptable salt thereof, wherein $R^4$ is selected from the group consisting of —Cl

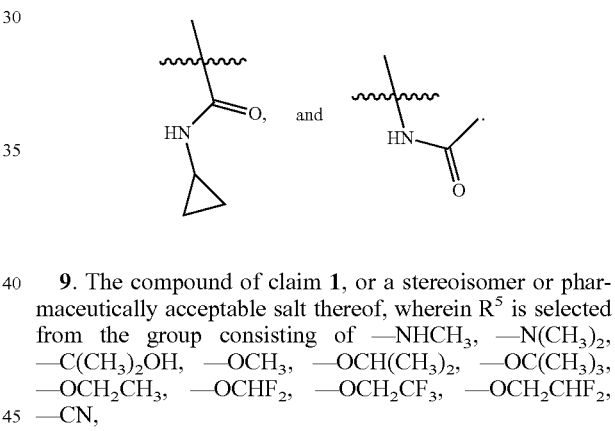

9. The compound of claim 1, or a stereoisomer or pharmaceutically acceptable salt thereof, wherein $R^5$ is selected from the group consisting of —NHCH$_3$, —N(CH$_3$)$_2$, —C(CH$_3$)$_2$OH, —OCH$_3$, —OCH(CH$_3$)$_2$, —OC(CH$_3$)$_3$, —OCH$_2$CH$_3$, —OCHF$_2$, —OCH$_2$CF$_3$, —OCH$_2$CHF$_2$, —CN,

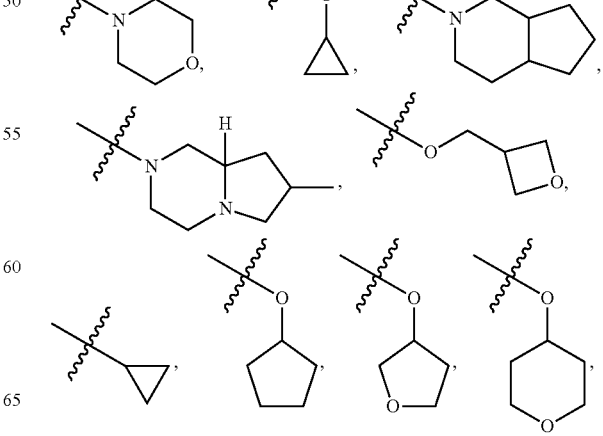

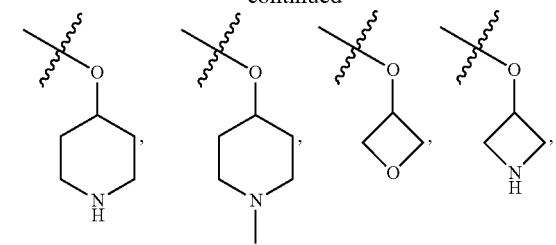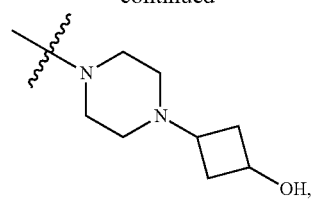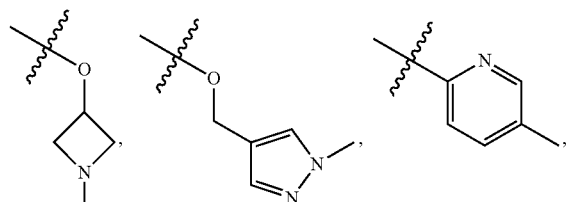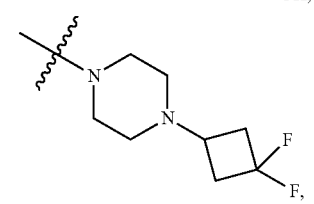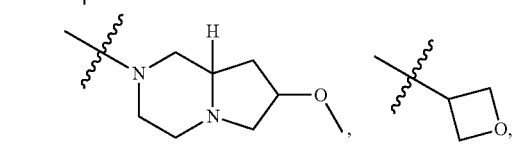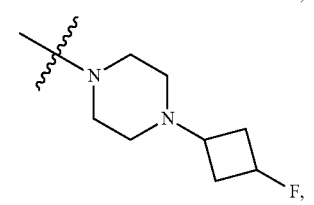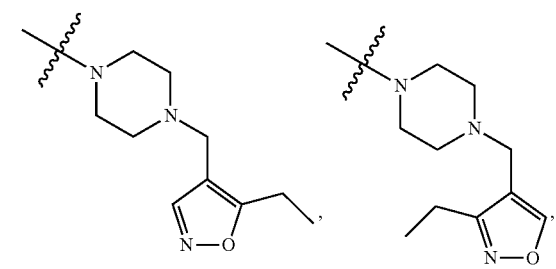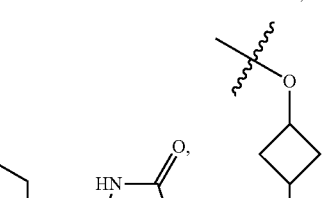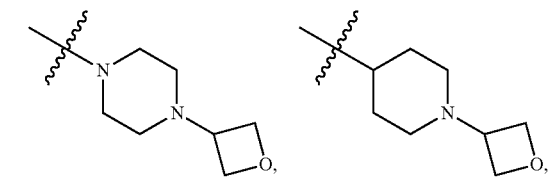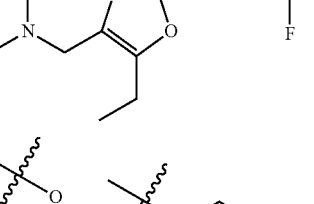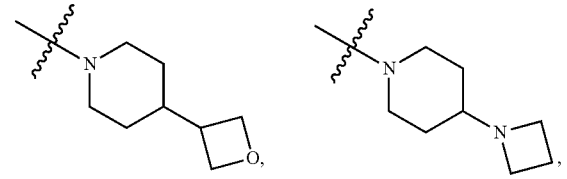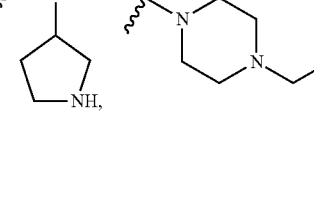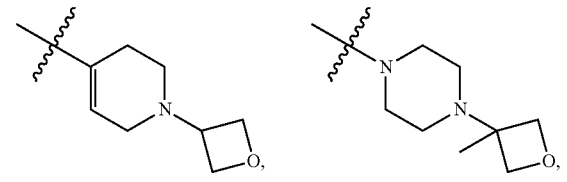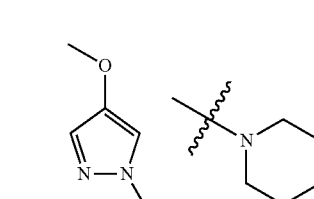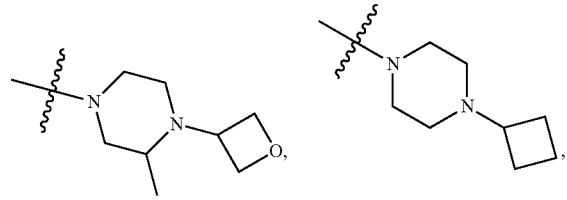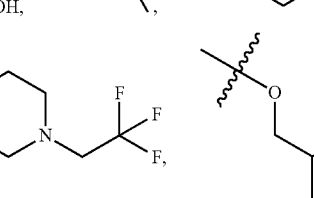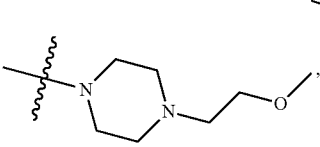

-continued
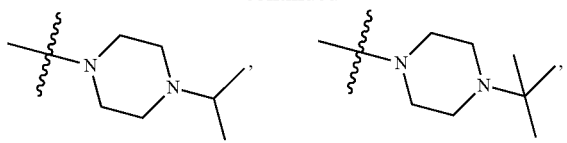
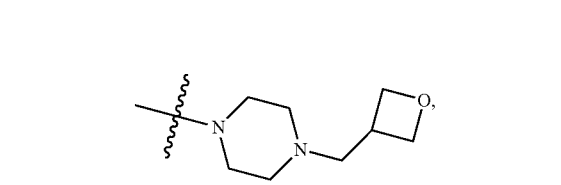
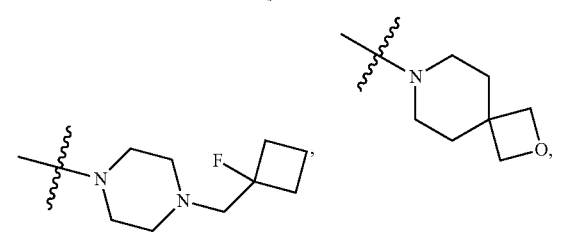
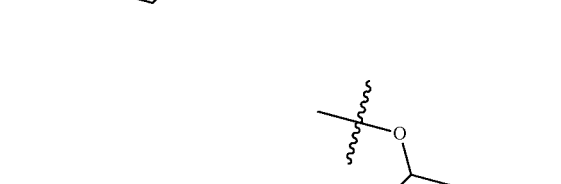
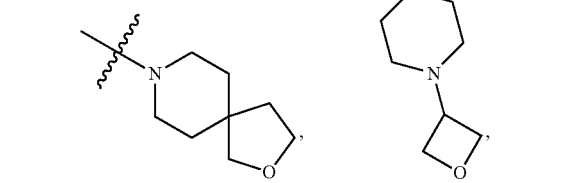
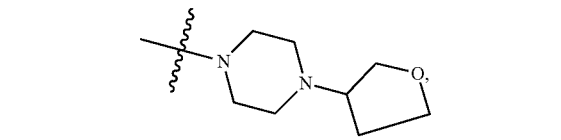
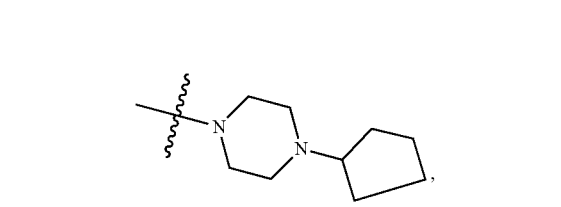
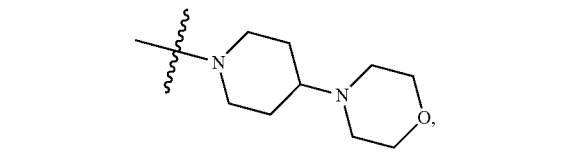
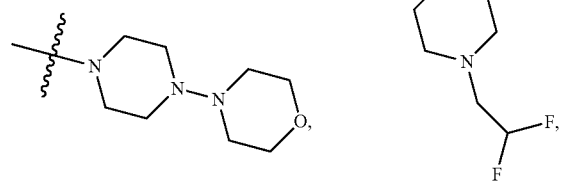
-continued
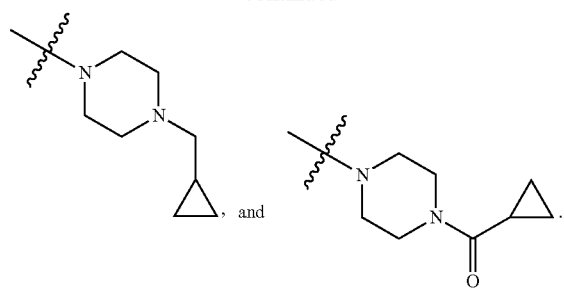
10. The compound of claim 9, or a stereoisomer or pharmaceutically acceptable salt thereof, wherein $R^5$ is selected from the group consisting of —OCHF$_2$, —OCH$_2$CHF$_2$,
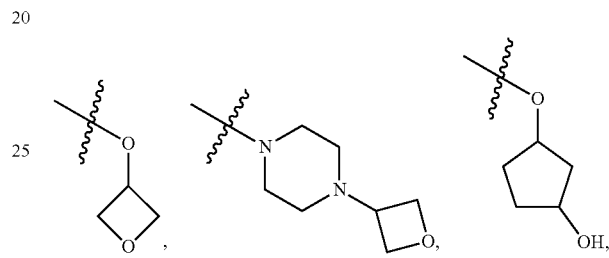
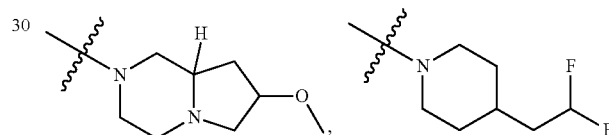
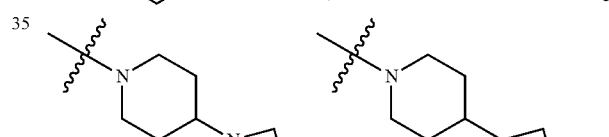
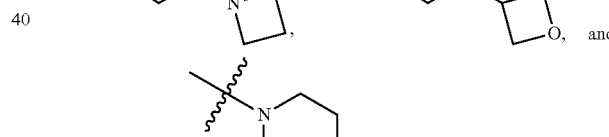
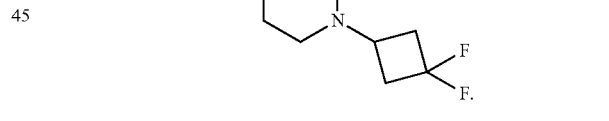
11. The compound of claim 1, or a stereoisomer or pharmaceutically acceptable salt thereof, wherein $R^{14}$ is selected from the group consisting of
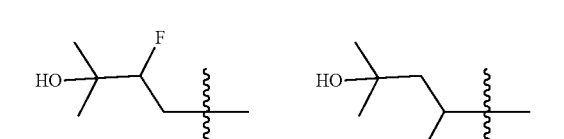
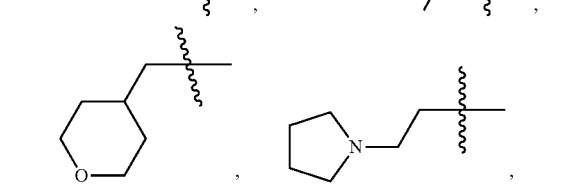

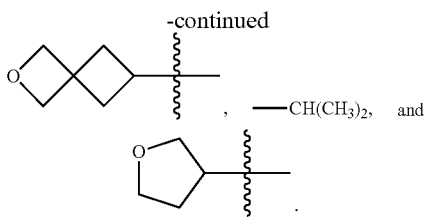
, —CH(CH₃)₂, and

12. The compound of claim 11, or a stereoisomer or pharmaceutically acceptable salt thereof, wherein R¹⁴ is

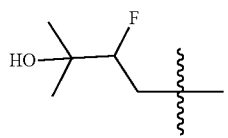

13. The compound of claim 1, or a stereoisomer or pharmaceutically acceptable salt thereof, wherein R¹⁶ is hydrogen.

14. The compound of claim 1, or a stereoisomer or pharmaceutically acceptable salt thereof, wherein R¹⁶ is —CH₂OH.

15. A pharmaceutical composition comprising a compound of claim 1, or a stereoisomer or pharmaceutically acceptable salt thereof, and a pharmaceutically acceptable excipient, carrier or diluent.

16. A compound according to claim 1 which compound is selected from the group consisting of:

(R)-N-(2-(2-Fluoro-3-hydroxy-3-methylbutyl)-6-((1-methyl-1H-pyrazol-4-yl)methoxy)-1-oxoisoindolin-5-yl)pyrazolo[1,5-a]pyrimidine-3-carboxamide;

(R)-N-(6-(2,2-Difluoroethoxy)-2-(2-fluoro-3-hydroxy-3-methylbutyl)-1-oxoisoindolin-5-yl)pyrazolo[1,5-a[pyrimidine-3-carboxamide;

N-(2-((R)-2-Fluoro-3-hydroxy-3-methylbutyl)-6-(((1S,3R)-3-hydroxycyclopentyl)oxy)-1-oxoisoindolin-5-yl)pyrazolo[1,5-a]pyrimidine-3-carboxamide;

N-(2-((R)-2-Fluoro-3-hydroxy-3-methylbutyl)-6-(((1R,3S)-3-hydroxycyclopentyl)oxy)-1-oxoisoindolin-5-yl)pyrazolo[1,5-a]pyrimidine-3-carboxamide;

(R)-N-(2-(2-Fluoro-3-hydroxy-3-methylbutyl)-6-((1-methylpiperidin-4-yl)oxy)-1-oxoisoindolin-5-yl)pyrazolo[1,5-a]pyrimidine-3-carboxamide;

(R)-N-(6-Cyclopropoxy-2-(2-fluoro-3-hydroxy-3-methylbutyl)-1-oxoisoindolin-5-yl)pyrazolo[1,5-a]pyrimidine-3-carboxamide;

(R)-N-(2-(2-Fluoro-3-hydroxy-3-methylbutyl)-6-(oxetan-3-ylmethoxy)-1-oxoisoindolin-5-yl)pyrazolo[1,5-a]pyrimidine-3-carboxamide;

(R)-N-(6-(Cyclopentyloxy)-2-(2-fluoro-3-hydroxy-3-methylbutyl)-1-oxoisoindolin-5-yl)pyrazolo[1,5-a]pyrimidine-3-carboxamide;

(R)-N-(6-Ethoxy-2-(2-fluoro-3-hydroxy-3-methylbutyl)-1-oxoisoindolin-5-yl)pyrazolo[1,5-a]pyrimidine-3-carboxamide;

(R)-N-(2-(2-Fluoro-3-hydroxy-3-methylbutyl)-6-methoxy-1-oxoisoindolin-5-yl)pyrazolo[1,5-a]pyrimidine-3-carboxamide;

(R)-N-(2-(2-Fluoro-3-hydroxy-3-methylbutyl)-6-(oxetan-3-yloxy)-1-oxoisoindolin-5-yl)pyrazolo[1,5-a]pyrimidine-3-carboxamide;

(R)-N-(6-(Difluoromethoxy)-2-(2-fluoro-3-hydroxy-3-methylbutyl)-1-oxoisoindolin-5-yl)pyrazolo[1,5-a]pyrimidine-3-carboxamide;

(R)-N-(2-(2-Fluoro-3-hydroxy-3-methylbutyl)-6-((1-methyl-1H-pyrazol-4-yl)oxy)-1-oxoisoindolin-5-yl)pyrazolo[1,5-a]pyrimidine-3-carboxamide;

(R)-N-(6-(tert-Butoxy)-2-(2-fluoro-3-hydroxy-3-methylbutyl)-1-oxoisoindolin-5-yl)pyrazolo[1,5-a]pyrimidine-3-carboxamide;

(R)-N-(6-(4-(2,2-Difluoroethyl)piperidin-1-yl)-2-(2-fluoro-3-hydroxy-3-methylbutyl)-1-oxoisoindolin-5-yl)pyrazolo[1,5-a]pyrimidine-3-carboxamide;

N-(6-Cyclopropyl-2-isopropyl-1-oxoisoindolin-5-yl)pyrazolo[1,5-a]pyrimidine-3-carboxamide;

(R)-N-(6-Cyano-2-(2-fluoro-3-hydroxy-3-methylbutyl)-1-oxoisoindolin-5-yl)pyrazolo[1,5-a]pyrimidine-3-carboxamide;

(R)-N-(2-(2-Fluoro-3-hydroxy-3-methylbutyl)-6-(4-morpholinopiperidin-1-yl)-1-oxoisoindolin-5-yl)pyrazolo[1,5-a]pyrimidine-3-carboxamide;

N-(2-((R)-2-Fluoro-3-hydroxy-3-methylbutyl)-6-((R)-hexahydropyrrolo[1,2-a]pyrazin-2(1H)-yl)-1-oxoisoindolin-5-yl)pyrazolo[1,5-a]pyrimidine-3-carboxamide;

N-(2-((R)-2-Fluoro-3-hydroxy-3-methylbutyl)-6-((7R,8aS)-7-methoxyhexahydropyrrolo[1,2-a]pyrazin-2(1H)-yl)-1-oxoisoindolin-5-yl)pyrazolo[1,5-a]pyrimidine-3-carboxamide;

(R)-5-Chloro-N-(2-(2-fluoro-3-hydroxy-3-methylbutyl)-6-morpholino-1-oxoisoindolin-5-yl)pyrazolo[1,5-a]pyrimidine-3-carboxamide;

(R)-N-(6-(4-((5-Ethylisoxazol-4-yl)methyl)piperazin-1-yl)-2-(2-fluoro-3-hydroxy-3-methylbutyl)-1-oxoisoindolin-5-yl)pyrazolo[1,5-a]pyrimidine-3-carboxamide;

(R)-N-(6-(4-((3-Ethylisoxazol-4-yl)methyl)piperazin-1-yl)-2-(2-fluoro-3-hydroxy-3-methylbutyl)-1-oxoisoindolin-5-yl)pyrazolo[1,5-a]pyrimidine-3-carboxamide;

(R)-N-(2-(2-Fluoro-3-hydroxy-3-methylbutyl)-6-(4-(oxetan-3-yl)piperazin-1-yl)-1-oxoisoindolin-5-yl)pyrazolo[1,5-a]pyrimidine-3-carboxamide;

(R)-N-(6-(4-(2-(1H-Imidazol-1-yl)ethyl)piperazin-1-yl)-2-(2-fluoro-3-hydroxy-3-methylbutyl)-1-oxoisoindolin-5-yl)pyrazolo[1,5-a]pyrimidine-3-carboxamide;

N-(2-((R)-2-Fluoro-3-hydroxy-3-methylbutyl)-6-((7R,8aR)-7-methoxyhexahydropyrrolo[1,2-a]pyrazin-2(1H)-yl)-1-oxoisoindolin-5-yl)pyrazolo[1,5-a]pyrimidine-3-carboxamide;

N-(2-((R)-2-Fluoro-3-hydroxy-3-methylbutyl)-6-((7S,8aR)-7-methoxyhexahydropyrrolo[1,2-a]pyrazin-2(1H)-yl)-1-oxoisoindolin-5-yl)pyrazolo[1,5-a]pyrimidine-3-carboxamide;

(R)-N-(2-(2-Fluoro-3-hydroxy-3-methylbutyl)-6-(4-(2-methoxyethyl)piperazin-1-yl)-1-oxoisoindolin-5-yl)pyrazolo[1,5-a]pyrimidine-3-carboxamide;

(R)-N-(2-(2-Fluoro-3-hydroxy-3-methylbutyl)-6-(4-isopropylpiperazin-1-yl)-1-oxoisoindolin-5-yl)pyrazolo[1,5-a]pyrimidine-3-carboxamide;

(R)-N-(2-(2-Fluoro-3-hydroxy-3-methylbutyl)-6-(4-(oxetan-3-ylmethyl)piperazin-1-yl)-1-oxoisoindolin-5-yl)pyrazolo[1,5-a]pyrimidine-3-carboxamide;

(R)-N-(2-(2-Fluoro-3-hydroxy-3-methylbutyl)-6-(4-(3-methyloxetan-3-yl)piperazin-1-yl)-1-oxoisoindolin-5-yl)pyrazolo[1,5-a]pyrimidine-3-carboxamide;

(R)-6-Chloro-N-(2-(2-fluoro-3-hydroxy-3-methylbutyl)-6-(4-(oxetan-3-yl)piperazin-1-yl)-1-oxoisoindolin-5-yl)pyrazolo[1,5-a]pyrimidine-3-carboxamide;

((R)-N-(2-(2-Fluoro-3-hydroxy-3-methylbutyl)-6-(4-(oxetan-3-yl)piperazin-1-yl)-1-oxoisoindolin-5-yl)-6-methylpyrazolo[1,5-a]pyrimidine-3-carboxamide;

(R)-N-(6-(4-(Azetidin-1-yl)piperidin-1-yl)-2-(2-fluoro-3-hydroxy-3-methylbutyl)-1-oxoisoindolin-5-yl)pyrazolo[1,5-a]pyrimidine-3-carboxamide;

(R)-N-(2-(2-Fluoro-3-hydroxy-3-methylbutyl)-6-(4-(oxetan-3-yl)piperidin-1-yl)-1-oxoisoindolin-5-yl)pyrazolo[1,5-a]pyrimidine-3-carboxamide;

(S)-N-(2-(4-Hydroxy-4-methylpentan-2-yl)-6-(4-(oxetan-3-yl)piperazin-1-yl)-1-oxoisoindolin-5-yl)pyrazolo[1,5-a]pyrimidine-3-carboxamide;

126  (R)-N-(2-(4-Hydroxy-4-methylpentan-2-yl)-6-(4-(oxetan-3-yl)piperazin-1-yl)-1-oxoisoindolin-5-yl)pyrazolo[1,5-a]pyrimidine-3-carboxamide;

(R)-N-(6-(4-(tert-Butyl)piperazin-1-yl)-2-(2-fluoro-3-hydroxy-3-methylbutyl)-1-oxoisoindolin-5-yl)pyrazolo[1,5-a]pyrimidine-3-carboxamide;

N-(2-((R)-2-Fluoro-3-hydroxy-3-methylbutyl)-6-(4-((1r,3R)-3-fluorocyclobutyl)piperazin-1-yl)-1-oxoisoindolin-5-yl)pyrazolo[1,5-a]pyrimidine-3-carboxamide;

N-(2-((R)-2-Fluoro-3-hydroxy-3-methylbutyl)-6-((S)-3-methyl-4-(oxetan-3-yl)piperazin-1-yl)-1-oxoisoindolin-5-yl)pyrazolo[1,5-a]pyrimidine-3-carboxamide;

N-(2-((R)-2-Fluoro-3-hydroxy-3-methylbutyl)-6-((R)-3-methyl-4-(oxetan-3-yl)piperazin-1-yl)-1-oxoisoindolin-5-yl)pyrazolo[1,5-a]pyrimidine-3-carboxamide;

(R)-5-Acetamido-N-(6-(dimethylamino)-2-(2-fluoro-3-hydroxy-3-methylbutyl)-1-oxoisoindolin-5-yl)pyrazolo[1,5-a]pyrimidine-3-carboxamide;

(R)-N-(6-((1-(2,2-Difluoroethyl)piperidin-4-yl)oxy)-2-(2-fluoro-3-hydroxy-3-methylbutyl)-1-oxoisoindolin-5-yl)pyrazolo[1,5-a]pyrimidine-3-carboxamide;

(R)-N-(6-(4-Cyclobutylpiperazin-1-yl)-2-(2-fluoro-3-hydroxy-3-methylbutyl)-1-oxoisoindolin-5-yl)pyrazolo[1,5-a]pyrimidine-3-carboxamide;

(R)-N-(6-(4-(3,3-difluorocyclobutyl)piperazin-1-yl)-2-(2-fluoro-3-hydroxy-3-methylbutyl)-1-oxoisoindolin-5-yl)pyrazolo[1,5-a]pyrimidine-3-carboxamide;

(R)-N-(2-(2-Fluoro-3-hydroxy-3-methylbutyl)-6-((1-(oxetan-3-yl)piperidin-4-yl)oxy)-1-oxoisoindolin-5-yl)pyrazolo[1,5-a]pyrimidine-3-carboxamide;

(R)-N-(2-(2-Fluoro-3-hydroxy-3-methylbutyl)-6-(5-methylpyridin-2-yl)-1-oxoisoindolin-5-yl)pyrazolo[1,5-a]pyrimidine-3-carboxamide;

(R)-N-(2-(2-Fluoro-3-hydroxy-3-methylbutyl)-6-(2-hydroxypropan-2-yl)-1-oxoisoindolin-5-yl)pyrazolo[1,5-a]pyrimidine-3-carboxamide;

N-(6-(Dimethylamino)-7-(hydroxymethyl)-2-isopropyl-1-oxoisoindolin-5-yl)pyrazolo[1,5-a]pyrimidine-3-carboxamide;

N-(2-((R)-2-fluoro-3-hydroxy-3-methylbutyl)-6-(6-(oxetan-3-yl)-3-azabicyclo[3.1.0]hexan-3-yl)-1-oxoisoindolin-5-yl)pyrazolo[1,5-a]pyrimidine-3-carboxamide;

N-(6-(4-(azetidin-1-yl)-3,3-difluoropiperidin-1-yl)-2-((R)-2-fluoro-3-hydroxy-3-methylbutyl)-1-oxoisoindolin-5-yl)pyrazolo[1,5-a]pyrimidine-3-carboxamide;

(R)-N-(6-(4-(3,3-difluoroazetidin-1-yl)piperidin-1-yl)-2-(2-fluoro-3-hydroxy-3-methylbutyl)-1-oxoisoindolin-5-yl)pyrazolo[1,5-a]pyrimidine-3-carboxamide;

(R)-N-(6-((difluoromethoxy)methyl)-2-(2-fluoro-3-hydroxy-3-methylbutyl)-1-oxoisoindolin-5-yl)pyrazolo[1,5-a]pyrimidine-3-carboxamide;

N-(2-((R)-2-fluoro-3-hydroxy-3-methylbutyl)-6-(octahydro-2H-cyclopenta[c]pyridin-2-yl)-1-oxoisoindolin-5-yl)pyrazolo[1,5-a]pyrimidine-3-carboxamide;

N-(2-((R)-2-fluoro-3-hydroxy-3-methylbutyl)-6-(hexahydrofuro[3,4-c]pyridin-5(3H)-yl)-1-oxoisoindolin-5-yl)pyrazolo[1,5-a]pyrimidine-3-carboxamide;

N-(2-(2-fluoro-2-(oxetan-3-yl)ethyl)-6-morpholino-1-oxoisoindolin-5-yl)pyrazolo[1,5-a]pyrimidine-3-carboxamide; and, N-(2-isopropyl-5-morpholino-3-oxo-2,3-dihydro-1H-indazol-6-yl)pyrazolo[1,5-a]pyrimidine-3-carboxamide.

* * * * *